US009212137B2

(12) United States Patent
DeLuca et al.

(10) Patent No.: US 9,212,137 B2
(45) Date of Patent: Dec. 15, 2015

(54) CRYSTALLIZATION OF (20R,22R)-2-METHYLENE-19-NOR-22-METHYL-1α,25-DIHYDROXYVITAMIN $D_3$ AND RELATED PRECURSORS

(71) Applicant: Wisconsin Alumni Research Foundation, Madison, WI (US)

(72) Inventors: Hector F. DeLuca, Deerfield, WI (US); Pawel Grzywacz, Madison, WI (US); Lori A. Plum, Arena, WI (US); Agnieszka Flores, Madison, WI (US); James B. Thoden, Madison, WI (US); Hazel M. Holden, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/828,302

(22) Filed: Mar. 14, 2013

(65) Prior Publication Data

US 2013/0324752 A1 Dec. 5, 2013

Related U.S. Application Data

(60) Provisional application No. 61/652,954, filed on May 30, 2012.

(51) Int. Cl.
*C07C 401/00* (2006.01)
*C07C 35/32* (2006.01)

(52) U.S. Cl.
CPC ............... *C07C 401/00* (2013.01); *C07C 35/32* (2013.01); *C07B 2200/07* (2013.01); *C07B 2200/13* (2013.01); *C07C 2102/24* (2013.01)

(58) Field of Classification Search
USPC .......................................... 552/653; 568/619
See application file for complete search history.

(56) References Cited

U.S. PATENT DOCUMENTS 5,086,191 A 2/1992 DeLuca et al.
5,536,713 A 7/1996 DeLuca et al.
5,843,928 A 12/1998 DeLuca et al.
8,664,206 B2 * 3/2014 DeLuca et al. ................ 514/167
2011/0237557 A1 9/2011 DeLuca et al.

FOREIGN PATENT DOCUMENTS

WO 0066548 A1 11/2000

OTHER PUBLICATIONS

Iwasaki, H.; Miyamoto, Y.; Hosotani, R.; Nakano, Y.; Konno, K.; Takayama, H. "Synthesis and Biological Evaluation of (23R)- and (23S)-24,24-Difluoro-1a,23,25-trihydroxyvitamin D3" Chem. Pharm. Bull. 1998, 46 (12), 1932-1935.*

Norris, J.F. "Experimental Organic Chemistry" McGraw-Hill Book Company. New York. 1924. Ch 1, pp. 1-3.*

Flores et al., "A 20S Combined with a 22R Configuration Markedly Increases both in Vivo and in Vitro Biological Activity of 1[alpha],25-Dihydroxy-22-methyl-2-methylene-19-norvitamin D3", Journal of Medical Chemistry, 2012, 55: 4352-4366.

Fujishaima et al., "Highly Potent Cell Differentiation—Inducing Analogues of 1[alpha],25-Dihydroxyvitamin d3: Synthesis and Biological activity of 2-methyl-1,25-dihydroxyvitamin D3 with side-chain Modifications", Bioorganic & Medicinal Chemistry, 2001, 9: 525-535.

International Search Report and Written Opinion, PCT International Application No. PCT/US2013/038886, mailed Aug. 12, 2013.

Andrews et al., "A Direct, Regio- and Stereoselective 1Alpha-Hydroxylation of (5E)-Calciferol Derivatives", Journal of Organic Chemistry, 1986, 51: 1635-1637.

Baggiolini et al., "Stereocontrolled Total Synthesis of 1[alpha],25-Dihydroxycholecaliferol and 1[alpha],25-Dihydroxyergocalciferol", Journal of Organic Chemistry, 1986, 51: 3098-3108.

Calverley et al., "A Biologically Active Vitamin D Metabolite Analogue", Tetrahedron, 1987, 43(20): 4609-4619.

Choudhry et al., "Synthesis of a Biologically Active Vitamin-D2 Metabolite", Journal of Organic Chemistry, 1993, 58:1496-1500.

Lythgoe et al., "Calciferol and its Relatives. Part 22. A Direct Total Synthesis of Vitamin D2 and Vitamin D3", J Chem. Soc. Perkin I, 1978, 590-595.

Lythgoe, "Synthetic Approaches to Vitamin D and its Relatives", Chem. Soc. Rev., 1983, 9: 449-475.

Paaren et al., "Direct C-1 Hydroxylation of Vitamin D Compounds: Convenient Preparation of 1alpha-Hydroxyvitamin D3,1alpha-Dihydroxyvitamin D3 and 1alpha,Hydroxyvitamin D2", Proc. Natl. Acad. Sci. USA, 1978, 75(5): 2080-2081.

Paaren et al., "Direct C-1 Hydroxylation of Vitamin D3 and Related Compounds", J. Org. Chem., 1980, 45: 3253-3258.

Perlman et al., "Novel Synthesis of 19-Nor-Vitamin D Compounds", Tetrahedron Letters, 1991, 32: 7663-7666.

Nerinckx et al., "An Improved Synthesis of 1Alpha-Hydroxy Vitamin D3", Tetrahedron, 1991, 47(45): 9419-9430.

Sardina et al., "Studies on the Synthesis of Side-Chain Hydroxylated Metabolites of Vitamin D. 2. Stereocontrolled Synthesis of 25-Hydroxyvitamin D2", Journal of Organic Chemistry, 1986, 51: 1264-1269.

Sicinski et al., "New 1alpha,25-Dihydroxy-19-norvitamin D3 Compounds of High Biological Activity: Synthesis and Biological Evaluation of 2-Hydroxymethyl, 2-Methyl, and 2-Methylene Analogs", J. Med. Chem., 1998, 41: 4662-4674.

Sheldrick, "Phase Annealing in SHELX-90: Direct Methods for Larger Structures", Acta Cryst., 1990, A46: 467-473.

(Continued)

*Primary Examiner* — Sabiha N Qazi
(74) *Attorney, Agent, or Firm* — Andrus Intellectual Property Law, LLP

(57) ABSTRACT

Disclosed are methods of purifying the compound (20R, 22R)-2-methylene-19-nor-22-methyl-1α,25-dihydroxyvitamin $D_3$ to obtain the compound in crystalline form. The methods typically include the steps of dissolving a product containing the compound in a solvent comprising hexane and 2-propanol, cooling the solvent and dissolved product below ambient temperature for a sufficient amount of time to form a precipitate of crystals, and recovering the crystals. Certain diol precursors formed during the synthesis of the compound and its diasteromers also may be obtained in crystalline form using ethyl acetate as a solvent.

33 Claims, 4 Drawing Sheets

(56) References Cited

OTHER PUBLICATIONS

Toh et al., "Studies on a Convergent Route to Side-Chain Analogues of Vitamin D:25-Hydroxy-23-oxavitamin D3", Journal of Organic Chemistry, 1983, 48: 1414-1417.

Vanmaele et al., "A Stereocontrolled Partial Synthesis of 1Alpha-Hydroxy Vitamin D3", Tetrahedron Letters, 1982, 23(9): 995-998.

Vanmaele et al., "1Alpha-Hydroxy Previtamin D3 and its Selective Formation From 1-Keto Previtamin D3", Tetrahedron, 1984, 40(7): 1179-1182.

Vanmaele et al., "An Efficient Synthesis of 1Alpha-25-Dihydroxy Vitamin D3", Tetrahedron, 1985, 41(1): 141-144.

International Preliminary Report on Patentability for PCT/US2013/038886 dated Dec. 11, 2014.

* cited by examiner

CRYSTALLIZATION OF (20R,22R)-2-METHYLENE-19-NOR-22-METHYL-1α,25-DIHYDROXYVITAMIN $D_3$ AND RELATED PRECURSORS

CROSS-REFERENCE TO RELATED PATENT APPLICATIONS

The present application claims the benefit under 35 U.S.C. §119(e) to U.S. Provisional Patent Application No. 61/652,954, filed on May 30, 2012, the content of which is incorporated herein by reference in its entirety.

STATEMENT REGARDING FEDERALLY SPONSORED RESEARCH OR DEVELOPMENT

This invention was made with government support under DK047814 awarded by the National Institutes of Health. The government has certain rights in the invention.

BACKGROUND

The field of the present invention relates to purification of organic compounds, and more particularly to the purification of the compounds (20R,22R)-2-methylene-19-nor-22-methyl-1α,25-dihydroxyvitamin D3 (referred to herein as "SAG-2") as well as certain diol precursors (referred to herein as "Diol-1," "Diol-2," and "Diol-3"), formed during the synthesis of the (20R,22S), (20R,22R), (20S,22R) and (20S,22S) diastereomers of 2-Methylene-19-nor-22-methyl-1α,25-dihydroxyvitamin $D_3$ (referred to herein as "SAG-1," "SAG-2," "AGS-1" and "AGS-2" respectively), by preparing the compounds in crystalline form.

Purification of organic compounds, especially those designated for pharmaceutical use, is of considerable importance for chemists synthesizing such compounds. Preparation of the compound usually requires many synthetic steps and, therefore, the final product can be contaminated not only with side-products derived from the last synthetic step of the procedure but also with compounds that were formed in previous steps. Even chromatographic purification, which is a very efficient but relatively time-consuming process, does not usually provide compounds which are sufficiently pure to be used as drugs.

Depending on the method used to synthesize 1α-hydroxyvitamin D compounds, different minor undesirable compounds can accompany the final product. Thus, for example, if direct C-1 hydroxylation of the 5,6-trans geometric isomer of vitamin D is performed, followed by $SeO_2$/NMO oxidation and photochemical irradiation, (see Andrews et al., *J. Org. Chem.* 51, 1635 (1986); Calverley et al., *Tetrahedron* 43, 4609 (1987); Choudry et al., *J. Org. Chem.* 58, 1496 (1993)), the final 1-hydroxyvitamin D product can be contaminated with 1β-hydroxy- as well as 5,6-trans isomers. If the method consists of C-1 allylic oxidation of the 4-phenyl-1,2,4-triazoline-3,5-dione adduct of the pre-vitamin D compound, followed by cycloreversion of the modified adduct under basic conditions, (see Nevinckx et al., *Tetrahedron* 47, 9419 (1991); Vanmaele et al., *Tetrahedron* 41, 141 (1985) and 40, 1179 (1994); Vanmaele et al., *Tetrahedron Lett.* 23, 995 (1982)), one can expect that the desired 1α-hydroxyvitamin can be contaminated with the pre-vitamin 5(10), 6,8-triene and 1β-hydroxy isomer. One of the most useful C-1 hydroxylation methods, of very broad scope and numerous applications, is the experimentally simple procedure elaborated by Paaren et al., *J. Org. Chem.* 45, 3253 (1980); and *Proc. Natl. Acad. Sci U.S.A.* 75, 2080 (1978). This method consists of allylic oxidation of 3,5-cyclovitamin D derivatives, readily obtained from the buffered solvolysis of vitamin D tosylates, with $SeO_2$/t-BuOOH and subsequent acid-catalyzed cycloreversion to the desired 1α-hydroxy compounds. Taking into account this synthetic path it is reasonable to assume that the final product can be contaminated with the 1α-hydroxy epimer, the 5,6-trans isomer and the pre-vitamin D form. 1α-hydroxyvitamin $D_4$ is another undesirable contaminant found in 1α-hydroxyvitamin D compounds synthesized from vitamin $D_2$ or from ergosterol. 1α-hydroxyvitamin $D_4$ results from C-1 oxidation of vitamin $D_4$, which in turn is derived from contamination of the commercial ergosterol material. Typically, the final product may contain up to about 1.5% by weight 1α-hydroxyvitamin $D_4$. Thus, a purification technique that would eliminate or substantially reduce the amount of 1α-hydroxyvitamin $D_4$ in the final product to less than about 0.1-0.2% would be highly desirable.

The vitamin D conjugated triene system is not only heat- and light-sensitive but it is also prone to oxidation, leading to the complex mixture of very polar compounds. Oxidation usually happens when a vitamin D compound has been stored for a prolonged time. Other types of processes that can lead to a partial decomposition of vitamin D compounds consist of some water-elimination reactions. The driving force for these reactions is the allylic (1α-) and homoallylic (3β-) position of the hydroxy groups. The presence of such above-mentioned oxidation and elimination products can be easily detected by thin-layer chromatography.

Usually, all 1α-hydroxylation procedures require at least one chromatographic purification. However, even chromatographically purified 1α-hydroxyvitamin D compounds, although showing consistent spectroscopic data that suggests homogeneity, do not meet the purity criteria required for therapeutic agents that can be orally, parenterally or transdermally administered. Therefore, it is evident that a suitable method of purification of 1α-hydroxylated vitamin D compounds such as SAG-2 is required.

SUMMARY

Disclosed herein are methods of purifying the compound SAG-2 as well as certain diol precursors of the compound (Diol-1, Diol-2, or Diol-3), which are formed during the synthesis of SAG- and SAG-2. The purification methods typically include a crystallization step to obtain SAG-2 as well as the desired diol precursors Diol-1 and Diol-2 in crystalline form. The solvent plays an important role in the crystallization process, and is typically an individual liquid substance or a suitable mixture of different liquids. For crystallizing SAG-2, as well as the desired diol precursors Diol-1, Diol-2, or Diol-3, the most appropriate solvent and/or solvent system is characterized by the following factors:

(1) low toxicity;

(2) low boiling point;

(3) significant dependence of solubility properties with regard to temperature (condition necessary for providing satisfactory crystallization yield); and (4) relatively low cost.

Interestingly, hexane, so frequently used for crystallization purposes, was found less suitable as the sole solvent for crystallization of SAG-2 or any of the diol precursors Diol-1, Diol-2 or Diol-3. However, it was found that ethyl acetate was most useful as the sole solvent for the crystallization of the diol precursors Diol-1, Diol-2 and Diol-3, and a mixture of 2-propanol and hexane, was most useful for the crystallization of the end product SAG-2. In particular, it was determined that a mixture of about 10% to about 20% 2-propanol (v/v) with about 90% to about 80% hexane (v/v) (and preferably 15% 2-propanol (v/v) with about 85% hexane (v/v)) performed well. The ethyl acetate solvent and the 2-propanol/hexane solvent mixture were easy to remove by evaporation or other well-known methods. In all cases the crystallization process occurred easily and efficiently. The precipitated crystals were sufficiently large to assure their recovery by filtration or other means, and thus were suitable for x-ray analysis.

Accordingly, disclosed is a compound having the formula:

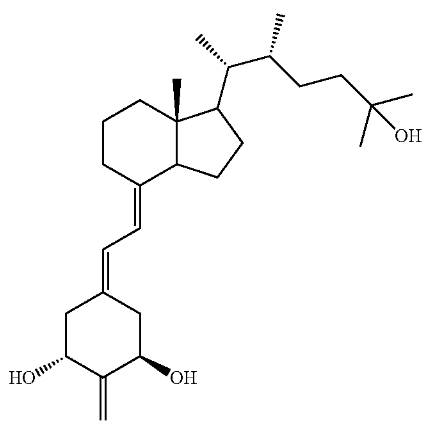 [SMILES: C=C1[C@H](O)CC(=C/C=C2\CCC[C@@]3(C)C2CCC3[C@H](C)[C@H](C)CCC(C)(C)O)C[C@H]1O]

in crystalline form. More specifically, the compound may be referred to as (20R,22R)-2-methylene-19-nor-22-methyl-1α,25-dihydroxyvitamin $D_3$ or "SAG-2", which has the above illustrated structural formula, in crystalline form.

Also disclosed is a compound having the formula

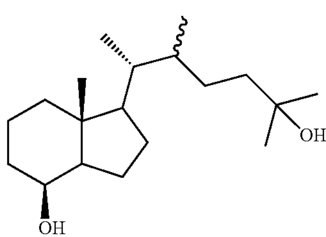 [SMILES: CC(CCC(C)(C)O)[C@@H](C)C1CCC2[C@@H](O)CCC[C@]12C]

in crystalline form, where the wavy line at carbon 22 indicates the methyl group attached to carbon 22 may be in its R or S orientation. More specifically, disclosed are (8S,20R,22S)-Des-A,B-22-methyl-cholestan-8,25-diol (Diol-1) in crystalline form, and (8S,20R,22R)-Des-A,B-22-methyl-cholestan-8,25-diol (Diol-2) in crystalline form.

Further, disclosed is a compound having the formula

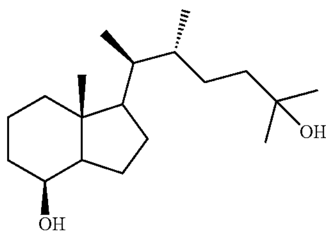 [SMILES: C[C@H](CCC(C)(C)O)[C@H](C)C1CCC2[C@@H](O)CCC[C@]12C]

in crystalline form. More specifically, the compound may be referred to as (8S,20S,22R)-Des-A,B-22-methyl-cholestan-8,25-diol (Diol-3) in crystalline form.

DETAILED DESCRIPTION

Figure 1:
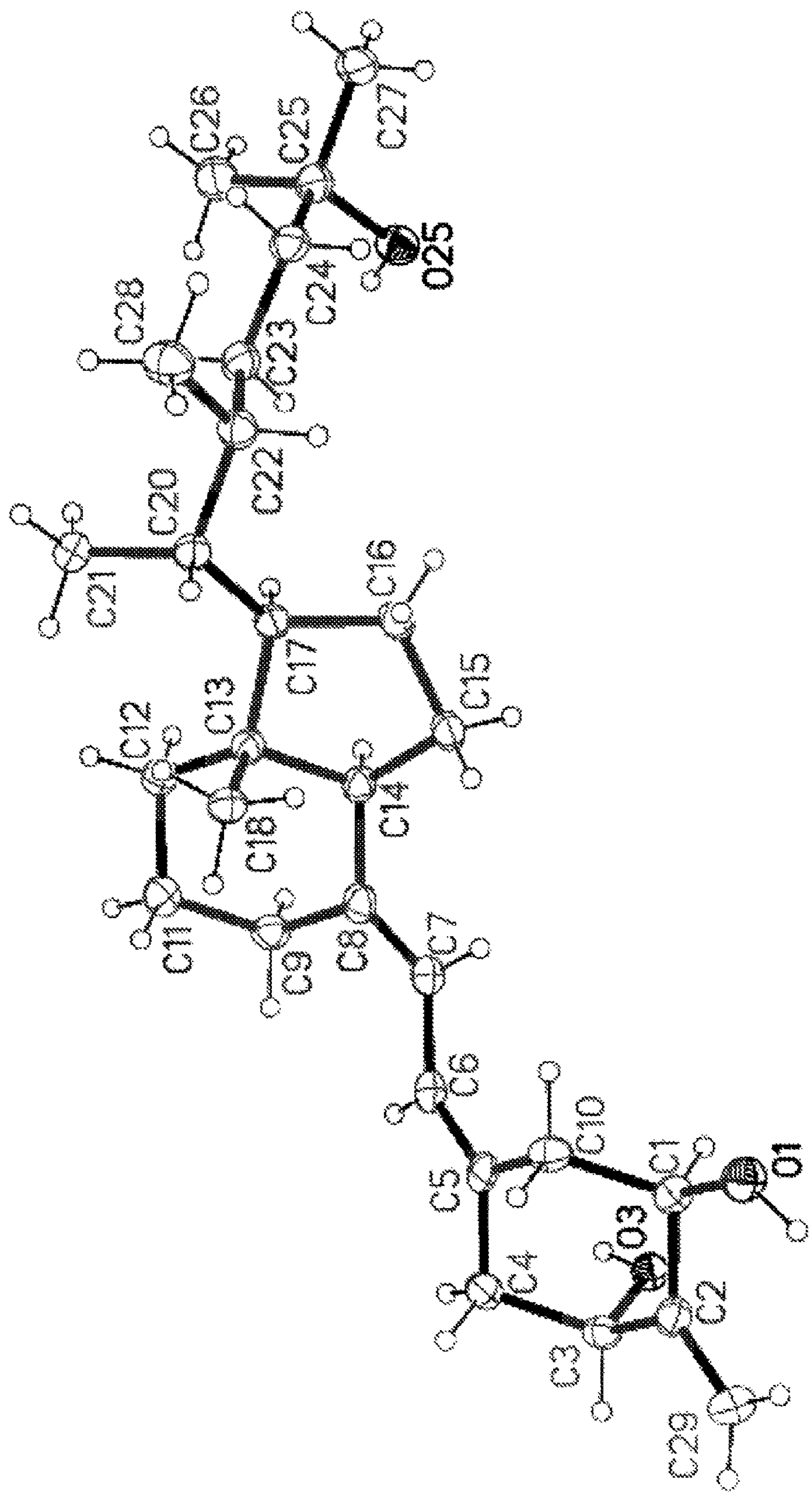
FIG. 1 is an illustration of the three dimensional molecular structure for SAG-2 as defined by the atomic positional parameters discovered and set forth herein.

Disclosed herein is the compound (20R,22S)-2-methylene-19-nor-22-methyl-1α,25-dihydroxyvitamin D3 (SAG-1), characterized by the formula I shown below:

I

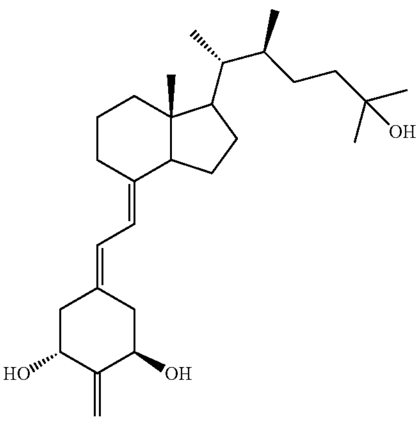

Also disclosed herein is the compound (20R,22R)-2-methylene-19-nor-22-methyl-1α,25-dihydroxyvitamin D3 (SAG-2) in crystalline form, a pharmacologically important compound, characterized by the formula II shown below:

II

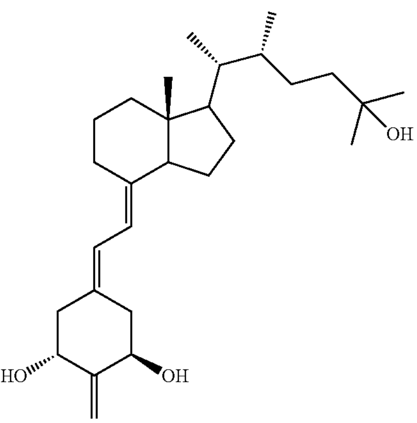 [SMILES: C=C1[C@H](O)CC(=C/C=C2\CCC[C@@]3(C)C2CCC3[C@H](C)[C@H](C)CCC(C)(C)O)C[C@H]1O]

Also disclosed herein is the compound (8S,20R,22S)-Des-A,B-22-methyl-cholestan-8,25-diol (Diol-1) in crystalline form. Diol-1 is the precursor of SAG-1 formed during the synthesis of SAG-1, and is characterized by the formula III shown below:

III

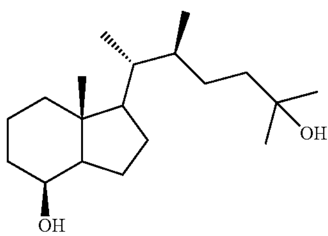

Also disclosed herein is the compound (8S,2R,22R)-Des-A,B-22-methyl-cholestan-8,25-diol (Diol-2) in crystalline form. Diol-2 is the precursor of SAG-2 formed during the synthesis of SAG-2, and is characterized by the formula IV shown below:

IV

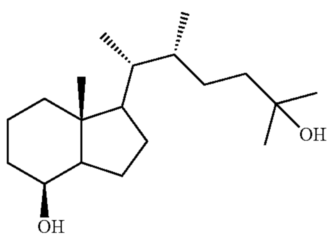

Also disclosed herein is the compound (20S,22R)-2-methylene-19-nor-22-methyl-1α,25-dihydroxyvitamin $D_3$ (AGS-1), characterized by the formula V shown below:

V

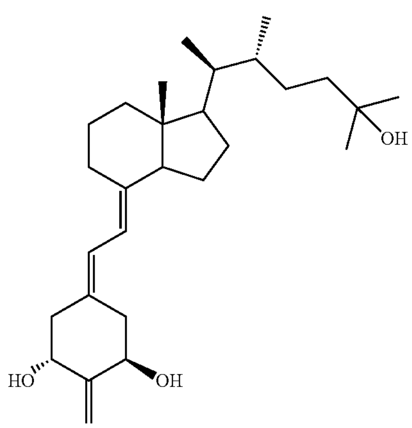

Also disclosed herein is the compound (20S,22S)-2-methylene-19-nor-22-methyl-1α,25-dihydroxyvitamin D3 (AGS-2), characterized by the formula VI shown below:

VI

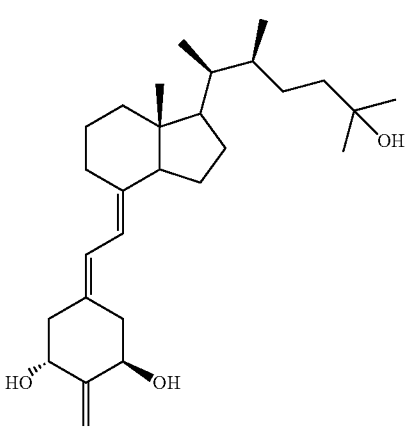

Also disclosed herein is the compound (8S,20S,22R)-Des-A,B-22-methyl-cholestan-8,25-diol (Diol-3) in crystalline form. Diol-3 is the precursor of AGS-1 formed during the synthesis of AGS-1, and is characterized by the formula VII shown below:

VII

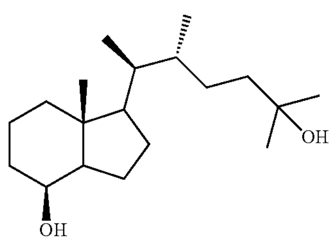

Also disclosed herein is the compound (8S,20S,22S)-Des-A,B-22-methyl-cholestan-8,25-diol (Diol-4). Diol-4 is the precursor of AGS-2 formed during the synthesis of AGS-2, and is characterized by the formula VIII shown below:

VIII

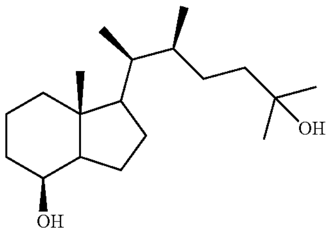

Also disclosed are methods of purifying SAG-2, Diol-1, Diol-2 and Diol-3. The purification technique typically involves obtaining the SAG-2, Diol-1, Diol-2 and Diol-3 products in crystalline form by utilizing a crystallization procedure wherein the material to be purified is dissolved using as the solvent either ethyl acetate as the sole solvent to obtain Diol-1, Diol-2 and Diol-3 in crystalline form, or a mixture comprised of 2-propanol and hexane to obtain SAG-2 in crystalline form. In particular, it was determined that a mixture of about 10% to about 20% 2-propanol (v/v) and 90% to about 80% hexane (v/v) performed well. Preferably the mixture comprises about 15% 2-propanol (v/v) and about 85% hexane (v/v). Thereafter, the solvent can be removed by evaporation, with or without vacuum, or other means as is well known, or the resultant crystals may be filtered from the mother liquor. The technique can be used to purify a wide range of final products containing Diol-1, Diol-2, Diol-3 and SAG-2 obtained from any known synthesis, and in varying concentrations, ranging from microgram amounts to kilogram amounts. As is well known to those skilled in this art, the amount of solvent utilized may be modulated according to the amount of Diol-1, Diol-2, Diol-3 and SAG-2 to be purified.

EXAMPLES

The following examples are illustrative and should not be interpreted as limiting the claimed subject matter.

The usefulness and advantages of the present crystallization procedure is shown in the following specific Examples. After crystallization, the precipitated material was observed under a microscope to confirm its crystalline form. Yields of crystals were relatively high and the obtained crystals showed a relatively sharp melting point of 159° C. (SAG-2), 147-148° C. (Diol-1), 108-110° C. (Diol-2), and 133-134° C. (Diol-3).

The described crystallization process of the synthetic Diol-1, Diol-2, Diol-3 and SAG-2 products represents a valuable purification method, which can remove most side products derived from the synthetic path. Such impurity is the result of the contamination of starting raw materials. The crystallization process occurred easily and efficiently; and the precipitated crystals were sufficiently large to assure their recovery by filtration, or other means, and thus were suitable for x-ray analysis.

Example 1

Crystallization of (20R,22R)-2-methylene-19-nor-22-methyl-1α,25-dihydroxyvitamin $D_3$ (SAG-2)

Crystallization from 2-Propanol/Hexane.

(20R,22R)-2-methylene-19-nor-22-methyl-1α,25-dihydroxyvitamin $D_3$ (13.5 mg), was suspended in hexane (4 mL) and then 2-propanol was added dropwise to the suspension. The mixture was heated in a water bath to dissolve the vitamin, then was left at room temperature for about 1 hour, and finally was kept in a refrigerator for about 48 hours. The precipitated crystals were filtered off, washed with a small volume of a cold (0° C.) 2-propanol/hexane (3:1) mixture, and dried to give crystalline material. It should be noted that an excess of 2-propanol should be avoided to get the point of saturation, (i.e., only about 1 mole or less of 2-propanol should be added).

Experimental.

A colorless prism-shaped crystal of SAG-2 having dimensions 0.25×0.36×0.65 mm was selected for structural analysis. Intensity data were collected using a Bruker AXS Platinum 135 CCD detector controlled with the PROTEUM software suite (Bruker AXS Inc., Madison, Wis.). The x-ray source was CuK radiation (1.54178 Å) from a Rigaku RU200 x-ray generator equipped with Montel optics, operated at 50 kV and 90 mA. The x-ray data were processed with SAINT version 7.06A (Bruker AXS Inc.) and internally scaled with SADABS version 2005/1 (Bruker AXS Inc.). The sample was mounted on a glass fiber using vacuum grease and cooled to 100 K. The intensity data were measured as a series of phi and omega oscillation frames each of 1° for 10-15 sec/frame. The detector was operated in 512×512 mode and was positioned 4.5 cm from the sample. Cell parameters were determined from a non-linear least squares fit of 3541 peaks in the range of 4.0<theta<55°. The data were merged to form a set of 4787 independent data with R(int)=0.042.

The monoclinic space group C2 was determined by systematic absences and statistical tests and verified by subsequent refinement. The structure was solved by direct methods and refined by full-matrix least-squares methods on F2, (a) G. M. Sheldrick (1994), SHELXTL Version 5 Reference Manual, Bruker AXS Inc.; (b) International Tables for Crystallography, Vol. C, Kluwer: Boston (1995). Hydrogen atom positions were determined from difference peaks and ultimately refined by a riding model with idealized geometry. Non-hydrogen atoms were refined with anisotropic displacement parameters. In addition to one molecule of compound SAG-2, there was also one molecule of 2-propanol in the asymmetric unit. A total of 316 parameters were refined against 1 restraint and 4787 data to give wR2=0.1903 and S=1.246 for weights of $w=1/[s^2(F^2)+(0.1150P^2)]$, where $P=[Fo^2+2Fc^2]/3$. The final R(F) was 0.0768 for the 4787 observed data. The largest shift/s.u. was 0.001 in the final refinement cycle and the final difference map had maxima and minima of 0.579 and −0.456 e/Å$^3$, respectively. The absolute structure was determined by refinement of the Flack parameter, H. D. Flack, Acta Cryst. A, vol. 39, 876-881 (1983).

The three dimensional structure of SAG-2 as defined by the following physical data and atomic positional parameters described and calculated herein (Tables 1-8) is illustrated in FIG. 1.

Example 2

Crystallization of (8S,20R,22S)-Des-A,B-22-methyl-cholestan-8,25-diol (Diol-1) and (8S,20R,22R)-Des-A,B-22-methyl-cholestan-8,25-diol (Diol-2)

Crystallization from ethyl acetate. A mixture of Diol-1 and Diol-2 (0.17 g) in 2:1 ratio (based on $^1$HNMR) was dissolved in ethyl acetate (less than 0.2 mL) and left in the refrigerator to cool. The pure crystals (96 mg) of Diol-1, which had the highest concentration, precipitated first. The 22S absolute configuration of Diol-1 was established. The filtrate was concentrated and the obtained oil dissolved in ethyl acetate (less than 0.2 mL). The mixture was left in the refrigerator and pure crystals of Diol-2 (44.6 mg) were obtained. The 22R absolute configuration of Diol-2 was established. A second batch of pure crystals (16 mg) of the Diol-1 was obtained from the filtrate after second crystallization.

Experimental Analysis of Diol-1.

A colorless prism-shaped crystal of Diol-1 having dimensions 0.11×0.18×0.45 mm was selected for structural analysis. Intensity data were collected using a Bruker AXS Platinum 135 CCD detector controlled with the PROTEUM software suite (Bruker AXS Inc., Madison, Wis.). The x-ray source was CuK radiation (1.54178 Å) from a Rigaku RU200 x-ray generator equipped with Montel optics, operated at 50 kV and 90 mA. The x-ray data were processed with SAINT version 7.06A (Bruker AXS Inc.) and internally scaled with SADABS version 2005/1 (Bruker AXS Inc.). The sample was mounted on a glass fiber using vacuum grease and cooled to 100 K. The intensity data were measured as a series of phi and omega oscillation frames each of 1° for 5 sec/frame. The detector was operated in 512×512 mode and was positioned 4.5 cm from the sample. Cell parameters were determined from a non-linear least squares fit of 3987 peaks in the range of 4.0<theta<55°. The data were merged to form a set of 2821 independent data with R(int)=0.042.

The monoclinic space group C2 was determined by systematic absences and statistical tests and verified by subsequent refinement. The structure was solved by direct methods and refined by full-matrix least-squares methods on F2, (a) G. M. Sheldrick (1994), SHELXTL Version 5 Reference Manual, Bruker AXS Inc.; (b) International Tables for Crystallography, Vol. C, Kluwer: Boston (1995). Hydrogen atom positions were determined from difference peaks and ultimately refined by a riding model with idealized geometry. Non-hydrogen atoms were refined with anisotropic displacement parameters. A total of 190 parameters were refined against 1 restraint and 2821 data to give wR2=0.1078 and S=1.134 for weights of $w=1/[s^2(F^2)+(0.0533P)^2]$, where $P=[Fo^2+2Fc^2]/3$. The final R(F) was 0.0401 for the 2821 observed data. The largest shift/s.u. was 0.001 in the final refinement cycle and the final difference map had maxima and minima of 0.410 and −0.347 e/Å$^3$, respectively. The absolute structure was determined by refinement of the Flack parameter, H. D. Flack, Acta Cryst. A, vol. 39, 876-881 (1983).

Figure 2:
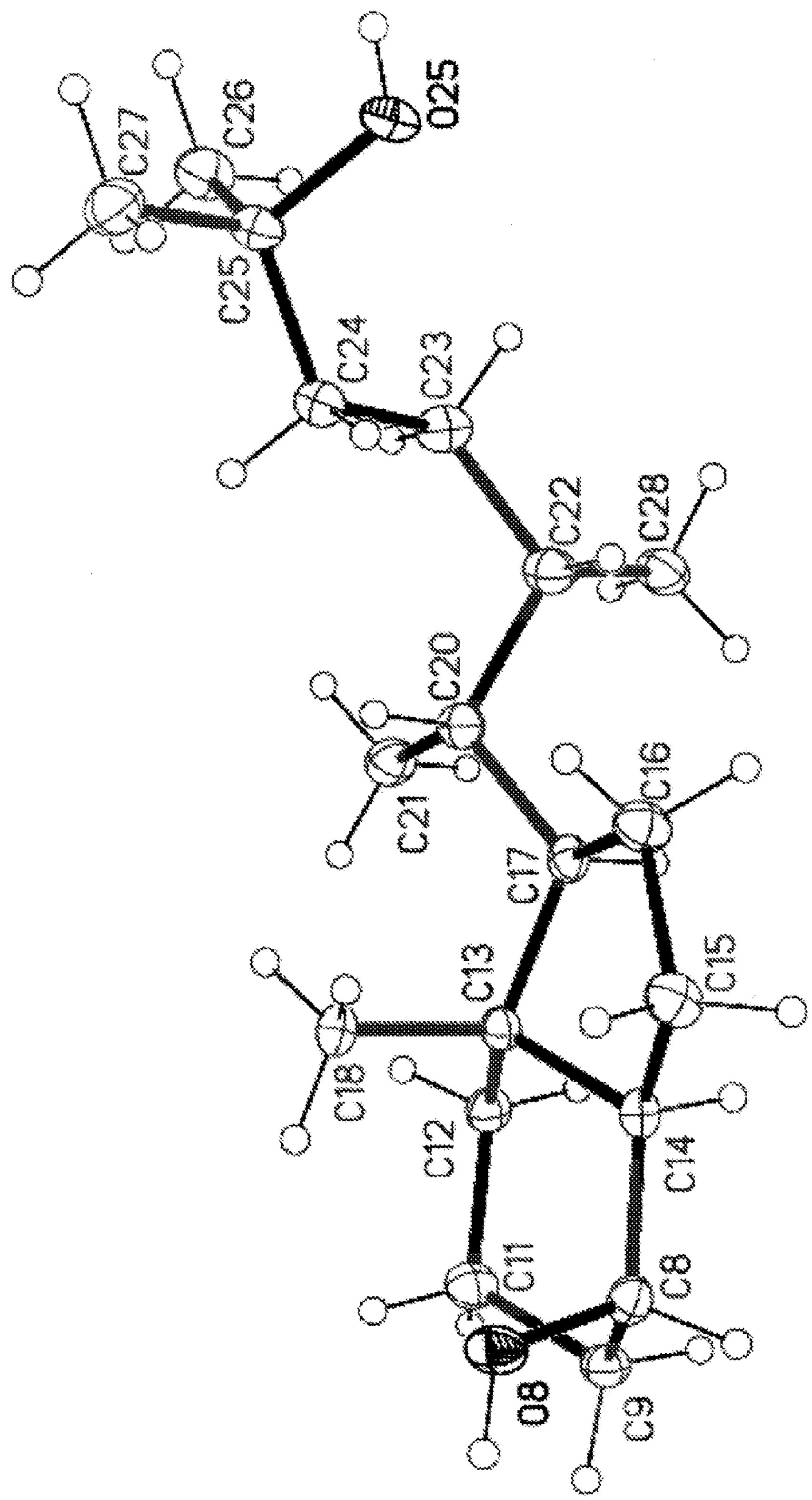
FIG. 2 is an illustration of the three dimensional molecular structure for Diol-1 as defined by the atomic positional parameters discovered and set forth herein.

The three dimensional structure of Diol-1 as defined by the following physical data and atomic positional parameters described and calculated herein (Tables 9-16) is illustrated in FIG. 2.

Experimental Analysis of Diol-2. A colorless prism-shaped crystal of Diol-2 having dimensions 0.15×0.19×0.55 mm was selected for structural analysis. Intensity data were collected using a Bruker AXS Platinum 135 CCD detector controlled with the PROTEUM software suite (Bruker AXS Inc., Madison, Wis.). The x-ray source was CuK radiation (1.54178 Å) from a Rigaku RU200 x-ray generator equipped with Montel optics, operated at 50 kV and 90 mA. The x-ray data were processed with SAINT version 7.06A (Bruker AXS Inc.) and internally scaled with SADABS version 2005/1 (Bruker AXS Inc.). The sample was mounted on a glass fiber using vacuum grease and cooled to 100 K. The intensity data were measured as a series of phi and omega oscillation frames each of 1° for 5-10 sec/frame. The detector was operated in 512×512 mode and was positioned 4.5 cm from the sample. Cell parameters were determined from a non-linear least squares fit of 4485 peaks in the range of 4.0<theta<55°. The data were merged to form a set of 5680 independent data with R(int)=0.047.

The monoclinic space group P2(1) was determined by systematic absences and statistical tests and verified by subsequent refinement. The structure was solved by direct methods and refined by full-matrix least-squares methods on F2, (a) G. M. Sheldrick (1994), SHELXTL Version 5 Reference Manual, Bruker AXS Inc.; (b) International Tables for Crystallography, Vol. C, Kluwer: Boston (1995). Two molecules of Diol-2 were present in the asymmetric unit. Hydrogen atom positions were determined from difference peaks and ultimately refined by a riding model with idealized geometry. Non-hydrogen atoms were refined with anisotropic displacement parameters. A total of 379 parameters were refined against 1 restraint and 5680 data to give wR2=0.1103 and S=1.030 for weights of $w=1/[s^2(F^2)+(0.0643P)^2]$, where $P=[Fo^2+2Fc^2]/3$. The final R(F) was 0.0478 for the 5680 observed data. The largest shift/s.u. was 0.001 in the final refinement cycle and the final difference map had maxima and minima of 0.250 and −0.330 e/Å$^3$, respectively. The absolute structure was determined by refinement of the Flack parameter, H. D. Flack, Acta Cryst. A, vol. 39, 876-881 (1983).

Figure 3:
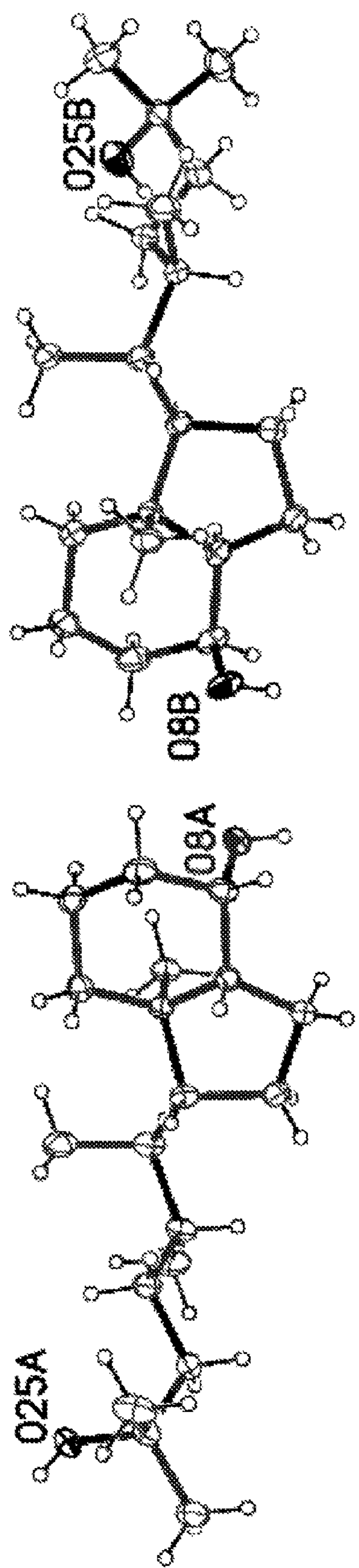
FIG. 3 is an illustration of the three dimensional molecular structure for Diol-2 as defined by the atomic positional parameters discovered and set forth herein.

The three dimensional structure of Diol-2 as defined by the following physical data and atomic positional parameters described and calculated herein (Tables 17-24) is illustrated in FIG. 3.

Example 3

Crystallization of (8S,20S,22R)-Des-A,B-22-methyl-cholestan-8,25-diol (Diol-3)

Crystallization from Ethyl Acetate.

A mixture of Diol-3 and Diol-4 (55 mg) in 2:1 ratio (based on HNMR) was dissolved in ethyl acetate (less than 0.2 mL) and left in the refrigerator to cool. The pure crystals (38.9 mg) of Diol-3, which had the highest concentration, precipitated first. The 22R absolute configuration of Diol-3 was established.

Experimental.

A colorless prism-shaped crystal of Diol-3 having dimensions 0.24×0.31×0.76 mm was selected for structural analysis. Intensity data were collected using a Bruker AXS Platinum 135 CCD detector controlled with the PROTEUM software suite (Bruker AXS Inc., Madison, Wis.). The x-ray source was CuK radiation (1.54178 Å) from a Rigaku RU200 x-ray generator equipped with Montel optics, operated at 50 kV and 90 mA. The x-ray data were processed with SAINT version 7.06A (Bruker AXS Inc.) and internally scaled with SADABS version 2005/1 (Bruker AXS Inc.). The sample was mounted on a glass fiber using vacuum grease and cooled to 100 K. The intensity data were measured as a series of phi and omega oscillation frames each of 1° for 5 sec/frame. The detector was operated in 512×512 mode and was positioned 4.5 cm from the sample. Cell parameters were determined from a non-linear least squares fit of 2476 peaks in the range of 4.0<theta<55°. The data were merged to form a set of 5350 independent data with R(int)=0.0689.

The monoclinic space group P2(1) was determined by systematic absences and statistical tests and verified by subsequent refinement. The structure was solved by direct methods and refined by full-matrix least-squares methods on F2, (a) G. M. Sheldrick (1994), SHELXTL Version 5 Reference Manual, Bruker AXS Inc.; (b) International Tables for Crystallography, Vol. C, Kluwer: Boston (1995). Hydrogen atom positions were determined from difference peaks and ultimately refined by a riding model with idealized geometry. Non-hydrogen atoms were refined with anisotropic displacement parameters. A total of 379 parameters were refined against 1 restraint and 5350 data to give wR2=0.1991 and S=1.047 for weights of $w=1/[s^2(F^2)+(0.1134P)^2]$, where $P=[Fo^2+2Fc^2]/3$. The final R(F) was 0.0872 for the 5350 observed data. The largest shift/s.u was 0.001 in the final refinement cycle and the final difference map had maxima and minima of 0.358 and −0.427 e/Å$^3$, respectively. The absolute structure was determined by refinement of the Flack parameter, H. D. Flack, Acta Cryst. A, vol. 39, 876-881 (1983).

Figure 4:
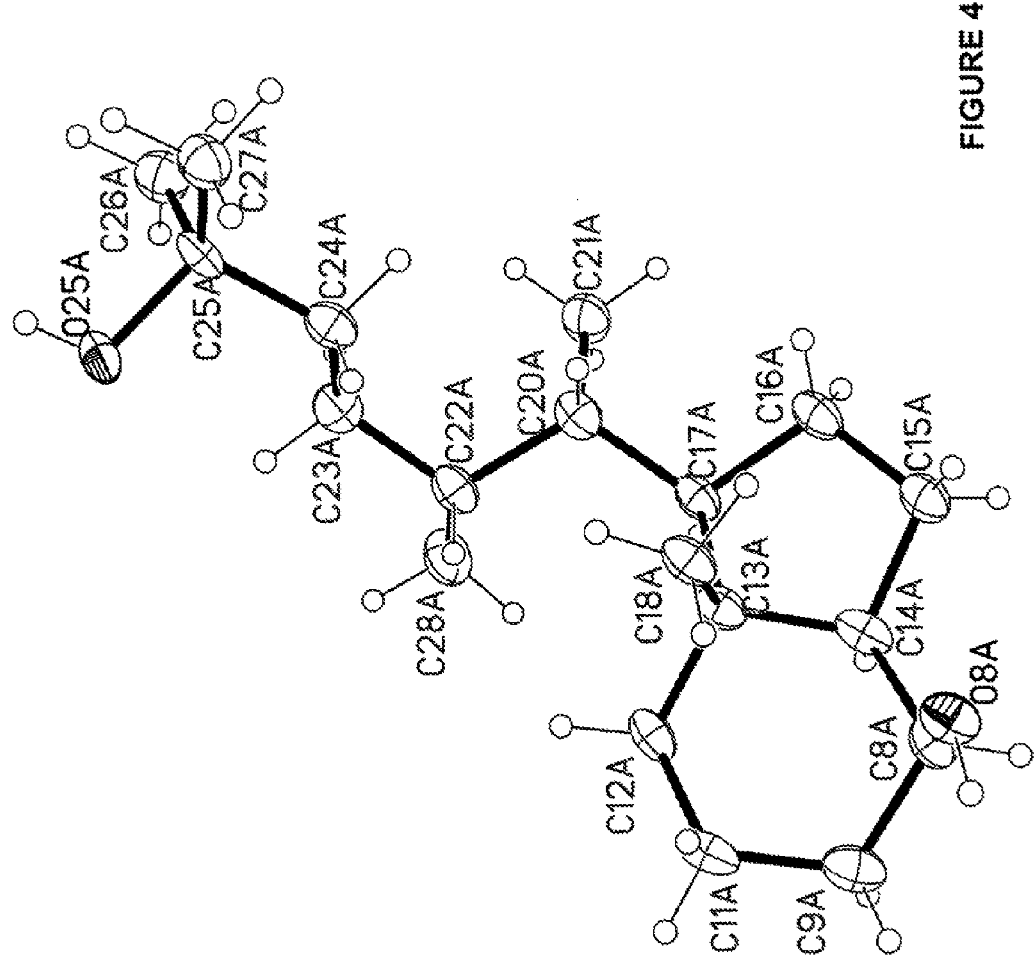
FIG. 4 is an illustration of the three dimensional molecular structure for Diol-3 as defined by the atomic positional parameters discovered and set forth herein.

The three dimensional structure of Diol-3 as defined by the following physical data and atomic positional parameters described and calculated herein (Tables 25-32) is illustrated in FIG. 4.

TABLE 1

| Crystal data and structure refinement for SAG-2. | |
| --- | --- |
| Empirical formula | C31H54O4 |
| Formula weight | 490.74 |

TABLE 1-continued

| Crystal data and structure refinement for SAG-2. | | |
|---|---|---|
| Temperature | 100(0) K | |
| Wavelength | 1.54178 Å | |
| Crystal system, space group | Monoclinic, C2 | |
| Unit cell dimensions | a = 27.039(5) Å | α = 90° |
| | b = 6.4790(13) Å | β = 103.35(3)° |
| | c = 17.412(4) Å | γ = 90° |
| Volume | 2967.9(10) $Å^3$ | |
| Z | 4 | |
| Calculated density | 1.098 $Mg/m^3$ | |
| Absorption coefficient | 0.544 $mm^{-1}$ | |
| F(000) | 1088 | |
| Crystal size | 0.25 × 0.36 × 0.65 mm | |
| Theta range for data collection | 2.61 to 64.53° | |
| Limiting indices | −30 <= h <= 29, −7 <= k <= 7, 0 <= l <= 20 | |
| Reflections collected/unique | 9654/4787 [R(int) = 0.0780] | |
| Data/restraints/parameters | 4787/1/316 | |
| Goodness-of-fit on F^2 | 1.246 | |
| Final R indices [I > 2□(I)] | R1 = 0.0738, wR2 = 0.1874 | |
| R indices (all data) | R1 = 0.0768, wR2 = 0.1903 | |
| Absolute structure parameter | 0.2(3) | |
| Largest diff. peak and hole | 0.579 and −0.456 e/$Å^3$ | |

TABLE 2

Atomic coordinates ($Å^2 \times 10^4$) and equivalent isotropic displacement parameters ($Å^2 \times 10^3$) for SAG-2 U(eq) is defined as one third of the trace of the orthogonalized Uij tensor.

| | x | y | z | U(eq) |
|---|---|---|---|---|
| O(3) | 7952(1) | 9146(3) | 6297(1) | 21(1) |
| O(1) | 8114(1) | 2849(3) | 7013(1) | 26(1) |
| O(25) | 11013(1) | 8186(3) | 13414(1) | 28(1) |
| O(50) | 9116(1) | 1933(4) | 7372(1) | 37(1) |
| C(6) | 7941(1) | 9084(5) | 8399(2) | 23(1) |
| C(14) | 8869(1) | 8980(5) | 10461(2) | 21(1) |
| C(7) | 8328(1) | 8548(5) | 9090(2) | 22(1) |
| C(2) | 7630(1) | 5724(5) | 6325(2) | 22(1) |
| C(23) | 9917(1) | 7161(5) | 13397(2) | 25(1) |
| C(22) | 9503(1) | 5626(5) | 13026(2) | 23(1) |
| C(1) | 8019(1) | 4999(4) | 7039(2) | 20(1) |
| C(10) | 7835(1) | 5535(5) | 7787(2) | 23(1) |
| C(8) | 8472(1) | 9665(5) | 9757(2) | 22(1) |
| C(25) | 10873(1) | 7438(5) | 14117(2) | 25(1) |
| C(18) | 8226(1) | 6929(5) | 11008(2) | 22(1) |
| C(24) | 10403(1) | 6076(5) | 13845(2) | 24(1) |
| C(3) | 7503(1) | 7995(5) | 6341(2) | 21(1) |
| C(9) | 8227(1) | 11671(5) | 9917(2) | 23(1) |
| C(27) | 11308(1) | 6101(5) | 14578(2) | 28(1) |
| C(11) | 8009(1) | 11478(5) | 10648(2) | 24(1) |
| C(12) | 8403(1) | 10663(5) | 11370(2) | 22(1) |
| C(5) | 7717(1) | 7793(5) | 7815(2) | 21(1) |
| C(17) | 9105(1) | 7790(5) | 11801(2) | 20(1) |
| C(13) | 8632(1) | 8618(4) | 11188(2) | 20(1) |
| C(20) | 9011(1) | 6654(5) | 12540(2) | 22(1) |
| C(29) | 7404(1) | 4522(5) | 5732(2) | 27(1) |
| C(16) | 9367(1) | 6372(5) | 11291(2) | 23(1) |
| C(28) | 9376(1) | 4146(5) | 13640(2) | 30(1) |
| C(50) | 9482(1) | 2186(5) | 8090(2) | 30(1) |
| C(15) | 9187(1) | 7052(5) | 10425(2) | 23(1) |
| C(26) | 10774(1) | 9277(6) | 14608(2) | 33(1) |
| C(4) | 7333(1) | 8540(5) | 7099(2) | 23(1) |
| C(52) | 9311(2) | 3957(6) | 8533(2) | 44(1) |
| C(21) | 8761(1) | 8064(5) | 13050(2) | 27(1) |
| C(51) | 9560(2) | 225(6) | 8562(2) | 42(1) |

TABLE 3

| Bond lengths [Å] for SAG-2. | | | |
|---|---|---|---|
| O(3)—C(3) | 1.441(4) | O(1)—C(1) | 1.419(4) |
| O(25)—C(25) | 1.445(4) | O(50)—C(50) | 1.413(4) |

TABLE 3-continued

| Bond lengths [Å] for SAG-2. | | | |
|---|---|---|---|
| C(6)—C(5) | 1.347(4) | C(6)—C(7) | 1.443(4) |
| C(14)—C(8) | 1.499(4) | C(14)—C(15) | 1.527(4) |
| C(14)—C(13) | 1.562(4) | C(7)—C(8) | 1.347(4) |
| C(2)—C(29) | 1.325(4) | C(2)—C(1) | 1.506(4) |
| C(2)—C(3) | 1.512(4) | C(23)—C(22) | 1.524(4) |
| C(23)—C(24) | 1.535(4) | C(22)—C(28) | 1.534(4) |
| C(22)—C(20) | 1.554(4) | C(1)—C(10) | 1.537(4) |
| C(10)—C(5) | 1.501(4) | C(8)—C(9) | 1.514(4) |
| C(25)—C(26) | 1.526(5) | C(25)—C(27) | 1.531(4) |
| C(25)—C(24) | 1.530(4) | C(18)—C(13) | 1.532(4) |
| C(3)—C(4) | 1.538(4) | C(9)—C(11) | 1.525(4) |
| C(11)—C(12) | 1.541(4) | C(12)—C(13) | 1.527(4) |
| C(5)—C(4) | 1.507(4) | C(17)—C(20) | 1.552(4) |
| C(17)—C(16) | 1.557(4) | C(17)—C(13) | 1.559(4) |
| C(20)—C(21) | 1.535(4) | C(16)—C(15) | 1.538(4) |
| C(50)—C(51) | 1.502(5) | C(50)—C(52) | 1.513(5) |

TABLE 4

| bond angles [°] for SAG-2. | |
|---|---|
| C(5)—C(6)—C(7) | 126.3(3) |
| C(8)—C(14)—C(15) | 120.9(2) |
| C(8)—C(14)—C(13) | 111.0(2) |
| C(15)—C(14)—C(13) | 104.5(2) |
| C(8)—C(7)—C(6) | 126.7(3) |
| C(29)—C(2)—C(1) | 124.6(3) |
| C(29)—C(2)—C(3) | 121.3(3) |
| C(1)—C(2)—C(3) | 114.0(2) |
| C(22)—C(23)—C(24) | 112.0(3) |
| C(23)—C(22)—C(28) | 111.9(2) |
| C(23)—C(22)—C(20) | 113.8(3) |
| C(28)—C(22)—C(20) | 110.3(3) |
| O(1)—C(1)—C(2) | 112.1(2) |
| O(1)—C(1)—C(10) | 110.2(2) |
| C(2)—C(1)—C(10) | 109.2(2) |
| C(5)—C(10)—C(1) | 111.1(2) |
| C(7)—C(8)—C(14) | 123.8(3) |
| C(7)—C(8)—C(9) | 124.7(3) |
| C(14)—C(8)—C(9) | 111.4(2) |
| O(25)—C(25)—C(26) | 109.1(3) |
| O(25)—C(25)—C(27) | 108.3(3) |
| C(26)—C(25)—C(27) | 111.2(3) |
| O(25)—C(25)—C(24) | 107.0(2) |
| C(26)—C(25)—C(24) | 112.4(3) |
| C(27)—C(25)—C(24) | 108.6(3) |
| C(23)—C(24)—C(25) | 116.5(3) |
| O(3)—C(3)—C(2) | 107.8(2) |
| O(3)—C(3)—C(4) | 110.5(2) |
| C(2)—C(3)—C(4) | 110.7(2) |
| C(8)—C(9)—C(11) | 110.7(2) |
| C(9)—C(11)—C(12) | 112.4(3) |
| C(13)—C(12)—C(11) | 111.5(2) |
| C(6)—C(5)—C(10) | 124.7(3) |
| C(6)—C(5)—C(4) | 121.9(3) |
| C(10)—C(5)—C(4) | 113.4(2) |
| C(20)—C(17)—C(16) | 112.1(2) |
| C(20)—C(17)—C(13) | 117.7(3) |
| C(16)—C(17)—C(13) | 102.8(2) |
| C(12)—C(13)—C(18) | 110.8(3) |
| C(12)—C(13)—C(17) | 117.7(2) |
| C(18)—C(13)—C(17) | 109.3(2) |
| C(12)—C(13)—C(14) | 107.4(2) |
| C(18)—C(13)—C(14) | 110.5(2) |
| C(17)—C(13)—C(14) | 100.5(2) |
| C(21)—C(20)—C(22) | 112.1(2) |
| C(21)—C(20)—C(17) | 112.1(2) |
| C(22)—C(20)—C(17) | 111.7(3) |
| C(15)—C(16)—C(17) | 107.9(2) |
| O(50)—C(50)—C(51) | 111.5(3) |
| O(50)—C(50)—C(52) | 107.8(3) |
| C(51)—C(50)—C(52) | 112.5(3) |
| C(14)—C(15)—C(16) | 104.4(2) |
| C(5)—C(4)—C(3) | 110.5(3) |

TABLE 5

Anisotropic displacement parameters ($Å^2 \times 10^3$) for SAG-2. The anisotropic displacement factor exponent takes the form "$-2\pi^2[h^2a * 2U_{11} + + 2hka * b * U_{12}]$

| | $U_{11}$ | $U_{22}$ | $U_{33}$ | $U_{23}$ | $U_{13}$ | $U_{12}$ |
|---|---|---|---|---|---|---|
| O(3) | 22(1) | 19(1) | 24(1) | −3(1) | 6(1) | −2(1) |
| O(1) | 30(1) | 19(1) | 28(1) | −5(1) | 4(1) | 1(1) |
| O(25) | 26(1) | 27(1) | 29(1) | 6(1) | 5(1) | 0(1) |
| O(50) | 31(1) | 32(1) | 45(1) | −7(1) | 2(1) | 7(1) |
| C(6) | 25(2) | 24(1) | 23(1) | 0(1) | 12(1) | 1(1) |
| C(14) | 21(2) | 22(1) | 20(1) | −5(1) | 6(1) | −2(1) |
| C(7) | 22(2) | 23(2) | 23(1) | 0(1) | 9(1) | 0(1) |
| C(2) | 22(2) | 25(2) | 20(1) | −3(1) | 7(1) | −1(1) |
| C(23) | 22(2) | 30(2) | 22(1) | −1(1) | 6(1) | −3(1) |
| C(22) | 21(2) | 24(1) | 23(1) | −1(1) | 5(1) | −1(1) |
| C(1) | 22(2) | 17(1) | 21(1) | −2(1) | 4(1) | −3(1) |
| C(10) | 22(2) | 25(2) | 20(1) | 4(1) | 1(1) | −2(1) |
| C(8) | 20(2) | 26(2) | 24(2) | −2(1) | 10(1) | −3(1) |
| C(25) | 21(2) | 30(2) | 23(1) | 2(1) | 6(1) | −1(1) |
| C(18) | 20(2) | 26(2) | 20(1) | −2(1) | 2(1) | −2(1) |
| C(24) | 21(2) | 30(2) | 21(1) | 3(1) | 6(1) | −1(1) |
| C(3) | 18(2) | 25(2) | 20(1) | 2(1) | 2(1) | −3(1) |
| C(9) | 22(2) | 23(2) | 22(1) | −2(1) | 3(1) | 0(1) |
| C(27) | 18(2) | 41(2) | 25(2) | 6(1) | 5(1) | −1(1) |
| C(11) | 25(2) | 18(1) | 28(2) | −4(1) | 7(1) | 0(1) |
| C(12) | 22(2) | 23(1) | 21(1) | −4(1) | 4(1) | −4(1) |
| C(5) | 23(2) | 25(2) | 17(1) | 0(1) | 11(1) | −1(1) |
| C(17) | 18(2) | 23(1) | 20(1) | −4(1) | 4(1) | −1(1) |
| C(13) | 19(2) | 24(2) | 18(1) | −3(1) | 5(1) | −2(1) |
| C(20) | 19(2) | 25(2) | 20(1) | −2(1) | 4(1) | −2(1) |
| C(29) | 29(2) | 29(2) | 21(1) | 0(1) | 0(1) | −2(1) |
| C(16) | 16(2) | 26(2) | 26(1) | −4(1) | 4(1) | 2(1) |
| C(28) | 26(2) | 32(2) | 33(2) | 5(1) | 4(1) | −3(1) |
| C(50) | 24(2) | 30(2) | 36(2) | −1(1) | 7(1) | −3(1) |
| C(15) | 18(2) | 27(2) | 26(1) | −4(1) | 7(1) | 1(1) |
| C(26) | 26(2) | 41(2) | 30(2) | −9(1) | 3(1) | −2(2) |
| C(4) | 20(2) | 26(2) | 24(1) | 1(1) | 5(1) | 2(1) |
| C(52) | 35(2) | 40(2) | 54(2) | −18(2) | 4(2) | −1(2) |
| C(21) | 26(2) | 36(2) | 20(1) | 0(1) | 7(1) | 4(1) |
| C(51) | 39(2) | 44(2) | 47(2) | 9(2) | 19(2) | 3(2) |

TABLE 6

Hydrogen coordinates ($Å^2 \times 10^4$) and isotropic displacement parameters ($Å^2 \times 10^3$) for SAG-2.

| | x | y | z | U(eq) |
|---|---|---|---|---|
| H(3A) | 7956 | 10240 | 6535 | 32 |
| H(1A) | 8059 | 2470 | 6552 | 39 |
| H(25A) | 10920 | 9388 | 13333 | 42 |
| H(50A) | 8839 | 2337 | 7425 | 56 |
| H(6A) | 7835 | 10453 | 8353 | 27 |
| H(14A) | 9108 | 10129 | 10600 | 25 |
| H(7A) | 8496 | 7303 | 9073 | 26 |
| H(23A) | 9791 | 8049 | 13757 | 30 |
| H(23B) | 9997 | 8022 | 12986 | 30 |
| H(22A) | 9641 | 4783 | 12657 | 27 |
| H(1B) | 8338 | 5737 | 7058 | 24 |
| H(10A) | 7533 | 4738 | 7796 | 27 |
| H(10B) | 8096 | 5165 | 8249 | 27 |
| H(18A) | 7935 | 7432 | 10628 | 33 |
| H(18B) | 8126 | 6557 | 11484 | 33 |
| H(18C) | 8361 | 5739 | 10799 | 33 |
| H(24A) | 10485 | 4996 | 13510 | 29 |
| H(24B) | 10330 | 5413 | 14307 | 29 |
| H(3B) | 7229 | 8326 | 5881 | 25 |
| H(9A) | 7957 | 12029 | 9465 | 27 |
| H(9B) | 8478 | 12768 | 9997 | 27 |
| H(27A) | 11606 | 6937 | 14751 | 42 |
| H(27B) | 11379 | 5015 | 14244 | 42 |
| H(27C) | 11212 | 5512 | 15028 | 42 |
| H(11A) | 7720 | 10549 | 10533 | 28 |
| H(11B) | 7889 | 12819 | 10773 | 28 |
| H(12A) | 8672 | 11675 | 11527 | 27 |
| H(12B) | 8241 | 10473 | 11807 | 27 |

TABLE 6-continued

Hydrogen coordinates ($Å^2 \times 10^4$) and isotropic displacement parameters ($Å^2 \times 10^3$) for SAG-2.

| | x | y | z | U(eq) |
|---|---|---|---|---|
| H(17A) | 9332 | 8959 | 11984 | 24 |
| H(20A) | 8769 | 5538 | 12347 | 26 |
| H(29A) | 7483 | 3123 | 5739 | 33 |
| H(29B) | 7167 | 5076 | 5308 | 33 |
| H(16A) | 9734 | 6499 | 11460 | 27 |
| H(16B) | 9276 | 4942 | 11348 | 27 |
| H(28A) | 9683 | 3526 | 13938 | 46 |
| H(28B) | 9151 | 3088 | 13377 | 46 |
| H(28C) | 9215 | 4898 | 13990 | 46 |
| H(50B) | 9806 | 2568 | 7967 | 36 |
| H(15A) | 9474 | 7366 | 10199 | 28 |
| H(15B) | 8984 | 5982 | 10112 | 28 |
| H(26A) | 10501 | 10090 | 14305 | 50 |
| H(26B) | 11075 | 10107 | 14750 | 50 |
| H(26C) | 10683 | 8789 | 15078 | 50 |
| H(4A) | 7294 | 10023 | 7131 | 28 |
| H(4B) | 7006 | 7905 | 7086 | 28 |
| H(52A) | 9266 | 5171 | 8208 | 66 |
| H(52B) | 9564 | 4718 | 9009 | 66 |
| H(52C) | 8995 | 3606 | 8663 | 66 |
| H(21A) | 8460 | 8671 | 12728 | 41 |
| H(21B) | 8995 | 9135 | 13277 | 41 |
| H(21C) | 8673 | 7268 | 13463 | 41 |
| H(51A) | 9670 | −847 | 8259 | 63 |
| H(51B) | 9246 | −175 | 8688 | 63 |
| H(51C) | 9813 | 442 | 9041 | 63 |

TABLE 7

Torsion angles [deg] for SAG-2.

| | |
|---|---|
| C(5)—C(6)—C(7)—C(8) | −163.6(3) |
| C(24)—C(23)—C(22)—C(28) | 56.3(4) |
| C(24)—C(23)—C(22)—C(20) | −177.9(2) |
| C(29)—C(2)—C(1)—O(1) | −0.8(4) |
| C(3)—C(2)—C(1)—O(1) | 178.0(3) |
| C(29)—C(2)—C(1)—C(10) | −123.2(3) |
| C(3)—C(2)—C(1)—C(10) | 55.6(3) |
| O(1)—C(1)—C(10)—C(5) | −178.3(3) |
| C(2)—C(1)—C(10)—C(5) | −54.8(3) |
| C(6)—C(7)—C(8)—C(14) | 178.2(3) |
| C(6)—C(7)—C(8)—C(9) | 3.3(5) |
| C(15)—C(14)—C(8)—C(7) | 7.7(5) |
| C(13)—C(14)—C(8)—C(7) | −115.1(3) |
| C(15)—C(14)—C(8)—C(9) | −176.8(3) |
| C(13)—C(14)—C(8)—C(9) | 60.4(3) |
| C(22)—C(23)—C(24)—C(25) | 169.5(2) |
| O(25)—C(25)—C(24)—C(23) | −65.5(3) |
| C(26)—C(25)—C(24)—C(23) | 54.3(3) |
| C(27)—C(25)—C(24)—C(23) | 177.7(3) |
| C(29)—C(2)—C(3)—O(3) | −115.2(3) |
| C(1)—C(2)—C(3)—O(3) | 66.0(3) |
| C(29)—C(2)—C(3)—C(4) | 123.9(3) |
| C(1)—C(2)—C(3)—C(4) | −54.9(3) |
| C(7)—C(8)—C(9)—C(11) | 119.9(3) |
| C(14)—C(8)—C(9)—C(11) | 55.5(3) |
| C(8)—C(9)—C(11)—C(12) | 52.5(3) |
| C(9)—C(11)—C(12)—C(13) | −54.9(3) |
| C(7)—C(6)—C(5)—C(10) | 0.3(5) |
| C(7)—C(6)—C(5)—C(4) | −177.1(3) |
| C(1)—C(10)—C(5)—C(6) | −121.3(3) |
| C(1)—C(10)—C(5)—C(4) | 56.3(3) |
| C(11)—C(12)—C(13)—C(18) | −64.0(3) |
| C(11)—C(12)—C(13)—C(17) | 169.1(3) |
| C(11)—C(12)—C(13)—C(14) | 56.8(3) |
| C(20)—C(17)—C(13)—C(12) | 80.6(3) |
| C(16)—C(17)—C(13)—C(12) | −155.7(3) |
| C(20)—C(17)—C(13)—C(18) | −47.0(3) |
| C(16)—C(17)—C(13)—C(18) | 76.7(3) |
| C(20)—C(17)—C(13)—C(14) | −163.3(2) |
| C(16)—C(17)—C(13)—C(14) | −39.5(3) |
| C(8)—C(14)—C(13)—C(12) | −60.2(3) |

TABLE 7-continued

| Torsion angles [deg] for SAG-2. | |
|---|---|
| C(15)—C(14)—C(13)—C(12) | 168.0(2) |
| C(8)—C(14)—C(13)—C(18) | 60.8(3) |
| C(15)—C(14)—C(13)—C(18) | −70.9(3) |
| C(8)—C(14)—C(13)—C(17) | 176.2(2) |
| C(15)—C(14)—C(13)—C(17) | 44.4(3) |
| C(23)—C(22)—C(20)—C(21) | −61.3(3) |
| C(28)—C(22)—C(20)—C(21) | 65.4(3) |
| C(23)—C(22)—C(20)—C(17) | 65.5(3) |
| C(28)—C(22)—C(20)—C(17) | −167.8(3) |
| C(16)—C(17)—C(20)—C(21) | 179.0(3) |
| C(13)—C(17)—C(20)—C(21) | −62.1(3) |
| C(16)—C(17)—C(20)—C(22) | 52.2(3) |
| C(13)—C(17)—C(20)—C(22) | 171.1(2) |
| C(20)—C(17)—C(16)—C(15) | 149.1(3) |
| C(13)—C(17)—C(16)—C(15) | 21.8(3) |
| C(8)—C(14)—C(15)—C(16) | −156.9(3) |
| C(13)—C(14)—C(15)—C(16) | −31.1(3) |
| C(17)—C(16)—C(15)—C(14) | 5.6(3) |
| C(6)—C(5)—C(4)—C(3) | 123.1(3) |
| C(10)—C(5)—C(4)—C(3) | −54.5(3) |
| O(3)—C(3)—C(4)—C(5) | −67.1(3) |
| C(2)—C(3)—C(4)—C(5) | 52.2(3) |

TABLE 8

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 1 | −7 | 0 | 32 | 33 | 15 | 10 | 0 | 0 | 253 | 272 | 6 | −3 | −7 | 1 | 177 | 154 | 7 | 3 | −3 | 1 | 245 | 217 | 8 | 10 | 0 | 1 | 13 | 43 | 13 |
| 3 | −7 | 0 | 0 | 19 | 1 | 12 | 0 | 0 | 145 | 158 | 5 | −1 | −7 | 1 | 34 | 48 | 14 | 5 | −3 | 1 | 140 | 132 | 6 | 12 | 0 | 1 | 109 | 169 | 4 |
| 5 | −7 | 0 | 144 | 131 | 6 | 16 | 0 | 0 | 0 | 39 | 1 | 1 | −7 | 1 | 68 | 65 | 7 | 7 | −3 | 1 | 406 | 370 | 21 | 14 | 0 | 1 | 195 | 223 | 7 |
| 7 | −7 | 0 | 157 | 146 | 7 | 18 | 0 | 0 | 132 | 154 | 18 | 3 | −7 | 1 | 147 | 142 | 7 | 9 | −3 | 1 | 603 | 529 | 15 | 16 | 0 | 1 | 395 | 329 | 20 |
| 9 | −7 | 0 | 146 | 140 | 6 | 20 | 0 | 0 | 298 | 278 | 10 | 5 | −7 | 1 | 137 | 133 | 6 | 11 | −3 | 1 | 201 | 182 | 6 | 18 | 0 | 1 | 544 | 711 | 26 |
| 11 | −7 | 0 | 66 | 58 | 7 | 22 | 0 | 0 | 124 | 136 | 6 | 7 | −7 | 1 | 75 | 72 | 7 | 13 | −3 | 1 | 506 | 450 | 13 | 20 | 0 | 1 | 28 | 8 | 11 |
| 0 | −6 | 0 | 114 | 108 | 9 | 24 | 0 | 0 | 235 | 234 | 12 | 9 | −7 | 1 | 103 | 96 | 6 | 15 | −3 | 1 | 162 | 143 | 5 | 22 | 0 | 1 | 27 | 8 | 13 |
| 2 | −6 | 0 | 166 | 159 | 6 | 26 | 0 | 0 | 64 | 61 | 7 | 11 | −7 | 1 | 141 | 141 | 6 | 17 | −3 | 1 | 270 | 249 | 6 | 24 | 0 | 1 | 5 | 10 | 5 |
| 4 | −6 | 0 | 148 | 141 | 7 | 28 | 0 | 0 | 220 | 188 | 11 | −16 | −6 | 1 | 162 | 149 | 6 | 19 | −3 | 1 | 300 | 298 | 11 | 26 | 0 | 1 | 11 | 9 | 10 |
| 6 | −6 | 0 | 149 | 141 | 7 | 1 | 1 | 0 | 1483 | 1433 | 29 | −14 | −6 | 1 | 152 | 145 | 6 | 21 | −3 | 1 | 121 | 139 | 6 | 28 | 0 | 1 | 32 | 3 | 12 |
| 8 | −6 | 0 | 135 | 108 | 7 | 3 | 1 | 0 | 1089 | 1001 | 24 | −12 | −6 | 1 | 150 | 131 | 7 | 23 | −3 | 1 | 22 | 20 | 22 | −23 | 1 | 1 | 265 | 289 | 20 |
| 10 | −6 | 0 | 94 | 84 | 7 | 5 | 1 | 0 | 869 | 834 | 19 | −10 | −6 | 1 | 249 | 224 | 8 | 25 | −3 | 1 | 286 | 294 | 15 | −21 | 1 | 1 | 228 | 218 | 18 |
| 12 | −6 | 0 | 109 | 102 | 9 | 7 | 1 | 0 | 524 | 491 | 14 | −8 | −6 | 1 | 136 | 102 | 7 | 27 | −3 | 1 | 66 | 62 | 9 | −19 | 1 | 1 | 70 | 83 | 34 |
| 14 | −6 | 0 | 231 | 234 | 11 | 9 | 1 | 0 | 873 | 792 | 23 | −6 | −6 | 1 | 68 | 66 | 9 | −28 | −2 | 1 | 116 | 123 | 9 | −17 | 1 | 1 | 317 | 304 | 17 |
| 16 | −6 | 0 | 97 | 99 | 6 | 15 | 1 | 0 | 245 | 253 | 16 | −4 | −6 | 1 | 165 | 164 | 6 | −26 | −2 | 1 | 151 | 133 | 10 | −15 | 1 | 1 | 211 | 192 | 13 |
| 18 | −6 | 0 | 163 | 178 | 10 | 17 | 1 | 0 | 423 | 389 | 20 | −2 | −6 | 1 | 82 | 76 | 6 | −24 | −2 | 1 | 70 | 65 | 10 | −9 | 1 | 1 | 563 | 528 | 25 |
| 1 | −5 | 0 | 168 | 171 | 5 | 19 | 1 | 0 | 257 | 246 | 16 | 0 | −6 | 1 | 355 | 319 | 9 | −22 | −2 | 1 | 326 | 300 | 16 | −7 | 1 | 1 | 934 | 858 | 21 |
| 3 | −5 | 0 | 351 | 307 | 9 | 21 | 1 | 0 | 111 | 117 | 22 | 2 | −6 | 1 | 84 | 58 | 6 | −20 | −2 | 1 | 369 | 356 | 18 | −5 | 1 | 1 | 1077 | 1013 | 23 |
| 5 | −5 | 0 | 563 | 478 | 15 | 0 | 2 | 0 | 539 | 509 | 14 | 4 | −6 | 1 | 236 | 238 | 7 | −18 | −2 | 1 | 99 | 101 | 4 | −3 | 1 | 1 | 1702 | 1655 | 37 |
| 7 | −5 | 0 | 351 | 322 | 10 | 2 | 2 | 0 | 599 | 538 | 12 | 6 | −6 | 1 | 202 | 188 | 8 | −16 | −2 | 1 | 161 | 167 | 4 | −1 | 1 | 1 | 618 | 592 | 12 |
| 9 | −5 | 0 | 352 | 301 | 11 | 4 | 2 | 0 | 505 | 472 | 11 | 8 | −6 | 1 | 388 | 356 | 14 | −14 | −2 | 1 | 256 | 213 | 5 | 1 | 1 | 1 | 813 | 741 | 18 |
| 13 | −5 | 0 | 226 | 255 | 11 | 6 | 2 | 0 | 496 | 491 | 11 | 10 | −6 | 1 | 116 | 91 | 6 | −12 | −2 | 1 | 256 | 191 | 7 | 3 | 1 | 1 | 1853 | 1706 | 46 |
| 15 | −5 | 0 | 275 | 238 | 9 | 8 | 2 | 0 | 453 | 378 | 9 | 12 | −6 | 1 | 74 | 69 | 7 | −10 | −2 | 1 | 950 | 845 | 25 | 5 | 1 | 1 | 469 | 450 | 10 |
| 17 | −5 | 0 | 181 | 184 | 10 | 10 | 2 | 0 | 772 | 708 | 25 | 14 | −6 | 1 | 136 | 107 | 6 | −8 | −2 | 1 | 680 | 638 | 19 | 7 | 1 | 1 | 570 | 570 | 16 |
| 19 | −5 | 0 | 129 | 133 | 5 | 14 | 2 | 0 | 371 | 342 | 19 | 16 | −6 | 1 | 103 | 109 | 6 | −6 | −2 | 1 | 664 | 636 | 18 | 9 | 1 | 1 | 662 | 611 | 22 |
| 21 | −5 | 0 | 155 | 143 | 8 | 16 | 2 | 0 | 141 | 137 | 8 | −21 | −5 | 1 | 39 | 49 | 9 | −4 | −2 | 1 | 843 | 795 | 23 | 11 | 1 | 1 | 436 | 435 | 15 |
| 0 | −4 | 0 | 84 | 72 | 6 | 18 | 2 | 0 | 183 | 181 | 9 | −19 | −5 | 1 | 141 | 144 | 6 | −2 | −2 | 1 | 670 | 632 | 17 | 15 | 1 | 1 | 206 | 217 | 16 |
| 2 | −4 | 0 | 334 | 283 | 7 | 20 | 2 | 0 | 112 | 120 | 9 | −17 | −5 | 1 | 282 | 275 | 10 | 0 | −2 | 1 | 540 | 512 | 16 | 17 | 1 | 1 | 457 | 435 | 22 |
| 4 | −4 | 0 | 289 | 255 | 7 | 1 | 3 | 0 | 226 | 256 | 9 | −15 | −5 | 1 | 335 | 305 | 10 | 2 | −2 | 1 | 191 | 168 | 6 | 19 | 1 | 1 | 105 | 130 | 8 |
| 6 | −4 | 0 | 52 | 56 | 6 | 3 | 3 | 0 | 645 | 602 | 21 | −13 | −5 | 1 | 351 | 397 | 16 | 4 | −2 | 1 | 136 | 140 | 5 | 23 | 1 | 1 | 162 | 190 | 9 |
| 8 | −4 | 0 | 507 | 451 | 13 | 5 | 3 | 0 | 449 | 368 | 11 | −11 | −5 | 1 | 152 | 132 | 8 | 6 | −2 | 1 | 24 | 8 | 9 | 25 | 1 | 1 | 55 | 53 | 7 |
| 10 | −4 | 0 | 350 | 319 | 8 | 7 | 3 | 0 | 227 | 240 | 6 | −9 | −5 | 1 | 180 | 142 | 8 | 8 | −2 | 1 | 830 | 774 | 41 | 27 | 1 | 1 | 157 | 137 | 8 |
| 12 | −4 | 0 | 297 | 277 | 7 | 9 | 3 | 0 | 293 | 280 | 5 | −7 | −5 | 1 | 340 | 317 | 9 | 10 | −2 | 1 | 371 | 330 | 11 | −22 | 2 | 1 | 321 | 299 | 20 |
| 14 | −4 | 0 | 287 | 262 | 8 | 11 | 3 | 0 | 477 | 384 | 9 | −5 | −5 | 1 | 376 | 336 | 9 | 12 | −2 | 1 | 667 | 625 | 17 | −20 | 2 | 1 | 360 | 354 | 21 |
| 16 | −4 | 0 | 173 | 145 | 7 | 13 | 3 | 0 | 530 | 483 | 13 | −3 | −5 | 1 | 335 | 296 | 3 | 14 | −2 | 1 | 194 | 163 | 5 | −18 | 2 | 1 | 95 | 101 | 9 |
| 18 | −4 | 0 | 190 | 194 | 6 | 15 | 3 | 0 | 200 | 184 | 8 | −1 | −5 | 1 | 73 | 47 | 6 | 16 | −2 | 1 | 538 | 484 | 11 | −16 | 2 | 1 | 163 | 167 | 8 |
| 20 | −4 | 0 | 120 | 106 | 7 | 17 | 3 | 0 | 158 | 142 | 7 | 1 | −5 | 1 | 207 | 215 | 6 | 18 | −2 | 1 | 259 | 240 | 6 | −14 | 2 | 1 | 255 | 213 | 16 |
| 22 | −4 | 0 | 218 | 223 | 12 | 19 | 3 | 0 | 139 | 127 | 7 | 3 | −5 | 1 | 149 | 168 | 5 | 20 | −2 | 1 | 341 | 322 | 8 | −10 | 2 | 1 | 948 | 846 | 30 |
| 24 | −4 | 0 | 43 | 51 | 16 | 21 | 3 | 0 | 60 | 63 | 8 | 5 | −5 | 1 | 116 | 113 | 5 | 22 | −2 | 1 | 70 | 48 | 9 | −8 | 2 | 1 | 718 | 637 | 15 |
| 1 | −3 | 0 | 248 | 255 | 8 | 23 | 3 | 0 | 139 | 122 | 11 | 7 | −5 | 1 | 205 | 187 | 6 | 24 | −2 | 1 | 98 | 90 | 9 | −6 | 2 | 1 | 694 | 637 | 15 |
| 3 | −3 | 0 | 658 | 603 | 20 | 25 | 3 | 0 | 89 | 93 | 10 | 9 | −5 | 1 | 329 | 302 | 11 | 26 | −2 | 1 | 102 | 103 | 8 | −4 | 2 | 1 | 881 | 794 | 19 |
| 5 | −3 | 0 | 434 | 369 | 14 | 27 | 3 | 0 | 179 | 172 | 11 | 13 | −5 | 1 | 153 | 183 | 11 | 28 | −2 | 1 | 92 | 87 | 8 | −2 | 2 | 1 | 670 | 635 | 15 |
| 7 | −3 | 0 | 225 | 239 | 11 | 0 | 4 | 0 | 68 | 72 | 5 | 15 | −5 | 1 | 138 | 134 | 7 | −29 | −1 | 1 | 117 | 120 | 8 | 0 | 2 | 1 | 525 | 513 | 11 |
| 9 | −3 | 0 | 286 | 280 | 8 | 2 | 4 | 0 | 342 | 283 | 6 | 17 | −5 | 1 | 129 | 111 | 6 | −27 | −1 | 1 | 104 | 86 | 8 | 2 | 2 | 1 | 193 | 167 | 4 |
| 11 | −3 | 0 | 482 | 385 | 12 | 4 | 4 | 0 | 293 | 255 | 4 | 19 | −5 | 1 | 16 | 16 | 95 | −25 | −1 | 1 | 341 | 302 | 17 | 4 | 2 | 1 | 138 | 141 | 4 |
| 13 | −3 | 0 | 526 | 484 | 12 | 6 | 4 | 0 | 53 | 56 | 3 | 21 | −5 | 1 | 130 | 111 | 5 | −23 | −1 | 1 | 300 | 290 | 11 | 6 | 2 | 1 | 32 | 6 | 7 |
| 15 | −3 | 0 | 203 | 186 | 5 | 8 | 4 | 0 | 498 | 451 | 8 | −26 | −4 | 1 | 197 | 234 | 12 | −21 | −1 | 1 | 226 | 216 | 9 | 8 | 2 | 1 | 839 | 776 | 21 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 17 | −3 | 0 | 147 | 143 | 5 | 10 | 4 | 0 | 339 | 320 | 6 | −24 | −4 | 1 | 73 | 81 | 11 | −19 | −1 | 1 | 92 | 84 | 6 | 10 | 2 | 1 | 351 | 332 | 10 |
| 19 | −3 | 0 | 131 | 125 | 8 | 12 | 4 | 0 | 281 | 277 | 7 | −22 | −4 | 1 | 279 | 296 | 14 | −17 | −1 | 1 | 298 | 303 | 11 | 12 | 2 | 1 | 642 | 627 | 18 |
| 21 | −3 | 0 | 47 | 62 | 6 | 14 | 4 | 0 | 301 | 263 | 11 | −20 | −4 | 1 | 77 | 82 | 8 | −15 | −1 | 1 | 184 | 192 | 6 | 14 | 2 | 1 | 195 | 164 | 6 |
| 23 | −3 | 0 | 136 | 122 | 10 | 16 | 4 | 0 | 163 | 145 | 8 | −18 | −4 | 1 | 201 | 183 | 7 | −13 | −1 | 1 | 230 | 204 | 6 | 16 | 2 | 1 | 538 | 483 | 15 |
| 25 | −3 | 0 | 91 | 93 | 9 | 18 | 4 | 0 | 187 | 195 | 8 | −16 | −4 | 1 | 415 | 395 | 11 | −11 | −1 | 1 | 460 | 406 | 12 | 18 | 2 | 1 | 242 | 240 | 10 |
| 27 | −3 | 0 | 174 | 172 | 10 | 20 | 4 | 0 | 113 | 106 | 7 | −14 | −4 | 1 | 345 | 339 | 9 | −9 | −1 | 1 | 576 | 529 | 18 | 20 | 2 | 1 | 329 | 320 | 18 |
| 0 | −2 | 0 | 546 | 508 | 23 | 22 | 4 | 0 | 213 | 223 | 8 | −12 | −4 | 1 | 304 | 271 | 7 | −7 | −1 | 1 | 927 | 858 | 25 | 22 | 2 | 1 | 56 | 48 | 8 |
| 2 | −2 | 0 | 591 | 538 | 15 | 24 | 4 | 0 | 38 | 54 | 13 | −10 | −4 | 1 | 197 | 180 | 5 | −5 | −1 | 1 | 1032 | 1012 | 24 | 24 | 2 | 1 | 88 | 90 | 7 |
| 4 | −2 | 0 | 489 | 472 | 13 | 1 | 5 | 0 | 172 | 170 | 4 | −8 | −4 | 1 | 94 | 68 | 5 | −3 | −1 | 1 | 1643 | 1654 | 38 | 26 | 2 | 1 | 93 | 103 | 7 |
| 6 | −2 | 0 | 479 | 489 | 13 | 3 | 5 | 0 | 362 | 307 | 6 | −6 | −4 | 1 | 156 | 133 | 4 | −1 | −1 | 1 | 601 | 593 | 16 | −27 | 3 | 1 | 199 | 205 | 11 |
| 8 | −2 | 0 | 412 | 379 | 15 | 5 | 5 | 0 | 557 | 479 | 10 | −4 | −4 | 1 | 64 | 65 | 5 | 1 | −1 | 1 | 802 | 742 | 21 | −25 | 3 | 1 | 86 | 72 | 11 |
| 10 | −2 | 0 | 787 | 709 | 25 | 7 | 5 | 0 | 351 | 322 | 6 | −2 | −4 | 1 | 352 | 352 | 7 | 3 | −1 | 1 | 1794 | 1706 | 47 | −23 | 3 | 1 | 248 | 246 | 13 |
| 12 | −2 | 0 | 722 | 635 | 23 | 9 | 5 | 0 | 331 | 301 | 6 | 0 | −4 | 1 | 384 | 339 | 8 | 5 | −1 | 1 | 470 | 450 | 10 | −21 | 3 | 1 | 161 | 178 | 7 |
| 14 | −2 | 0 | 374 | 344 | 8 | 11 | 5 | 0 | 372 | 354 | 8 | 2 | −4 | 1 | 152 | 156 | 4 | 7 | −1 | 1 | 599 | 569 | 15 | −19 | 3 | 1 | 238 | 205 | 9 |
| 16 | −2 | 0 | 148 | 138 | 4 | 13 | 5 | 0 | 219 | 254 | 8 | 4 | −4 | 1 | 281 | 272 | 7 | 9 | −1 | 1 | 697 | 611 | 18 | −17 | 3 | 1 | 128 | 137 | 6 |
| 18 | −2 | 0 | 184 | 181 | 5 | 15 | 5 | 0 | 243 | 237 | 17 | 6 | −4 | 1 | 271 | 251 | 7 | 11 | −1 | 1 | 466 | 433 | 12 | −15 | 3 | 1 | 264 | 228 | 8 |
| 20 | −2 | 0 | 100 | 118 | 4 | 17 | 5 | 0 | 173 | 184 | 8 | 8 | −4 | 1 | 167 | 137 | 6 | 13 | −1 | 1 | 281 | 264 | 8 | −13 | 3 | 1 | 300 | 279 | 10 |
| 22 | −2 | 0 | 557 | 534 | 27 | 19 | 5 | 0 | 124 | 133 | 7 | 10 | −4 | 1 | 204 | 201 | 5 | 15 | −1 | 1 | 224 | 218 | 5 | −11 | 3 | 1 | 329 | 323 | 6 |
| 24 | −2 | 0 | 101 | 91 | 9 | 21 | 5 | 0 | 133 | 143 | 7 | 12 | −4 | 1 | 97 | 89 | 5 | 17 | −1 | 1 | 447 | 435 | 9 | −9 | 3 | 1 | 308 | 272 | 6 |
| 26 | −2 | 0 | 161 | 161 | 10 | 23 | 5 | 0 | 92 | 98 | 9 | 14 | −4 | 1 | 211 | 208 | 7 | 19 | −1 | 1 | 122 | 131 | 7 | −7 | 3 | 1 | 842 | 739 | 18 |
| 28 | −2 | 0 | 97 | 94 | 8 | 0 | 6 | 0 | 91 | 107 | 7 | 16 | −4 | 1 | 109 | 92 | 7 | 21 | −1 | 1 | 182 | 199 | 10 | −5 | 3 | 1 | 809 | 698 | 18 |
| 1 | −1 | 0 | 1439 | 1434 | 38 | 2 | 6 | 0 | 161 | 160 | 5 | 18 | −4 | 1 | 127 | 132 | 6 | 23 | −1 | 1 | 180 | 191 | 9 | −3 | 3 | 1 | 430 | 386 | 11 |
| 3 | −1 | 0 | 1075 | 1002 | 24 | 4 | 6 | 0 | 161 | 141 | 5 | 20 | −4 | 1 | 92 | 97 | 7 | 25 | −1 | 1 | 55 | 52 | 9 | −1 | 3 | 1 | 689 | 631 | 38 |
| 5 | −1 | 0 | 867 | 834 | 19 | 6 | 6 | 0 | 143 | 141 | 5 | 22 | −4 | 1 | 193 | 199 | 12 | 27 | −1 | 1 | 160 | 138 | 9 | 1 | 3 | 1 | 974 | 916 | 50 |
| 7 | −1 | 0 | 531 | 490 | 14 | 8 | 6 | 0 | 119 | 107 | 4 | 24 | −4 | 1 | 26 | 42 | 26 | 29 | −1 | 1 | 64 | 51 | 8 | 3 | 3 | 1 | 233 | 216 | 7 |
| 9 | −1 | 0 | 902 | 792 | 23 | 10 | 6 | 0 | 87 | 85 | 5 | −27 | −3 | 1 | 179 | 204 | 11 | −26 | 0 | 1 | 57 | 46 | 8 | 5 | 3 | 1 | 145 | 132 | 5 |
| 11 | −1 | 0 | 401 | 352 | 11 | 12 | 6 | 0 | 102 | 102 | 6 | −25 | −3 | 1 | 77 | 73 | 10 | −24 | 0 | 1 | 149 | 159 | 7 | 7 | 3 | 1 | 451 | 370 | 10 |
| 13 | −1 | 0 | 278 | 276 | 8 | 14 | 6 | 0 | 213 | 235 | 13 | −23 | −3 | 1 | 228 | 246 | 13 | −22 | 0 | 1 | 179 | 164 | 19 | 9 | 3 | 1 | 606 | 528 | 11 |
| 15 | −1 | 0 | 248 | 253 | 5 | 16 | 6 | 0 | 79 | 100 | 12 | −21 | −3 | 1 | 160 | 178 | 7 | −20 | 0 | 1 | 329 | 283 | 15 | 11 | 3 | 1 | 192 | 183 | 4 |
| 17 | −1 | 0 | 408 | 389 | 9 | 18 | 6 | 0 | 157 | 179 | 10 | −19 | −3 | 1 | 233 | 207 | 9 | −18 | 0 | 1 | 169 | 130 | 16 | 13 | 3 | 1 | 500 | 451 | 10 |
| 19 | −1 | 0 | 235 | 244 | 9 | 1 | 7 | 0 | 29 | 32 | 29 | −17 | −3 | 1 | 126 | 137 | 4 | −16 | 0 | 1 | 70 | 68 | 26 | 15 | 3 | 1 | 166 | 143 | 7 |
| 21 | −1 | 0 | 135 | 116 | 7 | 3 | 7 | 0 | 17 | 20 | 16 | −15 | −3 | 1 | 249 | 226 | 6 | −8 | 0 | 1 | 1574 | 1606 | 42 | 17 | 3 | 1 | 274 | 249 | 10 |
| 23 | −1 | 0 | 233 | 227 | 12 | 5 | 7 | 0 | 131 | 131 | 4 | −13 | −3 | 1 | 294 | 279 | 7 | −6 | 0 | 1 | 2445 | 2410 | 55 | 19 | 3 | 1 | 298 | 298 | 11 |
| 25 | −1 | 0 | 216 | 206 | 11 | 7 | 7 | 0 | 151 | 146 | 6 | −11 | −3 | 1 | 333 | 323 | 8 | −4 | 0 | 1 | 1502 | 1496 | 40 | 21 | 3 | 1 | 130 | 139 | 7 |
| 27 | −1 | 0 | 120 | 110 | 9 | 9 | 7 | 0 | 144 | 139 | 7 | −9 | −3 | 1 | 304 | 272 | 10 | −2 | 0 | 1 | 166 | 161 | 3 | 23 | 3 | 1 | 22 | 20 | 21 |
| 29 | −1 | 0 | 140 | 132 | 8 | 11 | 7 | 0 | 66 | 58 | 12 | −7 | −3 | 1 | 799 | 741 | 38 | 0 | 0 | 1 | 275 | 308 | 6 | 25 | 3 | 1 | 304 | 294 | 15 |
| 2 | 0 | 0 | 742 | 704 | 16 | −11 | −7 | 1 | 79 | 63 | 6 | −5 | −3 | 1 | 793 | 697 | 25 | 2 | 0 | 1 | 477 | 522 | 10 | 27 | 3 | 1 | 74 | 61 | 9 |
| 4 | 0 | 0 | 442 | 392 | 11 | −9 | −7 | 1 | 50 | 49 | 9 | −3 | −3 | 1 | 446 | 386 | 13 | 4 | 0 | 1 | 346 | 385 | 7 | −26 | 4 | 1 | 222 | 235 | 11 |
| 6 | 0 | 0 | 1527 | 1445 | 40 | −7 | −7 | 1 | 97 | 89 | 6 | −1 | −3 | 1 | 744 | 632 | 22 | 6 | 0 | 1 | 111 | 123 | 3 | −24 | 4 | 1 | 77 | 81 | 7 |
| 8 | 0 | 0 | 1077 | 1060 | 28 | −5 | −7 | 1 | 57 | 38 | 9 | 1 | −3 | 1 | 1028 | 917 | 42 | 8 | 0 | 1 | 227 | 178 | 6 | −22 | 4 | 1 | 275 | 295 | 10 |
| −20 | 4 | 1 | 79 | 81 | 8 | 9 | −7 | 2 | 124 | 123 | 6 | 15 | −3 | 2 | 199 | 182 | 6 | 26 | 0 | 2 | 92 | 78 | 7 | −4 | 4 | 2 | 142 | 136 | 3 |
| −18 | 4 | 1 | 218 | 184 | 8 | −18 | −6 | 2 | 107 | 112 | 7 | 17 | −3 | 2 | 444 | 453 | 9 | 28 | 0 | 2 | 114 | 102 | 7 | −2 | 4 | 2 | 354 | 292 | 6 |
| −16 | 4 | 1 | 404 | 394 | 22 | −16 | −6 | 2 | 85 | 61 | 6 | 19 | −3 | 2 | 318 | 301 | 11 | −25 | 1 | 2 | 94 | 110 | 23 | 0 | 4 | 2 | 687 | 590 | 11 |
| −14 | 4 | 1 | 356 | 339 | 18 | −14 | −6 | 2 | 342 | 312 | 11 | 21 | −3 | 2 | 151 | 183 | 7 | −23 | 1 | 2 | 233 | 205 | 19 | 2 | 4 | 2 | 479 | 411 | 9 |
| −12 | 4 | 1 | 293 | 271 | 7 | −12 | −6 | 2 | 123 | 106 | 7 | 23 | −3 | 2 | 57 | 59 | 11 | −21 | 1 | 2 | 234 | 207 | 18 | 4 | 4 | 2 | 95 | 86 | 3 |
| −10 | 4 | 1 | 193 | 180 | 4 | −10 | −6 | 2 | 117 | 104 | 7 | 25 | −3 | 2 | 163 | 171 | 9 | −19 | 1 | 2 | 0 | 78 | 1 | 6 | 4 | 2 | 247 | 214 | 4 |
| −8 | 4 | 1 | 88 | 68 | 3 | −8 | −6 | 2 | 161 | 140 | 7 | 27 | −3 | 2 | 25 | 42 | 24 | −17 | 1 | 2 | 108 | 93 | 19 | 8 | 4 | 2 | 186 | 170 | 4 |
| −6 | 4 | 1 | 151 | 133 | 3 | −6 | −6 | 2 | 324 | 285 | 11 | −28 | −2 | 2 | 150 | 144 | 9 | −15 | 1 | 2 | 378 | 360 | 18 | 10 | 4 | 2 | 531 | 489 | 11 |
| −4 | 4 | 1 | 63 | 55 | 3 | −4 | −6 | 2 | 82 | 72 | 6 | −26 | −2 | 2 | 72 | 61 | 10 | −9 | 1 | 2 | 579 | 537 | 26 | 12 | 4 | 2 | 306 | 286 | 8 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −2 | 4 | 1 | 361 | 352 | 6 | −2 | −6 | 2 | 85 | 97 | 6 | −24 | −2 | 2 | 205 | 186 | 12 | −7 | 1 | 2 | 325 | 307 | 7 | 14 | 4 | 2 | 350 | 314 | 10 |
| 0 | 4 | 1 | 388 | 338 | 6 | 0 | −6 | 2 | 94 | 71 | 6 | −22 | −2 | 2 | 197 | 180 | 11 | −5 | 1 | 2 | 1610 | 1481 | 34 | 16 | 4 | 2 | 175 | 196 | 9 |
| 2 | 4 | 1 | 149 | 155 | 3 | 2 | −6 | 2 | 136 | 136 | 6 | −20 | −2 | 2 | 291 | 269 | 15 | −3 | 1 | 2 | 1505 | 1389 | 33 | 18 | 4 | 2 | 32 | 55 | 23 |
| 4 | 4 | 1 | 285 | 272 | 5 | 4 | −6 | 2 | 315 | 317 | 9 | −18 | −2 | 2 | 478 | 462 | 10 | −1 | 1 | 2 | 560 | 505 | 11 | 20 | 4 | 2 | 70 | 95 | 9 |
| 6 | 4 | 1 | 274 | 251 | 4 | 6 | −6 | 2 | 343 | 322 | 12 | −16 | −2 | 2 | 498 | 439 | 10 | 1 | 1 | 2 | 1222 | 1120 | 26 | 22 | 4 | 2 | 229 | 241 | 9 |
| 8 | 4 | 1 | 167 | 137 | 4 | 8 | −6 | 2 | 204 | 174 | 8 | −14 | −2 | 2 | 232 | 187 | 5 | 3 | 1 | 2 | 1057 | 1023 | 26 | 24 | 4 | 2 | 70 | 72 | 10 |
| 10 | 4 | 1 | 201 | 201 | 4 | 10 | −6 | 2 | 260 | 241 | 9 | −12 | −2 | 2 | 515 | 466 | 17 | 5 | 1 | 2 | 615 | 611 | 16 | −23 | 5 | 2 | 93 | 116 | 10 |
| 12 | 4 | 1 | 87 | 90 | 4 | 12 | −6 | 2 | 28 | 12 | 27 | −10 | −2 | 2 | 553 | 465 | 14 | 7 | 1 | 2 | 1020 | 1026 | 27 | −21 | 5 | 2 | 84 | 94 | 7 |
| 14 | 4 | 1 | 214 | 207 | 9 | 14 | −6 | 2 | 124 | 120 | 6 | −8 | −2 | 2 | 356 | 363 | 10 | 9 | 1 | 2 | 817 | 778 | 22 | −19 | 5 | 2 | 169 | 163 | 8 |
| 16 | 4 | 1 | 94 | 93 | 8 | 16 | −6 | 2 | 108 | 115 | 7 | −6 | −2 | 2 | 338 | 315 | 10 | 11 | 1 | 2 | 162 | 204 | 5 | −17 | 5 | 2 | 84 | 66 | 8 |
| 18 | 4 | 1 | 122 | 132 | 7 | −21 | −5 | 2 | 97 | 95 | 4 | −4 | −2 | 2 | 183 | 158 | 5 | 13 | 1 | 2 | 192 | 190 | 7 | −15 | 5 | 2 | 54 | 69 | 10 |
| 20 | 4 | 1 | 89 | 97 | 7 | −19 | −5 | 2 | 150 | 163 | 6 | −2 | −2 | 2 | 1185 | 1088 | 30 | 15 | 1 | 2 | 166 | 189 | 15 | −13 | 5 | 2 | 350 | 412 | 17 |
| 22 | 4 | 1 | 205 | 199 | 12 | −17 | −5 | 2 | 80 | 63 | 7 | 0 | −2 | 2 | 633 | 567 | 18 | 19 | 1 | 2 | 367 | 421 | 22 | −11 | 5 | 2 | 185 | 171 | 5 |
| 24 | 4 | 1 | 40 | 41 | 12 | −15 | −5 | 2 | 81 | 69 | 8 | 2 | −2 | 2 | 206 | 168 | 6 | 21 | 1 | 2 | 179 | 222 | 10 | −9 | 5 | 2 | 288 | 251 | 6 |
| −23 | 5 | 1 | 100 | 99 | 9 | −13 | −5 | 2 | 340 | 414 | 16 | 4 | −2 | 2 | 718 | 678 | 18 | 23 | 1 | 2 | 172 | 187 | 10 | −7 | 5 | 2 | 467 | 432 | 8 |
| −21 | 5 | 1 | 45 | 48 | 12 | −11 | −5 | 2 | 181 | 171 | 8 | 6 | −2 | 2 | 875 | 825 | 30 | 25 | 1 | 2 | 205 | 205 | 11 | −5 | 5 | 2 | 338 | 318 | 6 |
| −19 | 5 | 1 | 144 | 144 | 8 | −9 | −5 | 2 | 303 | 251 | 10 | 8 | −2 | 2 | 789 | 777 | 39 | 27 | 1 | 2 | 202 | 182 | 10 | −3 | 5 | 2 | 116 | 123 | 3 |
| −17 | 5 | 1 | 285 | 274 | 10 | −7 | −5 | 2 | 474 | 433 | 12 | 10 | −2 | 2 | 500 | 481 | 16 | −22 | 2 | 2 | 192 | 181 | 19 | −1 | 5 | 2 | 223 | 192 | 4 |
| −15 | 5 | 1 | 296 | 303 | 13 | −5 | −5 | 2 | 331 | 317 | 8 | 12 | −2 | 2 | 543 | 510 | 12 | −20 | 2 | 2 | 288 | 269 | 19 | 1 | 5 | 2 | 388 | 335 | 7 |
| −13 | 5 | 1 | 352 | 397 | 18 | −3 | −5 | 2 | 120 | 125 | 5 | 14 | −2 | 2 | 182 | 175 | 4 | −18 | 2 | 2 | 492 | 462 | 23 | 3 | 5 | 2 | 248 | 221 | 5 |
| −11 | 5 | 1 | 150 | 132 | 5 | −1 | −5 | 2 | 216 | 192 | 6 | 16 | −2 | 2 | 58 | 34 | 5 | −16 | 2 | 2 | 507 | 438 | 17 | 5 | 5 | 2 | 490 | 441 | 10 |
| −9 | 5 | 1 | 175 | 143 | 4 | 1 | −5 | 2 | 378 | 335 | 8 | 18 | −2 | 2 | 155 | 151 | 6 | −14 | 2 | 2 | 229 | 187 | 15 | 7 | 5 | 2 | 146 | 123 | 4 |
| −7 | 5 | 1 | 341 | 316 | 6 | 3 | −5 | 2 | 252 | 219 | 6 | 20 | −2 | 2 | 252 | 270 | 9 | −10 | 2 | 2 | 536 | 466 | 14 | 9 | 5 | 2 | 371 | 338 | 8 |
| −5 | 5 | 1 | 380 | 336 | 7 | 5 | −5 | 2 | 473 | 440 | 13 | 22 | −2 | 2 | 92 | 117 | 9 | −8 | 2 | 2 | 375 | 365 | 8 | 11 | 5 | 2 | 253 | 250 | 7 |
| −3 | 5 | 1 | 347 | 296 | 6 | 7 | −5 | 2 | 153 | 123 | 6 | 24 | −2 | 2 | 332 | 328 | 16 | −6 | 2 | 2 | 370 | 318 | 8 | 13 | 5 | 2 | 54 | 66 | 6 |
| −1 | 5 | 1 | 78 | 46 | 4 | 9 | −5 | 2 | 392 | 338 | 12 | 26 | −2 | 2 | 202 | 180 | 10 | −4 | 2 | 2 | 194 | 158 | 5 | 15 | 5 | 2 | 190 | 199 | 9 |
| 1 | 5 | 1 | 219 | 216 | 4 | 11 | −5 | 2 | 279 | 249 | 13 | 28 | −2 | 2 | 186 | 186 | 10 | −2 | 2 | 2 | 1181 | 1087 | 23 | 17 | 5 | 2 | 115 | 103 | 8 |
| 3 | 5 | 1 | 156 | 166 | 4 | 13 | −5 | 2 | 58 | 67 | 8 | −29 | −1 | 2 | 131 | 130 | 8 | 0 | 2 | 2 | 613 | 568 | 12 | 19 | 5 | 2 | 98 | 120 | 8 |
| 5 | 5 | 1 | 118 | 112 | 4 | 15 | −5 | 2 | 204 | 199 | 7 | −27 | −1 | 2 | 324 | 285 | 16 | 2 | 2 | 2 | 207 | 164 | 5 | 21 | 5 | 2 | 59 | 68 | 9 |
| 7 | 5 | 1 | 199 | 185 | 4 | 17 | −5 | 2 | 115 | 104 | 6 | −25 | −1 | 2 | 126 | 110 | 9 | 4 | 2 | 2 | 721 | 679 | 23 | −18 | 6 | 2 | 110 | 112 | 7 |
| 9 | 5 | 1 | 324 | 302 | 7 | 19 | −5 | 2 | 102 | 120 | 6 | −23 | −1 | 2 | 252 | 206 | 10 | 6 | 2 | 2 | 926 | 826 | 27 | −16 | 6 | 2 | 71 | 63 | 10 |
| 11 | 5 | 1 | 322 | 304 | 9 | 21 | −5 | 2 | 64 | 68 | 6 | −21 | −1 | 2 | 231 | 206 | 10 | 8 | 2 | 2 | 797 | 775 | 20 | −14 | 6 | 2 | 315 | 313 | 13 |
| 13 | 5 | 1 | 168 | 182 | 6 | −26 | −4 | 2 | 130 | 142 | 9 | −19 | −1 | 2 | 46 | 78 | 8 | 10 | 2 | 2 | 504 | 481 | 13 | −12 | 6 | 2 | 105 | 105 | 6 |
| 15 | 5 | 1 | 137 | 134 | 12 | −24 | −4 | 2 | 55 | 57 | 13 | −17 | −1 | 2 | 112 | 92 | 6 | 12 | 2 | 2 | 545 | 510 | 15 | −10 | 6 | 2 | 106 | 104 | 4 |
| 17 | 5 | 1 | 124 | 111 | 8 | −22 | −4 | 2 | 256 | 267 | 14 | −15 | −1 | 2 | 364 | 360 | 10 | 14 | 2 | 2 | 171 | 174 | 5 | −8 | 6 | 2 | 156 | 139 | 5 |
| 19 | 5 | 1 | 32 | 16 | 32 | −20 | −4 | 2 | 174 | 163 | 8 | −13 | −1 | 2 | 322 | 272 | 9 | 16 | 2 | 2 | 44 | 35 | 9 | −6 | 6 | 2 | 317 | 286 | 8 |
| 21 | 5 | 1 | 107 | 112 | 7 | −18 | −4 | 2 | 7 | 19 | 6 | −11 | −1 | 2 | 490 | 477 | 16 | 18 | 2 | 2 | 142 | 149 | 7 | −4 | 6 | 2 | 81 | 71 | 5 |
| −18 | 6 | 1 | 172 | 190 | 11 | −16 | −4 | 2 | 232 | 217 | 8 | −9 | −1 | 2 | 597 | 538 | 15 | 20 | 2 | 2 | 247 | 269 | 9 | −2 | 6 | 2 | 78 | 97 | 6 |
| −16 | 6 | 1 | 132 | 148 | 12 | −14 | −4 | 2 | 220 | 175 | 7 | −7 | −1 | 2 | 326 | 308 | 9 | 22 | 2 | 2 | 114 | 118 | 6 | 0 | 6 | 2 | 74 | 71 | 5 |
| −14 | 6 | 1 | 119 | 143 | 12 | −12 | −4 | 2 | 95 | 91 | 5 | −5 | −1 | 2 | 1523 | 1480 | 36 | 24 | 2 | 2 | 326 | 328 | 12 | 2 | 6 | 2 | 126 | 135 | 5 |
| −12 | 6 | 1 | 146 | 132 | 6 | −10 | −4 | 2 | 233 | 201 | 6 | −3 | −1 | 2 | 1460 | 1388 | 38 | 26 | 2 | 2 | 193 | 181 | 10 | 4 | 6 | 2 | 334 | 315 | 8 |
| −10 | 6 | 1 | 230 | 224 | 6 | −8 | −4 | 2 | 357 | 326 | 9 | −1 | −1 | 2 | 546 | 506 | 14 | −25 | 3 | 2 | 306 | 275 | 16 | 6 | 6 | 2 | 347 | 322 | 8 |
| −8 | 6 | 1 | 132 | 103 | 4 | −6 | −4 | 2 | 189 | 160 | 5 | 1 | −1 | 2 | 1188 | 1120 | 31 | −23 | 3 | 2 | 248 | 230 | 13 | 8 | 6 | 2 | 198 | 174 | 7 |
| −6 | 6 | 1 | 69 | 66 | 6 | −4 | −4 | 2 | 144 | 135 | 5 | 3 | −1 | 2 | 1030 | 1022 | 23 | −21 | 3 | 2 | 182 | 179 | 8 | 10 | 6 | 2 | 255 | 241 | 7 |
| −4 | 6 | 1 | 179 | 164 | 5 | −2 | −4 | 2 | 346 | 292 | 7 | 5 | −1 | 2 | 632 | 612 | 16 | −19 | 3 | 2 | 464 | 396 | 13 | 12 | 6 | 2 | 0 | 10 | 1 |
| −2 | 6 | 1 | 72 | 75 | 4 | 0 | −4 | 2 | 669 | 589 | 12 | 7 | −1 | 2 | 1052 | 1023 | 32 | −17 | 3 | 2 | 192 | 167 | 6 | 14 | 6 | 2 | 112 | 119 | 6 |
| 0 | 6 | 1 | 315 | 319 | 10 | 2 | −4 | 2 | 472 | 411 | 10 | 9 | −1 | 2 | 851 | 779 | 26 | −15 | 3 | 2 | 144 | 119 | 6 | 16 | 6 | 2 | 88 | 113 | 8 |
| 2 | 6 | 1 | 70 | 59 | 5 | 4 | −4 | 2 | 96 | 85 | 4 | 11 | −1 | 2 | 189 | 203 | 5 | −13 | 3 | 2 | 688 | 630 | 37 | −11 | 7 | 2 | 64 | 54 | 12 |
| 4 | 6 | 1 | 263 | 238 | 6 | 6 | −4 | 2 | 247 | 215 | 6 | 13 | −1 | 2 | 198 | 189 | 6 | −11 | 3 | 2 | 369 | 343 | 7 | −9 | 7 | 2 | 30 | 49 | 13 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 6 | 6 | 1 | 208 | 186 | 5 | 8 | −4 | 2 | 183 | 169 | 6 | 15 | −1 | 2 | 179 | 188 | 4 | −9 | 3 | 2 | 351 | 297 | 7 | −7 | 7 | 2 | 24 | 12 | 23 |
| 8 | 6 | 1 | 412 | 356 | 15 | 10 | −4 | 2 | 547 | 490 | 14 | 17 | −1 | 2 | 143 | 144 | 4 | −7 | 3 | 2 | 835 | 708 | 18 | −5 | 7 | 2 | 98 | 105 | 4 |
| 10 | 6 | 1 | 101 | 91 | 5 | 12 | −4 | 2 | 297 | 288 | 7 | 19 | −1 | 2 | 430 | 422 | 18 | −5 | 3 | 2 | 583 | 502 | 13 | −3 | 7 | 2 | 158 | 139 | 6 |
| 12 | 6 | 1 | 58 | 68 | 7 | 14 | −4 | 2 | 343 | 315 | 10 | 23 | −1 | 2 | 189 | 187 | 9 | −3 | 3 | 2 | 210 | 203 | 6 | −1 | 7 | 2 | 73 | 84 | 7 |
| 14 | 6 | 1 | 113 | 108 | 8 | 16 | −4 | 2 | 201 | 197 | 7 | 25 | −1 | 2 | 209 | 206 | 11 | −1 | 3 | 2 | 527 | 471 | 28 | 1 | 7 | 2 | 176 | 165 | 6 |
| 16 | 6 | 1 | 93 | 109 | 8 | 18 | −4 | 2 | 44 | 56 | 10 | 27 | −1 | 2 | 199 | 183 | 11 | 1 | 3 | 2 | 192 | 223 | 6 | 3 | 7 | 2 | 257 | 242 | 8 |
| 18 | 6 | 1 | 34 | 43 | 34 | 20 | −4 | 2 | 81 | 95 | 8 | 29 | −1 | 2 | 98 | 77 | 8 | 3 | 3 | 2 | 64 | 78 | 5 | 5 | 7 | 2 | 58 | 61 | 5 |
| −11 | 7 | 1 | 62 | 63 | 12 | 22 | −4 | 2 | 223 | 241 | 12 | −24 | 0 | 2 | 220 | 233 | 78 | 5 | 3 | 2 | 534 | 511 | 16 | 7 | 7 | 2 | 191 | 177 | 5 |
| −9 | 7 | 1 | 48 | 50 | 7 | 24 | −4 | 2 | 59 | 71 | 11 | −22 | 0 | 2 | 288 | 250 | 19 | 7 | 3 | 2 | 610 | 569 | 12 | 9 | 7 | 2 | 114 | 124 | 6 |
| −7 | 7 | 1 | 88 | 90 | 5 | −27 | −3 | 2 | 70 | 85 | 10 | −20 | 0 | 2 | 125 | 110 | 20 | 9 | 3 | 2 | 400 | 323 | 7 | −11 | −7 | 3 | 75 | 62 | 6 |
| −5 | 7 | 1 | 38 | 38 | 9 | −25 | −3 | 2 | 288 | 275 | 16 | −18 | 0 | 2 | 113 | 107 | 18 | 11 | 3 | 2 | 336 | 309 | 7 | −9 | −7 | 3 | 47 | 42 | 10 |
| −3 | 7 | 1 | 170 | 154 | 7 | −23 | −3 | 2 | 213 | 229 | 13 | −16 | 0 | 2 | 208 | 197 | 15 | 13 | 3 | 2 | 199 | 193 | 4 | −7 | −7 | 3 | 112 | 94 | 6 |
| −1 | 7 | 1 | 50 | 48 | 10 | −21 | −3 | 2 | 179 | 180 | 10 | −8 | 0 | 2 | 616 | 771 | 27 | 15 | 3 | 2 | 201 | 181 | 8 | −5 | −7 | 3 | 190 | 170 | 7 |
| 1 | 7 | 1 | 84 | 66 | 7 | −19 | −3 | 2 | 436 | 397 | 17 | −6 | 0 | 2 | 1159 | 1184 | 29 | 17 | 3 | 2 | 436 | 452 | 16 | −3 | −7 | 3 | 104 | 99 | 7 |
| 3 | 7 | 1 | 150 | 142 | 6 | −17 | −3 | 2 | 174 | 168 | 5 | −4 | 0 | 2 | 221 | 219 | 7 | 19 | 3 | 2 | 301 | 301 | 12 | −1 | −7 | 3 | 115 | 106 | 9 |
| 5 | 7 | 1 | 130 | 134 | 4 | −15 | −3 | 2 | 140 | 119 | 5 | −2 | 0 | 2 | 1102 | 1233 | 35 | 21 | 3 | 2 | 165 | 183 | 7 | 1 | −7 | 3 | 219 | 248 | 13 |
| 7 | 7 | 1 | 71 | 73 | 5 | −13 | −3 | 2 | 709 | 632 | 16 | 0 | 0 | 2 | 881 | 1029 | 22 | 23 | 3 | 2 | 57 | 59 | 9 | 3 | −7 | 3 | 105 | 100 | 7 |
| 9 | 7 | 1 | 91 | 97 | 6 | −11 | −3 | 2 | 368 | 341 | 8 | 2 | 0 | 2 | 1055 | 1145 | 27 | 25 | 3 | 2 | 151 | 171 | 6 | 5 | −7 | 3 | 40 | 31 | 13 |
| 11 | 7 | 1 | 136 | 141 | 11 | −9 | −3 | 2 | 354 | 295 | 11 | 4 | 0 | 2 | 1115 | 1282 | 28 | −26 | 4 | 2 | 136 | 142 | 10 | 7 | −7 | 3 | 187 | 187 | 11 |
| −11 | −7 | 2 | 67 | 54 | 7 | −7 | −3 | 2 | 806 | 707 | 37 | 6 | 0 | 2 | 194 | 235 | 4 | −24 | 4 | 2 | 50 | 57 | 9 | 9 | −7 | 3 | 191 | 220 | 8 |
| −9 | −7 | 2 | 60 | 49 | 8 | −5 | −3 | 2 | 556 | 504 | 18 | 8 | 0 | 2 | 433 | 451 | 9 | −22 | 4 | 2 | 263 | 268 | 10 | −18 | −6 | 3 | 104 | 113 | 10 |
| −7 | −7 | 2 | 24 | 12 | 24 | −3 | −3 | 2 | 206 | 202 | 7 | 10 | 0 | 2 | 885 | 868 | 23 | −20 | 4 | 2 | 175 | 164 | 8 | −16 | −6 | 3 | 337 | 319 | 11 |
| −5 | −7 | 2 | 109 | 104 | 6 | −1 | −3 | 2 | 549 | 472 | 16 | 12 | 0 | 2 | 837 | 863 | 27 | −18 | 4 | 2 | 26 | 20 | 26 | −14 | −6 | 3 | 161 | 136 | 7 |
| −3 | −7 | 2 | 157 | 139 | 7 | 3 | −3 | 2 | 71 | 77 | 6 | 14 | 0 | 2 | 67 | 49 | 4 | −16 | 4 | 2 | 254 | 218 | 9 | −12 | −6 | 3 | 123 | 106 | 7 |
| −1 | −7 | 2 | 72 | 84 | 10 | 5 | −3 | 2 | 510 | 511 | 16 | 16 | 0 | 2 | 464 | 375 | 12 | −14 | 4 | 2 | 221 | 175 | 9 | −10 | −6 | 3 | 211 | 196 | 8 |
| 1 | −7 | 2 | 157 | 165 | 7 | 7 | −3 | 2 | 609 | 569 | 27 | 18 | 0 | 2 | 258 | 330 | 13 | −12 | 4 | 2 | 99 | 91 | 4 | −8 | −6 | 3 | 96 | 80 | 7 |
| 3 | −7 | 2 | 249 | 243 | 14 | 9 | −3 | 2 | 399 | 324 | 10 | 20 | 0 | 2 | 566 | 605 | 27 | −10 | 4 | 2 | 234 | 201 | 5 | −6 | −6 | 3 | 153 | 140 | 7 |
| 5 | −7 | 2 | 59 | 60 | 9 | 11 | −3 | 2 | 334 | 309 | 9 | 22 | 0 | 2 | 251 | 257 | 13 | −8 | 4 | 2 | 348 | 326 | 6 | −4 | −6 | 3 | 134 | 117 | 8 |
| 7 | −7 | 2 | 191 | 176 | 7 | 13 | −3 | 2 | 201 | 193 | 6 | 24 | 0 | 2 | 66 | 65 | 7 | −6 | 4 | 2 | 187 | 160 | 3 | −2 | −6 | 3 | 176 | 159 | 6 |
| 0 | −6 | 3 | 171 | 164 | 6 | −22 | −2 | 3 | 370 | 320 | 18 | −3 | 1 | 3 | 1693 | 1608 | 52 | 18 | 4 | 3 | 213 | 231 | 9 | −11 | −5 | 4 | 239 | 212 | 9 |
| 2 | −6 | 3 | 268 | 247 | 8 | −20 | −2 | 3 | 372 | 326 | 19 | −1 | 1 | 3 | 1017 | 949 | 22 | 20 | 4 | 3 | 205 | 216 | 9 | −9 | −5 | 4 | 51 | 50 | 12 |
| 4 | −6 | 3 | 192 | 196 | 6 | −18 | −2 | 3 | 214 | 208 | 5 | 1 | 1 | 3 | 307 | 313 | 7 | 22 | 4 | 3 | 125 | 136 | 7 | −7 | −5 | 4 | 150 | 134 | 6 |
| 6 | −6 | 3 | 381 | 357 | 21 | −16 | −2 | 3 | 357 | 328 | 7 | 3 | 1 | 3 | 290 | 324 | 10 | 24 | 4 | 3 | 56 | 53 | 6 | −5 | −5 | 4 | 253 | 210 | 6 |
| 8 | −6 | 3 | 145 | 129 | 7 | −14 | −2 | 3 | 87 | 88 | 4 | 5 | 1 | 3 | 478 | 519 | 12 | −23 | 5 | 3 | 67 | 75 | 9 | −3 | −5 | 4 | 214 | 176 | 6 |
| 10 | −6 | 3 | 110 | 106 | 7 | −12 | −2 | 3 | 376 | 328 | 10 | 7 | 1 | 3 | 463 | 488 | 12 | −21 | 5 | 3 | 95 | 111 | 7 | −1 | −5 | 4 | 60 | 70 | 6 |
| 12 | −6 | 3 | 204 | 188 | 8 | −10 | −2 | 3 | 756 | 669 | 19 | 9 | 1 | 3 | 1097 | 1109 | 30 | −19 | 5 | 3 | 39 | 41 | 16 | 1 | −5 | 4 | 386 | 368 | 8 |
| 14 | −6 | 3 | 132 | 133 | 6 | −8 | −2 | 3 | 100 | 81 | 5 | 11 | 1 | 3 | 379 | 403 | 11 | −17 | 5 | 3 | 295 | 270 | 11 | 3 | −5 | 4 | 412 | 400 | 11 |
| 16 | −6 | 3 | 145 | 158 | 6 | −6 | −2 | 3 | 609 | 568 | 18 | 13 | 1 | 3 | 304 | 274 | 7 | −15 | 5 | 3 | 439 | 404 | 24 | 5 | −5 | 4 | 248 | 243 | 6 |
| −21 | −5 | 3 | 107 | 111 | 5 | −4 | −2 | 3 | 777 | 707 | 26 | 15 | 1 | 3 | 126 | 133 | 4 | −13 | 5 | 3 | 80 | 88 | 8 | 7 | −5 | 4 | 398 | 389 | 16 |
| −19 | −5 | 3 | 52 | 43 | 8 | −2 | −2 | 3 | 254 | 251 | 7 | 17 | 1 | 3 | 120 | 121 | 7 | −11 | 5 | 3 | 352 | 332 | 8 | 9 | −5 | 4 | 473 | 457 | 15 |
| −17 | −5 | 3 | 299 | 271 | 14 | 0 | −2 | 3 | 753 | 650 | 21 | 21 | 1 | 3 | 305 | 332 | 15 | −9 | 5 | 3 | 211 | 208 | 5 | 11 | −5 | 4 | 88 | 88 | 7 |
| −15 | −5 | 3 | 471 | 405 | 15 | 2 | −2 | 3 | 599 | 548 | 15 | 23 | 1 | 3 | 107 | 110 | 8 | −7 | 5 | 3 | 310 | 260 | 6 | 13 | −5 | 4 | 196 | 213 | 8 |
| −13 | −5 | 3 | 105 | 88 | 7 | 4 | −2 | 3 | 76 | 103 | 5 | 25 | 1 | 3 | 212 | 205 | 11 | −5 | 5 | 3 | 337 | 293 | 6 | 15 | −5 | 4 | 144 | 159 | 6 |
| −11 | −5 | 3 | 377 | 332 | 18 | 6 | −2 | 3 | 530 | 525 | 18 | 27 | 1 | 3 | 210 | 190 | 11 | −3 | 5 | 3 | 118 | 112 | 4 | 17 | −5 | 4 | 54 | 62 | 8 |
| −9 | −5 | 3 | 221 | 207 | 8 | 8 | −2 | 3 | 584 | 558 | 27 | −24 | 2 | 3 | 226 | 226 | 19 | −1 | 5 | 3 | 185 | 174 | 4 | 19 | −5 | 4 | 65 | 80 | 5 |
| −7 | −5 | 3 | 309 | 260 | 9 | 10 | −2 | 3 | 588 | 572 | 18 | −22 | 2 | 3 | 352 | 319 | 21 | 1 | 5 | 3 | 312 | 277 | 6 | −26 | −4 | 4 | 45 | 56 | 16 |
| −5 | −5 | 3 | 334 | 291 | 8 | 12 | −2 | 3 | 274 | 251 | 7 | −20 | 2 | 3 | 374 | 327 | 21 | 3 | 5 | 3 | 250 | 220 | 5 | −24 | −4 | 4 | 236 | 251 | 14 |
| −3 | −5 | 3 | 133 | 112 | 5 | 14 | −2 | 3 | 351 | 348 | 7 | −18 | 2 | 3 | 234 | 207 | 16 | 5 | 5 | 3 | 159 | 143 | 4 | −22 | −4 | 4 | 0 | 29 | 1 |
| −1 | −5 | 3 | 180 | 174 | 5 | 16 | −2 | 3 | 210 | 215 | 5 | −16 | 2 | 3 | 355 | 326 | 13 | 7 | 5 | 3 | 79 | 77 | 5 | −20 | −4 | 4 | 92 | 92 | 8 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 1 | −5 | 3 | 300 | 277 | 7 | 18 | −2 | 3 | 212 | 210 | 7 | −14 | 2 | 3 | 95 | 86 | 17 | 9 | 5 | 3 | 282 | 271 | 7 | −18 | −4 | 4 | 99 | 98 | 6 |
| 3 | −5 | 3 | 241 | 218 | 6 | 20 | −2 | 3 | 216 | 245 | 8 | −10 | 2 | 3 | 739 | 665 | 19 | 11 | 5 | 3 | 83 | 83 | 5 | −16 | −4 | 4 | 424 | 384 | 12 |
| 5 | −5 | 3 | 160 | 141 | 5 | 22 | −2 | 3 | 44 | 53 | 11 | −8 | 2 | 3 | 99 | 80 | 3 | 13 | 5 | 3 | 129 | 143 | 5 | −14 | −4 | 4 | 388 | 355 | 11 |
| 7 | −5 | 3 | 86 | 77 | 7 | 24 | −2 | 3 | 159 | 153 | 9 | −6 | 2 | 3 | 673 | 567 | 14 | 15 | 5 | 3 | 42 | 36 | 17 | −12 | −4 | 4 | 113 | 112 | 5 |
| 9 | −5 | 3 | 291 | 271 | 10 | 26 | −2 | 3 | 144 | 131 | 9 | −4 | 2 | 3 | 816 | 708 | 17 | 17 | 5 | 3 | 88 | 81 | 9 | −10 | −4 | 4 | 276 | 245 | 7 |
| 11 | −5 | 3 | 75 | 82 | 7 | 28 | −2 | 3 | 276 | 257 | 14 | −2 | 2 | 3 | 251 | 251 | 5 | 19 | 5 | 3 | 48 | 62 | 13 | −8 | −4 | 4 | 555 | 498 | 14 |
| 13 | −5 | 3 | 131 | 143 | 7 | −29 | −1 | 3 | 168 | 177 | 9 | 0 | 2 | 3 | 711 | 649 | 15 | 21 | 5 | 3 | 71 | 85 | 8 | −6 | −4 | 4 | 244 | 220 | 6 |
| 15 | −5 | 3 | 39 | 36 | 14 | −27 | −1 | 3 | 130 | 110 | 9 | 2 | 2 | 3 | 602 | 547 | 13 | −18 | 6 | 3 | 109 | 115 | 7 | −4 | −4 | 4 | 445 | 413 | 11 |
| 17 | −5 | 3 | 100 | 80 | 6 | −25 | −1 | 3 | 477 | 421 | 17 | 4 | 2 | 3 | 80 | 103 | 4 | −16 | 6 | 3 | 321 | 319 | 13 | −2 | −4 | 4 | 154 | 137 | 4 |
| 19 | −5 | 3 | 63 | 62 | 7 | −23 | −1 | 3 | 270 | 250 | 11 | 6 | 2 | 3 | 551 | 526 | 14 | −14 | 6 | 3 | 154 | 136 | 9 | 0 | −4 | 4 | 430 | 398 | 8 |
| −26 | −4 | 3 | 128 | 160 | 9 | −21 | −1 | 3 | 159 | 133 | 8 | 8 | 2 | 3 | 547 | 556 | 18 | −12 | 6 | 3 | 116 | 107 | 7 | 2 | −4 | 4 | 473 | 435 | 10 |
| −24 | −4 | 3 | 57 | 59 | 14 | −19 | −1 | 3 | 229 | 206 | 9 | 10 | 2 | 3 | 575 | 570 | 19 | −10 | 6 | 3 | 211 | 196 | 5 | 4 | −4 | 4 | 359 | 350 | 8 |
| −22 | −4 | 3 | 107 | 92 | 11 | −17 | −1 | 3 | 20 | 13 | 20 | 12 | 2 | 3 | 277 | 250 | 5 | −8 | 6 | 3 | 88 | 80 | 5 | 6 | −4 | 4 | 168 | 160 | 5 |
| −20 | −4 | 3 | 97 | 90 | 8 | −15 | −1 | 3 | 381 | 365 | 10 | 14 | 2 | 3 | 354 | 348 | 7 | −6 | 6 | 3 | 148 | 140 | 5 | 8 | −4 | 4 | 108 | 106 | 5 |
| −18 | −4 | 3 | 266 | 269 | 8 | −13 | −1 | 3 | 289 | 265 | 8 | 16 | 2 | 3 | 196 | 215 | 8 | −4 | 6 | 3 | 133 | 117 | 5 | 10 | −4 | 4 | 513 | 495 | 16 |
| −16 | −4 | 3 | 332 | 295 | 12 | −11 | −1 | 3 | 307 | 293 | 8 | 18 | 2 | 3 | 213 | 210 | 12 | −2 | 6 | 3 | 163 | 159 | 6 | 12 | −4 | 4 | 685 | 694 | 18 |
| −14 | −4 | 3 | 348 | 322 | 9 | −9 | −1 | 3 | 397 | 356 | 10 | 20 | 2 | 3 | 229 | 246 | 8 | 0 | 6 | 3 | 156 | 165 | 6 | 14 | −4 | 4 | 416 | 431 | 11 |
| −12 | −4 | 3 | 97 | 99 | 5 | −7 | −1 | 3 | 1274 | 1140 | 33 | 22 | 2 | 3 | 42 | 52 | 15 | 2 | 6 | 3 | 251 | 249 | 8 | 16 | −4 | 4 | 125 | 128 | 10 |
| −10 | −4 | 3 | 191 | 169 | 5 | −5 | −1 | 3 | 848 | 811 | 20 | 24 | 2 | 3 | 156 | 154 | 7 | 4 | 6 | 3 | 201 | 195 | 6 | 18 | −4 | 4 | 128 | 132 | 5 |
| −8 | −4 | 3 | 112 | 110 | 5 | −3 | −1 | 3 | 1642 | 1607 | 43 | 26 | 2 | 3 | 134 | 130 | 6 | 6 | 6 | 3 | 397 | 357 | 11 | 20 | −4 | 4 | 177 | 178 | 8 |
| −6 | −4 | 3 | 346 | 313 | 8 | −1 | −1 | 3 | 993 | 952 | 26 | −25 | 3 | 3 | 100 | 109 | 11 | 8 | 6 | 3 | 143 | 129 | 5 | 22 | −4 | 4 | 209 | 233 | 12 |
| −4 | −4 | 3 | 460 | 442 | 11 | 1 | −1 | 3 | 314 | 311 | 8 | −21 | 3 | 3 | 165 | 160 | 16 | 10 | 6 | 3 | 112 | 106 | 4 | −29 | −3 | 4 | 216 | 242 | 11 |
| −2 | −4 | 3 | 164 | 171 | 4 | 3 | −1 | 3 | 310 | 324 | 7 | −19 | 3 | 3 | 362 | 326 | 10 | 12 | 6 | 3 | 200 | 188 | 6 | −27 | −3 | 4 | 177 | 181 | 11 |
| 0 | −4 | 3 | 133 | 112 | 4 | 5 | −1 | 3 | 474 | 518 | 15 | −17 | 3 | 3 | 273 | 251 | 8 | 14 | 6 | 3 | 137 | 134 | 12 | −25 | −3 | 4 | 278 | 266 | 15 |
| 2 | −4 | 3 | 170 | 163 | 4 | 7 | −1 | 3 | 455 | 486 | 15 | −15 | 3 | 3 | 440 | 394 | 15 | −11 | 7 | 3 | 72 | 62 | 11 | −23 | −3 | 4 | 162 | 176 | 11 |
| 4 | −4 | 3 | 382 | 350 | 9 | 9 | −1 | 3 | 1146 | 1107 | 29 | −13 | 3 | 3 | 312 | 303 | 11 | −9 | 7 | 3 | 32 | 42 | 12 | −21 | −3 | 4 | 197 | 247 | 7 |
| 6 | −4 | 3 | 554 | 493 | 12 | 11 | −1 | 3 | 411 | 405 | 10 | −11 | 3 | 3 | 163 | 167 | 4 | −7 | 7 | 3 | 108 | 94 | 4 | −19 | −3 | 4 | 151 | 139 | 6 |
| 8 | −4 | 3 | 98 | 110 | 5 | 13 | −1 | 3 | 314 | 274 | 8 | −9 | 3 | 3 | 134 | 107 | 3 | −5 | 7 | 3 | 177 | 171 | 5 | −17 | −3 | 4 | 310 | 305 | 7 |
| 10 | −4 | 3 | 64 | 79 | 6 | 15 | −1 | 3 | 130 | 132 | 3 | −7 | 3 | 3 | 331 | 313 | 8 | −3 | 7 | 3 | 113 | 99 | 6 | −15 | −3 | 4 | 211 | 214 | 5 |
| 12 | −4 | 3 | 77 | 94 | 5 | 17 | −1 | 3 | 136 | 119 | 4 | −5 | 3 | 3 | 360 | 293 | 9 | −1 | 7 | 3 | 121 | 106 | 6 | −13 | −3 | 4 | 471 | 433 | 11 |
| 14 | −4 | 3 | 393 | 380 | 11 | 19 | −1 | 3 | 730 | 731 | 17 | −3 | 3 | 3 | 664 | 577 | 17 | 1 | 7 | 3 | 238 | 248 | 11 | −11 | −3 | 4 | 158 | 158 | 5 |
| 16 | −4 | 3 | 358 | 378 | 9 | 23 | −1 | 3 | 113 | 111 | 8 | −1 | 3 | 3 | 81 | 93 | 5 | 3 | 7 | 3 | 105 | 99 | 6 | −9 | −3 | 4 | 630 | 588 | 16 |
| 18 | −4 | 3 | 220 | 230 | 7 | 25 | −1 | 3 | 221 | 204 | 11 | 1 | 3 | 3 | 322 | 334 | 9 | 5 | 7 | 3 | 32 | 31 | 14 | −7 | −3 | 4 | 548 | 490 | 17 |
| 20 | −4 | 3 | 215 | 216 | 8 | 27 | −1 | 3 | 212 | 191 | 11 | 3 | 3 | 3 | 247 | 222 | 7 | 7 | 7 | 3 | 199 | 186 | 5 | −5 | −3 | 4 | 616 | 569 | 20 |
| 22 | −4 | 3 | 120 | 135 | 9 | −26 | 0 | 3 | 359 | 325 | 21 | 5 | 3 | 3 | 204 | 170 | 6 | 9 | 7 | 3 | 216 | 220 | 11 | −3 | −3 | 4 | 723 | 619 | 22 |
| 24 | −4 | 3 | 37 | 53 | 18 | −24 | 0 | 3 | 103 | 80 | 25 | 7 | 3 | 3 | 491 | 495 | 10 | −11 | −7 | 4 | 64 | 54 | 7 | −1 | −3 | 4 | 657 | 602 | 19 |
| −27 | −3 | 3 | 201 | 190 | 11 | −22 | 0 | 3 | 193 | 154 | 18 | 9 | 3 | 3 | 207 | 214 | 4 | −9 | −7 | 4 | 88 | 81 | 6 | 1 | −3 | 4 | 278 | 273 | 8 |
| −25 | −3 | 3 | 92 | 111 | 10 | −20 | 0 | 3 | 369 | 325 | 20 | 11 | 3 | 3 | 357 | 365 | 9 | −7 | −7 | 4 | 132 | 122 | 7 | 3 | −3 | 4 | 364 | 350 | 12 |
| −23 | −3 | 3 | 192 | 215 | 11 | −18 | 0 | 3 | 355 | 367 | 19 | 13 | 3 | 3 | 458 | 459 | 10 | −5 | −7 | 4 | 53 | 58 | 9 | 5 | −3 | 4 | 407 | 426 | 10 |
| −21 | −3 | 3 | 131 | 159 | 6 | −16 | 0 | 3 | 21 | 4 | 20 | 15 | 3 | 3 | 377 | 372 | 14 | −3 | −7 | 4 | 95 | 101 | 7 | 7 | −3 | 4 | 159 | 161 | 5 |
| −19 | −3 | 3 | 337 | 325 | 13 | −8 | 0 | 3 | 839 | 831 | 26 | 17 | 3 | 3 | 53 | 55 | 10 | −1 | −7 | 4 | 116 | 116 | 10 | 9 | −3 | 4 | 124 | 116 | 4 |
| −17 | −3 | 3 | 258 | 250 | 6 | −6 | 0 | 3 | 278 | 288 | 8 | 19 | 3 | 3 | 144 | 151 | 11 | 1 | −7 | 4 | 67 | 68 | 11 | 11 | −3 | 4 | 438 | 430 | 10 |
| −15 | −3 | 3 | 424 | 391 | 9 | −4 | 0 | 3 | 850 | 927 | 27 | 21 | 3 | 3 | 116 | 121 | 7 | 3 | −7 | 4 | 57 | 56 | 9 | 13 | −3 | 4 | 334 | 343 | 8 |
| −13 | −3 | 3 | 309 | 304 | 7 | −2 | 0 | 3 | 595 | 647 | 19 | 23 | 3 | 3 | 65 | 54 | 11 | 5 | −7 | 4 | 146 | 144 | 7 | 15 | −3 | 4 | 67 | 86 | 5 |
| −11 | −3 | 3 | 160 | 166 | 5 | 0 | 0 | 3 | 782 | 937 | 20 | 25 | 3 | 3 | 155 | 143 | 6 | 7 | −7 | 4 | 68 | 94 | 11 | 17 | −3 | 4 | 239 | 244 | 7 |
| −9 | −3 | 3 | 137 | 109 | 5 | 2 | 0 | 3 | 430 | 486 | 11 | −26 | 4 | 3 | 139 | 161 | 10 | −16 | −6 | 4 | 72 | 73 | 7 | 19 | −3 | 4 | 0 | 15 | 1 |
| −7 | −3 | 3 | 333 | 312 | 15 | 4 | 0 | 3 | 382 | 381 | 10 | −24 | 4 | 3 | 56 | 59 | 8 | −14 | −6 | 4 | 136 | 114 | 6 | 21 | −3 | 4 | 24 | 22 | 24 |
| −5 | −3 | 3 | 340 | 293 | 11 | 6 | 0 | 3 | 500 | 522 | 13 | −22 | 4 | 3 | 107 | 92 | 7 | −12 | −6 | 4 | 68 | 49 | 9 | 23 | −3 | 4 | 89 | 87 | 9 |
| −3 | −3 | 3 | 664 | 577 | 20 | 8 | 0 | 3 | 62 | 92 | 3 | −20 | 4 | 3 | 110 | 90 | 7 | −10 | −6 | 4 | 150 | 132 | 7 | 25 | −3 | 4 | 91 | 82 | 8 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −1 | −3 | 3 | 93 | 93 | 6 | 10 | 0 | 3 | 350 | 405 | 9 | −18 | 4 | 3 | 272 | 269 | 15 | −8 | −6 | 4 | 195 | 168 | 7 | −30 | −2 | 4 | 130 | 137 | 8 |
| 1 | −3 | 3 | 361 | 335 | 10 | 12 | 0 | 3 | 127 | 124 | 5 | −16 | 4 | 3 | 350 | 295 | 12 | −6 | −6 | 4 | 475 | 423 | 15 | −28 | −2 | 4 | 176 | 169 | 10 |
| 3 | −3 | 3 | 254 | 222 | 8 | 14 | 0 | 3 | 569 | 556 | 13 | −14 | 4 | 3 | 332 | 322 | 19 | −4 | −6 | 4 | 156 | 146 | 8 | −26 | −2 | 4 | 549 | 493 | 27 |
| 5 | −3 | 3 | 195 | 172 | 7 | 16 | 0 | 3 | 330 | 305 | 8 | −12 | 4 | 3 | 103 | 99 | 3 | −2 | −6 | 4 | 97 | 105 | 6 | −24 | −2 | 4 | 137 | 122 | 10 |
| 7 | −3 | 3 | 491 | 495 | 15 | 18 | 0 | 3 | 139 | 168 | 8 | −10 | 4 | 3 | 180 | 169 | 4 | 0 | −6 | 4 | 232 | 214 | 7 | −22 | −2 | 4 | 95 | 85 | 10 |
| 9 | −3 | 3 | 203 | 215 | 5 | 20 | 0 | 3 | 355 | 377 | 17 | −8 | 4 | 3 | 113 | 110 | 3 | 2 | −6 | 4 | 341 | 342 | 11 | −20 | −2 | 4 | 296 | 256 | 15 |
| 11 | −3 | 3 | 357 | 364 | 8 | 22 | 0 | 3 | 86 | 69 | 7 | −6 | 4 | 3 | 347 | 313 | 61 | 4 | −6 | 4 | 180 | 180 | 8 | −18 | −2 | 4 | 165 | 151 | 4 |
| 13 | −3 | 3 | 450 | 459 | 12 | 24 | 0 | 3 | 80 | 58 | 7 | −4 | 4 | 3 | 471 | 443 | 7 | 6 | −6 | 4 | 171 | 169 | 8 | −16 | −2 | 4 | 140 | 134 | 4 |
| 15 | −3 | 3 | 379 | 373 | 10 | 26 | 0 | 3 | 9 | 10 | 9 | −2 | 4 | 3 | 162 | 171 | 3 | 8 | −6 | 4 | 97 | 93 | 7 | −14 | −2 | 4 | 220 | 192 | 4 |
| 17 | −3 | 3 | 54 | 55 | 8 | 28 | 0 | 3 | 51 | 48 | 8 | 0 | 4 | 3 | 132 | 111 | 3 | 10 | −6 | 4 | 105 | 106 | 7 | −12 | −2 | 4 | 303 | 254 | 9 |
| 19 | −3 | 3 | 146 | 151 | 5 | −23 | 1 | 3 | 252 | 250 | 20 | 2 | 4 | 3 | 168 | 162 | 3 | 12 | −6 | 4 | 38 | 45 | 13 | −10 | −2 | 4 | 808 | 700 | 25 |
| 21 | −3 | 3 | 120 | 122 | 5 | −21 | 1 | 3 | 153 | 134 | 19 | 4 | 4 | 3 | 379 | 348 | 7 | 14 | −6 | 4 | 67 | 59 | 7 | −8 | −2 | 4 | 628 | 555 | 22 |
| 23 | −3 | 3 | 69 | 55 | 10 | −19 | 1 | 3 | 222 | 206 | 17 | 6 | 4 | 3 | 548 | 492 | 9 | −23 | −5 | 4 | 79 | 91 | 9 | −6 | −2 | 4 | 636 | 600 | 22 |
| 25 | −3 | 3 | 157 | 143 | 9 | −17 | 1 | 3 | 61 | 12 | 29 | 8 | 4 | 3 | 91 | 111 | 3 | −21 | −5 | 4 | 99 | 92 | 4 | −4 | −2 | 4 | 519 | 458 | 18 |
| −30 | −2 | 3 | 63 | 89 | 9 | −15 | 1 | 3 | 379 | 364 | 19 | 10 | 4 | 3 | 52 | 78 | 5 | −19 | −5 | 4 | 0 | 22 | 1 | −2 | −2 | 4 | 411 | 390 | 11 |
| −28 | −2 | 3 | 80 | 78 | 10 | −9 | 1 | 3 | 393 | 358 | 17 | 12 | 4 | 3 | 90 | 92 | 5 | −17 | −5 | 4 | 189 | 173 | 7 | 0 | −2 | 4 | 720 | 640 | 21 |
| −26 | −2 | 3 | 91 | 65 | 10 | −7 | 1 | 3 | 1260 | 1140 | 28 | 14 | 4 | 3 | 395 | 384 | 11 | −15 | −5 | 4 | 312 | 286 | 11 | 2 | −2 | 4 | 91 | 85 | 5 |
| −24 | −2 | 3 | 247 | 225 | 13 | −5 | 1 | 3 | 888 | 811 | 19 | 16 | 4 | 3 | 319 | 378 | 19 | −13 | −5 | 4 | 319 | 369 | 15 | 4 | −2 | 4 | 527 | 497 | 14 |
| 6 | −2 | 4 | 110 | 164 | 5 | 19 | 1 | 4 | 352 | 350 | 17 | −11 | 5 | 4 | 248 | 212 | 6 | 19 | −5 | 5 | 71 | 80 | 7 | −19 | −1 | 5 | 174 | 135 | 8 |
| 8 | −2 | 4 | 254 | 260 | 9 | 21 | 1 | 4 | 423 | 424 | 15 | −9 | 5 | 4 | 52 | 51 | 6 | −26 | −4 | 5 | 65 | 72 | 11 | −17 | −1 | 5 | 238 | 205 | 9 |
| 10 | −2 | 4 | 311 | 329 | 8 | 23 | 1 | 4 | 272 | 259 | 10 | −7 | 5 | 4 | 137 | 132 | 4 | −24 | −4 | 5 | 152 | 153 | 11 | −15 | −1 | 5 | 371 | 351 | 10 |
| 12 | −2 | 4 | 270 | 282 | 7 | 25 | 1 | 4 | 159 | 158 | 10 | −5 | 5 | 4 | 250 | 209 | 5 | −22 | −4 | 5 | 175 | 176 | 13 | −13 | −1 | 5 | 492 | 454 | 17 |
| 14 | −2 | 4 | 99 | 114 | 4 | 27 | 1 | 4 | 354 | 316 | 17 | −3 | 5 | 4 | 215 | 177 | 4 | −20 | −4 | 5 | 27 | 20 | 26 | −11 | −1 | 5 | 654 | 615 | 17 |
| 16 | −2 | 4 | 69 | 68 | 5 | −26 | 2 | 4 | 559 | 493 | 27 | −1 | 5 | 4 | 64 | 71 | 4 | −18 | −4 | 5 | 186 | 192 | 7 | −9 | −1 | 5 | 942 | 900 | 25 |
| 18 | −2 | 4 | 325 | 334 | 9 | −24 | 2 | 4 | 130 | 123 | 22 | 1 | 5 | 4 | 393 | 367 | 7 | −16 | −4 | 5 | 64 | 74 | 8 | −7 | −1 | 5 | 467 | 428 | 10 |
| 20 | −2 | 4 | 29 | 25 | 11 | −22 | 2 | 4 | 71 | 86 | 42 | 3 | 5 | 4 | 415 | 399 | 9 | −14 | −4 | 5 | 274 | 269 | 8 | −5 | −1 | 5 | 117 | 87 | 4 |
| 22 | −2 | 4 | 129 | 126 | 9 | −20 | 2 | 4 | 281 | 257 | 19 | 5 | 5 | 4 | 245 | 241 | 6 | −12 | −4 | 5 | 525 | 475 | 13 | −3 | −1 | 5 | 217 | 208 | 5 |
| 24 | −2 | 4 | 292 | 272 | 14 | −18 | 2 | 4 | 150 | 152 | 17 | 7 | 5 | 4 | 370 | 389 | 8 | −10 | −4 | 5 | 295 | 263 | 7 | −1 | −1 | 5 | 594 | 600 | 15 |
| 26 | −2 | 4 | 373 | 341 | 17 | −16 | 2 | 4 | 141 | 135 | 8 | 9 | 5 | 4 | 445 | 457 | 11 | −8 | −4 | 5 | 156 | 133 | 5 | 1 | −1 | 5 | 338 | 355 | 7 |
| −29 | −1 | 4 | 287 | 302 | 14 | −14 | 2 | 4 | 214 | 192 | 15 | 11 | 5 | 4 | 96 | 89 | 5 | −6 | −4 | 5 | 224 | 216 | 6 | 3 | −1 | 5 | 556 | 591 | 14 |
| −27 | −1 | 4 | 129 | 117 | 8 | −10 | 2 | 4 | 784 | 700 | 20 | 13 | 5 | 4 | 201 | 212 | 6 | −4 | −4 | 5 | 332 | 312 | 8 | 5 | −1 | 5 | 688 | 776 | 23 |
| −25 | −1 | 4 | 80 | 58 | 8 | −8 | 2 | 4 | 662 | 555 | 14 | 15 | 5 | 4 | 123 | 160 | 8 | −2 | −4 | 5 | 188 | 169 | 5 | 7 | −1 | 5 | 1076 | 1215 | 36 |
| −23 | −1 | 4 | 95 | 100 | 8 | −6 | 2 | 4 | 682 | 600 | 14 | 17 | 5 | 4 | 52 | 62 | 12 | 0 | −4 | 5 | 360 | 342 | 7 | 9 | −1 | 5 | 268 | 280 | 9 |
| −21 | −1 | 4 | 170 | 158 | 8 | −4 | 2 | 4 | 548 | 458 | 12 | 19 | 5 | 4 | 56 | 80 | 11 | 2 | −4 | 5 | 64 | 72 | 4 | 11 | −1 | 5 | 510 | 550 | 12 |
| −19 | −1 | 4 | 186 | 171 | 8 | −2 | 2 | 4 | 424 | 390 | 10 | −18 | 6 | 4 | 81 | 108 | 8 | 4 | −4 | 5 | 430 | 416 | 10 | 13 | −1 | 5 | 620 | 676 | 13 |
| −17 | −1 | 4 | 330 | 318 | 12 | 0 | 2 | 4 | 689 | 640 | 19 | −16 | 6 | 4 | 63 | 72 | 10 | 6 | −4 | 5 | 389 | 378 | 10 | 15 | −1 | 5 | 245 | 256 | 5 |
| −15 | −1 | 4 | 66 | 82 | 4 | 2 | 2 | 4 | 95 | 87 | 4 | −14 | 6 | 4 | 122 | 113 | 8 | 8 | −4 | 5 | 448 | 442 | 11 | 17 | −1 | 5 | 527 | 558 | 14 |
| −13 | −1 | 4 | 575 | 564 | 18 | 4 | 2 | 4 | 559 | 498 | 22 | −12 | 6 | 4 | 48 | 49 | 11 | 10 | −4 | 5 | 294 | 295 | 8 | 19 | −1 | 5 | 385 | 379 | 11 |
| −11 | −1 | 4 | 866 | 848 | 23 | 6 | 2 | 4 | 126 | 165 | 4 | −10 | 6 | 4 | 135 | 132 | 5 | 12 | −4 | 5 | 112 | 141 | 7 | 23 | −1 | 5 | 286 | 271 | 14 |
| −9 | −1 | 4 | 236 | 204 | 6 | 8 | 2 | 4 | 249 | 261 | 7 | −8 | 6 | 4 | 182 | 168 | 5 | 14 | −4 | 5 | 141 | 146 | 6 | 25 | −1 | 5 | 277 | 256 | 14 |
| −7 | −1 | 4 | 269 | 238 | 6 | 10 | 2 | 4 | 299 | 327 | 6 | −6 | 6 | 4 | 466 | 424 | 12 | 16 | −4 | 5 | 215 | 263 | 12 | 27 | −1 | 5 | 219 | 194 | 12 |
| −5 | −1 | 4 | 421 | 387 | 9 | 12 | 2 | 4 | 270 | 281 | 5 | −4 | 6 | 4 | 168 | 146 | 5 | 18 | −4 | 5 | 169 | 192 | 5 | −28 | 0 | 5 | 275 | 228 | 19 |
| −3 | −1 | 4 | 691 | 654 | 17 | 14 | 2 | 4 | 110 | 114 | 3 | −2 | 6 | 4 | 88 | 105 | 6 | 20 | −4 | 5 | 199 | 192 | 8 | −26 | 0 | 5 | 117 | 97 | 25 |
| −1 | −1 | 4 | 964 | 973 | 25 | 16 | 2 | 4 | 77 | 68 | 7 | 0 | 6 | 4 | 223 | 213 | 7 | 22 | −4 | 5 | 125 | 134 | 9 | −24 | 0 | 5 | 443 | 410 | 23 |
| 1 | −1 | 4 | 196 | 205 | 5 | 18 | 2 | 4 | 324 | 332 | 12 | 2 | 6 | 4 | 332 | 342 | 9 | −27 | −3 | 5 | 179 | 167 | 11 | −22 | 0 | 5 | 258 | 231 | 18 |
| 3 | −1 | 4 | 760 | 795 | 19 | 20 | 2 | 4 | 16 | 24 | 16 | 4 | 6 | 4 | 183 | 179 | 6 | −25 | −3 | 5 | 152 | 149 | 11 | −20 | 0 | 5 | 158 | 127 | 17 |
| 5 | −1 | 4 | 854 | 908 | 21 | 22 | 2 | 4 | 124 | 127 | 6 | 6 | 6 | 4 | 169 | 168 | 6 | −23 | −3 | 5 | 112 | 129 | 12 | −18 | 0 | 5 | 353 | 352 | 18 |
| 7 | −1 | 4 | 124 | 157 | 5 | 24 | 2 | 4 | 279 | 271 | 10 | 8 | 6 | 4 | 96 | 94 | 5 | −21 | −3 | 5 | 355 | 434 | 13 | −16 | 0 | 5 | 70 | 61 | 22 |
| 9 | −1 | 4 | 753 | 793 | 25 | 26 | 2 | 4 | 358 | 341 | 13 | 10 | 6 | 4 | 111 | 106 | 4 | −19 | −3 | 5 | 223 | 233 | 7 | −12 | 0 | 5 | 276 | 390 | 13 |

TABLE 8-continued

| Observed and calculated structure factors for SAG-2 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| 11 | -1 | 4 | 516 | 521 | 17 | -25 | 3 | 4 | 293 | 266 | 16 | 12 | 6 | 4 | 34 | 43 | 12 | -17 | -3 | 5 | 261 | 251 | 7 | -10 | 0 | 5 | 704 | 730 | 22 |
| 13 | -1 | 4 | 116 | 120 | 4 | -23 | 3 | 4 | 183 | 176 | 16 | 14 | 6 | 4 | 58 | 60 | 10 | -15 | -3 | 5 | 70 | 76 | 5 | -8 | 0 | 5 | 959 | 1071 | 31 |
| 15 | -1 | 4 | 148 | 144 | 4 | -21 | 3 | 4 | 233 | 248 | 16 | -11 | 7 | 4 | 62 | 54 | 12 | -13 | -3 | 5 | 176 | 170 | 5 | -6 | 0 | 5 | 1403 | 1534 | 45 |
| 17 | -1 | 4 | 478 | 499 | 10 | -19 | 3 | 4 | 152 | 138 | 10 | -9 | 7 | 4 | 86 | 81 | 6 | -11 | -3 | 5 | 559 | 534 | 14 | -4 | 0 | 5 | 812 | 842 | 21 |
| 19 | -1 | 4 | 337 | 349 | 7 | -17 | 3 | 4 | 321 | 303 | 9 | -7 | 7 | 4 | 134 | 123 | 4 | -9 | -3 | 5 | 227 | 223 | 6 | -2 | 0 | 5 | 121 | 112 | 4 |
| 21 | -1 | 4 | 429 | 424 | 21 | -15 | 3 | 4 | 218 | 215 | 8 | -5 | 7 | 4 | 53 | 57 | 6 | -7 | -3 | 5 | 415 | 368 | 12 | 0 | 0 | 5 | 293 | 295 | 7 |
| 23 | -1 | 4 | 270 | 259 | 14 | -13 | 3 | 4 | 467 | 435 | 16 | -3 | 7 | 4 | 95 | 100 | 5 | -5 | -3 | 5 | 556 | 523 | 23 | 2 | 0 | 5 | 59 | 34 | 4 |
| 25 | -1 | 4 | 187 | 157 | 9 | -11 | 3 | 4 | 163 | 159 | 4 | -1 | 7 | 4 | 124 | 115 | 6 | -3 | -3 | 5 | 387 | 359 | 12 | 4 | 0 | 5 | 594 | 587 | 13 |
| 27 | -1 | 4 | 357 | 315 | 17 | -9 | 3 | 4 | 622 | 587 | 11 | 1 | 7 | 4 | 76 | 68 | 7 | -1 | -3 | 5 | 254 | 251 | 8 | 6 | 0 | 5 | 160 | 112 | 4 |
| -28 | 0 | 4 | 356 | 299 | 20 | -7 | 3 | 4 | 554 | 490 | 11 | 3 | 7 | 4 | 59 | 55 | 8 | 1 | -3 | 5 | 114 | 116 | 6 | 8 | 0 | 5 | 530 | 538 | 12 |
| -26 | 0 | 4 | 64 | 58 | 64 | -5 | 3 | 4 | 657 | 570 | 16 | 5 | 7 | 4 | 167 | 145 | 6 | 3 | -3 | 5 | 281 | 313 | 7 | 10 | 0 | 5 | 135 | 120 | 5 |
| -24 | 0 | 4 | 311 | 293 | 20 | -3 | 3 | 4 | 719 | 618 | 18 | 7 | 7 | 4 | 84 | 95 | 5 | 5 | -3 | 5 | 327 | 330 | 6 | 12 | 0 | 5 | 353 | 430 | 7 |
| -22 | 0 | 4 | 613 | 540 | 29 | -1 | 3 | 4 | 626 | 602 | 17 | -9 | -7 | 5 | 170 | 168 | 7 | 7 | -3 | 5 | 215 | 250 | 5 | 14 | 0 | 5 | 192 | 193 | 4 |
| -20 | 0 | 4 | 406 | 375 | 21 | 1 | 3 | 4 | 255 | 274 | 9 | -7 | -7 | 5 | 218 | 223 | 8 | 9 | -3 | 5 | 221 | 223 | 6 | 16 | 0 | 5 | 572 | 631 | 11 |
| -18 | 0 | 4 | 205 | 166 | 15 | 3 | 3 | 4 | 371 | 350 | 10 | -5 | -7 | 5 | 133 | 120 | 6 | 11 | -3 | 5 | 148 | 160 | 5 | 18 | 0 | 5 | 251 | 289 | 5 |
| -16 | 0 | 4 | 331 | 331 | 17 | 5 | 3 | 4 | 419 | 427 | 7 | -3 | -7 | 5 | 74 | 80 | 7 | 13 | -3 | 5 | 54 | 45 | 6 | 20 | 0 | 5 | 21 | 29 | 20 |
| -10 | 0 | 4 | 83 | 99 | 3 | 7 | 3 | 4 | 156 | 161 | 3 | -1 | -7 | 5 | 98 | 120 | 9 | 15 | -3 | 5 | 252 | 252 | 9 | 22 | 0 | 5 | 175 | 168 | 10 |
| -8 | 0 | 4 | 507 | 640 | 15 | 9 | 3 | 4 | 129 | 117 | 3 | 3 | -7 | 5 | 180 | 195 | 7 | 17 | -3 | 5 | 276 | 319 | 8 | 24 | 0 | 5 | 185 | 163 | 10 |
| -6 | 0 | 4 | 553 | 562 | 17 | 11 | 3 | 4 | 411 | 430 | 15 | 5 | -7 | 5 | 59 | 66 | 8 | 19 | -3 | 5 | 196 | 183 | 6 | 26 | 0 | 5 | 25 | 9 | 24 |
| -4 | 0 | 4 | 1501 | 1606 | 40 | 13 | 3 | 4 | 343 | 344 | 7 | -18 | -6 | 5 | 103 | 116 | 9 | 21 | -3 | 5 | 332 | 315 | 9 | -27 | 1 | 5 | 217 | 195 | 18 |
| -2 | 0 | 4 | 954 | 1120 | 24 | 15 | 3 | 4 | 74 | 85 | 4 | -16 | -6 | 5 | 131 | 146 | 6 | 23 | -3 | 5 | 77 | 76 | 9 | -23 | 1 | 5 | 81 | 105 | 29 |
| 0 | 0 | 4 | 963 | 1129 | 25 | 17 | 3 | 4 | 225 | 244 | 9 | -14 | -6 | 5 | 207 | 189 | 8 | 25 | -3 | 5 | 260 | 264 | 14 | -21 | 1 | 5 | 136 | 119 | 20 |
| 2 | 0 | 4 | 354 | 459 | 11 | 19 | 3 | 4 | 32 | 15 | 23 | -12 | -6 | 5 | 92 | 74 | 7 | -30 | -2 | 5 | 60 | 65 | 9 | -19 | 1 | 5 | 178 | 135 | 17 |
| 4 | 0 | 4 | 164 | 186 | 4 | 21 | 3 | 4 | 33 | 22 | 19 | -10 | -6 | 5 | 241 | 231 | 9 | -28 | -2 | 5 | 150 | 157 | 10 | -17 | 1 | 5 | 241 | 205 | 16 |
| 6 | 0 | 4 | 386 | 368 | 8 | 23 | 3 | 4 | 80 | 87 | 6 | -8 | -6 | 5 | 89 | 87 | 8 | -26 | -2 | 5 | 179 | 170 | 11 | -15 | 1 | 5 | 383 | 351 | 18 |
| 10 | 0 | 4 | 997 | 1001 | 26 | 25 | 3 | 4 | 88 | 82 | 5 | -6 | -6 | 5 | 234 | 211 | 11 | -24 | -2 | 5 | 151 | 151 | 11 | -9 | 1 | 5 | 946 | 899 | 21 |
| 12 | 0 | 4 | 290 | 369 | 8 | -24 | 4 | 4 | 255 | 251 | 14 | -4 | -6 | 5 | 230 | 217 | 9 | -22 | -2 | 5 | 234 | 222 | 13 | -7 | 1 | 5 | 447 | 427 | 10 |
| 14 | 0 | 4 | 322 | 323 | 8 | -22 | 4 | 4 | 31 | 28 | 20 | -2 | -6 | 5 | 77 | 63 | 7 | -20 | -2 | 5 | 120 | 96 | 9 | -5 | 1 | 5 | 118 | 88 | 3 |
| 16 | 0 | 4 | 210 | 182 | 5 | -20 | 4 | 4 | 101 | 91 | 7 | 0 | -6 | 5 | 334 | 334 | 9 | -18 | -2 | 5 | 126 | 122 | 4 | -3 | 1 | 5 | 221 | 206 | 5 |
| 18 | 0 | 4 | 174 | 182 | 5 | -18 | 4 | 4 | 119 | 98 | 7 | 2 | -6 | 5 | 180 | 176 | 6 | -16 | -2 | 5 | 213 | 191 | 5 | -1 | 1 | 5 | 584 | 600 | 13 |
| 20 | 0 | 4 | 114 | 125 | 8 | -16 | 4 | 4 | 416 | 384 | 22 | 4 | -6 | 5 | 113 | 120 | 7 | -14 | -2 | 5 | 296 | 265 | 6 | 1 | 1 | 5 | 332 | 357 | 8 |
| 22 | 0 | 4 | 28 | 36 | 19 | -14 | 4 | 4 | 406 | 355 | 14 | 6 | -6 | 5 | 71 | 65 | 9 | -12 | -2 | 5 | 175 | 167 | 6 | 3 | 1 | 5 | 553 | 591 | 15 |
| 24 | 0 | 4 | 26 | 1 | 26 | -12 | 4 | 4 | 103 | 111 | 3 | 8 | -6 | 5 | 136 | 151 | 7 | -10 | -2 | 5 | 182 | 152 | 7 | 5 | 1 | 5 | 712 | 778 | 22 |
| 26 | 0 | 4 | 312 | 285 | 15 | -10 | 4 | 4 | 264 | 244 | 6 | 10 | -6 | 5 | 212 | 220 | 8 | -8 | -2 | 5 | 286 | 265 | 10 | 7 | 1 | 5 | 1113 | 1215 | 34 |
| 28 | 0 | 4 | 52 | 47 | 8 | -8 | 4 | 4 | 535 | 497 | 9 | 12 | -6 | 5 | 254 | 278 | 9 | -6 | -2 | 5 | 109 | 111 | 6 | 9 | 1 | 5 | 274 | 281 | 6 |
| -27 | 1 | 4 | 93 | 116 | 30 | -6 | 4 | 4 | 245 | 221 | 4 | 14 | -6 | 5 | 51 | 41 | 9 | -4 | -2 | 5 | 348 | 355 | 10 | 11 | 1 | 5 | 542 | 552 | 13 |
| -25 | 1 | 4 | 0 | 59 | 1 | -4 | 4 | 4 | 457 | 413 | 7 | -21 | -5 | 5 | 195 | 168 | 20 | -2 | -2 | 5 | 592 | 548 | 25 | 13 | 1 | 5 | 637 | 677 | 12 |
| -23 | 1 | 4 | 87 | 101 | 29 | -2 | 4 | 4 | 155 | 138 | 3 | -19 | -5 | 5 | 138 | 138 | 6 | 0 | -2 | 5 | 208 | 209 | 7 | 15 | 1 | 5 | 243 | 256 | 5 |
| -21 | 1 | 4 | 147 | 158 | 19 | 0 | 4 | 4 | 446 | 398 | 8 | -17 | -5 | 5 | 249 | 244 | 8 | 2 | -2 | 5 | 638 | 577 | 20 | 17 | 1 | 5 | 512 | 557 | 15 |
| -19 | 1 | 4 | 182 | 171 | 16 | 2 | 4 | 4 | 482 | 434 | 8 | -15 | -5 | 5 | 54 | 46 | 11 | 4 | -2 | 5 | 90 | 68 | 5 | 19 | 1 | 5 | 380 | 379 | 13 |
| -17 | 1 | 4 | 339 | 317 | 17 | 4 | 4 | 4 | 355 | 349 | 6 | -13 | -5 | 5 | 354 | 317 | 12 | 6 | -2 | 5 | 603 | 605 | 18 | 21 | 1 | 5 | 465 | 460 | 16 |
| -15 | 1 | 4 | 68 | 83 | 23 | 6 | 4 | 4 | 155 | 159 | 3 | -11 | -5 | 5 | 376 | 314 | 19 | 8 | -2 | 5 | 300 | 303 | 9 | 23 | 1 | 5 | 278 | 270 | 10 |
| -9 | 1 | 4 | 233 | 205 | 6 | 8 | 4 | 4 | 106 | 107 | 3 | -9 | -5 | 5 | 453 | 414 | 15 | 10 | -2 | 5 | 360 | 386 | 8 | 25 | 1 | 5 | 274 | 256 | 10 |
| -7 | 1 | 4 | 273 | 238 | 6 | 10 | 4 | 4 | 488 | 497 | 14 | -7 | -5 | 5 | 180 | 149 | 8 | 12 | -2 | 5 | 99 | 103 | 4 | 27 | 1 | 5 | 228 | 194 | 11 |
| -5 | 1 | 4 | 412 | 386 | 9 | 12 | 4 | 4 | 698 | 693 | 20 | -5 | -5 | 5 | 196 | 185 | 5 | 14 | -2 | 5 | 77 | 73 | 4 | -26 | 2 | 5 | 179 | 171 | 18 |
| -3 | 1 | 4 | 685 | 656 | 15 | 14 | 4 | 4 | 404 | 430 | 14 | -3 | -5 | 5 | 129 | 116 | 5 | 16 | -2 | 5 | 110 | 114 | 4 | -24 | 2 | 5 | 168 | 150 | 18 |
| -1 | 1 | 4 | 970 | 971 | 19 | 16 | 4 | 4 | 100 | 129 | 8 | -1 | -5 | 5 | 259 | 247 | 6 | 18 | -2 | 5 | 123 | 125 | 5 | -22 | 2 | 5 | 245 | 224 | 18 |
| 1 | 1 | 4 | 201 | 206 | 5 | 18 | 4 | 4 | 116 | 131 | 8 | 1 | -5 | 5 | 252 | 249 | 6 | 20 | -2 | 5 | 449 | 457 | 16 | -20 | 2 | 5 | 105 | 96 | 23 |
| 3 | 1 | 4 | 765 | 795 | 17 | 20 | 4 | 4 | 173 | 177 | 8 | 3 | -5 | 5 | 596 | 571 | 14 | 22 | -2 | 5 | 213 | 201 | 12 | -18 | 2 | 5 | 142 | 120 | 17 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 5 | 1 | 4 | 842 | 907 | 22 | 22 | 4 | 4 | 222 | 231 | 12 | 5 | −5 | 5 | 344 | 340 | 10 | 24 | −2 | 5 | 29 | 22 | 29 | −16 | 2 | 5 | 209 | 190 | 9 |
| 7 | 1 | 4 | 132 | 155 | 4 | −23 | 5 | 4 | 75 | 90 | 8 | 7 | −5 | 5 | 101 | 100 | 7 | 26 | −2 | 5 | 185 | 172 | 10 | −14 | 2 | 5 | 288 | 266 | 11 |
| 9 | 1 | 4 | 776 | 795 | 17 | −21 | 5 | 4 | 97 | 91 | 9 | 9 | −5 | 5 | 119 | 112 | 7 | −29 | −1 | 5 | 186 | 221 | 10 | −10 | 2 | 5 | 174 | 153 | 4 |
| 11 | 1 | 4 | 527 | 518 | 14 | −19 | 5 | 4 | 0 | 21 | 1 | 11 | −5 | 5 | 90 | 90 | 7 | −27 | −1 | 5 | 220 | 195 | 10 | −8 | 2 | 5 | 295 | 268 | 7 |
| 13 | 1 | 4 | 110 | 120 | 4 | −17 | 5 | 4 | 197 | 175 | 8 | 13 | −5 | 5 | 112 | 122 | 7 | −25 | −1 | 5 | 250 | 229 | 10 | −6 | 2 | 5 | 116 | 110 | 4 |
| 15 | 1 | 4 | 143 | 145 | 4 | −15 | 5 | 4 | 306 | 286 | 16 | 15 | −5 | 5 | 231 | 246 | 8 | −23 | −1 | 5 | 102 | 104 | 8 | −4 | 2 | 5 | 373 | 355 | 8 |
| 17 | 1 | 4 | 475 | 501 | 17 | −13 | 5 | 4 | 322 | 368 | 12 | 17 | −5 | 5 | 108 | 132 | 6 | −21 | −1 | 5 | 124 | 118 | 8 | −2 | 2 | 5 | 572 | 549 | 29 |
| 0 | 2 | 5 | 202 | 210 | 5 | −10 | 6 | 5 | 237 | 230 | 6 | 20 | −4 | 6 | 100 | 101 | 5 | −18 | 0 | 6 | 68 | 21 | 26 | −1 | 3 | 6 | 173 | 146 | 4 |
| 2 | 2 | 5 | 655 | 576 | 20 | −8 | 6 | 5 | 83 | 88 | 4 | −27 | −3 | 6 | 94 | 107 | 10 | −16 | 0 | 6 | 263 | 242 | 15 | 1 | 3 | 6 | 177 | 167 | 4 |
| 4 | 2 | 5 | 92 | 67 | 5 | −6 | 6 | 5 | 218 | 210 | 6 | −25 | −3 | 6 | 117 | 113 | 11 | −14 | 0 | 6 | 351 | 343 | 17 | 3 | 3 | 6 | 286 | 281 | 5 |
| 6 | 2 | 5 | 609 | 605 | 18 | −4 | 6 | 5 | 237 | 219 | 6 | −23 | −3 | 6 | 85 | 67 | 12 | −12 | 0 | 6 | 933 | 950 | 30 | 5 | 3 | 6 | 422 | 443 | 8 |
| 8 | 2 | 5 | 294 | 302 | 7 | −2 | 6 | 5 | 74 | 62 | 6 | −19 | −3 | 6 | 145 | 137 | 6 | −10 | 0 | 6 | 741 | 829 | 23 | 7 | 3 | 6 | 357 | 420 | 8 |
| 10 | 2 | 5 | 348 | 386 | 8 | 0 | 6 | 5 | 331 | 335 | 9 | −17 | −3 | 6 | 304 | 335 | 8 | −6 | 0 | 6 | 584 | 597 | 15 | 9 | 3 | 6 | 59 | 69 | 4 |
| 12 | 2 | 5 | 97 | 103 | 3 | 2 | 6 | 5 | 187 | 178 | 6 | −15 | −3 | 6 | 359 | 346 | 8 | −4 | 0 | 6 | 676 | 679 | 15 | 11 | 3 | 6 | 94 | 102 | 4 |
| 14 | 2 | 5 | 83 | 74 | 4 | 4 | 6 | 5 | 110 | 121 | 6 | −13 | −3 | 6 | 610 | 585 | 13 | −2 | 0 | 6 | 367 | 385 | 8 | 13 | 3 | 6 | 168 | 191 | 6 |
| 16 | 2 | 5 | 113 | 113 | 4 | 6 | 6 | 5 | 59 | 63 | 7 | −11 | −3 | 6 | 134 | 126 | 5 | 0 | 0 | 6 | 460 | 503 | 10 | 15 | 3 | 6 | 58 | 73 | 6 |
| 18 | 2 | 5 | 123 | 123 | 7 | 8 | 6 | 5 | 147 | 150 | 5 | −9 | −3 | 6 | 335 | 325 | 8 | 2 | 0 | 6 | 417 | 460 | 9 | 17 | 3 | 6 | 0 | 22 | 1 |
| 20 | 2 | 5 | 461 | 457 | 23 | 10 | 6 | 5 | 215 | 221 | 7 | −7 | −3 | 6 | 329 | 320 | 11 | 4 | 0 | 6 | 465 | 483 | 15 | 19 | 3 | 6 | 128 | 126 | 10 |
| 22 | 2 | 5 | 214 | 201 | 8 | 12 | 6 | 5 | 258 | 278 | 9 | −5 | −3 | 6 | 760 | 737 | 32 | 6 | 0 | 6 | 142 | 169 | 6 | 21 | 3 | 6 | 233 | 245 | 14 |
| 24 | 2 | 5 | 24 | 20 | 23 | 14 | 6 | 5 | 52 | 43 | 11 | −3 | −3 | 6 | 126 | 126 | 4 | 8 | 0 | 6 | 382 | 433 | 10 | 23 | 3 | 6 | 86 | 86 | 6 |
| 26 | 2 | 5 | 190 | 172 | 7 | −9 | 7 | 5 | 178 | 169 | 7 | −1 | −3 | 6 | 164 | 146 | 5 | 10 | 0 | 6 | 619 | 633 | 16 | −26 | 4 | 6 | 37 | 48 | 36 |
| −25 | 3 | 5 | 162 | 150 | 12 | −7 | 7 | 5 | 220 | 222 | 6 | 1 | −3 | 6 | 167 | 167 | 5 | 12 | 0 | 6 | 358 | 402 | 7 | −22 | 4 | 6 | 70 | 48 | 8 |
| −23 | 3 | 5 | 139 | 129 | 9 | −5 | 7 | 5 | 127 | 120 | 4 | 3 | −3 | 6 | 290 | 281 | 6 | 14 | 0 | 6 | 68 | 67 | 4 | −20 | 4 | 6 | 406 | 367 | 13 |
| −19 | 3 | 5 | 226 | 234 | 7 | −3 | 7 | 5 | 68 | 81 | 6 | 5 | −3 | 6 | 431 | 443 | 8 | 16 | 0 | 6 | 631 | 670 | 15 | −18 | 4 | 6 | 123 | 115 | 6 |
| −17 | 3 | 5 | 274 | 252 | 8 | −1 | 7 | 5 | 118 | 121 | 6 | 7 | −3 | 6 | 379 | 420 | 9 | 18 | 0 | 6 | 247 | 250 | 6 | −16 | 4 | 6 | 182 | 164 | 7 |
| −15 | 3 | 5 | 72 | 76 | 6 | 1 | 7 | 5 | 60 | 80 | 8 | 9 | −3 | 6 | 66 | 70 | 5 | 20 | 0 | 6 | 106 | 115 | 6 | −14 | 4 | 6 | 144 | 127 | 7 |
| 13 | 3 | 5 | 174 | 170 | 7 | 3 | 7 | 5 | 157 | 195 | 11 | 11 | −3 | 6 | 86 | 101 | 5 | 22 | 0 | 6 | 228 | 215 | 8 | −12 | 4 | 6 | 185 | 169 | 4 |
| −11 | 3 | 5 | 551 | 536 | 11 | 5 | 7 | 5 | 83 | 67 | 6 | 13 | −3 | 6 | 163 | 191 | 5 | 24 | 0 | 6 | 181 | 167 | 10 | −10 | 4 | 6 | 291 | 279 | 9 |
| −9 | 3 | 5 | 228 | 223 | 4 | 7 | 7 | 5 | 155 | 125 | 9 | 15 | −3 | 6 | 61 | 73 | 7 | 26 | 0 | 6 | 25 | 5 | 24 | −8 | 4 | 6 | 133 | 137 | 3 |
| −7 | 3 | 5 | 403 | 367 | 8 | −9 | −7 | 6 | 97 | 96 | 6 | 17 | −3 | 6 | 27 | 23 | 17 | −29 | 1 | 6 | 184 | 179 | 16 | −6 | 4 | 6 | 404 | 388 | 6 |
| −5 | 3 | 5 | 538 | 524 | 12 | −7 | −7 | 6 | 96 | 91 | 7 | 19 | −3 | 6 | 116 | 124 | 5 | −27 | 1 | 6 | 194 | 215 | 18 | −4 | 4 | 6 | 51 | 71 | 4 |
| −3 | 3 | 5 | 377 | 358 | 10 | −5 | −7 | 6 | 242 | 248 | 9 | 21 | −3 | 6 | 252 | 243 | 7 | −25 | 1 | 6 | 34 | 58 | 34 | −2 | 4 | 6 | 199 | 199 | 4 |
| −1 | 3 | 5 | 257 | 252 | 8 | −3 | −7 | 6 | 193 | 207 | 7 | 23 | −3 | 6 | 67 | 85 | 10 | −23 | 1 | 6 | 38 | 56 | 37 | 0 | 4 | 6 | 228 | 228 | 4 |
| 1 | 3 | 5 | 109 | 116 | 6 | −1 | −7 | 6 | 179 | 192 | 10 | −28 | −2 | 6 | 58 | 69 | 12 | −21 | 1 | 6 | 261 | 220 | 17 | 2 | 4 | 6 | 217 | 217 | 4 |
| 3 | 3 | 5 | 286 | 314 | 6 | −16 | −6 | 6 | 115 | 125 | 6 | −26 | −2 | 6 | 164 | 180 | 11 | −19 | 1 | 6 | 69 | 81 | 33 | 4 | 4 | 6 | 469 | 494 | 8 |
| 5 | 3 | 5 | 322 | 331 | 6 | −14 | −6 | 6 | 98 | 85 | 6 | −24 | −2 | 6 | 0 | 23 | 1 | −17 | 1 | 6 | 169 | 142 | 15 | 6 | 4 | 6 | 434 | 464 | 9 |
| 7 | 3 | 5 | 214 | 249 | 4 | −12 | −6 | 6 | 86 | 86 | 7 | −22 | −2 | 6 | 76 | 76 | 11 | −15 | 1 | 6 | 64 | 82 | 21 | 8 | 4 | 6 | 275 | 297 | 6 |
| 9 | 3 | 5 | 215 | 222 | 5 | −10 | −6 | 6 | 129 | 128 | 7 | −20 | −2 | 6 | 70 | 78 | 11 | −11 | 1 | 6 | 175 | 191 | 5 | 10 | 4 | 6 | 67 | 77 | 5 |
| 11 | 3 | 5 | 145 | 159 | 4 | −8 | −6 | 6 | 98 | 99 | 7 | −18 | −2 | 6 | 407 | 370 | 9 | −9 | 1 | 6 | 606 | 600 | 20 | 12 | 4 | 6 | 323 | 375 | 9 |
| 13 | 3 | 5 | 54 | 46 | 8 | −6 | −6 | 6 | 261 | 242 | 9 | −16 | −2 | 6 | 204 | 185 | 4 | −7 | 1 | 6 | 178 | 168 | 4 | 14 | 4 | 6 | 373 | 405 | 13 |
| 15 | 3 | 5 | 244 | 252 | 6 | −4 | −6 | 6 | 138 | 131 | 8 | −14 | −2 | 6 | 423 | 392 | 10 | −5 | 1 | 6 | 787 | 809 | 17 | 16 | 4 | 6 | 59 | 54 | 11 |
| 17 | 3 | 5 | 290 | 320 | 10 | −2 | −6 | 6 | 79 | 77 | 7 | −12 | −2 | 6 | 84 | 72 | 4 | −3 | 1 | 6 | 389 | 427 | 10 | 18 | 4 | 6 | 183 | 179 | 8 |
| 19 | 3 | 5 | 198 | 183 | 8 | 0 | −6 | 6 | 116 | 123 | 6 | −10 | −2 | 6 | 1142 | 1042 | 35 | −1 | 1 | 6 | 766 | 849 | 20 | 20 | 4 | 6 | 84 | 101 | 11 |
| 23 | 3 | 5 | 76 | 75 | 6 | 2 | −6 | 6 | 48 | 57 | 9 | −8 | −2 | 6 | 622 | 570 | 20 | 1 | 1 | 6 | 483 | 503 | 16 | 22 | 4 | 6 | 164 | 160 | 6 |
| 25 | 3 | 5 | 274 | 264 | 9 | 4 | −6 | 6 | 454 | 457 | 16 | −6 | −2 | 6 | 983 | 949 | 34 | 3 | 1 | 6 | 512 | 548 | 21 | −23 | 5 | 6 | 131 | 135 | 13 |
| −24 | 4 | 5 | 154 | 153 | 12 | 6 | −6 | 6 | 214 | 228 | 9 | −4 | −2 | 6 | 947 | 921 | 41 | 5 | 1 | 6 | 898 | 902 | 35 | −21 | 5 | 6 | 113 | 102 | 6 |
| −22 | 4 | 5 | 199 | 176 | 8 | 8 | −6 | 6 | 80 | 78 | 8 | −2 | −2 | 6 | 80 | 95 | 5 | 7 | 1 | 6 | 154 | 138 | 5 | −19 | 5 | 6 | 77 | 63 | 8 |
| −20 | 4 | 5 | 29 | 20 | 26 | 10 | −6 | 6 | 84 | 87 | 7 | 0 | −2 | 6 | 445 | 412 | 13 | 9 | 1 | 6 | 530 | 577 | 11 | −17 | 5 | 6 | 203 | 164 | 8 |
| −18 | 4 | 5 | 211 | 193 | 8 | 12 | −6 | 6 | 110 | 126 | 6 | 2 | −2 | 6 | 307 | 296 | 10 | 13 | 1 | 6 | 73 | 73 | 4 | −15 | 5 | 6 | 325 | 301 | 12 |

TABLE 8-continued

| Observed and calculated structure factors for SAG-2 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| −16 | 4 | 5 | 71 | 74 | 7 | 14 | −6 | 6 | 147 | 150 | 6 | 4 | −2 | 6 | 220 | 222 | 8 | 15 | 1 | 6 | 396 | 430 | 9 | −13 | 5 | 6 | 0 | 24 | 1 |
| −14 | 4 | 5 | 290 | 270 | 10 | −21 | −5 | 6 | 94 | 103 | 5 | 6 | −2 | 6 | 121 | 151 | 6 | 17 | 1 | 6 | 482 | 532 | 9 | −11 | 5 | 6 | 109 | 109 | 4 |
| −12 | 4 | 5 | 500 | 475 | 10 | −19 | −5 | 6 | 64 | 64 | 7 | 8 | −2 | 6 | 265 | 287 | 6 | 19 | 1 | 6 | 342 | 333 | 12 | −9 | 5 | 6 | 52 | 62 | 6 |
| −10 | 4 | 5 | 287 | 262 | 7 | −17 | −5 | 6 | 167 | 163 | 7 | 10 | −2 | 6 | 132 | 124 | 4 | 21 | 1 | 6 | 221 | 207 | 8 | −7 | 5 | 6 | 160 | 158 | 4 |
| −8 | 4 | 5 | 150 | 135 | 3 | −15 | −5 | 6 | 317 | 303 | 11 | 12 | −2 | 6 | 116 | 118 | 4 | 23 | 1 | 6 | 217 | 209 | 8 | −5 | 5 | 6 | 163 | 153 | 5 |
| −6 | 4 | 5 | 218 | 217 | 4 | −13 | −5 | 6 | 39 | 24 | 16 | 14 | −2 | 6 | 104 | 110 | 4 | 25 | 1 | 6 | 175 | 163 | 7 | −3 | 5 | 6 | 382 | 356 | 8 |
| −4 | 4 | 5 | 332 | 309 | 5 | −11 | −5 | 6 | 102 | 109 | 8 | 16 | −2 | 6 | 458 | 497 | 10 | −28 | 2 | 6 | 78 | 68 | 28 | −1 | 5 | 6 | 386 | 369 | 10 |
| −2 | 4 | 5 | 194 | 170 | 4 | −9 | −5 | 6 | 46 | 60 | 13 | 18 | −2 | 6 | 152 | 159 | 5 | −26 | 2 | 6 | 183 | 180 | 17 | 1 | 5 | 6 | 161 | 148 | 5 |
| 0 | 4 | 5 | 362 | 344 | 7 | −7 | −5 | 6 | 159 | 160 | 8 | 20 | −2 | 6 | 364 | 359 | 10 | −24 | 2 | 6 | 0 | 23 | 1 | 3 | 5 | 6 | 248 | 258 | 6 |
| 2 | 4 | 5 | 69 | 74 | 4 | −5 | −5 | 6 | 168 | 152 | 7 | 22 | −2 | 6 | 45 | 45 | 13 | −22 | 2 | 6 | 102 | 77 | 24 | 5 | 5 | 6 | 319 | 356 | 10 |
| 4 | 4 | 5 | 424 | 416 | 7 | −3 | −5 | 6 | 356 | 355 | 9 | 24 | −2 | 6 | 86 | 79 | 9 | −20 | 2 | 6 | 90 | 76 | 27 | 7 | 5 | 6 | 171 | 183 | 6 |
| 6 | 4 | 5 | 375 | 377 | 7 | −1 | −5 | 6 | 375 | 369 | 9 | 26 | −2 | 6 | 187 | 179 | 10 | −18 | 2 | 6 | 411 | 371 | 20 | 9 | 5 | 6 | 215 | 222 | 5 |
| 8 | 4 | 5 | 433 | 443 | 10 | 1 | −5 | 6 | 151 | 147 | 5 | −29 | −1 | 6 | 158 | 179 | 8 | −16 | 2 | 6 | 192 | 185 | 9 | 11 | 5 | 6 | 63 | 64 | 6 |
| 10 | 4 | 5 | 295 | 293 | 6 | 3 | −5 | 6 | 251 | 258 | 7 | −27 | −1 | 6 | 232 | 216 | 9 | −14 | 2 | 6 | 399 | 391 | 15 | 13 | 5 | 6 | 86 | 106 | 9 |
| 12 | 4 | 5 | 117 | 141 | 7 | 5 | −5 | 6 | 351 | 357 | 11 | −25 | −1 | 6 | 66 | 57 | 10 | −12 | 2 | 6 | 87 | 74 | 4 | 15 | 5 | 6 | 50 | 49 | 14 |
| 14 | 4 | 5 | 142 | 146 | 6 | 7 | −5 | 6 | 174 | 183 | 7 | −23 | −1 | 6 | 62 | 55 | 11 | −10 | 2 | 6 | 1105 | 1043 | 29 | 17 | 5 | 6 | 137 | 158 | 12 |
| 16 | 4 | 5 | 201 | 263 | 9 | 9 | −5 | 6 | 216 | 223 | 8 | −21 | −1 | 6 | 249 | 220 | 10 | −8 | 2 | 6 | 621 | 571 | 14 | −18 | 6 | 6 | 180 | 201 | 8 |
| 18 | 4 | 5 | 177 | 192 | 8 | 11 | −5 | 6 | 59 | 63 | 9 | −19 | −1 | 6 | 92 | 81 | 7 | −6 | 2 | 6 | 1033 | 950 | 22 | −16 | 6 | 6 | 116 | 124 | 7 |
| 20 | 4 | 5 | 214 | 191 | 12 | 13 | −5 | 6 | 104 | 107 | 7 | −17 | −1 | 6 | 158 | 142 | 8 | −4 | 2 | 6 | 949 | 920 | 30 | −14 | 6 | 6 | 73 | 85 | 9 |
| 22 | 4 | 5 | 137 | 134 | 6 | 15 | −5 | 6 | 36 | 48 | 15 | −15 | −1 | 6 | 65 | 82 | 3 | −2 | 2 | 6 | 75 | 94 | 5 | −12 | 6 | 6 | 77 | 86 | 9 |
| −23 | 5 | 5 | 195 | 194 | 13 | 17 | −5 | 6 | 155 | 158 | 6 | −13 | −1 | 6 | 417 | 376 | 14 | 0 | 2 | 6 | 430 | 413 | 15 | −10 | 6 | 6 | 130 | 127 | 4 |
| −21 | 5 | 5 | 191 | 169 | 11 | 19 | −5 | 6 | 13 | 42 | 13 | −11 | −1 | 6 | 172 | 193 | 5 | 2 | 2 | 6 | 318 | 297 | 10 | −8 | 6 | 6 | 95 | 98 | 5 |
| −19 | 5 | 5 | 150 | 136 | 9 | −26 | −4 | 6 | 32 | 48 | 32 | −9 | −1 | 6 | 622 | 599 | 16 | 4 | 2 | 6 | 230 | 220 | 8 | −6 | 6 | 6 | 255 | 243 | 6 |
| −17 | 5 | 5 | 277 | 245 | 13 | −24 | −4 | 6 | 102 | 102 | 11 | −7 | −1 | 6 | 188 | 168 | 4 | 6 | 2 | 6 | 130 | 152 | 4 | −4 | 6 | 6 | 145 | 132 | 6 |
| −15 | 5 | 5 | 54 | 45 | 12 | −22 | −4 | 6 | 67 | 48 | 15 | −5 | −1 | 6 | 760 | 807 | 25 | 8 | 2 | 5 | 266 | 286 | 5 | −2 | 6 | 6 | 95 | 76 | 6 |
| −11 | 5 | 5 | 374 | 314 | 9 | −20 | −4 | 6 | 384 | 368 | 12 | −3 | −1 | 6 | 374 | 426 | 12 | 10 | 2 | 6 | 142 | 125 | 3 | 0 | 6 | 6 | 125 | 122 | 4 |
| −9 | 5 | 5 | 455 | 414 | 9 | −18 | −4 | 6 | 100 | 115 | 6 | −1 | −1 | 6 | 756 | 848 | 23 | 12 | 2 | 6 | 131 | 118 | 4 | 2 | 6 | 6 | 65 | 56 | 6 |
| −7 | 5 | 5 | 172 | 151 | 4 | −16 | −4 | 6 | 172 | 165 | 7 | 1 | −1 | 6 | 498 | 504 | 15 | 14 | 2 | 6 | 118 | 111 | 5 | 4 | 6 | 6 | 488 | 457 | 20 |
| −5 | 5 | 5 | 199 | 185 | 4 | −14 | −4 | 6 | 141 | 127 | 7 | 3 | −1 | 6 | 486 | 548 | 13 | 16 | 2 | 6 | 472 | 497 | 9 | 6 | 6 | 6 | 224 | 228 | 7 |
| −3 | 5 | 5 | 121 | 116 | 4 | −12 | −4 | 6 | 182 | 168 | 5 | 5 | −1 | 6 | 839 | 904 | 28 | 18 | 2 | 6 | 159 | 160 | 10 | 8 | 6 | 6 | 87 | 78 | 5 |
| −1 | 5 | 5 | 257 | 247 | 5 | −10 | −4 | 6 | 307 | 279 | 8 | 7 | −1 | 6 | 142 | 138 | 7 | 20 | 2 | 6 | 344 | 358 | 13 | 10 | 6 | 6 | 89 | 87 | 4 |
| 1 | 5 | 5 | 252 | 250 | 5 | −8 | −4 | 6 | 146 | 138 | 6 | 9 | −1 | 6 | 515 | 578 | 12 | 22 | 2 | 6 | 42 | 44 | 10 | 12 | 6 | 6 | 120 | 126 | 6 |
| 3 | 5 | 5 | 613 | 572 | 14 | −6 | −4 | 6 | 411 | 387 | 11 | 13 | −1 | 6 | 72 | 73 | 4 | 24 | 2 | 6 | 98 | 80 | 6 | −9 | 7 | 6 | 119 | 96 | 9 |
| 5 | 5 | 5 | 347 | 341 | 8 | −4 | −4 | 6 | 47 | 70 | 7 | 15 | −1 | 6 | 379 | 429 | 9 | −25 | 3 | 6 | 121 | 111 | 9 | −7 | 7 | 6 | 110 | 90 | 6 |
| 7 | 5 | 5 | 105 | 100 | 4 | −2 | −4 | 6 | 199 | 200 | 5 | 17 | −1 | 6 | 483 | 530 | 20 | −23 | 3 | 6 | 81 | 69 | 12 | −5 | 7 | 6 | 261 | 249 | 13 |
| 9 | 5 | 5 | 105 | 112 | 4 | 0 | −4 | 6 | 223 | 229 | 5 | 19 | −1 | 6 | 332 | 333 | 10 | −21 | 3 | 6 | 239 | 232 | 11 | −3 | 7 | 6 | 197 | 207 | 6 |
| 11 | 5 | 5 | 97 | 89 | 5 | 2 | −4 | 6 | 212 | 218 | 4 | 21 | −1 | 6 | 186 | 207 | 12 | −19 | 3 | 6 | 144 | 136 | 6 | −1 | 7 | 6 | 174 | 192 | 6 |
| 13 | 5 | 5 | 114 | 121 | 6 | 4 | −4 | 6 | 482 | 494 | 11 | 23 | −1 | 6 | 211 | 209 | 12 | −17 | 3 | 6 | 325 | 335 | 9 | 1 | 7 | 6 | 86 | 101 | 6 |
| 15 | 5 | 5 | 218 | 245 | 14 | 6 | −4 | 6 | 458 | 465 | 10 | 25 | −1 | 6 | 170 | 162 | 10 | −15 | 3 | 6 | 362 | 347 | 13 | 3 | 7 | 6 | 77 | 80 | 6 |
| 17 | 5 | 5 | 104 | 132 | 8 | 8 | −4 | 6 | 294 | 298 | 8 | 27 | −1 | 6 | 149 | 141 | 9 | −13 | 3 | 6 | 598 | 584 | 21 | 5 | 7 | 6 | 93 | 96 | 8 |
| 19 | 5 | 5 | 74 | 80 | 8 | 10 | −4 | 6 | 73 | 76 | 8 | −28 | 0 | 6 | 109 | 97 | 25 | −11 | 3 | 6 | 143 | 126 | 4 | −7 | −7 | 7 | 0 | 3 | 1 |
| −18 | 6 | 5 | 99 | 117 | 7 | 12 | −4 | 6 | 338 | 374 | 17 | −26 | 0 | 6 | 57 | 16 | 56 | −9 | 3 | 6 | 339 | 325 | 5 | −5 | −7 | 7 | 125 | 149 | 6 |
| −16 | 6 | 5 | 138 | 147 | 7 | 14 | −4 | 6 | 359 | 405 | 12 | −24 | 0 | 6 | 50 | 41 | 50 | −7 | 3 | 6 | 342 | 321 | 7 | −16 | −6 | 7 | 144 | 157 | 6 |
| −14 | 6 | 5 | 198 | 188 | 9 | 16 | −4 | 6 | 50 | 54 | 10 | −22 | 0 | 6 | 0 | 24 | 1 | −5 | 3 | 6 | 743 | 736 | 15 | −14 | −6 | 7 | 149 | 139 | 7 |
| −12 | 6 | 5 | 80 | 74 | 8 | 18 | −4 | 6 | 174 | 179 | 6 | −20 | 0 | 6 | 337 | 299 | 19 | −3 | 3 | 6 | 125 | 127 | 3 | −12 | −6 | 7 | 11 | 12 | 10 |
| −10 | −6 | 7 | 26 | 24 | 25 | −18 | −2 | 7 | 392 | 379 | 11 | −13 | 1 | 7 | 304 | 301 | 15 | 6 | 4 | 7 | 413 | 460 | 7 | −14 | −4 | 8 | 208 | 206 | 7 |
| −8 | −6 | 7 | 117 | 106 | 7 | −16 | −2 | 7 | 526 | 490 | 12 | −11 | 1 | 7 | 562 | 584 | 15 | 8 | 4 | 7 | 312 | 338 | 7 | −12 | −4 | 8 | 168 | 175 | 6 |
| −6 | −6 | 7 | 85 | 94 | 13 | −14 | −2 | 7 | 388 | 416 | 10 | −9 | 1 | 7 | 289 | 292 | 6 | 10 | 4 | 7 | 123 | 142 | 5 | −10 | −4 | 8 | 363 | 353 | 8 |
| −4 | −6 | 7 | 138 | 151 | 8 | −12 | −2 | 7 | 262 | 251 | 6 | −7 | 1 | 7 | 428 | 468 | 9 | 12 | 4 | 7 | 358 | 399 | 10 | −8 | −4 | 8 | 455 | 442 | 12 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −2 | −6 | 7 | 104 | 103 | 7 | −10 | −2 | 7 | 492 | 494 | 13 | −5 | 1 | 7 | 664 | 733 | 14 | 14 | 4 | 7 | 82 | 91 | 5 | −6 | −4 | 8 | 99 | 117 | 6 |
| 0 | −6 | 7 | 121 | 133 | 6 | −8 | −2 | 7 | 259 | 253 | 9 | −3 | 1 | 7 | 407 | 470 | 13 | 16 | 4 | 7 | 154 | 168 | 8 | −4 | −4 | 8 | 394 | 397 | 10 |
| 2 | −6 | 7 | 194 | 212 | 6 | −6 | −2 | 7 | 373 | 355 | 12 | −1 | 1 | 7 | 329 | 374 | 12 | 18 | 4 | 7 | 50 | 81 | 19 | −2 | −4 | 8 | 352 | 362 | 10 |
| 4 | −6 | 7 | 98 | 110 | 8 | −4 | −2 | 7 | 793 | 820 | 26 | 1 | 1 | 7 | 109 | 104 | 6 | 20 | 4 | 7 | 81 | 86 | 6 | 0 | −4 | 8 | 385 | 419 | 7 |
| 6 | −6 | 7 | 123 | 121 | 11 | −2 | −2 | 7 | 520 | 505 | 16 | 3 | 1 | 7 | 400 | 358 | 12 | −23 | 5 | 7 | 159 | 173 | 13 | 2 | −4 | 8 | 312 | 335 | 7 |
| 8 | −6 | 7 | 56 | 72 | 10 | 0 | −2 | 7 | 309 | 306 | 10 | 5 | 1 | 7 | 197 | 169 | 7 | −21 | 5 | 7 | 56 | 48 | 8 | 4 | −4 | 8 | 145 | 139 | 5 |
| 10 | −6 | 7 | 115 | 131 | 7 | 2 | −2 | 7 | 311 | 325 | 10 | 7 | 1 | 7 | 334 | 356 | 8 | −19 | 5 | 7 | 147 | 146 | 8 | 6 | −4 | 8 | 139 | 148 | 6 |
| 12 | −6 | 7 | 180 | 195 | 7 | 4 | −2 | 7 | 78 | 72 | 5 | 9 | 1 | 7 | 353 | 364 | 6 | −17 | 5 | 7 | 95 | 83 | 7 | 8 | −4 | 8 | 201 | 242 | 9 |
| −21 | −5 | 7 | 40 | 48 | 19 | 6 | −2 | 7 | 296 | 324 | 6 | 11 | 1 | 7 | 235 | 264 | 5 | −15 | 5 | 7 | 226 | 214 | 10 | 10 | −4 | 8 | 157 | 202 | 8 |
| −19 | −5 | 7 | 158 | 146 | 11 | 8 | −2 | 7 | 305 | 347 | 7 | 13 | 1 | 7 | 322 | 322 | 7 | −13 | 5 | 7 | 125 | 122 | 8 | 12 | −4 | 8 | 93 | 129 | 7 |
| −17 | −5 | 7 | 74 | 81 | 10 | 10 | −2 | 7 | 101 | 120 | 4 | 15 | 1 | 7 | 377 | 402 | 9 | −11 | 5 | 7 | 37 | 44 | 11 | 14 | −4 | 8 | 149 | 159 | 7 |
| −15 | −5 | 7 | 221 | 214 | 9 | 12 | −2 | 7 | 132 | 149 | 5 | 17 | 1 | 7 | 177 | 194 | 5 | −9 | 5 | 7 | 54 | 47 | 6 | 16 | −4 | 8 | 87 | 91 | 7 |
| −13 | −5 | 7 | 135 | 123 | 7 | 14 | −2 | 7 | 315 | 317 | 9 | 19 | 1 | 7 | 120 | 120 | 7 | −7 | 5 | 7 | 170 | 144 | 4 | 18 | −4 | 8 | 90 | 88 | 5 |
| −11 | −5 | 7 | 43 | 45 | 14 | 16 | −2 | 7 | 355 | 381 | 10 | 21 | 1 | 7 | 59 | 45 | 8 | −5 | 5 | 7 | 350 | 351 | 8 | −27 | −3 | 8 | 94 | 94 | 10 |
| −9 | −5 | 7 | 65 | 46 | 9 | 18 | −2 | 7 | 67 | 68 | 5 | 23 | 1 | 7 | 150 | 139 | 6 | −3 | 5 | 7 | 198 | 187 | 5 | −25 | −3 | 8 | 89 | 101 | 12 |
| −7 | −5 | 7 | 173 | 143 | 8 | 20 | −2 | 7 | 281 | 289 | 7 | 25 | 1 | 7 | 97 | 88 | 5 | −1 | 5 | 7 | 153 | 151 | 5 | −23 | −3 | 8 | 86 | 99 | 13 |
| −5 | −5 | 7 | 333 | 350 | 12 | 22 | −2 | 7 | 66 | 55 | 10 | −28 | 2 | 7 | 81 | 129 | 28 | 1 | 5 | 7 | 222 | 254 | 6 | −21 | −3 | 8 | 57 | 72 | 15 |
| −3 | −5 | 7 | 172 | 186 | 7 | 24 | −2 | 7 | 130 | 127 | 9 | −26 | 2 | 7 | 359 | 351 | 18 | 3 | 5 | 7 | 209 | 221 | 7 | −19 | −3 | 8 | 440 | 490 | 26 |
| −1 | −5 | 7 | 136 | 151 | 6 | −29 | −1 | 7 | 190 | 203 | 8 | −24 | 2 | 7 | 71 | 89 | 37 | 5 | 5 | 7 | 58 | 74 | 7 | −17 | −3 | 8 | 449 | 467 | 12 |
| 1 | −5 | 7 | 246 | 253 | 6 | −27 | −1 | 7 | 462 | 448 | 16 | −22 | 2 | 7 | 272 | 276 | 18 | 7 | 5 | 7 | 160 | 170 | 5 | −15 | −3 | 8 | 74 | 85 | 5 |
| 3 | −5 | 7 | 209 | 222 | 7 | −25 | −1 | 7 | 83 | 90 | 9 | −20 | 2 | 7 | 356 | 336 | 15 | 9 | 5 | 7 | 179 | 194 | 5 | −13 | −3 | 8 | 200 | 212 | 6 |
| 5 | −5 | 7 | 47 | 73 | 12 | −23 | −1 | 7 | 227 | 208 | 9 | −18 | 2 | 7 | 396 | 381 | 14 | 11 | 5 | 7 | 113 | 124 | 5 | −11 | −3 | 8 | 110 | 119 | 5 |
| 7 | −5 | 7 | 165 | 170 | 11 | −21 | −1 | 7 | 72 | 47 | 9 | −16 | 2 | 7 | 515 | 491 | 18 | 13 | 5 | 7 | 108 | 119 | 8 | −9 | −3 | 8 | 340 | 370 | 10 |
| 9 | −5 | 7 | 186 | 194 | 7 | −19 | −1 | 7 | 206 | 196 | 9 | −14 | 2 | 7 | 389 | 416 | 14 | 15 | 5 | 7 | 132 | 148 | 8 | −7 | −3 | 8 | 60 | 62 | 6 |
| 11 | −5 | 7 | 101 | 123 | 7 | −17 | −1 | 7 | 211 | 190 | 9 | −12 | 2 | 7 | 263 | 260 | 5 | 17 | 5 | 7 | 105 | 115 | 10 | −5 | −3 | 8 | 183 | 165 | 6 |
| 13 | −5 | 7 | 120 | 119 | 6 | −15 | −1 | 7 | 542 | 528 | 10 | −10 | 2 | 7 | 499 | 496 | 11 | −18 | 6 | 7 | 84 | 99 | 8 | −3 | −3 | 8 | 334 | 326 | 8 |
| 15 | −5 | 7 | 141 | 148 | 6 | −13 | −1 | 7 | 294 | 298 | 6 | −8 | 2 | 7 | 255 | 252 | 6 | −16 | 6 | 7 | 142 | 157 | 7 | −1 | −3 | 8 | 345 | 355 | 7 |
| 17 | −5 | 7 | 105 | 114 | 5 | −11 | −1 | 7 | 583 | 582 | 19 | −6 | 2 | 7 | 378 | 356 | 10 | −14 | 6 | 7 | 149 | 139 | 8 | 1 | −3 | 8 | 72 | 70 | 4 |
| −26 | −4 | 7 | 121 | 140 | 9 | −9 | −1 | 7 | 288 | 293 | 10 | −4 | 2 | 7 | 836 | 821 | 20 | −12 | 6 | 7 | 24 | 12 | 24 | 3 | −3 | 8 | 134 | 114 | 4 |
| −24 | −4 | 7 | 78 | 86 | 12 | −7 | −1 | 7 | 412 | 468 | 13 | −2 | 2 | 7 | 545 | 506 | 23 | −10 | 6 | 7 | 41 | 24 | 8 | 5 | −3 | 8 | 121 | 124 | 5 |
| −22 | −4 | 7 | 0 | 7 | 1 | −5 | −1 | 7 | 611 | 734 | 31 | 0 | 2 | 7 | 300 | 304 | 10 | −8 | 6 | 7 | 106 | 106 | 5 | 7 | −3 | 8 | 177 | 192 | 6 |
| −20 | −4 | 7 | 300 | 281 | 9 | −3 | −1 | 7 | 397 | 479 | 18 | 2 | 2 | 7 | 306 | 327 | 10 | −6 | 6 | 7 | 98 | 93 | 4 | 9 | −3 | 8 | 229 | 276 | 7 |
| −18 | −4 | 7 | 246 | 230 | 10 | −1 | −1 | 7 | 348 | 374 | 10 | 4 | 2 | 7 | 70 | 74 | 6 | −4 | 6 | 7 | 155 | 152 | 5 | 11 | −3 | 8 | 49 | 56 | 11 |
| −16 | −4 | 7 | 430 | 445 | 15 | 1 | −1 | 7 | 109 | 105 | 5 | 6 | 2 | 7 | 304 | 325 | 7 | −2 | 6 | 7 | 104 | 104 | 6 | 13 | −3 | 8 | 263 | 284 | 7 |
| −14 | −4 | 7 | 281 | 287 | 10 | 3 | −1 | 7 | 382 | 358 | 12 | 8 | 2 | 7 | 319 | 346 | 6 | 0 | 6 | 7 | 126 | 133 | 5 | 15 | −3 | 8 | 135 | 128 | 5 |
| −12 | −4 | 7 | 79 | 79 | 5 | 5 | −1 | 7 | 180 | 168 | 7 | 10 | 2 | 7 | 114 | 120 | 4 | 2 | 6 | 7 | 212 | 213 | 8 | 17 | −3 | 8 | 193 | 203 | 5 |
| −10 | −4 | 7 | 197 | 179 | 6 | 7 | −1 | 7 | 330 | 355 | 8 | 12 | 2 | 7 | 140 | 148 | 4 | 4 | 6 | 7 | 100 | 111 | 7 | 19 | −3 | 8 | 186 | 193 | 6 |
| −8 | −4 | 7 | 375 | 373 | 10 | 9 | −1 | 7 | 358 | 364 | 9 | 14 | 2 | 7 | 327 | 318 | 8 | 6 | 6 | 7 | 123 | 120 | 5 | 21 | −3 | 8 | 88 | 87 | 6 |
| −6 | −4 | 7 | 373 | 347 | 10 | 11 | −1 | 7 | 236 | 263 | 6 | 16 | 2 | 7 | 369 | 379 | 13 | 8 | 6 | 7 | 59 | 72 | 6 | −28 | −2 | 8 | 182 | 186 | 11 |
| −4 | −4 | 7 | 297 | 292 | 8 | 13 | −1 | 7 | 306 | 322 | 9 | 18 | 2 | 7 | 59 | 69 | 8 | 10 | 6 | 7 | 140 | 131 | 5 | −26 | −2 | 8 | 174 | 184 | 11 |
| −2 | −4 | 7 | 172 | 159 | 5 | 15 | −1 | 7 | 362 | 401 | 8 | 20 | 2 | 7 | 274 | 289 | 10 | 12 | 6 | 7 | 169 | 197 | 12 | −24 | −2 | 8 | 109 | 129 | 10 |
| 0 | −4 | 7 | 106 | 89 | 4 | 17 | −1 | 7 | 181 | 192 | 5 | 22 | 2 | 7 | 66 | 55 | 7 | −5 | 7 | 7 | 120 | 148 | 10 | −22 | −2 | 8 | 120 | 135 | 9 |
| 2 | −4 | 7 | 250 | 274 | 5 | 19 | −1 | 7 | 132 | 118 | 5 | 24 | 2 | 7 | 137 | 126 | 6 | −3 | 7 | 7 | 125 | 147 | 7 | −20 | −2 | 8 | 256 | 233 | 10 |
| 4 | −4 | 7 | 113 | 111 | 5 | 21 | −1 | 7 | 67 | 46 | 7 | −25 | 3 | 7 | 67 | 61 | 32 | −1 | 7 | 7 | 71 | 73 | 6 | −18 | −2 | 8 | 278 | 266 | 7 |
| 6 | −4 | 7 | 430 | 460 | 11 | 23 | −1 | 7 | 150 | 139 | 9 | −23 | 3 | 7 | 224 | 246 | 16 | 1 | 7 | 7 | 126 | 138 | 6 | −16 | −2 | 8 | 496 | 503 | 13 |
| 8 | −4 | 7 | 308 | 337 | 9 | 25 | −1 | 7 | 87 | 89 | 8 | −21 | 3 | 7 | 108 | 94 | 5 | −16 | −6 | 8 | 35 | 49 | 16 | −14 | −2 | 8 | 146 | 146 | 4 |
| 10 | −4 | 7 | 102 | 143 | 7 | −30 | 0 | 7 | 0 | 23 | 1 | −19 | 3 | 7 | 245 | 242 | 8 | −14 | −6 | 8 | 159 | 153 | 6 | −12 | −2 | 8 | 674 | 701 | 18 |
| 12 | −4 | 7 | 328 | 399 | 20 | −28 | 0 | 7 | 381 | 349 | 21 | −17 | 3 | 7 | 395 | 376 | 11 | −12 | −6 | 8 | 87 | 92 | 7 | −10 | −2 | 8 | 203 | 224 | 5 |
| 14 | −4 | 7 | 69 | 91 | 8 | −26 | 0 | 7 | 257 | 233 | 18 | −15 | 3 | 7 | 437 | 444 | 15 | −10 | −6 | 8 | 183 | 188 | 10 | −8 | −2 | 8 | 137 | 128 | 4 |

TABLE 8-continued

| Observed and calculated structure factors for SAG-2 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| 16 | −4 | 7 | 161 | 168 | 7 | −24 | 0 | 7 | 0 | 26 | 1 | −13 | 3 | 7 | 235 | 225 | 6 | −8 | −6 | 8 | 96 | 103 | 7 | −6 | −2 | 8 | 246 | 263 | 8 |
| 18 | −4 | 7 | 64 | 81 | 6 | −22 | 0 | 7 | 400 | 420 | 21 | −11 | 3 | 7 | 285 | 278 | 6 | −6 | −6 | 8 | 37 | 39 | 20 | −4 | −2 | 8 | 138 | 145 | 6 |
| 20 | −4 | 7 | 85 | 86 | 5 | −20 | 0 | 7 | 0 | 13 | 1 | −9 | 3 | 7 | 117 | 115 | 3 | −4 | −6 | 8 | 212 | 228 | 8 | −2 | −2 | 8 | 190 | 187 | 7 |
| −27 | −3 | 7 | 82 | 102 | 11 | −18 | 0 | 7 | 206 | 165 | 15 | −7 | 3 | 7 | 371 | 375 | 6 | −2 | −6 | 8 | 192 | 196 | 8 | 0 | −2 | 8 | 321 | 339 | 8 |
| −25 | −3 | 7 | 58 | 63 | 16 | −16 | 0 | 7 | 186 | 193 | 14 | −5 | 3 | 7 | 108 | 89 | 3 | 0 | −6 | 8 | 108 | 101 | 5 | 2 | −2 | 8 | 73 | 66 | 4 |
| −23 | −3 | 7 | 223 | 247 | 13 | −14 | 0 | 7 | 309 | 370 | 8 | −3 | 3 | 7 | 194 | 190 | 4 | 2 | −6 | 8 | 178 | 200 | 7 | 4 | −2 | 8 | 113 | 136 | 3 |
| −21 | −3 | 7 | 83 | 93 | 13 | −12 | 0 | 7 | 26 | 19 | 7 | −1 | 3 | 7 | 427 | 442 | 7 | 4 | −6 | 8 | 191 | 230 | 8 | 6 | −2 | 8 | 144 | 153 | 4 |
| −19 | −3 | 7 | 223 | 243 | 15 | −10 | 0 | 7 | 579 | 611 | 15 | 1 | 3 | 7 | 139 | 136 | 3 | 6 | −6 | 8 | 90 | 126 | 8 | 8 | −2 | 8 | 205 | 238 | 5 |
| −17 | −3 | 7 | 392 | 377 | 14 | −8 | 0 | 7 | 18 | 34 | 17 | 3 | 3 | 7 | 170 | 176 | 3 | 8 | −6 | 8 | 91 | 94 | 7 | 10 | −2 | 8 | 74 | 80 | 5 |
| −15 | −3 | 7 | 440 | 443 | 10 | −6 | 0 | 7 | 135 | 167 | 4 | 5 | 3 | 7 | 176 | 195 | 4 | 10 | −6 | 8 | 102 | 106 | 6 | 12 | −2 | 8 | 25 | 29 | 18 |
| −13 | −3 | 7 | 234 | 226 | 7 | −4 | 0 | 7 | 954 | 961 | 25 | 7 | 3 | 7 | 186 | 215 | 4 | −21 | −5 | 8 | 0 | 51 | 1 | 14 | −2 | 8 | 574 | 579 | 18 |
| −11 | −3 | 7 | 296 | 278 | 8 | −2 | 0 | 7 | 367 | 403 | 9 | 9 | 3 | 7 | 108 | 108 | 4 | −19 | −5 | 8 | 106 | 95 | 10 | 16 | −2 | 8 | 153 | 146 | 5 |
| −9 | −3 | 7 | 125 | 116 | 4 | 0 | 0 | 7 | 366 | 338 | 9 | 11 | 3 | 7 | 173 | 184 | 5 | −17 | −5 | 8 | 0 | 42 | 1 | 18 | −2 | 8 | 201 | 202 | 5 |
| −7 | −3 | 7 | 373 | 375 | 12 | 2 | 0 | 7 | 0 | 9 | 1 | 13 | 3 | 7 | 27 | 36 | 26 | −15 | −5 | 8 | 84 | 77 | 8 | 20 | −2 | 8 | 57 | 63 | 6 |
| −5 | −3 | 7 | 98 | 88 | 4 | 4 | 0 | 7 | 45 | 49 | 5 | 15 | 3 | 7 | 120 | 139 | 6 | −13 | −5 | 8 | 111 | 113 | 7 | 22 | −2 | 8 | 108 | 102 | 6 |
| −3 | −3 | 7 | 194 | 189 | 5 | 6 | 0 | 7 | 207 | 237 | 6 | 17 | 3 | 7 | 189 | 218 | 9 | −11 | −5 | 8 | 108 | 113 | 7 | 24 | −2 | 8 | 154 | 134 | 10 |
| −1 | −3 | 7 | 408 | 443 | 8 | 8 | 0 | 7 | 628 | 624 | 11 | 19 | 3 | 7 | 60 | 51 | 8 | −9 | −5 | 8 | 79 | 81 | 9 | −29 | −1 | 8 | 195 | 204 | 8 |
| 1 | −3 | 7 | 136 | 137 | 3 | 10 | 0 | 7 | 100 | 112 | 3 | 21 | 3 | 7 | 226 | 223 | 8 | −7 | −5 | 8 | 181 | 176 | 8 | −27 | −1 | 8 | 62 | 54 | 10 |
| 3 | −3 | 7 | 174 | 177 | 4 | 12 | 0 | 7 | 188 | 170 | 4 | 23 | 3 | 7 | 176 | 182 | 6 | −5 | −5 | 8 | 185 | 190 | 8 | −25 | −1 | 8 | 106 | 118 | 9 |
| 5 | −3 | 7 | 184 | 195 | 5 | 14 | 0 | 7 | 248 | 229 | 5 | −24 | 4 | 7 | 121 | 87 | 14 | −3 | −5 | 8 | 294 | 318 | 10 | −23 | −1 | 8 | 322 | 326 | 11 |
| 7 | −3 | 7 | 187 | 215 | 6 | 16 | 0 | 7 | 66 | 77 | 5 | −22 | 4 | 7 | 24 | 7 | 23 | −1 | −5 | 8 | 208 | 231 | 6 | −21 | −1 | 8 | 239 | 250 | 10 |
| 9 | −3 | 7 | 101 | 109 | 6 | 18 | 0 | 7 | 262 | 272 | 8 | −20 | 4 | 7 | 315 | 282 | 14 | 3 | −5 | 8 | 280 | 268 | 8 | −19 | −1 | 8 | 110 | 101 | 8 |
| 11 | −3 | 7 | 156 | 186 | 5 | 20 | 0 | 7 | 91 | 131 | 8 | −18 | 4 | 7 | 253 | 228 | 12 | 5 | −5 | 8 | 336 | 346 | 16 | −17 | −1 | 8 | 432 | 437 | 10 |
| 13 | −3 | 7 | 29 | 35 | 17 | 22 | 0 | 7 | 69 | 50 | 7 | −16 | 4 | 7 | 485 | 446 | 20 | 7 | −5 | 8 | 128 | 149 | 8 | −15 | −1 | 8 | 381 | 378 | 8 |
| 15 | −3 | 7 | 126 | 140 | 5 | 24 | 0 | 7 | 72 | 75 | 6 | −14 | 4 | 7 | 307 | 287 | 14 | 9 | −5 | 8 | 68 | 82 | 9 | −13 | −1 | 8 | 539 | 548 | 10 |
| 17 | −3 | 7 | 202 | 218 | 5 | 26 | 0 | 7 | 413 | 374 | 20 | −12 | 4 | 7 | 67 | 79 | 4 | 11 | −5 | 8 | 243 | 257 | 9 | −11 | −1 | 8 | 247 | 226 | 5 |
| 19 | −3 | 7 | 54 | 53 | 6 | −29 | 1 | 7 | 191 | 203 | 15 | −10 | 4 | 7 | 202 | 180 | 6 | 13 | −5 | 8 | 179 | 191 | 7 | −9 | −1 | 8 | 264 | 246 | 11 |
| 21 | −3 | 7 | 229 | 225 | 8 | −27 | 1 | 7 | 480 | 449 | 21 | −8 | 4 | 7 | 371 | 374 | 6 | 15 | −5 | 8 | 92 | 94 | 6 | −7 | −1 | 8 | 316 | 352 | 15 |
| 23 | −3 | 7 | 163 | 182 | 10 | −25 | 1 | 7 | 68 | 89 | 35 | −6 | 4 | 7 | 367 | 346 | 7 | −26 | −4 | 8 | 212 | 240 | 12 | −5 | −1 | 8 | 672 | 716 | 31 |
| −28 | −2 | 7 | 103 | 130 | 9 | −23 | 1 | 7 | 200 | 209 | 18 | −4 | 4 | 7 | 301 | 293 | 5 | −24 | −4 | 8 | 55 | 70 | 16 | −3 | −1 | 8 | 576 | 655 | 26 |
| −26 | −2 | 7 | 327 | 351 | 18 | −21 | 1 | 7 | 84 | 48 | 27 | −2 | 4 | 7 | 180 | 159 | 3 | −22 | −4 | 8 | 179 | 189 | 13 | −1 | −1 | 8 | 595 | 634 | 19 |
| −24 | −2 | 7 | 88 | 89 | 10 | −19 | 1 | 7 | 237 | 196 | 15 | 0 | 4 | 7 | 111 | 88 | 3 | −20 | −4 | 8 | 110 | 107 | 6 | 1 | −1 | 8 | 388 | 360 | 11 |
| −22 | −2 | 7 | 267 | 276 | 11 | −17 | 1 | 7 | 203 | 190 | 15 | 2 | 4 | 7 | 255 | 274 | 5 | −18 | −4 | 8 | 69 | 81 | 7 | 3 | −1 | 8 | 218 | 247 | 7 |
| −20 | −2 | 7 | 344 | 337 | 18 | −15 | 1 | 7 | 548 | 529 | 25 | 4 | 4 | 7 | 109 | 109 | 3 | −16 | −4 | 8 | 138 | 138 | 6 | 5 | −1 | 8 | 576 | 618 | 17 |
| 7 | −1 | 8 | 441 | 475 | 9 | 14 | 2 | 8 | 555 | 580 | 13 | −12 | −6 | 9 | 0 | 10 | 1 | −4 | −2 | 9 | 61 | 65 | 4 | 7 | 1 | 9 | 125 | 127 | 3 |
| 9 | −1 | 8 | 396 | 436 | 11 | 16 | 2 | 8 | 141 | 148 | 5 | −10 | −6 | 9 | 0 | 32 | 1 | −2 | −2 | 9 | 317 | 347 | 7 | 9 | 1 | 9 | 148 | 159 | 4 |
| 11 | −1 | 8 | 269 | 259 | 7 | 18 | 2 | 8 | 190 | 201 | 8 | −8 | −6 | 9 | 87 | 106 | 8 | 0 | −2 | 9 | 82 | 97 | 3 | 11 | 1 | 9 | 158 | 148 | 5 |
| 13 | −1 | 8 | 222 | 217 | 5 | 20 | 2 | 8 | 54 | 63 | 8 | −6 | −6 | 9 | 371 | 408 | 12 | 2 | −2 | 9 | 133 | 130 | 3 | 13 | 1 | 9 | 271 | 276 | 5 |
| 15 | −1 | 8 | 75 | 54 | 4 | 22 | 2 | 8 | 105 | 102 | 6 | −4 | −6 | 9 | 72 | 73 | 8 | 4 | −2 | 9 | 315 | 334 | 6 | 15 | 1 | 9 | 400 | 410 | 10 |
| 17 | −1 | 8 | 108 | 108 | 4 | 24 | 2 | 8 | 165 | 136 | 6 | −2 | −6 | 9 | 103 | 104 | 7 | 6 | −2 | 9 | 491 | 531 | 13 | 17 | 1 | 9 | 77 | 92 | 5 |
| 19 | −1 | 8 | 152 | 158 | 5 | −25 | 3 | 8 | 112 | 101 | 11 | 0 | −6 | 9 | 127 | 112 | 6 | 8 | −2 | 9 | 314 | 324 | 10 | 19 | 1 | 9 | 48 | 36 | 10 |
| 21 | −1 | 8 | 201 | 167 | 8 | −23 | 3 | 8 | 91 | 98 | 14 | 2 | −6 | 9 | 67 | 94 | 9 | 10 | −2 | 9 | 95 | 97 | 5 | 21 | 1 | 9 | 23 | 6 | 23 |
| 23 | −1 | 8 | 237 | 210 | 9 | −21 | 3 | 8 | 87 | 71 | 6 | 4 | −6 | 9 | 105 | 122 | 7 | 12 | −2 | 9 | 254 | 273 | 7 | 23 | 1 | 9 | 22 | 3 | 21 |
| 25 | −1 | 8 | 146 | 132 | 9 | −19 | 3 | 8 | 483 | 491 | 15 | 6 | −6 | 9 | 115 | 122 | 7 | 14 | −2 | 9 | 186 | 189 | 6 | −28 | 2 | 9 | 97 | 99 | 19 |
| −30 | 0 | 8 | 239 | 215 | 16 | −17 | 3 | 8 | 472 | 467 | 15 | 8 | −6 | 9 | 137 | 139 | 6 | 16 | −2 | 9 | 291 | 290 | 7 | −26 | 2 | 9 | 96 | 113 | 23 |
| −28 | 0 | 8 | 402 | 375 | 21 | −15 | 3 | 8 | 81 | 86 | 8 | −19 | −5 | 9 | 107 | 89 | 9 | 18 | −2 | 9 | 164 | 159 | 5 | −24 | 2 | 9 | 204 | 193 | 15 |
| −26 | 0 | 8 | 257 | 224 | 18 | −13 | 3 | 8 | 196 | 211 | 6 | −17 | −5 | 9 | 41 | 54 | 15 | 20 | −2 | 9 | 81 | 85 | 4 | −22 | 2 | 9 | 229 | 238 | 9 |
| −24 | 0 | 8 | 33 | 5 | 18 | −11 | 3 | 8 | 100 | 118 | 4 | −15 | −5 | 9 | 84 | 82 | 7 | 22 | −2 | 9 | 128 | 109 | 6 | −20 | 2 | 9 | 308 | 320 | 9 |
| −22 | 0 | 8 | 37 | 41 | 14 | −9 | 3 | 8 | 355 | 370 | 6 | −13 | −5 | 9 | 111 | 116 | 7 | −29 | −1 | 9 | 84 | 94 | 7 | −18 | 2 | 9 | 441 | 426 | 12 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −20 | 0 | 8 | 29 | 19 | 28 | −7 | 3 | 8 | 62 | 63 | 4 | −11 | −5 | 9 | 186 | 199 | 8 | −27 | −1 | 9 | 2 | 22 | 2 | −16 | 2 | 9 | 136 | 146 | 6 |
| −18 | 0 | 8 | 33 | 33 | 16 | −5 | 3 | 8 | 187 | 164 | 3 | −9 | −5 | 9 | 214 | 238 | 14 | −25 | −1 | 9 | 86 | 96 | 9 | −14 | 2 | 9 | 116 | 115 | 6 |
| −16 | 0 | 8 | 198 | 225 | 8 | −3 | 3 | 8 | 337 | 327 | 6 | −7 | −5 | 9 | 271 | 289 | 11 | −23 | −1 | 9 | 178 | 191 | 9 | −12 | 2 | 9 | 59 | 71 | 4 |
| −14 | 0 | 8 | 311 | 351 | 6 | −1 | 3 | 8 | 349 | 356 | 6 | −5 | −5 | 9 | 116 | 140 | 12 | −21 | −1 | 9 | 454 | 462 | 14 | −10 | 2 | 9 | 102 | 99 | 3 |
| −12 | 0 | 8 | 551 | 558 | 11 | 1 | 3 | 8 | 72 | 69 | 4 | −3 | −5 | 9 | 82 | 98 | 8 | −19 | −1 | 9 | 483 | 508 | 26 | −8 | 2 | 9 | 258 | 281 | 4 |
| −10 | 0 | 8 | 959 | 957 | 25 | 3 | 3 | 8 | 133 | 114 | 3 | −1 | −5 | 9 | 330 | 374 | 10 | −17 | −1 | 9 | 437 | 452 | 9 | −6 | 2 | 9 | 198 | 184 | 4 |
| −8 | 0 | 8 | 442 | 438 | 10 | 5 | 3 | 8 | 118 | 124 | 3 | 1 | −5 | 9 | 396 | 456 | 10 | −15 | −1 | 9 | 368 | 390 | 7 | −4 | 2 | 9 | 59 | 64 | 4 |
| −6 | 0 | 8 | 285 | 271 | 8 | 7 | 3 | 8 | 184 | 193 | 4 | 3 | −5 | 9 | 278 | 336 | 11 | −13 | −1 | 9 | 118 | 114 | 3 | −2 | 2 | 9 | 324 | 347 | 6 |
| −4 | 0 | 8 | 155 | 169 | 5 | 9 | 3 | 8 | 240 | 274 | 5 | 5 | −5 | 9 | 51 | 76 | 14 | −11 | −1 | 9 | 193 | 196 | 4 | 0 | 2 | 9 | 79 | 97 | 4 |
| −2 | 0 | 8 | 113 | 313 | 7 | 11 | 3 | 8 | 57 | 57 | 7 | 7 | −5 | 9 | 99 | 113 | 8 | −9 | −1 | 9 | 760 | 827 | 18 | 2 | 2 | 9 | 134 | 129 | 3 |
| 0 | 0 | 8 | 126 | 137 | 6 | 13 | 3 | 8 | 262 | 284 | 9 | 9 | −5 | 9 | 108 | 115 | 7 | −7 | −1 | 9 | 137 | 146 | 5 | 4 | 2 | 9 | 318 | 335 | 6 |
| 2 | 0 | 8 | 229 | 269 | 8 | 15 | 3 | 8 | 135 | 129 | 7 | 11 | −5 | 9 | 164 | 176 | 7 | −5 | −1 | 9 | 122 | 121 | 6 | 6 | 2 | 9 | 492 | 532 | 8 |
| 4 | 0 | 8 | 66 | 74 | 6 | 17 | 3 | 8 | 178 | 203 | 8 | 13 | −5 | 9 | 248 | 275 | 8 | −3 | −1 | 9 | 434 | 500 | 14 | 8 | 2 | 9 | 320 | 324 | 6 |
| 6 | 0 | 8 | 219 | 248 | 5 | 19 | 3 | 8 | 184 | 194 | 11 | 15 | −5 | 9 | 87 | 103 | 6 | −1 | −1 | 9 | 507 | 555 | 15 | 10 | 2 | 9 | 101 | 97 | 6 |
| 8 | 0 | 8 | 337 | 400 | 6 | 21 | 3 | 8 | 97 | 88 | 6 | −24 | −4 | 9 | 126 | 152 | 12 | 1 | −1 | 9 | 263 | 241 | 8 | 12 | 2 | 9 | 269 | 274 | 6 |
| 10 | 0 | 8 | 68 | 67 | 4 | −24 | 4 | 8 | 69 | 70 | 23 | −22 | −4 | 9 | 112 | 121 | 11 | 3 | −1 | 9 | 52 | 68 | 5 | 14 | 2 | 9 | 179 | 191 | 5 |
| 12 | 0 | 8 | 63 | 66 | 4 | −22 | 4 | 8 | 202 | 188 | 8 | −20 | −4 | 9 | 191 | 196 | 6 | 5 | −1 | 9 | 240 | 287 | 5 | 16 | 2 | 9 | 269 | 290 | 9 |
| 14 | 0 | 8 | 264 | 289 | 5 | −20 | 4 | 8 | 128 | 107 | 7 | −18 | −4 | 9 | 101 | 98 | 6 | 7 | −1 | 9 | 133 | 127 | 3 | 18 | 2 | 9 | 170 | 158 | 10 |
| 16 | 0 | 8 | 456 | 437 | 11 | −18 | 4 | 8 | 72 | 78 | 7 | −16 | −4 | 9 | 416 | 475 | 13 | 9 | −1 | 9 | 144 | 157 | 4 | 20 | 2 | 9 | 78 | 84 | 6 |
| 18 | 0 | 8 | 125 | 118 | 5 | −16 | 4 | 8 | 150 | 139 | 7 | −14 | −4 | 9 | 116 | 113 | 6 | 11 | −1 | 3 | 153 | 149 | 5 | 22 | 2 | 9 | 138 | 108 | 8 |
| 20 | 0 | 8 | 72 | 67 | 7 | −14 | 4 | 8 | 218 | 206 | 9 | −12 | −4 | 9 | 346 | 363 | 9 | 13 | −1 | 9 | 270 | 276 | 6 | −25 | 3 | 9 | 33 | 42 | 32 |
| 22 | 0 | 8 | 165 | 158 | 7 | −12 | 4 | 8 | 173 | 176 | 5 | −10 | −4 | 9 | 420 | 453 | 14 | 15 | −1 | 9 | 418 | 409 | 10 | −23 | 3 | 9 | 150 | 146 | 6 |
| 24 | 0 | 8 | 127 | 119 | 6 | −10 | 4 | 8 | 351 | 354 | 8 | −8 | −4 | 9 | 280 | 294 | 8 | 17 | −1 | 9 | 79 | 92 | 5 | −21 | 3 | 9 | 85 | 68 | 5 |
| −29 | 1 | 8 | 191 | 204 | 15 | −8 | 4 | 8 | 441 | 441 | 8 | −6 | −4 | 9 | 338 | 349 | 9 | 19 | −1 | 9 | 54 | 37 | 7 | −19 | 3 | 9 | 302 | 293 | 9 |
| −27 | 1 | 8 | 21 | 54 | 21 | −6 | 4 | 8 | 102 | 117 | 4 | −4 | −4 | 9 | 471 | 498 | 12 | 21 | −1 | 9 | 23 | 6 | 22 | −17 | 3 | 9 | 172 | 179 | 8 |
| −25 | 1 | 8 | 130 | 118 | 18 | −4 | 4 | 8 | 394 | 397 | 7 | −2 | −4 | 9 | 121 | 128 | 5 | 23 | −1 | 9 | 0 | 3 | 1 | −13 | 3 | 9 | 272 | 274 | 5 |
| −23 | 1 | 8 | 285 | 324 | 19 | −2 | 4 | 8 | 363 | 361 | 6 | 0 | −4 | 9 | 120 | 131 | 4 | −30 | 0 | 9 | 258 | 246 | 16 | −11 | 3 | 9 | 128 | 141 | 5 |
| −21 | 1 | 8 | 238 | 250 | 17 | 0 | 4 | 8 | 394 | 417 | 9 | 2 | −4 | 9 | 28 | 38 | 15 | −28 | 0 | 9 | 178 | 176 | 17 | −9 | 3 | 9 | 226 | 237 | 5 |
| −19 | 1 | 8 | 123 | 100 | 18 | 2 | 4 | 8 | 314 | 336 | 7 | 4 | −4 | 9 | 488 | 590 | 17 | −26 | 0 | 9 | 55 | 40 | 10 | −7 | 3 | 9 | 235 | 250 | 4 |
| −17 | 1 | 8 | 441 | 436 | 20 | 4 | 4 | 8 | 131 | 138 | 5 | 6 | −4 | 9 | 177 | 198 | 11 | −24 | 0 | 9 | 266 | 307 | 10 | −5 | 3 | 9 | 132 | 147 | 3 |
| −15 | 1 | 8 | 407 | 378 | 18 | 6 | 4 | 8 | 147 | 149 | 4 | 8 | −4 | 9 | 91 | 109 | 7 | −22 | 0 | 9 | 92 | 99 | 7 | −3 | 3 | 9 | 120 | 116 | 3 |
| −13 | 1 | 8 | 557 | 549 | 12 | 8 | 4 | 8 | 221 | 243 | 5 | 10 | −4 | 9 | 34 | 52 | 16 | −20 | 0 | 9 | 452 | 509 | 22 | −1 | 3 | 9 | 133 | 139 | 3 |
| −11 | 1 | 8 | 254 | 225 | 9 | 10 | 4 | 8 | 188 | 202 | 5 | 12 | −4 | 9 | 125 | 139 | 7 | −18 | 0 | 9 | 288 | 285 | 10 | 1 | 3 | 9 | 197 | 219 | 5 |
| −9 | 1 | 8 | 256 | 245 | 7 | 12 | 4 | 8 | 114 | 130 | 5 | 14 | −4 | 9 | 258 | 274 | 10 | −16 | 0 | 9 | 0 | 38 | 1 | 3 | 3 | 9 | 233 | 245 | 4 |
| −7 | 1 | 8 | 326 | 353 | 7 | 14 | 4 | 8 | 156 | 160 | 5 | 16 | −4 | 9 | 8 | 82 | 6 | −14 | 0 | 9 | 92 | 88 | 3 | 5 | 3 | 9 | 343 | 370 | 6 |
| −5 | 1 | 8 | 698 | 717 | 17 | 16 | 4 | 8 | 78 | 91 | 13 | 18 | −4 | 9 | 156 | 140 | 8 | −12 | 0 | 9 | 93 | 109 | 3 | 7 | 3 | 9 | 199 | 220 | 4 |
| −3 | 1 | 8 | 594 | 656 | 19 | 18 | 4 | 8 | 84 | 88 | 7 | −27 | −3 | 9 | 55 | 85 | 14 | −10 | 0 | 9 | 55 | 78 | 4 | 9 | 3 | 9 | 239 | 255 | 5 |
| −1 | 1 | 8 | 616 | 634 | 26 | 20 | 4 | 8 | 136 | 135 | 6 | −25 | −3 | 9 | 47 | 40 | 20 | −8 | 0 | 9 | 154 | 122 | 6 | 11 | 3 | 9 | 197 | 200 | 6 |
| 1 | 1 | 8 | 362 | 358 | 12 | −21 | 5 | 8 | 46 | 50 | 9 | −23 | −3 | 9 | 128 | 144 | 12 | −6 | 0 | 9 | 448 | 436 | 12 | 13 | 3 | 9 | 263 | 284 | 9 |
| 3 | 1 | 8 | 190 | 248 | 8 | −19 | 5 | 8 | 89 | 94 | 8 | −21 | −3 | 9 | 45 | 68 | 23 | −4 | 0 | 9 | 294 | 282 | 10 | 15 | 3 | 9 | 210 | 225 | 6 |
| 5 | 1 | 8 | 561 | 617 | 13 | −17 | 5 | 8 | 29 | 43 | 28 | −19 | −3 | 9 | 298 | 293 | 11 | −2 | 0 | 9 | 64 | 87 | 7 | 17 | 3 | 9 | 42 | 38 | 12 |
| 7 | 1 | 8 | 430 | 473 | 10 | −15 | 5 | 8 | 94 | 77 | 8 | −17 | −3 | 9 | 161 | 179 | 7 | 0 | 0 | 9 | 185 | 145 | 7 | 19 | 3 | 9 | 89 | 77 | 6 |
| 9 | 1 | 8 | 405 | 438 | 7 | −13 | 5 | 8 | 110 | 113 | 8 | −15 | −3 | 9 | 422 | 472 | 11 | 2 | 0 | 9 | 102 | 116 | 6 | 21 | 3 | 9 | 95 | 70 | 6 |
| 11 | 1 | 8 | 265 | 260 | 5 | −11 | 5 | 8 | 108 | 113 | 5 | −13 | −3 | 9 | 242 | 274 | 8 | 4 | 0 | 9 | 105 | 106 | 4 | −24 | 4 | 9 | 153 | 152 | 6 |
| 13 | 1 | 8 | 220 | 216 | 5 | −9 | 5 | 8 | 82 | 81 | 4 | −11 | −3 | 9 | 124 | 142 | 4 | 6 | 0 | 9 | 257 | 234 | 5 | −22 | 4 | 9 | 122 | 121 | 7 |
| 15 | 1 | 8 | 75 | 54 | 5 | −7 | 5 | 8 | 193 | 177 | 4 | −9 | −3 | 9 | 229 | 237 | 6 | 8 | 0 | 9 | 567 | 588 | 10 | −20 | 4 | 9 | 192 | 194 | 8 |
| 17 | 1 | 8 | 96 | 108 | 5 | −5 | 5 | 8 | 193 | 190 | 6 | −7 | −3 | 9 | 243 | 250 | 6 | 10 | 0 | 9 | 470 | 494 | 10 | −18 | 4 | 9 | 98 | 97 | 7 |
| 19 | 1 | 8 | 143 | 157 | 7 | −3 | 5 | 8 | 307 | 318 | 9 | −5 | −3 | 9 | 134 | 147 | 5 | 12 | 0 | 9 | 332 | 323 | 8 | −16 | 4 | 9 | 388 | 474 | 24 |
| 21 | 1 | 8 | 198 | 167 | 8 | −1 | 5 | 8 | 185 | 230 | 8 | −3 | −3 | 9 | 116 | 116 | 5 | 14 | 0 | 9 | 0 | 12 | 1 | −14 | 4 | 9 | 110 | 113 | 7 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 23 | 1 | 8 | 237 | 210 | 9 | 1 | 5 | 8 | 191 | 272 | 5 | −1 | −3 | 9 | 127 | 137 | 4 | 16 | 0 | 9 | 129 | 120 | 5 | −12 | 4 | 9 | 349 | 364 | 13 |
| 25 | 1 | 8 | 158 | 132 | 8 | 3 | 5 | 8 | 267 | 269 | 8 | 1 | −3 | 9 | 194 | 218 | 5 | 18 | 0 | 9 | 239 | 224 | 6 | −10 | 4 | 9 | 427 | 454 | 10 |
| −28 | 2 | 8 | 196 | 184 | 14 | 5 | 5 | 8 | 344 | 347 | 10 | 3 | −3 | 9 | 234 | 244 | 5 | 20 | 0 | 9 | 14 | 18 | 14 | −8 | 4 | 9 | 285 | 293 | 6 |
| −26 | 2 | 8 | 183 | 184 | 16 | 7 | 5 | 8 | 144 | 149 | 5 | 5 | −3 | 9 | 339 | 370 | 8 | 22 | 0 | 9 | 248 | 209 | 9 | −6 | 4 | 9 | 340 | 347 | 6 |
| −24 | 2 | 8 | 149 | 129 | 17 | 9 | 5 | 8 | 86 | 83 | 5 | 7 | −3 | 9 | 194 | 221 | 6 | 24 | 0 | 9 | 111 | 78 | 8 | −4 | 4 | 9 | 455 | 499 | 9 |
| −22 | 2 | 8 | 134 | 133 | 19 | 11 | 5 | 8 | 247 | 256 | 7 | 9 | −3 | 9 | 224 | 255 | 7 | −29 | 1 | 9 | 56 | 94 | 56 | −2 | 4 | 9 | 132 | 127 | 4 |
| −20 | 2 | 8 | 270 | 231 | 16 | 13 | 5 | 8 | 176 | 191 | 7 | 11 | −3 | 9 | 154 | 202 | 8 | −27 | 1 | 9 | 0 | 23 | 1 | 0 | 4 | 9 | 126 | 130 | 4 |
| −18 | 2 | 8 | 256 | 265 | 8 | 15 | 5 | 8 | 90 | 93 | 11 | 13 | −3 | 9 | 247 | 285 | 9 | −25 | 1 | 9 | 92 | 96 | 24 | 2 | 4 | 9 | 29 | 39 | 12 |
| −16 | 2 | 8 | 494 | 503 | 13 | −16 | 6 | 8 | 30 | 49 | 19 | 15 | −3 | 9 | 208 | 225 | 8 | −23 | 1 | 9 | 161 | 190 | 16 | 4 | 4 | 9 | 514 | 592 | 13 |
| −14 | 2 | 8 | 131 | 146 | 8 | −14 | 6 | 8 | 151 | 154 | 8 | 17 | −3 | 9 | 40 | 37 | 12 | −21 | 1 | 9 | 424 | 463 | 15 | 6 | 4 | 9 | 183 | 197 | 4 |
| −12 | 2 | 8 | 771 | 701 | 13 | −12 | 6 | 8 | 85 | 92 | 8 | 19 | −3 | 9 | 96 | 78 | 7 | −19 | 1 | 9 | 527 | 508 | 23 | 8 | 4 | 9 | 104 | 109 | 5 |
| −10 | 2 | 8 | 217 | 224 | 4 | −10 | 6 | 8 | 173 | 188 | 8 | −28 | −2 | 9 | 76 | 100 | 10 | −17 | 1 | 9 | 431 | 452 | 21 | 10 | 4 | 9 | 49 | 51 | 7 |
| −8 | 2 | 8 | 136 | 126 | 4 | −8 | 6 | 8 | 106 | 104 | 5 | −26 | −2 | 9 | 109 | 113 | 10 | −15 | 1 | 9 | 367 | 391 | 13 | 12 | 4 | 9 | 136 | 139 | 5 |
| −6 | 2 | 8 | 256 | 263 | 5 | −6 | 6 | 8 | 41 | 38 | 7 | −24 | −2 | 9 | 178 | 194 | 9 | −13 | 1 | 9 | 119 | 113 | 3 | 14 | 4 | 9 | 278 | 273 | 8 |
| −4 | 2 | 8 | 143 | 143 | 5 | −4 | 6 | 8 | 216 | 228 | 8 | −22 | −2 | 9 | 224 | 239 | 10 | −11 | 1 | 9 | 199 | 200 | 5 | 16 | 4 | 9 | 80 | 82 | 7 |
| −2 | 2 | 8 | 187 | 185 | 7 | −2 | 6 | 8 | 188 | 196 | 6 | −20 | 2 | 9 | 298 | 320 | 11 | −9 | 1 | 9 | 785 | 829 | 15 | 18 | 4 | 9 | 163 | 140 | 7 |
| 0 | 2 | 8 | 315 | 340 | 8 | 0 | 6 | 8 | 102 | 100 | 5 | −18 | −2 | 9 | 434 | 426 | 9 | −7 | 1 | 9 | 142 | 145 | 4 | −21 | 5 | 9 | 138 | 151 | 7 |
| 2 | 2 | 8 | 72 | 67 | 4 | 2 | 6 | 8 | 197 | 200 | 7 | −16 | −2 | 9 | 143 | 145 | 4 | −5 | 1 | 9 | 121 | 121 | 5 | −19 | 5 | 9 | 97 | 90 | 7 |
| 4 | 2 | 8 | 112 | 136 | 3 | 4 | 6 | 8 | 200 | 230 | 7 | −14 | −2 | 9 | 101 | 116 | 4 | −3 | 1 | 9 | 448 | 500 | 13 | −17 | 5 | 9 | 44 | 55 | 12 |
| 6 | 2 | 8 | 139 | 151 | 3 | 6 | 6 | 8 | 108 | 126 | 5 | −12 | −2 | 9 | 59 | 73 | 5 | −1 | 1 | 9 | 488 | 557 | 16 | −15 | 5 | 9 | 97 | 81 | 8 |
| 8 | 2 | 8 | 209 | 238 | 4 | 8 | 6 | 8 | 99 | 95 | 4 | −10 | −2 | 9 | 95 | 99 | 3 | 1 | 1 | 9 | 255 | 241 | 9 | −13 | 5 | 9 | 120 | 115 | 8 |
| 10 | 2 | 8 | 72 | 80 | 5 | 10 | 6 | 8 | 106 | 105 | 6 | −8 | −2 | 9 | 255 | 281 | 6 | 3 | 1 | 9 | 44 | 67 | 5 | −11 | 5 | 9 | 197 | 199 | 6 |
| 12 | 2 | 8 | 29 | 29 | 14 | −14 | −6 | 9 | 73 | 93 | 7 | −6 | −2 | 9 | 189 | 183 | 5 | 5 | 1 | 9 | 231 | 288 | 5 | −9 | 5 | 9 | 218 | 236 | 5 |
| −7 | 5 | 9 | 288 | 288 | 6 | 5 | −3 | 10 | 429 | 475 | 10 | −25 | 1 | 10 | 353 | 336 | 17 | 4 | 4 | 10 | 152 | 164 | 6 | −7 | −3 | 11 | 113 | 111 | 6 |
| −5 | 5 | 9 | 154 | 140 | 5 | 7 | −3 | 10 | 82 | 86 | 8 | −23 | 1 | 10 | 362 | 407 | 14 | 6 | 4 | 10 | 293 | 313 | 9 | −5 | −3 | 11 | 125 | 120 | 6 |
| −3 | 5 | 9 | 94 | 98 | 6 | 11 | −3 | 10 | 137 | 152 | 8 | −21 | 1 | 10 | 331 | 360 | 12 | 8 | 4 | 10 | 244 | 271 | 6 | −3 | −3 | 11 | 320 | 297 | 8 |
| −1 | 5 | 9 | 288 | 374 | 11 | 13 | −3 | 10 | 102 | 105 | 7 | −19 | 1 | 10 | 262 | 280 | 10 | 10 | 4 | 10 | 179 | 194 | 5 | −1 | −3 | 11 | 296 | 320 | 6 |
| 1 | 5 | 9 | 359 | 456 | 16 | 15 | −3 | 10 | 89 | 87 | 7 | −17 | 1 | 10 | 401 | 436 | 14 | 12 | 4 | 10 | 134 | 128 | 6 | 1 | −3 | 11 | 204 | 210 | 4 |
| 3 | 5 | 9 | 291 | 335 | 9 | 17 | −3 | 10 | 96 | 107 | 6 | −15 | 1 | 10 | 233 | 253 | 8 | 14 | 4 | 10 | 102 | 99 | 6 | 3 | −3 | 11 | 354 | 399 | 7 |
| 5 | 5 | 9 | 66 | 77 | 7 | 19 | −3 | 10 | 46 | 64 | 9 | −13 | 1 | 10 | 467 | 492 | 9 | 16 | 4 | 10 | 86 | 73 | 6 | 5 | −3 | 11 | 130 | 156 | 8 |
| 7 | 5 | 9 | 96 | 113 | 6 | −28 | −2 | 10 | 216 | 232 | 12 | −11 | 1 | 10 | 117 | 105 | 5 | −21 | 5 | 10 | 23 | 32 | 23 | 7 | −3 | 11 | 278 | 314 | 14 |
| 9 | 5 | 9 | 111 | 115 | 4 | −26 | −2 | 10 | 117 | 125 | 10 | −9 | 1 | 10 | 489 | 515 | 8 | −19 | 5 | 10 | 191 | 202 | 8 | 9 | −3 | 11 | 89 | 115 | 12 |
| 11 | 5 | 9 | 164 | 175 | 7 | −24 | −2 | 10 | 97 | 99 | 10 | −7 | 1 | 10 | 458 | 508 | 7 | −17 | 5 | 10 | 57 | 55 | 9 | 11 | −3 | 11 | 170 | 207 | 9 |
| 13 | 5 | 9 | 240 | 275 | 10 | −22 | −2 | 10 | 290 | 319 | 12 | −5 | 1 | 10 | 333 | 354 | 5 | −15 | 5 | 10 | 156 | 141 | 8 | 13 | −3 | 11 | 218 | 212 | 9 |
| −16 | 6 | 9 | 76 | 77 | 8 | −20 | −2 | 10 | 392 | 387 | 19 | −3 | 1 | 10 | 433 | 448 | 7 | −13 | 5 | 10 | 48 | 58 | 13 | 15 | −3 | 11 | 61 | 58 | 9 |
| −14 | 6 | 9 | 88 | 92 | 6 | −18 | −2 | 10 | 106 | 109 | 5 | −1 | 1 | 10 | 443 | 521 | 9 | −11 | 5 | 10 | 90 | 102 | 5 | 17 | −3 | 11 | 151 | 131 | 6 |
| −12 | 6 | 9 | 17 | 9 | 16 | −16 | −2 | 10 | 267 | 276 | 7 | 1 | 1 | 10 | 138 | 164 | 3 | −9 | 5 | 10 | 66 | 65 | 7 | −28 | −2 | 11 | 165 | 173 | 9 |
| −10 | 6 | 9 | 33 | 31 | 15 | −14 | −2 | 10 | 342 | 341 | 7 | 3 | 1 | 10 | 184 | 206 | 4 | −7 | 5 | 10 | 128 | 129 | 4 | −26 | −2 | 11 | 148 | 165 | 10 |
| −8 | 6 | 9 | 100 | 106 | 4 | −12 | −2 | 10 | 120 | 113 | 4 | 5 | 1 | 10 | 147 | 154 | 3 | −5 | 5 | 10 | 248 | 275 | 7 | −24 | −2 | 11 | 234 | 258 | 10 |
| −6 | 6 | 9 | 365 | 407 | 13 | −10 | −2 | 10 | 176 | 171 | 4 | 7 | 1 | 10 | 253 | 263 | 5 | −3 | 5 | 10 | 131 | 150 | 6 | −22 | −2 | 11 | 229 | 262 | 11 |
| −4 | 6 | 9 | 74 | 73 | 6 | −8 | −2 | 10 | 594 | 652 | 13 | 9 | 1 | 10 | 108 | 120 | 4 | −1 | 5 | 10 | 285 | 287 | 17 | −20 | −2 | 11 | 286 | 271 | 16 |
| −2 | 6 | 9 | 89 | 104 | 6 | −6 | −2 | 10 | 213 | 228 | 5 | 11 | 1 | 10 | 160 | 157 | 5 | 1 | 5 | 10 | 145 | 141 | 6 | −18 | −2 | 11 | 209 | 192 | 7 |
| 0 | 6 | 9 | 106 | 112 | 7 | −4 | −2 | 10 | 398 | 434 | 10 | 13 | 1 | 10 | 138 | 139 | 6 | 3 | 5 | 10 | 79 | 95 | 5 | −16 | −2 | 11 | 179 | 169 | 5 |
| 2 | 6 | 9 | 77 | 93 | 7 | −2 | −2 | 10 | 104 | 126 | 3 | 15 | 1 | 10 | 273 | 255 | 7 | 5 | 5 | 10 | 40 | 35 | 12 | −14 | −2 | 11 | 435 | 454 | 8 |
| 4 | 6 | 9 | 96 | 123 | 7 | 0 | −2 | 10 | 225 | 272 | 4 | 17 | 1 | 10 | 259 | 245 | 7 | 7 | 5 | 10 | 135 | 146 | 6 | −12 | −2 | 11 | 109 | 113 | 4 |
| 6 | 6 | 9 | 130 | 122 | 5 | 2 | −2 | 10 | 251 | 265 | 5 | 19 | 1 | 10 | 116 | 97 | 6 | 9 | 5 | 10 | 264 | 273 | 7 | −10 | −2 | 11 | 341 | 368 | 7 |
| 8 | 6 | 9 | 131 | 139 | 8 | 4 | −2 | 10 | 411 | 470 | 7 | 21 | 1 | 10 | 38 | 25 | 11 | 11 | 5 | 10 | 122 | 140 | 5 | −8 | −2 | 11 | 265 | 279 | 5 |
| −14 | −6 | 10 | 173 | 165 | 6 | 6 | −2 | 10 | 138 | 140 | 5 | −28 | 2 | 10 | 216 | 233 | 14 | 13 | 5 | 10 | 111 | 115 | 11 | −6 | −2 | 11 | 302 | 325 | 6 |
| −12 | −6 | 10 | 49 | 58 | 9 | 8 | −2 | 10 | 154 | 171 | 6 | −26 | 2 | 10 | 127 | 125 | 16 | −14 | 6 | 10 | 173 | 165 | 10 | −4 | −2 | 11 | 195 | 216 | 5 |

TABLE 8-continued

| Observed and calculated structure factors for SAG-2 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| −10 | −6 | 10 | 85 | 88 | 7 | 10 | −2 | 10 | 185 | 196 | 6 | −24 | 2 | 10 | 119 | 100 | 18 | −12 | 6 | 10 | 52 | 59 | 9 | −2 | −2 | 11 | 225 | 247 | 5 |
| −8 | −6 | 10 | 25 | 29 | 24 | 12 | −2 | 10 | 242 | 250 | 9 | −22 | 2 | 10 | 304 | 319 | 9 | −10 | 6 | 10 | 86 | 89 | 7 | 0 | −2 | 11 | 155 | 154 | 3 |
| −6 | −6 | 10 | 267 | 259 | 9 | 14 | −2 | 10 | 151 | 159 | 6 | −20 | 2 | 10 | 383 | 385 | 11 | −8 | 6 | 10 | 34 | 31 | 9 | 2 | −2 | 11 | 225 | 236 | 4 |
| −4 | −6 | 10 | 124 | 118 | 6 | 16 | −2 | 10 | 176 | 182 | 5 | −18 | 2 | 10 | 109 | 110 | 6 | −6 | 6 | 10 | 267 | 259 | 7 | 4 | −2 | 11 | 155 | 169 | 4 |
| −2 | −6 | 10 | 213 | 206 | 8 | 18 | −2 | 10 | 188 | 181 | 5 | −16 | 2 | 10 | 276 | 275 | 8 | −4 | 6 | 10 | 114 | 117 | 5 | 6 | −2 | 11 | 124 | 135 | 6 |
| 0 | −6 | 10 | 101 | 101 | 6 | 20 | −2 | 10 | 52 | 49 | 8 | −14 | 2 | 10 | 344 | 340 | 7 | −2 | 6 | 10 | 208 | 205 | 6 | 8 | −2 | 11 | 304 | 345 | 12 |
| 4 | −6 | 10 | 99 | 122 | 7 | −29 | −1 | 10 | 111 | 125 | 7 | −12 | 2 | 10 | 116 | 113 | 4 | 0 | 6 | 10 | 95 | 102 | 7 | 12 | −2 | 11 | 89 | 126 | 8 |
| 6 | −6 | 10 | 85 | 99 | 7 | −27 | −1 | 10 | 86 | 97 | 8 | −10 | 2 | 10 | 177 | 170 | 4 | 2 | 6 | 10 | 223 | 240 | 8 | 14 | −2 | 11 | 171 | 165 | 8 |
| −19 | −5 | 10 | 204 | 202 | 7 | −25 | −1 | 10 | 339 | 337 | 12 | −8 | 2 | 10 | 602 | 651 | 9 | 4 | 6 | 10 | 113 | 122 | 7 | 16 | −2 | 11 | 109 | 106 | 6 |
| −17 | −5 | 10 | 58 | 56 | 7 | −23 | −1 | 10 | 399 | 406 | 13 | −6 | 2 | 10 | 215 | 229 | 4 | 6 | 6 | 10 | 100 | 99 | 8 | 18 | −2 | 11 | 69 | 59 | 9 |
| −15 | −5 | 10 | 151 | 142 | 7 | −21 | −1 | 10 | 347 | 360 | 12 | −4 | 2 | 10 | 422 | 434 | 7 | −12 | −6 | 11 | 216 | 220 | 8 | 20 | −2 | 11 | 117 | 103 | 9 |
| −13 | −5 | 10 | 60 | 58 | 10 | −19 | −1 | 10 | 260 | 279 | 10 | −2 | 2 | 10 | 108 | 127 | 3 | −10 | −6 | 11 | 71 | 77 | 7 | −27 | −1 | 11 | 69 | 76 | 9 |
| −11 | −5 | 10 | 86 | 102 | 6 | −17 | −1 | 10 | 412 | 436 | 8 | 0 | 2 | 10 | 215 | 273 | 4 | −8 | −6 | 11 | 61 | 77 | 9 | −25 | −1 | 11 | 167 | 182 | 8 |
| −9 | −5 | 10 | 51 | 65 | 13 | −15 | −1 | 10 | 239 | 252 | 6 | 2 | 2 | 10 | 242 | 266 | 4 | −6 | −6 | 11 | 117 | 110 | 5 | −23 | −1 | 11 | 135 | 137 | 9 |
| −7 | −5 | 10 | 116 | 129 | 8 | −13 | −1 | 10 | 478 | 491 | 10 | 4 | 2 | 10 | 409 | 469 | 7 | −4 | −6 | 11 | 206 | 218 | 6 | −21 | −1 | 11 | 100 | 112 | 9 |
| −5 | −5 | 10 | 248 | 274 | 9 | −11 | −1 | 10 | 112 | 105 | 3 | 6 | 2 | 10 | 135 | 140 | 4 | −2 | −6 | 11 | 188 | 198 | 7 | −19 | −1 | 11 | 192 | 208 | 9 |
| −3 | −5 | 10 | 134 | 150 | 7 | −9 | −1 | 10 | 496 | 513 | 9 | 8 | 2 | 10 | 161 | 170 | 4 | −19 | −5 | 11 | 51 | 52 | 8 | −17 | −1 | 11 | 253 | 284 | 6 |
| −1 | −5 | 10 | 271 | 287 | 8 | −7 | −1 | 10 | 461 | 509 | 9 | 10 | 2 | 10 | 203 | 196 | 5 | −17 | −5 | 11 | 141 | 137 | 5 | −15 | −1 | 11 | 279 | 294 | 7 |
| 1 | −5 | 10 | 143 | 143 | 5 | −5 | −1 | 10 | 327 | 354 | 6 | 12 | 2 | 10 | 257 | 250 | 7 | −15 | −5 | 11 | 102 | 97 | 7 | −13 | −1 | 11 | 94 | 97 | 3 |
| 3 | −5 | 10 | 76 | 93 | 7 | −3 | −1 | 10 | 414 | 446 | 8 | 14 | 2 | 10 | 161 | 158 | 6 | −23 | −5 | 11 | 43 | 44 | 14 | −11 | −1 | 11 | 118 | 121 | 3 |
| 5 | −5 | 10 | 29 | 36 | 28 | −1 | −1 | 10 | 452 | 522 | 10 | 16 | 2 | 10 | 177 | 182 | 5 | −11 | −5 | 11 | 39 | 63 | 17 | −9 | −1 | 11 | 132 | 139 | 4 |
| 7 | −5 | 10 | 130 | 146 | 7 | 1 | −1 | 10 | 145 | 164 | 3 | 18 | 2 | 10 | 197 | 181 | 7 | −9 | −5 | 11 | 192 | 188 | 6 | −7 | −1 | 11 | 304 | 311 | 6 |
| 9 | −5 | 10 | 259 | 273 | 9 | 3 | −1 | 10 | 185 | 206 | 4 | 20 | 2 | 10 | 57 | 49 | 7 | −7 | −5 | 11 | 74 | 78 | 9 | −5 | −1 | 11 | 504 | 546 | 10 |
| 11 | −5 | 10 | 122 | 140 | 6 | 5 | −1 | 10 | 148 | 153 | 4 | 22 | 2 | 10 | 33 | 21 | 16 | −5 | −5 | 11 | 204 | 207 | 8 | −3 | −1 | 11 | 300 | 312 | 5 |
| 13 | −5 | 10 | 117 | 116 | 6 | 7 | −1 | 10 | 244 | 264 | 6 | −25 | 3 | 10 | 84 | 103 | 18 | −3 | −5 | 11 | 122 | 127 | 7 | −1 | −1 | 11 | 308 | 292 | 5 |
| −24 | −4 | 10 | 133 | 141 | 10 | 9 | −1 | 10 | 114 | 120 | 4 | −23 | 3 | 10 | 184 | 180 | 6 | −1 | −5 | 11 | 131 | 135 | 7 | 1 | −1 | 11 | 41 | 54 | 5 |
| −22 | −4 | 10 | 189 | 217 | 13 | 11 | −1 | 10 | 153 | 157 | 5 | −21 | 3 | 10 | 187 | 194 | 7 | 1 | −5 | 11 | 187 | 203 | 5 | 3 | −1 | 11 | 104 | 102 | 3 |
| −20 | −4 | 10 | 65 | 72 | 6 | 13 | −1 | 10 | 134 | 139 | 5 | −19 | 3 | 10 | 341 | 332 | 10 | 3 | −5 | 11 | 88 | 117 | 9 | 5 | −1 | 11 | 57 | 40 | 5 |
| −18 | −4 | 10 | 226 | 247 | 9 | 15 | −1 | 10 | 275 | 255 | 7 | −17 | 3 | 10 | 33 | 37 | 15 | 5 | −5 | 11 | 147 | 181 | 8 | 7 | −1 | 11 | 432 | 450 | 11 |
| −16 | −4 | 10 | 173 | 193 | 7 | 17 | −1 | 10 | 258 | 245 | 6 | −15 | 3 | 10 | 182 | 167 | 8 | 7 | −5 | 11 | 50 | 53 | 12 | 9 | −1 | 11 | 237 | 264 | 7 |
| −14 | −4 | 10 | 270 | 289 | 7 | 19 | −1 | 10 | 105 | 97 | 5 | −13 | 3 | 10 | 95 | 104 | 4 | 9 | −5 | 11 | 146 | 154 | 7 | 11 | −1 | 11 | 503 | 503 | 14 |
| −12 | −4 | 10 | 231 | 244 | 6 | 21 | −1 | 10 | 35 | 24 | 13 | −11 | 3 | 10 | 80 | 96 | 6 | 11 | −5 | 11 | 153 | 173 | 7 | 13 | −1 | 11 | 171 | 161 | 6 |
| −8 | −4 | 10 | 408 | 470 | 15 | −30 | 0 | 10 | 326 | 317 | 17 | −9 | 3 | 10 | 315 | 334 | 6 | −22 | −4 | 11 | 215 | 238 | 13 | 15 | −1 | 11 | 273 | 270 | 7 |
| −6 | −4 | 10 | 125 | 129 | 7 | −28 | 0 | 10 | 25 | 12 | 24 | −7 | 3 | 10 | 120 | 138 | 3 | −20 | −4 | 11 | 100 | 103 | 6 | 17 | −1 | 11 | 191 | 177 | 5 |
| −4 | −4 | 10 | 146 | 156 | 6 | −26 | 0 | 10 | 220 | 239 | 9 | −5 | 3 | 10 | 195 | 211 | 4 | −18 | −4 | 11 | 160 | 152 | 8 | 19 | −1 | 11 | 57 | 40 | 6 |
| −2 | −4 | 10 | 211 | 227 | 7 | −24 | 0 | 10 | 52 | 59 | 12 | −3 | 3 | 10 | 20 | 39 | 17 | −16 | −4 | 11 | 199 | 219 | 6 | 21 | −1 | 11 | 167 | 147 | 7 |
| 0 | −4 | 10 | 347 | 392 | 8 | −22 | 0 | 10 | 328 | 393 | 12 | −1 | 3 | 10 | 262 | 311 | 5 | −14 | −4 | 11 | 100 | 103 | 6 | −28 | 0 | 11 | 157 | 167 | 15 |
| 2 | −4 | 10 | 224 | 258 | 7 | −20 | 0 | 10 | 232 | 233 | 9 | 1 | 3 | 10 | 472 | 513 | 9 | −12 | −4 | 11 | 205 | 214 | 7 | −26 | 0 | 11 | 212 | 225 | 9 |
| 4 | −4 | 10 | 166 | 164 | 6 | −18 | 0 | 10 | 22 | 38 | 21 | 3 | 3 | 10 | 264 | 289 | 6 | −10 | −4 | 11 | 179 | 186 | 8 | −24 | 0 | 11 | 65 | 55 | 9 |
| 6 | −4 | 10 | 315 | 312 | 14 | −16 | 0 | 10 | 23 | 21 | 22 | 5 | 3 | 10 | 428 | 476 | 7 | −8 | −4 | 11 | 191 | 234 | 8 | −22 | 0 | 11 | 198 | 218 | 9 |
| 8 | −4 | 10 | 253 | 271 | 12 | −14 | 0 | 10 | 22 | 11 | 17 | 7 | 3 | 10 | 73 | 85 | 5 | −6 | −4 | 11 | 19 | 33 | 18 | −20 | 0 | 11 | 4 | 28 | 3 |
| 10 | −4 | 10 | 165 | 194 | 8 | −12 | 0 | 10 | 0 | 25 | 1 | 9 | 3 | 10 | 434 | 452 | 11 | −4 | −4 | 11 | 180 | 188 | 8 | −18 | 0 | 11 | 174 | 185 | 8 |
| 12 | −4 | 10 | 109 | 128 | 7 | −10 | 0 | 10 | 331 | 364 | 6 | 11 | 3 | 10 | 163 | 154 | 7 | −2 | −4 | 11 | 255 | 252 | 8 | −16 | 0 | 11 | 160 | 169 | 5 |
| 14 | −4 | 10 | 93 | 99 | 7 | −8 | 0 | 10 | 478 | 483 | 9 | 13 | 3 | 10 | 116 | 105 | 5 | 0 | −4 | 11 | 196 | 231 | 6 | −14 | 0 | 11 | 137 | 135 | 4 |
| 16 | −4 | 10 | 85 | 73 | 6 | −6 | 0 | 10 | 561 | 595 | 10 | 15 | 3 | 10 | 88 | 86 | 5 | 2 | −4 | 11 | 115 | 127 | 5 | −12 | 0 | 11 | 402 | 425 | 7 |
| −27 | −3 | 10 | 107 | 112 | 9 | −4 | 0 | 10 | 152 | 154 | 3 | 17 | 3 | 10 | 106 | 108 | 6 | 4 | −4 | 11 | 140 | 158 | 8 | −10 | 0 | 11 | 45 | 25 | 5 |
| −25 | −3 | 10 | 79 | 103 | 11 | −2 | 0 | 10 | 540 | 534 | 11 | 19 | 3 | 10 | 61 | 63 | 7 | 6 | −4 | 11 | 223 | 256 | 9 | −8 | 0 | 11 | 27 | 24 | 8 |
| −23 | −3 | 10 | 169 | 180 | 12 | 0 | 0 | 10 | 186 | 195 | 4 | −24 | 4 | 10 | 130 | 140 | 14 | 8 | −4 | 11 | 243 | 258 | 10 | −6 | 0 | 11 | 405 | 406 | 7 |
| −21 | −3 | 10 | 158 | 194 | 13 | 2 | 0 | 10 | 124 | 138 | 3 | −22 | 4 | 10 | 216 | 217 | 8 | 10 | −4 | 11 | 77 | 87 | 8 | −4 | 0 | 11 | 360 | 385 | 7 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −19 | −3 | 10 | 351 | 332 | 18 | 4 | 0 | 10 | 185 | 216 | 4 | −20 | 4 | 10 | 68 | 72 | 7 | 12 | −4 | 11 | 151 | 157 | 7 | −2 | 0 | 11 | 204 | 201 | 4 |
| −17 | −3 | 10 | 36 | 37 | 12 | 6 | 0 | 10 | 567 | 573 | 9 | −18 | 4 | 10 | 247 | 245 | 9 | 14 | −4 | 11 | 74 | 74 | 7 | 0 | 0 | 11 | 174 | 161 | 4 |
| −15 | −3 | 10 | 158 | 166 | 8 | 8 | 0 | 10 | 130 | 112 | 4 | −16 | 4 | 10 | 176 | 193 | 8 | 16 | −4 | 11 | 6 | 19 | 5 | 2 | 0 | 11 | 155 | 188 | 3 |
| −13 | −3 | 10 | 93 | 104 | 5 | 10 | 0 | 10 | 197 | 179 | 5 | −14 | 4 | 10 | 226 | 288 | 15 | −25 | −3 | 11 | 131 | 126 | 10 | 4 | 0 | 11 | 434 | 476 | 8 |
| −11 | −3 | 10 | 75 | 94 | 5 | 12 | 0 | 10 | 193 | 188 | 5 | −12 | 4 | 10 | 216 | 245 | 8 | −23 | −3 | 11 | 64 | 70 | 15 | 6 | 0 | 11 | 204 | 211 | 4 |
| −9 | −3 | 10 | 309 | 333 | 8 | 14 | 0 | 10 | 360 | 380 | 10 | −10 | 4 | 10 | 416 | 434 | 12 | −21 | −3 | 11 | 57 | 64 | 16 | 8 | 0 | 11 | 147 | 160 | 4 |
| −7 | −3 | 10 | 117 | 138 | 6 | 16 | 0 | 10 | 188 | 170 | 5 | −8 | 4 | 10 | 428 | 471 | 10 | −19 | −3 | 11 | 194 | 190 | 8 | 10 | 0 | 11 | 27 | 18 | 15 |
| −5 | −3 | 10 | 193 | 211 | 6 | 18 | 0 | 10 | 190 | 184 | 5 | −6 | 4 | 10 | 123 | 130 | 4 | −17 | −3 | 11 | 160 | 159 | 6 | 12 | 0 | 11 | 41 | 52 | 9 |
| −3 | −3 | 10 | 13 | 38 | 13 | 20 | 0 | 10 | 188 | 162 | 8 | −4 | 4 | 10 | 161 | 156 | 4 | −15 | −3 | 11 | 236 | 232 | 7 | 14 | 0 | 11 | 184 | 192 | 5 |
| −1 | −3 | 10 | 265 | 309 | 7 | 22 | 0 | 10 | 301 | 256 | 11 | −2 | 4 | 10 | 210 | 226 | 5 | −13 | −3 | 11 | 253 | 260 | 8 | 16 | 0 | 11 | 24 | 27 | 23 |
| 1 | −3 | 10 | 459 | 515 | 11 | −29 | 1 | 10 | 103 | 125 | 18 | 0 | 4 | 10 | 328 | 392 | 11 | −11 | −3 | 11 | 154 | 160 | 4 | 18 | 0 | 11 | 88 | 76 | 5 |
| 3 | −3 | 10 | 269 | 288 | 5 | −27 | 1 | 10 | 81 | 96 | 26 | 2 | 4 | 10 | 212 | 256 | 6 | −9 | −3 | 11 | 355 | 391 | 7 | 20 | 0 | 11 | 95 | 71 | 6 |
| −29 | 1 | 11 | 161 | 179 | 13 | 6 | 4 | 11 | 231 | 257 | 7 | 15 | −3 | 12 | 176 | 177 | 7 | 1 | 1 | 12 | 192 | 188 | 4 | −6 | 6 | 12 | 138 | 151 | 6 |
| −27 | 1 | 11 | 56 | 77 | 52 | 8 | 4 | 11 | 263 | 258 | 7 | 17 | −3 | 12 | 62 | 56 | 8 | 3 | 1 | 12 | 85 | 78 | 4 | −4 | 6 | 12 | 110 | 122 | 7 |
| −25 | 1 | 11 | 161 | 180 | 8 | 10 | 4 | 11 | 79 | 86 | 5 | −26 | −2 | 12 | 104 | 107 | 9 | 5 | 1 | 12 | 352 | 345 | 8 | −2 | 6 | 12 | 83 | 79 | 12 |
| −23 | 1 | 11 | 145 | 135 | 7 | 12 | 4 | 11 | 153 | 157 | 6 | −24 | −2 | 12 | 178 | 185 | 9 | 7 | 1 | 12 | 336 | 339 | 7 | 0 | 6 | 12 | 160 | 170 | 11 |
| −21 | 1 | 11 | 108 | 113 | 7 | 14 | 4 | 11 | 84 | 74 | 6 | −22 | −2 | 12 | 149 | 158 | 9 | 9 | 1 | 12 | 133 | 129 | 5 | −15 | −5 | 13 | 70 | 73 | 6 |
| −19 | 1 | 11 | 195 | 209 | 8 | −19 | 5 | 11 | 49 | 52 | 8 | −20 | −2 | 12 | 178 | 213 | 9 | 11 | 1 | 12 | 334 | 315 | 9 | −13 | −5 | 13 | 24 | 29 | 23 |
| −17 | 1 | 11 | 258 | 283 | 8 | −17 | 5 | 11 | 146 | 138 | 7 | −18 | −2 | 12 | 61 | 56 | 7 | 13 | 1 | 12 | 82 | 80 | 5 | −11 | −5 | 13 | 47 | 52 | 12 |
| −15 | 1 | 11 | 276 | 295 | 7 | −15 | 5 | 11 | 117 | 97 | 7 | −16 | −2 | 12 | 319 | 331 | 8 | 15 | 1 | 12 | 144 | 129 | 5 | −9 | −5 | 13 | 150 | 159 | 7 |
| −13 | 1 | 11 | 97 | 96 | 4 | −13 | 5 | 11 | 42 | 43 | 14 | −14 | −21 | 2 | 161 | 179 | 5 | 17 | 1 | 12 | 215 | 191 | 6 | −7 | −5 | 13 | 381 | 371 | 10 |
| −11 | 1 | 11 | 115 | 123 | 6 | −11 | 5 | 11 | 38 | 63 | 17 | −12 | −2 | 12 | 191 | 196 | 5 | 19 | 1 | 12 | 126 | 124 | 6 | −5 | −5 | 13 | 151 | 153 | 6 |
| −9 | 1 | 11 | 139 | 139 | 3 | −9 | 5 | 11 | 184 | 188 | 6 | −10 | −2 | 12 | 287 | 310 | 6 | −26 | 2 | 12 | 110 | 108 | 15 | −3 | −5 | 13 | 132 | 132 | 6 |
| −7 | 1 | 11 | 301 | 311 | 5 | −7 | 5 | 11 | 69 | 77 | 5 | −8 | −2 | 12 | 164 | 171 | 4 | −24 | 2 | 12 | 183 | 187 | 8 | −1 | −5 | 13 | 110 | 112 | 5 |
| −5 | 1 | 11 | 515 | 546 | 9 | −5 | 5 | 11 | 196 | 206 | 6 | −6 | −2 | 12 | 192 | 193 | 5 | −22 | 2 | 12 | 151 | 159 | 6 | 1 | −5 | 13 | 84 | 92 | 7 |
| −3 | 1 | 11 | 299 | 310 | 5 | −3 | 5 | 11 | 127 | 127 | 6 | −4 | −2 | 12 | 31 | 28 | 12 | −20 | 2 | 12 | 202 | 213 | 7 | 3 | −5 | 13 | 36 | 50 | 26 |
| −1 | 1 | 11 | 302 | 292 | 5 | −1 | 5 | 11 | 123 | 136 | 6 | −2 | −2 | 12 | 117 | 115 | 3 | −18 | 2 | 12 | 61 | 56 | 8 | 5 | −5 | 13 | 38 | 54 | 15 |
| 1 | 1 | 11 | 42 | 54 | 5 | 1 | 5 | 11 | 190 | 204 | 6 | 0 | −2 | 12 | 259 | 288 | 4 | −16 | 2 | 12 | 325 | 332 | 9 | 7 | −5 | 13 | 94 | 94 | 9 |
| 3 | 1 | 11 | 99 | 101 | 3 | 3 | 5 | 11 | 107 | 116 | 6 | 2 | −2 | 12 | 237 | 244 | 5 | −14 | 2 | 12 | 164 | 178 | 5 | −20 | −4 | 13 | 95 | 102 | 10 |
| 5 | 1 | 11 | 63 | 40 | 4 | 5 | 5 | 11 | 155 | 181 | 7 | 4 | −2 | 12 | 288 | 291 | 6 | −12 | 2 | 12 | 194 | 195 | 5 | −18 | −4 | 13 | 50 | 54 | 11 |
| 7 | 1 | 11 | 469 | 451 | 10 | 7 | 5 | 11 | 54 | 52 | 8 | 6 | −2 | 12 | 158 | 159 | 8 | −10 | 2 | 12 | 290 | 309 | 5 | −16 | −4 | 13 | 152 | 133 | 5 |
| 9 | 1 | 11 | 255 | 265 | 6 | 9 | 5 | 11 | 161 | 153 | 6 | 8 | −2 | 12 | 112 | 131 | 7 | −8 | 2 | 12 | 166 | 172 | 4 | −14 | −4 | 13 | 75 | 69 | 8 |
| 11 | 1 | 11 | 533 | 503 | 13 | 11 | 5 | 11 | 172 | 172 | 6 | 12 | −2 | 12 | 189 | 189 | 8 | −6 | 2 | 12 | 190 | 195 | 4 | −12 | −4 | 13 | 110 | 136 | 8 |
| 13 | 1 | 11 | 173 | 162 | 6 | −10 | 6 | 11 | 78 | 79 | 7 | 14 | −2 | 12 | 191 | 185 | 8 | −4 | 2 | 12 | 32 | 27 | 7 | −10 | −4 | 13 | 154 | 160 | 6 |
| 15 | 1 | 11 | 271 | 270 | 7 | −8 | 6 | 11 | 72 | 75 | 9 | 16 | −2 | 12 | 152 | 138 | 6 | −2 | 2 | 12 | 113 | 114 | 3 | −8 | −4 | 13 | 181 | 183 | 6 |
| 17 | 1 | 11 | 186 | 177 | 5 | −6 | 6 | 11 | 107 | 111 | 6 | 18 | −2 | 12 | 173 | 162 | 6 | 0 | 2 | 12 | 251 | 289 | 5 | −6 | −4 | 13 | 207 | 212 | 7 |
| 19 | 1 | 11 | 49 | 39 | 9 | −4 | 6 | 11 | 197 | 218 | 5 | −27 | −1 | 12 | 232 | 239 | 9 | 2 | 2 | 12 | 235 | 244 | 5 | −4 | −4 | 13 | 48 | 49 | 11 |
| 21 | 1 | 11 | 165 | 147 | 7 | −2 | 6 | 11 | 182 | 199 | 7 | −25 | −1 | 12 | 205 | 200 | 9 | 4 | 2 | 12 | 288 | 289 | 5 | −2 | −4 | 13 | 199 | 198 | 6 |
| −28 | 2 | 11 | 158 | 173 | 13 | 0 | 6 | 11 | 41 | 50 | 12 | −23 | −1 | 12 | 227 | 241 | 10 | 6 | 2 | 12 | 158 | 158 | 4 | 0 | −4 | 13 | 270 | 287 | 8 |
| −26 | 2 | 11 | 137 | 166 | 15 | 2 | 6 | 11 | 68 | 75 | 8 | −21 | −1 | 12 | 434 | 442 | 15 | 8 | 2 | 12 | 131 | 129 | 4 | 2 | −4 | 13 | 83 | 81 | 5 |
| −24 | 2 | 11 | 241 | 257 | 9 | 4 | 6 | 11 | 35 | 53 | 17 | −19 | −1 | 12 | 220 | 264 | 10 | 10 | 2 | 12 | 354 | 320 | 10 | 4 | −4 | 13 | 165 | 164 | 8 |
| −22 | 2 | 11 | 244 | 262 | 8 | −8 | −6 | 12 | 154 | 152 | 6 | −17 | −1 | 12 | 103 | 100 | 5 | 12 | 2 | 12 | 208 | 189 | 6 | 6 | −4 | 13 | 187 | 185 | 8 |
| −20 | 2 | 11 | 274 | 270 | 9 | −6 | −6 | 12 | 144 | 152 | 6 | −15 | −1 | 12 | 397 | 404 | 9 | 14 | 2 | 12 | 192 | 186 | 5 | 8 | −4 | 13 | 70 | 73 | 8 |
| −18 | 2 | 11 | 211 | 192 | 7 | −4 | −6 | 12 | 121 | 122 | 5 | −13 | −1 | 12 | 92 | 99 | 4 | 16 | 2 | 12 | 150 | 138 | 5 | 10 | −4 | 13 | 83 | 84 | 7 |
| −16 | 2 | 11 | 188 | 170 | 7 | −2 | −6 | 12 | 86 | 80 | 12 | −11 | −1 | 12 | 373 | 370 | 7 | 18 | 2 | 12 | 179 | 162 | 10 | 12 | −4 | 13 | 135 | 134 | 6 |
| −14 | 2 | 11 | 447 | 453 | 8 | 0 | −6 | 12 | 175 | 171 | 12 | −9 | −1 | 12 | 272 | 285 | 6 | −25 | 3 | 12 | 123 | 140 | 15 | −25 | −3 | 13 | 193 | 199 | 11 |
| −12 | 2 | 11 | 112 | 114 | 5 | −17 | −5 | 12 | 82 | 61 | 6 | −7 | −1 | 12 | 185 | 189 | 4 | −23 | 3 | 12 | 105 | 103 | 6 | −23 | −3 | 13 | 237 | 227 | 13 |
| −10 | 2 | 11 | 342 | 369 | 7 | −15 | −5 | 12 | 102 | 88 | 5 | −5 | −1 | 12 | 19 | 18 | 19 | −21 | 3 | 12 | 154 | 151 | 7 | −21 | −3 | 13 | 212 | 207 | 12 |
| −8 | 2 | 11 | 266 | 278 | 5 | −13 | −5 | 12 | 136 | 130 | 7 | −3 | −1 | 12 | 38 | 35 | 7 | −19 | 3 | 12 | 120 | 124 | 7 | −19 | −3 | 13 | 54 | 58 | 9 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −6 | 2 | 11 | 314 | 324 | 5 | −11 | −5 | 12 | 262 | 278 | 9 | −1 | −1 | 12 | 354 | 358 | 6 | −17 | 3 | 12 | 33 | 34 | 18 | −17 | −3 | 13 | 212 | 219 | 6 |
| −4 | 2 | 11 | 193 | 214 | 4 | −9 | −5 | 12 | 75 | 74 | 6 | 1 | −1 | 12 | 195 | 188 | 4 | −15 | 3 | 12 | 381 | 439 | 25 | −15 | −3 | 13 | 63 | 64 | 7 |
| −2 | 2 | 11 | 218 | 246 | 4 | −7 | −5 | 12 | 250 | 246 | 7 | 3 | −1 | 12 | 90 | 78 | 4 | −13 | 3 | 12 | 255 | 281 | 7 | −13 | −3 | 13 | 216 | 211 | 6 |
| 0 | 2 | 11 | 151 | 153 | 4 | −5 | −5 | 12 | 175 | 182 | 6 | 5 | −1 | 12 | 337 | 344 | 7 | −11 | 3 | 12 | 228 | 255 | 8 | −11 | −3 | 13 | 216 | 218 | 7 |
| 2 | 2 | 11 | 217 | 238 | 4 | −3 | −5 | 12 | 169 | 165 | 7 | 7 | −1 | 12 | 324 | 339 | 8 | −9 | 3 | 12 | 294 | 316 | 7 | −9 | −3 | 13 | 199 | 195 | 9 |
| 4 | 2 | 11 | 151 | 171 | 4 | −1 | −5 | 12 | 147 | 144 | 7 | 9 | −1 | 12 | 125 | 129 | 7 | −7 | 3 | 12 | 101 | 104 | 5 | −7 | −3 | 13 | 171 | 201 | 7 |
| 6 | 2 | 11 | 131 | 135 | 4 | 1 | −5 | 12 | 123 | 125 | 6 | 11 | −1 | 12 | 287 | 316 | 17 | −5 | 3 | 12 | 173 | 177 | 4 | −5 | −3 | 13 | 146 | 145 | 6 |
| 8 | 2 | 11 | 329 | 346 | 7 | 3 | −5 | 12 | 103 | 117 | 7 | 13 | −1 | 12 | 87 | 80 | 7 | −3 | 3 | 12 | 281 | 287 | 5 | −3 | −3 | 13 | 142 | 149 | 5 |
| 10 | 2 | 11 | 225 | 185 | 7 | 5 | −5 | 12 | 28 | 37 | 28 | 15 | −1 | 12 | 142 | 130 | 5 | −1 | 3 | 12 | 355 | 388 | 8 | −1 | −3 | 13 | 73 | 65 | 6 |
| 12 | 2 | 11 | 112 | 127 | 5 | 7 | −5 | 12 | 87 | 93 | 7 | 17 | −1 | 12 | 223 | 189 | 7 | 1 | 3 | 12 | 280 | 314 | 8 | 1 | −3 | 13 | 240 | 228 | 5 |
| 14 | 2 | 11 | 181 | 166 | 5 | 9 | −5 | 12 | 109 | 111 | 6 | 19 | −1 | 12 | 126 | 123 | 6 | 3 | 3 | 12 | 239 | 259 | 8 | 3 | −3 | 13 | 270 | 272 | 6 |
| 16 | 2 | 11 | 107 | 106 | 5 | −22 | −4 | 12 | 154 | 155 | 10 | −28 | 0 | 12 | 50 | 60 | 8 | 5 | 3 | 12 | 175 | 184 | 8 | 5 | −3 | 13 | 366 | 367 | 10 |
| 18 | 2 | 11 | 75 | 60 | 7 | −20 | −4 | 12 | 79 | 73 | 11 | −26 | 0 | 12 | 117 | 111 | 7 | 7 | 3 | 12 | 148 | 145 | 5 | 7 | −3 | 13 | 186 | 188 | 7 |
| 20 | 2 | 11 | 111 | 103 | 6 | −18 | −4 | 12 | 167 | 149 | 7 | −24 | 0 | 12 | 95 | 96 | 8 | 9 | 3 | 12 | 109 | 107 | 5 | 9 | −3 | 13 | 154 | 161 | 6 |
| −25 | 3 | 11 | 121 | 126 | 15 | −16 | −4 | 12 | 214 | 212 | 6 | −22 | 0 | 12 | 205 | 187 | 9 | 11 | 3 | 12 | 120 | 117 | 5 | 11 | −3 | 13 | 179 | 175 | 7 |
| −23 | 3 | 11 | 75 | 69 | 6 | −14 | −4 | 12 | 154 | 149 | 7 | −20 | 0 | 12 | 246 | 288 | 10 | 13 | 3 | 12 | 122 | 132 | 6 | 13 | −3 | 13 | 115 | 97 | 6 |
| −21 | 3 | 11 | 64 | 64 | 7 | −12 | −4 | 12 | 191 | 202 | 7 | −18 | 0 | 12 | 57 | 47 | 11 | 15 | 3 | 12 | 182 | 179 | 7 | 15 | −3 | 13 | 174 | 161 | 7 |
| −19 | 3 | 11 | 203 | 190 | 8 | −10 | −4 | 12 | 158 | 172 | 6 | −16 | 0 | 12 | 365 | 405 | 9 | −22 | 4 | 12 | 155 | 156 | 7 | −26 | −2 | 13 | 178 | 185 | 10 |
| −17 | 3 | 11 | 164 | 159 | 8 | −8 | −4 | 12 | 251 | 298 | 16 | −14 | 0 | 12 | 281 | 307 | 6 | −20 | 4 | 12 | 67 | 74 | 7 | −24 | −2 | 13 | 203 | 215 | 11 |
| −15 | 3 | 11 | 229 | 232 | 10 | −6 | −4 | 12 | 247 | 265 | 10 | −12 | 0 | 12 | 419 | 479 | 7 | −18 | 4 | 12 | 156 | 149 | 8 | −22 | −2 | 13 | 233 | 224 | 10 |
| −13 | 3 | 11 | 259 | 259 | 7 | −4 | −4 | 12 | 169 | 170 | 10 | −10 | 0 | 12 | 395 | 408 | 7 | −16 | 4 | 12 | 211 | 213 | 9 | −20 | −2 | 13 | 222 | 226 | 10 |
| −11 | 3 | 11 | 149 | 158 | 6 | −2 | −4 | 12 | 235 | 252 | 9 | −8 | 0 | 12 | 193 | 216 | 4 | −14 | 4 | 12 | 139 | 150 | 8 | −18 | −2 | 13 | 73 | 67 | 6 |
| −9 | 3 | 11 | 348 | 390 | 7 | 0 | −4 | 12 | 250 | 269 | 7 | −6 | 0 | 12 | 116 | 94 | 3 | −12 | 4 | 12 | 177 | 201 | 7 | −16 | −2 | 13 | 309 | 315 | 7 |
| −7 | 3 | 11 | 112 | 111 | 4 | 2 | −4 | 12 | 235 | 265 | 6 | −4 | 0 | 12 | 226 | 264 | 4 | −10 | 4 | 12 | 172 | 173 | 6 | −14 | −2 | 13 | 419 | 413 | 9 |
| −5 | 3 | 11 | 118 | 120 | 3 | 4 | −4 | 12 | 267 | 286 | 10 | −2 | 0 | 12 | 400 | 386 | 7 | −8 | 4 | 12 | 264 | 297 | 8 | −12 | −2 | 13 | 148 | 137 | 5 |
| −3 | 3 | 11 | 312 | 296 | 5 | 6 | −4 | 12 | 56 | 60 | 12 | 0 | 0 | 12 | 534 | 511 | 8 | −6 | 4 | 12 | 256 | 265 | 6 | −10 | −2 | 13 | 359 | 370 | 7 |
| −1 | 3 | 11 | 293 | 318 | 5 | 8 | −4 | 12 | 197 | 206 | 8 | 2 | 0 | 12 | 85 | 93 | 3 | −4 | 4 | 12 | 167 | 169 | 5 | −8 | −2 | 13 | 186 | 207 | 4 |
| 1 | 3 | 11 | 195 | 211 | 5 | 10 | −4 | 12 | 141 | 151 | 7 | 4 | 0 | 12 | 137 | 148 | 4 | −2 | 4 | 12 | 235 | 252 | 8 | −6 | −2 | 13 | 351 | 355 | 7 |
| 3 | 3 | 11 | 349 | 398 | 7 | 12 | −4 | 12 | 98 | 95 | 6 | 6 | 0 | 12 | 286 | 317 | 6 | 0 | 4 | 12 | 243 | 269 | 8 | −4 | −2 | 13 | 116 | 103 | 4 |
| 5 | 3 | 11 | 150 | 157 | 4 | 14 | −4 | 12 | 156 | 153 | 6 | 8 | 0 | 12 | 69 | 70 | 7 | 2 | 4 | 12 | 206 | 265 | 6 | −2 | −2 | 13 | 288 | 309 | 5 |
| 7 | 3 | 11 | 288 | 312 | 6 | −25 | −3 | 12 | 140 | 141 | 9 | 10 | 0 | 12 | 335 | 344 | 9 | 4 | 4 | 12 | 275 | 286 | 9 | 0 | −2 | 13 | 316 | 316 | 5 |
| 9 | 3 | 11 | 120 | 116 | 5 | −23 | −3 | 12 | 87 | 102 | 12 | 12 | 0 | 12 | 344 | 317 | 12 | 6 | 4 | 12 | 50 | 61 | 10 | 2 | −2 | 13 | 254 | 245 | 5 |
| 11 | 3 | 11 | 208 | 209 | 5 | −21 | −3 | 12 | 147 | 152 | 11 | 14 | 0 | 12 | 148 | 150 | 5 | 8 | 4 | 12 | 199 | 206 | 6 | 4 | −2 | 13 | 92 | 85 | 5 |
| 13 | 3 | 11 | 233 | 212 | 6 | −19 | −3 | 12 | 121 | 125 | 7 | 16 | 0 | 12 | 218 | 204 | 6 | 10 | 4 | 12 | 154 | 151 | 6 | 6 | −2 | 13 | 169 | 153 | 7 |
| 15 | 3 | 11 | 68 | 58 | 6 | −17 | −3 | 12 | 39 | 35 | 12 | 18 | 0 | 12 | 215 | 171 | 6 | 12 | 4 | 12 | 110 | 96 | 6 | 8 | −2 | 13 | 345 | 331 | 17 |
| 17 | 3 | 11 | 158 | 131 | 6 | −15 | −3 | 12 | 420 | 439 | 11 | 20 | 0 | 12 | 48 | 40 | 13 | −17 | 5 | 12 | 76 | 61 | 7 | 10 | −2 | 13 | 180 | 180 | 8 |
| −22 | 4 | 11 | 230 | 237 | 9 | −13 | −3 | 12 | 254 | 281 | 8 | −27 | 1 | 12 | 243 | 239 | 14 | −15 | 5 | 12 | 102 | 88 | 7 | 12 | −2 | 13 | 220 | 193 | 8 |
| −20 | 4 | 11 | 107 | 105 | 7 | −11 | −3 | 12 | 237 | 256 | 6 | −25 | 1 | 12 | 205 | 200 | 8 | −13 | 5 | 12 | 133 | 130 | 8 | 14 | −2 | 13 | 38 | 45 | 15 |
| −18 | 4 | 11 | 155 | 150 | 8 | −9 | −3 | 12 | 297 | 316 | 9 | −23 | 1 | 12 | 235 | 242 | 9 | −11 | 5 | 12 | 256 | 278 | 10 | 16 | −2 | 13 | 211 | 188 | 7 |
| −16 | 4 | 11 | 204 | 218 | 9 | −7 | −3 | 12 | 89 | 104 | 7 | −21 | 1 | 12 | 424 | 442 | 15 | −9 | 5 | 12 | 72 | 74 | 5 | −27 | −1 | 13 | 75 | 92 | 8 |
| −14 | 4 | 11 | 90 | 104 | 8 | −5 | −3 | 12 | 171 | 177 | 5 | −19 | 1 | 12 | 237 | 265 | 7 | −7 | 5 | 12 | 242 | 247 | 6 | −25 | −1 | 13 | 20 | 41 | 20 |
| −12 | 4 | 11 | 178 | 215 | 7 | −3 | −3 | 12 | 294 | 288 | 7 | −17 | 1 | 12 | 119 | 101 | 6 | −5 | 5 | 12 | 174 | 182 | 5 | −23 | −1 | 13 | 47 | 22 | 14 |
| −10 | 4 | 11 | 166 | 187 | 7 | −1 | −3 | 12 | 376 | 388 | 7 | −15 | 1 | 12 | 387 | 402 | 8 | −3 | 5 | 12 | 165 | 166 | 8 | −21 | −1 | 13 | 132 | 148 | 9 |
| −8 | 4 | 11 | 201 | 234 | 5 | 1 | −3 | 12 | 293 | 314 | 6 | −13 | 1 | 12 | 95 | 98 | 5 | −1 | 5 | 12 | 133 | 143 | 6 | −19 | −1 | 13 | 94 | 101 | 9 |
| −6 | 4 | 11 | 41 | 33 | 8 | 3 | −3 | 12 | 253 | 257 | 6 | −11 | 1 | 12 | 368 | 369 | 11 | 1 | 5 | 12 | 121 | 125 | 6 | −17 | −1 | 13 | 131 | 141 | 6 |
| −4 | 4 | 11 | 172 | 187 | 5 | 5 | −3 | 12 | 177 | 185 | 7 | −9 | 1 | 12 | 260 | 286 | 5 | 3 | 5 | 12 | 117 | 116 | 5 | −15 | −1 | 13 | 154 | 170 | 5 |
| −2 | 4 | 11 | 265 | 251 | 8 | 7 | −3 | 12 | 132 | 144 | 8 | −7 | 1 | 12 | 185 | 189 | 4 | 5 | 5 | 12 | 41 | 36 | 10 | −13 | −1 | 13 | 295 | 307 | 6 |
| 0 | 4 | 11 | 167 | 230 | 6 | 9 | −3 | 12 | 95 | 107 | 8 | −5 | 1 | 12 | 18 | 19 | 18 | 7 | 5 | 12 | 99 | 93 | 4 | −11 | −1 | 13 | 429 | 439 | 9 |
| 2 | 4 | 11 | 98 | 127 | 5 | 11 | −3 | 12 | 106 | 116 | 8 | −3 | 1 | 12 | 38 | 34 | 6 | 9 | 5 | 12 | 115 | 112 | 5 | −9 | −1 | 13 | 88 | 81 | 4 |

TABLE 8-continued

| Observed and calculated structure factors for SAG-2 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| 4 | 4 | 11 | 142 | 158 | 6 | 13 | −3 | 12 | 126 | 133 | 7 | −1 | 1 | 12 | 344 | 359 | 6 | −8 | 6 | 12 | 156 | 152 | 12 | −7 | −1 | 13 | 123 | 123 | 4 |
| −5 | −1 | 13 | 242 | 229 | 5 | −11 | 3 | 13 | 223 | 219 | 9 | −20 | −2 | 14 | 71 | 87 | 12 | −14 | 2 | 14 | 150 | 147 | 7 | 3 | −3 | 15 | 278 | 260 | 6 |
| −3 | −1 | 13 | 366 | 357 | 7 | −9 | 3 | 13 | 187 | 195 | 5 | −18 | −2 | 14 | 270 | 261 | 6 | −12 | 2 | 14 | 56 | 51 | 7 | 5 | −3 | 15 | 114 | 109 | 8 |
| −1 | −1 | 13 | 365 | 368 | 6 | −7 | 3 | 13 | 195 | 201 | 5 | −16 | −2 | 14 | 155 | 152 | 6 | −10 | 2 | 14 | 128 | 125 | 4 | 7 | −3 | 15 | 42 | 47 | 14 |
| 1 | −1 | 13 | 392 | 402 | 6 | −5 | 3 | 13 | 156 | 146 | 5 | −14 | −2 | 14 | 151 | 145 | 5 | −8 | 2 | 14 | 291 | 286 | 7 | 9 | −3 | 15 | 175 | 181 | 8 |
| 3 | −1 | 13 | 148 | 152 | 3 | −3 | 3 | 13 | 133 | 149 | 5 | −12 | −2 | 14 | 50 | 51 | 8 | −6 | 2 | 14 | 188 | 194 | 5 | 11 | −3 | 15 | 87 | 68 | 9 |
| 5 | −1 | 13 | 397 | 385 | 11 | −1 | 3 | 13 | 56 | 63 | 7 | −10 | −2 | 14 | 132 | 124 | 5 | −4 | 2 | 14 | 77 | 75 | 5 | −24 | −2 | 15 | 99 | 94 | 9 |
| 7 | −1 | 13 | 126 | 124 | 6 | 1 | 3 | 13 | 218 | 227 | 7 | −8 | −2 | 14 | 289 | 285 | 7 | −2 | 2 | 14 | 299 | 300 | 7 | −22 | −2 | 15 | 168 | 159 | 8 |
| 9 | −1 | 13 | 75 | 68 | 8 | 3 | 3 | 13 | 263 | 270 | 10 | −6 | −2 | 14 | 180 | 196 | 6 | 0 | 2 | 14 | 212 | 203 | 6 | −20 | −2 | 15 | 120 | 111 | 8 |
| 11 | −1 | 13 | 348 | 342 | 13 | 5 | 3 | 13 | 347 | 367 | 11 | −4 | −2 | 14 | 83 | 73 | 6 | 2 | 2 | 14 | 149 | 143 | 5 | −18 | −2 | 15 | 156 | 145 | 7 |
| 13 | −1 | 13 | 128 | 110 | 7 | 7 | 3 | 13 | 180 | 188 | 6 | −2 | −2 | 14 | 322 | 300 | 7 | 4 | 2 | 14 | 215 | 234 | 6 | −16 | −2 | 15 | 120 | 117 | 6 |
| 15 | −1 | 13 | 0 | 16 | 1 | 9 | 3 | 13 | 161 | 162 | 6 | 0 | −2 | 14 | 218 | 202 | 5 | 6 | 2 | 14 | 201 | 209 | 6 | −14 | −2 | 15 | 336 | 331 | 9 |
| 17 | −1 | 13 | 28 | 26 | 27 | 11 | 3 | 13 | 185 | 174 | 5 | 2 | −2 | 14 | 147 | 143 | 4 | 8 | 2 | 14 | 41 | 53 | 10 | −12 | −2 | 15 | 116 | 103 | 5 |
| −28 | 0 | 13 | 0 | 40 | 1 | 13 | 3 | 13 | 108 | 96 | 7 | 4 | −2 | 14 | 231 | 233 | 5 | 10 | 2 | 14 | 0 | 26 | 1 | −10 | −2 | 15 | 70 | 70 | 8 |
| −26 | 0 | 13 | 147 | 131 | 7 | −20 | 4 | 13 | 100 | 103 | 6 | 6 | −2 | 14 | 221 | 208 | 7 | 12 | 2 | 14 | 56 | 48 | 9 | −8 | −2 | 15 | 309 | 295 | 11 |
| −24 | 0 | 13 | 32 | 30 | 32 | −18 | 4 | 13 | 46 | 52 | 9 | 8 | −2 | 14 | 38 | 53 | 18 | 14 | 2 | 14 | 32 | 27 | 18 | −6 | −2 | 15 | 288 | 298 | 12 |
| −22 | 0 | 13 | 98 | 87 | 8 | −16 | 4 | 13 | 137 | 132 | 8 | 10 | −2 | 14 | 20 | 27 | 20 | −23 | 3 | 14 | 89 | 105 | 6 | −4 | −2 | 15 | 149 | 148 | 6 |
| −20 | 0 | 13 | 22 | 46 | 22 | −14 | 4 | 13 | 77 | 70 | 9 | 12 | −2 | 14 | 41 | 48 | 15 | −21 | 3 | 14 | 98 | 88 | 6 | −2 | −2 | 15 | 386 | 368 | 8 |
| −18 | 0 | 13 | 28 | 2 | 27 | −12 | 4 | 13 | 124 | 136 | 5 | 14 | −2 | 14 | 33 | 27 | 18 | −19 | 3 | 14 | 88 | 91 | 7 | 0 | −2 | 15 | 444 | 402 | 9 |
| −16 | 0 | 13 | 81 | 83 | 6 | −10 | 4 | 13 | 142 | 159 | 9 | −25 | −1 | 14 | 158 | 147 | 8 | −17 | 3 | 14 | 17 | 28 | 16 | 2 | −2 | 15 | 90 | 90 | 5 |
| −14 | 0 | 13 | 117 | 129 | 5 | −8 | 4 | 13 | 179 | 184 | 5 | −23 | −1 | 14 | 137 | 136 | 8 | −15 | 3 | 14 | 35 | 44 | 16 | 4 | −2 | 15 | 77 | 55 | 5 |
| −12 | 0 | 13 | 649 | 692 | 12 | −6 | 4 | 13 | 200 | 212 | 5 | −21 | −1 | 14 | 240 | 246 | 10 | −13 | 3 | 14 | 133 | 132 | 5 | 6 | −2 | 15 | 102 | 94 | 7 |
| −10 | 0 | 13 | 263 | 273 | 5 | −4 | 4 | 13 | 37 | 49 | 15 | −19 | −1 | 14 | 134 | 141 | 9 | −11 | 3 | 14 | 312 | 320 | 11 | 8 | −2 | 15 | 156 | 155 | 8 |
| −8 | 0 | 13 | 77 | 84 | 4 | −2 | 4 | 13 | 179 | 198 | 7 | −17 | −1 | 14 | 138 | 151 | 5 | −9 | 3 | 14 | 58 | 55 | 6 | 10 | −2 | 15 | 218 | 192 | 7 |
| −6 | 0 | 13 | 108 | 109 | 4 | 0 | 4 | 13 | 259 | 288 | 7 | −15 | −1 | 14 | 151 | 152 | 4 | −7 | 3 | 14 | 123 | 119 | 5 | 12 | −2 | 15 | 142 | 135 | 7 |
| −4 | 0 | 13 | 403 | 398 | 6 | 2 | 4 | 13 | 77 | 81 | 6 | −13 | −1 | 14 | 260 | 253 | 6 | −5 | 3 | 14 | 24 | 16 | 24 | −25 | −1 | 15 | 123 | 117 | 7 |
| −2 | 0 | 13 | 147 | 156 | 4 | 4 | 4 | 13 | 166 | 164 | 6 | −11 | −1 | 14 | 332 | 329 | 9 | −3 | 3 | 14 | 459 | 468 | 14 | −23 | −1 | 15 | 64 | 42 | 10 |
| 0 | 0 | 13 | 97 | 110 | 4 | 6 | 4 | 13 | 191 | 184 | 6 | −9 | −1 | 14 | 290 | 293 | 6 | −1 | 3 | 14 | 155 | 173 | 7 | −21 | −1 | 15 | 76 | 78 | 10 |
| 2 | 0 | 13 | 489 | 468 | 8 | 8 | 4 | 13 | 69 | 73 | 6 | −7 | −1 | 14 | 288 | 269 | 5 | 1 | 3 | 14 | 378 | 389 | 11 | −19 | −1 | 15 | 105 | 93 | 7 |
| 4 | 0 | 13 | 77 | 70 | 4 | 10 | 4 | 13 | 88 | 85 | 4 | −5 | −1 | 14 | 318 | 320 | 7 | 3 | 3 | 14 | 154 | 164 | 5 | −17 | −1 | 15 | 124 | 133 | 6 |
| 6 | 0 | 13 | 419 | 442 | 10 | 12 | 4 | 13 | 131 | 134 | 6 | −3 | −1 | 14 | 188 | 189 | 4 | 5 | 3 | 14 | 230 | 233 | 6 | −15 | −1 | 15 | 293 | 291 | 9 |
| 8 | 0 | 13 | 373 | 444 | 17 | −15 | 5 | 13 | 72 | 74 | 8 | −1 | −1 | 14 | 159 | 163 | 4 | 7 | 3 | 14 | 108 | 110 | 6 | −13 | −1 | 15 | 89 | 90 | 5 |
| 10 | 0 | 13 | 97 | 96 | 7 | −13 | 5 | 13 | 29 | 28 | 25 | 1 | −1 | 14 | 411 | 407 | 8 | 9 | 3 | 14 | 180 | 177 | 6 | −11 | −1 | 15 | 107 | 101 | 5 |
| 12 | 0 | 13 | 214 | 177 | 8 | −11 | 5 | 13 | 52 | 52 | 9 | 3 | −1 | 14 | 198 | 188 | 5 | 11 | 3 | 14 | 120 | 113 | 6 | −9 | −1 | 15 | 94 | 81 | 5 |
| 14 | 0 | 13 | 0 | 19 | 1 | −9 | 5 | 13 | 162 | 158 | 5 | 5 | −1 | 14 | 227 | 216 | 6 | 13 | 3 | 14 | 122 | 111 | 7 | −7 | −1 | 15 | 244 | 255 | 8 |
| 16 | 0 | 13 | 161 | 140 | 8 | −7 | 5 | 13 | 349 | 371 | 11 | 7 | −1 | 14 | 63 | 64 | 9 | −20 | 4 | 14 | 139 | 150 | 7 | −5 | −1 | 15 | 102 | 118 | 5 |
| 18 | 0 | 13 | 38 | 12 | 19 | −5 | 5 | 13 | 140 | 154 | 5 | 9 | −1 | 14 | 85 | 84 | 8 | −18 | 4 | 14 | 156 | 153 | 7 | −3 | −1 | 15 | 395 | 384 | 8 |
| −27 | 1 | 13 | 94 | 91 | 16 | −3 | 5 | 13 | 126 | 133 | 6 | 11 | −1 | 14 | 106 | 110 | 7 | −16 | 4 | 14 | 217 | 216 | 9 | −1 | −1 | 15 | 294 | 285 | 7 |
| −25 | 1 | 13 | 35 | 41 | 12 | −1 | 5 | 13 | 102 | 112 | 6 | 13 | −1 | 14 | 162 | 155 | 7 | −14 | 4 | 14 | 80 | 66 | 8 | 1 | −1 | 15 | 333 | 317 | 7 |
| −23 | 1 | 13 | 65 | 20 | 30 | 1 | 5 | 13 | 96 | 95 | 7 | 15 | −1 | 14 | 175 | 147 | 6 | −12 | 4 | 14 | 113 | 111 | 8 | 3 | −1 | 15 | 90 | 89 | 5 |
| −21 | 1 | 13 | 142 | 148 | 6 | 3 | 5 | 13 | 42 | 51 | 13 | −26 | 0 | 14 | 108 | 96 | 7 | −10 | 4 | 14 | 97 | 90 | 5 | 5 | −1 | 15 | 206 | 208 | 5 |
| −19 | 1 | 13 | 103 | 101 | 6 | 5 | 5 | 13 | 49 | 53 | 6 | −24 | 0 | 14 | 375 | 360 | 13 | −8 | 4 | 14 | 169 | 168 | 4 | 7 | −1 | 15 | 352 | 335 | 11 |
| −17 | 1 | 13 | 149 | 142 | 6 | 7 | 5 | 13 | 96 | 95 | 8 | −22 | 0 | 14 | 181 | 160 | 8 | −6 | 4 | 14 | 72 | 83 | 6 | 9 | −1 | 15 | 334 | 302 | 9 |
| −15 | 1 | 13 | 162 | 169 | 6 | −13 | −5 | 14 | 184 | 178 | 7 | −20 | 0 | 14 | 191 | 199 | 7 | −4 | 4 | 14 | 92 | 104 | 6 | 11 | −1 | 15 | 23 | 36 | 22 |
| −13 | 1 | 13 | 300 | 309 | 7 | −11 | −5 | 14 | 238 | 222 | 8 | −18 | 0 | 14 | 121 | 147 | 7 | −2 | 4 | 14 | 232 | 245 | 8 | 13 | −1 | 15 | 34 | 26 | 16 |
| −11 | 1 | 13 | 421 | 437 | 12 | −9 | −5 | 14 | 236 | 232 | 8 | −16 | 0 | 14 | 318 | 408 | 9 | 0 | 4 | 14 | 223 | 216 | 6 | 15 | −1 | 15 | 0 | 47 | 1 |
| −9 | 1 | 13 | 81 | 81 | 4 | −7 | −5 | 14 | 138 | 131 | 6 | −14 | 0 | 14 | 16 | 11 | 15 | 2 | 4 | 14 | 160 | 154 | 5 | −26 | 0 | 15 | 129 | 119 | 14 |
| −7 | 1 | 13 | 120 | 124 | 4 | −5 | −5 | 14 | 173 | 157 | 5 | −12 | 0 | 14 | 146 | 131 | 4 | 4 | 4 | 14 | 81 | 75 | 6 | −24 | 0 | 15 | 31 | 25 | 30 |
| −5 | 1 | 13 | 240 | 230 | 4 | −3 | −5 | 14 | 239 | 244 | 7 | −10 | 0 | 14 | 115 | 99 | 4 | 6 | 4 | 14 | 95 | 99 | 5 | −22 | 0 | 15 | 87 | 86 | 8 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −3 | 1 | 13 | 363 | 357 | 6 | −1 | −5 | 14 | 99 | 102 | 5 | −8 | 0 | 14 | 12 | 28 | 12 | 8 | 4 | 14 | 130 | 127 | 5 | −20 | 0 | 15 | 0 | 10 | 1 |
| −1 | 1 | 13 | 358 | 367 | 6 | 1 | −5 | 14 | 188 | 191 | 13 | −6 | 0 | 14 | 264 | 275 | 5 | 10 | 4 | 14 | 56 | 49 | 9 | −18 | 0 | 15 | 81 | 75 | 8 |
| 1 | 1 | 13 | 381 | 402 | 6 | 3 | −5 | 14 | 121 | 131 | 12 | −4 | 0 | 14 | 29 | 16 | 12 | −13 | 5 | 14 | 176 | 178 | 10 | −16 | 0 | 15 | 155 | 176 | 5 |
| 3 | 1 | 13 | 138 | 152 | 4 | −18 | −4 | 14 | 166 | 152 | 7 | −2 | 0 | 14 | 187 | 202 | 4 | −9 | 5 | 14 | 207 | 230 | 17 | −14 | 0 | 15 | 239 | 230 | 10 |
| 5 | 1 | 13 | 393 | 385 | 9 | −16 | −4 | 14 | 231 | 215 | 7 | 0 | 0 | 14 | 257 | 235 | 5 | −7 | 5 | 14 | 126 | 132 | 6 | −12 | 0 | 15 | 235 | 228 | 6 |
| 7 | 1 | 13 | 124 | 125 | 5 | −14 | −4 | 14 | 71 | 67 | 8 | 2 | 0 | 14 | 690 | 706 | 14 | −5 | 5 | 14 | 155 | 157 | 5 | −10 | 0 | 15 | 18 | 9 | 18 |
| 9 | 1 | 13 | 76 | 68 | 8 | −12 | −4 | 14 | 122 | 111 | 7 | 4 | 0 | 14 | 955 | 953 | 18 | −3 | 5 | 14 | 217 | 244 | 7 | −8 | 0 | 15 | 241 | 241 | 7 |
| 11 | 1 | 13 | 396 | 342 | 15 | −10 | −4 | 14 | 93 | 90 | 8 | 6 | 0 | 14 | 293 | 274 | 7 | −1 | 5 | 14 | 101 | 103 | 6 | −6 | 0 | 15 | 102 | 107 | 5 |
| 13 | 1 | 13 | 129 | 110 | 5 | −8 | −4 | 14 | 185 | 169 | 6 | 8 | 0 | 14 | 61 | 72 | 9 | 1 | 5 | 14 | 189 | 190 | 7 | −4 | 0 | 15 | 293 | 312 | 6 |
| 15 | 1 | 13 | 20 | 15 | 19 | −6 | −4 | 14 | 91 | 83 | 6 | 10 | 0 | 14 | 202 | 185 | 8 | 3 | 5 | 14 | 128 | 130 | 6 | −2 | 0 | 15 | 908 | 892 | 19 |
| 17 | 1 | 13 | 0 | 25 | 1 | −4 | −4 | 14 | 99 | 104 | 6 | 12 | 0 | 14 | 16 | 2 | 15 | −9 | −5 | 15 | 92 | 89 | 6 | 0 | 0 | 15 | 284 | 247 | 6 |
| −26 | 2 | 13 | 169 | 186 | 13 | −2 | −4 | 14 | 250 | 245 | 7 | 14 | 0 | 14 | 65 | 44 | 8 | −7 | −5 | 15 | 194 | 180 | 7 | 2 | 0 | 15 | 87 | 81 | 5 |
| −24 | 2 | 13 | 199 | 216 | 7 | 0 | −4 | 14 | 222 | 216 | 6 | 16 | 0 | 14 | 54 | 44 | 9 | −5 | −5 | 15 | 103 | 112 | 8 | 4 | 0 | 15 | 228 | 228 | 5 |
| −22 | 2 | 13 | 233 | 224 | 8 | 2 | −4 | 14 | 155 | 155 | 6 | −25 | 1 | 14 | 153 | 148 | 7 | −3 | −5 | 15 | 245 | 224 | 14 | 6 | 0 | 15 | 116 | 101 | 5 |
| −20 | 2 | 13 | 234 | 226 | 8 | 4 | −4 | 14 | 67 | 75 | 8 | −23 | 1 | 14 | 134 | 134 | 7 | −1 | −5 | 15 | 94 | 91 | 12 | 8 | 0 | 15 | 212 | 188 | 7 |
| −18 | 2 | 13 | 61 | 65 | 8 | 6 | −4 | 14 | 97 | 99 | 7 | −21 | 1 | 14 | 237 | 245 | 8 | −16 | −4 | 15 | 178 | 167 | 8 | 10 | 0 | 15 | 200 | 163 | 8 |
| −16 | 2 | 13 | 299 | 314 | 12 | 8 | −4 | 14 | 127 | 125 | 6 | −19 | 1 | 14 | 136 | 141 | 7 | −14 | −4 | 15 | 125 | 124 | 5 | 12 | 0 | 15 | 27 | 4 | 27 |
| −14 | 2 | 13 | 399 | 414 | 12 | 10 | −4 | 14 | 31 | 48 | 31 | −17 | 1 | 14 | 143 | 152 | 6 | −12 | −4 | 15 | 107 | 94 | 6 | 14 | 0 | 15 | 18 | 28 | 18 |
| −12 | 2 | 13 | 142 | 137 | 6 | −23 | −3 | 14 | 91 | 105 | 9 | −15 | 1 | 14 | 147 | 151 | 5 | −10 | −4 | 15 | 132 | 109 | 6 | −25 | 1 | 15 | 115 | 116 | 6 |
| −10 | 2 | 13 | 355 | 370 | 6 | −21 | −3 | 14 | 96 | 87 | 10 | −13 | 1 | 14 | 247 | 253 | 7 | −8 | −4 | 15 | 120 | 117 | 6 | −23 | 1 | 15 | 49 | 42 | 9 |
| −8 | 2 | 13 | 184 | 208 | 5 | −19 | −3 | 14 | 66 | 92 | 13 | −11 | 1 | 14 | 331 | 329 | 7 | −6 | −4 | 15 | 194 | 183 | 6 | −21 | 1 | 15 | 86 | 79 | 7 |
| −6 | 2 | 13 | 344 | 355 | 6 | −17 | −3 | 14 | 0 | 28 | 1 | −9 | 1 | 14 | 277 | 293 | 9 | −4 | −4 | 15 | 138 | 126 | 6 | −19 | 1 | 15 | 101 | 93 | 7 |
| −4 | 2 | 13 | 99 | 103 | 3 | −15 | −3 | 14 | 41 | 44 | 10 | −7 | 1 | 14 | 273 | 269 | 6 | −2 | −4 | 15 | 78 | 78 | 7 | −17 | 1 | 15 | 126 | 133 | 7 |
| −2 | 2 | 13 | 274 | 307 | 5 | −13 | −3 | 14 | 143 | 132 | 6 | −5 | 1 | 14 | 311 | 320 | 6 | 0 | −4 | 15 | 157 | 152 | 7 | −15 | 1 | 15 | 277 | 292 | 7 |
| 0 | 2 | 13 | 307 | 317 | 6 | −11 | −3 | 14 | 315 | 321 | 11 | −3 | 1 | 14 | 180 | 190 | 4 | 2 | −4 | 15 | 65 | 66 | 7 | −13 | 1 | 15 | 84 | 89 | 6 |
| 2 | 2 | 13 | 253 | 245 | 6 | −9 | −3 | 14 | 53 | 54 | 9 | −1 | 1 | 14 | 155 | 163 | 4 | 4 | −4 | 15 | 122 | 121 | 7 | −11 | 1 | 15 | 108 | 102 | 5 |
| 4 | 2 | 13 | 93 | 85 | 5 | −7 | −3 | 14 | 104 | 119 | 8 | 1 | 1 | 14 | 400 | 406 | 10 | 6 | −4 | 15 | 120 | 115 | 9 | −9 | 1 | 15 | 77 | 81 | 8 |
| 6 | 2 | 13 | 160 | 152 | 5 | −5 | −3 | 14 | 29 | 16 | 28 | 3 | 1 | 14 | 195 | 188 | 7 | −21 | −3 | 15 | 124 | 121 | 10 | −7 | 1 | 15 | 247 | 255 | 8 |
| 8 | 2 | 13 | 334 | 332 | 8 | −3 | −3 | 14 | 476 | 470 | 11 | 5 | 1 | 14 | 211 | 215 | 5 | −19 | −3 | 15 | 58 | 58 | 14 | −5 | 1 | 15 | 118 | 117 | 6 |
| 10 | 2 | 13 | 194 | 180 | 8 | −1 | −3 | 14 | 177 | 175 | 5 | 7 | 1 | 14 | 57 | 65 | 6 | −17 | −3 | 15 | 15 | 38 | 15 | −3 | 1 | 15 | 401 | 384 | 11 |
| 12 | 2 | 13 | 214 | 192 | 7 | 1 | −3 | 14 | 404 | 390 | 8 | 9 | 1 | 14 | 94 | 84 | 7 | −15 | −3 | 15 | 157 | 151 | 5 | −1 | 1 | 15 | 293 | 285 | 8 |
| 14 | 2 | 13 | 31 | 45 | 17 | 3 | −3 | 14 | 158 | 164 | 5 | 11 | 1 | 14 | 116 | 110 | 6 | −13 | −3 | 15 | 29 | 29 | 28 | 1 | 1 | 15 | 334 | 317 | 9 |
| 16 | 2 | 13 | 213 | 188 | 8 | 5 | −3 | 14 | 240 | 234 | 7 | 13 | 1 | 14 | 156 | 153 | 5 | −11 | −3 | 15 | 240 | 227 | 8 | 3 | 1 | 15 | 104 | 91 | 5 |
| −23 | 3 | 13 | 232 | 228 | 9 | 7 | −3 | 14 | 104 | 111 | 7 | 15 | 1 | 14 | 186 | 148 | 8 | −9 | −3 | 15 | 65 | 61 | 9 | 5 | 1 | 15 | 206 | 207 | 6 |
| −21 | 3 | 13 | 200 | 206 | 9 | 9 | −3 | 14 | 189 | 178 | 6 | −24 | 2 | 14 | 36 | 38 | 9 | −7 | −3 | 15 | 130 | 125 | 6 | 7 | 1 | 15 | 344 | 334 | 7 |
| −19 | 3 | 13 | 53 | 57 | 9 | 11 | −3 | 14 | 128 | 112 | 6 | −22 | 2 | 14 | 25 | 27 | 25 | −5 | −3 | 15 | 498 | 482 | 12 | 9 | 1 | 15 | 334 | 302 | 9 |
| −17 | 3 | 13 | 216 | 218 | 9 | 13 | −3 | 14 | 125 | 110 | 6 | −20 | 2 | 14 | 88 | 87 | 6 | −3 | −3 | 15 | 225 | 214 | 6 | 11 | 1 | 15 | 48 | 35 | 10 |
| −15 | 3 | 13 | 55 | 65 | 9 | −24 | −2 | 14 | 52 | 37 | 14 | −18 | 2 | 14 | 263 | 260 | 8 | −1 | −3 | 15 | 171 | 171 | 5 | 13 | 1 | 15 | 48 | 26 | 8 |
| −13 | 3 | 13 | 198 | 211 | 6 | −22 | −2 | 14 | 0 | 27 | 1 | −16 | 2 | 14 | 134 | 152 | 7 | 1 | −3 | 15 | 231 | 229 | 6 | 15 | 1 | 15 | 42 | 46 | 15 |
| −24 | 2 | 15 | 106 | 93 | 7 | 0 | −2 | 16 | 212 | 190 | 5 | −1 | 3 | 16 | 116 | 100 | 6 | −3 | 1 | 17 | 258 | 241 | 6 | −13 | 1 | 18 | 93 | 93 | 5 |
| −22 | 2 | 15 | 175 | 160 | 6 | 2 | −2 | 16 | 132 | 116 | 5 | 1 | 3 | 16 | 150 | 143 | 5 | −1 | 1 | 17 | 58 | 59 | 7 | −11 | 1 | 18 | 105 | 118 | 4 |
| −20 | 2 | 15 | 114 | 110 | 6 | 4 | −2 | 16 | 46 | 31 | 11 | 3 | 3 | 16 | 205 | 196 | 5 | 1 | 1 | 17 | 210 | 191 | 5 | −9 | 1 | 18 | 206 | 196 | 6 |
| −18 | 2 | 15 | 150 | 144 | 6 | 6 | −2 | 16 | 205 | 193 | 6 | 5 | 3 | 16 | 223 | 212 | 6 | 3 | 1 | 17 | 260 | 236 | 6 | −7 | 1 | 18 | 364 | 317 | 10 |
| −16 | 2 | 15 | 110 | 118 | 7 | 8 | −2 | 16 | 242 | 225 | 9 | 7 | 3 | 16 | 107 | 98 | 5 | 5 | 1 | 17 | 307 | 274 | 7 | −5 | 1 | 18 | 122 | 122 | 6 |
| −14 | 2 | 15 | 312 | 331 | 8 | 10 | −2 | 16 | 38 | 34 | 13 | −14 | 4 | 16 | 126 | 129 | 7 | 7 | 1 | 17 | 53 | 50 | 8 | −3 | 1 | 18 | 196 | 174 | 6 |
| −12 | 2 | 15 | 122 | 104 | 6 | −23 | −1 | 16 | 188 | 174 | 8 | −12 | 4 | 16 | 119 | 110 | 7 | 9 | 1 | 17 | 82 | 70 | 7 | −1 | 1 | 18 | 55 | 49 | 7 |
| −10 | 2 | 15 | 74 | 71 | 5 | −21 | −1 | 16 | 112 | 111 | 8 | −10 | 4 | 16 | 100 | 110 | 7 | −20 | 2 | 17 | 133 | 128 | 6 | 1 | 1 | 18 | 87 | 76 | 5 |
| −8 | 2 | 15 | 291 | 296 | 8 | −19 | −1 | 16 | 176 | 158 | 7 | −8 | 4 | 16 | 62 | 76 | 12 | −18 | 2 | 17 | 239 | 240 | 8 | 3 | 1 | 18 | 75 | 61 | 5 |
| −6 | 2 | 15 | 293 | 299 | 8 | −17 | −1 | 16 | 15 | 14 | 15 | −6 | 4 | 16 | 53 | 60 | 7 | −16 | 2 | 17 | 19 | 12 | 18 | 5 | 1 | 18 | 266 | 233 | 6 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −4 | 2 | 15 | 154 | 148 | 5 | −15 | −1 | 16 | 100 | 106 | 6 | −4 | 4 | 16 | 56 | 60 | 8 | −14 | 2 | 17 | 192 | 195 | 7 | 7 | 1 | 18 | 147 | 125 | 7 |
| −2 | 2 | 15 | 362 | 368 | 10 | −13 | −1 | 16 | 161 | 148 | 5 | −2 | 4 | 16 | 109 | 110 | 5 | −12 | 2 | 17 | 44 | 22 | 8 | −18 | 2 | 18 | 54 | 56 | 7 |
| 0 | 2 | 15 | 422 | 402 | 13 | −11 | −1 | 16 | 101 | 93 | 5 | 0 | 4 | 16 | 148 | 135 | 5 | −10 | 2 | 17 | 215 | 194 | 5 | −16 | 2 | 18 | 198 | 197 | 7 |
| 2 | 2 | 15 | 93 | 90 | 5 | −9 | −1 | 16 | 123 | 103 | 7 | 2 | 4 | 16 | 181 | 185 | 7 | −8 | 2 | 17 | 192 | 189 | 6 | −14 | 2 | 18 | 53 | 33 | 8 |
| 4 | 2 | 15 | 72 | 56 | 7 | −7 | −1 | 16 | 126 | 132 | 5 | 4 | 4 | 16 | 121 | 120 | 9 | −6 | 2 | 17 | 235 | 229 | 6 | −12 | 2 | 18 | 115 | 125 | 5 |
| 6 | 2 | 15 | 97 | 92 | 5 | −5 | −1 | 16 | 394 | 370 | 21 | −10 | −4 | 17 | 47 | 53 | 9 | −4 | 2 | 17 | 94 | 82 | 6 | −10 | 2 | 18 | 167 | 166 | 7 |
| 8 | 2 | 15 | 148 | 154 | 6 | −3 | −1 | 16 | 251 | 246 | 6 | −8 | −4 | 17 | 12 | 31 | 12 | −2 | 2 | 17 | 98 | 94 | 6 | −8 | 2 | 18 | 54 | 67 | 8 |
| 10 | 2 | 15 | 216 | 193 | 9 | −1 | −1 | 16 | 67 | 62 | 6 | −6 | −4 | 17 | 67 | 52 | 7 | 0 | 2 | 17 | 170 | 161 | 5 | −6 | 2 | 18 | 173 | 162 | 7 |
| 12 | 2 | 15 | 134 | 135 | 6 | 1 | −1 | 16 | 239 | 231 | 6 | −4 | −4 | 17 | 103 | 79 | 7 | 2 | 2 | 17 | 48 | 42 | 9 | −4 | 2 | 18 | 116 | 110 | 6 |
| −21 | 3 | 15 | 122 | 122 | 6 | 3 | −1 | 16 | 85 | 79 | 6 | −15 | −3 | 17 | 49 | 52 | 12 | 4 | 2 | 17 | 82 | 68 | 6 | −2 | 2 | 18 | 27 | 2 | 26 |
| −19 | 3 | 15 | 62 | 58 | 8 | 5 | −1 | 16 | 163 | 143 | 5 | −13 | −3 | 17 | 113 | 112 | 5 | 6 | 2 | 17 | 171 | 148 | 5 | 0 | 2 | 18 | 76 | 75 | 7 |
| −17 | 3 | 15 | 20 | 37 | 20 | 7 | −1 | 16 | 110 | 105 | 6 | −11 | −3 | 17 | 140 | 117 | 6 | 8 | 2 | 17 | 129 | 124 | 7 | 2 | 2 | 18 | 98 | 90 | 4 |
| −15 | 3 | 15 | 159 | 149 | 8 | 9 | −1 | 16 | 157 | 137 | 6 | −9 | −3 | 17 | 90 | 85 | 7 | −17 | 3 | 17 | 76 | 80 | 6 | 4 | 2 | 18 | 259 | 237 | 7 |
| −13 | 3 | 15 | 26 | 28 | 25 | 11 | −1 | 16 | 271 | 231 | 9 | −7 | −3 | 17 | 41 | 35 | 14 | −15 | 3 | 17 | 51 | 53 | 8 | −9 | 3 | 18 | 103 | 97 | 6 |
| −11 | 3 | 15 | 222 | 228 | 8 | −24 | 0 | 16 | 151 | 125 | 7 | −5 | −3 | 17 | 87 | 78 | 6 | −13 | 3 | 17 | 101 | 111 | 7 | −7 | 3 | 18 | 65 | 63 | 6 |
| −9 | 3 | 15 | 63 | 61 | 6 | −22 | 0 | 16 | 238 | 214 | 8 | −3 | −3 | 17 | 82 | 77 | 6 | −11 | 3 | 17 | 128 | 119 | 5 | −5 | 3 | 18 | 143 | 142 | 5 |
| −7 | 3 | 15 | 110 | 125 | 6 | −20 | 0 | 16 | 71 | 50 | 8 | −1 | −3 | 17 | 80 | 62 | 7 | −9 | 3 | 17 | 78 | 85 | 11 | −3 | 3 | 18 | 130 | 123 | 5 |
| −5 | 3 | 15 | 489 | 483 | 13 | −18 | 0 | 16 | 33 | 16 | 19 | 1 | −3 | 17 | 180 | 166 | 5 | −7 | 3 | 17 | 27 | 36 | 27 | −1 | 3 | 18 | 56 | 69 | 7 |
| −3 | 3 | 15 | 216 | 215 | 7 | −16 | 0 | 16 | 47 | 45 | 8 | 3 | −3 | 17 | 75 | 73 | 6 | −5 | 3 | 17 | 79 | 78 | 7 | 1 | 3 | 18 | 161 | 136 | 10 |
| −1 | 3 | 15 | 167 | 171 | 6 | −14 | 0 | 16 | 104 | 110 | 6 | 5 | −3 | 17 | 125 | 123 | 11 | −3 | 3 | 17 | 75 | 76 | 7 | −14 | −2 | 19 | 24 | 31 | 23 |
| 1 | 3 | 15 | 226 | 228 | 6 | −12 | 0 | 16 | 320 | 344 | 13 | −20 | −2 | 17 | 134 | 129 | 9 | −1 | 3 | 17 | 75 | 60 | 7 | −12 | −2 | 19 | 174 | 161 | 11 |
| 3 | 3 | 15 | 279 | 259 | 7 | −10 | 0 | 16 | 77 | 115 | 12 | −18 | −2 | 17 | 254 | 241 | 8 | 1 | 3 | 17 | 179 | 167 | 6 | −10 | −2 | 19 | 122 | 107 | 5 |
| 5 | 3 | 15 | 124 | 110 | 5 | −8 | 0 | 16 | 25 | 18 | 24 | −16 | −2 | 17 | 0 | 13 | 1 | 3 | 3 | 17 | 73 | 73 | 7 | −8 | −2 | 19 | 178 | 146 | 6 |
| 7 | 3 | 15 | 56 | 48 | 7 | −6 | 0 | 16 | 195 | 238 | 8 | −14 | −2 | 17 | 198 | 194 | 5 | 5 | 3 | 17 | 120 | 123 | 6 | −6 | −2 | 19 | 49 | 46 | 9 |
| 9 | 3 | 15 | 179 | 180 | 6 | −4 | 0 | 16 | 305 | 342 | 8 | −12 | −2 | 17 | 33 | 21 | 15 | −8 | 4 | 17 | 25 | 31 | 24 | −4 | −2 | 19 | 118 | 106 | 7 |
| 11 | 3 | 15 | 74 | 68 | 8 | −2 | 0 | 16 | 329 | 334 | 7 | −10 | −2 | 17 | 224 | 193 | 7 | −6 | 4 | 17 | 43 | 52 | 19 | −2 | −2 | 19 | 110 | 103 | 6 |
| −18 | 4 | 15 | 87 | 77 | 6 | 0 | 0 | 16 | 22 | 26 | 22 | −8 | −2 | 17 | 204 | 189 | 7 | −4 | 4 | 17 | 89 | 80 | 15 | −15 | −1 | 19 | 200 | 200 | 9 |
| −16 | 4 | 15 | 174 | 167 | 10 | 2 | 0 | 16 | 245 | 220 | 6 | −6 | −2 | 17 | 258 | 230 | 6 | −13 | −3 | 18 | 55 | 30 | 10 | −13 | −1 | 19 | 196 | 169 | 7 |
| −14 | 4 | 15 | 124 | 124 | 7 | 4 | 0 | 16 | 325 | 313 | 8 | −4 | −2 | 17 | 97 | 83 | 6 | −11 | −3 | 18 | 91 | 84 | 6 | −11 | −1 | 19 | 81 | 71 | 12 |
| −12 | 4 | 15 | 103 | 95 | 7 | 6 | 0 | 16 | 53 | 44 | 11 | −2 | −2 | 17 | 114 | 95 | 5 | −9 | −3 | 18 | 111 | 96 | 6 | −9 | −1 | 19 | 132 | 109 | 9 |
| −10 | 4 | 15 | 116 | 109 | 5 | 8 | 0 | 16 | 104 | 87 | 5 | 0 | −2 | 17 | 171 | 161 | 5 | −7 | −3 | 18 | 61 | 62 | 8 | −7 | −1 | 19 | 205 | 172 | 7 |
| −8 | 4 | 15 | 116 | 117 | 4 | 10 | 0 | 16 | 162 | 139 | 6 | 2 | −2 | 17 | 50 | 42 | 9 | −5 | −3 | 18 | 147 | 141 | 6 | −5 | −1 | 19 | 288 | 240 | 8 |
| −6 | 4 | 15 | 173 | 183 | 6 | 12 | 0 | 16 | 0 | 7 | 1 | 4 | −2 | 17 | 79 | 67 | 6 | −3 | −3 | 18 | 133 | 123 | 8 | −3 | −1 | 19 | 165 | 155 | 6 |
| −4 | 4 | 15 | 126 | 126 | 6 | −23 | 1 | 16 | 185 | 175 | 7 | 6 | −2 | 17 | 161 | 150 | 7 | −1 | −3 | 18 | 73 | 70 | 6 | −1 | −1 | 19 | 52 | 31 | 9 |
| −2 | 4 | 15 | 81 | 77 | 7 | −21 | 1 | 16 | 98 | 111 | 7 | 8 | −2 | 17 | 128 | 125 | 7 | 1 | −3 | 18 | 158 | 136 | 11 | 1 | −1 | 19 | 157 | 123 | 6 |
| 0 | 4 | 15 | 157 | 152 | 6 | −19 | 1 | 16 | 170 | 158 | 7 | −21 | −1 | 17 | 163 | 141 | 6 | −16 | −2 | 18 | 213 | 198 | 9 | 3 | −1 | 19 | 136 | 118 | 8 |
| 2 | 4 | 15 | 71 | 67 | 8 | −17 | 1 | 16 | 23 | 14 | 22 | −19 | −1 | 17 | 110 | 101 | 6 | −14 | −2 | 18 | 64 | 32 | 9 | −18 | 0 | 19 | 157 | 132 | 13 |
| 4 | 4 | 15 | 125 | 121 | 5 | −15 | 1 | 16 | 93 | 106 | 5 | −17 | −1 | 17 | 117 | 99 | 7 | −12 | −2 | 18 | 130 | 126 | 5 | −16 | 0 | 19 | 164 | 146 | 6 |
| 6 | 4 | 15 | 122 | 115 | 5 | −13 | 1 | 16 | 161 | 149 | 6 | −15 | −1 | 17 | 141 | 130 | 6 | −10 | −2 | 18 | 174 | 167 | 6 | −14 | 0 | 19 | 35 | 9 | 34 |
| −9 | 5 | 15 | 72 | 89 | 17 | −11 | 1 | 16 | 88 | 92 | 5 | −13 | −1 | 17 | 332 | 320 | 7 | −8 | −2 | 18 | 62 | 67 | 8 | −12 | 0 | 19 | 55 | 28 | 13 |
| −7 | 5 | 15 | 190 | 181 | 6 | −9 | 1 | 16 | 117 | 103 | 5 | −11 | −1 | 17 | 131 | 125 | 5 | −6 | −2 | 18 | 191 | 161 | 6 | −10 | 0 | 19 | 209 | 176 | 6 |
| −5 | 5 | 15 | 95 | 112 | 8 | −7 | 1 | 16 | 143 | 132 | 5 | −9 | −1 | 17 | 153 | 134 | 6 | −4 | −2 | 18 | 128 | 112 | 5 | −8 | 0 | 19 | 32 | 13 | 21 |
| −3 | 5 | 15 | 226 | 225 | 12 | −5 | 1 | 16 | 389 | 371 | 10 | −7 | −1 | 17 | 147 | 137 | 6 | −2 | −2 | 18 | 34 | 2 | 16 | −6 | 0 | 19 | 177 | 152 | 6 |
| −1 | 5 | 15 | 107 | 92 | 10 | −3 | 1 | 16 | 258 | 246 | 6 | −5 | −1 | 17 | 397 | 371 | 10 | 0 | −2 | 18 | 81 | 75 | 6 | −4 | 0 | 19 | 162 | 127 | 7 |
| −14 | −4 | 16 | 137 | 129 | 10 | −1 | 1 | 16 | 73 | 61 | 6 | −3 | −1 | 17 | 260 | 241 | 7 | 2 | −2 | 18 | 107 | 90 | 5 | −2 | 0 | 19 | 236 | 216 | 6 |
| −12 | −4 | 16 | 129 | 110 | 6 | 1 | 1 | 16 | 248 | 232 | 6 | −1 | −1 | 17 | 61 | 59 | 7 | 4 | −2 | 18 | 250 | 238 | 8 | 0 | 0 | 19 | 83 | 79 | 5 |
| −10 | −4 | 16 | 122 | 110 | 6 | 3 | 1 | 16 | 87 | 78 | 6 | 1 | −1 | 17 | 204 | 190 | 5 | −19 | −1 | 18 | 88 | 78 | 6 | 2 | 0 | 19 | 215 | 192 | 6 |
| −8 | −4 | 16 | 77 | 76 | 7 | 5 | 1 | 16 | 165 | 144 | 5 | 3 | −1 | 17 | 257 | 238 | 6 | −17 | −1 | 18 | 25 | 36 | 25 | 4 | 0 | 19 | 94 | 80 | 7 |
| −6 | −4 | 16 | 64 | 60 | 8 | 7 | 1 | 16 | 114 | 108 | 5 | 5 | −1 | 17 | 304 | 274 | 9 | −15 | −1 | 18 | 99 | 78 | 4 | −17 | 1 | 19 | 85 | 77 | 14 |

TABLE 8-continued

Observed and calculated structure factors for SAG-2

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −4 | −4 | 16 | 68 | 60 | 6 | 9 | 1 | 16 | 148 | 136 | 7 | 7 | −1 | 17 | 52 | 50 | 12 | −13 | −1 | 18 | 98 | 93 | 11 | −15 | 1 | 19 | 198 | 201 | 7 |
| −2 | −4 | 16 | 110 | 111 | 5 | 11 | 1 | 16 | 247 | 231 | 8 | 9 | −1 | 17 | 78 | 70 | 8 | −11 | −1 | 18 | 118 | 119 | 5 | −13 | 1 | 19 | 178 | 170 | 7 |
| 0 | −4 | 16 | 146 | 136 | 7 | −22 | 2 | 16 | 265 | 253 | 13 | −22 | 0 | 17 | 161 | 153 | 7 | −9 | −1 | 18 | 208 | 196 | 7 | −11 | 1 | 19 | 82 | 71 | 9 |
| 2 | −4 | 16 | 182 | 185 | 13 | −20 | 2 | 16 | 79 | 90 | 6 | −20 | 0 | 17 | 102 | 92 | 6 | −7 | −1 | 18 | 368 | 316 | 10 | −9 | 1 | 19 | 122 | 108 | 5 |
| −19 | −3 | 16 | 132 | 118 | 9 | −18 | 2 | 16 | 80 | 73 | 7 | −18 | 0 | 17 | 45 | 57 | 12 | −5 | −1 | 18 | 135 | 121 | 6 | −7 | 1 | 19 | 195 | 171 | 7 |
| −17 | −3 | 16 | 84 | 78 | 5 | −16 | 2 | 16 | 107 | 104 | 6 | −16 | 0 | 17 | 213 | 219 | 8 | −3 | −1 | 18 | 204 | 174 | 5 | −5 | 1 | 19 | 283 | 239 | 10 |
| −15 | −3 | 16 | 174 | 157 | 6 | −14 | 2 | 16 | 389 | 279 | 9 | −14 | 0 | 17 | 97 | 79 | 5 | −1 | −1 | 18 | 51 | 48 | 8 | −3 | 1 | 19 | 160 | 155 | 5 |
| −13 | −3 | 16 | 95 | 77 | 6 | −12 | 2 | 16 | 251 | 251 | 7 | −12 | 0 | 17 | 117 | 123 | 7 | 1 | −1 | 18 | 89 | 76 | 5 | −1 | 1 | 19 | 45 | 31 | 9 |
| −11 | −3 | 16 | 129 | 118 | 6 | −10 | 2 | 16 | 107 | 106 | 5 | −10 | 0 | 17 | 103 | 95 | 6 | 3 | −1 | 18 | 74 | 62 | 8 | 1 | 1 | 19 | 144 | 122 | 5 |
| −7 | −3 | 16 | 170 | 150 | 6 | −8 | 2 | 16 | 184 | 174 | 5 | −8 | 0 | 17 | 147 | 147 | 6 | 5 | −1 | 18 | 259 | 233 | 8 | 3 | 1 | 19 | 123 | 118 | 10 |
| −5 | −3 | 16 | 92 | 82 | 6 | −6 | 2 | 16 | 31 | 31 | 19 | −6 | 0 | 17 | 61 | 65 | 8 | 7 | −1 | 18 | 148 | 126 | 6 | −12 | 2 | 19 | 165 | 162 | 13 |
| −3 | −3 | 16 | 249 | 235 | 7 | −4 | 2 | 16 | 175 | 181 | 5 | −4 | 0 | 17 | 167 | 146 | 5 | −20 | 0 | 18 | 224 | 220 | 7 | −10 | 2 | 19 | 115 | 106 | 6 |
| −1 | −3 | 16 | 116 | 100 | 5 | −2 | 2 | 16 | 87 | 83 | 5 | −2 | 0 | 17 | 290 | 268 | 6 | −18 | 0 | 18 | 151 | 137 | 6 | −8 | 2 | 19 | 158 | 145 | 6 |
| 1 | −3 | 16 | 156 | 145 | 5 | 0 | 2 | 16 | 208 | 191 | 5 | 0 | 0 | 17 | 198 | 179 | 5 | −16 | 0 | 18 | 190 | 157 | 7 | −6 | 2 | 19 | 50 | 47 | 9 |
| 3 | −3 | 16 | 206 | 198 | 6 | 2 | 2 | 16 | 130 | 116 | 5 | 2 | 0 | 17 | 42 | 40 | 16 | −14 | 0 | 18 | 14 | 24 | 13 | −4 | 2 | 19 | 107 | 107 | 6 |
| 5 | −3 | 16 | 210 | 212 | 7 | 4 | 2 | 16 | 47 | 32 | 9 | 4 | 0 | 17 | 120 | 97 | 5 | −12 | 0 | 18 | 74 | 55 | 5 | −2 | 2 | 19 | 109 | 102 | 5 |
| 7 | −3 | 16 | 103 | 98 | 7 | 6 | 2 | 16 | 203 | 193 | 6 | 6 | 0 | 17 | 135 | 117 | 5 | −10 | 0 | 18 | 91 | 79 | 10 | 0 | 2 | 19 | 61 | 51 | 8 |
| −22 | −2 | 16 | 263 | 254 | 14 | 8 | 2 | 16 | 242 | 226 | 7 | 8 | 0 | 17 | 138 | 125 | 6 | −8 | 0 | 18 | 175 | 130 | 10 | −11 | −1 | 20 | 72 | 91 | 24 |
| −20 | −2 | 16 | 81 | 90 | 9 | 10 | 2 | 16 | 40 | 35 | 13 | 10 | 0 | 17 | 267 | 226 | 9 | −6 | 0 | 18 | 118 | 92 | 10 | −9 | −1 | 20 | 102 | 86 | 18 |
| −18 | −2 | 16 | 90 | 73 | 7 | −19 | 3 | 16 | 129 | 120 | 6 | −21 | 1 | 17 | 153 | 141 | 6 | −4 | 0 | 18 | 130 | 103 | 8 | −7 | −1 | 20 | 116 | 93 | 16 |
| −16 | −2 | 16 | 108 | 104 | 5 | −17 | 3 | 16 | 88 | 78 | 7 | −19 | 1 | 17 | 100 | 100 | 6 | −2 | 0 | 18 | 15 | 15 | 14 | −5 | −1 | 20 | 112 | 81 | 17 |
| −14 | −2 | 16 | 301 | 278 | 6 | −15 | 3 | 16 | 162 | 156 | 8 | −17 | 1 | 17 | 114 | 99 | 6 | 0 | 0 | 18 | 243 | 205 | 8 | −3 | −1 | 20 | 150 | 121 | 14 |
| −12 | −2 | 16 | 263 | 251 | 7 | −13 | 3 | 16 | 99 | 78 | 7 | −15 | 1 | 17 | 141 | 130 | 6 | 2 | 0 | 18 | 106 | 92 | 5 | −12 | 0 | 20 | 157 | 133 | 6 |
| −10 | −2 | 16 | 123 | 106 | 6 | −11 | 3 | 16 | 107 | 119 | 5 | −13 | 1 | 17 | 335 | 321 | 8 | 4 | 0 | 18 | 78 | 79 | 6 | −10 | 0 | 20 | 188 | 171 | 7 |
| −8 | −2 | 16 | 193 | 175 | 5 | −9 | 3 | 16 | 239 | 255 | 7 | −11 | 1 | 17 | 131 | 125 | 5 | 6 | 0 | 18 | 274 | 240 | 8 | −8 | 0 | 20 | 376 | 347 | 12 |
| −6 | −2 | 16 | 23 | 31 | 22 | −7 | 3 | 16 | 156 | 151 | 5 | −9 | 1 | 17 | 150 | 135 | 5 | −19 | 1 | 18 | 93 | 77 | 6 | −6 | 0 | 20 | 153 | 133 | 7 |
| −4 | −2 | 16 | 182 | 180 | 6 | −5 | 3 | 16 | 78 | 83 | 7 | −7 | 1 | 17 | 143 | 137 | 7 | −17 | 1 | 18 | 39 | 35 | 11 | −4 | 0 | 20 | 270 | 245 | 8 |
| −2 | −2 | 16 | 102 | 82 | 5 | −3 | 3 | 16 | 239 | 236 | 8 | −5 | 1 | 17 | 395 | 371 | 9 | −15 | 1 | 18 | 100 | 79 | 6 | −2 | 0 | 20 | 231 | 189 | 7 |
| −9 | 1 | 20 | 93 | 85 | 13 | −7 | 1 | 20 | 105 | 94 | 16 | | | | | | | | | | | | | | | | | | |

TABLE 9

| Crystal data and structure refinement for Diol-1. | | |
|---|---|---|
| Empirical formula | C19H36O2 | |
| Formula weight | 296.48 | |
| Temperature | 100(1) K | |
| Wavelength | 1.54178 Å | |
| Crystal system, space group | Monoclinic, C2 | |
| Unit cell dimensions | a = 26.391(5) Å | α = 90° |
| | b = 6.0830(12) Å | β = 118.38(3)° |
| | c = 12.688(3) Å | γ = 90° |
| Volume | 1792.1(6) $Å^3$ | |
| Z | 4 | |
| Calculated density | 1.099 $Mg/m^3$ | |
| Absorption coefficient | 0.522 $mm^{-1}$ | |
| F(000) | 664 | |
| Crystal size | 0.11 × 0.18 × 0.45 mm | |
| Theta range for data collection | 3.81 to 64.54° | |
| Limiting indices | −30 <= h <= 26, −6 <= k <= 6, 0 <= l <= 14 | |
| Reflections collected/unique | 4452/2821 [R(int) = 0.0420] | |
| Data/restraints/parameters | 2821/1/190 | |
| Goodness-of-fit on $F^2$ | 1.134 | |
| Final R indices [I > 2□(I)] | R1 = 0.0399, wR2 = 0.1075 | |
| R indices (all data) | R1 = 0.0401, wR2 = 0.1078 | |
| Absolute structure parameter | 0.1(3) | |
| Largest diff. peak and hole | 0.410 and −0.347 e/$Å^3$ | |

TABLE 10

Atomic coordinates ($Å^2 \times 10^4$) and equivalent isotropic displacement parameters ($Å^2 \times 10^3$) for Diol-1 U(eq) is defined as one third of the trace of the orthogonalized Uij tensor.

| | x | y | z | U(eq) |
|---|---|---|---|---|
| O(8) | 584(1) | −102(2) | 9286(1) | 19(1) |
| O(25) | 594(1) | −820(3) | 1455(1) | 19(1) |
| C(20) | 1536(1) | −144(3) | 6131(2) | 17(1) |
| C(13) | 1366(1) | 221(3) | 8042(2) | 14(1) |
| C(11) | 1901(1) | −325(4) | 10306(2) | 19(1) |
| C(14) | 1018(1) | 2008(3) | 8290(2) | 15(1) |
| C(8) | 947(1) | 1735(3) | 9405(2) | 16(1) |
| C(9) | 1547(1) | 1473(4) | 10489(2) | 17(1) |
| C(21) | 2136(1) | −1171(4) | 6844(2) | 21(1) |
| C(22) | 1484(1) | 1202(4) | 5042(2) | 20(1) |
| C(16) | 739(1) | 2158(4) | 6189(2) | 20(1) |
| C(24) | 988(1) | −1925(4) | 3526(2) | 19(1) |
| C(17) | 1362(1) | 1259(3) | 6915(2) | 15(1) |
| C(23) | 1471(1) | −215(4) | 4031(2) | 21(1) |
| C(25) | 824(1) | −2683(4) | 2253(2) | 18(1) |
| C(18) | 1065(1) | −2035(4) | 7726(2) | 19(1) |
| C(28) | 1952(1) | 2940(4) | 5409(2) | 23(1) |
| C(15) | 493(1) | 2396(4) | 7073(2) | 20(1) |
| C(26) | 1342(1) | −3479(4) | 2133(2) | 24(1) |
| C(12) | 1956(1) | 35(4) | 9165(2) | 17(1) |
| C(27) | 372(1) | −4480(4) | 1853(2) | 25(1) |

TABLE 11

Bond lengths [Å] for Diol-1.

| | | | |
|---|---|---|---|
| O(8)—C(8) | 1.433(2) | O(25)—C(25) | 1.446(2) |
| C(20)—C(21) | 1.534(3) | C(20)—C(17) | 1.536(3) |
| C(20)—C(22) | 1.555(3) | C(13)—C(18) | 1.540(3) |
| C(13)—C(14) | 1.549(3) | C(13)—C(12) | 1.536(2) |
| C(13)—C(17) | 1.559(3) | C(11)—C(9) | 1.527(3) |
| C(11)—C(12) | 1.539(2) | C(14)—C(8) | 1.521(2) |
| C(14)—C(15) | 1.526(3) | C(8)—C(9) | 1.534(3) |
| C(22)—C(28) | 1.523(3) | C(22)—C(23) | 1.533(3) |
| C(16)—C(15) | 1.548(3) | C(16)—C(17) | 1.554(3) |
| C(24)—C(25) | 1.532(3) | C(24)—C(23) | 1.530(3) |
| C(25)—C(27) | 1.516(3) | C(25)—C(26) | 1.524(3) |

TABLE 12

Bond lengths [°] for Diol-1.

| | |
|---|---|
| C(21)—C(20)—C(17) | 112.66(15) |
| C(21)—C(20)—C(22) | 111.66(16) |
| C(17)—C(20)—C(22) | 110.83(17) |
| C(18)—C(13)—C(14) | 113.36(15) |
| C(18)—C(13)—C(12) | 110.28(16) |
| C(14)—C(13)—C(12) | 107.53(15) |
| C(18)—C(13)—C(17) | 110.16(15) |
| C(14)—C(13)—C(17) | 99.01(15) |
| C(12)—C(13)—C(17) | 116.14(15) |
| C(9)—C(11)—C(12) | 112.30(17) |
| C(8)—C(14)—C(15) | 120.27(15) |
| C(8)—C(14)—C(13) | 117.32(16) |
| C(15)—C(14)—C(13) | 104.12(15) |
| O(8)—C(8)—C(14) | 111.00(15) |
| O(8)—C(8)—C(9) | 111.54(16) |
| C(14)—C(8)—C(9) | 108.35(15) |
| C(11)—C(9)—C(8) | 112.57(16) |
| C(28)—C(22)—C(23) | 109.68(17) |
| C(28)—C(22)—C(20) | 112.22(16) |
| C(23)—C(22)—C(20) | 113.94(18) |
| C(15)—C(16)—C(17) | 107.12(15) |
| C(25)—C(24)—C(23) | 114.06(16) |
| C(20)—C(17)—C(16) | 111.63(15) |
| C(20)—C(17)—C(13) | 119.70(16) |
| C(16)—C(17)—C(13) | 103.25(15) |
| C(22)—C(23)—C(24) | 114.43(16) |
| O(25)—C(25)—C(27) | 109.20(15) |
| O(25)—C(25)—C(26) | 106.13(16) |
| C(27)—C(25)—C(26) | 109.73(18) |
| O(25)—C(25)—C(24) | 108.44(17) |
| C(27)—C(25)—C(24) | 110.67(16) |
| C(26)—C(25)—C(24) | 112.51(16) |
| C(14)—C(15)—C(16) | 103.09(15) |
| C(11)—C(12)—C(13) | 112.03(15) |

TABLE 13

Anisotropic displacement parameters ($Å^2 \times 10^3$) for Diol-1. The anisotropic displacement factor exponent takes the form: $-2\pi^2[h^2a^{*2}U_{11} + \ldots + 2hka^* b^* U_{12}$.

| | $U_{11}$ | $U_{22}$ | $U_{33}$ | $U_{23}$ | $U_{13}$ | $U_{12}$ |
|---|---|---|---|---|---|---|
| O(8) | 18(1) | 24(1) | 18(1) | −1(1) | 10(1) | −5(1) |
| O(25) | 20(1) | 25(1) | 14(1) | 4(1) | 8(1) | 3(1) |
| C(20) | 16(1) | 17(1) | 17(1) | −2(1) | 8(1) | −4(1) |
| C(13) | 15(1) | 12(1) | 15(1) | 0(1) | 7(1) | −1(1) |
| C(11) | 17(1) | 23(1) | 14(1) | 1(1) | 5(1) | 2(1) |
| C(14) | 16(1) | 12(1) | 17(1) | 0(1) | 8(1) | 0(1) |
| C(8) | 17(1) | 14(1) | 18(1) | −2(1) | 9(1) | −1(1) |
| C(9) | 20(1) | 18(1) | 14(1) | −1(1) | 9(1) | −3(1) |
| C(21) | 22(1) | 23(1) | 21(1) | 0(1) | 12(1) | 3(1) |
| C(22) | 21(1) | 23(1) | 17(1) | 0(1) | 8(1) | −2(1) |
| C(16) | 18(1) | 24(1) | 17(1) | 4(1) | 8(1) | 3(1) |
| C(24) | 21(1) | 19(1) | 17(1) | 2(1) | 10(1) | 1(1) |
| C(17) | 15(1) | 13(1) | 16(1) | −1(1) | 6(1) | −2(1) |
| C(23) | 19(1) | 26(1) | 17(1) | 0(1) | 8(1) | 2(1) |
| C(25) | 18(1) | 21(1) | 14(1) | 2(1) | 7(1) | 1(1) |
| C(18) | 26(1) | 13(1) | 20(1) | −3(1) | 12(1) | −4(1) |
| C(28) | 28(1) | 23(1) | 19(1) | 1(1) | 11(1) | −6(1) |
| C(15) | 16(1) | 23(1) | 20(1) | 4(1) | 8(1) | 5(1) |
| C(26) | 23(1) | 27(1) | 22(1) | 4(1) | 12(1) | 5(1) |
| C(12) | 16(1) | 17(1) | 17(1) | 0(1) | 8(1) | 2(1) |
| C(27) | 27(1) | 26(1) | 22(1) | −4(1) | 12(1) | −6(1) |

TABLE 14

Hydrogen coordinates ($Å^2 \times 10^4$) and isotropic displacement parameters ($Å^2 \times 10^3$) for Diol-1.

| | x | y | z | U(eq) |
|---|---|---|---|---|
| H(8A) | 587 | −324 | 9926 | 29 |
| H(25A) | 643 | −1001 | 870 | 29 |
| H(20A) | 1259 | −1357 | 5811 | 20 |

TABLE 14-continued

Hydrogen coordinates (Å$^2$ × $10^4$) and isotropic displacement parameters (Å$^2$ × $10^3$) for Diol-1.

| | x | y | z | U(eq) |
|---|---|---|---|---|
| H(11A) | 1721 | −1739 | 10257 | 23 |
| H(11B) | 2283 | −359 | 10994 | 23 |
| H(14A) | 1249 | 3347 | 8440 | 18 |
| H(8B) | 769 | 3069 | 9513 | 20 |
| H(9A) | 1752 | 2858 | 10638 | 21 |
| H(9B) | 1505 | 1125 | 11190 | 21 |
| H(21A) | 2152 | −1990 | 7507 | 32 |
| H(21B) | 2421 | −28 | 7139 | 32 |
| H(21C) | 2209 | −2136 | 6334 | 32 |
| H(22A) | 1115 | 1985 | 4708 | 24 |
| H(16A) | 742 | 3572 | 5839 | 24 |
| H(16B) | 505 | 1149 | 5549 | 24 |
| H(24A) | 1107 | −3196 | 4051 | 23 |
| H(24B) | 650 | −1309 | 3530 | 23 |
| H(17A) | 1621 | 2530 | 7189 | 18 |
| H(23A) | 1838 | −968 | 4328 | 25 |
| H(23B) | 1431 | 744 | 3384 | 25 |
| H(18A) | 1067 | −2655 | 8424 | 29 |
| H(18B) | 1265 | −2998 | 7450 | 29 |
| H(18C) | 674 | −1858 | 7106 | 29 |
| H(28A) | 1905 | 3728 | 4712 | 35 |
| H(28B) | 2323 | 2243 | 5783 | 35 |
| H(28C) | 1925 | 3947 | 5962 | 35 |
| H(15A) | 334 | 3852 | 7027 | 24 |
| H(15B) | 196 | 1308 | 6913 | 24 |
| H(26A) | 1218 | −3926 | 1321 | 35 |
| H(26B) | 1516 | −4704 | 2660 | 35 |
| H(26C) | 1617 | −2309 | 2342 | 35 |
| H(12A) | 2168 | −1182 | 9066 | 20 |
| H(12B) | 2174 | 1369 | 9251 | 20 |
| H(27A) | 274 | −4932 | 1054 | 37 |
| H(27B) | 34 | −3932 | 1867 | 37 |
| H(27C) | 522 | −5713 | 2386 | 37 |

TABLE 15

Torsion angles [deg] for Diol-1.

| | |
|---|---|
| C(18)—C(13)—C(14)—C(8) | 67.4(2) |
| C(12)—C(13)—C(14)—C(8) | −54.7(2) |
| C(17)—C(13)—C(14)—C(8) | −175.91(15) |
| C(18)—C(13)—C(14)—C(15) | −68.20(19) |
| C(12)—C(13)—C(14)—C(15) | 169.64(16) |
| C(17)—C(13)—C(14)—C(15) | 48.45(17) |
| C(15)—C(14)—C(8)—O(8) | 59.6(2) |
| C(13)—C(14)—C(8)—O(8) | −68.6(2) |
| C(15)—C(14)—C(8)—C(9) | −177.56(18) |
| C(13)—C(14)—C(8)—C(9) | 54.2(2) |
| C(12)—C(11)—C(9)—C(8) | 55.3(2) |
| O(8)—C(8)—C(9)—C(11) | 70.4(2) |
| C(14)—C(8)—C(9)—C(11) | −52.1(2) |
| C(21)—C(20)—C(22)—C(28) | −54.6(2) |
| C(17)—C(20)—C(22)—C(28) | 71.9(2) |
| C(21)—C(20)—C(22)—C(23) | 70.8(2) |
| C(17)—C(20)—C(22)—C(23) | −162.74(16) |
| C(21)—C(20)—C(17)—C(16) | −176.42(18) |
| C(22)—C(20)—C(17)—C(16) | 57.7(2) |
| C(21)—C(20)—C(17)—C(13) | −55.8(2) |
| C(22)—C(20)—C(17)—C(13) | 178.32(15) |
| C(15)—C(16)—C(17)—C(20) | 150.05(16) |
| C(15)—C(16)—C(17)—C(13) | 20.2(2) |
| C(18)—C(13)—C(17)—C(20) | −46.7(2) |
| C(14)—C(13)—C(17)—C(20) | −165.79(15) |
| C(12)—C(13)—C(17)—C(20) | 79.5(2) |
| C(18)—C(13)—C(17)—C(16) | 78.05(19) |
| C(14)—C(13)—C(17)—C(16) | −41.02(18) |
| C(12)—C(13)—C(17)—C(16) | −155.70(17) |
| C(28)—C(22)—C(23)—C(24) | −176.00(18) |
| C(20)—C(22)—C(23)—C(24) | 57.3(2) |
| C(25)—C(24)—C(23)—C(22) | 157.17(18) |
| C(23)—C(24)—C(25)—O(25) | −64.0(2) |
| C(23)—C(24)—C(25)—C(27) | 176.22(18) |
| C(23)—C(24)—C(25)—C(26) | 53.1(3) |
| C(8)—C(14)—C(15)—C(16) | −170.25(18) |
| C(13)—C(14)—C(15)—C(16) | −36.2(2) |
| C(17)—C(16)—C(15)—C(14) | 9.5(2) |
| C(9)—C(11)—C(12)—C(13) | −56.0(2) |
| C(18)—C(13)—C(12)—C(11) | −71.3(2) |
| C(14)—C(13)—C(12)—C(11) | 52.8(2) |
| C(17)—C(13)—C(12)—C(11) | 162.55(18) |

TABLE 16

Observed and calculated structure factors for Diol-1

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 2 | −6 | 0 | 182 | 180 | 3 | 17 | 1 | 0 | 119 | 126 | 1 | −8 | −4 | 1 | 256 | 254 | 3 | 15 | −1 | 1 | 374 | 388 | 3 | −21 | 3 | 1 | 93 | 93 | 2 |
| 4 | −6 | 0 | 283 | 277 | 5 | 19 | 1 | 0 | 237 | 251 | 2 | −6 | −4 | 1 | 168 | 157 | 3 | 17 | −1 | 1 | 240 | 257 | 2 | −19 | 3 | 1 | 87 | 87 | 2 |
| 6 | −6 | 0 | 234 | 229 | 4 | 21 | 1 | 0 | 266 | 274 | 4 | −4 | −4 | 1 | 159 | 162 | 2 | 19 | −1 | 1 | 104 | 95 | 2 | −17 | 3 | 1 | 243 | 253 | 5 |
| 8 | −6 | 0 | 122 | 122 | 2 | 23 | 1 | 0 | 289 | 275 | 4 | −2 | −4 | 1 | 183 | 186 | 3 | 21 | −1 | 1 | 93 | 94 | 2 | −15 | 3 | 1 | 378 | 390 | 7 |
| 10 | −6 | 0 | 74 | 79 | 2 | 25 | 1 | 0 | 230 | 221 | 4 | 0 | −4 | 1 | 272 | 264 | 3 | 23 | −1 | 1 | 189 | 181 | 3 | −13 | 3 | 1 | 215 | 222 | 4 |
| 12 | −6 | 0 | 13 | 20 | 5 | 2 | 2 | 0 | 264 | 276 | 8 | 2 | −4 | 1 | 160 | 166 | 2 | 25 | −1 | 1 | 32 | 31 | 2 | −11 | 3 | 1 | 55 | 40 | 2 |
| 1 | −5 | 0 | 330 | 315 | 4 | 4 | 2 | 0 | 714 | 703 | 11 | 4 | −4 | 1 | 182 | 175 | 3 | −28 | 0 | 1 | 109 | 97 | 2 | −9 | 3 | 1 | 275 | 255 | 8 |
| 3 | −5 | 0 | 120 | 121 | 2 | 6 | 2 | 0 | 802 | 776 | 17 | 6 | −4 | 1 | 45 | 48 | 1 | −26 | 0 | 1 | 84 | 82 | 2 | 7 | 3 | 1 | 80 | 81 | 3 |
| 5 | −5 | 0 | 208 | 216 | 4 | 8 | 2 | 0 | 666 | 666 | 13 | 8 | −4 | 1 | 167 | 167 | 2 | −24 | 0 | 1 | 119 | 122 | 2 | 9 | 3 | 1 | 327 | 333 | 6 |
| 7 | −5 | 0 | 47 | 48 | 2 | 10 | 2 | 0 | 740 | 725 | 10 | 10 | −4 | 1 | 139 | 147 | 1 | −22 | 0 | 1 | 45 | 42 | 1 | 11 | 3 | 1 | 213 | 210 | 4 |
| 9 | −5 | 0 | 146 | 153 | 3 | 12 | 2 | 0 | 310 | 292 | 4 | 12 | −4 | 1 | 269 | 268 | 3 | −20 | 0 | 1 | 64 | 68 | 1 | 13 | 3 | 1 | 141 | 134 | 3 |
| 11 | −5 | 0 | 159 | 146 | 2 | 14 | 2 | 0 | 252 | 267 | 2 | 14 | −4 | 1 | 187 | 185 | 3 | −18 | 0 | 1 | 213 | 232 | 2 | 15 | 3 | 1 | 232 | 233 | 4 |
| 13 | −5 | 0 | 114 | 124 | 2 | 16 | 2 | 0 | 295 | 294 | 3 | 16 | −4 | 1 | 90 | 89 | 2 | −16 | 0 | 1 | 208 | 225 | 2 | 17 | 3 | 1 | 158 | 154 | 3 |
| 15 | −5 | 0 | 157 | 152 | 3 | 18 | 2 | 0 | 254 | 259 | 3 | 18 | −4 | 1 | 112 | 116 | 2 | −14 | 0 | 1 | 72 | 59 | 1 | 19 | 3 | 1 | 151 | 146 | 3 |
| 17 | −5 | 0 | 106 | 99 | 2 | 20 | 2 | 0 | 75 | 78 | 2 | 20 | −4 | 1 | 132 | 133 | 2 | −12 | 0 | 1 | 84 | 104 | 1 | 21 | 3 | 1 | 97 | 100 | 2 |
| 19 | −5 | 0 | 100 | 100 | 3 | 22 | 2 | 0 | 139 | 141 | 2 | −25 | −3 | 1 | 169 | 156 | 5 | −10 | 0 | 1 | 178 | 201 | 2 | 23 | 3 | 1 | 82 | 77 | 2 |
| 0 | −4 | 0 | 394 | 382 | 10 | 24 | 2 | 0 | 146 | 150 | 2 | −23 | −3 | 1 | 61 | 59 | 3 | −8 | 0 | 1 | 27 | 38 | 1 | −22 | 4 | 1 | 116 | 121 | 2 |
| 2 | −4 | 0 | 143 | 141 | 2 | 7 | 3 | 0 | 446 | 466 | 14 | −21 | −3 | 1 | 91 | 93 | 2 | −6 | 0 | 1 | 312 | 366 | 4 | −20 | 4 | 1 | 174 | 170 | 3 |
| 4 | −4 | 0 | 108 | 111 | 1 | 9 | 3 | 0 | 395 | 406 | 8 | −19 | −3 | 1 | 89 | 88 | 1 | −4 | 0 | 1 | 483 | 478 | 6 | −18 | 4 | 1 | 150 | 152 | 3 |
| 6 | −4 | 0 | 196 | 193 | 2 | 11 | 3 | 0 | 184 | 187 | 4 | −17 | −3 | 1 | 245 | 253 | 2 | −2 | 0 | 1 | 131 | 127 | 1 | −16 | 4 | 1 | 289 | 292 | 5 |
| 8 | −4 | 0 | 358 | 330 | 4 | 13 | 3 | 0 | 164 | 156 | 3 | −15 | −3 | 1 | 374 | 389 | 3 | 0 | 0 | 1 | 354 | 364 | 5 | −14 | 4 | 1 | 239 | 237 | 4 |
| 10 | −4 | 0 | 122 | 134 | 1 | 15 | 3 | 0 | 482 | 477 | 9 | −13 | −3 | 1 | 215 | 221 | 2 | 2 | 0 | 1 | 889 | 924 | 12 | −12 | 4 | 1 | 137 | 137 | 3 |
| 12 | −4 | 0 | 132 | 135 | 1 | 17 | 3 | 0 | 195 | 185 | 6 | −11 | −3 | 1 | 55 | 41 | 1 | 4 | 0 | 1 | 69 | 80 | 1 | −10 | 4 | 1 | 228 | 205 | 6 |
| 14 | −4 | 0 | 190 | 200 | 3 | 19 | 3 | 0 | 220 | 231 | 4 | −9 | −3 | 1 | 281 | 254 | 2 | 6 | 0 | 1 | 275 | 296 | 2 | −8 | 4 | 1 | 252 | 255 | 8 |
| 16 | −4 | 0 | 103 | 109 | 2 | 21 | 3 | 0 | 86 | 82 | 2 | −7 | −3 | 1 | 592 | 565 | 6 | 8 | 0 | 1 | 708 | 759 | 8 | 6 | 4 | 1 | 45 | 49 | 3 |
| 18 | −4 | 0 | 71 | 63 | 1 | 23 | 3 | 0 | 100 | 102 | 2 | −5 | −3 | 1 | 190 | 191 | 2 | 10 | 0 | 1 | 334 | 332 | 3 | 8 | 4 | 1 | 174 | 167 | 5 |
| 20 | −4 | 0 | 126 | 122 | 2 | 6 | 4 | 0 | 181 | 193 | 6 | −3 | −3 | 1 | 261 | 241 | 4 | 12 | 0 | 1 | 49 | 27 | 1 | 10 | 4 | 1 | 137 | 147 | 3 |
| 22 | −4 | 0 | 11 | 13 | 11 | 8 | 4 | 0 | 362 | 330 | 10 | −1 | −3 | 1 | 253 | 251 | 5 | 14 | 0 | 1 | 321 | 321 | 2 | 12 | 4 | 1 | 278 | 268 | 5 |
| 1 | −3 | 0 | 282 | 394 | 4 | 10 | 4 | 0 | 127 | 133 | 4 | 1 | −3 | 1 | 195 | 181 | 3 | 16 | 0 | 1 | 168 | 182 | 1 | 14 | 4 | 1 | 189 | 184 | 3 |
| 3 | −3 | 0 | 306 | 288 | 4 | 12 | 4 | 0 | 139 | 135 | 3 | 3 | −3 | 1 | 43 | 35 | 1 | 18 | 0 | 1 | 53 | 57 | 1 | 16 | 4 | 1 | 88 | 90 | 2 |
| 5 | −3 | 0 | 484 | 448 | 6 | 14 | 4 | 0 | 198 | 199 | 4 | 5 | −3 | 1 | 66 | 72 | 1 | 20 | 0 | 1 | 94 | 121 | 2 | 18 | 4 | 1 | 113 | 117 | 2 |
| 7 | −3 | 0 | 468 | 467 | 4 | 16 | 4 | 0 | 105 | 110 | 2 | 7 | −3 | 1 | 82 | 82 | 1 | 22 | 0 | 1 | 129 | 127 | 2 | 20 | 4 | 1 | 136 | 132 | 3 |
| 9 | −3 | 0 | 408 | 406 | 3 | 18 | 4 | 0 | 68 | 62 | 2 | 9 | −3 | 1 | 333 | 334 | 3 | 24 | 0 | 1 | 29 | 17 | 3 | −19 | 5 | 1 | 7 | 11 | 7 |
| 11 | −3 | 0 | 184 | 187 | 2 | 20 | 4 | 0 | 129 | 122 | 2 | 11 | −3 | 1 | 216 | 211 | 2 | 26 | 0 | 1 | 136 | 135 | 3 | −17 | 5 | 1 | 20 | 20 | 3 |
| 13 | −3 | 0 | 162 | 156 | 1 | 22 | 4 | 0 | 20 | 14 | 6 | 13 | −3 | 1 | 139 | 135 | 1 | −27 | 1 | 1 | 100 | 95 | 2 | −15 | 5 | 1 | 159 | 155 | 5 |
| 15 | −3 | 0 | 476 | 476 | 4 | 5 | 5 | 0 | 205 | 217 | 6 | 15 | −3 | 1 | 235 | 232 | 2 | −25 | 1 | 1 | 192 | 196 | 3 | −13 | 5 | 1 | 211 | 198 | 6 |
| 17 | −3 | 0 | 199 | 186 | 3 | 7 | 5 | 0 | 50 | 49 | 3 | 17 | −3 | 1 | 161 | 153 | 2 | −23 | 1 | 1 | 125 | 120 | 2 | −11 | 5 | 1 | 141 | 143 | 5 |
| 19 | −3 | 0 | 228 | 232 | 3 | 9 | 5 | 0 | 140 | 153 | 5 | 19 | −3 | 1 | 155 | 146 | 2 | −21 | 1 | 1 | 217 | 224 | 4 | −9 | 5 | 1 | 166 | 162 | 5 |
| 21 | −3 | 0 | 88 | 82 | 2 | 11 | 5 | 0 | 158 | 146 | 5 | 21 | −3 | 1 | 98 | 100 | 2 | −19 | 1 | 1 | 333 | 345 | 3 | −7 | 5 | 1 | 85 | 84 | 3 |
| 23 | −3 | 0 | 104 | 101 | 3 | 13 | 5 | 0 | 115 | 124 | 4 | 23 | −3 | 1 | 77 | 77 | 3 | −17 | 1 | 1 | 320 | 328 | 3 | 5 | 5 | 1 | 257 | 262 | 8 |
| 0 | −2 | 0 | 176 | 162 | 4 | 15 | 5 | 0 | 153 | 152 | 5 | −26 | −2 | 1 | 72 | 64 | 2 | −15 | 1 | 1 | 352 | 357 | 3 | 7 | 5 | 1 | 351 | 341 | 10 |
| 2 | −2 | 0 | 279 | 276 | 3 | 17 | 5 | 0 | 104 | 99 | 2 | −24 | −2 | 1 | 96 | 93 | 2 | −13 | 1 | 1 | 156 | 151 | 2 | 9 | 5 | 1 | 25 | 15 | 4 |
| 4 | −2 | 0 | 732 | 703 | 10 | 19 | 5 | 0 | 102 | 100 | 3 | −22 | −2 | 1 | 148 | 152 | 3 | −11 | 1 | 1 | 361 | 368 | 4 | 11 | 5 | 1 | 154 | 148 | 5 |
| 6 | −2 | 0 | 829 | 777 | 8 | 4 | 6 | 0 | 280 | 277 | 8 | −20 | −2 | 1 | 135 | 140 | 2 | −9 | 1 | 1 | 602 | 612 | 9 | 13 | 5 | 1 | 153 | 154 | 5 |
| 8 | −2 | 0 | 663 | 668 | 7 | 6 | 6 | 0 | 228 | 229 | 7 | −18 | −2 | 1 | 139 | 147 | 1 | −7 | 1 | 1 | 769 | 820 | 13 | 15 | 5 | 1 | 55 | 47 | 3 |
| 10 | −2 | 0 | 740 | 724 | 7 | 8 | 6 | 0 | 118 | 122 | 4 | −16 | −2 | 1 | 254 | 251 | 2 | −5 | 1 | 1 | 655 | 669 | 8 | 17 | 5 | 1 | 85 | 80 | 2 |
| 12 | −2 | 0 | 304 | 292 | 2 | 10 | 6 | 0 | 73 | 78 | 3 | −14 | −2 | 1 | 117 | 117 | 1 | −3 | 1 | 1 | 1117 | 1169 | 17 | −14 | 6 | 1 | 17 | 13 | 5 |

TABLE 16-continued

| Observed and calculated structure factors for Diol-1 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| 14 | −2 | 0 | 255 | 266 | 2 | 12 | 6 | 0 | 17 | 20 | 5 | −12 | −2 | 1 | 201 | 215 | 1 | −1 | 1 | 1 | 794 | 834 | 14 | −12 | 6 | 1 | 36 | 25 | 3 |
| 16 | −2 | 0 | 286 | 294 | 2 | −14 | −6 | 1 | 20 | 14 | 3 | −10 | −2 | 1 | 534 | 537 | 6 | 1 | 1 | 1 | 859 | 918 | 14 | −10 | 6 | 1 | 129 | 125 | 4 |
| 18 | −2 | 0 | 251 | 261 | 2 | −12 | −6 | 1 | 34 | 25 | 4 | −8 | −2 | 1 | 644 | 640 | 7 | 3 | 1 | 1 | 949 | 977 | 13 | −8 | 6 | 1 | 181 | 179 | 6 |
| 20 | −2 | 0 | 73 | 77 | 2 | −10 | −6 | 1 | 131 | 125 | 4 | −6 | −2 | 1 | 107 | 120 | 1 | 5 | 1 | 1 | 114 | 103 | 1 | −6 | 6 | 1 | 75 | 75 | 3 |
| 22 | −2 | 0 | 141 | 142 | 2 | −8 | −6 | 1 | 185 | 180 | 3 | −4 | −2 | 1 | 920 | 887 | 10 | 7 | 1 | 1 | 756 | 761 | 9 | 2 | 6 | 1 | 81 | 80 | 3 |
| 24 | −2 | 0 | 149 | 149 | 3 | −6 | −6 | 1 | 85 | 75 | 2 | −2 | −2 | 1 | 367 | 359 | 3 | 9 | 1 | 1 | 234 | 233 | 3 | 4 | 6 | 1 | 145 | 135 | 5 |
| 1 | −1 | 0 | 1294 | 1329 | 37 | −4 | −6 | 1 | 105 | 102 | 3 | 0 | −2 | 1 | 580 | 581 | 6 | 11 | 1 | 1 | 386 | 393 | 5 | 6 | 6 | 1 | 42 | 37 | 3 |
| 3 | −1 | 0 | 1181 | 1274 | 18 | 0 | −6 | 1 | 145 | 144 | 4 | 2 | −2 | 1 | 106 | 108 | 1 | 13 | 1 | 1 | 394 | 396 | 4 | 8 | 6 | 1 | 97 | 100 | 3 |
| 5 | – | 0 | 159 | 172 | 1 | 2 | −6 | 1 | 82 | 79 | 2 | 4 | −2 | 1 | 227 | 223 | 2 | 15 | 1 | 1 | 370 | 388 | 4 | 10 | 6 | 1 | 11 | 5 | 10 |
| 7 | −1 | 0 | 244 | 259 | 2 | 4 | −6 | 1 | 148 | 136 | 3 | 6 | −2 | 1 | 454 | 424 | 5 | 17 | 1 | 1 | 242 | 257 | 3 | 12 | 6 | 1 | 48 | 41 | 3 |
| 9 | −1 | 0 | 478 | 513 | 5 | 6 | −6 | 1 | 42 | 36 | 2 | 8 | −2 | 1 | 544 | 547 | 6 | 19 | 1 | 1 | 100 | 95 | 2 | −14 | −6 | 2 | 90 | 92 | 3 |
| 11 | −1 | 0 | 309 | 306 | 3 | 8 | −6 | 1 | 94 | 100 | 2 | 10 | −2 | 1 | 82 | 76 | 1 | 21 | 1 | 1 | 92 | 94 | 2 | −12 | −6 | 2 | 45 | 41 | 2 |
| 13 | −1 | 0 | 305 | 315 | 2 | 10 | −6 | 1 | 6 | 4 | 6 | 12 | −2 | 1 | 333 | 342 | 2 | 23 | 1 | 1 | 185 | 181 | 2 | −10 | −6 | 2 | 39 | 39 | 2 |
| 15 | −1 | 0 | 310 | 333 | 2 | 12 | −6 | 1 | 46 | 40 | 2 | 14 | −2 | 1 | 138 | 146 | 1 | 25 | 1 | 1 | 36 | 29 | 3 | −8 | −6 | 2 | 118 | 113 | 2 |
| 17 | −1 | 0 | 119 | 127 | 1 | −19 | −5 | 1 | 15 | 11 | 3 | 16 | −2 | 1 | 605 | 629 | 5 | −26 | 2 | 1 | 74 | 64 | 1 | −6 | −6 | 2 | 170 | 170 | 4 |
| 19 | −1 | 0 | 237 | 251 | 3 | −17 | −5 | 1 | 25 | 20 | 2 | 18 | −2 | 1 | 37 | 38 | 1 | −24 | 2 | 1 | 95 | 93 | 2 | −4 | −6 | 2 | 186 | 188 | 5 |
| 21 | −1 | 0 | 270 | 274 | 4 | −15 | −5 | 1 | 163 | 155 | 2 | 20 | −2 | 1 | 97 | 90 | 2 | −22 | 2 | 1 | 146 | 152 | 2 | −2 | −6 | 2 | 123 | 119 | 2 |
| 23 | −1 | 0 | 293 | 274 | 4 | −13 | −5 | 1 | 209 | 197 | 3 | 22 | −2 | 1 | 167 | 159 | 4 | −20 | 2 | 1 | 137 | 141 | 2 | 0 | −6 | 2 | 270 | 256 | 7 |
| 25 | −1 | 0 | 226 | 221 | 3 | −11 | −5 | 1 | 147 | 144 | 2 | 24 | −2 | 1 | 135 | 134 | 3 | −18 | 2 | 1 | 142 | 145 | 1 | 2 | −6 | 2 | 251 | 246 | 4 |
| 2 | 0 | 0 | 200 | 206 | 2 | −9 | −5 | 1 | 168 | 163 | 3 | −27 | −1 | 1 | 97 | 94 | 1 | −16 | 2 | 1 | 246 | 251 | 2 | 4 | −6 | 2 | 270 | 266 | 5 |
| 4 | 0 | 0 | 1531 | 1736 | 42 | −7 | −5 | 1 | 82 | 84 | 2 | −25 | −1 | 1 | 189 | 194 | 3 | −14 | 2 | 1 | 113 | 117 | 2 | 6 | −6 | 2 | 228 | 209 | 6 |
| 6 | 0 | 0 | 204 | 218 | 2 | −5 | −5 | 1 | 167 | 172 | 3 | −23 | −1 | 1 | 128 | 120 | 2 | −12 | 2 | 1 | 198 | 216 | 3 | 8 | −6 | 2 | 318 | 321 | 6 |
| 8 | 0 | 0 | 566 | 599 | 6 | −3 | −5 | 1 | 401 | 397 | 6 | −21 | −1 | 1 | 223 | 224 | 4 | −10 | 2 | 1 | 519 | 535 | 9 | 10 | −6 | 2 | 96 | 96 | 2 |
| 10 | 0 | 0 | 379 | 392 | 5 | −1 | −5 | 1 | 210 | 203 | 2 | −19 | −1 | 1 | 326 | 344 | 3 | −8 | 2 | 1 | 644 | 641 | 12 | −21 | −5 | 2 | 182 | 180 | 5 |
| 12 | 0 | 0 | 308 | 322 | 5 | 1 | −5 | 1 | 205 | 200 | 4 | −17 | −1 | 1 | 323 | 329 | 3 | −6 | 2 | 1 | 106 | 119 | 2 | −19 | −5 | 2 | 70 | 65 | 2 |
| 14 | 0 | 0 | 385 | 405 | 3 | 3 | −5 | 1 | 144 | 142 | 3 | −15 | −1 | 1 | 357 | 358 | 3 | −4 | 2 | 1 | 868 | 888 | 19 | −17 | −5 | 2 | 62 | 50 | 2 |
| 16 | 0 | 0 | 32 | 25 | 1 | 5 | −5 | 1 | 257 | 262 | 5 | −13 | −1 | 1 | 153 | 150 | 2 | 2 | 2 | 1 | 97 | 107 | 2 | −15 | −5 | 2 | 174 | 175 | 3 |
| 18 | 0 | 0 | 136 | 141 | 1 | 7 | −5 | 1 | 352 | 340 | 5 | −11 | −1 | 1 | 350 | 370 | 4 | 4 | 2 | 1 | 223 | 223 | 4 | −13 | −5 | 2 | 135 | 146 | 2 |
| 20 | 0 | 0 | 445 | 474 | 6 | 9 | −5 | 1 | 22 | 14 | 2 | −9 | −1 | 1 | 600 | 612 | 6 | 6 | 2 | 1 | 447 | 425 | 9 | −11 | −5 | 2 | 171 | 166 | 2 |
| 22 | 0 | 0 | 82 | 90 | 1 | 11 | −5 | 1 | 150 | 147 | 2 | −7 | −1 | 1 | 797 | 820 | 8 | 8 | 2 | 1 | 548 | 547 | 9 | −9 | −5 | 2 | 20 | 14 | 2 |
| 24 | 0 | 0 | 319 | 295 | 5 | 13 | −5 | 1 | 154 | 155 | 2 | −5 | −1 | 1 | 679 | 669 | 6 | 10 | 2 | 1 | 81 | 75 | 1 | −7 | −5 | 2 | 168 | 162 | 2 |
| 26 | 0 | 0 | 41 | 40 | 2 | 15 | −5 | 1 | 53 | 47 | 2 | −3 | −1 | 1 | 1134 | 1170 | 14 | 12 | 2 | 1 | 329 | 341 | 4 | −5 | −5 | 2 | 43 | 34 | 1 |
| 1 | 1 | 0 | 1246 | 1330 | 58 | 17 | −5 | 1 | 87 | 81 | 2 | −1 | −1 | 1 | 810 | 836 | 7 | 14 | 2 | 1 | 139 | 146 | 1 | −3 | −5 | 2 | 209 | 213 | 3 |
| 3 | 1 | 0 | 1175 | 1274 | 23 | −22 | −4 | 1 | 112 | 121 | 2 | 1 | −1 | 1 | 884 | 917 | 8 | 16 | 2 | 1 | 621 | 630 | 8 | −1 | −5 | 2 | 279 | 274 | 5 |
| 5 | 1 | 0 | 155 | 172 | 2 | −20 | −4 | 1 | 169 | 170 | 3 | 3 | −1 | 1 | 940 | 976 | 9 | 18 | 2 | 1 | 43 | 39 | 2 | 1 | −5 | 2 | 238 | 231 | 3 |
| 7 | 1 | 0 | 238 | 258 | 3 | −18 | −4 | 1 | 152 | 153 | 2 | 5 | −1 | 1 | 117 | 103 | 1 | 20 | 2 | 1 | 98 | 90 | 2 | 3 | −5 | 2 | 291 | 292 | 4 |
| 9 | 1 | 0 | 501 | 515 | 6 | −16 | −4 | 1 | 284 | 291 | 4 | 7 | −1 | 1 | 747 | 761 | 8 | 22 | 2 | 1 | 163 | 159 | 2 | 5 | −5 | 2 | 113 | 110 | 2 |
| 11 | 1 | 0 | 310 | 307 | 4 | −14 | −4 | 1 | 228 | 237 | 2 | 9 | −1 | 1 | 233 | 235 | 2 | 24 | 2 | 1 | 136 | 133 | 2 | 7 | −5 | 2 | 162 | 162 | 2 |
| 13 | 1 | 0 | 300 | 315 | 3 | −12 | −4 | 1 | 140 | 136 | 1 | 11 | −1 | 1 | 389 | 393 | 4 | −25 | 3 | 1 | 170 | 165 | 3 | 9 | −5 | 2 | 212 | 209 | 3 |
| 15 | 1 | 0 | 312 | 333 | 3 | −10 | −4 | 1 | 222 | 205 | 2 | 13 | −1 | 1 | 398 | 397 | 3 | −23 | 3 | 1 | 53 | 59 | 2 | 11 | −5 | 2 | 96 | 90 | 2 |
| 13 | −5 | 2 | 22 | 20 | 3 | 1 | −1 | 2 | 689 | 705 | 6 | 18 | 2 | 2 | 273 | 269 | 4 | 5 | −5 | 3 | 193 | 202 | 3 | −9 | −1 | 3 | 431 | 409 | 5 |
| 15 | −5 | 2 | 67 | 62 | 2 | 3 | −1 | 2 | 615 | 597 | 6 | 20 | 2 | 2 | 221 | 219 | 3 | 7 | −5 | 3 | 154 | 150 | 2 | −7 | −1 | 3 | 409 | 402 | 4 |
| −22 | −4 | 2 | 140 | 131 | 3 | 5 | −1 | 2 | 244 | 217 | 2 | 22 | 2 | 2 | 82 | 76 | 1 | 9 | −5 | 3 | 234 | 241 | 3 | −5 | −1 | 3 | 525 | 533 | 5 |
| −20 | −4 | 2 | 144 | 141 | 3 | 7 | −1 | 2 | 267 | 242 | 3 | −25 | 3 | 2 | 13 | 14 | 12 | 11 | −5 | 3 | 60 | 59 | 2 | −3 | −1 | 3 | 409 | 372 | 3 |
| −18 | −4 | 2 | 103 | 112 | 2 | 9 | −1 | 2 | 395 | 373 | 4 | −23 | 3 | 2 | 86 | 88 | 2 | 13 | −5 | 3 | 77 | 81 | 2 | −1 | −1 | 3 | 521 | 556 | 5 |
| −16 | −4 | 2 | 135 | 127 | 2 | 11 | −1 | 2 | 336 | 319 | 2 | −21 | 3 | 2 | 84 | 84 | 2 | 15 | −5 | 3 | 65 | 71 | 2 | 1 | −1 | 3 | 421 | 427 | 4 |
| −14 | −4 | 2 | 267 | 277 | 3 | 13 | −1 | 2 | 122 | 112 | 1 | −19 | 3 | 2 | 132 | 142 | 3 | −24 | −4 | 3 | 33 | 43 | 3 | 3 | −1 | 3 | 402 | 419 | 4 |
| −12 | −4 | 2 | 158 | 163 | 2 | 15 | −1 | 2 | 92 | 77 | 1 | −17 | 3 | 2 | 76 | 69 | 2 | −22 | −4 | 3 | 59 | 67 | 2 | 5 | −1 | 3 | 529 | 540 | 7 |
| −10 | −4 | 2 | 65 | 71 | 1 | 17 | −1 | 2 | 229 | 229 | 3 | −15 | 3 | 2 | 48 | 47 | 2 | −20 | −4 | 3 | 36 | 39 | 2 | 7 | −1 | 3 | 143 | 141 | 2 |

TABLE 16-continued

Observed and calculated structure factors for Diol-1

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −8 | −4 | 2 | 158 | 159 | 2 | 19 | −1 | 2 | 125 | 122 | 2 | −13 | 3 | 2 | 195 | 204 | 4 | −18 | −4 | 3 | 148 | 153 | 2 | 9 | −1 | 3 | 609 | 619 | 5 |
| −6 | −4 | 2 | 113 | 109 | 2 | 21 | −1 | 2 | 65 | 59 | 2 | −11 | 3 | 2 | 370 | 352 | 7 | −16 | −4 | 3 | 28 | 8 | 2 | 11 | −1 | 3 | 20 | 23 | 1 |
| −4 | −4 | 2 | 205 | 193 | 2 | 23 | −1 | 2 | 50 | 48 | 2 | −9 | 3 | 2 | 258 | 241 | 8 | −14 | −4 | 3 | 102 | 108 | 1 | 13 | −1 | 3 | 188 | 192 | 2 |
| −2 | −4 | 2 | 368 | 379 | 4 | −28 | 0 | 2 | 20 | 8 | 4 | 5 | 3 | 2 | 457 | 460 | 14 | −12 | −4 | 3 | 205 | 206 | 2 | 15 | −1 | 3 | 110 | 116 | 1 |
| 0 | −4 | 2 | 125 | 136 | 2 | −26 | 0 | 2 | 303 | 289 | 8 | 7 | 3 | 2 | 196 | 194 | 4 | −10 | −4 | 3 | 36 | 34 | 1 | 17 | −1 | 3 | 165 | 166 | 2 |
| 2 | −4 | 2 | 145 | 147 | 2 | −24 | 0 | 2 | 323 | 340 | 6 | 9 | 3 | 2 | 261 | 254 | 5 | −8 | −4 | 3 | 209 | 198 | 3 | 19 | −1 | 3 | 79 | 82 | 2 |
| 4 | −4 | 2 | 178 | 177 | 2 | −22 | 0 | 2 | 377 | 418 | 6 | 11 | 3 | 2 | 204 | 211 | 3 | −6 | −4 | 3 | 426 | 420 | 6 | 21 | −1 | 3 | 130 | 130 | 2 |
| 6 | −4 | 2 | 29 | 19 | 1 | −20 | 0 | 2 | 237 | 231 | 2 | 13 | 3 | 2 | 572 | 578 | 11 | −4 | −4 | 3 | 117 | 112 | 1 | 23 | −1 | 3 | 100 | 103 | 4 |
| 8 | −4 | 2 | 64 | 57 | 1 | −18 | 0 | 2 | 106 | 98 | 1 | 15 | 3 | 2 | 159 | 167 | 3 | −2 | −4 | 3 | 222 | 217 | 2 | −28 | 0 | 3 | 25 | 29 | 3 |
| 10 | −4 | 2 | 214 | 213 | 2 | −16 | 0 | 2 | 247 | 259 | 2 | 17 | 3 | 2 | 226 | 235 | 4 | 0 | −4 | 3 | 64 | 78 | 1 | −26 | 0 | 3 | 147 | 143 | 3 |
| 12 | −4 | 2 | 291 | 301 | 5 | −14 | 0 | 2 | 68 | 64 | 1 | 19 | 3 | 2 | 236 | 231 | 5 | 2 | −4 | 3 | 222 | 215 | 2 | −24 | 0 | 3 | 143 | 146 | 2 |
| 14 | −4 | 2 | 107 | 107 | 2 | −12 | 0 | 2 | 245 | 236 | 3 | 21 | 3 | 2 | 23 | 25 | 5 | 4 | −4 | 3 | 243 | 248 | 2 | −22 | 0 | 3 | 66 | 61 | 1 |
| 16 | −4 | 2 | 270 | 264 | 4 | −10 | 0 | 2 | 98 | 68 | 1 | −22 | 4 | 2 | 145 | 131 | 2 | 6 | −4 | 3 | 195 | 210 | 2 | −20 | 0 | 3 | 73 | 76 | 1 |
| 18 | −4 | 2 | 75 | 73 | 1 | −8 | 0 | 2 | 61 | 97 | 1 | −20 | 4 | 2 | 146 | 141 | 2 | 8 | −4 | 3 | 246 | 247 | 3 | −18 | 0 | 3 | 48 | 50 | 1 |
| 20 | −4 | 2 | 13 | 31 | 8 | −6 | 0 | 2 | 1381 | 1398 | 20 | −18 | 4 | 2 | 104 | 112 | 2 | 10 | −4 | 3 | 304 | 325 | 5 | −16 | 0 | 3 | 383 | 406 | 3 |
| −25 | −3 | 2 | 16 | 13 | 5 | −4 | 0 | 2 | 157 | 177 | 2 | −16 | 4 | 2 | 140 | 127 | 3 | 12 | −4 | 3 | 50 | 51 | 1 | −14 | 0 | 3 | 188 | 187 | 3 |
| −23 | −3 | 2 | 94 | 89 | 3 | −2 | 0 | 2 | 543 | 525 | 7 | −14 | 4 | 2 | 261 | 277 | 5 | 14 | −4 | 3 | 105 | 110 | 2 | −12 | 0 | 3 | 277 | 261 | 3 |
| −21 | −3 | 2 | 85 | 83 | 2 | 0 | 0 | 2 | 335 | 316 | 4 | −12 | 4 | 2 | 159 | 164 | 5 | 16 | −4 | 3 | 158 | 156 | 2 | −10 | 0 | 3 | 536 | 483 | 7 |
| −19 | −3 | 2 | 138 | 142 | 3 | 2 | 0 | 2 | 802 | 836 | 10 | −10 | 4 | 2 | 65 | 71 | 3 | 18 | −4 | 3 | 113 | 121 | 2 | −8 | 0 | 3 | 117 | 117 | 1 |
| −17 | −3 | 2 | 74 | 69 | 1 | 4 | 0 | 2 | 263 | 243 | 3 | −8 | 4 | 2 | 156 | 160 | 5 | −25 | −3 | 3 | 160 | 153 | 4 | −6 | 0 | 3 | 527 | 510 | 6 |
| −15 | −3 | 2 | 50 | 47 | 1 | 6 | 0 | 2 | 146 | 140 | 1 | 4 | 4 | 2 | 177 | 178 | 5 | −23 | −3 | 3 | 181 | 181 | 5 | −4 | 0 | 3 | 172 | 137 | 2 |
| −13 | −3 | 2 | 196 | 204 | 1 | 8 | 0 | 2 | 1001 | 964 | 13 | 6 | 4 | 2 | 28 | 19 | 3 | −21 | −3 | 3 | 182 | 188 | 3 | −2 | 0 | 3 | 438 | 415 | 5 |
| −11 | −3 | 2 | 373 | 353 | 3 | 10 | 0 | 2 | 134 | 127 | 1 | 8 | 4 | 2 | 64 | 58 | 3 | −19 | −3 | 3 | 110 | 106 | 2 | 0 | 0 | 3 | 28 | 3 | 1 |
| −9 | −3 | 2 | 263 | 240 | 3 | 12 | 0 | 2 | 624 | 635 | 5 | 10 | 4 | 2 | 218 | 214 | 4 | −17 | −3 | 3 | 125 | 131 | 1 | 2 | 0 | 3 | 216 | 214 | 2 |
| −7 | −3 | 2 | 730 | 723 | 9 | 14 | 0 | 2 | 60 | 74 | 1 | 12 | 4 | 2 | 311 | 301 | 5 | −15 | −3 | 3 | 88 | 91 | 1 | 4 | 0 | 3 | 399 | 400 | 5 |
| −5 | −3 | 2 | 210 | 207 | 2 | 16 | 0 | 2 | 51 | 44 | 1 | 14 | 4 | 2 | 107 | 106 | 2 | −13 | −3 | 3 | 133 | 121 | 1 | 6 | 0 | 3 | 398 | 389 | 5 |
| −3 | −3 | 2 | 48 | 26 | 1 | 18 | 0 | 2 | 152 | 159 | 2 | 16 | 4 | 2 | 269 | 265 | 4 | −11 | −3 | 3 | 119 | 106 | 1 | 8 | 0 | 3 | 441 | 418 | 5 |
| −1 | −3 | 2 | 231 | 230 | 4 | 20 | 0 | 2 | 103 | 113 | 2 | 18 | 4 | 2 | 75 | 74 | 2 | −9 | −3 | 3 | 137 | 141 | 1 | 10 | 0 | 3 | 236 | 226 | 2 |
| 1 | −3 | 2 | 275 | 262 | 3 | 22 | 0 | 2 | 27 | 30 | 4 | 20 | 4 | 2 | 32 | 33 | 4 | −7 | −3 | 3 | 225 | 215 | 2 | 12 | 0 | 3 | 110 | 122 | 1 |
| 3 | −3 | 2 | 308 | 307 | 3 | 24 | 0 | 2 | 51 | 55 | 2 | −19 | 5 | 2 | 71 | 65 | 2 | −5 | −3 | 3 | 238 | 244 | 2 | 14 | 0 | 3 | 58 | 53 | 1 |
| 5 | −3 | 2 | 465 | 460 | 4 | −27 | 1 | 2 | 158 | 155 | 4 | −17 | 5 | 2 | 58 | 50 | 3 | −3 | −3 | 3 | 170 | 166 | 2 | 16 | 0 | 3 | 71 | 69 | 1 |
| 7 | −3 | 2 | 202 | 194 | 2 | −25 | 1 | 2 | 82 | 82 | 2 | −15 | 5 | 2 | 172 | 175 | 5 | −1 | −3 | 3 | 350 | 337 | 4 | 18 | 0 | 3 | 103 | 101 | 2 |
| 9 | −3 | 2 | 258 | 253 | 2 | −23 | 1 | 2 | 239 | 240 | 3 | −13 | 5 | 2 | 134 | 146 | 4 | 1 | −3 | 3 | 109 | 137 | 1 | 20 | 0 | 3 | 62 | 56 | 2 |
| 11 | −3 | 2 | 206 | 210 | 1 | −21 | 1 | 2 | 177 | 174 | 2 | −11 | 5 | 2 | 174 | 166 | 5 | 3 | −3 | 3 | 287 | 282 | 2 | 22 | 0 | 3 | 64 | 67 | 2 |
| 13 | −3 | 2 | 566 | 579 | 6 | −19 | 1 | 2 | 243 | 238 | 3 | −9 | 5 | 2 | 23 | 15 | 4 | 5 | −3 | 3 | 112 | 110 | 1 | −29 | 1 | 3 | 66 | 66 | 3 |
| 15 | −3 | 2 | 163 | 166 | 2 | −17 | 1 | 2 | 182 | 183 | 2 | −7 | 5 | 2 | 168 | 163 | 5 | 7 | −3 | 3 | 181 | 176 | 1 | −27 | 1 | 3 | 56 | 58 | 3 |
| 17 | −3 | 2 | 229 | 236 | 3 | −15 | 1 | 2 | 107 | 94 | 1 | 3 | 5 | 2 | 289 | 293 | 9 | 9 | −3 | 3 | 168 | 162 | 1 | −25 | 1 | 3 | 193 | 192 | 3 |
| 19 | −3 | 2 | 238 | 230 | 4 | −13 | 1 | 2 | 219 | 223 | 3 | 5 | 5 | 2 | 114 | 109 | 4 | 11 | −3 | 3 | 99 | 91 | 1 | −23 | 1 | 3 | 128 | 123 | 2 |
| 21 | −3 | 2 | 27 | 25 | 3 | −11 | 1 | 2 | 316 | 322 | 4 | 7 | 5 | 2 | 158 | 162 | 5 | 13 | −3 | 3 | 215 | 214 | 3 | −21 | 1 | 3 | 208 | 206 | 2 |
| −26 | −2 | 2 | 42 | 36 | 2 | −9 | 1 | 2 | 428 | 472 | 5 | 9 | 5 | 2 | 212 | 208 | 6 | 15 | −3 | 3 | 190 | 190 | 3 | −19 | 1 | 3 | 220 | 225 | 2 |
| −24 | −2 | 2 | 117 | 115 | 2 | −7 | 1 | 2 | 36 | 26 | 1 | 11 | 5 | 2 | 94 | 89 | 3 | 17 | −3 | 3 | 45 | 51 | 2 | −17 | 1 | 3 | 126 | 135 | 1 |
| −22 | −2 | 2 | 197 | 203 | 3 | −5 | 1 | 2 | 322 | 340 | 4 | 13 | 5 | 2 | 26 | 22 | 4 | 19 | −3 | 3 | 97 | 93 | 2 | −15 | 1 | 3 | 233 | 222 | 2 |
| −20 | −2 | 2 | 174 | 183 | 2 | −3 | 1 | 2 | 649 | 664 | 9 | 15 | 5 | 2 | 64 | 62 | 2 | −28 | −2 | 3 | 57 | 54 | 3 | −13 | 1 | 3 | 166 | 159 | 2 |
| −18 | −2 | 2 | 249 | 247 | 2 | −1 | 1 | 2 | 721 | 744 | 9 | −14 | 6 | 2 | 89 | 91 | 3 | −26 | −2 | 3 | 69 | 69 | 2 | −11 | 1 | 3 | 533 | 509 | 7 |
| −16 | −2 | 2 | 281 | 290 | 2 | 1 | 1 | 2 | 689 | 705 | 9 | −12 | 6 | 2 | 41 | 41 | 3 | −24 | −2 | 3 | 132 | 132 | 2 | −9 | 1 | 3 | 434 | 410 | 6 |
| −14 | −2 | 2 | 250 | 250 | 2 | 3 | 1 | 2 | 591 | 597 | 8 | −10 | 6 | 2 | 45 | 39 | 3 | −22 | −2 | 3 | 237 | 256 | 3 | −7 | 1 | 3 | 410 | 402 | 5 |
| −12 | −2 | 2 | 402 | 380 | 4 | 5 | 1 | 2 | 247 | 216 | 3 | −8 | 6 | 2 | 118 | 112 | 4 | −20 | −2 | 3 | 172 | 176 | 1 | −5 | 1 | 3 | 513 | 534 | 7 |
| −10 | −2 | 2 | 258 | 248 | 3 | 7 | 1 | 2 | 268 | 243 | 3 | −6 | 6 | 2 | 167 | 170 | 5 | −18 | −2 | 3 | 118 | 116 | 1 | −3 | 1 | 3 | 398 | 372 | 5 |
| −8 | −2 | 2 | 520 | 502 | 5 | 9 | 1 | 2 | 398 | 372 | 5 | 2 | 6 | 2 | 247 | 24 | 7 | −16 | −2 | 3 | 437 | 445 | 3 | −1 | 1 | 3 | 523 | 555 | 6 |

TABLE 16-continued

Observed and calculated structure factors for Diol-1

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −6 | −2 | 2 | 695 | 698 | 6 | 11 | 1 | 2 | 338 | 320 | 3 | 4 | 6 | 2 | 271 | 265 | 8 | −14 | −2 | 3 | 150 | 154 | 1 | 1 | 1 | 3 | 424 | 42 | 5 |
| −4 | −2 | 2 | 25 | 18 | 1 | 13 | 1 | 2 | 121 | 113 | 1 | 6 | 6 | 2 | 227 | 208 | 7 | −12 | −2 | 3 | 77 | 42 | 1 | 3 | 1 | 3 | 419 | 420 | 5 |
| −2 | −2 | 2 | 98 | 89 | 1 | 15 | 1 | 2 | 90 | 76 | 1 | 8 | 6 | 2 | 328 | 321 | 9 | −10 | −2 | 3 | 348 | 308 | 4 | 5 | 1 | 3 | 538 | 541 | 7 |
| 0 | −2 | 2 | 500 | 486 | 4 | 17 | 1 | 2 | 227 | 229 | 3 | 10 | 6 | 2 | 98 | 95 | 3 | −8 | −2 | 3 | 187 | 184 | 2 | 7 | 1 | 3 | 143 | 140 | 2 |
| 2 | −2 | 2 | 240 | 248 | 2 | 19 | 1 | 2 | 125 | 123 | 2 | −14 | −6 | 3 | 131 | 125 | 4 | −6 | −2 | 3 | 166 | 171 | 1 | 9 | 1 | 3 | 599 | 619 | 6 |
| 4 | −2 | 2 | 315 | 295 | 3 | 21 | 1 | 2 | 63 | 59 | 1 | −12 | −6 | 3 | 116 | 118 | 3 | −4 | −2 | 3 | 330 | 323 | 3 | 11 | 1 | 3 | 22 | 24 | 1 |
| 6 | −2 | 2 | 152 | 142 | 1 | 23 | 1 | 2 | 49 | 49 | 2 | −10 | −6 | 3 | 48 | 46 | 2 | −2 | −2 | 3 | 410 | 397 | 4 | 13 | 1 | 3 | 188 | 191 | 2 |
| 8 | −2 | 2 | 274 | 261 | 2 | −26 | 2 | 2 | 43 | 36 | 2 | −8 | −6 | 3 | 86 | 85 | 3 | 0 | −2 | 3 | 230 | 211 | 2 | 15 | 1 | 3 | 110 | 116 | 1 |
| 10 | −2 | 2 | 90 | 104 | 1 | −24 | 2 | 2 | 112 | 115 | 2 | −6 | −6 | 3 | 165 | 155 | 3 | 2 | −2 | 3 | 413 | 407 | 4 | 17 | 1 | 3 | 162 | 166 | 2 |
| 12 | −2 | 2 | 301 | 301 | 2 | −22 | 2 | 2 | 202 | 204 | 3 | −4 | −6 | 3 | 88 | 89 | 2 | 4 | −2 | 3 | 228 | 232 | 2 | 19 | 1 | 3 | 81 | 82 | 1 |
| 14 | −2 | 2 | 246 | 249 | 2 | −20 | 2 | 2 | 179 | 183 | 2 | −2 | −6 | 3 | 165 | 163 | 3 | 6 | −2 | 3 | 279 | 257 | 2 | 21 | 1 | 3 | 136 | 130 | 3 |
| 16 | −2 | 2 | 386 | 336 | 4 | −18 | 2 | 2 | 24 | 247 | 3 | 0 | −6 | 3 | 140 | 142 | 3 | 8 | −2 | 3 | 349 | 354 | 3 | 23 | 1 | 3 | 101 | 104 | 2 |
| 18 | −2 | 2 | 276 | 269 | 4 | −16 | 2 | 2 | 275 | 290 | 3 | 2 | −6 | 3 | 130 | 124 | 2 | 10 | −2 | 3 | 295 | 237 | 2 | −28 | 2 | 3 | 52 | 53 | 1 |
| 20 | −2 | 2 | 218 | 219 | 3 | −14 | 2 | 2 | 245 | 250 | 3 | 4 | −6 | 3 | 167 | 162 | 3 | 12 | −2 | 3 | 135 | 132 | 1 | −26 | 2 | 3 | 65 | 70 | 2 |
| 22 | −2 | 2 | 81 | 76 | 2 | −12 | 2 | 2 | 396 | 379 | 6 | 6 | −6 | 3 | 113 | 111 | 2 | 14 | −2 | 3 | 181 | 186 | 1 | −24 | 2 | 3 | 134 | 131 | 2 |
| −27 | −1 | 2 | 150 | 156 | 2 | −10 | 2 | 2 | 254 | 247 | 4 | 8 | −6 | 3 | 124 | 129 | 2 | 16 | −2 | 3 | 265 | 272 | 4 | −22 | 2 | 3 | 244 | 256 | 3 |
| −25 | −1 | 2 | 84 | 81 | 2 | −8 | 2 | 2 | 524 | 501 | 10 | 10 | −6 | 3 | 45 | 49 | 3 | 18 | −2 | 3 | 146 | 140 | 2 | −20 | 2 | 3 | 174 | 176 | 2 |
| −23 | −1 | 2 | 244 | 240 | 4 | −6 | 2 | 2 | 678 | 698 | 14 | −21 | −5 | 3 | 95 | 31 | 3 | 20 | −2 | 3 | 224 | 226 | 4 | −18 | 2 | 3 | 114 | 115 | 1 |
| −21 | −1 | 2 | 178 | 174 | 3 | −4 | 2 | 2 | 31 | 18 | 1 | −17 | −5 | 3 | 70 | 69 | 2 | 22 | −2 | 3 | 61 | 58 | 3 | −16 | 2 | 3 | 428 | 444 | 5 |
| −19 | −1 | 2 | 238 | 238 | 2 | −2 | 2 | 2 | 93 | 89 | 2 | −15 | −5 | 3 | 113 | 104 | 2 | −29 | −1 | 3 | 63 | 66 | 2 | −14 | 2 | 3 | 149 | 153 | 2 |
| −17 | −1 | 2 | 184 | 183 | 1 | 0 | 2 | 2 | 480 | 485 | 8 | −13 | −5 | 3 | 176 | 170 | 3 | −27 | −1 | 3 | 58 | 58 | 2 | −12 | 2 | 3 | 78 | 41 | 1 |
| −15 | −1 | 2 | 110 | 94 | 1 | 2 | 2 | 2 | 230 | 247 | 5 | −11 | −5 | 3 | 175 | 181 | 3 | −25 | −1 | 3 | 192 | 191 | 4 | −10 | 2 | 3 | 341 | 309 | 5 |
| −13 | −1 | 2 | 216 | 223 | 3 | 4 | 2 | 2 | 318 | 296 | 6 | −9 | −5 | 3 | 242 | 237 | 3 | −23 | −1 | 3 | 130 | 123 | 2 | −8 | 2 | 3 | 184 | 183 | 3 |
| −11 | −1 | 2 | 313 | 322 | 4 | 6 | 2 | 2 | 143 | 141 | 3 | −7 | −5 | 3 | 327 | 334 | 5 | −21 | −1 | 3 | 204 | 206 | 2 | −6 | 2 | 3 | 160 | 171 | 3 |
| −9 | −1 | 2 | 426 | 472 | 4 | 8 | 2 | 2 | 276 | 261 | 4 | −5 | −5 | 3 | 183 | 188 | 3 | −19 | −1 | 3 | 218 | 224 | 2 | −4 | 2 | 3 | 313 | 323 | 6 |
| −7 | −1 | 2 | 36 | 26 | 1 | 10 | 2 | 2 | 88 | 104 | 1 | −3 | −5 | 3 | 302 | 293 | 4 | −17 | −1 | 3 | 128 | 135 | 1 | −2 | 2 | 3 | 393 | 398 | 12 |
| −5 | −1 | 2 | 327 | 340 | 3 | 12 | 2 | 2 | 298 | 300 | 3 | −1 | −5 | 3 | 85 | 85 | 1 | −15 | −1 | 3 | 238 | 222 | 2 | 0 | 2 | 3 | 225 | 212 | 3 |
| −3 | −1 | 2 | 668 | 665 | 6 | 14 | 2 | 2 | 248 | 249 | 3 | 1 | −5 | 3 | 169 | 164 | 2 | −13 | −1 | 3 | 163 | 159 | 2 | 2 | 2 | 3 | 412 | 408 | 8 |
| −1 | −1 | 2 | 735 | 743 | 7 | 16 | 2 | 2 | 387 | 396 | 5 | 3 | −5 | 3 | 111 | 108 | 2 | −11 | −1 | 3 | 520 | 511 | 8 | 4 | 2 | 3 | 226 | 233 | 4 |
| 6 | 2 | 3 | 271 | 258 | 4 | −11 | −5 | 4 | 144 | 144 | 3 | −19 | −1 | 4 | 354 | 359 | 3 | −2 | 2 | 4 | 225 | 209 | 6 | 0 | −6 | 5 | 111 | 111 | 2 |
| 8 | 2 | 3 | 343 | 354 | 5 | −9 | −5 | 4 | 95 | 93 | 2 | −17 | −1 | 4 | 140 | 126 | 1 | 0 | 2 | 4 | 518 | 494 | 15 | 2 | −6 | 5 | 26 | 22 | 1 |
| 10 | 2 | 3 | 291 | 298 | 3 | −5 | −5 | 4 | 89 | 115 | 2 | −15 | −1 | 4 | 140 | 147 | 1 | 2 | 2 | 4 | 239 | 250 | 5 | 4 | −6 | 5 | 169 | 177 | 3 |
| 12 | 2 | 3 | 133 | 131 | 1 | −3 | −5 | 4 | 268 | 292 | 5 | −13 | −1 | 4 | 289 | 281 | 3 | 4 | 2 | 4 | 193 | 197 | 3 | −21 | −5 | 5 | 52 | 46 | 2 |
| 14 | 2 | 3 | 183 | 185 | 2 | −1 | −5 | 4 | 37 | 34 | 1 | −11 | −1 | 4 | 414 | 416 | 6 | 6 | 2 | 4 | 155 | 158 | 2 | −19 | −5 | 5 | 77 | 82 | 2 |
| 16 | 2 | 3 | 268 | 273 | 4 | 1 | −5 | 4 | 157 | 159 | 2 | −9 | −1 | 4 | 678 | 673 | 10 | 8 | 2 | 4 | 13 | 13 | 3 | −17 | −5 | 5 | 44 | 44 | 2 |
| 18 | 2 | 3 | 147 | 141 | 2 | 3 | −5 | 4 | 121 | 128 | 2 | −7 | −1 | 4 | 276 | 276 | 3 | 10 | 2 | 4 | 197 | 199 | 2 | −15 | −5 | 5 | 80 | 79 | 2 |
| 20 | 2 | 3 | 226 | 226 | 3 | 5 | −5 | 4 | 113 | 116 | 2 | −5 | −1 | 4 | 366 | 345 | 4 | 12 | 2 | 4 | 191 | 191 | 2 | −13 | −5 | 5 | 59 | 64 | 2 |
| 22 | 2 | 3 | 61 | 58 | 1 | 7 | −5 | 4 | 180 | 181 | 3 | −3 | −1 | 4 | 217 | 243 | 2 | 14 | 2 | 4 | 185 | 181 | 2 | −11 | −5 | 5 | 191 | 184 | 5 |
| −25 | 3 | 3 | 154 | 154 | 3 | 9 | −5 | 4 | 60 | 51 | 2 | −1 | −1 | 4 | 523 | 526 | 6 | 16 | 2 | 4 | 37 | 43 | 2 | −9 | −5 | 5 | 117 | 110 | 3 |
| −23 | 3 | 3 | 177 | 181 | 3 | 11 | −5 | 4 | 138 | 145 | 3 | 1 | −1 | 4 | 318 | 308 | 5 | 18 | 2 | 4 | 94 | 96 | 2 | −7 | −5 | 5 | 316 | 328 | 9 |
| −21 | 3 | 3 | 182 | 188 | 3 | 13 | −5 | 4 | 131 | 128 | 2 | 3 | −1 | 4 | 138 | 120 | 2 | 20 | 2 | 4 | 138 | 128 | 2 | −5 | −5 | 5 | 80 | 93 | 1 |
| −19 | 3 | 3 | 98 | 106 | 3 | −24 | −4 | 4 | 220 | 226 | 6 | 5 | −1 | 4 | 441 | 432 | 5 | −27 | 3 | 4 | 91 | 84 | 2 | −3 | −5 | 5 | 285 | 299 | 8 |
| −17 | 3 | 3 | 127 | 131 | 3 | −22 | −4 | 4 | 54 | 61 | 2 | 7 | −1 | 4 | 188 | 177 | 1 | −25 | 3 | 4 | 84 | 81 | 2 | −1 | −5 | 5 | 155 | 162 | 4 |
| −15 | 3 | 3 | 89 | 92 | 2 | −20 | −4 | 4 | 171 | 176 | 3 | 9 | −1 | 4 | 113 | 101 | 1 | −23 | 3 | 4 | 124 | 129 | 2 | 1 | −5 | 5 | 161 | 160 | 3 |
| −13 | 3 | 3 | 130 | 120 | 2 | −18 | −4 | 4 | 163 | 166 | 3 | 11 | −1 | 4 | 96 | 103 | 1 | −21 | 3 | 4 | 251 | 263 | 5 | 3 | −5 | 5 | 212 | 217 | 3 |
| −11 | 3 | 3 | 120 | 107 | 2 | −16 | −4 | 4 | 262 | 281 | 4 | 13 | −1 | 4 | 278 | 283 | 3 | −19 | 3 | 4 | 280 | 288 | 5 | 5 | −5 | 5 | 237 | 230 | 3 |
| −9 | 3 | 3 | 133 | 140 | 4 | −14 | −4 | 4 | 116 | 129 | 2 | 15 | −1 | 4 | 147 | 151 | 2 | −17 | 3 | 4 | 264 | 256 | 5 | 7 | −5 | 5 | 183 | 180 | 3 |
| 3 | 3 | 3 | 296 | 282 | 8 | −12 | −4 | 4 | 49 | 55 | 1 | 7 | −1 | 4 | 71 | 68 | 2 | −15 | 3 | 4 | 130 | 123 | 3 | 9 | −5 | 5 | 73 | 72 | 2 |
| 5 | 3 | 3 | 106 | 111 | 2 | −10 | −4 | 4 | 423 | 413 | 5 | 19 | −1 | 4 | 110 | 122 | 1 | −13 | 3 | 4 | 148 | 154 | 2 | 11 | −5 | 5 | 85 | 71 | 2 |

TABLE 16-continued

| Observed and calculated structure factors for Diol-1 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| 7 | 3 | 3 | 183 | 177 | 3 | −8 | −4 | 4 | 345 | 325 | 5 | 21 | −1 | 4 | 138 | 140 | 2 | −11 | 3 | 4 | 362 | 384 | 6 | −24 | −4 | 5 | 160 | 172 | 5 |
| 9 | 3 | 3 | 167 | 161 | 3 | −6 | −4 | 4 | 410 | 409 | 6 | −30 | 0 | 4 | 50 | 44 | 2 | −9 | 3 | 4 | 176 | 171 | 5 | −22 | −4 | 5 | 33 | 34 | 2 |
| 11 | 3 | 3 | 102 | 92 | 2 | −4 | −4 | 4 | 62 | 66 | 1 | −28 | 0 | 4 | 60 | 58 | 3 | −7 | 3 | 4 | 239 | 230 | 8 | −20 | −4 | 5 | 82 | 87 | 2 |
| 13 | 3 | 3 | 198 | 215 | 4 | −2 | −4 | 4 | 291 | 284 | 4 | −26 | 0 | 4 | 31 | 44 | 2 | −1 | 3 | 4 | 375 | 380 | 12 | −8 | −4 | 5 | 246 | 232 | 4 |
| 15 | 3 | 3 | 188 | 191 | 3 | 0 | −4 | 4 | 153 | 164 | 2 | −24 | 0 | 4 | 111 | 117 | 2 | 1 | 3 | 4 | 219 | 209 | 6 | −16 | −4 | 5 | 212 | 214 | 2 |
| 17 | 3 | 3 | 47 | 50 | 2 | 2 | −4 | 4 | 144 | 141 | 1 | −22 | 0 | 4 | 261 | 264 | 3 | 3 | 3 | 4 | 349 | 353 | 7 | −14 | −4 | 5 | 389 | 396 | 5 |
| 19 | 3 | 3 | 95 | 93 | 2 | 4 | −4 | 4 | 318 | 315 | 3 | −20 | 0 | 4 | 18 | 19 | 2 | 5 | 3 | 4 | 326 | 331 | 5 | −12 | −4 | 5 | 352 | 349 | 4 |
| −24 | 4 | 3 | 34 | 43 | 4 | 6 | −4 | 4 | 33 | 31 | 1 | −18 | 0 | 4 | 187 | 182 | 1 | 7 | 3 | 4 | 279 | 265 | 4 | −10 | −4 | 5 | 207 | 196 | 2 |
| −22 | 4 | 3 | 57 | 67 | 2 | 8 | −4 | 4 | 41 | 35 | 2 | −16 | 0 | 4 | 52 | 61 | 1 | 9 | 3 | 4 | 248 | 243 | 4 | −8 | −4 | 5 | 192 | 181 | 3 |
| −20 | 4 | 3 | 40 | 39 | 3 | 10 | −4 | 4 | 73 | 81 | 2 | −14 | 0 | 4 | 179 | 155 | 2 | 11 | 3 | 4 | 19 | 15 | 4 | −6 | −4 | 5 | 33 | 36 | 2 |
| −18 | 4 | 3 | 149 | 153 | 3 | 12 | −4 | 4 | 120 | 125 | 2 | −12 | 0 | 4 | 398 | 390 | 5 | 13 | 3 | 4 | 295 | 308 | 5 | −4 | −4 | 5 | 264 | 260 | 4 |
| −16 | 4 | 3 | 26 | 7 | 3 | 14 | −4 | 4 | 144 | 14 | 2 | −10 | 0 | 4 | 20 | 16 | 1 | 15 | 3 | 4 | 78 | 73 | 2 | −2 | −4 | 5 | 158 | 159 | 2 |
| −14 | 4 | 3 | 99 | 109 | 2 | 16 | −4 | 4 | 17 | 20 | 2 | −8 | 0 | 4 | 68 | 65 | 1 | 17 | 3 | 4 | 120 | 118 | 3 | 0 | −4 | 5 | 269 | 277 | 3 |
| −12 | 4 | 3 | 201 | 207 | 6 | −27 | −3 | 4 | 86 | 85 | 3 | −6 | 0 | 4 | 423 | 394 | 5 | 19 | 3 | 4 | 74 | 74 | 2 | 2 | −4 | 5 | 289 | 288 | 3 |
| −10 | 4 | 3 | 38 | 34 | 3 | −25 | −3 | 4 | 82 | 81 | 3 | −4 | 0 | 4 | 787 | 746 | 9 | −24 | 4 | 4 | 230 | 227 | 4 | 4 | −4 | 5 | 332 | 326 | 4 |
| −8 | 4 | 3 | 204 | 198 | 6 | −23 | −3 | 4 | 118 | 128 | 3 | −2 | 0 | 4 | 575 | 534 | 6 | −22 | 4 | 4 | 60 | 62 | 2 | 6 | −4 | 5 | 166 | 158 | 2 |
| 2 | 4 | 3 | 220 | 214 | 7 | −21 | −3 | 4 | 261 | 262 | 4 | 0 | 0 | 4 | 132 | 120 | 1 | −20 | 4 | 4 | 172 | 177 | 4 | 8 | −4 | 5 | 213 | 211 | 3 |
| 4 | 4 | 3 | 255 | 247 | 7 | −19 | −3 | 4 | 280 | 286 | 3 | 2 | 0 | 4 | 17 | 36 | 1 | −18 | 4 | 4 | 164 | 166 | 3 | 10 | −4 | 5 | 11 | 5 | 7 |
| 6 | 4 | 3 | 196 | 210 | 6 | −17 | −3 | 4 | 264 | 257 | 2 | 4 | 0 | 4 | 436 | 435 | 6 | −16 | 4 | 4 | 269 | 280 | 5 | 12 | −4 | 5 | 75 | 66 | 2 |
| 8 | 4 | 3 | 249 | 246 | 5 | −15 | −3 | 4 | 129 | 123 | 1 | 6 | 0 | 4 | 764 | 728 | 9 | −14 | 4 | 4 | 109 | 129 | 4 | 14 | −4 | 5 | 105 | 109 | 2 |
| 10 | 4 | 3 | 322 | 324 | 5 | −13 | −3 | 4 | 149 | 154 | 1 | 8 | 0 | 4 | 175 | 198 | 1 | −12 | 4 | 4 | 47 | 55 | 2 | −27 | −3 | 5 | 45 | 40 | 3 |
| 12 | 4 | 3 | 50 | 50 | 2 | −11 | −3 | 4 | 375 | 384 | 3 | 10 | 0 | 4 | 139 | 152 | 1 | −10 | 4 | 4 | 419 | 415 | 13 | −25 | −3 | 5 | 68 | 61 | 3 |
| 14 | 4 | 3 | 104 | 111 | 2 | −9 | −3 | 4 | 178 | 169 | 1 | 12 | 0 | 4 | 333 | 341 | 3 | −8 | 4 | 4 | 328 | 328 | 10 | −23 | −3 | 5 | 197 | 199 | 6 |
| 16 | 4 | 3 | 161 | 155 | 3 | −7 | −3 | 4 | 253 | 231 | 2 | 14 | 0 | 4 | 271 | 276 | 2 | −6 | 4 | 4 | 391 | 410 | 12 | −21 | −3 | 5 | 48 | 50 | 2 |
| 18 | 4 | 3 | 116 | 122 | 3 | −5 | −3 | 4 | 97 | 108 | 1 | 16 | 0 | 4 | 73 | 57 | 1 | −2 | 4 | 4 | 279 | 283 | 9 | −19 | −3 | 5 | 236 | 239 | 3 |
| −21 | 5 | 3 | 93 | 92 | 3 | −3 | −3 | 4 | 178 | 170 | 1 | 18 | 0 | 4 | 138 | 128 | 2 | 0 | 4 | 4 | 151 | 164 | 5 | −17 | −3 | 5 | 386 | 378 | 4 |
| −17 | 5 | 3 | 68 | 69 | 3 | −1 | −3 | 4 | 400 | 380 | 3 | 20 | 0 | 4 | 63 | 53 | 2 | 2 | 4 | 4 | 144 | 140 | 4 | −15 | −3 | 5 | 200 | 196 | 2 |
| −15 | 5 | 3 | 113 | 103 | 4 | 1 | −3 | 4 | 217 | 209 | 1 | 22 | 0 | 4 | 36 | 28 | 2 | 4 | 4 | 4 | 312 | 315 | 9 | −13 | −3 | 5 | 518 | 531 | 4 |
| −13 | 5 | 3 | 173 | 171 | 5 | 3 | −3 | 4 | 359 | 353 | 3 | −29 | 1 | 4 | 111 | 105 | 3 | 6 | 4 | 4 | 32 | 32 | 3 | −11 | −3 | 5 | 208 | 208 | 1 |
| −11 | 5 | 3 | 174 | 181 | 5 | 5 | −3 | 4 | 327 | 332 | 2 | −27 | 1 | 4 | 114 | 113 | 2 | 8 | 4 | 4 | 43 | 36 | 2 | −9 | −3 | 5 | 98 | 93 | 1 |
| −9 | 5 | 3 | 240 | 237 | 7 | 7 | −3 | 4 | 283 | 267 | 2 | −25 | 1 | 4 | 167 | 163 | 2 | 10 | 4 | 4 | 73 | 81 | 2 | −7 | −3 | 5 | 238 | 240 | 1 |
| −7 | 5 | 3 | 329 | 335 | 9 | 9 | −3 | 4 | 238 | 243 | 2 | −23 | 1 | 4 | 197 | 191 | 3 | 12 | 4 | 4 | 119 | 125 | 2 | −5 | −3 | 5 | 235 | 226 | 1 |
| 1 | 5 | 3 | 168 | 165 | 5 | 11 | −3 | 4 | 14 | 14 | 2 | −21 | 1 | 4 | 280 | 289 | 3 | 14 | 4 | 4 | 148 | 148 | 2 | −3 | −3 | 5 | 342 | 328 | 3 |
| 3 | 5 | 3 | 113 | 109 | 4 | 13 | −3 | 4 | 303 | 309 | 5 | −19 | 1 | 4 | 351 | 359 | 4 | 16 | 4 | 4 | 23 | 21 | 3 | −1 | −3 | 5 | 100 | 99 | 1 |
| 5 | 5 | 3 | 192 | 201 | 6 | 15 | −3 | 4 | 78 | 74 | 2 | −17 | 1 | 4 | 136 | 125 | 1 | −21 | 5 | 4 | 148 | 152 | 5 | 1 | −3 | 5 | 147 | 132 | 1 |
| 7 | 5 | 3 | 153 | 150 | 5 | 17 | −3 | 4 | 121 | 118 | 3 | −15 | 1 | 4 | 140 | 148 | 1 | −17 | 5 | 4 | 171 | 178 | 5 | 3 | −3 | 5 | 401 | 390 | 3 |
| 9 | 5 | 3 | 241 | 241 | 5 | 19 | −3 | 4 | 72 | 74 | 2 | −13 | 1 | 4 | 286 | 278 | 4 | −15 | 5 | 4 | 101 | 103 | 4 | 5 | −3 | 5 | 159 | 155 | 1 |
| 11 | 5 | 3 | 66 | 59 | 2 | −28 | −2 | 4 | 148 | 150 | 3 | −11 | 1 | 4 | 426 | 415 | 5 | −13 | 5 | 4 | 110 | 125 | 3 | 7 | −3 | 5 | 597 | 612 | 5 |
| 13 | 5 | 3 | 77 | 82 | 2 | −26 | −2 | 4 | 142 | 133 | 3 | −9 | 1 | 4 | 691 | 674 | 9 | −11 | 5 | 4 | 142 | 144 | 5 | 9 | −3 | 5 | 20 | 20 | 2 |
| 15 | 5 | 3 | 65 | 71 | 3 | −24 | −2 | 4 | 197 | 200 | 3 | −7 | 1 | 4 | 282 | 277 | 3 | −9 | 5 | 4 | 98 | 94 | 3 | 11 | −3 | 5 | 331 | 333 | 5 |
| −14 | 6 | 3 | 129 | 125 | 4 | −22 | −2 | 4 | 158 | 158 | 2 | −5 | 1 | 4 | 377 | 345 | 5 | −3 | 5 | 4 | 285 | 292 | 8 | 13 | −3 | 5 | 77 | 75 | 2 |
| −12 | 6 | 3 | 117 | 118 | 4 | −20 | −2 | 4 | 477 | 507 | 5 | −3 | 1 | 4 | 223 | 245 | 3 | −1 | 5 | 4 | 42 | 35 | 3 | 15 | −3 | 5 | 78 | 82 | 2 |
| −10 | 6 | 3 | 46 | 46 | 3 | −18 | −2 | 4 | 72 | 82 | 1 | −1 | 1 | 4 | 543 | 526 | 6 | 1 | 5 | 4 | 166 | 160 | 5 | 17 | −3 | 5 | 120 | 118 | 2 |
| −8 | 6 | 3 | 83 | 86 | 3 | −16 | −2 | 4 | 203 | 201 | 2 | 1 | 1 | 4 | 322 | 309 | 4 | 3 | 5 | 4 | 122 | 128 | 4 | −28 | −2 | 5 | 63 | 55 | 2 |
| −6 | 6 | 3 | 154 | 155 | 5 | −14 | −2 | 4 | 325 | 315 | 3 | 3 | 1 | 4 | 137 | 121 | 2 | 5 | 5 | 4 | 117 | 117 | 4 | −26 | −2 | 5 | 120 | 107 | 3 |
| −2 | 6 | 3 | 158 | 163 | 5 | −12 | −2 | 4 | 325 | 290 | 3 | 5 | 1 | 4 | 436 | 434 | 5 | 7 | 5 | 4 | 186 | 182 | 4 | −24 | −2 | 5 | 70 | 79 | 1 |
| 0 | 6 | 3 | 138 | 141 | 4 | −10 | −2 | 4 | 582 | 563 | 6 | 7 | 1 | 4 | 184 | 177 | 2 | 9 | 5 | 4 | 60 | 52 | 2 | −22 | −2 | 5 | 247 | 250 | 4 |
| 2 | 6 | 3 | 126 | 125 | 4 | −8 | −2 | 4 | 209 | 198 | 2 | 9 | 1 | 4 | 111 | 100 | 1 | 11 | 5 | 4 | 137 | 145 | 4 | −20 | −2 | 5 | 30 | 17 | 1 |
| 4 | 6 | 3 | 174 | 163 | 5 | −6 | −2 | 4 | 564 | 540 | 5 | 11 | 1 | 4 | 99 | 104 | 1 | 13 | 5 | 4 | 128 | 129 | 3 | −18 | −2 | 5 | 234 | 233 | 2 |

TABLE 16-continued

| Observed and calculated structure factors for Diol-1 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| 6 | 6 | 3 | 113 | 111 | 4 | −4 | −2 | 4 | 296 | 307 | 2 | 13 | 1 | 4 | 278 | 283 | 3 | −14 | 6 | 4 | 51 | 51 | 3 | −16 | −2 | 5 | 119 | 123 | 1 |
| 8 | 6 | 3 | 125 | 130 | 4 | −2 | −2 | 4 | 228 | 207 | 2 | 15 | 1 | 4 | 143 | 153 | 2 | −12 | 6 | 4 | 131 | 138 | 4 | −14 | −2 | 5 | 104 | 102 | 1 |
| −14 | −6 | 4 | 51 | 51 | 2 | 0 | −2 | 4 | 530 | 493 | 5 | 17 | 1 | 4 | 72 | 69 | 1 | −10 | 6 | 4 | 18 | 9 | 3 | −12 | −2 | 5 | 295 | 307 | 2 |
| −12 | −6 | 4 | 136 | 138 | 2 | 2 | −2 | 4 | 245 | 249 | 2 | 19 | 1 | 4 | 113 | 122 | 2 | −8 | 6 | 4 | 113 | 121 | 2 | −10 | −2 | 5 | 258 | 253 | 3 |
| −10 | −6 | 4 | 22 | 8 | 2 | 4 | −2 | 4 | 192 | 197 | 1 | 21 | 1 | 4 | 145 | 141 | 3 | −6 | 6 | 4 | 205 | 215 | 4 | −8 | −2 | 5 | 138 | 133 | 1 |
| −8 | −6 | 4 | 120 | 122 | 2 | 6 | −2 | 4 | 160 | 159 | 1 | −28 | 2 | 4 | 147 | 151 | 3 | −4 | 6 | 4 | 98 | 102 | 2 | −6 | −2 | 5 | 428 | 430 | 4 |
| −6 | −6 | 4 | 218 | 214 | 4 | 8 | −2 | 4 | 19 | 12 | 1 | −26 | 2 | 4 | 138 | 133 | 2 | −2 | 6 | 4 | 60 | 54 | 3 | −4 | −2 | 5 | 689 | 636 | 7 |
| −4 | −6 | 4 | 105 | 102 | 2 | 10 | −2 | 4 | 198 | 199 | 1 | −24 | 2 | 4 | 207 | 201 | 3 | 0 | 6 | 4 | 116 | 120 | 4 | −2 | −2 | 5 | 396 | 374 | 4 |
| −2 | −6 | 4 | 63 | 55 | 1 | 12 | −2 | 4 | 190 | 192 | 1 | −22 | 2 | 4 | 158 | 158 | 2 | 2 | 6 | 4 | 37 | 33 | 3 | 0 | −2 | 5 | 53 | 18 | 2 |
| 0 | −6 | 4 | 123 | 120 | 2 | 14 | −2 | 4 | 182 | 181 | 2 | −20 | 2 | 4 | 482 | 507 | 6 | 4 | 6 | 4 | 40 | 31 | 3 | 2 | −2 | 5 | 181 | 186 | 1 |
| 2 | −6 | 4 | 37 | 33 | 2 | 16 | −2 | 4 | 36 | 42 | 2 | −18 | 2 | 4 | 69 | 82 | 1 | 6 | 6 | 4 | 182 | 190 | 4 | 4 | −2 | 5 | 271 | 248 | 2 |
| 4 | −6 | 4 | 34 | 32 | 2 | 18 | −2 | 4 | 95 | 96 | 2 | −16 | 2 | 4 | 198 | 201 | 3 | −14 | −6 | 5 | 79 | 74 | 1 | 6 | −2 | 5 | 450 | 457 | 3 |
| 6 | −6 | 4 | 180 | 190 | 3 | 20 | −2 | 4 | 138 | 129 | 2 | −14 | 2 | 4 | 324 | 316 | 5 | −12 | −6 | 5 | 206 | 198 | 3 | 8 | −2 | 5 | 175 | 182 | 1 |
| 8 | −6 | 4 | 66 | 70 | 3 | −29 | −1 | 4 | 104 | 105 | 2 | −12 | 2 | 4 | 314 | 288 | 5 | −10 | −6 | 5 | 153 | 144 | 3 | 10 | −2 | 5 | 346 | 359 | 3 |
| −21 | −5 | 4 | 151 | 152 | 4 | −27 | −1 | 4 | 115 | 114 | 2 | −10 | 2 | 4 | 567 | 562 | 12 | −8 | −6 | 5 | 341 | 338 | 6 | 12 | −2 | 5 | 286 | 294 | 5 |
| −17 | −5 | 4 | 167 | 179 | 2 | −25 | −1 | 4 | 172 | 163 | 2 | −8 | 2 | 4 | 202 | 199 | 6 | −6 | −6 | 5 | 94 | 90 | 2 | 14 | −2 | 5 | 45 | 44 | 2 |
| −15 | −5 | 4 | 103 | 103 | 2 | −23 | −1 | 4 | 203 | 190 | 3 | −6 | 2 | 4 | 558 | 540 | 15 | −4 | −6 | 5 | 185 | 183 | 3 | 16 | −2 | 5 | 65 | 59 | 2 |
| −13 | −5 | 4 | 121 | 125 | 2 | −21 | −1 | 4 | 276 | 290 | 3 | −4 | 2 | 4 | 274 | 308 | 8 | −2 | −6 | 5 | 184 | 180 | 5 | 18 | −2 | 5 | 48 | 43 | 2 |
| −29 | −1 | 5 | 123 | 122 | 2 | −4 | 2 | 5 | 655 | 635 | 14 | −4 | −6 | 6 | 149 | 142 | 3 | −23 | −1 | 6 | 71 | 71 | 2 | 6 | 2 | 6 | 227 | 228 | 3 |
| −27 | −1 | 5 | 240 | 217 | 4 | −2 | 2 | 5 | 381 | 372 | 8 | −2 | −6 | 6 | 123 | 123 | 3 | −21 | −1 | 6 | 295 | 289 | 3 | 8 | 2 | 6 | 182 | 195 | 2 |
| −25 | −1 | 5 | 154 | 149 | 2 | 0 | 2 | 5 | 50 | 17 | 3 | 0 | −6 | 6 | 161 | 168 | 3 | −19 | −1 | 6 | 116 | 120 | 1 | 10 | 2 | 6 | 160 | 154 | 2 |
| −23 | −1 | 5 | 250 | 245 | 4 | 2 | 2 | 5 | 181 | 186 | 2 | 2 | −6 | 6 | 141 | 147 | 2 | −17 | −1 | 6 | 168 | 181 | 2 | 12 | 2 | 6 | 217 | 223 | 3 |
| −21 | −1 | 5 | 130 | 128 | 1 | 4 | 2 | 5 | 266 | 249 | 3 | −21 | −5 | 6 | 73 | 72 | 2 | −15 | −1 | 6 | 295 | 276 | 3 | 14 | 2 | 6 | 69 | 72 | 1 |
| −19 | −1 | 5 | 241 | 230 | 2 | 6 | 2 | 5 | 437 | 457 | 5 | −19 | −5 | 6 | 131 | 123 | 3 | −13 | −1 | 6 | 298 | 302 | 3 | 16 | 2 | 6 | 33 | 32 | 1 |
| −17 | −1 | 5 | 101 | 93 | 1 | 8 | 2 | 5 | 174 | 181 | 2 | −17 | −5 | 6 | 155 | 160 | 3 | −11 | −1 | 6 | 162 | 150 | 2 | −27 | 3 | 6 | 30 | 28 | 4 |
| −15 | −1 | 5 | 127 | 117 | 1 | 10 | 2 | 5 | 356 | 359 | 4 | −15 | −5 | 6 | 297 | 298 | 5 | −9 | −1 | 6 | 430 | 391 | 5 | −25 | 3 | 6 | 50 | 54 | 2 |
| −13 | −1 | 5 | 382 | 392 | 5 | 12 | 2 | 5 | 291 | 294 | 4 | −13 | −5 | 6 | 66 | 63 | 2 | −7 | −1 | 6 | 664 | 668 | 9 | −23 | 3 | 6 | 134 | 127 | 2 |
| −11 | −1 | 5 | 401 | 403 | 6 | 14 | 2 | 5 | 48 | 43 | 1 | −11 | −5 | 6 | 174 | 167 | 3 | −5 | −1 | 6 | 428 | 412 | 6 | −21 | 3 | 6 | 191 | 199 | 3 |
| −9 | −1 | 5 | 262 | 259 | 4 | 16 | 2 | 5 | 64 | 60 | 1 | −9 | −5 | 6 | 155 | 158 | 4 | −3 | −1 | 6 | 543 | 553 | 6 | −19 | 3 | 6 | 141 | 149 | 2 |
| −7 | −1 | 5 | 711 | 747 | 11 | 18 | 2 | 5 | 44 | 43 | 1 | −7 | −5 | 6 | 134 | 136 | 3 | −1 | −1 | 6 | 103 | 110 | 1 | −17 | 3 | 6 | 224 | 239 | 4 |
| −5 | −1 | 5 | 622 | 589 | 10 | −27 | 3 | 5 | 3 | 38 | 3 | −5 | −5 | 6 | 43 | 49 | 2 | 1 | −1 | 6 | 52 | 64 | 1 | −15 | 3 | 6 | 277 | 263 | 4 |
| −3 | −1 | 5 | 850 | 845 | 16 | −25 | 3 | 5 | 72 | 61 | 2 | −3 | −5 | 6 | 25 | 27 | 2 | 3 | −1 | 6 | 237 | 241 | 2 | −13 | 3 | 6 | 224 | 225 | 3 |
| −1 | −1 | 5 | 381 | 380 | 7 | −23 | 3 | 5 | 198 | 198 | 3 | −1 | −5 | 6 | 284 | 284 | 5 | 5 | −1 | 6 | 82 | 86 | 1 | −11 | 3 | 6 | 457 | 465 | 7 |
| 1 | −1 | 5 | 364 | 374 | 5 | −21 | 3 | 5 | 50 | 52 | 2 | 1 | −5 | 6 | 77 | 69 | 2 | 7 | −1 | 6 | 73 | 77 | 1 | −9 | 3 | 6 | 199 | 187 | 3 |
| 3 | −1 | 5 | 192 | 191 | 2 | −19 | 3 | 5 | 236 | 239 | 5 | 3 | −5 | 6 | 173 | 169 | 3 | 9 | −1 | 6 | 185 | 188 | 1 | −7 | 3 | 6 | 173 | 173 | 3 |
| 5 | −1 | 5 | 236 | 224 | 2 | −17 | 3 | 5 | 390 | 378 | 7 | 5 | −5 | 6 | 203 | 201 | 4 | 11 | −1 | 6 | 91 | 93 | 2 | −5 | 3 | 6 | 62 | 57 | 1 |
| 7 | −1 | 5 | 211 | 214 | 2 | −15 | 3 | 5 | 202 | 196 | 4 | 7 | −5 | 6 | 29 | 24 | 2 | 13 | −1 | 6 | 112 | 117 | 2 | −3 | 3 | 6 | 132 | 130 | 2 |
| 9 | −1 | 5 | 88 | 97 | 1 | −13 | 3 | 5 | 518 | 532 | 10 | 9 | −5 | 6 | 104 | 108 | 2 | 15 | −1 | 6 | 167 | 162 | 2 | −1 | 3 | 6 | 272 | 264 | 4 |
| 11 | −1 | 5 | 133 | 143 | 1 | −11 | 3 | 5 | 204 | 207 | 3 | −24 | −4 | 6 | 73 | 74 | 3 | 17 | −1 | 6 | 57 | 52 | 1 | 1 | 3 | 6 | 235 | 225 | 4 |
| 13 | −1 | 5 | 36 | 27 | 2 | −9 | 3 | 5 | 99 | 94 | 2 | −22 | −4 | 6 | 140 | 153 | 2 | −30 | 0 | 6 | 102 | 93 | 4 | 3 | 3 | 6 | 329 | 329 | 5 |
| 15 | −1 | 5 | 162 | 160 | 2 | −7 | 3 | 5 | 230 | 239 | 5 | −20 | −4 | 6 | 151 | 169 | 2 | −28 | 0 | 6 | 301 | 283 | 4 | 5 | 3 | 6 | 74 | 77 | 2 |
| 17 | −1 | 5 | 180 | 174 | 2 | −5 | 3 | 5 | 225 | 226 | 5 | −18 | −4 | 6 | 148 | 157 | 2 | −26 | 0 | 6 | 28 | 22 | 2 | 7 | 3 | 6 | 322 | 310 | 6 |
| 19 | −1 | 5 | 82 | 84 | 1 | −3 | 3 | 5 | 342 | 328 | 7 | −16 | −4 | 6 | 229 | 220 | 5 | −24 | 0 | 6 | 10 | 11 | 9 | 9 | 3 | 6 | 274 | 277 | 4 |
| −30 | 0 | 5 | 202 | 188 | 5 | −1 | 3 | 5 | 95 | 98 | 2 | −14 | −4 | 6 | 280 | 279 | 5 | −22 | 0 | 6 | 42 | 46 | 1 | 11 | 3 | 6 | 151 | 147 | 2 |
| −28 | 0 | 5 | 389 | 361 | 6 | 1 | 3 | 5 | 144 | 132 | 3 | −12 | −4 | 6 | 271 | 272 | 5 | −20 | 0 | 6 | 301 | 294 | 3 | 13 | 3 | 6 | 122 | 122 | 2 |
| −26 | 0 | 5 | 163 | 153 | 3 | 3 | 3 | 5 | 397 | 389 | 6 | −10 | −4 | 6 | 233 | 226 | 3 | −18 | 0 | 6 | 146 | 146 | 1 | 15 | 3 | 6 | 78 | 81 | 2 |
| −24 | 0 | 5 | 118 | 128 | 2 | 5 | 3 | 5 | 160 | 154 | 2 | −8 | −4 | 6 | 47 | 47 | 2 | −16 | 0 | 6 | 50 | 44 | 1 | −24 | 4 | 6 | 75 | 74 | 2 |
| −22 | 0 | 5 | 252 | 248 | 2 | 7 | 3 | 5 | 598 | 612 | 10 | −6 | −4 | 6 | 285 | 276 | 4 | −14 | 0 | 6 | 196 | 198 | 2 | −22 | 4 | 6 | 144 | 152 | 3 |
| −20 | 0 | 5 | 242 | 241 | 2 | 9 | 3 | 5 | 16 | 20 | 4 | −4 | −4 | 6 | 185 | 191 | 2 | −12 | 0 | 6 | 61 | 62 | 1 | −20 | 4 | 6 | 151 | 169 | 3 |

TABLE 16-continued

Observed and calculated structure factors for Diol-1

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −18 | 0 | 5 | 178 | 176 | 1 | 11 | 3 | 5 | 325 | 334 | 5 | −2 | −4 | 6 | 131 | 134 | 1 | −10 | 0 | 6 | 208 | 220 | 3 | −18 | 4 | 6 | 148 | 158 | 3 |
| −16 | 0 | 5 | 154 | 130 | 1 | 13 | 3 | 5 | 73 | 74 | 1 | 0 | −4 | 6 | 314 | 305 | 4 | −8 | 0 | 6 | 467 | 486 | 6 | −16 | 4 | 6 | 225 | 220 | 4 |
| −14 | 0 | 5 | 301 | 291 | 3 | 15 | 3 | 5 | 75 | 81 | 1 | 2 | −4 | 6 | 169 | 165 | 2 | −6 | 0 | 6 | 256 | 232 | 3 | −14 | 4 | 6 | 269 | 278 | 4 |
| −12 | 0 | 5 | 286 | 268 | 4 | 17 | 3 | 5 | 121 | 118 | 2 | 4 | −4 | 6 | 185 | 181 | 3 | −4 | 0 | 6 | 459 | 422 | 6 | −12 | 4 | 6 | 277 | 272 | 8 |
| −10 | 0 | 5 | 83 | 101 | 1 | −24 | 4 | 5 | 169 | 172 | 3 | 6 | −4 | 6 | 255 | 247 | 3 | −2 | 0 | 6 | 284 | 270 | 4 | −10 | 4 | 6 | 225 | 225 | 5 |
| −8 | 0 | 5 | 600 | 615 | 8 | −22 | 4 | 5 | 38 | 35 | 2 | 8 | −4 | 6 | 206 | 203 | 3 | 0 | 0 | 6 | 39 | 57 | 1 | −8 | 4 | 6 | 47 | 46 | 2 |
| −6 | 0 | 5 | 505 | 457 | 6 | −20 | 4 | 5 | 83 | 87 | 2 | 10 | −4 | 6 | 204 | 209 | 3 | 2 | 0 | 6 | 69 | 88 | 1 | −6 | 4 | 6 | 283 | 276 | 6 |
| −4 | 0 | 5 | 1247 | 1241 | 16 | −18 | 4 | 5 | 246 | 232 | 5 | 12 | −4 | 6 | 119 | 126 | 2 | 4 | 0 | 6 | 310 | 324 | 2 | −4 | 4 | 6 | 187 | 191 | 4 |
| −2 | 0 | 5 | 21 | 6 | 1 | −16 | 4 | 5 | 213 | 214 | 4 | −27 | −3 | 6 | 36 | 29 | 3 | 6 | 0 | 6 | 84 | 83 | 1 | −2 | 4 | 6 | 133 | 134 | 3 |
| 0 | 0 | 5 | 150 | 142 | 1 | −14 | 4 | 5 | 381 | 397 | 10 | −25 | −3 | 6 | 58 | 55 | 3 | 8 | 0 | 6 | 15 | 4 | 2 | 0 | 4 | 6 | 310 | 304 | 7 |
| 2 | 0 | 5 | 246 | 246 | 3 | −12 | 4 | 5 | 333 | 349 | 11 | −23 | −3 | 6 | 136 | 128 | 3 | 10 | 0 | 6 | 102 | 107 | 1 | 2 | 4 | 6 | 171 | 166 | 3 |
| 4 | 0 | 5 | 56 | 75 | 1 | −10 | 4 | 5 | 202 | 195 | 4 | −21 | −3 | 6 | 192 | 199 | 3 | 12 | 0 | 6 | 193 | 192 | 3 | 4 | 4 | 6 | 185 | 181 | 3 |
| 6 | 0 | 5 | 288 | 296 | 2 | −8 | 4 | 5 | 188 | 182 | 4 | −19 | −3 | 6 | 143 | 149 | 3 | 14 | 0 | 6 | 18 | 24 | 3 | 6 | 4 | 6 | 253 | 247 | 4 |
| 8 | 0 | 5 | 85 | 76 | 1 | −6 | 4 | 5 | 28 | 35 | 2 | −17 | −3 | 6 | 222 | 238 | 2 | 16 | 0 | 6 | 104 | 113 | 2 | 8 | 4 | 6 | 206 | 204 | 3 |
| 10 | 0 | 5 | 0 | 0 | 1 | −4 | 4 | 5 | 255 | 260 | 5 | −15 | −3 | 6 | 271 | 263 | 3 | 18 | 0 | 6 | 114 | 38 | 2 | 10 | 4 | 6 | 208 | 209 | 3 |
| 12 | 0 | 5 | 207 | 216 | 2 | −2 | 4 | 5 | 160 | 160 | 5 | −13 | −3 | 6 | 221 | 224 | 2 | −29 | 1 | 6 | 186 | 170 | 3 | 12 | 4 | 6 | 123 | 127 | 2 |
| 14 | 0 | 5 | 227 | 218 | 3 | 0 | 4 | 5 | 274 | 277 | 5 | −11 | −3 | 6 | 461 | 466 | 4 | −2 | 1 | 6 | 182 | 173 | 2 | −21 | 5 | 6 | 69 | 72 | 3 |
| 16 | 0 | 5 | 221 | 240 | 3 | 2 | 4 | 5 | 284 | 288 | 6 | −9 | −3 | 6 | 202 | 188 | 1 | −25 | 1 | 6 | 180 | 177 | 2 | −19 | 5 | 6 | 120 | 122 | 4 |
| 18 | 0 | 5 | 153 | 160 | 2 | 4 | 4 | 5 | 323 | 324 | 6 | −7 | −3 | 6 | 174 | 172 | 1 | −23 | 1 | 6 | 71 | 71 | 2 | −17 | 5 | 6 | 159 | 162 | 5 |
| 20 | 0 | 5 | 30 | 18 | 3 | 6 | 4 | 5 | 173 | 159 | 3 | −5 | −3 | 6 | 66 | 58 | 1 | −21 | 1 | 6 | 298 | 287 | 3 | −15 | 5 | 6 | 289 | 298 | 9 |
| −29 | 1 | 5 | 129 | 123 | 4 | 8 | 4 | 5 | 213 | 211 | 3 | −3 | −3 | 6 | 138 | 131 | 1 | −19 | 1 | 6 | 118 | 120 | 1 | −13 | 5 | 6 | 69 | 62 | 2 |
| −27 | 1 | 5 | 237 | 216 | 3 | 10 | 4 | 5 | 10 | 5 | 9 | −1 | −3 | 6 | 269 | 264 | 2 | −17 | 1 | 6 | 170 | 182 | 2 | −11 | 5 | 6 | 172 | 168 | 5 |
| −25 | 1 | 5 | 149 | 148 | 2 | 12 | 4 | 5 | 77 | 66 | 2 | 1 | −3 | 6 | 236 | 226 | 2 | −15 | 1 | 6 | 288 | 276 | 3 | −9 | 5 | 6 | 157 | 158 | 3 |
| −23 | 1 | 5 | 251 | 245 | 4 | 14 | 4 | 5 | 106 | 109 | 2 | 3 | −3 | 6 | 324 | 329 | 3 | −13 | 1 | 6 | 297 | 301 | 3 | −7 | 5 | 6 | 140 | 135 | 3 |
| −21 | 1 | 5 | 131 | 129 | 2 | −21 | 5 | 5 | 48 | 46 | 3 | 5 | −3 | 6 | 75 | 78 | 1 | −11 | 1 | 6 | 161 | 150 | 2 | −5 | 5 | 6 | 47 | 49 | 2 |
| −19 | 1 | 5 | 238 | 229 | 2 | −19 | 5 | 5 | 71 | 82 | 3 | 7 | −3 | 6 | 317 | 309 | 4 | −9 | 1 | 6 | 441 | 393 | 5 | −3 | 5 | 6 | 26 | 28 | 2 |
| −17 | 1 | 5 | 103 | 94 | 1 | −17 | 5 | 5 | 41 | 44 | 3 | 9 | −3 | 6 | 273 | 278 | 4 | −7 | 1 | 6 | 690 | 668 | 9 | −1 | 5 | 6 | 285 | 285 | 6 |
| −15 | 1 | 5 | 124 | 116 | 1 | −15 | 5 | 5 | 78 | 79 | 3 | 11 | −3 | 6 | 151 | 146 | 2 | −5 | 1 | 6 | 432 | 413 | 6 | 1 | 5 | 6 | 72 | 68 | 2 |
| −13 | 1 | 5 | 376 | 393 | 5 | −13 | 5 | 5 | 63 | 65 | 2 | 13 | −3 | 6 | 124 | 122 | 3 | −3 | 1 | 6 | 564 | 554 | 6 | 3 | 5 | 6 | 176 | 170 | 4 |
| −11 | 1 | 5 | 413 | 405 | 6 | −11 | 5 | 5 | 191 | 183 | 6 | 15 | −3 | 6 | 83 | 80 | 2 | −1 | 1 | 6 | 103 | 109 | 1 | 5 | 5 | 6 | 198 | 200 | 4 |
| −9 | 1 | 5 | 267 | 261 | 3 | −9 | 5 | 5 | 115 | 111 | 2 | −28 | −2 | 6 | 124 | 127 | 3 | 1 | 1 | 6 | 55 | 64 | 1 | 7 | 5 | 6 | 27 | 24 | 3 |
| −7 | 1 | 5 | 751 | 746 | 10 | −7 | 5 | 5 | 325 | 328 | 6 | −26 | −2 | 6 | 139 | 140 | 2 | 3 | 1 | 6 | 238 | 241 | 2 | 9 | 5 | 6 | 99 | 108 | 2 |
| −5 | 1 | 5 | 633 | 590 | 8 | −5 | 5 | 5 | 93 | 93 | 2 | −24 | −2 | 6 | 74 | 79 | 2 | 5 | 1 | 6 | 83 | 85 | 1 | −12 | 6 | 6 | 54 | 64 | 2 |
| −3 | 1 | 5 | 867 | 845 | 12 | −3 | 5 | 5 | 292 | 300 | 6 | −22 | −2 | 6 | 76 | 70 | 2 | 7 | 1 | 6 | 72 | 77 | 1 | −10 | 6 | 6 | 67 | 77 | 2 |
| −1 | 1 | 5 | 398 | 382 | 6 | −1 | 5 | 5 | 155 | 162 | 3 | −20 | −2 | 6 | 254 | 256 | 3 | 9 | 1 | 6 | 182 | 187 | 2 | −8 | 6 | 6 | 118 | 117 | 4 |
| 1 | 1 | 5 | 385 | 374 | 5 | 1 | 5 | 5 | 163 | 161 | 5 | −18 | −2 | 6 | 67 | 68 | 1 | 11 | 1 | 6 | 89 | 94 | 2 | −6 | 6 | 6 | 67 | 71 | 2 |
| 3 | 1 | 5 | 189 | 191 | 2 | 3 | 5 | 5 | 225 | 216 | 4 | −16 | −2 | 6 | 76 | 61 | 1 | 13 | 1 | 6 | 108 | 116 | 1 | −4 | 6 | 6 | 146 | 142 | 3 |
| 5 | 1 | 5 | 233 | 225 | 2 | 5 | 5 | 5 | 243 | 230 | 5 | −14 | −2 | 6 | 142 | 146 | 1 | 15 | 1 | 6 | 167 | 161 | 2 | −2 | 6 | 6 | 127 | 124 | 3 |
| 7 | 1 | 5 | 208 | 213 | 2 | 7 | 5 | 5 | 175 | 180 | 4 | −12 | −2 | 6 | 434 | 441 | 4 | 17 | 1 | 6 | 59 | 52 | 2 | 0 | 6 | 6 | 164 | 167 | 3 |
| 9 | 1 | 5 | 87 | 97 | 1 | 9 | 5 | 5 | 71 | 73 | 3 | −10 | −2 | 6 | 79 | 80 | 1 | −28 | 2 | 6 | 118 | 128 | 2 | −12 | −6 | 7 | 107 | 106 | 2 |
| 11 | 1 | 5 | 131 | 142 | 1 | 11 | 5 | 5 | 80 | 71 | 2 | −8 | −2 | 6 | 606 | 591 | 5 | −26 | 2 | 6 | 139 | 141 | 2 | −10 | −6 | 7 | 31 | 26 | 1 |
| 13 | 1 | 5 | 40 | 26 | 2 | −14 | 6 | 5 | 82 | 74 | 3 | −6 | −2 | 6 | 127 | 112 | 1 | −24 | 2 | 6 | 4 | 79 | 2 | −8 | −6 | 7 | 175 | 169 | 3 |
| 15 | 1 | 5 | 159 | 159 | 2 | −12 | 6 | 5 | 198 | 197 | 6 | −4 | −2 | 6 | 69 | 61 | 1 | −22 | 2 | 6 | 71 | 70 | 1 | −6 | −6 | 7 | 92 | 90 | 2 |
| 17 | 1 | 5 | 178 | 173 | 2 | −10 | 6 | 5 | 148 | 143 | 5 | −2 | −2 | 6 | 235 | 224 | 2 | −20 | 2 | 6 | 261 | 257 | 3 | −4 | −6 | 7 | 36 | 33 | 1 |
| 19 | 1 | 5 | 86 | 84 | 2 | −8 | 6 | 5 | 330 | 338 | 10 | 0 | −2 | 6 | 97 | 97 | 1 | −18 | 2 | 6 | 70 | 69 | 1 | −2 | −6 | 7 | 64 | 68 | 2 |
| −28 | 2 | 5 | 59 | 55 | 1 | −6 | 6 | 5 | 95 | 90 | 2 | 2 | −2 | 6 | 286 | 276 | 2 | −16 | 2 | 6 | 76 | 61 | 1 | −21 | −5 | 7 | 47 | 52 | 2 |
| −26 | 2 | 5 | 112 | 106 | 1 | −4 | 6 | 5 | 183 | 183 | 4 | 4 | −2 | 6 | 185 | 183 | 1 | −14 | 2 | 6 | 145 | 146 | 2 | −17 | −5 | 7 | 30 | 30 | 2 |
| −24 | 2 | 5 | 68 | 79 | 2 | −2 | 6 | 5 | 186 | 180 | 4 | 6 | −2 | 6 | 222 | 227 | 2 | −12 | 2 | 6 | 432 | 441 | 6 | −15 | −5 | 7 | 103 | 103 | 2 |
| −22 | 2 | 5 | 251 | 248 | 4 | 0 | 6 | 5 | 113 | 111 | 2 | 8 | −2 | 6 | 179 | 196 | 1 | −10 | 2 | 6 | 79 | 79 | 1 | −13 | −5 | 7 | 72 | 73 | 2 |

TABLE 16-continued

Observed and calculated structure factors for Diol-1

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −20 | 2 | 5 | 30 | 17 | 2 | 2 | 6 | 5 | 26 | 23 | 2 | 10 | −2 | 6 | 155 | 154 | 3 | −8 | 2 | 6 | 605 | 592 | 12 | −11 | −5 | 7 | 30 | 30 | 2 |
| −18 | 2 | 5 | 232 | 233 | 3 | 4 | 6 | 5 | 180 | 177 | 5 | 12 | −2 | 6 | 214 | 223 | 4 | −6 | 2 | 6 | 128 | 112 | 2 | −9 | −5 | 7 | 157 | 155 | 4 |
| −16 | 2 | 5 | 116 | 123 | 2 | −14 | −6 | 6 | 91 | 91 | 2 | 14 | −2 | 6 | 70 | 72 | 2 | −4 | 2 | 5 | 71 | 61 | 2 | −7 | −5 | 7 | 340 | 332 | 6 |
| −14 | 2 | 5 | 100 | 102 | 1 | −12 | −6 | 6 | 56 | 64 | 1 | 16 | −2 | 6 | 32 | 32 | 2 | −2 | 2 | 6 | 229 | 224 | 3 | −5 | −5 | 7 | 93 | 86 | 2 |
| −12 | 2 | 5 | 290 | 306 | 4 | −10 | −6 | 6 | 71 | 76 | 1 | −29 | −1 | 6 | 174 | 169 | 3 | 0 | 2 | 6 | 96 | 96 | 1 | −3 | −5 | 7 | 108 | 98 | 2 |
| −10 | 2 | 5 | 248 | 252 | 4 | −8 | −6 | 6 | 123 | 117 | 2 | −27 | −1 | 6 | 185 | 172 | 2 | 2 | 2 | 6 | 281 | 277 | 3 | −1 | −5 | 7 | 49 | 42 | 2 |
| −8 | 2 | 5 | 127 | 133 | 2 | −6 | −6 | 6 | 72 | 70 | 1 | −25 | −1 | 6 | 184 | 177 | 3 | 4 | 2 | 6 | 182 | 182 | 2 | 1 | −5 | 7 | 317 | 323 | 6 |
| 3 | −5 | 7 | 86 | 83 | 2 | −30 | 0 | 7 | 178 | 177 | 3 | 9 | 3 | 7 | 194 | 193 | 3 | 11 | −3 | 8 | 70 | 71 | 2 | 11 | 1 | 8 | 60 | 60 | 1 |
| 5 | −5 | 7 | 64 | 71 | 2 | −28 | 0 | 7 | 156 | 161 | 2 | 11 | 3 | 7 | 90 | 90 | 2 | −28 | −2 | 8 | 165 | 157 | 3 | 13 | 1 | 8 | 16 | 167 | 2 |
| 7 | −5 | 7 | 72 | 68 | 2 | −26 | 0 | 7 | 15 | 9 | 4 | 13 | 3 | 7 | 30 | 28 | 2 | −26 | −2 | 8 | 146 | 139 | 3 | −28 | 2 | 8 | 164 | 158 | 2 |
| −24 | −4 | 7 | 191 | 203 | 6 | −24 | 0 | 7 | 246 | 245 | 3 | −24 | 4 | 7 | 207 | 204 | 4 | −24 | −2 | 8 | 89 | 93 | 2 | −26 | 2 | 8 | 148 | 139 | 2 |
| −22 | −4 | 7 | 12 | 8 | 7 | −22 | 0 | 7 | 57 | 50 | 1 | −22 | 4 | 7 | 16 | 8 | 5 | −22 | −2 | 8 | 223 | 225 | 5 | −24 | 2 | 8 | 91 | 93 | 2 |
| −20 | −4 | 7 | 129 | 132 | 4 | −20 | 0 | 7 | 19 | 12 | 2 | −20 | 4 | 7 | 134 | 133 | 3 | −20 | −2 | 8 | 90 | 87 | 3 | −22 | 2 | 8 | 223 | 224 | 3 |
| −18 | −4 | 7 | 254 | 276 | 5 | −18 | 0 | 7 | 267 | 278 | 2 | −18 | 4 | 7 | 269 | 278 | 5 | −18 | −2 | 8 | 93 | 91 | 1 | −20 | 2 | 8 | 81 | 87 | 2 |
| −16 | −4 | 7 | 210 | 205 | 4 | −16 | 0 | 7 | 56 | 73 | 1 | −16 | 4 | 7 | 209 | 206 | 4 | −16 | −2 | 8 | 67 | 72 | 1 | −18 | 2 | 8 | 97 | 92 | 2 |
| −14 | −4 | 7 | 241 | 244 | 4 | −14 | 0 | 7 | 91 | 100 | 1 | −14 | 4 | 7 | 240 | 243 | 4 | −14 | −2 | 8 | 364 | 358 | 3 | −16 | 2 | 8 | 68 | 72 | 2 |
| −12 | −4 | 7 | 183 | 195 | 3 | −12 | 0 | 7 | 121 | 95 | 1 | −12 | 4 | 7 | 185 | 195 | 5 | −12 | −2 | 8 | 38 | 30 | 1 | −14 | 2 | 8 | 369 | 358 | 5 |
| −10 | −4 | 7 | 123 | 124 | 2 | −10 | 0 | 7 | 441 | 434 | 4 | −10 | 4 | 7 | 122 | 126 | 3 | −10 | −2 | 8 | 123 | 132 | 1 | −12 | 2 | 8 | 37 | 28 | 1 |
| −8 | −4 | 7 | 125 | 127 | 2 | −8 | 0 | 7 | 81 | 77 | 1 | −8 | 4 | 7 | 114 | 125 | 3 | −8 | −2 | 8 | 55 | 56 | 1 | −10 | 2 | 8 | 126 | 133 | 1 |
| −6 | −4 | 7 | 227 | 230 | 3 | −6 | 0 | 7 | 349 | 313 | 5 | −6 | 4 | 7 | 218 | 229 | 5 | −6 | −2 | 8 | 210 | 216 | 2 | −8 | 2 | 8 | 54 | 55 | 1 |
| −4 | −4 | 7 | 195 | 203 | 2 | −4 | 0 | 7 | 355 | 366 | 3 | −4 | 4 | 7 | 201 | 202 | 6 | −4 | −2 | 8 | 173 | 172 | 1 | −6 | 2 | 8 | 212 | 217 | 3 |
| −2 | −4 | 7 | 55 | 38 | 1 | −2 | 0 | 7 | 95 | 94 | 1 | −2 | 4 | 7 | 48 | 38 | 2 | −2 | −2 | 8 | 366 | 368 | 3 | −4 | 2 | 8 | 174 | 173 | 2 |
| 0 | −4 | 7 | 147 | 159 | 2 | 0 | 0 | 7 | 419 | 421 | 3 | 0 | 4 | 7 | 149 | 159 | 2 | 0 | −2 | 8 | 215 | 212 | 2 | −2 | 2 | 8 | 368 | 369 | 5 |
| 2 | −4 | 7 | 122 | 121 | 2 | 2 | 0 | 7 | 90 | 71 | 1 | 2 | 4 | 7 | 122 | 121 | 2 | 2 | −2 | 8 | 377 | 381 | 3 | 0 | 2 | 8 | 219 | 213 | 3 |
| 4 | −4 | 7 | 157 | 145 | 3 | 4 | 0 | 7 | 328 | 324 | 2 | 4 | 4 | 7 | 153 | 145 | 3 | 4 | −2 | 8 | 240 | 238 | 4 | 2 | 2 | 8 | 385 | 382 | 5 |
| 6 | −4 | 7 | 90 | 95 | 2 | 6 | 0 | 7 | 67 | 70 | 1 | 6 | 4 | 7 | 92 | 95 | 2 | 6 | −2 | 8 | 63 | 60 | 2 | 4 | 2 | 8 | 231 | 238 | 3 |
| 8 | −4 | 7 | 165 | 161 | 3 | 8 | 0 | 7 | 176 | 177 | 2 | 8 | 4 | 7 | 168 | 161 | 3 | 8 | −2 | 8 | 149 | 146 | 2 | 6 | 2 | 8 | 65 | 59 | 1 |
| 10 | −4 | 7 | 109 | 121 | 2 | 10 | 0 | 7 | 55 | 50 | 1 | 10 | 4 | 7 | 112 | 121 | 2 | 10 | −2 | 8 | 97 | 100 | 2 | 8 | 2 | 8 | 148 | 145 | 2 |
| −27 | −3 | 7 | 116 | 111 | 4 | 12 | 0 | 7 | 159 | 163 | 2 | −21 | 5 | 7 | 44 | 52 | 3 | 12 | −2 | 8 | 91 | 90 | 2 | 10 | 2 | 8 | 99 | 101 | 2 |
| −25 | −3 | 7 | 123 | 113 | 4 | 14 | 0 | 7 | 86 | 77 | 1 | −17 | 5 | 7 | 31 | 29 | 4 | −29 | −1 | 8 | 82 | 87 | 1 | 12 | 2 | 8 | 90 | 91 | 1 |
| −23 | −3 | 7 | 122 | 103 | 3 | 16 | 0 | 7 | 183 | 189 | 3 | −15 | 5 | 7 | 105 | 104 | 4 | −27 | −1 | 8 | 281 | 278 | 4 | −27 | 3 | 8 | 39 | 35 | 2 |
| −21 | −3 | 7 | 71 | 69 | 2 | −29 | 1 | 7 | 181 | 169 | 3 | −13 | 5 | 7 | 70 | 72 | 2 | −25 | −1 | 8 | 147 | 145 | 2 | −25 | 3 | 8 | 35 | 37 | 2 |
| −19 | −3 | 7 | 186 | 188 | 3 | −27 | 1 | 7 | 236 | 224 | 3 | −11 | 5 | 7 | 31 | 30 | 2 | −23 | −1 | 8 | 60 | 69 | 2 | −23 | 3 | 8 | 238 | 231 | 4 |
| −17 | −3 | 7 | 222 | 219 | 3 | −25 | 1 | 7 | 162 | 155 | 2 | −9 | 5 | 7 | 156 | 155 | 3 | −21 | −1 | 8 | 326 | 327 | 5 | −21 | 3 | 8 | 102 | 106 | 2 |
| −15 | −3 | 7 | 335 | 347 | 4 | −23 | 1 | 7 | 128 | 123 | 2 | −7 | 5 | 7 | 321 | 331 | 7 | −19 | −1 | 8 | 246 | 246 | 2 | −19 | 3 | 8 | 160 | 160 | 3 |
| −13 | −3 | 7 | 94 | 98 | 1 | −21 | 1 | 7 | 109 | 118 | 2 | −5 | 5 | 7 | 94 | 86 | 2 | −17 | −1 | 8 | 209 | 217 | 2 | −17 | 3 | 8 | 234 | 235 | 4 |
| −11 | −3 | 7 | 349 | 357 | 3 | −19 | 1 | 1 | 161 | 163 | 2 | −3 | 5 | 7 | 104 | 97 | 2 | −15 | −1 | 8 | 482 | 460 | 5 | −15 | 3 | 8 | 411 | 404 | 6 |
| −9 | −3 | 7 | 43 | 32 | 1 | −17 | 1 | 7 | 159 | 157 | 2 | −1 | 5 | 7 | 49 | 42 | 2 | −13 | −1 | 8 | 237 | 251 | 2 | −13 | 3 | 8 | 83 | 77 | 1 |
| −7 | −3 | 7 | 34 | 37 | 1 | −15 | 1 | 7 | 169 | 166 | 2 | 1 | 5 | 7 | 330 | 322 | 6 | −11 | −1 | 8 | 128 | 134 | 1 | −11 | 3 | 8 | 150 | 140 | 2 |
| −5 | −3 | 7 | 116 | 120 | 1 | −13 | 1 | 7 | 280 | 280 | 3 | 3 | 5 | 7 | 78 | 83 | 2 | −9 | −1 | 8 | 209 | 202 | 2 | −9 | 3 | 8 | 286 | 278 | 3 |
| −3 | −3 | 7 | 108 | 94 | 1 | −11 | 1 | 7 | 334 | 324 | 3 | 5 | 5 | 7 | 65 | 71 | 3 | −7 | −1 | 8 | 326 | 332 | 3 | −7 | 3 | 8 | 246 | 248 | 3 |
| −1 | −3 | 7 | 201 | 200 | 1 | −9 | 1 | 7 | 317 | 330 | 3 | 7 | 5 | 7 | 74 | 69 | 3 | −5 | −1 | 8 | 35 | 17 | 1 | −5 | 3 | 8 | 74 | 71 | 1 |
| 1 | −3 | 7 | 232 | 234 | 2 | −7 | 1 | 7 | 168 | 164 | 1 | −10 | 6 | 7 | 28 | 27 | 2 | −3 | −1 | 8 | 202 | 194 | 1 | −3 | 3 | 8 | 14 | 17 | 3 |
| 3 | −3 | 7 | 174 | 166 | 2 | −5 | 1 | 7 | 111 | 96 | 1 | −8 | 6 | 7 | 173 | 171 | 5 | −1 | −1 | 8 | 265 | 261 | 2 | −1 | 3 | 8 | 105 | 100 | 2 |
| 5 | −3 | 7 | 109 | 112 | 2 | −3 | 1 | 7 | 107 | 105 | 1 | −6 | 6 | 7 | 89 | 91 | 3 | 1 | −1 | 8 | 340 | 336 | 3 | 1 | 3 | 8 | 159 | 160 | 3 |
| 7 | −3 | 7 | 133 | 135 | 2 | −1 | 1 | 7 | 74 | 85 | 1 | −4 | 6 | 7 | 34 | 33 | 2 | 3 | −1 | 8 | 157 | 156 | 1 | 3 | 3 | 8 | 61 | 60 | 1 |
| 9 | −3 | 7 | 197 | 193 | 4 | 1 | 1 | 7 | 249 | 254 | 2 | −19 | −5 | 8 | 51 | 52 | 2 | 5 | −1 | 8 | 245 | 251 | 3 | 5 | 3 | 8 | 123 | 115 | 2 |
| 11 | −3 | 7 | 95 | 90 | 2 | 3 | 1 | 7 | 245 | 240 | 2 | −17 | −5 | 8 | 49 | 54 | 3 | 7 | −1 | 8 | 81 | 82 | 2 | 7 | 3 | 8 | 11 | 8 | 6 |
| 13 | −3 | 7 | 36 | 27 | 2 | 5 | 1 | 7 | 165 | 165 | 1 | −15 | −5 | 8 | 21 | 12 | 3 | 9 | −1 | 8 | 69 | 63 | 1 | 9 | 3 | 8 | 191 | 191 | 4 |

TABLE 16-continued

Observed and calculated structure factors for Diol-1

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −28 | −2 | 7 | 213 | 208 | 4 | 7 | 1 | 7 | 103 | 112 | 1 | −13 | −5 | 8 | 70 | 73 | 2 | 11 | −1 | 8 | 60 | 61 | 1 | 11 | 3 | 8 | 65 | 70 | 2 |
| −26 | −2 | 7 | 131 | 117 | 2 | 9 | 1 | 7 | 218 | 217 | 3 | −11 | −5 | 8 | 108 | 107 | 3 | 13 | −1 | 8 | 163 | 166 | 2 | −22 | 4 | 8 | 42 | 52 | 2 |
| −24 | −2 | 7 | 131 | 138 | 2 | 11 | 1 | 7 | 170 | 171 | 2 | −9 | −5 | 8 | 132 | 136 | 2 | −30 | 0 | 8 | 265 | 263 | 4 | −20 | 4 | 8 | 226 | 225 | 4 |
| −22 | −2 | 7 | 159 | 164 | 4 | 13 | 1 | 7 | 133 | 123 | 2 | −7 | −5 | 8 | 122 | 115 | 2 | −28 | 0 | 8 | 103 | 99 | 2 | −18 | 4 | 8 | 86 | 89 | 2 |
| −20 | −2 | 7 | 203 | 203 | 3 | 15 | 1 | 7 | 181 | 174 | 3 | −5 | −5 | 8 | 25 | 23 | 2 | −26 | 0 | 8 | 125 | 130 | 2 | −16 | 4 | 8 | 141 | 140 | 3 |
| −18 | −2 | 7 | 184 | 194 | 2 | −28 | 2 | 7 | 206 | 208 | 3 | −3 | −5 | 8 | 94 | 92 | 2 | −24 | 0 | 9 | 233 | 222 | 3 | −14 | 4 | 9 | 143 | 132 | 2 |
| −16 | −2 | 7 | 251 | 252 | 2 | −26 | 2 | 7 | 132 | 117 | 2 | −1 | −5 | 8 | 71 | 64 | 2 | −22 | 0 | 9 | 56 | 53 | 1 | −12 | 4 | 8 | 253 | 253 | 5 |
| −14 | −2 | 7 | 245 | 240 | 2 | −24 | 2 | 7 | 131 | 138 | 2 | 1 | −5 | 8 | 139 | 144 | 4 | −20 | 0 | 8 | 20 | 23 | 2 | −10 | 4 | 8 | 229 | 278 | 5 |
| −12 | −2 | 7 | 568 | 590 | 5 | −22 | 2 | 7 | 155 | 163 | 3 | 3 | −5 | 8 | 101 | 97 | 3 | −18 | 0 | 8 | 91 | 79 | 1 | −8 | 4 | 8 | 102 | 109 | 2 |
| −10 | −2 | 7 | 245 | 249 | 2 | −20 | 2 | 7 | 206 | 202 | 3 | −24 | −4 | 8 | 93 | 129 | 3 | −16 | 0 | 8 | 28 | 25 | 1 | −6 | 4 | 8 | 154 | 150 | 5 |
| −8 | −2 | 7 | 180 | 175 | 1 | −18 | 2 | 7 | 188 | 193 | 4 | −22 | −4 | 8 | 40 | 52 | 2 | −14 | 0 | 8 | 270 | 259 | 2 | −4 | 4 | 8 | 236 | 244 | 4 |
| −6 | −2 | 7 | 166 | 156 | 1 | −16 | 2 | 7 | 249 | 252 | 4 | −20 | −4 | 8 | 218 | 226 | 5 | −12 | 0 | 8 | 355 | 348 | 3 | −2 | 4 | 8 | 43 | 44 | 2 |
| −4 | −2 | 7 | 252 | 251 | 2 | −14 | 2 | 7 | 242 | 240 | 3 | −18 | −4 | 8 | 83 | 90 | 2 | −10 | 0 | 8 | 146 | 126 | 1 | 0 | 4 | 8 | 24 | 25 | 2 |
| −2 | −2 | 7 | 163 | 133 | 1 | −12 | 2 | 7 | 573 | 590 | 7 | −16 | −4 | 8 | 136 | 139 | 4 | −8 | 0 | 8 | 180 | 170 | 1 | 2 | 4 | 8 | 140 | 130 | 3 |
| 0 | −2 | 7 | 266 | 267 | 2 | −10 | 2 | 7 | 244 | 250 | 3 | −14 | −4 | 8 | 133 | 131 | 2 | −6 | 0 | 8 | 260 | 259 | 2 | 4 | 4 | 8 | 124 | 123 | 2 |
| 2 | −2 | 7 | 88 | 101 | 1 | −8 | 2 | 7 | 181 | 175 | 2 | −12 | −4 | 8 | 252 | 254 | 5 | −4 | 0 | 8 | 384 | 405 | 3 | 6 | 4 | 8 | 38 | 35 | 2 |
| 4 | −2 | 7 | 159 | 157 | 1 | −6 | 2 | 7 | 165 | 156 | 2 | −10 | −4 | 8 | 221 | 277 | 8 | −2 | 0 | 8 | 46 | 36 | 1 | 8 | 4 | 8 | 151 | 152 | 4 |
| 6 | −2 | 7 | 393 | 384 | 6 | −4 | 2 | 7 | 245 | 250 | 3 | −8 | −4 | 8 | 101 | 109 | 4 | 0 | 0 | 8 | 311 | 328 | 2 | −17 | 5 | 8 | 52 | 54 | 3 |
| 8 | −2 | 7 | 123 | 121 | 2 | −2 | 2 | 7 | 161 | 134 | 2 | −6 | −4 | 8 | 160 | 151 | 2 | 2 | 0 | 8 | 64 | 40 | 1 | −15 | 5 | 8 | 9 | 13 | 8 |
| 10 | −2 | 7 | 243 | 244 | 3 | 0 | 2 | 7 | 266 | 268 | 3 | −4 | −4 | 8 | 240 | 245 | 4 | 4 | 0 | 8 | 229 | 228 | 2 | −13 | 5 | 8 | 65 | 73 | 2 |
| 12 | −2 | 7 | 64 | 62 | 2 | 2 | 2 | 7 | 88 | 100 | 1 | −2 | −4 | 8 | 47 | 45 | 2 | 6 | 0 | 8 | 208 | 215 | 2 | −11 | 5 | 8 | 106 | 108 | 2 |
| 14 | −2 | 7 | 153 | 149 | 2 | 4 | 2 | 7 | 164 | 157 | 2 | 0 | −4 | 8 | 31 | 25 | 3 | 8 | 0 | 8 | 92 | 96 | 1 | −9 | 5 | 8 | 133 | 135 | 3 |
| −29 | −1 | 7 | 173 | 169 | 2 | 6 | 2 | 7 | 390 | 384 | 5 | 2 | −4 | 8 | 134 | 129 | 2 | 10 | 0 | 8 | 18 | 14 | 3 | −7 | 5 | 8 | 124 | 114 | 3 |
| −27 | −1 | 7 | 233 | 224 | 4 | 8 | 2 | 7 | 121 | 120 | 2 | 4 | −4 | 8 | 120 | 123 | 2 | 12 | 0 | 8 | 231 | 216 | 3 | −5 | 5 | 8 | 27 | 23 | 2 |
| −25 | −1 | 7 | 168 | 154 | 3 | 10 | 2 | 7 | 246 | 244 | 3 | 6 | −4 | 8 | 36 | 36 | 2 | 14 | 0 | 8 | 211 | 210 | 3 | −3 | 5 | 8 | 92 | 91 | 2 |
| −23 | −1 | 7 | 125 | 123 | 2 | 12 | 2 | 7 | 63 | 62 | 1 | 8 | −4 | 8 | 149 | 151 | 2 | −29 | 1 | 8 | 84 | 88 | 2 | −1 | 5 | 8 | 69 | 65 | 2 |
| −21 | −1 | 7 | 112 | 118 | 1 | 14 | 2 | 7 | 151 | 150 | 2 | −27 | −3 | 8 | 36 | 34 | 3 | −27 | 1 | 8 | 278 | 277 | 4 | 1 | 5 | 8 | 136 | 143 | 4 |
| −19 | −1 | 7 | 159 | 163 | 1 | −27 | 3 | 7 | 120 | 110 | 2 | −25 | −3 | 8 | 38 | 36 | 3 | −25 | 1 | 8 | 146 | 146 | 2 | 3 | 5 | 8 | 102 | 97 | 2 |
| −17 | −1 | 7 | 162 | 156 | 1 | −25 | 3 | 7 | 124 | 113 | 2 | −23 | −3 | 8 | 236 | 231 | 7 | −23 | 1 | 8 | 62 | 68 | 2 | −15 | −5 | 9 | 137 | 155 | 3 |
| −15 | −1 | 7 | 171 | 166 | 2 | −23 | 3 | 7 | 122 | 103 | 2 | −21 | −3 | 8 | 101 | 105 | 3 | −21 | 1 | 8 | 328 | 326 | 5 | −13 | −5 | 9 | 59 | 48 | 2 |
| −13 | −1 | 7 | 287 | 279 | 2 | −21 | 3 | 7 | 69 | 69 | 2 | −19 | −3 | 8 | 166 | 161 | 4 | −19 | 1 | 8 | 244 | 246 | 3 | −11 | −5 | 9 | 87 | 79 | 3 |
| −11 | −1 | 7 | 342 | 324 | 3 | −19 | 3 | 7 | 185 | 189 | 3 | −17 | −3 | 8 | 239 | 234 | 4 | −17 | 1 | 8 | 209 | 216 | 2 | −9 | −5 | 9 | 71 | 81 | 3 |
| −9 | −1 | 7 | 321 | 329 | 3 | −17 | 3 | 7 | 227 | 220 | 4 | −15 | −3 | 8 | 403 | 403 | 5 | −15 | 1 | 8 | 476 | 459 | 5 | −7 | −5 | 9 | 188 | 188 | 3 |
| −7 | −1 | 7 | 171 | 165 | 1 | −15 | 3 | 7 | 345 | 346 | 4 | −13 | −3 | 8 | 79 | 77 | 1 | −13 | 1 | 8 | 237 | 251 | 2 | −5 | −5 | 9 | 58 | 53 | 2 |
| −5 | −1 | 7 | 114 | 97 | 1 | −13 | 3 | 7 | 94 | 97 | 1 | −11 | −3 | 8 | 147 | 141 | 1 | −11 | 1 | 8 | 127 | 135 | 1 | −3 | −5 | 9 | 153 | 146 | 4 |
| −3 | −1 | 7 | 107 | 104 | 1 | −11 | 3 | 7 | 356 | 357 | 4 | −9 | −3 | 8 | 274 | 277 | 2 | −9 | 1 | 8 | 207 | 203 | 2 | −1 | −5 | 9 | 66 | 65 | 2 |
| −1 | −1 | 7 | 75 | 85 | 1 | −9 | 3 | 7 | 43 | 31 | 1 | −7 | −3 | 8 | 242 | 248 | 2 | −7 | 1 | 8 | 319 | 333 | 2 | −22 | −4 | 9 | 127 | 143 | 5 |
| 1 | −1 | 7 | 255 | 254 | 2 | −7 | 3 | 7 | 37 | 37 | 1 | −5 | −3 | 8 | 72 | 70 | 1 | −5 | 1 | 8 | 36 | 19 | 1 | −20 | −4 | 9 | 177 | 181 | 4 |
| 3 | −1 | 7 | 247 | 240 | 2 | −5 | 3 | 7 | 116 | 121 | 2 | −3 | −3 | 8 | 18 | 17 | 1 | −3 | 1 | 8 | 201 | 195 | 2 | −18 | −4 | 9 | 77 | 86 | 2 |
| 5 | −1 | 7 | 168 | 165 | 1 | −3 | 3 | 7 | 109 | 94 | 1 | −1 | −3 | 8 | 101 | 100 | 1 | −1 | 1 | 8 | 263 | 261 | 2 | −16 | −4 | 9 | 110 | 121 | 2 |
| 7 | −1 | 7 | 101 | 112 | 1 | −1 | 3 | 7 | 203 | 201 | 3 | 1 | −3 | 8 | 164 | 161 | 2 | 1 | 1 | 8 | 343 | 336 | 3 | −14 | 4 | 9 | 166 | 182 | 4 |
| 9 | −1 | 7 | 215 | 217 | 3 | 1 | 3 | 7 | 236 | 235 | 3 | 3 | −3 | 8 | 61 | 59 | 1 | 3 | 1 | 8 | 154 | 155 | 2 | −12 | −4 | 9 | 189 | 186 | 4 |
| 11 | −1 | 7 | 173 | 170 | 3 | 3 | 3 | 7 | 170 | 165 | 3 | 5 | −3 | 8 | 120 | 114 | 2 | 5 | 1 | 8 | 244 | 250 | 3 | −10 | −4 | 9 | 151 | 166 | 3 |
| 13 | −1 | 7 | 135 | 123 | 2 | 5 | 3 | 7 | 109 | 112 | 2 | 7 | −3 | 8 | 14 | 9 | 2 | 7 | 1 | 8 | 81 | 82 | 1 | −8 | −4 | 9 | 66 | 60 | 1 |
| 15 | −1 | 7 | 177 | 174 | 2 | 7 | 3 | 7 | 132 | 136 | 2 | 9 | −3 | 8 | 194 | 192 | 4 | 9 | 1 | 8 | 67 | 63 | 1 | −6 | −4 | 9 | 300 | 310 | 5 |
| −4 | −4 | 9 | 194 | 191 | 4 | −27 | 1 | 9 | 95 | 84 | 2 | −6 | −4 | 10 | 163 | 164 | 3 | −13 | 1 | 10 | 115 | 126 | 1 | 2 | −2 | 11 | 25 | 26 | 3 |
| −2 | −4 | 9 | 22 | 15 | 3 | −25 | 1 | 9 | 157 | 151 | 2 | −4 | −4 | 10 | 132 | 139 | 2 | −11 | 1 | 10 | 261 | 258 | 3 | 4 | −2 | 11 | 102 | 95 | 2 |
| 0 | −4 | 9 | 236 | 232 | 5 | −23 | 1 | 9 | 347 | 337 | 6 | −2 | −4 | 10 | 278 | 277 | 6 | −9 | 1 | 10 | 184 | 186 | 2 | −27 | −1 | 11 | 107 | 104 | 2 |
| 2 | −4 | 9 | 78 | 75 | 2 | −21 | 1 | 9 | 165 | 167 | 3 | 0 | −4 | 10 | 72 | 79 | 1 | −7 | 1 | 10 | 468 | 471 | 5 | −25 | −1 | 11 | 16 | 15 | 3 |

TABLE 16-continued

Observed and calculated structure factors for Diol-1

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 4 | −4 | 9 | 106 | 110 | 2 | −19 | 1 | 9 | 237 | 239 | 3 | −25 | −3 | 10 | 100 | 98 | 3 | −5 | 1 | 10 | 136 | 137 | 1 | −23 | −1 | 11 | 125 | 118 | 2 |
| 6 | −4 | 9 | 90 | 88 | 3 | −17 | 1 | 9 | 227 | 229 | 3 | −23 | −3 | 10 | 218 | 204 | 6 | −3 | 1 | 10 | 223 | 223 | 3 | −21 | −1 | 11 | 73 | 64 | 2 |
| −25 | −3 | 9 | 42 | 54 | 3 | −15 | 1 | 9 | 274 | 294 | 3 | −21 | −3 | 10 | 216 | 207 | 4 | −1 | 1 | 10 | 197 | 200 | 3 | −19 | −1 | 11 | 102 | 98 | 2 |
| −23 | −3 | 9 | 87 | 83 | 2 | −13 | 1 | 9 | 531 | 540 | 6 | −19 | −3 | 10 | 93 | 91 | 2 | 1 | 1 | 10 | 181 | 172 | 4 | −17 | −1 | 11 | 133 | 141 | 5 |
| −21 | −3 | 9 | 137 | 128 | 3 | −11 | 1 | 9 | 200 | 197 | 2 | −17 | −3 | 10 | 34 | 32 | 2 | 3 | 1 | 10 | 294 | 291 | 4 | −15 | −1 | 11 | 161 | 155 | 3 |
| −19 | −3 | 9 | 164 | 156 | 4 | −9 | 1 | 9 | 247 | 250 | 2 | −15 | −3 | 10 | 347 | 354 | 5 | 5 | 1 | 10 | 128 | 133 | 2 | −13 | −1 | 11 | 70 | 81 | 2 |
| −17 | −3 | 9 | 146 | 150 | 3 | −7 | 1 | 9 | 103 | 100 | 1 | −13 | −3 | 10 | 73 | 70 | 2 | 7 | 1 | 10 | 32 | 27 | 2 | −11 | −1 | 11 | 247 | 276 | 3 |
| −15 | −3 | 9 | 170 | 178 | 2 | −5 | 1 | 9 | 311 | 315 | 3 | −11 | −3 | 10 | 97 | 81 | 2 | 9 | 1 | 10 | 80 | 75 | 1 | −9 | −1 | 11 | 99 | 116 | 2 |
| −13 | −3 | 9 | 105 | 99 | 2 | −3 | 1 | 9 | 372 | 379 | 3 | −9 | −3 | 10 | 83 | 81 | 2 | −28 | 2 | 10 | 27 | 29 | 3 | −7 | −1 | 11 | 335 | 348 | 6 |
| −11 | −3 | 9 | 118 | 125 | 2 | −1 | 1 | 9 | 370 | 366 | 4 | −7 | −3 | 10 | 264 | 267 | 4 | −26 | 2 | 10 | 109 | 109 | 1 | −5 | −1 | 11 | 77 | 74 | 2 |
| −9 | −3 | 9 | 58 | 58 | 2 | 1 | 1 | 9 | 554 | 561 | 7 | −5 | −3 | 10 | 194 | 189 | 3 | −24 | 2 | 10 | 116 | 105 | 2 | −3 | −1 | 11 | 29 | 19 | 2 |
| −7 | −3 | 9 | 227 | 233 | 3 | 3 | 1 | 9 | 81 | 79 | 2 | −3 | −3 | 10 | 202 | 195 | 4 | −22 | 2 | 10 | 271 | 271 | 5 | −1 | −1 | 11 | 160 | 160 | 3 |
| −5 | −3 | 9 | 350 | 356 | 4 | 5 | 1 | 9 | 327 | 327 | 5 | −1 | −3 | 10 | 300 | 295 | 5 | −20 | 2 | 10 | 208 | 255 | 5 | 1 | −1 | 11 | 151 | 146 | 2 |
| −3 | −3 | 9 | 120 | 124 | 2 | 7 | 1 | 9 | 214 | 207 | 2 | 1 | −3 | 10 | 118 | 113 | 2 | −18 | 2 | 10 | 196 | 231 | 7 | 3 | −1 | 11 | 123 | 124 | 2 |
| −1 | −3 | 9 | 213 | 217 | 4 | 9 | 1 | 9 | 295 | 288 | 4 | 3 | −3 | 10 | 153 | 150 | 3 | −16 | 2 | 10 | 345 | 350 | 6 | 5 | −1 | 11 | 138 | 134 | 2 |
| 1 | −3 | 9 | 190 | 197 | 3 | 11 | 1 | 9 | 67 | 67 | 2 | 5 | −3 | 10 | 75 | 73 | 2 | −14 | 2 | 10 | 222 | 225 | 3 | −28 | 0 | 11 | 132 | 118 | 2 |
| 3 | −3 | 9 | 59 | 59 | 1 | −28 | 2 | 9 | 57 | 56 | 1 | −28 | −2 | 10 | 19 | 28 | 3 | −12 | 2 | 10 | 88 | 98 | 2 | −26 | 0 | 11 | 45 | 44 | 2 |
| 5 | −3 | 9 | 160 | 150 | 3 | −26 | 2 | 9 | 88 | 85 | 1 | −26 | −2 | 10 | 109 | 109 | 2 | −10 | 2 | 10 | 126 | 118 | 2 | −24 | 0 | 11 | 101 | 88 | 2 |
| 7 | −3 | 9 | 128 | 135 | 2 | −24 | 2 | 9 | 74 | 67 | 2 | −24 | −2 | 10 | 116 | 107 | 2 | −8 | 2 | 10 | 312 | 315 | 4 | −22 | 0 | 11 | 83 | 64 | 1 |
| −28 | −2 | 9 | 56 | 55 | 2 | −22 | 2 | 9 | 192 | 192 | 3 | −22 | −2 | 10 | 271 | 270 | 4 | −6 | 2 | 10 | 191 | 191 | 3 | −20 | 0 | 11 | 63 | 66 | 2 |
| −26 | −2 | 9 | 90 | 85 | 2 | −20 | 2 | 9 | 219 | 295 | 5 | −20 | −2 | 10 | 199 | 255 | 6 | −4 | 2 | 10 | 335 | 343 | 5 | −18 | 0 | 11 | 26 | 10 | 2 |
| −24 | −2 | 9 | 74 | 65 | 2 | −18 | 2 | 9 | 269 | 279 | 4 | −18 | −2 | 10 | 220 | 230 | 7 | −2 | 2 | 10 | 205 | 206 | 4 | −16 | 0 | 11 | 33 | 44 | 2 |
| −22 | −2 | 9 | 188 | 190 | 4 | −16 | 2 | 9 | 342 | 355 | 5 | −16 | −2 | 10 | 353 | 350 | 9 | 0 | 2 | 10 | 248 | 254 | 5 | −14 | 0 | 11 | 342 | 339 | 4 |
| −20 | −2 | 9 | 239 | 296 | 6 | −14 | 2 | 9 | 424 | 426 | 6 | −14 | −2 | 10 | 225 | 225 | 4 | 2 | 2 | 10 | 138 | 130 | 2 | −12 | 0 | 11 | 122 | 127 | 2 |
| −18 | −2 | 9 | 276 | 279 | 6 | −12 | 2 | 9 | 56 | 59 | 1 | −12 | −2 | 10 | 87 | 97 | 2 | 4 | 2 | 10 | 96 | 92 | 1 | −10 | 0 | 11 | 204 | 205 | 3 |
| −16 | −2 | 9 | 347 | 356 | 6 | −10 | 2 | 9 | 82 | 78 | 1 | −10 | −2 | 10 | 130 | 117 | 3 | 6 | 2 | 10 | 105 | 105 | 1 | −8 | 0 | 11 | 257 | 258 | 3 |
| −14 | −2 | 9 | 413 | 425 | 5 | −8 | 2 | 9 | 95 | 85 | 1 | −8 | −2 | 10 | 324 | 314 | 6 | 8 | 2 | 10 | 123 | 119 | 2 | −6 | 0 | 11 | 15 | 7 | 4 |
| −12 | −2 | 9 | 58 | 58 | 1 | −6 | 2 | 9 | 186 | 188 | 2 | −6 | −2 | 10 | 193 | 191 | 3 | −25 | 3 | 10 | 100 | 97 | 2 | −4 | 0 | 11 | 212 | 201 | 2 |
| −10 | −2 | 9 | 79 | 78 | 1 | −4 | 2 | 9 | 68 | 65 | 1 | −4 | −2 | 10 | 335 | 344 | 7 | −23 | 3 | 10 | 216 | 203 | 4 | −2 | 0 | 11 | 20 | 11 | 2 |
| −8 | −2 | 9 | 93 | 84 | 1 | −2 | 2 | 9 | 148 | 148 | 2 | −2 | −2 | 10 | 212 | 206 | 5 | −21 | 3 | 10 | 216 | 207 | 3 | 0 | 0 | 11 | 193 | 187 | 2 |
| −6 | −2 | 9 | 188 | 189 | 2 | 0 | 2 | 9 | 239 | 250 | 3 | 0 | −2 | 10 | 251 | 255 | 5 | −19 | 3 | 10 | 91 | 91 | 2 | 2 | 0 | 11 | 76 | 82 | 1 |
| −4 | −2 | 9 | 68 | 66 | 1 | 2 | 2 | 9 | 96 | 93 | 2 | 2 | −2 | 10 | 134 | 129 | 2 | −17 | 3 | 10 | 34 | 33 | 2 | 4 | 0 | 11 | 197 | 201 | 2 |
| −2 | −2 | 9 | 145 | 147 | 2 | 4 | 2 | 9 | 234 | 232 | 4 | 4 | −2 | 10 | 96 | 90 | 2 | −15 | 3 | 10 | 352 | 354 | 5 | 6 | 0 | 11 | 70 | 62 | 1 |
| 0 | −2 | 9 | 244 | 248 | 3 | 6 | 2 | 9 | 250 | 242 | 3 | 6 | −2 | 10 | 103 | 105 | 2 | −13 | 3 | 10 | 73 | 71 | 2 | −27 | 1 | 11 | 103 | 104 | 2 |
| 2 | −2 | 9 | 97 | 93 | 2 | 8 | 2 | 9 | 81 | 80 | 1 | 8 | −2 | 10 | 122 | 118 | 2 | −11 | 3 | 10 | 93 | 81 | 2 | −25 | 1 | 11 | 20 | 16 | 3 |
| 4 | −2 | 9 | 240 | 234 | 4 | 10 | 2 | 9 | 154 | 157 | 2 | −29 | −1 | 10 | 98 | 85 | 2 | −9 | 3 | 10 | 86 | 82 | 1 | −23 | 1 | 11 | 127 | 118 | 2 |
| 6 | −2 | 9 | 250 | 242 | 3 | −27 | 3 | 9 | 56 | 42 | 2 | −27 | −1 | 10 | 202 | 193 | 3 | −7 | 3 | 10 | 266 | 269 | 4 | −21 | 1 | 11 | 76 | 64 | 2 |
| 8 | −2 | 9 | 80 | 80 | 1 | −25 | 3 | 9 | 36 | 53 | 4 | −25 | −1 | 10 | 219 | 213 | 3 | −5 | 3 | 10 | 193 | 188 | 3 | −19 | 1 | 11 | 103 | 98 | 3 |
| 10 | −2 | 9 | 152 | 157 | 2 | −23 | 3 | 9 | 87 | 84 | 2 | −23 | −1 | 10 | 96 | 91 | 2 | −3 | 3 | 10 | 201 | 195 | 3 | −17 | 1 | 11 | 138 | 141 | 2 |
| −29 | −1 | 9 | 69 | 61 | 2 | −21 | 3 | 9 | 135 | 128 | 2 | −21 | −1 | 10 | 308 | 301 | 6 | −1 | 3 | 10 | 300 | 294 | 4 | −15 | 1 | 11 | 161 | 154 | 3 |
| −27 | −1 | 9 | 93 | 84 | 2 | −19 | 3 | 9 | 159 | 156 | 3 | −19 | −1 | 10 | 172 | 187 | 3 | 1 | 3 | 10 | 119 | 114 | 2 | −13 | 1 | 11 | 71 | 80 | 1 |
| −25 | −1 | 9 | 155 | 150 | 2 | −17 | 3 | 9 | 142 | 149 | 2 | −17 | −1 | 10 | 195 | 209 | 4 | 3 | 3 | 10 | 154 | 151 | 2 | −11 | 1 | 11 | 249 | 277 | 3 |
| −23 | −1 | 9 | 332 | 337 | 5 | −15 | 3 | 9 | 168 | 178 | 3 | −15 | −1 | 10 | 49 | 41 | 1 | 5 | 3 | 10 | 77 | 73 | 1 | −9 | 1 | 11 | 102 | 116 | 2 |
| −21 | −1 | 9 | 170 | 169 | 3 | −13 | 3 | 9 | 105 | 98 | 2 | −13 | −1 | 10 | 117 | 128 | 1 | −22 | 4 | 10 | 79 | 72 | 3 | −7 | 1 | 11 | 344 | 347 | 4 |
| −19 | −1 | 9 | 241 | 239 | 4 | −11 | 3 | 9 | 120 | 124 | 2 | −11 | −1 | 10 | 256 | 258 | 2 | −20 | 4 | 10 | 88 | 96 | 2 | −5 | 1 | 11 | 72 | 74 | 2 |
| −17 | −1 | 9 | 224 | 230 | 2 | −9 | 3 | 9 | 55 | 59 | 1 | −9 | −1 | 10 | 180 | 187 | 1 | −18 | 4 | 10 | 112 | 106 | 2 | −3 | 1 | 11 | 27 | 19 | 2 |
| −15 | −1 | 9 | 275 | 295 | 3 | −7 | 3 | 9 | 229 | 234 | 3 | −7 | −1 | 10 | 465 | 470 | 4 | −16 | 4 | 10 | 100 | 106 | 2 | −1 | 1 | 11 | 159 | 161 | 2 |
| −13 | −1 | 9 | 526 | 538 | 5 | −5 | 3 | 9 | 359 | 356 | 5 | −5 | −1 | 10 | 131 | 137 | 1 | −14 | 4 | 10 | 96 | 96 | 2 | 1 | 1 | 11 | 151 | 146 | 2 |
| −11 | −1 | 9 | 200 | 197 | 2 | −3 | 3 | 9 | 119 | 124 | 2 | −3 | −1 | 10 | 219 | 222 | 3 | −12 | 4 | 10 | 66 | 73 | 2 | 3 | 1 | 11 | 124 | 124 | 2 |

TABLE 16-continued

Observed and calculated structure factors for Diol-1

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −9 | −1 | 9 | 249 | 249 | 2 | −1 | 3 | 9 | 210 | 217 | 3 | −1 | −1 | 10 | 194 | 201 | 3 | −10 | 4 | 10 | 218 | 236 | 3 | 5 | 1 | 11 | 136 | 134 | 2 |
| −7 | −1 | 9 | 104 | 99 | 1 | 1 | 3 | 9 | 192 | 196 | 2 | 1 | −1 | 10 | 179 | 172 | 3 | −8 | 4 | 10 | 121 | 119 | 2 | −26 | 2 | 11 | 70 | 68 | 2 |
| −5 | −1 | 9 | 311 | 313 | 3 | 3 | 3 | 9 | 64 | 58 | 1 | 3 | −1 | 10 | 301 | 290 | 4 | −6 | 4 | 10 | 163 | 165 | 3 | −24 | 2 | 11 | 128 | 126 | 2 |
| −3 | −1 | 9 | 379 | 378 | 3 | 5 | 3 | 9 | 157 | 151 | 2 | 5 | −1 | 10 | 132 | 132 | 2 | −4 | 4 | 10 | 135 | 138 | 2 | −22 | 2 | 11 | 113 | 101 | 2 |
| −1 | −1 | 9 | 365 | 366 | 3 | 7 | 3 | 9 | 128 | 135 | 2 | 7 | −1 | 10 | 35 | 27 | 2 | −2 | 4 | 10 | 283 | 277 | 4 | −20 | 2 | 11 | 81 | 71 | 3 |
| 1 | −1 | 9 | 555 | 559 | 7 | 9 | 3 | 9 | 130 | 133 | 3 | 9 | −1 | 10 | 76 | 74 | 1 | 0 | 4 | 10 | 74 | 78 | 1 | −18 | 2 | 11 | 89 | 89 | 2 |
| 3 | −1 | 9 | 84 | 81 | 2 | −22 | 4 | 9 | 145 | 144 | 3 | −28 | 0 | 10 | 217 | 214 | 3 | 2 | 4 | 10 | 276 | 274 | 7 | −16 | 2 | 11 | 64 | 73 | 2 |
| 5 | −1 | 9 | 332 | 328 | 4 | −20 | 4 | 9 | 184 | 181 | 3 | −26 | 0 | 10 | 127 | 121 | 2 | −23 | −3 | 11 | 56 | 52 | 3 | −14 | 2 | 11 | 197 | 204 | 4 |
| 7 | −1 | 9 | 214 | 207 | 3 | −18 | 4 | 9 | 81 | 85 | 2 | −24 | 0 | 10 | 71 | 70 | 2 | −21 | −3 | 11 | 42 | 44 | 2 | −12 | 2 | 11 | 42 | 35 | 2 |
| 9 | −1 | 9 | 291 | 289 | 4 | −16 | 4 | 9 | 115 | 122 | 2 | −22 | 0 | 10 | 389 | 387 | 5 | −19 | −3 | 11 | 164 | 173 | 3 | −10 | 2 | 11 | 142 | 142 | 2 |
| 11 | −1 | 9 | 69 | 69 | 1 | −14 | 4 | 9 | 176 | 183 | 3 | −20 | 0 | 10 | 167 | 167 | 2 | −17 | −3 | 11 | 131 | 133 | 3 | −8 | 2 | 11 | 217 | 215 | 4 |
| −30 | 0 | 9 | 72 | 71 | 2 | −12 | 4 | 9 | 191 | 185 | 3 | −18 | 0 | 10 | 199 | 243 | 3 | −15 | −3 | 11 | 67 | 49 | 1 | −6 | 2 | 11 | 252 | 242 | 5 |
| −28 | 0 | 9 | 156 | 149 | 2 | −10 | 4 | 9 | 151 | 166 | 3 | −16 | 0 | 10 | 103 | 113 | 1 | −13 | −3 | 11 | 163 | 170 | 2 | −4 | 2 | 11 | 254 | 250 | 4 |
| −26 | 0 | 9 | 84 | 72 | 2 | −8 | 4 | 9 | 68 | 61 | 2 | −14 | 0 | 10 | 182 | 171 | 2 | −11 | −3 | 11 | 172 | 169 | 3 | −2 | 2 | 11 | 133 | 126 | 2 |
| −24 | 0 | 9 | 435 | 434 | 6 | −6 | 4 | 9 | 303 | 310 | 5 | −12 | 0 | 10 | 357 | 339 | 3 | −9 | −3 | 11 | 74 | 74 | 1 | 0 | 2 | 11 | 50 | 50 | 2 |
| −22 | 0 | 9 | 315 | 337 | 4 | −4 | 4 | 9 | 194 | 190 | 3 | −10 | 0 | 10 | 618 | 650 | 6 | −7 | −3 | 11 | 95 | 96 | 2 | 2 | 2 | 11 | 26 | 26 | 2 |
| −20 | 0 | 9 | 202 | 208 | 3 | −2 | 4 | 9 | 20 | 15 | 3 | −8 | 0 | 10 | 218 | 223 | 2 | −5 | −3 | 11 | 246 | 254 | 4 | 4 | 2 | 11 | 95 | 94 | 2 |
| −18 | 0 | 9 | 120 | 118 | 1 | 0 | 4 | 9 | 230 | 232 | 4 | −6 | 0 | 10 | 369 | 363 | 3 | −3 | −3 | 11 | 106 | 104 | 2 | −23 | 3 | 11 | 57 | 51 | 2 |
| −16 | 0 | 9 | 181 | 148 | 2 | 2 | 4 | 9 | 80 | 74 | 2 | −4 | 0 | 10 | 15 | 3 | 2 | −1 | −3 | 11 | 147 | 152 | 3 | −21 | 3 | 11 | 43 | 44 | 2 |
| −14 | 0 | 9 | 371 | 370 | 3 | 4 | 4 | 9 | 110 | 111 | 2 | −2 | 0 | 10 | 300 | 285 | 3 | 1 | −3 | 11 | 62 | 67 | 2 | −19 | 3 | 11 | 166 | 173 | 3 |
| −12 | 0 | 9 | 301 | 304 | 3 | 6 | 4 | 9 | 90 | 88 | 3 | 0 | 0 | 10 | 99 | 97 | 1 | −26 | −2 | 11 | 70 | 67 | 3 | −17 | 3 | 11 | 130 | 132 | 2 |
| −10 | 0 | 9 | 313 | 324 | 3 | −15 | 5 | 9 | 140 | 156 | 4 | 2 | 0 | 10 | 392 | 388 | 4 | −24 | −2 | 11 | 126 | 125 | 2 | −15 | 3 | 11 | 62 | 49 | 2 |
| −8 | 0 | 9 | 63 | 46 | 1 | −13 | 5 | 9 | 61 | 48 | 3 | 4 | 0 | 10 | 112 | 101 | 2 | −22 | −2 | 11 | 110 | 102 | 2 | −13 | 3 | 11 | 166 | 170 | 2 |
| −6 | 0 | 9 | 122 | 125 | 1 | −11 | 5 | 9 | 86 | 78 | 2 | 6 | 0 | 10 | 109 | 116 | 2 | −20 | −2 | 11 | 81 | 71 | 2 | −11 | 3 | 11 | 174 | 169 | 3 |
| −4 | 0 | 9 | 207 | 208 | 2 | −9 | 5 | 9 | 73 | 81 | 2 | 8 | 0 | 10 | 174 | 174 | 2 | −18 | −2 | 11 | 90 | 89 | 2 | −9 | 3 | 11 | 75 | 74 | 2 |
| −2 | 0 | 9 | 216 | 210 | 2 | −7 | 5 | 9 | 188 | 189 | 4 | 10 | 0 | 10 | 22 | 23 | 3 | −16 | −2 | 11 | 68 | 72 | 2 | −7 | 3 | 11 | 96 | 97 | 1 |
| 0 | 0 | 9 | 280 | 292 | 2 | −5 | 5 | 9 | 55 | 53 | 2 | −29 | 1 | 10 | 96 | 84 | 2 | −14 | −2 | 11 | 199 | 203 | 4 | −5 | 3 | 11 | 250 | 254 | 4 |
| 2 | 0 | 9 | 417 | 423 | 4 | −3 | 5 | 9 | 147 | 147 | 3 | −27 | 1 | 10 | 202 | 193 | 3 | −12 | −2 | 11 | 38 | 34 | 3 | −3 | 3 | 11 | 106 | 105 | 2 |
| 4 | 0 | 9 | 49 | 57 | 1 | −1 | 5 | 9 | 68 | 65 | 3 | −25 | 1 | 10 | 219 | 212 | 3 | −10 | −2 | 11 | 150 | 143 | 3 | −1 | 3 | 11 | 146 | 151 | 2 |
| 6 | 0 | 9 | 173 | 169 | 2 | −11 | −5 | 10 | 94 | 106 | 3 | −23 | 1 | 10 | 94 | 92 | 1 | −8 | −2 | 11 | 220 | 215 | 4 | 1 | 3 | 11 | 54 | 67 | 1 |
| 8 | 0 | 9 | 161 | 150 | 2 | −7 | −5 | 10 | 81 | 72 | 3 | −21 | 1 | 10 | 304 | 302 | 6 | −6 | −2 | 11 | 248 | 242 | 5 | 3 | 3 | 11 | 135 | 133 | 3 |
| 10 | 0 | 9 | 272 | 278 | 3 | −18 | −4 | 10 | 107 | 106 | 4 | −19 | 1 | 10 | 177 | 188 | 3 | −4 | −2 | 11 | 253 | 250 | 4 | −20 | 4 | 11 | 204 | 212 | 4 |
| 12 | 0 | 9 | 42 | 39 | 2 | −16 | −4 | 10 | 91 | 107 | 4 | −17 | 1 | 10 | 211 | 211 | 2 | −2 | −2 | 11 | 133 | 126 | 2 | −18 | 4 | 11 | 66 | 60 | 2 |
| −29 | 1 | 9 | 72 | 62 | 2 | −8 | −4 | 10 | 118 | 120 | 2 | −15 | 1 | 10 | 47 | 40 | 1 | 0 | −2 | 11 | 51 | 50 | 2 | −16 | 4 | 11 | 26 | 17 | 3 |
| −14 | 4 | 11 | 76 | 65 | 2 | −3 | −1 | 12 | 62 | 66 | 4 | −10 | 2 | 12 | 134 | 128 | 2 | −11 | −1 | 13 | 141 | 138 | 3 | −17 | 3 | 13 | 116 | 112 | 3 |
| −12 | 4 | 11 | 199 | 203 | 3 | −1 | −1 | 12 | 121 | 120 | 3 | −8 | 2 | 12 | 147 | 137 | 2 | −9 | −1 | 13 | 75 | 68 | 2 | −15 | 3 | 13 | 102 | 103 | 2 |
| −10 | 4 | 11 | 153 | 150 | 3 | 1 | −1 | 12 | 62 | 59 | 2 | −6 | 2 | 12 | 113 | 114 | 2 | −7 | −1 | 13 | 190 | 191 | 4 | −13 | 3 | 13 | 107 | 101 | 2 |
| −8 | 4 | 11 | 41 | 36 | 2 | 3 | −1 | 12 | 85 | 90 | 2 | −4 | 2 | 12 | 151 | 155 | 2 | −5 | −1 | 13 | 154 | 143 | 3 | −11 | 3 | 13 | 119 | 114 | 2 |
| −6 | 4 | 11 | 194 | 213 | 6 | −26 | 0 | 12 | 143 | 151 | 2 | −2 | 2 | 12 | 22 | 23 | 2 | −3 | −1 | 13 | 151 | 142 | 3 | −9 | 3 | 13 | 124 | 124 | 2 |
| −4 | 4 | 11 | 53 | 74 | 4 | −24 | 0 | 12 | 86 | 87 | 2 | 0 | 2 | 12 | 145 | 143 | 2 | −1 | −1 | 13 | 114 | 119 | 2 | −7 | 3 | 13 | 26 | 23 | 4 |
| −2 | 4 | 11 | 107 | 109 | 2 | −22 | 0 | 12 | 28 | 19 | 2 | −21 | 3 | 12 | 184 | 188 | 3 | −26 | 0 | 13 | 35 | 44 | 4 | −16 | −2 | 14 | 106 | 110 | 2 |
| −21 | −3 | 12 | 188 | 188 | 5 | −20 | 0 | 12 | 95 | 82 | 2 | −19 | 3 | 12 | 191 | 195 | 5 | −24 | 0 | 13 | 11 | 17 | 6 | −14 | −2 | 14 | 141 | 128 | 3 |
| −19 | −3 | 12 | 199 | 196 | 4 | −18 | 0 | 12 | 28 | 28 | 2 | −17 | 3 | 12 | 68 | 70 | 1 | −22 | 0 | 13 | 102 | 101 | 2 | −12 | −2 | 14 | 42 | 42 | 3 |
| −17 | −3 | 12 | 72 | 70 | 2 | −16 | 0 | 12 | 159 | 159 | 2 | −15 | 3 | 12 | 96 | 86 | 2 | −20 | 0 | 13 | 82 | 71 | 2 | −10 | −2 | 14 | 54 | 65 | 3 |
| −15 | −3 | 12 | 97 | 87 | 2 | −14 | 0 | 12 | 41 | 41 | 2 | −13 | 3 | 12 | 55 | 55 | 1 | −18 | 0 | 13 | 84 | 94 | 2 | −21 | −1 | 14 | 98 | 85 | 2 |
| −13 | −3 | 12 | 55 | 54 | 1 | −12 | 0 | 12 | 163 | 173 | 2 | −11 | 3 | 12 | 113 | 112 | 2 | −16 | 0 | 13 | 86 | 97 | 1 | −19 | −1 | 14 | 112 | 110 | 2 |
| −11 | −3 | 12 | 109 | 112 | 2 | −10 | 0 | 12 | 138 | 149 | 2 | −9 | 3 | 12 | 130 | 132 | 2 | −14 | 0 | 13 | 108 | 103 | 2 | −17 | −1 | 14 | 205 | 209 | 4 |
| −9 | −3 | 12 | 126 | 132 | 3 | −8 | 0 | 12 | 65 | 79 | 1 | −7 | 3 | 12 | 131 | 132 | 2 | −12 | 0 | 13 | 37 | 26 | 2 | −15 | −1 | 14 | 106 | 105 | 2 |
| −7 | −3 | 12 | 128 | 133 | 3 | −6 | 0 | 12 | 18 | 13 | 3 | −5 | 3 | 12 | 51 | 48 | 1 | −10 | 0 | 13 | 31 | 30 | 2 | −13 | −1 | 14 | 90 | 93 | 2 |

TABLE 16-continued

Observed and calculated structure factors for Diol-1

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −5 | −3 | 12 | 48 | 49 | 1 | −4 | 0 | 12 | 82 | 68 | 1 | −3 | 3 | 12 | 75 | 72 | 1 | −8 | 0 | 13 | 129 | 142 | 2 | −11 | −1 | 14 | 12 | 15 | 7 |
| −3 | −3 | 12 | 71 | 70 | 2 | −2 | 0 | 12 | 114 | 120 | 2 | −1 | 3 | 12 | 104 | 100 | 2 | −6 | 0 | 13 | 92 | 95 | 2 | −9 | −1 | 14 | 90 | 86 | 2 |
| −24 | −2 | 12 | 72 | 82 | 2 | 0 | 0 | 12 | 125 | 113 | 2 | −16 | 4 | 12 | 150 | 159 | 5 | −4 | 0 | 13 | 59 | 62 | 2 | −7 | −1 | 14 | 153 | 147 | 3 |
| −22 | −2 | 12 | 114 | 115 | 2 | 2 | 0 | 12 | 124 | 106 | 2 | −12 | 4 | 12 | 20 | 55 | 19 | −2 | 0 | 13 | 13 | 13 | 4 | −22 | 0 | 14 | 28 | 28 | 4 |
| −20 | −2 | 12 | 51 | 41 | 2 | 4 | 0 | 12 | 36 | 49 | 3 | −19 | −3 | 13 | 93 | 125 | 4 | 0 | 0 | 13 | 185 | 208 | 5 | −20 | 0 | 14 | 39 | 37 | 1 |
| −18 | −2 | 12 | 73 | 59 | 2 | −27 | 11 | 2 | 73 | 73 | 2 | −17 | −3 | 13 | 113 | 113 | 3 | −25 | 1 | 13 | 163 | 159 | 4 | −18 | 0 | 14 | 264 | 285 | 5 |
| −16 | −2 | 12 | 100 | 104 | 2 | −25 | 1 | 12 | 25 | 32 | 2 | −15 | −3 | 13 | 102 | 104 | 4 | −23 | 1 | 13 | 81 | 75 | 1 | −16 | 0 | 14 | 143 | 156 | 3 |
| −14 | −2 | 12 | 176 | 172 | 3 | −23 | 1 | 12 | 19 | 25 | 3 | −13 | −3 | 13 | 103 | 101 | 4 | −21 | 1 | 13 | 137 | 128 | 3 | −14 | 0 | 14 | 51 | 44 | 1 |
| −12 | −2 | 12 | 126 | 120 | 3 | −21 | 1 | 12 | 156 | 144 | 3 | −11 | −3 | 13 | 119 | 115 | 5 | −19 | 1 | 13 | 182 | 168 | 3 | −12 | 0 | 14 | 23 | 15 | 2 |
| −10 | −2 | 12 | 136 | 129 | 3 | −19 | 1 | 12 | 80 | 76 | 2 | −9 | −3 | 13 | 122 | 124 | 5 | −17 | 1 | 13 | 162 | 175 | 2 | −10 | 0 | 14 | 151 | 156 | 2 |
| −8 | −2 | 12 | 149 | 137 | 3 | −17 | 1 | 12 | 210 | 200 | 3 | −7 | −3 | 13 | 26 | 23 | 5 | −15 | 1 | 13 | 62 | 54 | 1 | −8 | 0 | 14 | 101 | 94 | 2 |
| −6 | −2 | 12 | 114 | 115 | 2 | −15 | 1 | 12 | 120 | 113 | 2 | −22 | −2 | 13 | 91 | 92 | 2 | −13 | 1 | 13 | 207 | 211 | 3 | −6 | 0 | 14 | 196 | 197 | 4 |
| −4 | −2 | 12 | 151 | 155 | 3 | −13 | 1 | 12 | 92 | 89 | 1 | −20 | −2 | 13 | 87 | 81 | 2 | −11 | 1 | 13 | 142 | 138 | 2 | −21 | 1 | 14 | 99 | 85 | 3 |
| −2 | −2 | 12 | 24 | 24 | 3 | −11 | 1 | 12 | 134 | 139 | 2 | −18 | −2 | 13 | 195 | 194 | 3 | −9 | 1 | 13 | 73 | 69 | 1 | −19 | 1 | 14 | 110 | 111 | 2 |
| 0 | −2 | 12 | 146 | 143 | 2 | −9 | 1 | 12 | 167 | 165 | 2 | −16 | −2 | 13 | 29 | 38 | 3 | −7 | 1 | 13 | 193 | 192 | 3 | −17 | 1 | 14 | 197 | 208 | 4 |
| 2 | −2 | 12 | 75 | 73 | 2 | −7 | 1 | 12 | 171 | 172 | 2 | −14 | −2 | 13 | 116 | 113 | 2 | −5 | 1 | 13 | 146 | 142 | 2 | −15 | 1 | 14 | 101 | 104 | 1 |
| −27 | −1 | 12 | 74 | 73 | 2 | −5 | 1 | 12 | 46 | 41 | 2 | −12 | −2 | 13 | 84 | 83 | 2 | −3 | 1 | 13 | 145 | 142 | 2 | −13 | 1 | 14 | 90 | 93 | 1 |
| −25 | −1 | 12 | 27 | 31 | 3 | −3 | 1 | 12 | 59 | 67 | 1 | −10 | −2 | 13 | 108 | 106 | 2 | −1 | 1 | 13 | 120 | 120 | 3 | −11 | 1 | 14 | 13 | 13 | 4 |
| −23 | −1 | 12 | 17 | 25 | 4 | −1 | 1 | 12 | 119 | 119 | 2 | −8 | −2 | 13 | 58 | 47 | 2 | −22 | 2 | 13 | 101 | 93 | 2 | −9 | 1 | 14 | 88 | 88 | 2 |
| −21 | −1 | 12 | 159 | 144 | 3 | 1 | 1 | 12 | 57 | 59 | 1 | −6 | −2 | 13 | 73 | 72 | 2 | −20 | 2 | 13 | 87 | 81 | 3 | −7 | 1 | 14 | 153 | 148 | 4 |
| −19 | −1 | 12 | 78 | 77 | 2 | 3 | 1 | 12 | 87 | 90 | 2 | −4 | −2 | 13 | 73 | 76 | 2 | −18 | 2 | 13 | 204 | 194 | 3 | −16 | 2 | 14 | 107 | 110 | 2 |
| −17 | −1 | 12 | 208 | 200 | 4 | −24 | 2 | 12 | 76 | 82 | 2 | −25 | −1 | 13 | 163 | 161 | 5 | −16 | 2 | 13 | 28 | 39 | 3 | −14 | 2 | 14 | 143 | 129 | 3 |
| −15 | −1 | 12 | 115 | 112 | 3 | −22 | 2 | 12 | 120 | 116 | 3 | −23 | −1 | 13 | 84 | 77 | 2 | −14 | 2 | 13 | 114 | 113 | 2 | −12 | 2 | 14 | 43 | 41 | 2 |
| −13 | −1 | 12 | 90 | 89 | 2 | −20 | 2 | 12 | 55 | 40 | 3 | −21 | −1 | 13 | 142 | 128 | 3 | −12 | 2 | 13 | 85 | 83 | 2 | −10 | 2 | 14 | 53 | 63 | 2 |
| −11 | −1 | 12 | 128 | 138 | 3 | −18 | 2 | 12 | 71 | 59 | 2 | −19 | −1 | 13 | 182 | 169 | 4 | −10 | 2 | 13 | 104 | 105 | 2 | | | | | | |
| −9 | −1 | 12 | 161 | 165 | 3 | −16 | 2 | 12 | 101 | 104 | 2 | −17 | −1 | 13 | 166 | 173 | 3 | −8 | 2 | 13 | 60 | 48 | 2 | | | | | | |
| −7 | −1 | 12 | 169 | 172 | 3 | −14 | 2 | 12 | 173 | 172 | 3 | −15 | −1 | 13 | 63 | 52 | 2 | −6 | 2 | 13 | 77 | 73 | 2 | | | | | | |
| −5 | −1 | 12 | 48 | 40 | 2 | −12 | 2 | 12 | 124 | 120 | 2 | −13 | −1 | 13 | 213 | 211 | 4 | −4 | 2 | 13 | 78 | 76 | 2 | | | | | | |

TABLE 17

| Crystal data and structure refinement for Diol-2. | | |
|---|---|---|
| Empirical formula | C19H36O2 | |
| Formula weight | 296.48 | |
| Temperature | 100(1) K | |
| Wavelength | 1.54178 Å | |
| Crystal system, space group | Monoclinic, P2(1) | |
| Unit cell dimensions | a = 11.394(2) Å | α = 90° |
| | b = 16.535(3) Å | β = 119.26(3)° |
| | c = 11.450(2) Å | γ = 90° |
| Volume | 1881.9(7) $A^3$ | |
| Z | 4 | |
| Calculated density | 1.046 $Mg/m^3$ | |
| Absorption coefficient | 0.497 $mm^{-1}$ | |
| F(000) | 664 | |
| Crystal size | 0.15 × 0.19 × 0.55 mm | |
| Theta range for data collection | 4.43 to 64.72° | |
| Limiting indices | −13 <= h <= 11, −19 <= k <= 16, 0 <= l <= 13 | |
| Reflections collected/unique | 8253/5680 [R(int) = 0.0470] | |
| Data/restraints/parameters | 5680/1/379 | |
| Goodness-of-fit on $F^2$ | 1.030 | |
| Final R indices [I > 2□(I)] | R1 = 0.0421, wR2 = 0.1062 | |
| R indices (all data) | R1 = 0.0478, wR2 = 0.1103 | |
| Absolute structure parameter | −0.2(2) | |
| Largest diff. peak and hole | 0.250 and −0.330 e/$Å^3$ | |

TABLE 18

Atomic coordinates ($Å^2 \times 10^4$) and equivalent isotropic displacement parameters ($Å^2 \times 10^3$) for Diol-2 U(eq) is defined as one third of the trace of the orthogonalized Uij tensor.

| | x | y | z | U(eq) |
|---|---|---|---|---|
| O(8A) | 7009(1) | 1054(1) | 343(1) | 22(1) |
| O(25A) | 12097(2) | 4501(1) | 9078(2) | 29(1) |
| C(23A) | 10679(2) | 3214(2) | 7126(2) | 22(1) |
| C(17A) | 9015(2) | 2275(2) | 4307(2) | 19(1) |
| C(16A) | 9538(2) | 1393(2) | 4652(2) | 22(1) |
| C(15A) | 9271(2) | 983(2) | 3327(2) | 22(1) |
| C(24A) | 11896(2) | 3094(1) | 8510(2) | 23(1) |
| C(13A) | 8009(2) | 2235(1) | 2769(2) | 17(1) |
| C(14A) | 8839(2) | 1686(1) | 2347(2) | 19(1) |
| C(25A) | 12854(2) | 3814(2) | 9041(2) | 23(1) |
| C(20A) | 8505(2) | 2600(2) | 5234(2) | 25(1) |
| C(8A) | 8224(2) | 1527(2) | 858(2) | 21(1) |
| C(18A) | 6679(2) | 1851(2) | 2518(2) | 21(1) |
| C(27A) | 13970(2) | 3638(2) | 10462(2) | 29(1) |
| C(22A) | 9602(2) | 2555(2) | 6736(2) | 22(1) |
| C(11A) | 7075(2) | 2885(2) | 475(2) | 24(1) |
| C(9A) | 7911(2) | 2324(2) | 110(2) | 24(1) |
| C(12A) | 7733(2) | 3031(1) | 1989(2) | 21(1) |
| C(26A) | 13435(3) | 4031(2) | 8141(2) | 34(1) |
| C(21A) | 7921(3) | 3453(2) | 4862(2) | 35(1) |
| C(28A) | 8960(3) | 2575(2) | 7639(2) | 36(1) |
| O(8B) | 6008(2) | 844(1) | −2333(2) | 29(1) |
| O(25B) | −1758(2) | −138(1) | −11229(2) | 31(1) |
| C(20B) | 3276(2) | 896(1) | −7960(2) | 20(1) |
| C(23B) | 1088(2) | 258(1) | −9811(2) | 23(1) |
| C(8B) | 4624(2) | 615(2) | −2947(2) | 24(1) |
| C(25B) | −951(2) | −457(1) | −11765(2) | 21(1) |
| C(15B) | 4781(2) | −316(2) | −4716(2) | 22(1) |
| C(13B) | 3930(2) | 1048(1) | −5393(2) | 18(1) |
| C(16B) | 4136(2) | −269(2) | −6261(2) | 23(1) |
| C(18B) | 5282(2) | 1414(2) | −5116(2) | 22(1) |
| C(17B) | 3314(2) | 531(1) | −6707(2) | 19(1) |
| C(21B) | 2592(2) | 1722(2) | −8340(2) | 27(1) |
| C(24B) | 494(2) | −514(2) | −10619(2) | 24(1) |
| C(14B) | 4088(2) | 366(1) | −4397(2) | 20(1) |
| C(12B) | 3031(2) | 1699(2) | −5298(2) | 24(1) |
| C(26B) | −1474(2) | −1295(2) | −12333(3) | 32(1) |
| C(22B) | 2623(2) | 297(1) | −9166(2) | 21(1) |
| C(11B) | 3587(2) | 1997(2) | −3844(2) | 29(1) |
| C(28B | 3045(2) | 500(2) | −10211(2) | 30(1) |
| C(9B) | 3782(2) | 1313(2) | −2879(2) | 29(1) |
| C(27B) | −1056(2) | 106(2) | −12854(2) | 30(1) |

TABLE 19

| Bond lengths [Å] for Diol-2. | | | |
|---|---|---|---|
| O(8A)—C(8A) | 1.442(3) | O(25A)—C(25A) | 1.440(3) |
| C(23A)—C(24A) | 1.524(3) | C(23A)—C(22A) | 1.536(3) |
| C(17A)—C(20A) | 1.536(3) | C(17A)—C(16A) | 1.553(3) |
| C(17A)—C(13A) | 1.564(3) | C(16A)—C(15A) | 1.549(3) |
| C(15A)—C(14A) | 1.521(3) | C(24A)—C(25A) | 1.526(3) |
| C(13A)—C(18A) | 1.534(3) | C(13A)—C(12A) | 1.535(3) |
| C(13A)—C(14A) | 1.549(3) | C(14A)—C(8A) | 1.516(3) |
| C(25A)—C(26A) | 1.515(3) | C(25A)—C(27A) | 1.525(3) |
| C(20A)—C(21A) | 1.527(4) | C(20A)—C(22A) | 1.557(3) |
| C(8A)—C(9A) | 1.515(3) | C(22A)—C(28A) | 1.531(3) |
| C(11A)—C(9A) | 1.526(3) | C(11A)—C(12A) | 1.535(3) |
| O(8B)—C(8B) | 1.428(3) | O(25B)—C(25B) | 1.432(3) |
| C(20B)—C(21B) | 1.526(3) | C(20B)—C(17B) | 1.537(3) |
| C(20B)—C(22B) | 1.561(3) | C(23B)—C(24B) | 1.528(3) |
| C(23B)—C(22B) | 1.531(3) | C(8B)—C(14B) | 1.519(3) |
| C(8B)—C(9B) | 1.528(4) | C(25B)—C(27B) | 1.513(3) |
| C(25B)—C(26B) | 1.523(4) | C(25B)—C(24B) | 1.526(3) |
| C(15B)—C(14B) | 1.520(3) | C(15B)—C(16B) | 1.550(3) |
| C(13B)—C(12B) | 1.525(3) | C(13B)—C(18B) | 1.537(3) |
| C(13B)—C(14B) | 1.550(3) | C(13B)—C(17B) | 1.567(3) |
| C(16B)—C(17B) | 1.556(3) | C(12B)—C(11B) | 1.545(3) |
| C(22B)—C(28B) | 1.529(3) | C(11B)—C(9B) | 1.520(4) |

TABLE 20

| bond angles [°] for Diol-2. | |
|---|---|
| C(24A)—C(23A)—C(22A) | 113.68(19) |
| C(20A)—C(17A)—C(16A) | 112.36(18) |
| C(20A)—C(17A)—C(13A) | 118.44(17) |
| C(16A)—C(17A)—C(13A) | 103.00(17) |
| C(15A)—C(16A)—C(17A) | 107.12(17) |
| C(14A)—C(15A)—C(16A) | 103.10(19) |
| C(23A)—C(24A)—C(25A) | 115.03(19) |
| C(18A)—C(13A)—C(12A) | 110.07(17) |
| C(18A)—C(13A)—C(14A) | 113.38(18) |
| C(12A)—C(13A)—C(14A) | 107.63(16) |
| C(18A)—C(13A)—C(17A) | 110.06(17) |
| C(12A)—C(13A)—C(17A) | 116.57(19) |
| C(14A)—C(13A)—C(17A) | 98.79(16) |
| C(8A)—C(14A)—C(15A) | 120.18(19) |
| C(8A)—C(14A)—C(13A) | 115.82(17) |
| C(15A)—C(14A)—C(13A) | 104.12(16) |
| O(25A)—C(25A)—C(26A) | 107.5(2) |
| O(25A)—C(25A)—C(27A) | 108.53(18) |
| C(26A)—C(25A)—C(27A) | 110.92(19) |
| O(25A)—C(25A)—C(24A) | 107.75(18) |
| C(26A)—C(25A)—C(24A) | 112.30(19) |
| C(27A)—C(25A)—C(24A) | 109.7(2) |
| C(21A)—C(20A)—C(17A) | 113.0(2) |
| C(21A)—C(20A)—C(22A) | 110.95(19) |
| C(17A)—C(20A)—C(22A) | 112.09(17) |
| O(8A)—C(8A)—C(14A) | 112.21(16) |
| O(8A)—C(8A)—C(9A) | 109.01(17) |
| C(14A)—C(8A)—C(9A) | 109.69(19) |
| C(28A)—C(22A)—C(23A) | 111.49(19) |
| C(28A)—C(22A)—C(20A) | 110.75(18) |
| C(23A)—C(22A)—C(20A) | 112.53(19) |
| C(9A)—C(11A)—C(12A) | 112.28(18) |
| C(8A)—C(9A)—C(11A) | 112.32(18) |
| C(13A)—C(12A)—C(11A) | 111.75(18) |
| C(21B)—C(20B)—C(17B) | 113.30(18) |
| C(21B)—C(20B)—C(22B) | 111.07(17) |
| C(17B)—C(20B)—C(22B) | 111.08(18) |
| C(24B)—C(23B)—C(22B) | 112.97(18) |
| O(8B)—C(8B)—C(14B) | 111.57(17) |
| O(8B)—C(8B)—C(9B) | 110.1(2) |
| C(14B)—C(8B)—C(9B) | 109.48(18) |
| O(25B)—C(25B)—C(27B) | 108.53(19) |
| O(25B)—C(25B)—C(26B) | 108.61(18) |
| C(27B)—C(25B)—C(26B) | 110.5(2) |
| O(25B)—C(25B)—C(24B) | 107.65(18) |
| C(27B)—C(25B)—C(24B) | 111.33(19) |
| C(26B)—C(25B)—C(24B) | 110.08(19) |
| C(14B)—C(15B)—C(16B) | 102.99(17) |

TABLE 20-continued

| bond angles [°] for Diol-2. | |
|---|---|
| C(12B)—C(13B)—C(18B) | 110.33(19) |
| C(12B)—C(13B)—C(14B) | 107.54(17) |
| C(18B)—C(13B)—C(14B) | 113.00(17) |
| C(12B)—C(13B)—C(17B) | 116.87(17) |
| C(18B)—C(13B)—C(17B) | 110.25(17) |
| C(14B)—C(13B)—C(17B) | 98.39(18) |
| C(15B)—C(16B)—C(17B) | 106.92(18) |
| C(20B)—C(17B)—C(16B) | 112.29(18) |
| C(20B)—C(17B)—C(13B) | 118.48(19) |
| C(16B)—C(17B)—C(13B) | 103.50(16) |
| C(23B)—C(24B)—C(25B) | 116.19(19) |
| C(8B)—C(14B)—C(15B) | 118.99(18) |
| C(8B)—C(14B)—C(13B) | 116.6(2) |
| C(15B)—C(14B)—C(13B) | 104.49(17) |
| C(13B)—C(12B)—C(11B) | 111.47(18) |
| C(28B)—C(22B)—C(23B) | 110.72(18) |
| C(28B)—C(22B)—C(20B) | 110.89(19) |
| C(23B)—C(22B)—C(20B) | 113.04(18) |
| C(9B)—C(11B)—C(12B) | 112.6(2) |
| C(11B)—C(9B)—C(8B) | 113.39(19) |

TABLE 21

Anisotropic displacement parameters ($Å^2 \times 10^3$) for Diol-2. The anisotropic displacement factor exponent takes the form "$-2\pi^2[h^2a * 2U_{11} + + 2hka * b * U_{12}]$

| | $U_{11}$ | $U_{22}$ | $U_{33}$ | $U_{23}$ | $U_{13}$ | $U_{12}$ |
|---|---|---|---|---|---|---|
| O(8A) | 25(1) | 17(1) | 23(1) | −3(1) | 11(1) | −2(1) |
| O(25A) | 32(1) | 16(1) | 29(1) | −6(1) | 8(1) | 1(1) |
| C(23A) | 24(1) | 21(1) | 19(1) | −1(1) | 9(1) | −2(1) |
| C(17A) | 17(1) | 23(1) | 16(1) | −1(1) | 8(1) | −2(1) |
| C(16A) | 23(1) | 23(1) | 17(1) | 2(1) | 7(1) | 1(1) |
| C(15A) | 23(1) | 20(1) | 18(1) | −2(1) | 6(1) | 0(1) |
| C(24A) | 27(1) | 19(1) | 19(1) | 0(1) | 9(1) | 2(1) |
| C(13A) | 17(1) | 19(1) | 15(1) | −2(1) | 8(1) | −1(1) |
| C(14A) | 18(1) | 18(1) | 19(1) | −1(1) | 9(1) | 0(1) |
| C(25A) | 26(1) | 20(1) | 21(1) | −5(1) | 9(1) | 1(1) |
| C(20A) | 19(1) | 34(2) | 21(1) | −7(1) | 9(1) | −2(1) |
| C(8A) | 18(1) | 25(1) | 19(1) | −4(1) | 10(1) | −1(1) |
| C(18A) | 20(1) | 25(1) | 18(1) | −3(1) | 10(1) | −3(1) |
| C(27A) | 25(1) | 31(2) | 25(1) | −7(1) | 7(1) | −1(1) |
| C(22A) | 24(1) | 26(1) | 17(1) | −6(1) | 10(1) | −4(1) |
| C(11A) | 27(1) | 21(1) | 21(1) | 4(1) | 10(1) | −1(1) |
| C(9A) | 27(1) | 29(1) | 18(1) | 1(1) | 13(1) | −5(1) |
| C(12A) | 21(1) | 18(1) | 23(1) | 0(1) | 11(1) | −1(1) |
| C(26A) | 32(1) | 41(2) | 30(1) | −10(1) | 16(1) | −13(1) |
| C(21A) | 31(1) | 45(2) | 21(1) | −9(1) | 7(1) | 13(1) |
| C(28A) | 34(1) | 53(2) | 25(1) | −9(1) | 17(1) | −10(1) |
| O(8B) | 19(1) | 42(1) | 18(1) | 3(1) | 4(1) | 3(1) |
| O(25B) | 31(1) | 30(1) | 40(1) | −4(1) | 24(1) | −1(1) |
| C(20B) | 22(1) | 19(1) | 17(1) | 1(1) | 7(1) | −3(1) |
| C(23B) | 24(1) | 22(1) | 18(1) | −2(1) | 7(1) | 3(1) |
| C(8B) | 21(1) | 34(2) | 17(1) | 5(1) | 8(1) | 2(1) |
| C(25B) | 21(1) | 22(1) | 21(1) | −2(1) | 10(1) | 1(1) |
| C(15B) | 21(1) | 19(1) | 20(1) | 2(1) | 6(1) | 0(1) |
| C(13B) | 18(1) | 17(1) | 17(1) | −1(1) | 7(1) | −1(1) |
| C(16B) | 27(1) | 21(1) | 20(1) | −1(1) | 10(1) | 0(1) |
| C(18B) | 22(1) | 24(1) | 19(1) | −3(1) | 8(1) | −6(1) |
| C(17B) | 18(1) | 20(1) | 17(1) | 0(1) | 7(1) | −2(1) |
| C(21B) | 40(1) | 20(1) | 17(1) | 2(1) | 10(1) | 1(1) |
| C(24B) | 24(1) | 21(1) | 24(1) | −1(1) | 10(1) | 3(1) |
| C(14B) | 16(1) | 21(1) | 19(1) | 4(1) | 6(1) | 1(1) |
| C(12B) | 24(1) | 24(1) | 20(1) | 1(1) | 8(1) | 3(1) |
| C(26B) | 25(1) | 25(2) | 38(1) | −8(1) | 10(1) | −1(1) |
| C(22B) | 24(1) | 19(1) | 16(1) | 0(1) | 8(1) | 3(1) |
| C(11B) | 32(1) | 31(2) | 24(1) | −4(1) | 13(1) | 7(1) |
| C(28B) | 36(1) | 34(2) | 21(1) | −2(1) | 14(1) | −1(1) |
| C(9B) | 25(1) | 43(2) | 20(1) | −1(1) | 11(1) | 3(1) |
| C(27B) | 26(1) | 35(2) | 23(1) | 3(1) | 8(1) | −6(1) |

TABLE 22

Hydrogen coordinates ($Å^2 \times 10^4$) and isotropic displacement parameters ($Å^2 \times 10^3$) for Diol-2.

| | x | y | z | U(eq) |
|---|---|---|---|---|
| H(8AA) | 7202 | 573 | 485 | 33 |
| H(25A) | 12570 | 4907 | 9278 | 44 |
| H(23A) | 10981 | 3224 | 6468 | 26 |
| H(23B) | 10277 | 3735 | 7101 | 26 |
| H(17A) | 9774 | 2615 | 4434 | 23 |
| H(16A) | 10493 | 1389 | 5291 | 27 |
| H(16B) | 9068 | 1106 | 5040 | 27 |
| H(15A) | 10079 | 728 | 3421 | 27 |
| H(15B) | 8564 | 581 | 3044 | 27 |
| H(24A) | 12395 | 2627 | 8480 | 27 |
| H(24B) | 11578 | 2975 | 9137 | 27 |
| H(14A) | 9666 | 1989 | 2591 | 22 |
| H(20A) | 7769 | 2245 | 5123 | 30 |
| H(8AB) | 8879 | 1232 | 700 | 25 |
| H(18A) | 6068 | 1828 | 1572 | 31 |
| H(18B) | 6292 | 2171 | 2942 | 31 |
| H(18C) | 6846 | 1314 | 2881 | 31 |
| H(27A) | 14571 | 4092 | 10792 | 44 |
| H(27B) | 14458 | 3166 | 10459 | 44 |
| H(27C) | 13582 | 3547 | 11030 | 44 |
| H(22A) | 10054 | 2032 | 6876 | 27 |
| H(11A) | 6191 | 2649 | 160 | 28 |
| H(11B) | 6959 | 3399 | 23 | 28 |
| H(9AA) | 7423 | 2218 | −845 | 29 |
| H(9AB) | 8747 | 2591 | 314 | 29 |
| H(12A) | 8574 | 3319 | 2288 | 25 |
| H(12B) | 7146 | 3367 | 2175 | 25 |
| H(26A) | 12716 | 4138 | 7253 | 51 |
| H(26B) | 13968 | 3589 | 8116 | 51 |
| H(26C) | 13989 | 4504 | 8484 | 51 |
| H(21A) | 7245 | 3465 | 3935 | 52 |
| H(21B) | 8625 | 3827 | 5013 | 52 |
| H(21C) | 7526 | 3601 | 5404 | 52 |
| H(28A) | 9651 | 2547 | 8559 | 55 |
| H(28B) | 8363 | 2123 | 7434 | 55 |
| H(28C) | 8463 | 3069 | 7490 | 55 |
| H(8BA) | 6481 | 439 | −2080 | 43 |
| H(25B) | −1614 | −395 | −10559 | 46 |
| H(20B) | 4211 | 976 | −7751 | 24 |
| H(23C) | 839 | 293 | −9115 | 28 |
| H(23D) | 702 | 722 | −10396 | 28 |
| H(8BB) | 4541 | 153 | −2455 | 29 |
| H(15C) | 4604 | −835 | −4437 | 26 |
| H(15D) | 5745 | −230 | −4285 | 26 |
| H(16C) | 3550 | −730 | −6675 | 28 |
| H(16D) | 4828 | −269 | −6522 | 28 |
| H(18D) | 5651 | 1727 | −4307 | 33 |
| H(18E) | 5144 | 1757 | −5850 | 33 |
| H(18F) | 5895 | 988 | −5019 | 33 |
| H(17B) | 2386 | 401 | −6940 | 23 |
| H(21D) | 3014 | 2080 | −7585 | 41 |
| H(21E) | 1657 | 1664 | −8602 | 41 |
| H(21F) | 2675 | 1942 | −9072 | 41 |
| H(24C) | 533 | −934 | −10010 | 29 |
| H(24D) | 1062 | −684 | −10987 | 29 |
| H(14B) | 3172 | 171 | −4696 | 23 |
| H(12C) | 2134 | 1482 | −5624 | 29 |
| H(12D) | 2968 | 2152 | −5864 | 29 |
| H(26D) | −2384 | −1253 | −13048 | 48 |
| H(26E) | −1445 | −1636 | −11640 | 48 |
| H(26F) | −922 | −1524 | −12667 | 48 |
| H(22B) | 2970 | −244 | −8819 | 25 |
| H(11C) | 4442 | 2265 | −3555 | 35 |
| H(11D) | 2969 | 2390 | −3817 | 35 |
| H(28D) | 2629 | 126 | −10944 | 45 |
| H(28E) | 4005 | 460 | −9811 | 45 |
| H(28F) | 2766 | 1040 | −10533 | 45 |
| H(9BA) | 2907 | 1107 | −3075 | 35 |
| H(9BB) | 4216 | 1525 | −1974 | 35 |
| H(27D) | −1973 | 129 | −13560 | 45 |
| H(27E) | −497 | −92 | −13204 | 45 |
| H(27F) | −763 | 637 | −12489 | 45 |

TABLE 23

| Torsion angles [deg] for Diol-2. | |
|---|---|
| C(20A)—C(17A)—C(16A)—C(15A) | 149.10(17) |
| C(13A)—C(17A)—C(16A)—C(15A) | 20.5(2) |
| C(17A)—C(16A)—C(15A)—C(14A) | 9.4(2) |
| C(22A)—C(23A)—C(24A)—C(25A) | −168.75(19) |
| C(20A)—C(17A)—C(13A)—C(18A) | −47.1(3) |
| C(16A)—C(17A)—C(13A)—C(18A) | 77.5(2) |
| C(20A)—C(17A)—C(13A)—C(12A) | 79.1(3) |
| C(16A)—C(17A)—C(13A)—C(12A) | −156.23(17) |
| C(20A)—C(17A)—C(13A)—C(14A) | −166.1(2) |
| C(16A)—C(17A)—C(13A)—C(14A) | −41.40(19) |
| C(16A)—C(15A)—C(14A)—C(8A) | −168.25(18) |
| C(16A)—C(15A)—C(14A)—C(13A) | −36.5(2) |
| C(18A)—C(13A)—C(14A)—C(8A) | 66.7(2) |
| C(12A)—C(13A)—C(14A)—C(8A) | −55.3(2) |
| C(17A)—C(13A)—C(14A)—C(8A) | −176.87(19) |
| C(18A)—C(13A)—C(14A)—C(15A) | −67.5(2) |
| C(12A)—C(13A)—C(14A)—C(15A) | 170.49(17) |
| C(17A)—C(13A)—C(14A)—C(15A) | 48.9(2) |
| C(23A)—C(24A)—C(25A)—O(25A) | 58.3(2) |
| C(23A)—C(24A)—C(25A)—C(26A) | −59.9(3) |
| C(23A)—C(24A)—C(25A)—C(27A) | 176.25(19) |
| C(16A)—C(17A)—C(20A)—C(21A) | −177.05(18) |
| C(13A)—C(17A)—C(20A)—C(21A) | −57.1(3) |
| C(16A)—C(17A)—C(20A)—C(22A) | 56.7(2) |
| C(13A)—C(17A)—C(20A)—C(22A) | 176.68(19) |
| C(15A)—C(14A)—C(8A)—O(8A) | 59.8(3) |
| C(13A)—C(14A)—C(8A)—O(8A) | −66.7(2) |
| C(15A)—C(14A)—C(8A)—C(9A) | −178.85(18) |
| C(13A)—C(14A)—C(8A)—C(9A) | 54.6(2) |
| C(24A)—C(23A)—C(22A)—C(28A) | 65.4(3) |
| C(24A)—C(23A)—C(22A)—C(20A) | −169.45(18) |
| C(21A)—C(20A)—C(22A)—C(28A) | 73.7(3) |
| C(17A)—C(20A)—C(22A)—C(28A) | −159.0(2) |
| C(21A)—C(20A)—C(22A)—C(23A) | −51.8(3) |
| C(17A)—C(20A)—C(22A)—C(23A) | 75.5(3) |
| O(8A)—C(8A)—C(9A)—C(11A) | 71.0(2) |
| C(14A)—C(8A)—C(9A)—C(11A) | −52.2(2) |
| C(12A)—C(11A)—C(9A)—C(8A) | 54.6(3) |
| C(18A)—C(13A)—C(12A)—C(11A) | −70.1(2) |
| C(14A)—C(13A)—C(12A)—C(11A) | 53.9(2) |
| C(17A)—C(13A)—C(12A)—C(11A) | 163.67(17) |
| C(9A)—C(11A)—C(12A)—C(13A) | −56.1(2) |
| C(14B)—C(15B)—C(16B)—C(17B) | 10.3(2) |

TABLE 23-continued

| Torsion angles [deg] for Diol-2. | |
|---|---|
| C(21B)—C(20B)—C(17B)—C(16B) | −174.45(18) |
| C(22B)—C(20B)—C(17B)—C(16B) | 59.7(2) |
| C(21B)—C(20B)—C(17B)—C(13B) | −53.8(2) |
| C(22B)—C(20B)—C(17B)—C(13B) | −179.67(17) |
| C(15B)—C(16B)—C(17B)—C(20B) | 148.55(18) |
| C(15B)—C(16B)—C(17B)—C(13B) | 19.6(2) |
| C(12B)—C(13B)—C(17B)—C(20B) | 79.7(2) |
| C(18B)—C(13B)—C(17B)—C(20B) | −47.3(3) |
| C(14B)—C(13B)—C(17B)—C(20B) | −165.72(18) |
| C(12B)—C(13B)—C(17B)—C(16B) | −155.29(19) |
| C(18B)—C(13B)—C(17B)—C(16B) | 77.7(2) |
| C(14B)—C(13B)—C(17B)—C(16B) | −40.70(18) |
| C(22B)—C(23B)—C(24B)—C(25B) | −153.23(19) |
| O(25B)—C(25B)—C(24B)—C(23B) | −53.0(3) |
| C(27B)—C(25B)—C(24B)—C(23B) | 65.8(3) |
| C(26B)—C(25B)—C(24B)—C(23B) | −171.2(2) |
| O(8B)—C(8B)—C(14B)—C(15B) | 57.2(3) |
| C(9B)—C(8B)—C(14B)—C(15B) | 179.4(2) |
| O(8B)—C(8B)—C(14B)—C(13B) | −69.4(2) |
| C(9B)—C(8B)—C(14B)—C(13B) | 52.7(2) |
| C(16B)—C(15B)—C(14B)—C(8B) | −169.37(19) |
| C(16B)—C(15B)—C(14B)—C(13B) | −37.2(2) |
| C(12B)—C(13B)—C(14B)—C(8B) | −55.9(2) |
| C(18B)—C(13B)—C(14B)—C(8B) | 66.1(2) |
| C(17B)—C(13B)—C(14B)—C(8B) | −177.65(17) |
| C(12B)—C(13B)—C(14B)—C(15B) | 170.54(16) |
| C(18B)—C(13B)—C(14B)—C(15B) | −67.5(2) |
| C(17B)—C(13B)—C(14B)—C(15B) | 48.82(18) |
| C(18B)—C(13B)—C(12B)—C(11B) | −68.8(2) |
| C(14B)—C(13B)—C(12B)—C(11B) | 54.9(2) |
| C(17B)—C(13B)—C(12B)—C(11B) | 164.25(19) |
| C(24B)—C(23B)—C(22B)—C(28B) | 75.7(3) |
| C(24B)—C(23B)—C(22B)—C(20B) | −159.22(19) |
| C(21B)—C(20B)—C(22B)—C(28B) | 74.3(2) |
| C(17B)—C(20B)—C(22B)—C(28B) | −158.59(18) |
| C(21B)—C(20B)—C(22B)—C(23B) | −50.7(2) |
| C(17B)—C(20B)—C(22B)—C(23B) | 76.4(2) |
| C(13B)—C(12B)—C(11B)—C(9B) | −56.2(3) |
| C(12B)—C(11B)—C(9B)—C(8B) | 52.8(3) |
| O(8B)—C(8B)—C(9B)—C(11B) | 73.6(2) |
| C(14B)—C(8B)—C(9B)—C(11B) | −49.4(3) |

TABLE 24

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 1 | −18 | 0 | 66 | 65 | 3 | 2 | −7 | 0 | 373 | 369 | 7 | 1 | 1 | 0 | 266 | 267 | 4 | 7 | 10 | 0 | 168 | 178 | 4 | 7 | −14 | 1 | 35 | 31 | 3 |
| 2 | −18 | 0 | 111 | 109 | 3 | 3 | −7 | 0 | 167 | 163 | 2 | 2 | 1 | 0 | 1113 | 1151 | 15 | 8 | 10 | 0 | 15 | 9 | 15 | −9 | −13 | 1 | 95 | 91 | 3 |
| 3 | −18 | 0 | 51 | 29 | 16 | 4 | −7 | 0 | 179 | 180 | 1 | 3 | 1 | 0 | 167 | 163 | 3 | 9 | 10 | 0 | 59 | 57 | 3 | −8 | −13 | 1 | 62 | 64 | 4 |
| 4 | −18 | 0 | 77 | 62 | 10 | 5 | −7 | 0 | 138 | 138 | 1 | 4 | 1 | 0 | 121 | 127 | 3 | 4 | 11 | 0 | 162 | 169 | 6 | −7 | −13 | 1 | 8 | 10 | 7 |
| 1 | −17 | 0 | 114 | 118 | 3 | 6 | −7 | 0 | 156 | 160 | 1 | 5 | 1 | 0 | 216 | 218 | 5 | 5 | 11 | 0 | 130 | 117 | 4 | −6 | −13 | 1 | 67 | 63 | 4 |
| 2 | −17 | 0 | 104 | 108 | 3 | 7 | −7 | 0 | 172 | 180 | 2 | 6 | 1 | 0 | 117 | 111 | 2 | 6 | 11 | 0 | 135 | 126 | 5 | −5 | −13 | 1 | 11 | 20 | 10 |
| 3 | −17 | 0 | 41 | 47 | 4 | 8 | −7 | 0 | 84 | 84 | 2 | 7 | 1 | 0 | 73 | 79 | 2 | 7 | 11 | 0 | 71 | 73 | 5 | −4 | −13 | 1 | 68 | 64 | 2 |
| 4 | −17 | 0 | 49 | 46 | 10 | 9 | −7 | 0 | 190 | 186 | 3 | 8 | 1 | 0 | 72 | 70 | 3 | 8 | 11 | 0 | 109 | 111 | 3 | −3 | −13 | 1 | 144 | 145 | 3 |
| 5 | −17 | 0 | 36 | 42 | 5 | 10 | −7 | 0 | 48 | 50 | 5 | 9 | 1 | 0 | 109 | 111 | 4 | 9 | 11 | 0 | 61 | 61 | 3 | −2 | −13 | 1 | 199 | 193 | 3 |
| 0 | −16 | 0 | 81 | 90 | 8 | 1 | −6 | 0 | 183 | 193 | 3 | 10 | 1 | 0 | 107 | 111 | 4 | 5 | 12 | 0 | 107 | 109 | 7 | −1 | −13 | 1 | 105 | 101 | 4 |
| 1 | −16 | 0 | 122 | 128 | 2 | 2 | −6 | 0 | 293 | 291 | 4 | 11 | 1 | 0 | 96 | 89 | 3 | 6 | 12 | 0 | 108 | 106 | 5 | 0 | −13 | 1 | 40 | 31 | 6 |
| 2 | −16 | 0 | 182 | 178 | 3 | 3 | −6 | 0 | 380 | 373 | 5 | 1 | 2 | 0 | 724 | 745 | 13 | 7 | 12 | 0 | 80 | 87 | 6 | 1 | −13 | 1 | 115 | 114 | 2 |
| 3 | −16 | 0 | 18 | 23 | 10 | 4 | −6 | 0 | 134 | 149 | 2 | 2 | 2 | 0 | 355 | 360 | 6 | 8 | 12 | 0 | 94 | 97 | 3 | 2 | −13 | 1 | 119 | 114 | 3 |
| 4 | −16 | 0 | 31 | 11 | 7 | 5 | −6 | 0 | 78 | 83 | 1 | 3 | 2 | 0 | 472 | 471 | 7 | 9 | 12 | 0 | 35 | 41 | 8 | 3 | −13 | 1 | 63 | 58 | 1 |
| 5 | −16 | 0 | 6 | 12 | 6 | 6 | −6 | 0 | 47 | 27 | 2 | 4 | 2 | 0 | 186 | 175 | 5 | 5 | 13 | 0 | 86 | 86 | 7 | 4 | −13 | 1 | 52 | 53 | 3 |
| 6 | −16 | 0 | 56 | 64 | 4 | 7 | −6 | 0 | 100 | 104 | 2 | 5 | 2 | 0 | 177 | 190 | 5 | 6 | 13 | 0 | 71 | 80 | 8 | 5 | −13 | 1 | 31 | 29 | 6 |
| 1 | −15 | 0 | 135 | 166 | 2 | 8 | −6 | 0 | 99 | 104 | 2 | 6 | 2 | 0 | 113 | 108 | 2 | 7 | 13 | 0 | 114 | 113 | 5 | 6 | −13 | 1 | 26 | 29 | 8 |
| 2 | −15 | 0 | 39 | 41 | 4 | 9 | −6 | 0 | 132 | 128 | 2 | 7 | 2 | 0 | 88 | 83 | 2 | 8 | 13 | 0 | 29 | 25 | 8 | 7 | −13 | 1 | 69 | 64 | 4 |
| 3 | −15 | 0 | 50 | 51 | 4 | 10 | −6 | 0 | 20 | 13 | 10 | 8 | 2 | 0 | 29 | 26 | 7 | 5 | 14 | 0 | 129 | 121 | 7 | 8 | −13 | 1 | 0 | 13 | 1 |
| 4 | −15 | 0 | 125 | 115 | 2 | 11 | −6 | 0 | 42 | 59 | 19 | 9 | 2 | 0 | 31 | 28 | 7 | 6 | 14 | 0 | 179 | 169 | 7 | −9 | −12 | 1 | 50 | 50 | 5 |
| 5 | −15 | 0 | 63 | 62 | 4 | 1 | −5 | 0 | 285 | 277 | 4 | 10 | 2 | 0 | 61 | 61 | 4 | 7 | 14 | 0 | 38 | 38 | 14 | −8 | −12 | 1 | 67 | 72 | 3 |
| 6 | −15 | 0 | 39 | 51 | 8 | 2 | −5 | 0 | 483 | 466 | 4 | 11 | 2 | 0 | 5 | 15 | 5 | 8 | 14 | 0 | 17 | 4 | 17 | −7 | −12 | 1 | 43 | 45 | 5 |
| 7 | −15 | 0 | 19 | 19 | 18 | 3 | −5 | 0 | 299 | 309 | 3 | 1 | 3 | 0 | 921 | 985 | 25 | 5 | 15 | 0 | 72 | 62 | 8 | −6 | −12 | 1 | 166 | 164 | 4 |
| 0 | −14 | 0 | 308 | 304 | 6 | 4 | −5 | 0 | 266 | 250 | 3 | 2 | 3 | 0 | 98 | 82 | 4 | 6 | 15 | 0 | 40 | 52 | 12 | −5 | −12 | 1 | 195 | 190 | 2 |
| 1 | −14 | 0 | 174 | 167 | 2 | 5 | −5 | 0 | 181 | 185 | 2 | 3 | 3 | 0 | 578 | 573 | 10 | 7 | 15 | 0 | 17 | 19 | 17 | −4 | −12 | 1 | 98 | 99 | 3 |
| 2 | −14 | 0 | 123 | 128 | 2 | 6 | −5 | 0 | 216 | 211 | 2 | 4 | 3 | 0 | 107 | 88 | 5 | 5 | 16 | 0 | 0 | 11 | 1 | −3 | −12 | 1 | 124 | 117 | 2 |
| 3 | −14 | 0 | 151 | 152 | 3 | 7 | −5 | 0 | 171 | 166 | 2 | 5 | 3 | 0 | 176 | 191 | 5 | 6 | 16 | 0 | 58 | 64 | 8 | −2 | −12 | 1 | 229 | 222 | 2 |
| 4 | −14 | 0 | 20 | 29 | 5 | 8 | −5 | 0 | 232 | 238 | 3 | 6 | 3 | 0 | 132 | 120 | 2 | −2 | −19 | 1 | 36 | 39 | 4 | −1 | −12 | 1 | 69 | 72 | 4 |
| 5 | −14 | 0 | 131 | 121 | 2 | 9 | −5 | 0 | 62 | 61 | 4 | 7 | 3 | 0 | 116 | 120 | 2 | −4 | −18 | 1 | 102 | 92 | 9 | 0 | −12 | 1 | 148 | 146 | 3 |
| 6 | −14 | 0 | 182 | 169 | 2 | 10 | −5 | 0 | 56 | 50 | 4 | 8 | 3 | 0 | 94 | 104 | 2 | −3 | −18 | 1 | 67 | 63 | 3 | 1 | −12 | 1 | 254 | 248 | 3 |
| 7 | −14 | 0 | 46 | 38 | 3 | 11 | −5 | 0 | 26 | 25 | 7 | 9 | 3 | 0 | 15 | 10 | 14 | −2 | −18 | 1 | 94 | 100 | 3 | 2 | −12 | 1 | 223 | 218 | 2 |
| 1 | −13 | 0 | 72 | 63 | 4 | 1 | −4 | 0 | 500 | 498 | 7 | 10 | 3 | 0 | 98 | 100 | 3 | −1 | −18 | 1 | 62 | 63 | 3 | 3 | −12 | 1 | 44 | 40 | 3 |
| 2 | −13 | 0 | 61 | 60 | 2 | 2 | −4 | 0 | 63 | 69 | 1 | 11 | 3 | 0 | 59 | 52 | 5 | 0 | −18 | 1 | 74 | 72 | 10 | 4 | −12 | 1 | 120 | 110 | 2 |
| 3 | −13 | 0 | 184 | 180 | 2 | 3 | −4 | 0 | 490 | 473 | 4 | 1 | 4 | 0 | 493 | 499 | 12 | 1 | −18 | 1 | 53 | 59 | 13 | 5 | −12 | 1 | 198 | 208 | 2 |
| 4 | −13 | 0 | 136 | 135 | 1 | 4 | −4 | 0 | 120 | 100 | 3 | 2 | 4 | 0 | 63 | 69 | 4 | 2 | −18 | 1 | 92 | 75 | 6 | 6 | −12 | 1 | 98 | 100 | 2 |
| 5 | −13 | 0 | 89 | 86 | 3 | 5 | −4 | 0 | 39 | 32 | 4 | 3 | 4 | 0 | 489 | 474 | 9 | 3 | −18 | 1 | 78 | 64 | 6 | 7 | −12 | 1 | 68 | 67 | 3 |
| 6 | −13 | 0 | 80 | 80 | 3 | 6 | −4 | 0 | 154 | 148 | 2 | 4 | 4 | 0 | 127 | 100 | 5 | −5 | −17 | 1 | 60 | 61 | 4 | 8 | −12 | 1 | 61 | 67 | 4 |
| 7 | −13 | 0 | 113 | 113 | 4 | 7 | −4 | 0 | 138 | 133 | 2 | 5 | 4 | 0 | 41 | 32 | 6 | −4 | −17 | 1 | 81 | 74 | 4 | −9 | −11 | 1 | 19 | 11 | 19 |
| 8 | −13 | 0 | 21 | 25 | 16 | 8 | −4 | 0 | 34 | 34 | 5 | 6 | 4 | 0 | 151 | 148 | 2 | −3 | −17 | 1 | 85 | 83 | 3 | −8 | −11 | 1 | 25 | 19 | 13 |
| 0 | −12 | 0 | 112 | 112 | 5 | 9 | −4 | 0 | 151 | 153 | 3 | 7 | 4 | 0 | 141 | 133 | 2 | −2 | −17 | 1 | 17 | 16 | 9 | −7 | −11 | 1 | 80 | 81 | 3 |
| 1 | −12 | 0 | 126 | 128 | 3 | 10 | −4 | 0 | 59 | 51 | 4 | 8 | 4 | 0 | 28 | 34 | 5 | −1 | −17 | 1 | 162 | 160 | 3 | −6 | −11 | 1 | 80 | 77 | 3 |
| 2 | −12 | 0 | 70 | 69 | 2 | 11 | −4 | 0 | 68 | 74 | 3 | 9 | 4 | 0 | 155 | 154 | 3 | 0 | −17 | 1 | 146 | 148 | 2 | −5 | −11 | 1 | 140 | 136 | 2 |
| 3 | −12 | 0 | 212 | 208 | 2 | 1 | −3 | 0 | 967 | 986 | 8 | 10 | 4 | 0 | 52 | 50 | 4 | 1 | −17 | 1 | 57 | 58 | 3 | −4 | −11 | 1 | 151 | 145 | 1 |
| 4 | −12 | 0 | 131 | 131 | 2 | 2 | −3 | 0 | 98 | 82 | 1 | 11 | 4 | 0 | 75 | 74 | 3 | 2 | −17 | 1 | 103 | 103 | 6 | −3 | −11 | 1 | 150 | 145 | 2 |
| 5 | −12 | 0 | 108 | 109 | 2 | 3 | −3 | 0 | 572 | 572 | 5 | 1 | 5 | 0 | 273 | 276 | 7 | 3 | −17 | 1 | 105 | 105 | 5 | −2 | −11 | 1 | 89 | 93 | 2 |
| 6 | −12 | 0 | 102 | 106 | 4 | 4 | −3 | 0 | 96 | 88 | 3 | 2 | 5 | 0 | 484 | 467 | 12 | 4 | −17 | 1 | 66 | 72 | 3 | −1 | −11 | 1 | 47 | 46 | 4 |
| 7 | −12 | 0 | 88 | 87 | 3 | 5 | −3 | 0 | 180 | 191 | 4 | 3 | 5 | 0 | 301 | 309 | 8 | −6 | −16 | 1 | 139 | 142 | 8 | 0 | −11 | 1 | 113 | 110 | 3 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 8 | −12 | 0 | 93 | 96 | 2 | 6 | −3 | 0 | 132 | 119 | 2 | 4 | 5 | 0 | 268 | 250 | 8 | −5 | −16 | 1 | 50 | 46 | 4 | 1 | −11 | 1 | 57 | 53 | 2 |
| 9 | −12 | 0 | 33 | 41 | 8 | 7 | −3 | 0 | 121 | 120 | 2 | 5 | 5 | 0 | 181 | 185 | 3 | −4 | −16 | 1 | 47 | 43 | 4 | 2 | −11 | 1 | 186 | 17 | 2 |
| 1 | −11 | 0 | 135 | 138 | 3 | 8 | −3 | 0 | 105 | 104 | 2 | 6 | 5 | 0 | 212 | 211 | 2 | −3 | −16 | 1 | 6 | 55 | 4 | 3 | −11 | 1 | 96 | 100 | 1 |
| 2 | −11 | 0 | 201 | 196 | 2 | 9 | −3 | 0 | 14 | 9 | 14 | 7 | 5 | 0 | 171 | 166 | 2 | −2 | −16 | 1 | 20 | 196 | 3 | 4 | −11 | 1 | 237 | 232 | 2 |
| 3 | −11 | 0 | 227 | 224 | 3 | 10 | −3 | 0 | 100 | 100 | 3 | 8 | 5 | 0 | 230 | 238 | 3 | −1 | −16 | 1 | 70 | 78 | 2 | 5 | −11 | 1 | 134 | 140 | 2 |
| 4 | −11 | 0 | 172 | 169 | 1 | 11 | −3 | 0 | 59 | 53 | 3 | 9 | 5 | 0 | 59 | 62 | 4 | 0 | −16 | 1 | 54 | 55 | 8 | 6 | −11 | 1 | 127 | 124 | 2 |
| 5 | −11 | 0 | 132 | 117 | 2 | 0 | −2 | 0 | 746 | 767 | 9 | 10 | 5 | 0 | 53 | 51 | 4 | 1 | −16 | 1 | 32 | 28 | 4 | 7 | −11 | 1 | 72 | 71 | 3 |
| 6 | −11 | 0 | 127 | 126 | 3 | 1 | −2 | 0 | 735 | 746 | 7 | 11 | 5 | 0 | 15 | 24 | 14 | 2 | −16 | 1 | 73 | 73 | 3 | 8 | −11 | 1 | 79 | 78 | 3 |
| 7 | −11 | 0 | 77 | 73 | 4 | 2 | −2 | 0 | 353 | 360 | 3 | 2 | 6 | 0 | 294 | 292 | 8 | 3 | −16 | 1 | 79 | 82 | 2 | −10 | −10 | 1 | 36 | 32 | 6 |
| 8 | −11 | 0 | 112 | 112 | 3 | 3 | −2 | 0 | 476 | 472 | 5 | 3 | 6 | 0 | 365 | 372 | 11 | 4 | −16 | 1 | 68 | 71 | 3 | −9 | −10 | 1 | 133 | 131 | 2 |
| 9 | −11 | 0 | 55 | 61 | 3 | 4 | −2 | 0 | 184 | 175 | 3 | 4 | 6 | 0 | 140 | 149 | 7 | 5 | −16 | 1 | 90 | 91 | 3 | −8 | −10 | 1 | 59 | 65 | 3 |
| 0 | −10 | 0 | 198 | 200 | 4 | 5 | −2 | 0 | 173 | 191 | 4 | 5 | 6 | 0 | 81 | 83 | 4 | −7 | −15 | 1 | 54 | 62 | 5 | −7 | −10 | 1 | 81 | 80 | 3 |
| 1 | −10 | 0 | 241 | 229 | 3 | 6 | −2 | 0 | 115 | 108 | 2 | 6 | 6 | 0 | 43 | 28 | 5 | −6 | −15 | 1 | 69 | 62 | 4 | −6 | −10 | 1 | 115 | 112 | 2 |
| 2 | −10 | 0 | 153 | 158 | 1 | 7 | −2 | 0 | 88 | 84 | 2 | 7 | 6 | 0 | 101 | 103 | 3 | −5 | −15 | 1 | 32 | 26 | 6 | −5 | −10 | 1 | 123 | 115 | 1 |
| 3 | −10 | 0 | 196 | 200 | 2 | 8 | −2 | 0 | 31 | 25 | 8 | 8 | 6 | 0 | 99 | 103 | 3 | −4 | −15 | 1 | 88 | 96 | 2 | −4 | −10 | 1 | 181 | 175 | 2 |
| 4 | −10 | 0 | 83 | 83 | 1 | 9 | −2 | 0 | 33 | 28 | 8 | 9 | 6 | 0 | 127 | 129 | 3 | −3 | −15 | 1 | 196 | 189 | 3 | −3 | −10 | 1 | 166 | 154 | 1 |
| 5 | −10 | 0 | 65 | 62 | 2 | 10 | −2 | 0 | 53 | 60 | 5 | 10 | 6 | 0 | 21 | 14 | 13 | −2 | −15 | 1 | 108 | 103 | 2 | −2 | −10 | 1 | 61 | 52 | 2 |
| 6 | −10 | 0 | 120 | 122 | 2 | 11 | −2 | 0 | 8 | 15 | 8 | 5 | 7 | 0 | 138 | 138 | 4 | −1 | −15 | 1 | 119 | 115 | 2 | −1 | −10 | 1 | 276 | 280 | 4 |
| 7 | −10 | 0 | 168 | 179 | 3 | 1 | −1 | 0 | 262 | 265 | 3 | 6 | 7 | 0 | 151 | 159 | 4 | 0 | −15 | 1 | 243 | 271 | 5 | 0 | −10 | 1 | 95 | 90 | 3 |
| 8 | −10 | 0 | 10 | 8 | 9 | 2 | −1 | 0 | 1112 | 1150 | 12 | 7 | 7 | 0 | 167 | 181 | 3 | 1 | −15 | 1 | 63 | 74 | 3 | 1 | −10 | 1 | 205 | 196 | 2 |
| 9 | −10 | 0 | 55 | 57 | 2 | 3 | −1 | 0 | 168 | 163 | 2 | 8 | 7 | 0 | 87 | 85 | 3 | 2 | −15 | 1 | 58 | 52 | 3 | 2 | −10 | 1 | 14 | 10 | 3 |
| 2 | −9 | 0 | 150 | 142 | 2 | 4 | −1 | 0 | 121 | 126 | 3 | 9 | 7 | 0 | 191 | 186 | 3 | 3 | −15 | 1 | 51 | 49 | 3 | 3 | −10 | 1 | 40 | 36 | 2 |
| 3 | −9 | 0 | 170 | 167 | 1 | 5 | −1 | 0 | 208 | 218 | 4 | 10 | 7 | 0 | 58 | 43 | 4 | 4 | −15 | 1 | 91 | 92 | 3 | 4 | −10 | 1 | 286 | 290 | 2 |
| 4 | −9 | 0 | 102 | 101 | 1 | 6 | −1 | 0 | 115 | 110 | 2 | 4 | 8 | 0 | 137 | 129 | 4 | 5 | −15 | 1 | 100 | 100 | 3 | 5 | −10 | 1 | 107 | 109 | 2 |
| 5 | −9 | 0 | 98 | 95 | 2 | 7 | −1 | 0 | 76 | 79 | 2 | 5 | 8 | 0 | 212 | 214 | 5 | 6 | −15 | 1 | 67 | 67 | 4 | 6 | −10 | 1 | 214 | 218 | 4 |
| 6 | −9 | 0 | 78 | 76 | 2 | 8 | −1 | 0 | 69 | 70 | 3 | 6 | 8 | 0 | 62 | 63 | 5 | −8 | −14 | 1 | 28 | 25 | 5 | 7 | −10 | 1 | 86 | 85 | 3 |
| 7 | −9 | 0 | 263 | 259 | 3 | 9 | −1 | 0 | 108 | 111 | 5 | 7 | 8 | 0 | 198 | 200 | 4 | −7 | −14 | 1 | 112 | 107 | 2 | 8 | −10 | 1 | 111 | 113 | 2 |
| 8 | −9 | 0 | 110 | 105 | 3 | 10 | −1 | 0 | 113 | 111 | 3 | 8 | 8 | 0 | 133 | 130 | 3 | −6 | −14 | 1 | 71 | 75 | 2 | 9 | −10 | 1 | 14 | 18 | 13 |
| 9 | −9 | 0 | 92 | 90 | 3 | 11 | −1 | 0 | 96 | 88 | 4 | 9 | 8 | 0 | 135 | 133 | 2 | −5 | −14 | 1 | 44 | 50 | 3 | −10 | −9 | 1 | 16 | 22 | 15 |
| 10 | −9 | 0 | 0 | 18 | 1 | 1 | 0 | 0 | 121 | 131 | 2 | 10 | 8 | 0 | 113 | 116 | 3 | −4 | −14 | 1 | 121 | 115 | 3 | −9 | −9 | 1 | 160 | 156 | 3 |
| 2 | −8 | 0 | 137 | 131 | 3 | 2 | 0 | 0 | 660 | 684 | 8 | 4 | 9 | 0 | 104 | 100 | 4 | −3 | −14 | 1 | 37 | 31 | 4 | −8 | −9 | 1 | 105 | 102 | 3 |
| 3 | −8 | 0 | 130 | 136 | 2 | 3 | 0 | 0 | 68 | 77 | 2 | 5 | 9 | 0 | 95 | 95 | 5 | −2 | −14 | 1 | 219 | 223 | 3 | −7 | −9 | 1 | 13 | 18 | 13 |
| 4 | −8 | 0 | 134 | 129 | 1 | 4 | 0 | 0 | 361 | 358 | 5 | 6 | 9 | 0 | 74 | 76 | 5 | −1 | −14 | 1 | 68 | 72 | 4 | −6 | −9 | 1 | 155 | 151 | 2 |
| 5 | −8 | 0 | 217 | 214 | 1 | 5 | 0 | 0 | 114 | 135 | 4 | 7 | 9 | 0 | 254 | 259 | 4 | 0 | −14 | 1 | 231 | 227 | 4 | −5 | −9 | 1 | 43 | 43 | 2 |
| 6 | −8 | 0 | 62 | 62 | 2 | 6 | 0 | 0 | 117 | 113 | 2 | 8 | 9 | 0 | 103 | 104 | 3 | 1 | −14 | 1 | 99 | 102 | 2 | −4 | −9 | 1 | 149 | 150 | 1 |
| 7 | −8 | 0 | 204 | 200 | 2 | 7 | 0 | 0 | 94 | 82 | 2 | 9 | 9 | 0 | 87 | 90 | 3 | 2 | −14 | 1 | 123 | 115 | 3 | −3 | −9 | 1 | 233 | 242 | 2 |
| 8 | −8 | 0 | 134 | 131 | 3 | 8 | 0 | 0 | 174 | 171 | 2 | 10 | 9 | 0 | 21 | 18 | 21 | 3 | −14 | 1 | 109 | 121 | 2 | −2 | −9 | 1 | 47 | 40 | 1 |
| 9 | −8 | 0 | 135 | 133 | 3 | 9 | 0 | 0 | 53 | 59 | 3 | 4 | 10 | 0 | 89 | 84 | 6 | 4 | −14 | 1 | 138 | 128 | 3 | 0 | −9 | 1 | 82 | 76 | 2 |
| 10 | −8 | 0 | 103 | 116 | 2 | 10 | 0 | 0 | 209 | 201 | 4 | 5 | 10 | 0 | 62 | 61 | 6 | 5 | −14 | 1 | 203 | 201 | 3 | 1 | −9 | 1 | 285 | 289 | 4 |
| 1 | −7 | 0 | 491 | 460 | 8 | 11 | 0 | 0 | 39 | 48 | 6 | 6 | 10 | 0 | 125 | 122 | 5 | 6 | −14 | 1 | 43 | 49 | 3 | 2 | −9 | 1 | 254 | 242 | 2 |
| 3 | −9 | 1 | 84 | 83 | 1 | 6 | −5 | 1 | 213 | 221 | 2 | 4 | −1 | 1 | 576 | 562 | 10 | −3 | 3 | 1 | 369 | 342 | 7 | 7 | 7 | 1 | 85 | 91 | 3 |
| 4 | −9 | 1 | 52 | 45 | 2 | 7 | −5 | 1 | 160 | 160 | 2 | 5 | −1 | 1 | 73 | 66 | 4 | −2 | 3 | 1 | 237 | 250 | 5 | 8 | 7 | 1 | 58 | 64 | 3 |
| 5 | −9 | 1 | 127 | 133 | 2 | 8 | −5 | 1 | 99 | 96 | 3 | 6 | −1 | 1 | 66 | 58 | 2 | −1 | 3 | 1 | 818 | 826 | 15 | 9 | 7 | 1 | 72 | 66 | 3 |
| 6 | −9 | 1 | 50 | 46 | 4 | 9 | −5 | 1 | 90 | 86 | 3 | 7 | −1 | 1 | 104 | 95 | 2 | 0 | 3 | 1 | 560 | 581 | 10 | 10 | 7 | 1 | 48 | 52 | 4 |
| 7 | −9 | 1 | 36 | 37 | 5 | 10 | −5 | 1 | 30 | 22 | 7 | 8 | −1 | 1 | 133 | 132 | 3 | 1 | 3 | 1 | 823 | 865 | 15 | −11 | 8 | 1 | 88 | 94 | 8 |
| 8 | −9 | 1 | 175 | 172 | 3 | −11 | −4 | 1 | 55 | 46 | 4 | 9 | −1 | 1 | 210 | 218 | 4 | 2 | 3 | 1 | 115 | 116 | 4 | −10 | 8 | 1 | 75 | 75 | 3 |
| 9 | −9 | 1 | 64 | 67 | 3 | −10 | −4 | 1 | 170 | 175 | 3 | 10 | −1 | 1 | 20 | 17 | 20 | 3 | 3 | 1 | 148 | 134 | 4 | −9 | 8 | 1 | 53 | 53 | 4 |
| −11 | −8 | 1 | 82 | 94 | 3 | −9 | −4 | 1 | 36 | 34 | 6 | 11 | −1 | 1 | 101 | 107 | 4 | 4 | 3 | 1 | 207 | 204 | 5 | −8 | 8 | 1 | 35 | 41 | 7 |
| −10 | −8 | 1 | 76 | 74 | 3 | −8 | −4 | 1 | 34 | 28 | 5 | −12 | 0 | 1 | 46 | 35 | 17 | 5 | 3 | 1 | 129 | 134 | 2 | −7 | 8 | 1 | 119 | 125 | 3 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −9 | −8 | 1 | 51 | 53 | 3 | −7 | −4 | 1 | 212 | 208 | 2 | −11 | 0 | 1 | 33 | 27 | 9 | 6 | 3 | 1 | 57 | 54 | 3 | −6 | 8 | 1 | 105 | 103 | 4 |
| −8 | −8 | 1 | 31 | 42 | 4 | −6 | −4 | 1 | 182 | 193 | 2 | −10 | 0 | 1 | 149 | 153 | 4 | 7 | 3 | 1 | 0 | 12 | 1 | −5 | 8 | 1 | 81 | 77 | 4 |
| −7 | −8 | 1 | 123 | 125 | 2 | −5 | −4 | 1 | 657 | 641 | 9 | −9 | 0 | 1 | 13 | 20 | 13 | 8 | 3 | 1 | 226 | 233 | 3 | 4 | 8 | 1 | 117 | 132 | 4 |
| −6 | −8 | 1 | 103 | 103 | 1 | −4 | −4 | 1 | 494 | 489 | 6 | −8 | 0 | 1 | 101 | 104 | 2 | 9 | 3 | 1 | 66 | 59 | 3 | 5 | 8 | 1 | 203 | 185 | 4 |
| −5 | −8 | 1 | 80 | 78 | 1 | −3 | −4 | 1 | 382 | 392 | 4 | −7 | 0 | 1 | 74 | 59 | 2 | 10 | 3 | 1 | 99 | 101 | 3 | 6 | 8 | 1 | 99 | 100 | 4 |
| −4 | −8 | 1 | 164 | 164 | 2 | −2 | −4 | 1 | 380 | 379 | 3 | −6 | 0 | 1 | 141 | 150 | 2 | −11 | 4 | 1 | 48 | 46 | 5 | 7 | 8 | 1 | 39 | 43 | 6 |
| −3 | −8 | 1 | 301 | 284 | 4 | −1 | −4 | 1 | 522 | 516 | 4 | −5 | 0 | 1 | 179 | 192 | 4 | −10 | 4 | 1 | 171 | 174 | 3 | 8 | 8 | 1 | 160 | 156 | 3 |
| −2 | −8 | 1 | 292 | 288 | 4 | 0 | −4 | 1 | 179 | 189 | 1 | −4 | 0 | 1 | 151 | 145 | 3 | −9 | 4 | 1 | 31 | 34 | 8 | 9 | 8 | 1 | 19 | 13 | 19 |
| 1 | −8 | 1 | 360 | 362 | 5 | 1 | −4 | 1 | 522 | 517 | 5 | −3 | 0 | 1 | 222 | 241 | 3 | −8 | 4 | 1 | 33 | 28 | 5 | 10 | 8 | 1 | 76 | 69 | 4 |
| 2 | −8 | 1 | 451 | 439 | 6 | 2 | −4 | 1 | 364 | 366 | 3 | −2 | 0 | 1 | 991 | 1016 | 10 | −7 | 4 | 1 | 212 | 208 | 2 | −10 | 9 | 1 | 26 | 21 | 9 |
| 3 | −8 | 1 | 75 | 86 | 1 | 3 | −4 | 1 | 339 | 332 | 4 | −1 | 0 | 1 | 142 | 140 | 2 | −6 | 4 | 1 | 180 | 194 | 2 | −9 | 9 | 1 | 157 | 157 | 3 |
| 4 | −8 | 1 | 122 | 132 | 1 | 4 | −4 | 1 | 117 | 105 | 3 | 0 | 0 | 1 | 272 | 277 | 3 | −5 | 4 | 1 | 664 | 641 | 17 | −8 | 9 | 1 | 98 | 102 | 3 |
| 5 | −8 | 1 | 193 | 185 | 2 | 5 | −4 | 1 | 52 | 44 | 2 | 1 | 0 | 1 | 511 | 544 | 6 | −4 | 4 | 1 | 503 | 489 | 9 | −7 | 9 | 1 | 13 | 18 | 12 |
| 6 | −8 | 1 | 98 | 100 | 2 | 6 | −4 | 1 | 36 | 33 | 4 | 2 | 0 | 1 | 1033 | 1049 | 12 | −3 | 4 | 1 | 384 | 391 | 7 | −6 | 9 | 1 | 157 | 151 | 4 |
| 7 | −8 | 1 | 32 | 43 | 4 | 7 | −4 | 1 | 169 | 165 | 2 | 3 | 0 | 1 | 106 | 122 | 3 | −2 | 4 | 1 | 360 | 378 | 7 | −5 | 9 | 1 | 48 | 44 | 6 |
| 8 | −8 | 1 | 150 | 156 | 2 | 8 | −4 | 1 | 58 | 58 | 4 | 4 | 0 | 1 | 129 | 126 | 3 | −1 | 4 | 1 | 498 | 516 | 13 | −4 | 9 | 1 | 143 | 149 | 6 |
| 9 | −8 | 1 | 0 | 13 | 1 | 9 | −4 | 1 | 37 | 44 | 6 | 5 | 0 | 1 | 38 | 46 | 4 | 0 | 4 | 1 | 172 | 189 | 5 | 4 | 9 | 1 | 47 | 44 | 6 |
| 10 | −8 | 1 | 63 | 69 | 3 | 10 | −4 | 1 | 53 | 57 | 4 | 6 | 0 | 1 | 113 | 127 | 2 | 1 | 4 | 1 | 500 | 517 | 9 | 5 | 9 | 1 | 132 | 133 | 4 |
| −11 | −7 | 1 | 93 | 99 | 3 | −11 | −3 | 1 | 128 | 124 | 3 | 7 | 0 | 1 | 246 | 243 | 2 | 2 | 4 | 1 | 365 | 366 | 7 | 6 | 9 | 1 | 53 | 46 | 6 |
| −10 | −7 | 1 | 46 | 45 | −3 | −10 | −3 | 1 | 75 | 84 | 4 | 8 | 0 | 1 | 224 | 233 | 3 | 3 | 4 | 1 | 333 | 333 | 7 | 7 | 9 | 1 | 34 | 37 | 7 |
| −9 | −7 | 1 | 166 | 170 | 3 | −9 | −3 | 1 | 50 | 48 | 4 | 9 | 0 | 1 | 37 | 34 | 7 | 4 | 4 | 1 | 121 | 106 | 7 | 8 | 9 | 1 | 177 | 172 | 3 |
| −8 | −7 | 1 | 223 | 228 | 3 | −8 | −3 | 1 | 100 | 103 | 2 | 10 | 0 | 1 | 23 | 3 | 15 | 5 | 4 | 1 | 47 | 45 | 4 | 9 | 9 | 1 | 65 | 66 | 4 |
| −7 | −7 | 1 | 101 | 102 | 2 | −7 | −3 | 1 | 99 | 107 | 2 | 11 | 0 | 1 | 100 | 108 | 5 | 6 | 4 | 1 | 31 | 32 | 5 | −10 | 10 | 1 | 33 | 32 | 7 |
| −6 | −7 | 1 | 157 | 156 | 1 | −6 | −3 | 1 | 96 | 97 | 2 | −12 | 1 | 1 | 10 | 27 | 10 | 7 | 4 | 1 | 174 | 165 | 2 | −9 | 10 | 1 | 129 | 130 | 3 |
| −5 | −7 | 1 | 178 | 176 | 1 | −5 | −3 | 1 | 547 | 519 | 8 | −11 | 1 | 1 | 40 | 38 | 8 | 8 | 4 | 1 | 60 | 58 | 3 | −8 | 10 | 1 | 64 | 65 | 4 |
| −4 | −7 | 1 | 265 | 271 | 2 | −4 | −3 | 1 | 82 | 69 | 2 | −10 | 1 | 1 | 59 | 62 | 4 | 9 | 4 | 1 | 50 | 44 | 4 | −7 | 10 | 1 | 80 | 80 | 6 |
| −3 | −7 | 1 | 330 | 320 | 5 | −3 | −3 | 1 | 365 | 342 | 3 | −9 | 1 | 1 | 42 | 46 | 5 | 10 | 4 | 1 | 51 | 57 | 5 | −6 | 10 | 1 | 120 | 112 | 5 |
| −2 | −7 | 1 | 259 | 247 | 5 | −2 | −3 | 1 | 242 | 249 | 2 | −8 | 1 | 1 | 61 | 51 | 3 | −11 | 5 | 1 | 107 | 104 | 3 | −5 | 10 | 1 | 124 | 115 | 4 |
| −1 | −7 | 1 | 135 | 145 | 2 | −1 | −3 | 1 | 840 | 826 | 8 | −7 | 1 | 1 | 29 | 32 | 5 | −10 | 5 | 1 | 52 | 46 | 4 | 4 | 10 | 1 | 273 | 290 | 6 |
| 1 | −7 | 1 | 366 | 367 | 6 | 0 | −3 | 1 | 573 | 582 | 5 | −6 | 1 | 1 | 214 | 198 | 2 | −9 | 5 | 1 | 45 | 43 | 5 | 5 | 10 | 1 | 108 | 108 | 5 |
| 2 | −7 | 1 | 190 | 181 | 2 | 1 | −3 | 1 | 846 | 866 | 8 | −5 | 1 | 1 | 426 | 426 | 6 | −8 | 5 | 1 | 19 | 28 | 18 | 6 | 10 | 1 | 215 | 217 | 4 |
| 3 | −7 | 1 | 83 | 81 | 1 | 2 | −3 | 1 | 117 | 115 | 2 | −4 | 1 | 1 | 440 | 422 | 6 | −7 | 5 | 1 | 233 | 234 | 2 | 7 | 10 | 1 | 93 | 86 | 3 |
| 4 | −7 | 1 | 189 | 186 | 1 | 3 | −3 | 1 | 144 | 135 | 2 | −3 | 1 | 1 | 471 | 485 | 7 | −6 | 5 | 1 | 191 | 185 | 2 | 8 | 10 | 1 | 119 | 113 | 3 |
| 5 | −7 | 1 | 70 | 69 | 1 | 4 | −3 | 1 | 207 | 204 | 3 | −2 | 1 | 1 | 1170 | 1216 | 20 | −5 | 5 | 1 | 144 | 139 | 8 | 9 | 10 | 1 | 25 | 19 | 10 |
| 6 | −7 | 1 | 116 | 114 | 2 | 5 | −3 | 1 | 127 | 135 | 2 | −1 | 1 | 1 | 494 | 510 | 9 | −4 | 5 | 1 | 316 | 292 | 9 | −9 | 11 | 1 | 0 | 11 | 1 |
| 7 | −7 | 1 | 85 | 91 | 2 | 6 | −3 | 1 | 56 | 55 | 3 | 0 | 1 | 1 | 239 | 253 | 4 | −3 | 5 | 1 | 230 | 216 | 7 | −8 | 11 | 1 | 29 | 19 | 8 |
| 8 | −7 | 1 | 59 | 63 | 3 | 7 | −3 | 1 | 0 | 13 | 1 | 1 | 1 | 1 | 480 | 498 | 7 | −2 | 5 | 1 | 399 | 397 | 10 | −7 | 11 | 1 | 79 | 81 | 6 |
| 9 | −7 | 1 | 62 | 65 | 3 | 8 | −3 | 1 | 224 | 232 | 3 | 2 | 1 | 1 | 72 | 74 | 3 | −1 | 5 | 1 | 227 | 222 | 6 | −6 | 11 | 1 | 80 | 77 | 5 |
| 10 | −7 | 1 | 45 | 53 | 4 | 9 | −3 | 1 | 67 | 59 | 4 | 3 | 1 | 1 | 364 | 382 | 5 | 1 | 5 | 1 | 248 | 249 | 7 | −5 | 11 | 1 | 144 | 137 | 6 |
| −11 | −6 | 1 | 70 | 74 | 2 | 10 | −3 | 1 | 99 | 101 | 3 | 4 | 1 | 1 | 561 | 562 | 8 | 2 | 5 | 1 | 236 | 236 | 7 | 4 | 11 | 1 | 226 | 231 | 7 |
| −10 | −6 | 1 | 142 | 139 | 2 | −11 | −2 | 1 | 24 | 33 | 24 | 5 | 1 | 1 | 77 | 67 | 3 | 3 | 5 | 1 | 232 | 217 | 8 | 5 | 11 | 1 | 139 | 140 | 5 |
| −9 | −6 | 1 | 64 | 67 | 3 | −10 | −2 | 1 | 54 | 49 | 5 | 6 | 1 | 1 | 62 | 58 | 2 | 4 | 5 | 1 | 147 | 159 | 7 | 6 | 11 | 1 | 128 | 123 | 5 |
| −8 | −6 | 1 | 166 | 163 | 2 | −9 | −2 | 1 | 118 | 120 | 3 | 7 | 1 | 1 | 105 | 94 | 2 | 5 | 5 | 1 | 213 | 223 | 3 | 7 | 11 | 1 | 75 | 72 | 4 |
| −7 | −6 | 1 | 72 | 75 | 2 | −8 | −2 | 1 | 104 | 108 | 3 | 8 | 1 | 1 | 134 | 132 | 2 | 6 | 5 | 1 | 214 | 222 | 2 | 8 | 11 | 1 | 83 | 79 | 3 |
| −6 | −6 | 1 | 103 | 105 | 2 | −7 | −2 | 1 | 113 | 103 | 2 | 9 | 1 | 1 | 206 | 219 | 3 | 7 | 5 | 1 | 164 | 160 | 3 | 9 | 11 | 1 | 47 | 39 | 10 |
| −5 | −6 | 1 | 201 | 190 | 1 | −6 | −2 | 1 | 218 | 211 | 2 | 10 | 1 | 1 | 0 | 17 | 1 | 8 | 5 | 1 | 89 | 95 | 2 | −9 | 12 | 1 | 44 | 49 | 4 |
| −4 | −6 | 1 | 320 | 305 | 3 | −5 | −2 | 1 | 376 | 382 | 5 | 11 | 1 | 1 | 109 | 107 | 5 | 9 | 5 | 1 | 85 | 86 | 3 | −8 | 12 | 1 | 61 | 72 | 5 |
| −3 | −6 | 1 | 483 | 456 | 5 | −4 | −2 | 1 | 237 | 250 | 3 | −11 | 2 | 1 | 42 | 33 | 7 | 10 | 5 | 1 | 0 | 22 | 1 | −7 | 12 | 1 | 52 | 45 | 8 |
| −2 | −6 | 1 | 505 | 485 | 7 | −3 | −2 | 1 | 591 | 602 | 6 | −10 | 2 | 1 | 46 | 50 | 5 | −11 | 6 | 1 | 76 | 74 | 3 | −6 | 12 | 1 | 169 | 164 | 6 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −1 | −6 | 1 | 168 | 164 | 3 | −2 | −2 | 1 | 670 | 673 | 6 | −9 | 2 | 1 | 116 | 119 | 3 | −10 | 6 | 1 | 142 | 139 | 3 | −5 | 12 | 1 | 196 | 190 | 7 |
| 0 | −6 | 1 | 89 | 87 | 1 | −1 | −2 | 1 | 1223 | 1241 | 12 | −8 | 2 | 1 | 107 | 108 | 3 | −9 | 6 | 1 | 66 | 67 | 3 | 4 | 12 | 1 | 110 | 110 | 7 |
| 1 | −6 | 1 | 414 | 403 | 7 | 0 | −2 | 1 | 708 | 727 | 7 | −7 | 2 | 1 | 113 | 103 | 2 | −8 | 6 | 1 | 166 | 163 | 3 | 5 | 12 | 1 | 205 | 208 | 7 |
| 2 | −6 | 1 | 149 | 143 | 2 | 1 | −2 | 1 | 37 | 39 | 2 | −6 | 2 | 1 | 212 | 211 | 2 | −7 | 6 | 1 | 67 | 75 | 3 | 6 | 12 | 1 | 95 | 101 | 6 |
| 3 | −6 | 1 | 196 | 187 | 2 | 2 | −2 | 1 | 189 | 196 | 2 | −5 | 2 | 1 | 399 | 382 | 7 | −6 | 6 | 1 | 104 | 105 | 3 | 7 | 12 | 1 | 73 | 68 | 4 |
| 4 | −6 | 1 | 79 | 85 | 2 | 3 | −2 | 1 | 140 | 150 | 2 | −4 | 2 | 1 | 249 | 249 | 4 | −5 | 6 | 1 | 197 | 190 | 4 | 8 | 12 | 1 | 64 | 67 | 3 |
| 5 | −6 | 1 | 94 | 96 | 2 | 4 | −2 | 1 | 37 | 43 | 4 | −3 | 2 | 1 | 590 | 602 | 8 | −4 | 6 | 1 | 315 | 305 | 9 | −9 | 13 | 1 | 86 | 91 | 5 |
| 6 | −6 | 1 | 157 | 145 | 2 | 5 | −2 | 1 | 178 | 190 | 2 | −2 | 2 | 1 | 661 | 674 | 12 | −3 | 6 | 1 | 475 | 456 | 13 | −8 | 13 | 1 | 54 | 65 | 6 |
| 7 | −6 | 1 | 72 | 70 | 2 | 6 | −2 | 1 | 45 | 52 | 3 | −1 | 2 | 1 | 1206 | 1241 | 21 | −2 | 6 | 1 | 487 | 486 | 13 | −7 | 13 | 1 | 20 | 10 | 20 |
| 8 | −6 | 1 | 113 | 119 | 2 | 7 | −2 | 1 | 88 | 86 | 3 | 0 | 2 | 1 | 700 | 725 | 12 | 1 | 6 | 1 | 393 | 403 | 11 | −6 | 13 | 1 | 72 | 63 | 8 |
| 9 | −6 | 1 | 115 | 118 | 2 | 8 | −2 | 1 | 60 | 61 | 5 | 1 | 2 | 1 | 40 | 39 | 4 | 2 | 6 | 1 | 149 | 143 | 6 | −5 | 13 | 1 | 0 | 21 | 1 |
| 10 | −6 | 1 | 21 | 35 | 8 | 9 | −2 | 1 | 137 | 145 | 3 | 2 | 2 | 1 | 189 | 197 | 3 | 3 | 6 | 1 | 196 | 187 | 7 | 4 | 13 | 1 | 52 | 54 | 10 |
| −11 | −5 | 1 | 105 | 104 | 3 | 10 | −2 | 1 | 54 | 67 | 6 | 3 | 2 | 1 | 146 | 149 | 3 | 4 | 6 | 1 | 72 | 85 | 5 | 5 | 13 | 1 | 12 | 30 | 12 |
| −10 | −5 | 1 | 49 | 45 | 4 | −12 | −1 | 1 | 18 | 27 | 17 | 4 | 2 | 1 | 47 | 44 | 8 | 5 | 6 | 1 | 91 | 95 | 3 | 6 | 13 | 1 | 40 | 29 | 13 |
| −9 | −5 | 1 | 46 | 43 | 4 | −11 | −1 | 1 | 42 | 39 | 6 | 5 | 2 | 1 | 174 | 189 | 2 | 6 | 6 | 1 | 148 | 145 | 3 | 7 | 13 | 1 | 60 | 64 | 6 |
| −8 | −5 | 1 | 21 | 28 | 9 | −10 | −1 | 1 | 62 | 63 | 5 | 6 | 2 | 1 | 46 | 51 | 2 | 7 | 6 | 1 | 76 | 70 | 3 | 8 | 13 | 1 | 5 | 13 | 5 |
| −7 | −5 | 1 | 230 | 234 | 2 | −9 | −1 | 1 | 48 | 46 | 5 | 7 | 2 | 1 | 81 | 85 | 3 | 8 | 6 | 1 | 112 | 119 | 3 | −8 | 14 | 1 | 0 | 26 | 1 |
| −6 | −5 | 1 | 191 | 186 | 2 | −8 | −1 | 1 | 61 | 51 | 3 | 8 | 2 | 1 | 55 | 62 | 4 | 9 | 6 | 1 | 120 | 118 | 3 | −7 | 14 | 1 | 111 | 108 | 7 |
| −5 | −5 | 1 | 153 | 139 | 3 | −7 | −1 | 1 | 32 | 32 | 4 | 9 | 2 | 1 | 149 | 145 | 3 | 10 | 6 | 1 | 26 | 35 | 9 | −6 | 14 | 1 | 69 | 75 | 8 |
| −4 | −5 | 1 | 306 | 291 | 3 | −6 | −1 | 1 | 212 | 198 | 3 | 10 | 2 | 1 | 65 | 67 | 5 | −11 | 7 | 1 | 97 | 99 | 3 | −5 | 14 | 1 | 49 | 50 | 10 |
| −3 | −5 | 1 | 225 | 215 | 2 | −5 | −1 | 1 | 431 | 425 | 8 | 11 | 2 | 1 | 54 | 56 | 15 | −10 | 7 | 1 | 41 | 45 | 6 | 4 | 14 | 1 | 137 | 128 | 7 |
| −2 | −5 | 1 | 399 | 398 | 3 | −4 | −1 | 1 | 432 | 421 | 5 | −11 | 3 | 1 | 131 | 125 | 3 | −9 | 7 | 1 | 165 | 170 | 3 | 5 | 14 | 1 | 205 | 201 | 7 |
| −1 | −5 | 1 | 239 | 222 | 3 | −3 | −1 | 1 | 472 | 484 | 5 | −10 | 3 | 1 | 82 | 83 | 3 | −8 | 7 | 1 | 228 | 229 | 3 | 6 | 14 | 1 | 44 | 49 | 11 |
| 0 | −5 | 1 | 351 | 361 | 3 | −2 | −1 | 1 | 1182 | 1217 | 12 | −9 | 3 | 1 | 44 | 49 | 5 | −7 | 7 | 1 | 95 | 102 | 3 | 7 | 14 | 1 | 36 | 31 | 8 |
| 1 | −5 | 1 | 255 | 249 | 2 | −1 | −1 | 1 | 502 | 510 | 5 | −8 | 3 | 1 | 103 | 103 | 2 | −6 | 7 | 1 | 156 | 155 | 4 | −7 | 15 | 1 | 60 | 62 | 8 |
| 2 | −5 | 1 | 243 | 236 | 2 | 0 | −1 | 1 | 244 | 253 | 2 | −7 | 3 | 1 | 98 | 107 | 2 | −5 | 7 | 1 | 176 | 176 | 4 | −6 | 15 | 1 | 74 | 61 | 8 |
| 3 | −5 | 1 | 236 | 217 | 3 | 1 | −1 | 1 | 484 | 499 | 5 | −6 | 3 | 1 | 94 | 97 | 2 | 4 | 7 | 1 | 182 | 186 | 4 | −5 | 15 | 1 | 45 | 27 | 11 |
| 4 | −5 | 1 | 147 | 158 | 3 | 2 | −1 | 1 | 69 | 73 | 2 | −5 | 3 | 1 | 556 | 520 | 10 | 5 | 7 | 1 | 71 | 68 | 4 | 5 | 15 | 1 | 98 | 100 | 8 |
| 5 | −5 | 1 | 212 | 223 | 2 | 3 | −1 | 1 | 364 | 382 | 5 | −4 | 3 | 1 | 81 | 70 | 5 | 6 | 7 | 1 | 114 | 114 | 3 | 6 | 15 | 1 | 64 | 66 | 7 |
| −6 | 16 | 1 | 132 | 142 | 7 | −2 | −12 | 2 | 231 | 224 | 2 | 8 | −8 | 2 | 164 | 165 | 3 | 8 | −4 | 2 | 84 | 92 | 3 | 3 | 0 | 2 | 386 | 386 | 6 |
| 5 | 16 | 1 | 85 | 91 | 6 | −1 | −12 | 2 | 118 | 102 | 3 | 9 | −8 | 2 | 128 | 131 | 3 | 9 | −4 | 2 | 65 | 71 | 4 | 4 | 0 | 2 | 299 | 311 | 7 |
| −2 | −19 | 2 | 28 | 28 | 4 | 0 | −12 | 2 | 243 | 233 | 4 | −11 | −7 | 2 | 76 | 68 | 3 | 10 | −4 | 2 | 45 | 41 | 5 | 5 | 0 | 2 | 69 | 58 | 2 |
| −4 | −18 | 2 | 79 | 80 | 3 | 1 | −12 | 2 | 125 | 119 | 2 | −10 | −7 | 2 | 179 | 174 | 3 | −12 | −3 | 2 | 88 | 89 | 3 | 6 | 0 | 2 | 68 | 57 | 3 |
| −3 | −18 | 2 | 118 | 126 | 3 | 2 | −12 | 2 | 91 | 93 | 1 | −9 | −7 | 2 | 62 | 58 | 3 | −11 | −3 | 2 | 154 | 150 | 3 | 7 | 0 | 2 | 237 | 252 | 2 |
| −2 | −18 | 2 | 17 | 26 | 9 | 3 | −12 | 2 | 91 | 75 | 2 | −8 | −7 | 2 | 235 | 213 | 3 | −10 | −3 | 2 | 121 | 117 | 3 | 8 | 0 | 2 | 9 | 1 | 9 |
| −1 | −18 | 2 | 92 | 97 | 2 | 4 | −12 | 2 | 35 | 37 | 3 | −7 | −7 | 2 | 48 | 47 | 2 | −9 | −3 | 2 | 114 | 120 | 3 | 9 | 0 | 2 | 219 | 207 | 3 |
| 0 | −18 | 2 | 31 | 22 | 30 | 5 | −12 | 2 | 133 | 139 | 3 | −6 | −7 | 2 | 45 | 50 | 2 | −8 | −3 | 2 | 170 | 170 | 2 | 10 | 0 | 2 | 196 | 197 | 3 |
| 1 | −18 | 2 | 106 | 98 | 8 | 6 | −12 | 2 | 102 | 102 | 2 | −5 | −7 | 2 | 258 | 262 | 1 | −7 | −3 | 2 | 387 | 389 | 3 | −12 | 1 | 2 | 60 | 54 | 4 |
| 2 | −18 | 2 | 170 | 170 | 3 | 7 | −12 | 2 | 69 | 69 | 4 | −4 | −7 | 2 | 226 | 221 | 3 | −6 | −3 | 2 | 197 | 203 | 3 | −11 | 1 | 2 | 79 | 75 | 5 |
| −6 | −17 | 2 | 69 | 86 | 3 | −10 | −11 | 2 | 55 | 34 | 12 | −3 | −7 | 2 | 316 | 301 | 4 | −5 | −3 | 2 | 347 | 340 | 5 | −10 | 1 | 2 | 164 | 179 | 4 |
| −5 | −17 | 2 | 81 | 70 | 10 | −9 | −11 | 2 | 67 | 66 | 5 | −2 | −7 | 2 | 310 | 322 | 6 | −4 | −3 | 2 | 178 | 180 | 3 | −9 | 1 | 2 | 131 | 128 | 2 |
| −4 | −17 | 2 | 125 | 130 | 3 | −8 | −11 | 2 | 109 | 107 | 4 | −1 | −7 | 2 | 336 | 337 | 4 | −3 | −3 | 2 | 311 | 313 | 3 | −8 | 1 | 2 | 57 | 61 | 3 |
| −3 | −17 | 2 | 59 | 62 | 4 | −7 | −11 | 2 | 72 | 73 | 2 | 0 | −7 | 2 | 360 | 345 | 4 | −2 | −3 | 2 | 334 | 336 | 3 | −7 | 1 | 2 | 322 | 323 | 2 |
| −2 | −17 | 2 | 56 | 59 | 3 | −6 | −11 | 2 | 122 | 132 | 2 | 1 | −7 | 2 | 415 | 418 | 4 | −1 | −3 | 2 | 90 | 95 | 1 | −6 | 1 | 2 | 93 | 81 | 6 |
| −1 | −17 | 2 | 26 | 36 | 4 | −5 | −11 | 2 | 139 | 139 | 2 | 2 | −7 | 2 | 219 | 217 | 3 | 0 | −3 | 2 | 173 | 163 | 2 | −5 | 1 | 2 | 114 | 123 | 4 |
| 0 | −17 | 2 | 79 | 85 | 2 | −4 | −11 | 2 | 130 | 133 | 1 | 3 | −7 | 2 | 144 | 144 | 1 | 1 | −3 | 2 | 24 | 24 | 3 | −4 | 1 | 2 | 84 | 99 | 3 |
| 1 | −17 | 2 | 47 | 54 | 3 | −3 | −11 | 2 | 77 | 71 | 2 | 4 | −7 | 2 | 21 | 19 | 4 | 2 | −3 | 2 | 167 | 150 | 2 | −3 | 1 | 2 | 470 | 473 | 7 |
| 2 | −17 | 2 | 0 | 34 | 1 | −2 | −11 | 2 | 147 | 144 | 2 | 5 | −7 | 2 | 260 | 267 | 2 | 3 | −3 | 2 | 243 | 240 | 4 | −2 | 1 | 2 | 719 | 745 | 10 |
| 3 | −17 | 2 | 13 | 23 | 13 | −1 | −11 | 2 | 121 | 124 | 3 | 6 | −7 | 2 | 395 | 395 | 3 | 4 | −3 | 2 | 246 | 254 | 3 | −1 | 1 | 2 | 648 | 661 | 9 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 4 | −17 | 2 | 95 | 98 | 2 | 0 | −11 | 2 | 102 | 99 | 3 | 7 | −7 | 2 | 31 | 31 | 5 | 5 | −3 | 2 | 87 | 82 | 2 | 0 | 1 | 2 | 256 | 277 | 4 |
| −7 | −16 | 2 | 31 | 50 | 9 | 1 | −11 | 2 | 90 | 77 | 1 | 8 | −7 | 2 | 133 | 136 | 2 | 6 | −3 | 2 | 180 | 175 | 2 | 1 | 1 | 2 | 240 | 243 | 4 |
| −6 | −16 | 2 | 27 | 23 | 9 | 2 | −11 | 2 | 38 | 36 | 3 | 9 | −7 | 2 | 60 | 60 | 4 | 7 | −3 | 2 | 206 | 201 | 3 | 2 | 1 | 2 | 159 | 166 | 3 |
| −5 | −16 | 2 | 33 | 18 | 5 | 3 | −11 | 2 | 285 | 281 | 3 | −11 | −6 | 2 | 66 | 67 | 3 | 8 | −3 | 2 | 143 | 150 | 3 | 3 | 1 | 2 | 314 | 326 | 5 |
| −4 | −16 | 2 | 158 | 152 | 4 | 4 | −11 | 2 | 143 | 142 | 2 | −10 | −6 | 2 | 145 | 139 | 2 | 9 | −3 | 2 | 107 | 110 | 3 | 4 | 1 | 2 | 273 | 277 | 6 |
| −3 | −16 | 2 | 110 | 101 | 3 | 5 | −11 | 2 | 97 | 95 | 2 | −9 | −6 | 2 | 86 | 86 | 2 | 10 | −3 | 2 | 25 | 37 | 9 | 5 | 1 | 2 | 58 | 62 | 2 |
| −2 | −16 | 2 | 98 | 95 | 3 | 6 | −11 | 2 | 133 | 136 | 4 | −8 | −6 | 2 | 120 | 120 | 2 | −12 | −2 | 2 | 22 | 28 | 12 | 6 | 1 | 2 | 48 | 43 | 3 |
| −1 | −16 | 2 | 77 | 83 | 2 | 7 | −11 | 2 | 46 | 44 | 4 | −7 | −6 | 2 | 115 | 109 | 2 | −11 | −2 | 2 | 22 | 39 | 21 | 7 | 1 | 2 | 152 | 155 | 2 |
| 0 | −16 | 2 | 159 | 162 | 2 | 8 | −11 | 2 | 82 | 79 | 2 | −6 | −6 | 2 | 182 | 181 | 1 | −10 | −2 | 2 | 70 | 67 | 4 | 8 | 1 | 2 | 93 | 98 | 3 |
| 1 | −16 | 2 | 116 | 117 | 2 | −10 | −10 | 2 | 50 | 31 | 4 | −5 | −6 | 2 | 159 | 164 | 2 | −9 | −2 | 2 | 24 | 23 | 13 | 9 | 1 | 2 | 93 | 94 | 4 |
| 2 | −16 | 2 | 125 | 121 | 3 | −9 | −10 | 2 | 62 | 64 | 2 | −4 | −6 | 2 | 459 | 431 | 5 | −8 | −2 | 2 | 136 | 145 | 2 | 10 | 1 | 2 | 0 | 19 | 1 |
| 3 | −16 | 2 | 129 | 130 | 3 | −8 | −10 | 2 | 110 | 113 | 2 | −3 | −6 | 2 | 92 | 89 | 2 | −7 | −2 | 2 | 72 | 74 | 2 | −12 | 2 | 2 | 19 | 27 | 18 |
| 4 | −16 | 2 | 30 | 27 | 6 | −7 | −10 | 2 | 240 | 251 | 2 | −2 | −6 | 2 | 171 | 186 | 2 | −6 | −2 | 2 | 192 | 195 | 4 | −11 | 2 | 2 | 40 | 40 | 6 |
| 5 | −16 | 2 | 98 | 101 | 3 | −6 | −10 | 2 | 137 | 136 | 1 | −1 | −6 | 2 | 373 | 359 | 4 | −5 | −2 | 2 | 46 | 57 | 4 | −10 | 2 | 2 | 72 | 67 | 3 |
| −7 | −15 | 2 | 131 | 133 | 4 | −5 | −10 | 2 | 186 | 181 | 1 | 0 | −6 | 2 | 191 | 191 | 2 | −4 | −2 | 2 | 202 | 213 | 2 | −9 | 2 | 2 | 21 | 23 | 12 |
| −6 | −15 | 2 | 69 | 71 | 4 | −4 | −10 | 2 | 69 | 57 | 2 | 1 | −6 | 2 | 436 | 422 | 5 | −3 | −2 | 2 | 127 | 119 | 2 | −8 | 2 | 2 | 132 | 146 | 2 |
| −5 | −15 | 2 | 78 | 81 | 3 | −3 | −10 | 2 | 95 | 97 | 1 | 2 | −6 | 2 | 160 | 161 | 2 | −2 | −2 | 2 | 319 | 321 | 3 | −7 | 2 | 2 | 67 | 74 | 2 |
| −4 | −15 | 2 | 135 | 133 | 2 | −2 | −10 | 2 | 119 | 116 | 2 | 3 | −6 | 2 | 171 | 161 | 2 | −1 | −2 | 2 | 636 | 630 | 6 | −6 | 2 | 2 | 195 | 196 | 6 |
| −3 | −15 | 2 | 169 | 165 | 3 | −1 | −10 | 2 | 105 | 96 | 3 | 4 | −6 | 2 | 98 | 95 | 1 | 0 | −2 | 2 | 198 | 213 | 2 | −5 | 2 | 2 | 51 | 57 | 6 |
| −2 | −15 | 2 | 236 | 232 | 4 | 0 | −10 | 2 | 294 | 300 | 3 | 5 | −6 | 2 | 67 | 68 | 2 | 1 | −2 | 2 | 119 | 122 | 2 | −4 | 2 | 2 | 206 | 213 | 4 |
| −1 | −15 | 2 | 110 | 104 | 3 | 1 | −10 | 2 | 61 | 51 | 2 | 6 | −6 | 2 | 288 | 296 | 2 | 2 | −2 | 2 | 167 | 184 | 2 | −3 | 2 | 2 | 123 | 120 | 3 |
| 0 | −15 | 2 | 65 | 74 | 3 | 2 | −10 | 2 | 95 | 97 | 1 | 7 | −6 | 2 | 80 | 81 | 3 | 3 | −2 | 2 | 108 | 93 | 3 | −2 | 2 | 2 | 324 | 322 | 6 |
| 1 | −15 | 2 | 87 | 84 | 3 | 3 | −10 | 2 | 92 | 93 | 2 | 8 | −6 | 2 | 114 | 113 | 2 | 4 | −2 | 2 | 208 | 212 | 4 | −1 | 2 | 2 | 628 | 630 | 11 |
| 2 | −15 | 2 | 147 | 146 | 2 | 4 | −10 | 2 | 156 | 152 | 1 | 9 | −6 | 2 | 92 | 100 | 3 | 5 | −2 | 2 | 271 | 259 | 2 | 0 | 2 | 2 | 203 | 214 | 4 |
| 3 | −15 | 2 | 142 | 132 | 3 | 5 | −10 | 2 | 117 | 115 | 2 | −12 | −5 | 2 | 51 | 52 | 3 | 6 | −2 | 2 | 60 | 53 | 3 | 1 | 2 | 2 | 116 | 122 | 3 |
| 4 | −15 | 2 | 55 | 42 | 4 | 6 | −10 | 2 | 129 | 137 | 2 | −11 | −5 | 2 | 74 | 71 | 3 | 7 | −2 | 2 | 120 | 117 | 3 | 2 | 2 | 2 | 167 | 183 | 3 |
| 5 | −15 | 2 | 54 | 61 | 4 | 7 | −10 | 2 | 74 | 76 | 2 | −10 | −5 | 2 | 30 | 23 | 8 | 8 | −2 | 2 | 75 | 71 | 4 | 3 | 2 | 2 | 118 | 92 | 5 |
| 6 | −15 | 2 | 93 | 91 | 8 | 8 | −10 | 2 | 62 | 65 | 4 | −9 | −5 | 2 | 51 | 56 | 4 | 9 | −2 | 2 | 80 | 83 | 4 | 4 | 2 | 2 | 208 | 211 | 6 |
| −8 | −14 | 2 | 49 | 41 | 3 | −11 | −9 | 2 | 12 | 22 | 11 | −8 | −5 | 2 | 176 | 179 | 2 | 10 | −2 | 2 | 55 | 58 | 4 | 5 | 2 | 2 | 264 | 259 | 2 |
| −7 | −14 | 2 | 106 | 108 | 3 | −10 | −9 | 2 | 37 | 32 | 4 | −7 | −5 | 2 | 264 | 255 | 2 | −12 | −1 | 2 | 62 | 54 | 5 | 6 | 2 | 2 | 61 | 53 | 2 |
| −6 | −14 | 2 | 87 | 84 | 2 | −9 | −9 | 2 | 59 | 57 | 3 | −6 | −5 | 2 | 276 | 260 | 2 | −11 | −1 | 2 | 82 | 75 | 4 | 7 | 2 | 2 | 122 | 117 | 3 |
| −5 | −14 | 2 | 77 | 80 | 3 | −8 | −9 | 2 | 61 | 61 | 3 | −5 | −5 | 2 | 235 | 210 | 3 | −10 | −1 | 2 | 160 | 179 | 4 | 8 | 2 | 2 | 74 | 71 | 3 |
| −4 | −14 | 2 | 158 | 153 | 3 | −7 | −9 | 2 | 116 | 118 | 2 | −4 | −5 | 2 | 413 | 383 | 4 | −9 | −1 | 2 | 125 | 128 | 2 | 9 | 2 | 2 | 89 | 83 | 3 |
| −3 | −14 | 2 | 197 | 190 | 3 | −6 | −9 | 2 | 83 | 81 | 2 | −3 | −5 | 2 | 20 | 27 | 3 | −8 | −1 | 2 | 55 | 61 | 3 | 10 | 2 | 2 | 66 | 58 | 4 |
| −2 | −14 | 2 | 55 | 55 | 2 | −5 | −9 | 2 | 197 | 195 | 2 | −2 | −5 | 2 | 255 | 249 | 2 | −7 | −1 | 2 | 320 | 323 | 2 | −12 | 3 | 2 | 82 | 89 | 4 |
| −1 | −14 | 2 | 173 | 179 | 2 | −4 | −9 | 2 | 395 | 391 | 3 | −1 | −5 | 2 | 302 | 283 | 3 | −6 | −1 | 2 | 91 | 80 | 4 | −11 | 3 | 2 | 149 | 150 | 2 |
| 0 | −14 | 2 | 35 | 27 | 2 | −3 | −9 | 2 | 288 | 288 | 2 | 0 | −5 | 2 | 51 | 47 | 1 | −5 | −1 | 2 | 118 | 124 | 4 | −10 | 3 | 2 | 126 | 117 | 3 |
| 1 | −14 | 2 | 92 | 89 | 3 | −2 | −9 | 2 | 116 | 112 | 2 | 1 | −5 | 2 | 344 | 349 | 3 | −4 | −1 | 2 | 82 | 101 | 3 | −9 | 3 | 2 | 120 | 121 | 3 |
| 2 | −14 | 2 | 122 | 119 | 2 | −1 | −9 | 2 | 129 | 138 | 2 | 2 | −5 | 2 | 313 | 309 | 3 | −3 | −1 | 2 | 472 | 473 | 5 | −8 | 3 | 2 | 171 | 169 | 2 |
| 3 | −14 | 2 | 17 | 7 | 17 | 0 | −9 | 2 | 193 | 175 | 3 | 3 | −5 | 2 | 108 | 101 | 3 | −2 | −1 | 2 | 724 | 745 | 8 | −7 | 3 | 2 | 392 | 388 | 3 |
| 4 | −14 | 2 | 109 | 107 | 2 | 1 | −9 | 2 | 130 | 132 | 1 | 4 | −5 | 2 | 174 | 187 | 2 | −1 | −1 | 2 | 651 | 661 | 8 | −6 | 3 | 2 | 200 | 203 | 3 |
| 5 | −14 | 2 | 32 | 20 | 4 | 2 | −9 | 2 | 67 | 55 | 1 | 5 | −5 | 2 | 62 | 50 | 2 | 0 | −1 | 2 | 258 | 277 | 3 | −5 | 3 | 2 | 354 | 339 | 7 |
| 6 | −14 | 2 | 90 | 86 | 3 | 3 | −9 | 2 | 249 | 251 | 2 | 6 | −5 | 2 | 240 | 242 | 2 | 1 | −1 | 2 | 248 | 243 | 3 | −4 | 3 | 2 | 182 | 179 | 4 |
| −9 | −13 | 2 | 76 | 69 | 9 | 4 | −9 | 2 | 229 | 228 | 2 | 7 | −5 | 2 | 76 | 79 | 3 | 2 | −1 | 2 | 161 | 165 | 3 | −3 | 3 | 2 | 311 | 312 | 6 |
| −8 | −13 | 2 | 69 | 66 | 11 | 5 | −9 | 2 | 231 | 236 | 2 | 8 | −5 | 2 | 36 | 40 | 6 | 3 | −1 | 2 | 310 | 326 | 5 | −2 | 3 | 2 | 336 | 336 | 6 |
| −7 | −13 | 2 | 85 | 87 | 4 | 6 | −9 | 2 | 145 | 148 | 2 | 9 | −5 | 2 | 107 | 108 | 2 | 4 | −1 | 2 | 268 | 277 | 5 | −1 | 3 | 2 | 91 | 95 | 3 |
| −6 | −13 | 2 | 96 | 88 | 3 | 7 | −9 | 2 | 0 | 21 | 1 | 10 | −5 | 2 | 54 | 52 | 3 | 5 | −1 | 2 | 58 | 62 | 2 | 0 | 3 | 2 | 174 | 163 | 4 |
| −5 | −13 | 2 | 9 | 9 | 8 | 8 | −9 | 2 | 12 | 12 | 11 | −12 | −4 | 2 | 158 | 156 | 4 | 6 | −1 | 2 | 46 | 43 | 3 | 1 | 3 | 2 | 20 | 24 | 10 |
| −4 | −13 | 2 | 27 | 23 | 4 | 9 | −9 | 2 | 182 | 186 | 3 | −11 | −4 | 2 | 20 | 4 | 20 | 7 | −1 | 2 | 154 | 155 | 2 | 2 | 3 | 2 | 168 | 151 | 5 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −3 | −13 | 2 | 282 | 273 | 4 | −11 | −8 | 2 | 0 | 11 | 1 | −10 | −4 | 2 | 193 | 193 | 3 | 8 | −1 | 2 | 85 | 97 | 4 | 3 | 3 | 2 | 239 | 235 | 6 |
| −2 | −13 | 2 | 197 | 189 | 2 | −10 | −8 | 2 | 50 | 52 | 4 | −9 | −4 | 2 | 39 | 41 | 5 | 9 | −1 | 2 | 94 | 95 | 3 | 4 | 3 | 2 | 242 | 254 | 4 |
| −1 | −13 | 2 | 23 | 27 | 12 | −9 | −8 | 2 | 52 | 59 | 3 | −8 | −4 | 2 | 166 | 158 | 2 | 10 | −1 | 2 | 4 | 19 | 4 | 5 | 3 | 2 | 88 | 82 | 2 |
| 0 | −13 | 2 | 153 | 151 | 2 | −8 | −8 | 2 | 36 | 45 | 4 | −7 | −4 | 2 | 164 | 158 | 2 | −12 | 0 | 2 | 88 | 88 | 4 | 6 | 3 | 2 | 174 | 175 | 2 |
| 1 | −13 | 2 | 98 | 101 | 3 | −7 | −8 | 2 | 64 | 56 | 2 | 6 | −4 | 2 | 121 | 122 | 2 | −11 | 0 | 2 | 108 | 103 | 3 | 7 | 3 | 2 | 205 | 201 | 3 |
| 2 | −13 | 2 | 75 | 75 | 2 | −6 | −8 | 2 | 114 | 111 | 1 | −5 | −4 | 2 | 157 | 153 | 3 | −10 | 0 | 2 | 22 | 19 | 19 | 8 | 3 | 2 | 149 | 151 | 3 |
| 3 | −13 | 2 | 179 | 184 | 2 | −5 | −8 | 2 | 168 | 163 | 1 | −4 | −4 | 2 | 375 | 342 | 4 | −9 | 0 | 2 | 110 | 109 | 3 | 9 | 3 | 2 | 114 | 110 | 3 |
| 4 | −13 | 2 | 117 | 122 | 3 | −4 | −8 | 2 | 193 | 185 | 2 | −3 | −4 | 2 | 527 | 511 | 5 | −8 | 0 | 2 | 187 | 180 | 2 | 10 | 3 | 2 | 52 | 37 | 5 |
| 5 | −13 | 2 | 37 | 43 | 5 | −3 | −8 | 2 | 101 | 95 | 2 | −2 | −4 | 2 | 389 | 390 | 4 | −7 | 0 | 2 | 23 | 31 | 6 | −12 | 4 | 2 | 156 | 156 | 4 |
| 6 | −13 | 2 | 44 | 44 | 6 | −2 | −8 | 2 | 112 | 107 | 2 | −1 | −4 | 2 | 146 | 151 | 1 | −6 | 0 | 2 | 62 | 69 | 7 | −11 | 4 | 2 | 0 | 4 | 1 |
| 7 | −13 | 2 | 52 | 44 | 4 | 0 | −8 | 2 | 312 | 297 | 4 | 0 | −4 | 2 | 144 | 146 | 2 | −5 | 0 | 2 | 0 | 21 | 1 | −10 | 4 | 2 | 198 | 193 | 3 |
| −9 | −12 | 2 | 65 | 64 | 3 | 1 | −8 | 2 | 255 | 254 | 4 | 1 | −4 | 2 | 176 | 167 | 2 | −4 | 0 | 2 | 542 | 542 | 7 | −9 | 4 | 2 | 35 | 42 | 6 |
| −8 | −12 | 2 | 12 | 12 | 12 | 2 | −8 | 2 | 208 | 223 | 1 | 2 | −4 | 2 | 258 | 262 | 3 | −3 | 0 | 2 | 349 | 359 | 4 | −8 | 4 | 2 | 166 | 159 | 2 |
| −7 | −12 | 2 | 37 | 36 | 4 | 3 | −8 | 2 | 113 | 107 | 1 | 3 | −4 | 2 | 100 | 91 | 3 | −2 | 0 | 2 | 122 | 112 | 2 | −7 | 4 | 2 | 169 | 158 | 2 |
| −6 | −12 | 2 | 104 | 106 | 3 | 4 | −8 | 2 | 87 | 95 | 1 | 4 | −4 | 2 | 130 | 129 | 2 | −1 | 0 | 2 | 440 | 457 | 5 | −6 | 4 | 2 | 128 | 122 | 3 |
| −5 | −12 | 2 | 156 | 166 | 3 | 5 | −8 | 2 | 176 | 171 | 2 | 5 | −4 | 2 | 164 | 173 | 2 | 0 | 0 | 2 | 149 | 163 | 2 | −5 | 4 | 2 | 165 | 153 | 7 |
| −4 | −12 | 2 | 39 | 29 | 4 | 6 | −8 | 2 | 97 | 104 | 2 | 6 | −4 | 2 | 128 | 135 | 2 | 1 | 0 | 2 | 113 | 99 | 2 | −4 | 4 | 2 | 372 | 343 | 7 |
| −3 | −12 | 2 | 251 | 241 | 3 | 7 | −8 | 2 | 188 | 188 | 3 | 7 | −4 | 2 | 137 | 131 | 2 | 2 | 0 | 2 | 223 | 242 | 3 | −3 | 4 | 2 | 518 | 510 | 9 |
| −2 | 4 | 2 | 374 | 389 | 7 | −6 | 9 | 2 | 84 | 80 | 5 | −4 | −16 | 3 | 28 | 26 | 3 | −10 | −10 | 3 | 79 | 77 | 2 | −5 | −6 | 3 | 212 | 210 | 2 |
| −1 | 4 | 2 | 139 | 150 | 3 | −5 | 9 | 2 | 192 | 194 | 4 | −3 | −16 | 3 | 132 | 135 | 2 | −9 | −10 | 3 | 74 | 71 | 2 | −4 | −6 | 3 | 206 | 201 | 2 |
| 0 | 4 | 2 | 141 | 146 | 4 | 3 | 9 | 2 | 242 | 251 | 5 | −2 | −16 | 3 | 7 | 15 | 7 | −8 | −10 | 3 | 66 | 69 | 3 | −3 | −6 | 3 | 471 | 452 | 4 |
| 1 | 4 | 2 | 170 | 167 | 4 | 4 | 9 | 2 | 230 | 228 | 5 | −1 | −16 | 3 | 115 | 110 | 3 | −7 | −10 | 3 | 103 | 94 | 2 | −2 | −6 | 3 | 210 | 191 | 2 |
| 2 | 4 | 2 | 253 | 261 | 6 | 5 | 9 | 2 | 235 | 236 | 4 | 0 | −16 | 3 | 57 | 61 | 3 | −6 | −10 | 3 | 103 | 105 | 1 | −1 | −6 | 3 | 286 | 279 | 3 |
| 3 | 4 | 2 | 101 | 91 | 6 | 6 | 9 | 2 | 137 | 147 | 4 | 1 | −16 | 3 | 163 | 158 | 3 | −5 | −10 | 3 | 112 | 108 | 1 | 0 | −6 | 3 | 496 | 472 | 5 |
| 4 | 4 | 2 | 127 | 130 | 3 | 7 | 9 | 2 | 30 | 20 | 7 | 2 | −16 | 3 | 122 | 229 | 3 | −4 | −10 | 3 | 56 | 55 | 1 | 1 | −6 | 3 | 368 | 354 | 4 |
| 5 | 4 | 2 | 163 | 173 | 2 | 8 | 9 | 2 | 22 | 13 | 11 | 3 | −16 | 3 | 29 | 33 | 5 | 3 | 10 | 3 | 195 | 190 | 1 | 2 | −6 | 3 | 211 | 208 | 2 |
| 6 | 4 | 2 | 131 | 135 | 2 | 9 | 9 | 2 | 189 | 186 | 3 | 4 | −16 | 3 | 53 | 51 | 3 | −2 | −10 | 3 | 328 | 324 | 3 | 3 | −6 | 3 | 66 | 67 | 2 |
| 7 | 4 | 2 | 131 | 130 | 2 | −10 | 10 | 2 | 34 | 30 | 8 | −7 | −15 | 3 | 172 | 168 | 4 | −1 | −10 | 3 | 218 | 213 | 2 | 4 | −6 | 3 | 388 | 397 | 3 |
| 8 | 4 | 2 | 93 | 92 | 3 | −9 | 10 | 2 | 64 | 63 | 4 | −6 | −15 | 3 | 39 | 30 | 5 | 0 | −10 | 3 | 164 | 171 | 2 | 5 | −6 | 3 | 90 | 87 | 2 |
| 9 | 4 | 2 | 70 | 71 | 3 | −8 | 10 | 2 | 104 | 113 | 4 | −5 | −15 | 3 | 71 | 73 | 3 | 1 | −10 | 3 | 63 | 63 | 1 | 6 | −6 | 3 | 45 | 48 | 4 |
| 10 | 4 | 2 | 49 | 41 | 6 | −7 | 10 | 2 | 240 | 251 | 5 | −4 | −15 | 3 | 0 | 8 | 1 | 2 | −10 | 3 | 129 | 125 | 2 | 7 | −6 | 3 | 226 | 229 | 3 |
| −12 | 5 | 2 | 62 | 52 | 7 | −6 | 10 | 2 | 137 | 135 | 5 | −3 | −15 | 3 | 107 | 111 | 2 | 3 | −10 | 3 | 105 | 106 | 1 | 8 | −6 | 3 | 108 | 104 | 2 |
| −11 | 5 | 2 | 70 | 71 | 3 | −5 | 10 | 2 | 184 | 181 | 6 | −2 | −15 | 3 | 204 | 194 | 3 | 4 | −10 | 3 | 99 | 95 | 2 | 9 | −6 | 3 | 107 | 112 | 2 |
| −10 | 5 | 2 | 30 | 23 | 8 | 3 | 10 | 2 | 89 | 92 | 5 | −1 | −15 | 3 | 96 | 92 | 3 | 5 | −10 | 3 | 202 | 207 | 2 | −12 | −5 | 3 | 19 | 30 | 18 |
| −9 | 5 | 2 | 55 | 56 | 3 | 4 | 10 | 2 | 151 | 150 | 5 | 0 | −15 | 3 | 146 | 156 | 3 | 6 | −10 | 3 | 193 | 189 | 2 | −11 | −5 | 3 | 107 | 101 | 3 |
| −8 | 5 | 2 | 176 | 178 | 2 | 5 | 10 | 2 | 119 | 115 | 5 | 1 | −15 | 3 | 152 | 157 | 3 | 7 | −10 | 3 | 42 | 41 | 4 | −10 | −5 | 3 | 58 | 59 | 4 |
| −7 | 5 | 2 | 266 | 255 | 3 | 6 | 10 | 2 | 126 | 137 | 4 | 2 | −15 | 3 | 64 | 60 | 3 | 8 | −10 | 3 | 52 | 49 | 4 | −9 | −5 | 3 | 249 | 249 | 3 |
| −6 | 5 | 2 | 276 | 260 | 4 | 7 | 10 | 2 | 85 | 77 | 3 | 3 | −15 | 3 | 112 | 109 | 3 | −11 | −9 | 3 | 37 | 36 | 2 | −8 | −5 | 3 | 113 | 112 | 2 |
| −5 | 5 | 2 | 235 | 211 | 8 | 8 | 10 | 2 | 63 | 64 | 3 | 4 | −15 | 3 | 44 | 34 | 4 | −10 | −9 | 3 | 50 | 46 | 4 | −7 | −5 | 3 | 81 | 81 | 2 |
| −4 | 5 | 2 | 414 | 383 | 11 | −10 | 11 | 2 | 13 | 34 | 12 | 5 | −15 | 3 | 88 | 84 | 8 | −9 | −9 | 3 | 81 | 85 | 3 | −6 | −5 | 3 | 273 | 283 | 2 |
| −3 | 5 | 2 | 0 | 26 | 1 | −9 | 11 | 2 | 69 | 67 | 3 | −8 | −14 | 3 | 67 | 78 | 3 | −8 | −9 | 3 | 70 | 71 | 3 | −5 | −5 | 3 | 224 | 214 | 3 |
| −2 | 5 | 2 | 249 | 248 | 5 | −8 | 11 | 2 | 105 | 108 | 4 | −7 | −14 | 3 | 103 | 103 | 2 | −7 | −9 | 3 | 259 | 261 | 2 | −4 | −5 | 3 | 174 | 187 | 2 |
| −1 | 5 | 2 | 290 | 283 | 6 | −7 | 11 | 2 | 74 | 74 | 6 | −6 | −14 | 3 | 19 | 29 | 12 | −6 | −9 | 3 | 238 | 228 | 2 | −3 | −5 | 3 | 269 | 253 | 3 |
| 0 | 5 | 2 | 52 | 46 | 4 | −6 | 11 | 2 | 127 | 133 | 5 | −5 | −14 | 3 | 92 | 93 | 3 | −5 | −9 | 3 | 208 | 207 | 2 | −2 | −5 | 3 | 343 | 334 | 4 |
| 1 | 5 | 2 | 343 | 348 | 6 | −5 | 11 | 2 | 139 | 139 | 6 | −4 | −14 | 3 | 125 | 122 | 2 | −4 | −9 | 3 | 151 | 148 | 1 | −1 | −5 | 3 | 243 | 244 | 2 |
| 2 | 5 | 2 | 300 | 310 | 9 | 3 | 11 | 2 | 267 | 281 | 8 | −3 | −14 | 3 | 166 | 165 | 2 | −3 | −9 | 3 | 231 | 235 | 1 | 0 | −5 | 3 | 333 | 325 | 3 |
| 3 | 5 | 2 | 102 | 100 | 8 | 4 | 11 | 2 | 145 | 143 | 5 | −2 | −14 | 3 | 113 | 112 | 2 | −2 | −9 | 3 | 142 | 141 | 1 | 1 | −5 | 3 | 228 | 222 | 3 |
| 4 | 5 | 2 | 172 | 187 | 3 | 5 | 11 | 2 | 104 | 95 | 5 | −1 | −14 | 3 | 135 | 144 | 3 | −1 | −9 | 3 | 152 | 152 | 2 | 2 | −5 | 3 | 53 | 40 | 3 |
| 5 | 5 | 2 | 61 | 50 | 3 | 6 | 11 | 2 | 137 | 135 | 3 | 0 | −14 | 3 | 79 | 86 | 3 | 0 | −9 | 3 | 143 | 152 | 1 | 3 | −5 | 3 | 162 | 160 | 2 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 6 | 5 | 2 | 243 | 243 | 2 | 7 | 11 | 2 | 42 | 44 | 5 | 1 | −14 | 3 | 206 | 209 | 4 | 1 | −9 | 3 | 192 | 191 | 1 | 4 | −5 | 3 | 131 | 128 | 2 |
| 7 | 5 | 2 | 72 | 79 | 3 | 8 | 11 | 2 | 82 | 79 | 3 | 2 | −14 | 3 | 75 | 70 | 3 | 2 | −9 | 3 | 115 | 113 | 1 | 5 | −5 | 3 | 359 | 378 | 3 |
| 8 | 5 | 2 | 40 | 40 | 5 | −9 | 12 | 2 | 58 | 64 | 4 | 3 | −14 | 3 | 60 | 66 | 4 | 3 | −9 | 3 | 33 | 38 | 2 | 6 | −5 | 3 | 261 | 263 | 3 |
| 9 | 5 | 2 | 105 | 107 | 3 | −8 | 12 | 2 | 0 | 12 | 1 | 4 | −14 | 3 | 32 | 33 | 3 | 4 | −9 | 3 | 140 | 146 | 1 | 7 | −5 | 3 | 75 | 79 | 3 |
| 10 | 5 | 2 | 55 | 52 | 5 | −7 | 12 | 2 | 48 | 36 | 8 | 5 | −14 | 3 | 12 | 7 | 11 | 5 | −9 | 3 | 123 | 127 | 2 | 8 | −5 | 3 | 112 | 119 | 3 |
| −11 | 6 | 2 | 62 | 67 | 3 | −6 | 12 | 2 | 104 | 106 | 7 | −8 | −13 | 3 | 65 | 72 | 11 | 6 | −9 | 3 | 76 | 78 | 3 | 9 | −5 | 3 | 84 | 83 | 3 |
| −10 | 6 | 2 | 144 | 138 | 3 | −5 | 12 | 2 | 156 | 166 | 6 | −7 | −13 | 3 | 79 | 76 | 4 | 7 | −9 | 3 | 43 | 41 | 4 | −12 | −4 | 3 | 81 | 81 | 3 |
| −9 | 6 | 2 | 82 | 86 | 3 | 3 | 12 | 2 | 92 | 75 | 7 | −6 | −13 | 3 | 65 | 66 | 3 | 8 | −9 | 3 | 104 | 104 | 2 | −11 | −4 | 3 | 139 | 141 | 3 |
| −8 | 6 | 2 | 125 | 121 | 3 | 4 | 12 | 2 | 43 | 36 | 12 | −5 | −13 | 3 | 112 | 111 | 2 | −11 | −8 | 3 | 38 | 34 | 5 | −10 | −4 | 3 | 113 | 112 | 3 |
| −7 | 6 | 2 | 114 | 108 | 3 | 5 | 12 | 2 | 142 | 138 | 5 | −4 | −13 | 3 | 137 | 129 | 1 | −10 | −8 | 3 | 135 | 132 | 3 | −9 | −4 | 3 | 163 | 155 | 2 |
| −6 | 6 | 2 | 183 | 181 | 3 | 6 | 12 | 2 | 94 | 102 | 4 | −3 | −13 | 3 | 77 | 74 | 3 | −9 | −8 | 3 | 133 | 125 | 3 | −8 | −4 | 3 | 239 | 235 | 2 |
| −5 | 6 | 2 | 156 | 165 | 8 | 7 | 12 | 2 | 69 | 69 | 3 | −2 | −13 | 3 | 370 | 363 | 4 | −8 | −8 | 3 | 133 | 134 | 2 | −7 | −4 | 3 | 179 | 187 | 2 |
| −4 | 6 | 2 | 462 | 433 | 12 | −9 | 13 | 2 | 65 | 69 | 4 | −1 | −13 | 3 | 229 | 225 | 3 | −7 | −8 | 3 | 96 | 91 | 2 | −6 | −4 | 3 | 149 | 140 | 2 |
| −3 | 6 | 2 | 94 | 88 | 6 | −8 | 13 | 2 | 56 | 66 | 7 | 0 | −13 | 3 | 86 | 89 | 2 | −6 | −8 | 3 | 110 | 108 | 1 | −5 | −4 | 3 | 352 | 327 | 5 |
| −2 | 6 | 2 | 170 | 185 | 6 | −7 | 13 | 2 | 85 | 87 | 7 | 1 | −13 | 3 | 160 | 170 | 3 | −5 | −8 | 3 | 21 | 23 | 2 | −4 | −4 | 3 | 150 | 145 | 2 |
| 2 | 6 | 2 | 156 | 160 | 7 | −6 | 13 | 2 | 90 | 88 | 7 | 2 | −13 | 3 | 93 | 100 | 2 | −4 | −8 | 3 | 189 | 177 | 1 | −3 | −4 | 3 | 304 | 299 | 3 |
| 3 | 6 | 2 | 166 | 161 | 8 | −5 | 13 | 2 | 22 | 9 | 21 | 3 | −13 | 3 | 92 | 94 | 2 | −3 | −8 | 3 | 84 | 93 | 1 | −2 | −4 | 3 | 452 | 425 | 4 |
| 4 | 6 | 2 | 105 | 95 | 3 | 4 | 13 | 2 | 114 | 122 | 7 | 4 | −13 | 3 | 78 | 67 | 3 | −2 | −8 | 3 | 287 | 286 | 3 | −1 | −4 | 3 | 153 | 156 | 2 |
| 5 | 6 | 2 | 72 | 68 | 3 | 5 | 13 | 2 | 54 | 44 | 10 | 5 | −13 | 3 | 69 | 66 | 4 | −1 | −8 | 3 | 99 | 92 | 1 | 0 | −4 | 3 | 494 | 492 | 5 |
| 6 | 6 | 2 | 294 | 297 | 3 | 6 | 13 | 2 | 33 | 44 | 12 | 6 | −13 | 3 | 45 | 40 | 4 | 0 | −8 | 3 | 83 | 83 | 1 | 1 | −4 | 3 | 217 | 213 | 3 |
| 7 | 6 | 2 | 82 | 81 | 3 | 7 | 13 | 2 | 48 | 43 | 4 | −9 | −12 | 3 | 17 | 7 | 16 | 1 | −8 | 3 | 92 | 86 | 1 | 2 | −4 | 3 | 188 | 192 | 3 |
| 8 | 6 | 2 | 121 | 114 | 2 | −8 | 14 | 2 | 47 | 41 | 9 | −8 | −12 | 3 | 42 | 37 | 5 | 2 | −8 | 3 | 34 | 28 | 2 | 3 | −4 | 3 | 273 | 289 | 3 |
| 9 | 6 | 2 | 106 | 100 | 2 | −7 | 14 | 2 | 97 | 108 | 7 | −7 | −12 | 3 | 69 | 75 | 3 | 3 | −8 | 3 | 31 | 33 | 2 | 4 | −4 | 3 | 152 | 166 | 2 |
| −11 | 7 | 2 | 73 | 68 | 3 | −6 | 14 | 2 | 83 | 84 | 7 | −6 | −12 | 3 | 154 | 157 | 2 | 4 | −8 | 3 | 260 | 262 | 2 | 5 | −4 | 3 | 493 | 510 | 4 |
| −10 | 7 | 2 | 180 | 174 | 3 | −5 | 14 | 2 | 69 | 80 | 8 | −5 | −12 | 3 | 125 | 114 | 3 | 5 | −8 | 3 | 112 | 111 | 2 | 6 | −4 | 3 | 110 | 107 | 2 |
| −9 | 7 | 2 | 56 | 58 | 4 | 4 | 14 | 2 | 106 | 107 | 7 | −4 | −12 | 3 | 152 | 151 | 2 | 6 | −8 | 3 | 294 | 291 | 3 | 7 | −4 | 3 | 175 | 173 | 3 |
| −8 | 7 | 2 | 227 | 213 | 3 | 5 | 14 | 2 | 31 | 20 | 10 | −3 | −12 | 3 | 132 | 128 | 2 | 7 | −8 | 3 | 45 | 41 | 3 | 8 | −4 | 3 | 135 | 130 | 3 |
| −7 | 7 | 2 | 44 | 47 | 5 | 6 | 14 | 2 | 85 | 87 | 6 | −2 | −12 | 3 | 267 | 256 | 3 | 8 | −8 | 3 | 145 | 143 | 3 | 9 | −4 | 3 | 91 | 95 | 3 |
| −6 | 7 | 2 | 48 | 50 | 6 | −8 | −15 | 2 | 80 | 76 | 6 | −1 | −12 | 3 | 218 | 216 | 2 | −11 | −7 | 3 | 40 | 45 | 3 | −12 | −3 | 3 | 57 | 58 | 4 |
| −5 | 7 | 2 | 246 | 261 | 5 | −7 | 15 | 2 | 144 | 133 | 6 | 0 | −12 | 3 | 127 | 119 | 2 | −10 | −7 | 3 | 174 | 180 | 3 | −11 | −3 | 3 | 126 | 125 | 3 |
| 3 | 7 | 2 | 137 | 143 | 4 | −6 | 15 | 2 | 76 | 71 | 7 | 1 | −12 | 3 | 125 | 126 | 1 | −9 | −7 | 3 | 169 | 169 | 2 | −10 | −3 | 3 | 73 | 78 | 3 |
| 4 | 7 | 2 | 32 | 18 | 7 | 4 | 15 | 2 | 61 | 42 | 5 | 2 | −12 | 3 | 116 | 112 | 3 | −8 | −7 | 3 | 106 | 100 | 2 | −9 | −3 | 3 | 374 | 375 | 4 |
| 5 | 7 | 2 | 258 | 267 | 3 | 5 | 15 | 2 | 64 | 62 | 7 | 3 | −12 | 3 | 77 | 77 | 3 | −7 | −7 | 3 | 62 | 57 | 2 | −8 | −3 | 3 | 98 | 98 | 2 |
| 6 | 7 | 2 | 395 | 396 | 4 | 6 | 15 | 2 | 88 | 90 | 6 | 4 | −12 | 3 | 15 | 12 | 11 | −6 | −7 | 3 | 85 | 83 | 1 | −7 | −3 | 3 | 160 | 167 | 2 |
| 7 | 7 | 2 | 24 | 32 | 9 | −7 | 16 | 2 | 37 | 50 | 12 | 5 | −12 | 3 | 56 | 62 | 3 | −5 | −7 | 3 | 225 | 224 | 1 | −6 | −3 | 3 | 192 | 207 | 3 |
| 8 | 7 | 2 | 137 | 136 | 3 | −6 | 16 | 2 | 35 | 23 | 14 | 6 | −12 | 3 | 53 | 50 | 2 | −4 | −7 | 3 | 162 | 147 | 1 | −5 | −3 | 3 | 214 | 212 | 3 |
| 9 | 7 | 2 | 63 | 60 | 3 | 4 | 16 | 2 | 46 | 28 | 9 | 7 | −12 | 3 | 132 | 129 | 3 | −3 | −7 | 3 | 215 | 213 | 2 | −4 | −3 | 3 | 195 | 186 | 2 |
| −11 | 8 | 2 | 13 | 11 | 13 | 5 | 16 | 2 | 90 | 101 | 6 | −10 | −11 | 3 | 101 | 93 | 4 | −2 | −7 | 3 | 242 | 239 | 3 | −3 | −3 | 3 | 424 | 421 | 4 |
| −10 | 8 | 2 | 41 | 52 | 6 | −3 | −18 | 3 | 72 | 82 | 3 | −9 | −11 | 3 | 119 | 118 | 3 | −1 | −7 | 3 | 140 | 148 | 2 | −2 | −3 | 3 | 203 | 197 | 2 |
| −9 | 8 | 2 | 60 | 59 | 4 | −2 | −18 | 3 | 90 | 91 | 3 | −8 | −11 | 3 | 105 | 108 | 4 | 0 | −7 | 3 | 231 | 224 | 2 | −1 | −3 | 3 | 497 | 495 | 5 |
| −8 | 8 | 2 | 28 | 45 | 9 | −1 | 18 | 3 | 60 | 63 | 2 | −7 | −11 | 3 | 119 | 110 | 3 | 1 | −7 | 3 | 235 | 230 | 2 | 0 | −3 | 3 | 255 | 255 | 3 |
| −7 | 8 | 2 | 67 | 56 | 5 | 0 | −18 | 3 | 80 | 76 | 3 | −6 | −11 | 3 | 206 | 190 | 3 | 2 | −7 | 3 | 118 | 117 | 1 | 1 | −3 | 3 | 412 | 401 | 5 |
| −6 | 8 | 2 | 109 | 112 | 4 | 1 | −18 | 3 | 57 | 59 | 2 | −5 | −11 | 3 | 277 | 264 | 3 | 3 | −7 | 3 | 138 | 139 | 1 | 2 | −3 | 3 | 114 | 107 | 3 |
| −5 | 8 | 2 | 161 | 163 | 4 | −6 | −17 | 3 | 60 | 63 | 3 | −4 | −11 | 3 | 324 | 320 | 3 | 4 | −7 | 3 | 342 | 342 | 3 | 3 | −3 | 3 | 44 | 46 | 6 |
| 3 | 8 | 2 | 111 | 108 | 4 | −5 | −17 | 3 | 20 | 30 | 7 | −3 | −11 | 3 | 163 | 153 | 2 | 5 | −7 | 3 | 124 | 133 | 2 | 4 | −3 | 3 | 156 | 149 | 2 |
| 4 | 8 | 2 | 92 | 96 | 5 | −4 | −17 | 3 | 75 | 72 | 2 | −2 | −11 | 3 | 76 | 74 | 2 | 6 | −7 | 3 | 142 | 141 | 2 | 5 | −3 | 3 | 233 | 237 | 3 |
| 5 | 8 | 2 | 177 | 171 | 4 | −3 | −17 | 3 | 107 | 110 | 2 | −1 | −11 | 3 | 149 | 153 | 2 | 7 | −7 | 3 | 119 | 122 | 3 | 6 | −3 | 3 | 106 | 102 | 3 |
| 6 | 8 | 2 | 97 | 103 | 3 | −2 | −17 | 3 | 78 | 87 | 2 | 0 | −11 | 3 | 112 | 111 | 1 | 8 | −7 | 3 | 147 | 147 | 2 | 7 | −3 | 3 | 102 | 105 | 3 |
| 7 | 8 | 2 | 191 | 188 | 3 | −1 | −17 | 3 | 74 | 70 | 2 | 1 | −11 | 3 | 235 | 234 | 2 | 9 | −7 | 3 | 39 | 59 | 17 | 8 | −3 | 3 | 48 | 47 | 5 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 8 | 8 | 2 | 168 | 164 | 2 | 0 | −17 | 3 | 0 | 13 | 1 | 2 | −11 | 3 | 77 | 76 | 1 | −12 | −6 | 3 | 68 | 75 | 4 | 9 | −3 | 3 | 43 | 46 | 5 |
| 9 | 8 | 2 | 134 | 132 | 2 | 1 | −17 | 3 | 138 | 137 | 2 | 3 | −11 | 3 | 76 | 63 | 2 | −11 | −6 | 3 | 62 | 65 | 3 | −12 | −2 | 3 | 131 | 123 | 4 |
| −11 | 9 | 2 | 23 | 22 | 13 | 2 | −17 | 3 | 54 | 55 | 3 | 4 | −11 | 3 | 213 | 215 | 2 | −10 | −6 | 3 | 66 | 64 | 3 | −12 | −2 | 3 | 150 | 155 | 3 |
| −10 | 9 | 2 | 40 | 32 | 6 | 3 | −17 | 3 | 14 | 15 | 14 | 5 | −11 | 3 | 47 | 48 | 4 | −9 | −6 | 3 | 120 | 125 | 2 | −10 | −2 | 3 | 131 | 132 | 3 |
| −9 | 9 | 2 | 53 | 57 | 4 | −7 | −16 | 3 | 0 | 2 | 1 | 6 | −11 | 3 | 39 | 37 | 4 | −8 | −6 | 3 | 167 | 167 | 2 | −9 | −2 | 3 | 224 | 225 | 3 |
| −8 | 9 | 2 | 44 | 60 | 5 | −6 | −16 | 3 | 126 | 131 | 3 | 7 | −11 | 3 | 39 | 36 | 4 | −7 | −6 | 3 | 80 | 72 | 2 | −8 | −2 | 3 | 123 | 127 | 2 |
| −7 | 9 | 2 | 113 | 119 | 4 | −5 | −16 | 3 | 67 | 68 | 3 | −11 | −10 | 3 | 41 | 43 | 6 | −6 | −6 | 3 | 174 | 174 | 1 | −7 | −2 | 3 | 141 | 143 | 2 |
| −6 | −2 | 3 | 211 | 219 | 4 | −7 | 2 | 3 | 142 | 143 | 2 | −8 | 6 | 3 | 163 | 167 | 3 | −5 | 12 | 3 | 124 | 114 | 7 | −1 | −13 | 4 | 68 | 67 | 3 |
| −5 | −2 | 3 | 277 | 280 | 5 | −6 | 2 | 3 | 218 | 219 | 6 | −7 | 6 | 3 | 74 | 72 | 3 | 3 | 12 | 3 | 86 | 77 | 8 | 0 | −13 | 4 | 155 | 162 | 3 |
| −4 | −2 | 3 | 80 | 90 | 3 | −5 | 2 | 3 | 287 | 280 | 6 | −6 | 6 | 3 | 177 | 175 | 3 | 4 | 12 | 3 | 0 | 11 | 1 | 1 | −13 | 4 | 18 | 19 | 6 |
| −3 | −2 | 3 | 331 | 331 | 4 | −4 | 2 | 3 | 79 | 90 | 3 | −5 | 6 | 3 | 210 | 210 | 8 | 5 | 12 | 3 | 57 | 62 | 7 | 2 | −13 | 4 | 48 | 53 | 2 |
| −2 | −2 | 3 | 144 | 141 | 2 | −3 | 2 | 3 | 329 | 330 | 5 | −4 | 6 | 3 | 205 | 200 | 7 | 6 | 12 | 3 | 47 | 49 | 5 | 3 | −13 | 4 | 59 | 62 | 3 |
| −1 | −2 | 3 | 220 | 207 | 2 | −2 | 2 | 3 | 143 | 140 | 4 | −3 | 6 | 3 | 469 | 452 | 12 | 7 | 12 | 3 | 128 | 129 | 2 | 4 | −13 | 4 | 65 | 62 | 4 |
| 0 | −2 | 3 | 247 | 263 | 3 | −1 | 2 | 3 | 218 | 206 | 5 | 3 | 6 | 3 | 68 | 67 | 4 | −9 | 13 | 3 | 74 | 73 | 4 | 5 | −13 | 4 | 95 | 94 | 3 |
| 1 | −2 | 3 | 170 | 182 | 3 | 0 | 2 | 3 | 242 | 262 | 4 | 4 | 6 | 3 | 385 | 397 | 4 | −8 | 13 | 3 | 62 | 72 | 7 | −9 | −12 | 4 | 69 | 71 | 3 |
| 2 | −2 | 3 | 447 | 457 | 7 | 1 | 2 | 3 | 175 | 182 | 3 | 5 | 6 | 3 | 90 | 87 | 3 | −7 | 13 | 3 | 81 | 76 | 7 | −8 | −12 | 4 | 10 | 13 | 9 |
| 3 | −2 | 3 | 71 | 82 | 5 | 2 | 2 | 3 | 463 | 456 | 8 | 6 | 6 | 3 | 43 | 47 | 5 | −6 | 13 | 3 | 73 | 66 | 8 | −7 | −12 | 4 | 90 | 96 | 3 |
| 4 | −2 | 3 | 23 | 15 | 5 | 3 | 2 | 3 | 79 | 83 | 7 | 7 | 6 | 3 | 222 | 229 | 3 | −5 | 13 | 3 | 113 | 112 | 7 | −6 | −12 | 4 | 101 | 99 | 2 |
| 5 | −2 | 3 | 88 | 91 | 2 | 4 | 2 | 3 | 23 | 15 | 5 | 8 | 6 | 3 | 106 | 103 | 3 | 3 | 13 | 3 | 91 | 94 | 5 | −5 | −12 | 4 | 25 | 25 | 6 |
| 6 | −2 | 3 | 196 | 191 | 3 | 5 | 2 | 3 | 88 | 90 | 2 | 9 | 6 | 3 | 116 | 112 | 3 | 4 | 13 | 3 | 69 | 67 | 7 | −4 | −12 | 4 | 293 | 293 | 3 |
| 7 | −2 | 3 | 118 | 119 | 3 | 6 | 2 | 3 | 195 | 191 | 3 | −11 | 7 | 3 | 40 | 45 | 6 | 5 | 13 | 3 | 57 | 65 | 9 | −3 | −12 | 4 | 41 | 45 | 2 |
| 8 | −2 | 3 | 0 | 4 | 1 | 7 | 2 | 3 | 113 | 120 | 3 | −10 | 7 | 3 | 179 | 180 | 2 | 6 | 13 | 3 | 42 | 40 | 6 | −2 | −12 | 4 | 96 | 94 | 2 |
| 9 | −2 | 3 | 42 | 35 | 7 | 8 | 2 | 3 | 0 | 4 | 1 | −9 | 7 | 3 | 164 | 169 | 3 | −9 | 14 | 3 | 0 | 25 | 1 | −1 | −12 | 4 | 80 | 88 | 3 |
| −12 | −1 | 3 | 141 | 136 | 4 | 9 | 2 | 3 | 39 | 35 | 7 | −8 | 7 | 3 | 102 | 100 | 3 | −8 | 14 | 3 | 74 | 78 | 7 | 0 | −12 | 4 | 118 | 120 | 2 |
| −11 | −1 | 3 | 90 | 92 | 4 | −12 | 3 | 3 | 63 | 59 | 5 | −7 | 7 | 3 | 57 | 57 | 4 | −7 | 14 | 3 | 103 | 103 | 7 | 1 | −12 | 4 | 91 | 89 | 2 |
| −10 | −1 | 3 | 121 | 128 | 3 | −11 | 3 | 3 | 128 | 125 | 3 | −6 | 7 | 3 | 87 | 82 | 4 | −6 | 14 | 3 | 29 | 29 | 24 | 2 | −12 | 4 | 147 | 142 | 2 |
| −9 | −1 | 3 | 281 | 276 | 3 | −10 | 3 | 3 | 73 | 78 | 3 | −5 | 7 | 3 | 216 | 225 | 4 | 3 | 14 | 3 | 60 | 66 | 7 | 3 | −12 | 4 | 49 | 42 | 2 |
| −8 | −1 | 3 | 152 | 158 | 2 | −9 | 3 | 3 | 373 | 375 | 3 | 2 | 7 | 3 | 121 | 116 | 5 | 4 | 14 | 3 | 37 | 33 | 11 | 4 | −12 | 4 | 123 | 120 | 2 |
| −7 | −1 | 3 | 109 | 106 | 2 | −8 | 3 | 3 | 103 | 98 | 2 | 3 | 7 | 3 | 135 | 140 | 3 | 5 | 14 | 3 | 0 | 7 | 1 | 5 | −12 | 4 | 30 | 18 | 9 |
| −6 | −1 | 3 | 269 | 265 | 5 | −7 | 3 | 3 | 164 | 168 | 2 | 4 | 7 | 3 | 337 | 342 | 4 | 6 | 14 | 3 | 0 | 20 | 1 | 6 | −12 | 4 | 60 | 56 | 4 |
| −5 | −1 | 3 | 190 | 181 | 4 | −6 | 3 | 3 | 195 | 207 | 4 | 5 | 7 | 3 | 129 | 134 | 2 | −8 | 15 | 3 | 22 | 21 | 22 | −10 | −11 | 4 | 103 | 99 | 4 |
| −4 | −1 | 3 | 154 | 146 | 3 | −5 | 3 | 3 | 214 | 212 | 5 | 6 | 7 | 3 | 144 | 141 | 3 | −7 | 15 | 3 | 179 | 168 | 6 | −9 | −11 | 4 | 99 | 102 | 5 |
| −3 | −1 | 3 | 459 | 452 | 5 | −4 | 3 | 3 | 204 | 187 | 5 | 7 | 7 | 3 | 120 | 122 | 2 | −6 | 15 | 3 | 36 | 30 | 14 | −8 | −11 | 4 | 28 | 37 | 12 |
| −2 | −1 | 3 | 326 | 323 | 4 | −3 | 3 | 3 | 442 | 421 | 8 | 8 | 7 | 3 | 150 | 147 | 3 | 3 | 15 | 3 | 107 | 109 | 7 | −7 | −11 | 4 | 211 | 209 | 3 |
| −1 | −1 | 3 | 275 | 275 | 3 | −2 | 3 | 3 | 206 | 197 | 4 | 9 | 7 | 3 | 59 | 59 | 6 | 4 | 15 | 3 | 40 | 34 | 10 | −6 | −11 | 4 | 192 | 188 | 3 |
| 0 | −1 | 3 | 384 | 400 | 5 | −1 | 3 | 3 | 502 | 495 | 9 | −11 | 8 | 3 | 35 | 34 | 7 | 5 | 15 | 3 | 73 | 84 | 7 | −5 | −11 | 4 | 113 | 111 | 2 |
| 1 | −1 | 3 | 190 | 185 | 3 | 0 | 3 | 3 | 255 | 254 | 5 | −10 | 8 | 3 | 146 | 132 | 3 | −7 | 16 | 3 | 0 | 2 | 3 | −4 | −11 | 4 | 190 | 183 | 2 |
| 2 | −1 | 3 | 338 | 331 | 5 | 1 | 3 | 3 | 422 | 401 | 8 | −9 | 8 | 3 | 128 | 125 | 3 | −6 | 16 | 3 | 136 | 132 | 6 | −3 | −11 | 4 | 122 | 118 | 2 |
| 3 | −1 | 3 | 271 | 280 | 5 | 2 | 3 | 3 | 122 | 107 | 4 | −8 | 8 | 3 | 135 | 134 | 3 | 4 | 16 | 3 | 48 | 51 | 9 | −2 | −11 | 4 | 150 | 144 | 2 |
| 4 | −1 | 3 | 136 | 135 | 2 | 3 | 3 | 3 | 40 | 46 | 10 | −7 | 8 | 3 | 99 | 91 | 4 | −4 | −19 | 4 | 43 | 50 | 3 | −1 | −11 | 4 | 95 | 94 | 2 |
| 5 | −1 | 3 | 66 | 67 | 2 | 4 | 3 | 3 | 155 | 149 | 2 | −6 | 8 | 3 | 110 | 108 | 4 | −3 | −18 | 4 | 53 | 52 | 2 | 0 | −11 | 4 | 124 | 121 | 2 |
| 6 | −1 | 3 | 175 | 175 | 2 | 5 | 3 | 3 | 232 | 237 | 2 | −5 | 8 | 3 | 24 | 23 | 12 | −2 | −18 | 4 | 52 | 53 | 2 | 1 | −11 | 4 | 27 | 24 | 3 |
| 7 | −1 | 3 | 109 | 113 | 4 | 6 | 3 | 3 | 102 | 101 | 2 | 2 | 8 | 3 | 44 | 2 | 6 | −1 | −18 | 4 | 119 | 122 | 3 | 2 | −11 | 4 | 181 | 186 | 3 |
| 8 | −1 | 3 | 90 | 83 | 3 | 7 | 3 | 3 | 102 | 106 | 3 | 3 | 8 | 3 | 23 | 32 | 14 | 0 | −18 | 4 | 40 | 48 | 3 | 3 | −11 | 4 | 171 | 182 | 3 |
| 9 | −1 | 3 | 12 | 5 | 12 | 8 | 3 | 3 | 49 | 47 | 4 | 4 | 8 | 3 | 253 | 262 | 4 | −6 | −17 | 4 | 88 | 84 | 3 | 4 | −11 | 4 | 68 | 75 | 3 |
| −12 | 0 | 3 | 87 | 87 | 4 | 9 | 3 | 3 | 49 | 46 | 5 | 5 | 8 | 3 | 112 | 110 | 3 | −5 | −17 | 4 | 36 | 40 | 4 | 5 | −11 | 4 | 61 | 63 | 3 |
| −11 | 0 | 3 | 90 | 89 | 4 | −12 | 4 | 3 | 81 | 81 | 3 | 6 | 8 | 3 | 295 | 290 | 3 | −4 | −17 | 4 | 38 | 39 | 3 | 6 | −11 | 4 | 34 | 16 | 4 |
| −10 | 0 | 3 | 14 | 29 | 14 | −11 | 4 | 3 | 139 | 141 | 3 | 7 | 8 | 3 | 46 | 41 | 4 | −3 | −17 | 4 | 74 | 75 | 2 | −11 | −10 | 4 | 74 | 64 | 4 |
| −9 | 0 | 3 | 115 | 110 | 2 | −10 | 4 | 3 | 111 | 112 | 3 | 8 | 8 | 3 | 151 | 143 | 3 | −2 | −17 | 4 | 63 | 62 | 2 | −10 | −10 | 4 | 59 | 55 | 2 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −8 | 0 | 3 | 125 | 124 | 2 | −9 | 4 | 3 | 160 | 155 | 2 | −11 | 9 | 3 | 30 | 36 | 8 | −1 | −17 | 4 | 30 | 26 | 3 | −9 | −10 | 4 | 72 | 76 | 2 |
| −7 | 0 | 3 | 41 | 26 | 3 | −8 | 4 | 3 | 242 | 235 | 3 | −10 | 9 | 3 | 44 | 47 | 4 | 0 | −17 | 4 | 70 | 73 | 2 | −8 | −10 | 4 | 158 | 157 | 3 |
| −6 | 0 | 3 | 12 | 37 | 11 | −7 | 4 | 3 | 177 | 187 | 2 | −9 | 9 | 3 | 78 | 84 | 3 | 1 | −17 | 4 | 23 | 11 | 6 | −7 | −10 | 4 | 124 | 121 | 2 |
| −5 | 0 | 3 | 217 | 245 | 4 | −6 | 4 | 3 | 148 | 140 | 3 | −8 | 9 | 3 | 70 | 71 | 4 | 2 | −17 | 4 | 97 | 39 | 3 | −6 | −10 | 4 | 221 | 216 | 2 |
| −4 | 0 | 3 | 258 | 266 | 3 | −5 | 4 | 3 | 352 | 327 | 7 | −7 | 9 | 3 | 266 | 260 | 5 | −7 | −16 | 4 | 72 | 34 | 3 | −5 | −10 | 4 | 153 | 154 | 1 |
| −3 | 0 | 3 | 461 | 470 | 6 | −4 | 4 | 3 | 149 | 145 | 5 | −6 | 9 | 3 | 239 | 228 | 5 | −6 | −16 | 4 | 76 | 81 | 3 | −4 | −10 | 4 | 214 | 210 | 2 |
| −2 | 0 | 3 | 54 | 49 | 3 | −3 | 4 | 3 | 300 | 299 | 6 | −5 | 9 | 3 | 199 | 206 | 4 | −5 | −16 | 4 | 48 | 54 | 3 | −3 | −10 | 4 | 91 | 90 | 1 |
| −1 | 0 | 3 | 178 | 183 | 2 | −2 | 4 | 3 | 446 | 425 | 8 | 2 | 9 | 3 | 114 | 113 | 4 | −4 | −16 | 4 | 33 | 34 | 3 | −2 | −10 | 4 | 178 | 174 | 1 |
| 0 | 0 | 3 | 105 | 104 | 2 | −1 | 4 | 3 | 149 | 155 | 4 | 3 | 9 | 3 | 33 | 38 | 10 | −3 | −16 | 4 | 112 | 123 | 2 | −1 | −10 | 4 | 209 | 210 | 3 |
| 1 | 0 | 3 | 317 | 322 | 4 | 0 | 4 | 3 | 489 | 491 | 9 | 4 | 9 | 3 | 145 | 146 | 4 | −2 | −16 | 4 | 84 | 80 | 2 | 0 | −10 | 4 | 96 | 98 | 1 |
| 2 | 0 | 3 | 338 | 327 | 5 | 1 | 4 | 3 | 224 | 212 | 5 | 5 | 9 | 3 | 115 | 128 | 4 | −1 | −16 | 4 | 25 | 29 | 5 | 1 | −10 | 4 | 10 | 104 | 2 |
| 3 | 0 | 3 | 426 | 398 | 8 | 2 | 4 | 3 | 187 | 191 | 5 | 6 | 9 | 3 | 77 | 79 | 3 | 0 | −16 | 4 | 36 | 37 | 3 | 2 | −10 | 4 | 215 | 217 | 2 |
| 4 | 0 | 3 | 115 | 106 | 2 | 3 | 4 | 3 | 273 | 288 | 4 | 7 | 9 | 3 | 43 | 40 | 5 | 1 | −16 | 4 | 28 | 28 | 6 | 3 | −10 | 4 | 157 | 156 | 3 |
| 5 | 0 | 3 | 73 | 73 | 2 | 4 | 4 | 3 | 154 | 166 | 2 | 8 | 9 | 3 | 107 | 105 | 3 | 2 | −16 | 4 | 158 | 157 | 3 | 4 | −10 | 4 | 117 | 108 | 2 |
| 6 | 0 | 3 | 109 | 34 | 2 | 5 | 4 | 3 | 496 | 509 | 4 | −11 | 10 | 3 | 33 | 43 | 8 | 3 | −16 | 4 | 52 | 58 | 3 | 5 | −10 | 4 | 62 | 62 | 3 |
| 7 | 0 | 3 | 34 | 35 | 5 | 6 | 4 | 3 | 110 | 107 | 2 | −10 | 10 | 3 | 79 | 76 | 3 | −7 | −15 | 4 | 46 | 40 | 5 | 6 | −10 | 4 | 81 | 77 | 3 |
| 8 | 0 | 3 | 45 | 39 | 6 | 7 | 4 | 3 | 165 | 173 | 3 | −9 | 10 | 3 | 67 | 71 | 4 | −6 | −15 | 4 | 21 | 25 | 10 | 7 | −10 | 4 | 25 | 26 | 8 |
| 9 | 0 | 3 | 59 | 54 | 4 | 8 | 4 | 3 | 140 | 131 | 2 | −8 | 10 | 3 | 66 | 68 | 5 | −5 | −15 | 4 | 85 | 93 | 3 | −11 | −9 | 4 | 69 | 71 | 3 |
| −12 | 1 | 3 | 147 | 135 | 4 | 9 | 4 | 3 | 96 | 94 | 3 | −7 | 10 | 3 | 108 | 95 | 5 | −4 | −15 | 4 | 12 | 15 | 11 | −10 | −9 | 4 | 82 | 83 | 3 |
| −11 | 1 | 3 | 85 | 92 | 4 | −12 | 5 | 3 | 33 | 29 | 8 | −6 | 10 | 3 | 105 | 105 | 5 | −3 | −15 | 4 | 110 | 110 | 2 | −9 | −9 | 4 | 165 | 155 | 3 |
| −10 | 1 | 3 | 119 | 128 | 3 | −11 | 5 | 3 | 114 | 101 | 3 | −5 | 10 | 3 | 112 | 103 | 6 | −2 | −15 | 4 | 112 | 106 | 2 | −8 | −9 | 4 | 116 | 121 | 3 |
| −9 | 1 | 3 | 286 | 276 | 3 | −10 | 5 | 3 | 56 | 60 | 4 | 2 | 10 | 3 | 131 | 127 | 6 | −1 | −15 | 4 | 29 | 24 | 4 | −7 | −9 | 4 | 194 | 198 | 2 |
| −8 | 1 | 3 | 153 | 158 | 2 | −9 | 5 | 3 | 250 | 250 | 3 | 3 | 10 | 3 | 105 | 106 | 5 | 0 | −15 | 4 | 120 | 117 | 2 | −6 | −9 | 4 | 164 | 165 | 2 |
| −7 | 1 | 3 | 110 | 106 | 2 | −8 | 5 | 3 | 122 | 112 | 2 | 4 | 10 | 3 | 93 | 94 | 5 | 1 | −15 | 4 | 48 | 43 | 3 | −5 | −9 | 4 | 191 | 190 | 2 |
| −6 | 1 | 3 | 273 | 265 | 6 | −7 | 5 | 3 | 82 | 81 | 2 | 5 | 10 | 3 | 202 | 208 | 4 | 2 | −15 | 4 | 103 | 98 | 3 | −4 | −9 | 4 | 97 | 105 | 1 |
| −5 | 1 | 3 | 190 | 180 | 4 | −6 | 5 | 3 | 270 | 283 | 4 | 6 | 10 | 3 | 192 | 189 | 3 | 3 | −15 | 4 | 97 | 91 | 3 | −3 | 9 | 4 | 173 | 170 | 2 |
| −4 | 1 | 3 | 156 | 147 | 3 | −5 | 5 | 3 | 228 | 214 | 8 | 7 | 10 | 3 | 37 | 42 | 5 | 4 | −15 | 4 | 99 | 102 | 5 | −2 | −9 | 4 | 72 | 66 | 1 |
| −3 | 1 | 3 | 452 | 452 | 6 | −4 | 5 | 3 | 178 | 188 | 7 | 8 | 10 | 3 | 51 | 49 | 5 | −7 | −14 | 4 | 125 | 132 | 3 | −1 | −9 | 4 | 126 | 113 | 1 |
| −2 | 1 | 3 | 320 | 322 | 4 | −3 | 5 | 3 | 266 | 253 | 8 | −10 | 11 | 3 | 96 | 93 | 3 | −6 | −14 | 4 | 90 | 91 | 4 | 0 | −9 | 4 | 83 | 81 | 1 |
| −1 | 1 | 3 | 267 | 274 | 3 | −2 | 5 | 3 | 337 | 334 | 6 | −9 | 11 | 3 | 118 | 118 | 3 | −5 | −14 | 4 | 138 | 130 | 4 | 1 | −9 | 4 | 51 | 55 | 1 |
| 0 | 1 | 3 | 378 | 400 | 5 | −1 | 5 | 3 | 247 | 244 | 5 | −8 | 11 | 3 | 107 | 108 | 4 | −4 | −14 | 4 | 279 | 278 | 4 | 2 | −9 | 4 | 225 | 231 | 1 |
| 1 | 1 | 3 | 192 | 186 | 3 | 0 | 5 | 3 | 332 | 325 | 6 | −7 | 11 | 3 | 116 | 110 | 5 | −3 | −14 | 4 | 28 | 27 | 4 | 3 | −9 | 4 | 116 | 121 | 1 |
| 2 | 1 | 3 | 342 | 331 | 5 | 1 | 5 | 3 | 229 | 223 | 8 | −6 | 11 | 3 | 203 | 190 | 5 | −2 | −14 | 4 | 77 | 74 | 2 | 4 | −9 | 4 | 230 | 233 | 2 |
| 3 | 1 | 3 | 288 | 280 | 6 | 2 | 5 | 3 | 66 | 40 | 10 | −5 | 11 | 3 | 274 | 264 | 8 | −1 | −14 | 4 | 119 | 115 | 3 | 5 | −9 | 4 | 83 | 78 | 3 |
| 4 | 1 | 3 | 132 | 136 | 2 | 3 | 5 | 3 | 164 | 161 | 3 | 2 | 11 | 3 | 78 | 76 | 7 | 0 | −14 | 4 | 41 | 47 | 4 | 6 | −9 | 4 | 32 | 34 | 5 |
| 5 | 1 | 3 | 70 | 66 | 3 | 4 | 5 | 3 | 131 | 128 | 2 | 3 | 11 | 3 | 63 | 62 | 8 | 1 | −14 | 4 | 82 | 90 | 3 | 7 | −9 | 4 | 38 | 34 | 3 |
| 6 | 1 | 3 | 176 | 175 | 2 | 5 | 5 | 3 | 365 | 379 | 3 | 4 | 11 | 3 | 213 | 215 | 4 | 2 | −14 | 4 | 28 | 24 | 7 | −11 | −8 | 4 | 46 | 47 | 4 |
| 7 | 1 | 3 | 108 | 113 | 3 | 6 | 5 | 3 | 265 | 264 | 3 | 5 | 11 | 3 | 43 | 49 | 7 | 3 | −14 | 4 | 64 | 69 | 3 | −10 | −8 | 4 | 60 | 63 | 2 |
| 8 | 1 | 3 | 90 | 83 | 3 | 7 | 5 | 3 | 70 | 79 | 3 | 6 | 11 | 3 | 43 | 36 | 5 | 4 | −14 | 4 | 9 | 30 | 8 | −9 | −8 | 4 | 39 | 34 | 4 |
| 9 | 1 | 3 | 5 | 5 | 5 | 8 | 5 | 3 | 114 | 119 | 2 | 7 | 11 | 3 | 39 | 36 | 5 | −7 | −13 | 4 | 75 | 84 | 4 | −8 | −8 | 4 | 90 | 78 | 2 |
| −12 | 2 | 3 | 124 | 123 | 4 | 9 | 5 | 3 | 81 | 84 | 3 | −10 | 12 | 3 | 45 | 49 | 4 | −6 | −13 | 4 | 159 | 164 | 4 | −7 | −8 | 4 | 43 | 40 | 3 |
| −11 | 2 | 3 | 154 | 154 | 2 | −12 | 6 | 3 | 72 | 75 | 4 | −9 | 12 | 3 | 0 | 7 | 1 | −5 | −13 | 4 | 275 | 270 | 4 | −6 | −8 | 4 | 113 | 109 | 1 |
| −10 | 2 | 3 | 139 | 132 | 3 | −11 | 6 | 3 | 67 | 65 | 3 | −8 | 12 | 3 | 47 | 37 | 8 | −4 | −13 | 4 | 66 | 79 | 2 | −5 | −8 | 4 | 295 | 292 | 2 |
| −9 | 2 | 3 | 228 | 225 | 2 | −10 | 6 | 3 | 60 | 64 | 4 | −7 | 12 | 3 | 81 | 75 | 6 | −3 | −13 | 4 | 131 | 125 | 2 | −4 | −8 | 4 | 54 | 55 | 1 |
| −8 | 2 | 3 | 126 | 127 | 2 | −9 | 6 | 3 | 122 | 125 | 3 | −6 | 12 | 3 | 151 | 158 | 6 | −2 | −13 | 4 | 74 | 66 | 3 | −3 | −8 | 4 | 154 | 152 | 1 |
| −2 | −8 | 4 | 162 | 154 | 1 | 1 | −4 | 4 | 260 | 246 | 4 | 0 | 0 | 4 | 652 | 702 | 8 | −2 | 4 | 4 | 141 | 132 | 5 | 1 | 9 | 4 | 51 | 55 | 5 |
| −1 | −8 | 4 | 303 | 293 | 2 | 2 | −4 | 4 | 171 | 184 | 2 | 1 | 0 | 4 | 254 | 254 | 4 | −1 | 4 | 4 | 436 | 439 | 8 | 2 | 9 | 4 | 223 | 231 | 4 |
| 0 | −8 | 4 | 112 | 116 | 1 | 3 | −4 | 4 | 225 | 233 | 2 | 2 | 0 | 4 | 139 | 122 | 5 | 0 | 4 | 4 | 422 | 434 | 8 | 3 | 9 | 4 | 119 | 121 | 4 |
| 1 | −8 | 4 | 95 | 96 | 1 | 4 | −4 | 4 | 81 | 83 | 2 | 3 | 0 | 4 | 129 | 109 | 2 | 1 | 4 | 4 | 262 | 246 | 6 | 4 | 9 | 4 | 228 | 233 | 5 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 2 | −8 | 4 | 154 | 149 | 1 | 5 | −4 | 4 | 137 | 135 | 2 | 4 | 0 | 4 | 59 | 54 | 3 | 2 | 4 | 4 | 162 | 183 | 3 | 5 | 9 | 4 | 82 | 78 | 3 |
| 3 | −8 | 4 | 268 | 258 | 2 | 6 | −4 | 4 | 228 | 226 | 3 | 5 | 0 | 4 | 159 | 160 | 2 | 3 | 4 | 4 | 224 | 233 | 2 | 6 | 9 | 4 | 28 | 34 | 8 |
| 4 | −8 | 4 | 225 | 228 | 2 | 7 | −4 | 4 | 77 | 81 | 3 | 6 | 0 | 4 | 53 | 55 | 3 | 4 | 4 | 4 | 84 | 84 | 2 | 7 | 9 | 4 | 36 | 33 | 6 |
| 5 | −8 | 4 | 176 | 178 | 3 | 8 | −4 | 4 | 20 | 22 | 15 | 7 | 0 | 4 | 80 | 86 | 4 | 5 | 4 | 4 | 136 | 136 | 2 | −11 | 10 | 4 | 73 | 65 | 4 |
| 6 | −8 | 4 | 108 | 107 | 2 | −12 | −3 | 4 | 80 | 85 | 4 | 8 | 0 | 4 | 98 | 102 | 3 | 6 | 4 | 4 | 221 | 226 | 3 | −10 | 10 | 4 | 53 | 56 | 4 |
| 7 | −8 | 4 | 86 | 89 | 3 | −11 | −3 | 4 | 50 | 47 | 6 | 9 | 0 | 4 | 51 | 44 | 8 | 7 | 4 | 4 | 82 | 81 | 3 | −9 | 10 | 4 | 70 | 76 | 4 |
| 8 | −8 | 4 | 79 | 82 | 3 | −10 | −3 | 4 | 122 | 122 | 3 | −13 | 1 | 4 | 49 | 55 | 16 | 8 | 4 | 4 | 25 | 23 | 11 | −8 | 10 | 4 | 158 | 157 | 4 |
| −12 | −7 | 4 | 69 | 65 | 4 | −9 | −3 | 4 | 108 | 106 | 3 | −12 | 1 | 4 | 109 | 105 | 4 | −12 | 5 | 4 | 78 | 77 | 3 | −7 | 10 | 4 | 128 | 122 | 5 |
| −11 | −7 | 4 | 88 | 85 | 3 | −8 | −3 | 4 | 240 | 241 | 3 | −11 | 1 | 4 | 124 | 128 | 3 | −11 | 5 | 4 | 155 | 153 | 3 | −6 | 10 | 4 | 222 | 226 | 5 |
| −10 | −7 | 4 | 62 | 60 | 4 | −7 | −3 | 4 | 100 | 99 | 2 | −10 | 1 | 4 | 175 | 180 | 2 | −10 | 5 | 4 | 141 | 146 | 3 | −5 | 10 | 4 | 153 | 154 | 6 |
| −9 | −7 | 4 | 77 | 74 | 3 | −6 | −3 | 4 | 144 | 140 | 2 | −9 | 1 | 4 | 86 | 87 | 3 | −9 | 5 | 4 | 159 | 155 | 2 | 1 | 10 | 4 | 107 | 104 | 4 |
| −8 | −7 | 4 | 133 | 130 | 2 | −5 | −3 | 4 | 174 | 172 | 3 | −8 | 1 | 4 | 223 | 223 | 2 | −8 | 5 | 4 | 85 | 86 | 2 | 2 | 10 | 4 | 210 | 217 | 4 |
| −7 | −7 | 4 | 157 | 155 | 2 | −4 | −3 | 4 | 83 | 64 | 3 | −7 | 1 | 4 | 181 | 189 | 2 | −7 | 5 | 4 | 255 | 260 | 2 | 3 | 10 | 4 | 155 | 157 | 4 |
| −6 | −7 | 4 | 193 | 195 | 1 | −3 | −3 | 4 | 224 | 218 | 4 | −6 | 1 | 4 | 190 | 195 | 5 | −6 | 5 | 4 | 142 | 144 | 3 | 4 | 10 | 4 | 108 | 108 | 4 |
| −5 | −7 | 4 | 121 | 112 | 1 | −2 | −3 | 4 | 165 | 166 | 3 | −5 | 1 | 4 | 84 | 69 | 6 | −5 | 5 | 4 | 350 | 332 | 10 | 5 | 10 | 4 | 63 | 63 | 4 |
| −4 | −7 | 4 | 196 | 198 | 1 | −1 | −3 | 4 | 398 | 409 | 6 | −4 | 1 | 4 | 400 | 408 | 6 | −4 | 5 | 4 | 271 | 266 | 9 | 6 | 10 | 4 | 79 | 77 | 3 |
| −3 | −7 | 4 | 137 | 122 | 2 | 0 | −3 | 4 | 294 | 280 | 5 | −3 | 1 | 4 | 219 | 214 | 3 | −3 | 5 | 4 | 184 | 171 | 7 | 7 | 10 | 4 | 0 | 26 | 1 |
| −2 | −7 | 4 | 198 | 196 | 2 | 1 | −3 | 4 | 336 | 322 | 5 | −2 | 1 | 4 | 401 | 400 | 5 | −2 | 5 | 4 | 90 | 71 | 5 | −10 | 11 | 4 | 97 | 99 | 3 |
| −1 | −7 | 4 | 103 | 84 | 2 | 2 | −3 | 4 | 198 | 197 | 3 | −1 | 1 | 4 | 426 | 431 | 5 | −1 | 5 | 4 | 293 | 287 | 6 | −9 | 11 | 4 | 97 | 102 | 3 |
| 0 | −7 | 4 | 111 | 115 | 1 | 3 | −3 | 4 | 274 | 288 | 2 | 0 | 1 | 4 | 219 | 202 | 4 | 0 | 5 | 4 | 188 | 184 | 7 | −8 | 11 | 4 | 28 | 37 | 12 |
| 1 | −7 | 4 | 111 | 112 | 1 | 4 | −3 | 4 | 91 | 87 | 3 | 1 | 1 | 4 | 624 | 608 | 11 | 1 | 5 | 4 | 163 | 153 | 8 | −7 | 11 | 4 | 213 | 210 | 5 |
| 2 | −7 | 4 | 78 | 85 | 1 | 5 | −3 | 4 | 123 | 120 | 3 | 2 | 1 | 4 | 212 | 197 | 5 | 2 | 5 | 4 | 241 | 254 | 3 | −6 | 11 | 4 | 190 | 188 | 5 |
| 3 | −7 | 4 | 155 | 162 | 1 | 6 | −3 | 4 | 114 | 109 | 3 | 3 | 1 | 4 | 224 | 233 | 2 | 3 | 5 | 4 | 136 | 134 | 2 | −5 | 11 | 4 | 113 | 111 | 6 |
| 4 | −7 | 4 | 27 | 29 | 4 | 7 | −3 | 4 | 109 | 95 | 4 | 4 | 1 | 4 | 39 | 32 | 3 | 4 | 5 | 4 | 159 | 164 | 2 | 1 | 11 | 4 | 30 | 25 | 15 |
| 5 | −7 | 4 | 243 | 236 | 3 | 8 | −3 | 4 | 44 | 43 | 5 | 5 | 1 | 4 | 101 | 99 | 2 | 5 | 5 | 4 | 151 | 144 | 2 | 2 | 11 | 4 | 180 | 186 | 6 |
| 6 | −7 | 4 | 208 | 202 | 2 | −12 | −2 | 4 | 37 | 27 | 12 | 6 | 1 | 4 | 62 | 75 | 3 | 6 | 5 | 4 | 115 | 112 | 2 | 3 | 11 | 4 | 176 | 182 | 5 |
| 7 | −7 | 4 | 96 | 96 | 2 | −11 | −2 | 4 | 84 | 81 | 4 | 7 | 1 | 4 | 81 | 84 | 3 | 7 | 5 | 4 | 96 | 92 | 3 | 4 | 11 | 4 | 72 | 75 | 5 |
| 8 | −7 | 4 | 85 | 91 | 3 | −10 | −2 | 4 | 208 | 208 | 4 | 8 | 1 | 4 | 82 | 82 | 4 | 8 | 5 | 4 | 94 | 95 | 3 | 5 | 11 | 4 | 64 | 64 | 4 |
| −12 | −6 | 4 | 113 | 116 | 3 | −9 | −2 | 4 | 72 | 75 | 4 | 9 | 1 | 4 | 44 | 42 | 9 | −12 | 6 | 4 | 112 | 116 | 3 | 6 | 11 | 4 | 7 | 17 | 7 |
| −11 | −6 | 4 | 67 | 59 | 3 | −8 | −2 | 4 | 176 | 176 | 2 | −12 | 2 | 4 | 14 | 27 | 14 | −11 | 6 | 4 | 64 | 59 | 4 | −10 | 12 | 4 | 70 | 66 | 3 |
| −10 | −6 | 4 | 87 | 83 | 3 | −7 | −2 | 4 | 32 | 28 | 4 | −11 | 2 | 4 | 85 | 82 | 3 | −10 | 6 | 4 | 83 | 82 | 3 | −9 | 12 | 4 | 75 | 71 | 3 |
| −9 | −6 | 4 | 86 | 80 | 3 | −6 | −2 | 4 | 222 | 221 | 4 | −10 | 2 | 4 | 216 | 208 | 3 | −9 | 6 | 4 | 88 | 80 | 3 | −8 | 12 | 4 | 23 | 13 | 23 |
| −8 | −6 | 4 | 117 | 110 | 2 | −5 | −2 | 4 | 360 | 353 | 5 | −9 | 2 | 4 | 78 | 75 | 3 | −8 | 6 | 4 | 114 | 110 | 3 | −7 | 12 | 4 | 102 | 96 | 5 |
| −7 | −6 | 4 | 262 | 262 | 2 | −4 | −2 | 4 | 75 | 90 | 3 | −8 | 2 | 4 | 179 | 176 | 2 | −7 | 6 | 4 | 263 | 262 | 3 | −6 | 12 | 4 | 103 | 99 | 7 |
| −6 | −6 | 4 | 100 | 99 | 1 | −3 | −2 | 4 | 299 | 313 | 4 | −7 | 2 | 4 | 32 | 28 | 3 | −6 | 6 | 4 | 97 | 99 | 3 | −5 | 12 | 4 | 34 | 25 | 15 |
| −5 | −6 | 4 | 273 | 266 | 2 | −2 | −2 | 4 | 494 | 498 | 6 | −6 | 2 | 4 | 226 | 221 | 6 | −5 | 6 | 4 | 267 | 267 | 5 | 2 | 12 | 4 | 128 | 142 | 7 |
| −4 | −6 | 4 | 93 | 96 | 2 | −1 | −2 | 4 | 616 | 641 | 8 | −5 | 2 | 4 | 368 | 353 | 7 | 2 | 6 | 4 | 138 | 136 | 3 | 3 | 12 | 4 | 49 | 43 | 9 |
| −3 | −6 | 4 | 235 | 239 | 3 | 0 | −2 | 4 | 505 | 498 | 8 | −4 | 2 | 4 | 80 | 90 | 5 | 3 | 6 | 4 | 339 | 347 | 3 | 4 | 12 | 4 | 122 | 120 | 4 |
| −2 | −6 | 4 | 299 | 294 | 3 | 1 | −2 | 4 | 245 | 252 | 4 | −3 | 2 | 4 | 302 | 314 | 5 | 4 | 6 | 4 | 226 | 223 | 3 | 5 | 12 | 4 | 13 | 17 | 13 |
| −1 | −6 | 4 | 644 | 610 | 7 | 2 | −2 | 4 | 437 | 425 | 6 | −2 | 2 | 4 | 492 | 499 | 7 | 5 | 6 | 4 | 268 | 260 | 3 | 6 | 12 | 4 | 53 | 56 | 4 |
| 0 | −6 | 4 | 185 | 176 | 3 | 3 | −2 | 4 | 204 | 214 | 2 | −1 | 2 | 4 | 633 | 642 | 11 | 6 | 6 | 4 | 18 | 23 | 17 | −9 | 13 | 4 | 123 | 124 | 4 |
| 1 | −6 | 4 | 136 | 118 | 2 | 4 | −2 | 4 | 122 | 127 | 2 | 0 | 2 | 4 | 517 | 498 | 9 | 7 | 6 | 4 | 124 | 115 | 3 | −8 | 13 | 4 | 96 | 94 | 7 |
| 2 | −6 | 4 | 139 | 135 | 1 | 5 | −2 | 4 | 114 | 109 | 3 | 1 | 2 | 4 | 267 | 252 | 6 | 8 | 6 | 4 | 99 | 98 | 2 | −7 | 13 | 4 | 73 | 84 | 8 |
| 3 | −6 | 4 | 336 | 347 | 2 | 6 | −2 | 4 | 87 | 90 | 3 | 2 | 2 | 4 | 440 | 425 | 9 | −12 | 7 | 4 | 63 | 66 | 4 | −6 | 13 | 4 | 165 | 164 | 6 |
| 4 | −6 | 4 | 225 | 224 | 2 | 7 | −2 | 4 | 59 | 63 | 4 | 3 | 2 | 4 | 208 | 214 | 2 | −11 | 7 | 4 | 88 | 84 | 3 | −5 | 13 | 4 | 271 | 270 | 8 |
| 5 | −6 | 4 | 269 | 260 | 3 | 8 | −2 | 4 | 38 | 41 | 7 | 4 | 2 | 4 | 128 | 128 | 2 | −10 | 7 | 4 | 62 | 60 | 3 | 2 | 13 | 4 | 54 | 52 | 9 |
| 6 | −6 | 4 | 23 | 23 | 10 | 9 | −2 | 4 | 41 | 31 | 10 | 5 | 2 | 4 | 120 | 110 | 2 | −9 | 7 | 4 | 78 | 74 | 3 | 3 | 13 | 4 | 59 | 62 | 8 |
| 7 | −6 | 4 | 122 | 116 | 2 | −13 | −1 | 4 | 30 | 55 | 29 | 6 | 2 | 4 | 85 | 90 | 3 | −8 | 7 | 4 | 134 | 131 | 3 | 4 | 13 | 4 | 69 | 62 | 8 |
| 8 | −6 | 4 | 94 | 97 | 2 | −12 | −1 | 4 | 113 | 106 | 3 | 7 | 2 | 4 | 60 | 63 | 4 | −7 | 7 | 4 | 156 | 154 | 3 | 5 | 13 | 4 | 92 | 94 | 5 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −12 | −5 | 4 | 77 | 77 | 4 | −11 | −1 | 4 | 128 | 128 | 4 | 8 | 2 | 4 | 31 | 40 | 9 | −6 | 7 | 4 | 192 | 196 | 3 | −9 | 14 | 4 | 115 | 114 | 6 |
| −11 | −5 | 4 | 158 | 153 | 3 | −10 | −1 | 4 | 163 | 180 | 3 | 9 | 2 | 4 | 42 | 31 | 9 | −5 | 7 | 4 | 121 | 112 | 4 | −8 | 14 | 4 | 35 | 27 | 13 |
| −10 | −5 | 4 | 149 | 146 | 3 | −9 | −1 | 4 | 83 | 86 | 2 | −12 | 3 | 4 | 87 | 85 | 4 | 1 | 7 | 4 | 108 | 111 | 3 | −7 | 14 | 4 | 136 | 132 | 6 |
| −9 | −5 | 4 | 162 | 156 | 3 | −8 | −1 | 4 | 222 | 223 | 2 | −11 | 3 | 4 | 58 | 47 | 4 | 2 | 7 | 4 | 80 | 85 | 3 | −6 | 14 | 4 | 94 | 92 | 7 |
| −8 | −5 | 4 | 85 | 87 | 2 | −7 | −1 | 4 | 182 | 189 | 2 | −10 | 3 | 4 | 121 | 122 | 3 | 3 | 7 | 4 | 158 | 163 | 3 | −5 | 14 | 4 | 140 | 130 | 7 |
| −7 | −5 | 4 | 260 | 260 | 2 | −6 | −1 | 4 | 187 | 195 | 4 | −9 | 3 | 4 | 102 | 104 | 2 | 4 | 7 | 4 | 23 | 29 | 12 | 2 | 14 | 4 | 35 | 24 | 13 |
| −6 | −5 | 4 | 144 | 144 | 2 | −5 | −1 | 4 | 76 | 68 | 4 | −8 | 3 | 4 | 240 | 241 | 2 | 5 | 7 | 4 | 244 | 236 | 3 | 3 | 14 | 4 | 75 | 69 | 7 |
| −5 | −5 | 4 | 354 | 332 | 4 | −4 | −1 | 4 | 401 | 409 | 6 | −7 | 3 | 4 | 100 | 99 | 2 | 6 | 7 | 4 | 203 | 203 | 3 | 4 | 14 | 4 | 30 | 29 | 16 |
| −4 | −5 | 4 | 280 | 266 | 4 | 3 | −1 | 4 | 215 | 215 | 3 | −6 | 3 | 4 | 137 | 140 | 3 | 7 | 7 | 4 | 97 | 96 | 3 | 5 | 14 | 4 | 60 | 61 | 7 |
| −3 | −5 | 4 | 180 | 171 | 2 | −2 | −1 | 4 | 403 | 400 | 5 | −5 | 3 | 4 | 181 | 173 | 5 | 8 | 7 | 4 | 94 | 92 | 2 | −8 | 15 | 4 | 43 | 53 | 10 |
| −2 | −5 | 4 | 86 | 70 | 2 | −1 | −1 | 4 | 421 | 431 | 5 | −4 | 3 | 4 | 80 | 64 | 5 | −11 | 8 | 4 | 55 | 47 | 5 | −7 | 15 | 4 | 47 | 40 | 9 |
| −1 | −5 | 4 | 300 | 287 | 4 | 0 | −1 | 4 | 213 | 202 | 3 | −3 | 3 | 4 | 229 | 218 | 5 | −10 | 8 | 4 | 65 | 63 | 3 | −6 | 15 | 4 | 0 | 25 | 1 |
| 0 | −5 | 4 | 188 | 184 | 3 | 1 | −1 | 4 | 616 | 608 | 8 | −2 | 3 | 4 | 170 | 165 | 4 | −9 | 8 | 4 | 41 | 34 | 5 | 2 | 15 | 4 | 108 | 98 | 7 |
| 1 | −5 | 4 | 169 | 155 | 3 | 2 | −1 | 4 | 209 | 198 | 4 | −1 | 3 | 4 | 413 | 410 | 7 | −8 | 8 | 4 | 80 | 79 | 4 | 3 | 15 | 4 | 96 | 90 | 7 |
| 2 | −5 | 4 | 247 | 254 | 2 | 3 | −1 | 4 | 224 | 233 | 2 | 0 | 3 | 4 | 290 | 280 | 6 | −7 | 8 | 4 | 31 | 40 | 9 | 4 | 15 | 4 | 107 | 102 | 6 |
| 3 | −5 | 4 | 132 | 135 | 2 | 4 | −1 | 4 | 42 | 32 | 3 | 1 | 3 | 4 | 339 | 322 | 7 | −6 | 8 | 4 | 116 | 109 | 4 | −7 | 16 | 4 | 90 | 93 | 6 |
| 4 | −5 | 4 | 158 | 163 | 2 | 5 | −1 | 4 | 103 | 99 | 2 | 2 | 3 | 4 | 197 | 197 | 3 | −5 | 8 | 4 | 286 | 292 | 5 | −6 | 16 | 4 | 85 | 82 | 7 |
| 5 | −5 | 4 | 145 | 144 | 3 | 6 | −1 | 4 | 68 | 75 | 4 | 3 | 3 | 4 | 271 | 287 | 2 | −4 | 8 | 4 | 43 | 54 | 10 | 3 | 16 | 4 | 52 | 59 | 9 |
| 6 | −5 | 4 | 113 | 113 | 3 | 7 | −1 | 4 | 94 | 85 | 3 | 4 | 3 | 4 | 89 | 88 | 2 | 1 | 8 | 4 | 102 | 96 | 3 | −5 | −17 | 5 | 63 | 67 | 3 |
| 7 | −5 | 4 | 96 | 92 | 3 | 8 | −1 | 4 | 82 | 82 | 4 | 5 | 3 | 4 | 120 | 120 | 2 | 2 | 8 | 4 | 151 | 148 | 3 | −4 | −17 | 5 | 87 | 91 | 3 |
| 8 | −5 | 4 | 96 | 96 | 3 | 9 | −1 | 4 | 43 | 42 | 10 | 6 | 3 | 4 | 106 | 109 | 3 | 3 | 8 | 4 | 264 | 258 | 4 | −3 | −17 | 5 | 46 | 50 | 3 |
| −12 | −4 | 4 | 56 | 55 | 4 | −13 | 0 | 4 | 193 | 202 | 7 | 7 | 3 | 4 | 96 | 95 | 3 | 4 | 8 | 4 | 221 | 227 | 3 | −2 | −17 | 5 | 38 | 37 | 3 |
| −11 | −4 | 4 | 82 | 86 | 4 | −12 | 0 | 4 | 64 | 61 | 5 | 8 | 3 | 4 | 53 | 43 | 4 | 5 | 8 | 4 | 179 | 179 | 3 | −1 | −17 | 5 | 36 | 28 | 3 |
| −10 | −4 | 4 | 136 | 136 | 3 | −11 | 0 | 4 | 200 | 202 | 4 | 9 | 3 | 4 | 71 | 61 | 7 | 6 | 8 | 4 | 105 | 108 | 3 | 0 | −17 | 5 | 60 | 70 | 3 |
| −9 | −4 | 4 | 136 | 139 | 3 | −10 | 0 | 4 | 286 | 283 | 3 | −12 | 4 | 4 | 54 | 55 | 5 | 7 | 8 | 4 | 92 | 88 | 3 | 1 | −17 | 5 | 59 | 77 | 10 |
| −8 | −4 | 4 | 107 | 112 | 2 | −9 | 0 | 4 | 284 | 272 | 2 | −11 | 4 | 4 | 88 | 86 | 3 | 8 | 8 | 4 | 80 | 82 | 3 | −6 | −16 | 5 | 55 | 64 | 3 |
| −7 | −4 | 4 | 120 | 120 | 2 | −8 | 0 | 4 | 79 | 85 | 2 | −10 | 4 | 4 | 123 | 136 | 3 | −11 | 9 | 4 | 64 | 71 | 4 | −5 | −16 | 5 | 73 | 81 | 3 |
| −6 | −4 | 4 | 112 | 114 | 2 | −7 | 0 | 4 | 81 | 87 | 2 | −9 | 4 | 4 | 140 | 139 | 2 | −10 | 9 | 4 | 73 | 82 | 3 | −4 | −16 | 5 | 93 | 105 | 4 |
| −5 | −4 | 4 | 229 | 231 | 3 | −6 | 0 | 4 | 112 | 112 | 6 | −8 | 4 | 4 | 109 | 113 | 2 | −9 | 9 | 4 | 159 | 155 | 3 | −3 | −16 | 5 | 98 | 96 | 2 |
| −4 | −4 | 4 | 426 | 409 | 6 | −5 | 0 | 4 | 283 | 298 | 5 | −7 | 4 | 4 | 119 | 120 | 2 | −8 | 9 | 4 | 112 | 121 | 4 | −2 | −16 | 5 | 11 | 12 | 11 |
| −3 | −4 | 4 | 265 | 255 | 3 | −4 | 0 | 4 | 402 | 429 | 5 | −6 | 4 | 4 | 109 | 114 | 3 | −7 | 9 | 4 | 197 | 198 | 4 | −1 | −16 | 5 | 64 | 69 | 2 |
| −2 | −4 | 4 | 141 | 132 | 2 | −3 | 0 | 4 | 189 | 198 | 3 | −5 | 4 | 4 | 228 | 231 | 6 | −6 | 9 | 4 | 164 | 165 | 4 | 0 | −16 | 5 | 135 | 134 | 3 |
| −1 | −4 | 4 | 440 | 439 | 5 | −2 | 0 | 4 | 109 | 119 | 3 | −4 | 4 | 4 | 420 | 409 | 8 | −5 | 9 | 4 | 181 | 190 | 4 | 1 | −16 | 5 | 117 | 121 | 3 |
| 0 | −4 | 4 | 426 | 434 | 6 | −1 | 0 | 4 | 423 | 423 | 5 | −3 | 4 | 4 | 263 | 254 | 6 | −4 | 9 | 4 | 85 | 105 | 7 | 2 | −16 | 5 | 77 | 89 | 8 |
| −7 | −15 | 5 | 76 | 86 | 4 | −8 | −9 | 5 | 43 | 40 | 5 | 0 | −5 | 5 | 236 | 234 | 2 | 1 | −1 | 5 | 307 | 307 | 4 | 0 | 3 | 5 | 226 | 207 | 6 |
| −6 | −15 | 5 | 44 | 49 | 4 | −1 | −9 | 5 | 70 | 65 | 2 | 1 | −5 | 5 | 274 | 270 | 2 | 2 | −1 | 5 | 30 | 36 | 4 | 1 | 3 | 5 | 130 | 133 | 3 |
| −5 | −15 | 5 | 66 | 68 | 4 | −6 | −9 | 5 | 109 | 112 | 1 | 2 | −5 | 5 | 41 | 38 | 3 | 3 | −1 | 5 | 111 | 112 | 2 | 2 | 3 | 5 | 190 | 186 | 2 |
| −4 | −15 | 5 | 66 | 73 | 4 | −5 | −9 | 5 | 74 | 70 | 1 | 3 | −5 | 5 | 141 | 135 | 2 | 4 | −1 | 5 | 44 | 40 | 3 | 3 | 3 | 5 | 68 | 72 | 2 |
| −3 | −15 | 5 | 81 | 85 | 2 | −4 | −9 | 5 | 158 | 154 | 1 | 4 | −5 | 5 | 431 | 427 | 4 | 5 | −1 | 5 | 104 | 103 | 3 | 4 | 3 | 5 | 104 | 99 | 2 |
| −2 | −15 | 5 | 78 | 80 | 2 | −3 | −9 | 5 | 175 | 175 | 1 | 5 | −5 | 5 | 85 | 81 | 3 | 6 | −1 | 5 | 126 | 125 | 3 | 5 | 3 | 5 | 64 | 66 | 3 |
| −1 | −15 | 5 | 156 | 153 | 2 | −2 | −9 | 5 | 75 | 75 | 1 | 6 | −5 | 5 | 142 | 137 | 3 | 7 | −1 | 5 | 98 | 95 | 3 | 6 | 3 | 5 | 31 | 36 | 6 |
| 0 | −15 | 5 | 92 | 89 | 3 | −1 | −9 | 5 | 86 | 77 | 1 | 7 | −5 | 5 | 143 | 141 | 2 | 8 | −1 | 5 | 60 | 50 | 5 | 7 | 3 | 5 | 84 | 81 | 3 |
| 1 | −15 | 5 | 94 | 94 | 3 | 0 | −9 | 5 | 135 | 136 | 1 | −12 | −4 | 5 | 22 | 9 | 17 | −13 | 0 | 5 | 34 | 30 | 15 | 8 | 3 | 5 | 97 | 89 | 4 |
| 2 | −15 | 5 | 102 | 100 | 3 | 1 | −9 | 5 | 53 | 45 | 2 | −11 | −4 | 5 | 81 | 76 | 4 | −12 | 0 | 5 | 54 | 43 | 6 | −12 | 4 | 5 | 0 | 10 | 1 |
| 3 | −15 | 5 | 56 | 63 | 11 | 2 | −9 | 5 | 269 | 280 | 2 | −10 | −4 | 5 | 141 | 140 | 3 | −11 | 0 | 5 | 149 | 154 | 4 | −11 | 4 | 5 | 82 | 76 | 3 |
| −7 | −14 | 5 | 39 | 44 | 6 | 3 | −9 | 5 | 69 | 69 | 2 | −9 | −4 | 5 | 104 | 104 | 3 | −10 | 0 | 5 | 64 | 56 | 4 | −10 | 4 | 5 | 138 | 139 | 3 |
| −6 | −14 | 5 | 50 | 63 | 4 | 4 | −9 | 5 | 59 | 60 | 2 | −8 | −4 | 5 | 143 | 147 | 2 | −9 | 0 | 5 | 247 | 256 | 2 | −9 | 4 | 5 | 102 | 104 | 2 |
| −5 | −14 | 5 | 20 | 29 | 11 | 5 | −9 | 5 | 135 | 132 | 3 | −7 | −4 | 5 | 104 | 104 | 2 | −8 | 0 | 5 | 155 | 165 | 2 | −8 | 4 | 5 | 142 | 147 | 2 |
| −4 | −14 | 5 | 87 | 86 | 3 | 6 | −9 | 5 | 136 | 133 | 3 | −6 | −4 | 5 | 434 | 437 | 3 | −7 | 0 | 5 | 243 | 257 | 2 | −7 | 4 | 5 | 102 | 104 | 2 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −3 | −14 | 5 | 105 | 94 | 2 | −12 | −8 | 5 | 54 | 51 | 3 | −5 | −4 | 5 | 186 | 184 | 3 | −6 | 0 | 5 | 116 | 107 | 2 | −6 | 4 | 5 | 431 | 437 | 4 |
| −2 | −14 | 5 | 101 | 100 | 2 | −11 | −8 | 5 | 76 | 79 | 3 | −4 | −4 | 5 | 142 | 130 | 3 | −5 | 0 | 5 | 359 | 361 | 7 | −5 | 4 | 5 | 182 | 184 | 4 |
| −1 | −14 | 5 | 72 | 68 | 2 | −10 | −8 | 5 | 56 | 58 | 3 | −3 | −4 | 5 | 278 | 278 | 4 | −4 | 0 | 5 | 656 | 638 | 12 | −4 | 4 | 5 | 137 | 130 | 6 |
| 0 | −14 | 5 | 76 | 74 | 3 | −9 | −8 | 5 | 119 | 113 | 3 | −2 | −4 | 5 | 286 | 272 | 4 | −3 | 0 | 5 | 447 | 469 | 7 | −3 | 4 | 5 | 285 | 278 | 6 |
| 1 | −14 | 5 | 35 | 51 | 6 | −8 | −8 | 5 | 170 | 176 | 2 | −1 | −4 | 5 | 189 | 180 | 3 | −2 | 0 | 5 | 126 | 107 | 3 | −2 | 4 | 5 | 288 | 273 | 6 |
| 2 | −14 | 5 | 127 | 128 | 5 | −7 | −8 | 5 | 150 | 153 | 2 | 0 | −4 | 5 | 70 | 75 | 3 | −1 | 0 | 5 | 480 | 462 | 7 | −1 | 4 | 5 | 196 | 180 | 5 |
| 3 | −14 | 5 | 91 | 83 | 5 | −6 | −8 | 5 | 147 | 142 | 1 | 1 | −4 | 5 | 183 | 178 | 2 | 0 | 0 | 5 | 321 | 317 | 7 | 0 | 4 | 5 | 71 | 74 | 7 |
| −7 | −13 | 5 | 60 | 59 | 5 | −5 | −8 | 5 | 116 | 111 | 1 | 2 | −4 | 5 | 328 | 330 | 3 | 1 | 0 | 5 | 54 | 51 | 8 | 1 | 4 | 5 | 178 | 178 | 3 |
| −6 | −13 | 5 | 106 | 102 | 4 | −4 | −8 | 5 | 161 | 153 | 1 | 3 | −4 | 5 | 214 | 222 | 2 | 2 | 0 | 5 | 17 | 6 | 6 | 2 | 4 | 5 | 326 | 330 | 3 |
| −5 | −13 | 5 | 88 | 84 | 3 | −3 | −8 | 5 | 226 | 225 | 1 | 4 | −4 | 5 | 185 | 189 | 2 | 3 | 0 | 5 | 94 | 91 | 2 | 3 | 4 | 5 | 218 | 222 | 2 |
| −4 | −13 | 5 | 47 | 41 | 3 | −2 | −8 | 5 | 195 | 197 | 1 | 5 | −4 | 5 | 24 | 30 | 11 | 4 | 0 | 5 | 45 | 43 | 4 | 4 | 4 | 5 | 189 | 189 | 2 |
| −3 | −13 | 5 | 175 | 179 | 3 | −1 | −8 | 5 | 127 | 116 | 1 | 6 | −4 | 5 | 0 | 11 | 1 | 5 | 0 | 5 | 85 | 87 | 2 | 5 | 4 | 5 | 21 | 29 | 11 |
| −2 | −13 | 5 | 22 | 27 | 6 | 0 | −8 | 5 | 140 | 141 | 1 | 7 | −4 | 5 | 105 | 102 | 3 | 6 | 0 | 5 | 99 | 91 | 3 | 6 | 4 | 5 | 0 | 11 | 1 |
| −1 | −13 | 5 | 127 | 123 | 3 | 1 | −8 | 5 | 94 | 92 | 1 | 8 | −4 | 5 | 39 | 31 | 6 | 7 | 0 | 5 | 210 | 215 | 3 | 7 | 4 | 5 | 100 | 101 | 3 |
| 0 | −13 | 5 | 42 | 61 | 3 | 2 | −8 | 5 | 132 | 136 | 2 | −13 | −3 | 5 | 18 | 42 | 17 | 8 | 0 | 5 | 44 | 36 | 7 | 8 | 4 | 5 | 36 | 32 | 9 |
| 1 | −13 | 5 | 103 | 91 | 2 | 3 | −8 | 5 | 98 | 103 | 2 | −12 | −3 | 5 | 7 | 23 | 7 | −13 | 1 | 5 | 94 | 92 | 7 | −12 | 5 | 5 | 48 | 49 | 5 |
| 2 | −13 | 5 | 61 | 57 | 4 | 4 | −8 | 5 | 54 | 57 | 3 | −11 | −3 | 5 | 30 | 25 | 10 | −12 | 1 | 5 | 150 | 151 | 4 | −11 | 5 | 5 | 35 | 32 | 6 |
| 3 | −13 | 5 | 96 | 99 | 3 | 5 | −8 | 5 | 70 | 63 | 2 | −10 | −3 | 5 | 202 | 199 | 3 | −11 | 1 | 5 | 120 | 114 | 4 | −10 | 5 | 5 | 102 | 106 | 3 |
| 4 | −13 | 5 | 24 | 19 | 8 | 6 | −8 | 5 | 82 | 82 | 3 | −9 | −3 | 5 | 34 | 40 | 8 | −10 | 1 | 5 | 96 | 100 | 3 | −9 | 5 | 5 | 76 | 79 | 3 |
| 5 | −13 | 5 | 65 | 60 | 3 | 7 | −8 | 5 | 123 | 120 | 3 | −8 | −3 | 5 | 280 | 272 | 3 | −9 | 1 | 5 | 200 | 196 | 2 | −8 | 5 | 5 | 69 | 65 | 3 |
| −9 | −12 | 5 | 105 | 103 | 3 | −12 | −7 | 5 | 61 | 71 | 4 | −7 | −3 | 5 | 181 | 177 | 2 | −8 | 1 | 5 | 139 | 144 | 2 | −7 | 5 | 5 | 69 | 67 | 3 |
| −8 | −12 | 5 | 61 | 58 | 4 | −11 | −7 | 5 | 123 | 119 | 2 | −6 | −3 | 5 | 141 | 146 | 2 | −7 | 1 | 5 | 212 | 205 | 2 | −6 | 5 | 5 | 97 | 102 | 3 |
| −7 | −12 | 5 | 45 | 44 | 3 | −10 | −7 | 5 | 40 | 40 | 5 | −5 | −3 | 5 | 432 | 426 | 7 | −6 | 1 | 5 | 109 | 113 | 2 | −5 | 5 | 5 | 167 | 174 | 3 |
| −6 | −12 | 5 | 123 | 124 | 2 | −9 | −7 | 5 | 108 | 112 | 2 | −4 | −3 | 5 | 286 | 274 | 4 | −5 | 1 | 5 | 186 | 194 | 5 | −4 | 5 | 5 | 145 | 142 | 8 |
| −5 | −12 | 5 | 95 | 90 | 4 | −8 | −7 | 5 | 116 | 124 | 2 | −3 | −3 | 5 | 425 | 396 | 8 | −4 | 1 | 5 | 182 | 182 | 5 | −3 | 5 | 5 | 180 | 180 | 8 |
| −4 | −12 | 5 | 160 | 162 | 2 | −7 | −7 | 5 | 92 | 97 | 2 | −2 | −3 | 5 | 341 | 334 | 6 | −3 | 1 | 5 | 72 | 62 | 6 | −2 | 5 | 5 | 156 | 145 | 5 |
| −3 | −12 | 5 | 176 | 173 | 3 | −6 | −7 | 5 | 221 | 217 | 2 | −1 | −3 | 5 | 143 | 116 | 3 | −2 | 1 | 5 | 525 | 506 | 9 | −1 | 5 | 5 | 61 | 92 | 11 |
| −2 | −12 | 5 | 181 | 179 | 2 | −5 | −7 | 5 | 103 | 105 | 1 | 0 | −3 | 5 | 219 | 208 | 4 | −1 | 1 | 5 | 92 | 91 | 5 | 0 | 5 | 5 | 230 | 234 | 4 |
| −1 | −12 | 5 | 37 | 45 | 2 | −4 | −7 | 5 | 118 | 124 | 1 | 1 | −3 | 5 | 136 | 134 | 2 | 0 | 1 | 5 | 504 | 477 | 9 | 1 | 5 | 5 | 268 | 271 | 3 |
| 0 | −12 | 5 | 61 | 61 | 3 | −3 | −7 | 5 | 168 | 169 | 1 | 2 | −3 | 5 | 191 | 186 | 2 | 1 | 1 | 5 | 307 | 308 | 4 | 2 | 5 | 5 | 37 | 38 | 5 |
| 1 | −12 | 5 | 167 | 170 | 3 | −2 | −7 | 5 | 143 | 144 | 1 | 3 | −3 | 5 | 69 | 72 | 3 | 2 | 1 | 5 | 34 | 35 | 3 | 3 | 5 | 5 | 144 | 134 | 3 |
| 2 | −12 | 5 | 40 | 44 | 6 | −1 | −7 | 5 | 118 | 114 | 1 | 4 | −3 | 5 | 99 | 99 | 3 | 3 | 1 | 5 | 114 | 111 | 2 | 4 | 5 | 5 | 424 | 427 | 4 |
| 3 | −12 | 5 | 157 | 149 | 3 | 0 | −7 | 5 | 69 | 79 | 1 | 5 | −3 | 5 | 70 | 67 | 4 | 4 | 1 | 5 | 39 | 40 | 4 | 5 | 5 | 5 | 80 | 80 | 2 |
| 4 | −12 | 5 | 30 | 27 | 7 | 1 | −7 | 5 | 23 | 27 | 4 | 6 | −3 | 5 | 38 | 36 | 8 | 5 | 1 | 5 | 103 | 103 | 2 | 6 | 5 | 5 | 140 | 138 | 3 |
| 5 | −12 | 5 | 77 | 76 | 4 | 2 | −7 | 5 | 93 | 90 | 2 | 7 | −3 | 5 | 85 | 80 | 3 | 6 | 1 | 5 | 128 | 126 | 3 | 7 | 5 | 5 | 139 | 141 | 2 |
| −10 | −11 | 5 | 27 | 18 | 10 | 3 | −7 | 5 | 199 | 203 | 2 | 8 | −3 | 5 | 91 | 89 | 3 | 7 | 1 | 5 | 100 | 96 | 3 | −12 | 6 | 5 | 59 | 58 | 4 |
| −9 | −11 | 5 | 92 | 83 | 5 | 4 | −7 | 5 | 66 | 68 | 3 | −13 | −2 | 5 | 68 | 69 | 6 | 8 | 1 | 5 | 50 | 52 | 7 | −11 | 6 | 5 | 45 | 49 | 5 |
| −8 | −11 | 5 | 190 | 184 | 5 | 5 | −7 | 5 | 61 | 63 | 3 | −12 | −2 | 5 | 108 | 98 | 5 | −13 | 2 | 5 | 57 | 69 | 10 | −10 | 6 | 5 | 99 | 100 | 3 |
| −7 | −11 | 5 | 146 | 143 | 3 | 6 | −7 | 5 | 61 | 60 | 3 | −11 | −2 | 5 | 60 | 56 | 5 | −12 | 2 | 5 | 99 | 99 | 4 | −9 | 6 | 5 | 22 | 28 | 11 |
| −6 | −11 | 5 | 96 | 101 | 2 | 7 | −7 | 5 | 93 | 109 | 4 | −10 | −2 | 5 | 42 | 53 | 7 | −11 | 2 | 5 | 56 | 56 | 4 | −8 | 6 | 5 | 121 | 119 | 3 |
| −5 | −11 | 5 | 25 | 21 | 3 | −12 | −6 | 5 | 53 | 57 | 3 | −9 | −2 | 5 | 52 | 47 | 5 | −10 | 2 | 5 | 53 | 52 | 4 | −7 | 6 | 5 | 185 | 192 | 3 |
| −4 | −11 | 5 | 147 | 143 | 1 | −11 | −6 | 5 | 48 | 49 | 4 | −8 | −2 | 5 | 116 | 121 | 2 | −9 | 2 | 5 | 50 | 46 | 4 | −6 | 6 | 5 | 123 | 120 | 3 |
| −3 | −11 | 5 | 130 | 127 | 2 | −10 | −6 | 5 | 98 | 100 | 3 | −7 | −2 | 5 | 76 | 82 | 2 | −8 | 2 | 5 | 116 | 120 | 2 | −5 | 6 | 5 | 189 | 195 | 3 |
| −2 | −11 | 5 | 141 | 137 | 2 | −9 | −6 | 5 | 28 | 29 | 7 | −6 | −2 | 5 | 87 | 106 | 2 | −7 | 2 | 5 | 74 | 82 | 2 | −4 | 6 | 5 | 167 | 185 | 6 |
| −1 | −11 | 5 | 157 | 161 | 2 | −8 | −6 | 5 | 121 | 120 | 2 | −5 | −2 | 5 | 144 | 130 | 4 | −6 | 2 | 5 | 90 | 105 | 2 | 0 | 6 | 5 | 211 | 229 | 3 |
| 0 | −11 | 5 | 153 | 142 | 2 | −7 | −6 | 5 | 184 | 192 | 2 | −4 | −2 | 5 | 44 | 33 | 4 | −5 | 2 | 5 | 144 | 130 | 5 | 1 | 6 | 5 | 72 | 78 | 4 |
| 1 | −11 | 5 | 199 | 200 | 2 | −6 | −6 | 5 | 118 | 121 | 1 | −3 | −2 | 5 | 226 | 239 | 4 | −4 | 2 | 5 | 50 | 33 | 7 | 2 | 6 | 5 | 91 | 98 | 3 |
| 2 | −11 | 5 | 101 | 98 | 4 | −5 | −6 | 5 | 196 | 200 | 1 | −2 | −2 | 5 | 325 | 333 | 6 | −3 | 2 | 5 | 229 | 239 | 5 | 3 | 6 | 5 | 127 | 133 | 3 |
| 3 | −11 | 5 | 246 | 240 | 3 | −4 | −6 | 5 | 175 | 187 | 2 | −1 | −2 | 5 | 121 | 135 | 3 | −2 | 2 | 5 | 335 | 333 | 7 | 4 | 6 | 5 | 170 | 172 | 3 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 4 | −11 | 5 | 39 | 31 | 4 | −3 | −6 | 5 | 226 | 222 | 3 | 0 | −2 | 5 | 161 | 153 | 3 | −1 | 2 | 5 | 129 | 135 | 5 | 5 | 6 | 5 | 7 | 21 | 7 |
| 5 | −11 | 5 | 70 | 68 | 3 | −2 | −6 | 5 | 170 | 167 | 2 | 1 | −2 | 5 | 179 | 186 | 2 | 0 | 2 | 5 | 166 | 154 | 5 | 6 | 6 | 5 | 99 | 91 | 3 |
| −11 | −10 | 5 | 29 | 37 | 10 | −1 | −6 | 5 | 131 | 140 | 1 | 2 | −2 | 5 | 94 | 101 | 2 | 1 | 2 | 5 | 175 | 185 | 2 | 7 | 6 | 5 | 82 | 79 | 3 |
| −10 | −10 | 5 | 97 | 93 | 2 | 0 | −6 | 5 | 214 | 229 | 2 | 3 | −2 | 5 | 117 | 124 | 2 | 2 | 2 | 5 | 98 | 100 | 2 | −12 | 7 | 5 | 65 | 71 | 3 |
| −9 | −10 | 5 | 78 | 76 | 3 | 1 | −6 | 5 | 77 | 78 | 2 | 4 | −2 | 5 | 182 | 183 | 3 | 3 | 2 | 5 | 119 | 125 | 2 | −11 | 7 | 5 | 117 | 119 | 3 |
| −8 | −10 | 5 | 123 | 127 | 3 | 2 | −6 | 5 | 90 | 98 | 2 | 5 | −2 | 5 | 98 | 99 | 3 | 4 | 2 | 5 | 182 | 183 | 2 | −10 | 7 | 5 | 44 | 40 | 4 |
| −7 | −10 | 5 | 124 | 122 | 3 | 3 | −6 | 5 | 127 | 133 | 2 | 6 | −2 | 5 | 76 | 75 | 4 | 5 | 2 | 5 | 88 | 100 | 3 | −9 | 7 | 5 | 105 | 112 | 3 |
| −6 | −10 | 5 | 331 | 323 | 3 | 4 | −6 | 5 | 171 | 172 | 3 | 7 | −2 | 5 | 146 | 149 | 4 | 6 | 2 | 5 | 76 | 76 | 2 | −8 | 7 | 5 | 119 | 124 | 3 |
| −5 | −10 | 5 | 181 | 180 | 2 | 5 | −6 | 5 | 18 | 21 | 17 | 8 | −2 | 5 | 33 | 42 | 12 | 7 | 2 | 5 | 149 | 148 | 3 | −7 | 7 | 5 | 97 | 98 | 3 |
| −4 | −10 | 5 | 138 | 128 | 2 | 6 | −6 | 5 | 97 | 90 | 3 | −13 | −1 | 5 | 100 | 92 | 5 | 8 | 2 | 5 | 47 | 41 | 6 | −6 | 7 | 5 | 218 | 217 | 3 |
| −3 | −10 | 5 | 244 | 251 | 2 | 7 | −6 | 5 | 80 | 78 | 3 | −12 | −1 | 5 | 152 | 151 | 3 | −13 | 3 | 5 | 52 | 42 | 11 | −5 | 7 | 5 | 98 | 105 | 3 |
| −2 | −10 | 5 | 43 | 42 | 1 | −12 | −5 | 5 | 58 | 49 | 4 | −11 | −1 | 5 | 124 | 114 | 4 | −12 | 3 | 5 | 31 | 23 | 9 | −4 | 7 | 5 | 121 | 125 | 4 |
| −1 | −10 | 5 | 29 | 29 | 2 | −11 | −5 | 5 | 17 | 32 | 17 | −10 | −1 | 5 | 99 | 100 | 5 | −11 | 3 | 5 | 29 | 24 | 8 | −3 | 7 | 5 | 165 | 170 | 6 |
| 0 | −10 | 5 | 194 | 186 | 2 | −10 | −5 | 5 | 103 | 107 | 3 | −9 | −1 | 5 | 195 | 185 | 2 | −10 | 3 | 5 | 203 | 193 | 3 | −1 | 7 | 5 | 110 | 114 | 4 |
| 1 | −10 | 5 | 166 | 171 | 2 | −9 | −5 | 5 | 76 | 79 | 3 | −8 | −1 | 5 | 136 | 144 | 2 | −9 | 3 | 5 | 34 | 41 | 3 | 0 | 7 | 5 | 71 | 80 | 4 |
| 2 | −10 | 5 | 99 | 88 | 3 | −8 | −5 | 5 | 62 | 65 | 3 | −7 | −1 | 5 | 212 | 205 | 2 | −8 | 3 | 5 | 276 | 272 | 2 | 1 | 7 | 5 | 22 | 27 | 13 |
| 3 | −10 | 5 | 133 | 132 | 2 | −7 | −5 | 5 | 70 | 67 | 2 | −6 | −1 | 5 | 108 | 113 | 2 | −7 | 3 | 5 | 178 | 177 | 2 | 2 | 7 | 5 | 96 | 90 | 4 |
| 4 | −10 | 5 | 87 | 75 | 3 | −6 | −5 | 5 | 96 | 102 | 2 | −5 | −1 | 5 | 177 | 195 | 4 | −6 | 3 | 5 | 143 | 147 | 2 | 3 | 7 | 5 | 200 | 203 | 3 |
| 5 | −10 | 5 | 73 | 71 | 3 | −5 | −5 | 5 | 167 | 173 | 2 | −4 | −1 | 5 | 176 | 181 | 4 | −5 | 3 | 5 | 442 | 427 | 8 | 4 | 7 | 5 | 64 | 67 | 4 |
| 6 | −10 | 5 | 139 | 130 | 3 | −4 | −5 | 5 | 152 | 142 | 3 | −3 | −1 | 5 | 73 | 61 | 3 | −4 | 3 | 5 | 287 | 274 | 6 | 5 | 7 | 5 | 61 | 63 | 3 |
| −11 | −9 | 5 | 136 | 137 | 2 | −3 | −5 | 5 | 189 | 180 | 3 | −2 | −1 | 5 | 498 | 506 | 7 | −3 | 3 | 5 | 434 | 397 | 8 | 6 | 7 | 5 | 65 | 59 | 3 |
| −10 | −9 | 5 | 54 | 47 | 4 | −2 | −5 | 5 | 163 | 145 | 3 | −1 | −1 | 5 | 92 | 92 | 3 | −2 | 3 | 5 | 341 | 334 | 7 | 7 | 7 | 5 | 113 | 110 | 2 |
| −9 | −9 | 5 | 109 | 110 | 3 | −1 | −5 | 5 | 69 | 93 | 3 | 0 | −1 | 5 | 493 | 476 | 7 | −1 | 3 | 5 | 147 | 115 | 5 | −12 | 8 | 5 | 49 | 51 | 5 |
| −11 | 8 | 5 | 84 | 79 | 3 | −9 | 14 | 5 | 61 | 64 | 7 | −4 | −10 | 6 | 35 | 36 | 3 | −9 | −5 | 6 | 138 | 142 | 3 | −6 | −1 | 6 | 176 | 159 | 2 |
| −10 | 8 | 5 | 58 | 58 | 4 | −8 | 14 | 5 | 81 | 89 | 6 | −3 | −10 | 6 | 146 | 150 | 1 | −8 | −5 | 6 | 258 | 262 | 3 | −5 | −1 | 6 | 134 | 120 | 2 |
| −9 | 8 | 5 | 111 | 113 | 3 | −7 | 14 | 5 | 37 | 44 | 13 | −2 | −10 | 6 | 121 | 125 | 2 | −7 | −5 | 6 | 72 | 71 | 3 | −4 | −1 | 6 | 35 | 42 | 10 |
| −8 | 8 | 5 | 167 | 176 | 3 | −6 | 14 | 5 | 62 | 63 | 8 | −1 | −10 | 6 | 68 | 63 | 2 | −6 | −5 | 6 | 147 | 156 | 2 | −3 | −1 | 6 | 119 | 110 | 6 |
| −7 | 8 | 5 | 150 | 154 | 4 | −5 | 14 | 5 | 0 | 28 | 1 | 0 | −10 | 6 | 40 | 36 | 3 | −5 | −5 | 6 | 151 | 138 | 2 | −2 | −1 | 6 | 146 | 131 | 5 |
| −6 | 8 | 5 | 144 | 142 | 4 | 1 | 14 | 5 | 49 | 52 | 10 | 1 | −10 | 6 | 202 | 199 | 3 | −4 | −5 | 6 | 253 | 254 | 2 | −1 | −1 | 6 | 295 | 317 | 3 |
| −5 | 8 | 5 | 112 | 111 | 4 | 2 | 14 | 5 | 120 | 128 | 5 | 2 | −10 | 6 | 150 | 143 | 3 | −3 | −5 | 6 | 33 | 338 | 3 | 0 | −1 | 6 | 143 | 136 | 2 |
| −4 | 8 | 5 | 159 | 153 | 4 | 3 | 14 | 5 | 78 | 84 | 7 | 3 | −10 | 6 | 24 | 19 | 7 | −2 | −5 | 6 | 141 | 149 | 2 | 1 | −1 | 6 | 148 | 137 | 2 |
| −3 | 8 | 5 | 219 | 224 | 5 | 4 | 14 | 5 | 33 | 31 | 10 | 4 | −10 | 6 | 130 | 124 | 4 | −1 | −5 | 6 | 106 | 109 | 2 | 2 | −1 | 6 | 72 | 68 | 2 |
| −2 | 8 | 5 | 182 | 197 | 7 | −8 | 15 | 5 | 122 | 115 | 6 | 5 | −10 | 6 | 90 | 85 | 4 | 0 | −5 | 6 | 80 | 81 | 2 | 3 | −1 | 6 | 143 | 148 | 3 |
| −1 | 8 | 5 | 116 | 115 | 4 | −7 | 15 | 5 | 79 | 86 | 7 | −11 | −9 | 6 | 20 | 24 | 10 | 1 | −5 | 6 | 56 | 63 | 3 | 4 | −1 | 6 | 130 | 117 | 3 |
| 0 | 8 | 5 | 135 | 141 | 4 | −6 | 15 | 5 | 44 | 49 | 10 | −10 | −9 | 6 | 53 | 49 | 4 | 2 | −5 | 6 | 226 | 234 | 3 | 5 | −1 | 6 | 186 | 185 | 4 |
| 1 | 8 | 5 | 90 | 93 | 4 | −5 | 15 | 5 | 71 | 68 | 8 | −9 | −9 | 6 | 58 | 54 | 4 | 3 | −5 | 6 | 148 | 141 | 3 | 6 | −1 | 6 | 81 | 74 | 4 |
| 2 | 8 | 5 | 134 | 136 | 4 | 1 | 15 | 5 | 112 | 94 | 7 | −8 | −9 | 6 | 325 | 323 | 3 | 4 | −5 | 6 | 180 | 181 | 3 | 7 | −1 | 6 | 44 | 45 | 6 |
| 3 | 8 | 5 | 99 | 103 | 4 | 2 | 15 | 5 | 108 | 100 | 6 | −7 | −9 | 6 | 139 | 136 | 2 | 5 | −5 | 6 | 91 | 97 | 3 | −13 | 0 | 6 | 157 | 154 | 4 |
| 4 | 8 | 5 | 57 | 57 | 4 | 3 | 15 | 5 | 59 | 64 | 7 | −6 | −9 | 6 | 100 | 96 | 1 | 6 | −5 | 6 | 109 | 114 | 3 | −12 | 0 | 6 | 49 | 43 | 6 |
| 5 | 8 | 5 | 68 | 63 | 3 | −7 | 16 | 5 | 59 | 57 | 7 | −5 | −9 | 6 | 160 | 163 | 1 | 7 | −5 | 6 | 86 | 77 | 3 | −11 | 0 | 6 | 22 | 14 | 21 |
| 6 | 8 | 5 | 92 | 81 | 4 | −6 | 16 | 5 | 58 | 64 | 9 | −4 | −9 | 6 | 320 | 323 | 2 | −13 | −4 | 6 | 47 | 48 | 5 | −10 | 0 | 6 | 96 | 94 | 3 |
| 7 | 8 | 5 | 118 | 121 | 3 | −6 | −16 | 6 | 44 | 50 | 4 | −3 | −9 | 6 | 44 | 44 | 2 | −12 | −4 | 6 | 0 | 14 | 1 | −9 | 0 | 6 | 52 | 58 | 3 |
| −11 | 9 | 5 | 143 | 136 | 3 | −5 | −16 | 6 | 64 | 71 | 3 | −2 | −9 | 6 | 178 | 177 | 2 | −11 | −4 | 6 | 100 | 97 | 4 | −8 | 0 | 6 | 175 | 177 | 2 |
| −10 | 9 | 5 | 53 | 46 | 4 | −4 | −16 | 6 | 59 | 58 | 4 | −1 | −9 | 6 | 266 | 262 | 2 | −10 | −4 | 6 | 33 | 39 | 8 | −7 | 0 | 6 | 213 | 211 | 2 |
| −9 | 9 | 5 | 102 | 111 | 3 | −3 | −16 | 6 | 99 | 111 | 3 | 0 | −9 | 6 | 82 | 77 | 2 | −9 | −4 | 6 | 197 | 198 | 3 | −6 | 0 | 6 | 268 | 282 | 2 |
| −8 | 9 | 5 | 44 | 39 | 6 | −2 | −16 | 6 | 106 | 104 | 3 | 1 | −9 | 6 | 165 | 157 | 2 | −8 | −4 | 6 | 184 | 192 | 2 | −5 | 0 | 6 | 112 | 105 | 2 |
| −7 | 9 | 5 | 71 | 65 | 5 | −1 | −16 | 6 | 133 | 135 | 7 | 2 | −9 | 6 | 110 | 117 | 3 | −7 | −4 | 6 | 64 | 59 | 2 | −4 | 0 | 6 | 99 | 95 | 6 |
| −6 | 9 | 5 | 107 | 112 | 5 | 0 | −16 | 6 | 59 | 50 | 10 | 3 | −9 | 6 | 195 | 190 | 4 | −6 | −4 | 6 | 251 | 258 | 2 | −3 | 0 | 6 | 485 | 485 | 13 |
| −5 | 9 | 5 | 71 | 70 | 5 | −7 | −15 | 6 | 65 | 77 | 4 | 4 | −9 | 6 | 84 | 85 | 4 | −5 | −4 | 6 | 154 | 161 | 2 | −2 | 0 | 6 | 18 | 27 | 17 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −4 | 9 | 5 | 159 | 155 | 4 | −5 | −15 | 6 | 93 | 95 | 4 | 5 | −9 | 6 | 60 | 52 | 4 | −4 | −4 | 6 | 68 | 73 | 3 | −1 | 0 | 6 | 65 | 77 | 7 |
| −3 | 9 | 5 | 173 | 175 | 7 | −4 | −15 | 6 | 47 | 51 | 4 | −12 | −8 | 6 | 52 | 63 | 4 | −3 | −4 | 6 | 179 | 170 | 3 | 0 | 0 | 6 | 14 | 2 | 11 |
| −1 | 9 | 5 | 77 | 77 | 7 | −3 | −15 | 6 | 98 | 94 | 3 | −11 | −8 | 6 | 69 | 73 | 3 | −2 | −4 | 6 | 195 | 193 | 3 | 1 | 0 | 6 | 52 | 63 | 2 |
| 0 | 9 | 5 | 133 | 136 | 5 | −2 | −15 | 6 | 77 | 82 | 3 | −10 | −8 | 6 | 117 | 114 | 2 | −1 | −4 | 6 | 166 | 172 | 2 | 2 | 0 | 6 | 80 | 78 | 2 |
| 1 | 9 | 5 | 52 | 44 | 6 | −1 | −15 | 6 | 51 | 57 | 12 | −9 | −8 | 6 | 67 | 71 | 3 | 0 | −4 | 6 | 174 | 181 | 2 | 3 | 0 | 6 | 201 | 204 | 2 |
| 2 | 9 | 5 | 274 | 280 | 4 | 0 | −15 | 6 | 153 | 152 | 7 | −8 | −8 | 6 | 118 | 114 | 2 | 1 | −4 | 6 | 152 | 151 | 2 | 4 | 0 | 6 | 254 | 261 | 3 |
| 3 | 9 | 5 | 67 | 69 | 6 | 1 | −15 | 6 | 53 | 51 | 12 | −7 | −8 | 6 | 132 | 134 | 2 | 2 | −4 | 6 | 108 | 104 | 3 | 5 | 0 | 6 | 152 | 155 | 3 |
| 4 | 9 | 5 | 52 | 60 | 4 | 2 | −15 | 6 | 0 | 24 | 1 | −6 | −8 | 6 | 105 | 108 | 2 | 3 | −4 | 6 | 141 | 140 | 3 | 6 | 0 | 6 | 14 | 8 | 13 |
| 5 | 9 | 5 | 131 | 131 | 3 | −6 | −14 | 6 | 35 | 42 | 6 | −5 | −8 | 6 | 109 | 118 | 2 | 4 | −4 | 6 | 57 | 51 | 4 | 7 | 0 | 6 | 50 | 62 | 6 |
| 6 | 9 | 5 | 133 | 133 | 3 | −5 | −14 | 6 | 143 | 144 | 4 | −4 | −8 | 6 | 150 | 150 | 1 | 5 | −4 | 6 | 50 | 46 | 5 | −13 | 1 | 6 | 86 | 81 | 5 |
| −11 | 10 | 5 | 34 | 37 | 7 | −4 | −14 | 6 | 32 | 36 | 7 | −3 | −8 | 6 | 90 | 87 | 1 | 6 | −4 | 6 | 131 | 138 | 3 | −12 | 1 | 6 | 169 | 161 | 4 |
| −10 | 10 | 5 | 100 | 93 | 3 | −3 | −14 | 6 | 0 | 9 | 1 | −2 | −8 | 6 | 38 | 30 | 2 | 7 | −4 | 6 | 145 | 143 | 4 | −11 | 1 | 6 | 45 | 42 | 6 |
| −9 | 10 | 5 | 75 | 77 | 4 | −2 | −14 | 6 | 38 | 49 | 6 | −1 | −8 | 6 | 141 | 141 | 1 | −13 | −3 | 6 | 40 | 42 | 7 | −10 | 1 | 6 | 70 | 68 | 3 |
| −8 | 10 | 5 | 122 | 127 | 4 | −1 | −14 | 6 | 65 | 57 | 10 | 0 | −8 | 6 | 33 | 35 | 3 | −12 | −3 | 6 | 62 | 61 | 4 | −9 | 1 | 6 | 158 | 152 | 2 |
| −7 | 10 | 5 | 119 | 122 | 5 | 0 | −14 | 6 | 142 | 129 | 7 | 1 | −8 | 6 | 51 | 54 | 3 | −11 | −3 | 6 | 123 | 118 | 5 | −8 | 1 | 6 | 55 | 66 | 3 |
| −6 | 10 | 5 | 334 | 323 | 6 | 1 | −14 | 6 | 86 | 98 | 9 | 2 | −8 | 6 | 155 | 159 | 2 | −10 | −3 | 6 | 71 | 71 | 5 | −7 | 1 | 6 | 184 | 190 | 2 |
| −5 | 10 | 5 | 180 | 180 | 5 | 2 | −14 | 6 | 24 | 45 | 24 | 3 | −8 | 6 | 55 | 49 | 3 | −9 | −3 | 6 | 109 | 108 | 3 | −6 | 1 | 6 | 173 | 159 | 2 |
| −4 | 10 | 5 | 123 | 128 | 7 | −6 | −13 | 6 | 72 | 72 | 4 | 4 | −8 | 6 | 68 | 69 | 3 | −8 | −3 | 6 | 76 | 78 | 3 | −5 | 1 | 6 | 132 | 120 | 2 |
| 0 | 10 | 5 | 181 | 186 | 7 | −5 | −13 | 6 | 30 | 45 | 8 | 5 | −8 | 6 | 61 | 64 | 2 | −7 | −3 | 6 | 78 | 73 | 3 | −4 | 1 | 6 | 27 | 41 | 15 |
| 1 | 10 | 5 | 173 | 171 | 5 | −4 | −13 | 6 | 74 | 82 | 4 | 6 | −8 | 6 | 16 | 13 | 16 | −6 | −3 | 6 | 142 | 142 | 2 | −3 | 1 | 6 | 128 | 110 | 6 |
| 2 | 10 | 5 | 94 | 88 | 5 | −3 | −13 | 6 | 85 | 82 | 4 | −12 | −7 | 6 | 62 | 68 | 4 | −5 | −3 | 6 | 90 | 81 | 2 | −2 | 1 | 6 | 147 | 132 | 5 |
| 3 | 10 | 5 | 131 | 132 | 4 | −2 | −13 | 6 | 123 | 120 | 4 | −11 | −7 | 6 | 61 | 60 | 3 | −4 | −3 | 6 | 98 | 107 | 2 | −1 | 1 | 6 | 294 | 317 | 4 |
| 4 | 10 | 5 | 76 | 75 | 4 | 0 | −13 | 6 | 43 | 52 | 3 | −10 | −7 | 6 | 129 | 130 | 3 | −3 | −3 | 6 | 146 | 147 | 3 | 0 | 1 | 6 | 144 | 136 | 2 |
| 5 | 10 | 5 | 72 | 71 | 3 | 1 | −13 | 6 | 185 | 185 | 3 | −9 | −7 | 6 | 91 | 84 | 2 | −2 | −3 | 6 | 180 | 166 | 3 | 1 | 1 | 6 | 148 | 138 | 2 |
| 6 | 10 | 5 | 132 | 129 | 3 | 2 | −13 | 6 | 26 | 26 | 8 | −8 | −7 | 6 | 0 | 18 | 1 | −1 | −3 | 6 | 112 | 121 | 2 | 2 | 1 | 6 | 72 | 69 | 2 |
| −10 | 11 | 5 | 22 | 18 | 11 | 3 | −13 | 6 | 68 | 67 | 3 | −7 | −7 | 6 | 262 | 260 | 2 | 0 | −3 | 6 | 406 | 428 | 3 | 3 | 1 | 6 | 145 | 149 | 2 |
| −9 | 11 | 5 | 89 | 83 | 3 | −8 | −12 | 6 | 82 | 78 | 3 | −6 | −7 | 6 | 113 | 120 | 2 | 1 | −3 | 6 | 167 | 160 | 3 | 4 | 1 | 6 | 126 | 117 | 2 |
| −8 | 11 | 5 | 185 | 183 | 4 | −7 | −12 | 6 | 36 | 31 | 5 | −5 | −7 | 6 | 173 | 172 | 1 | 2 | −3 | 6 | 94 | 99 | 3 | 5 | 1 | 6 | 175 | 185 | 3 |
| −7 | 11 | 5 | 153 | 143 | 5 | −6 | −12 | 6 | 40 | 40 | 6 | −4 | −7 | 6 | 315 | 311 | 2 | 3 | −3 | 6 | 108 | 98 | 3 | 6 | 1 | 6 | 85 | 72 | 4 |
| −6 | 11 | 5 | 103 | 102 | 5 | −5 | −12 | 6 | 147 | 151 | 4 | −3 | −7 | 6 | 142 | 148 | 1 | 4 | −3 | 6 | 55 | 57 | 5 | 7 | 1 | 6 | 58 | 45 | 6 |
| −5 | 11 | 5 | 0 | 20 | 1 | −4 | −12 | 6 | 222 | 229 | 4 | −2 | −7 | 6 | 248 | 249 | 2 | 5 | −3 | 6 | 145 | 135 | 4 | −13 | 2 | 6 | 102 | 103 | 4 |
| −4 | 11 | 5 | 127 | 143 | 7 | −3 | −12 | 6 | 151 | 144 | 3 | −1 | −7 | 6 | 46 | 35 | 2 | 6 | −3 | 6 | 57 | 59 | 4 | −12 | 2 | 6 | 33 | 40 | 9 |
| 0 | 11 | 5 | 146 | 142 | 7 | −2 | −12 | 6 | 172 | 168 | 3 | 0 | −7 | 6 | 164 | 165 | 2 | 7 | −3 | 6 | 60 | 64 | 4 | −11 | 2 | 6 | 137 | 142 | 3 |
| 1 | 11 | 5 | 200 | 200 | 7 | −1 | −12 | 6 | 56 | 55 | 5 | 1 | −7 | 6 | 260 | 267 | 2 | −13 | −2 | 6 | 110 | 103 | 4 | −10 | 2 | 6 | 160 | 157 | 3 |
| 2 | 11 | 5 | 110 | 98 | 5 | 0 | −12 | 6 | 84 | 84 | 5 | 2 | −7 | 6 | 199 | 198 | 2 | −12 | −2 | 6 | 43 | 40 | 10 | −9 | 2 | 6 | 238 | 238 | 3 |
| 3 | 11 | 5 | 239 | 239 | 4 | 1 | −12 | 6 | 177 | 173 | 5 | 3 | −7 | 6 | 62 | 66 | 3 | −11 | −2 | 6 | 145 | 142 | 3 | −8 | 2 | 6 | 125 | 125 | 2 |
| 4 | 11 | 5 | 0 | 31 | 1 | 2 | −12 | 6 | 29 | 30 | 10 | 4 | −7 | 6 | 112 | 107 | 2 | −10 | −2 | 6 | 146 | 156 | 4 | −7 | 2 | 6 | 188 | 1.71 | 2 |
| 5 | 11 | 5 | 75 | 69 | 3 | 3 | −12 | 6 | 118 | 117 | 4 | 5 | −7 | 6 | 35 | 31 | 5 | −9 | −2 | 6 | 236 | 238 | 3 | −6 | 2 | 6 | 112 | 103 | 2 |
| 6 | 11 | 5 | 73 | 77 | 5 | 4 | −12 | 6 | 0 | 20 | 1 | 6 | −7 | 6 | 195 | 189 | 3 | −8 | −2 | 6 | 124 | 125 | 3 | −5 | 2 | 6 | 364 | 372 | 3 |
| −10 | 12 | 5 | 58 | 68 | 3 | −10 | −11 | 6 | 57 | 58 | 5 | −12 | −6 | 6 | 138 | 145 | 3 | −7 | −2 | 6 | 187 | 172 | 2 | −4 | 2 | 6 | 431 | 421 | 8 |
| −9 | 12 | 5 | 100 | 103 | 3 | −9 | −11 | 6 | 32 | 33 | 9 | −11 | −6 | 6 | 33 | 11 | 6 | −6 | −2 | 6 | 109 | 102 | 2 | −3 | 2 | 6 | 213 | 200 | 6 |
| −8 | 12 | 5 | 53 | 58 | 8 | −8 | −11 | 6 | 85 | 84 | 3 | −10 | −6 | 6 | 85 | 89 | 3 | −5 | −2 | 6 | 361 | 372 | 3 | −2 | 2 | 6 | 151 | 141 | 5 |
| −7 | 12 | 5 | 56 | 45 | 7 | −7 | −11 | 6 | 134 | 133 | 3 | −9 | −6 | 6 | 17 | 15 | 16 | −4 | −2 | 6 | 418 | 421 | 7 | −1 | 2 | 6 | 95 | 93 | 3 |
| −6 | 12 | 5 | 137 | 124 | 6 | −6 | −11 | 6 | 176 | 191 | 2 | −8 | −6 | 6 | 171 | 170 | 2 | −3 | −2 | 6 | 202 | 200 | 3 | 0 | 2 | 6 | 34 | 33 | 3 |
| −5 | 12 | 5 | 100 | 90 | 7 | −5 | −11 | 6 | 215 | 224 | 2 | −7 | −6 | 6 | 82 | 86 | 2 | −2 | −2 | 6 | 147 | 141 | 3 | 1 | 2 | 6 | 96 | 102 | 2 |
| 0 | 12 | 5 | 76 | 61 | 8 | −4 | −11 | 6 | 107 | 104 | 1 | −6 | −6 | 6 | 34 | 39 | 3 | −1 | −2 | 6 | 94 | 92 | 2 | 2 | 2 | 6 | 235 | 241 | 2 |
| 1 | 12 | 5 | 166 | 170 | 7 | −3 | −11 | 6 | 89 | 79 | 2 | −5 | −6 | 6 | 181 | 183 | 2 | 0 | −2 | 6 | 38 | 33 | 4 | 3 | 2 | 6 | 34 | 27 | 5 |
| 2 | 12 | 5 | 52 | 45 | 9 | −2 | −11 | 6 | 186 | 174 | 5 | −4 | −6 | 6 | 139 | 140 | 1 | 1 | −2 | 6 | 93 | 102 | 2 | 4 | 2 | 6 | 145 | 147 | 3 |
| 3 | 12 | 5 | 155 | 149 | 4 | −1 | −11 | 6 | 208 | 198 | 3 | −3 | −6 | 6 | 89 | 81 | 2 | 2 | −2 | 6 | 230 | 241 | 2 | 5 | 2 | 6 | 253 | 254 | 3 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 4 | 12 | 5 | 29 | 27 | 11 | 0 | −11 | 6 | 110 | 111 | 3 | −2 | −6 | 6 | 54 | 62 | 2 | 3 | −2 | 6 | 32 | 26 | 8 | 6 | 2 | 6 | 127 | 122 | 4 |
| 5 | 12 | 5 | 81 | 75 | 3 | 1 | −11 | 6 | 68 | 79 | 3 | −1 | −6 | 6 | 152 | 148 | 2 | 4 | −2 | 6 | 148 | 147 | 3 | 7 | 2 | 6 | 30 | 10 | 9 |
| −9 | 13 | 5 | 62 | 74 | 5 | 2 | −11 | 6 | 139 | 138 | 3 | 0 | −6 | 6 | 132 | 130 | 2 | 5 | −2 | 6 | 256 | 254 | 4 | −13 | 3 | 6 | 55 | 43 | 6 |
| −8 | 13 | 5 | 130 | 126 | 6 | 3 | −11 | 6 | 85 | 82 | 3 | 1 | −6 | 6 | 63 | 62 | 2 | 6 | −2 | 6 | 123 | 122 | 4 | −12 | 3 | 6 | 65 | 62 | 4 |
| −7 | 13 | 5 | 63 | 59 | 8 | 4 | −11 | 6 | 18 | 12 | 9 | 2 | −6 | 6 | 93 | 90 | 3 | 7 | −2 | 6 | 0 | 10 | 1 | −11 | 3 | 6 | 129 | 118 | 2 |
| −6 | 13 | 5 | 111 | 103 | 7 | −11 | −10 | 6 | 65 | 55 | 5 | 3 | −6 | 6 | 109 | 114 | 3 | −13 | −1 | 6 | 90 | 81 | 5 | −10 | 3 | 6 | 75 | 71 | 3 |
| −5 | 13 | 5 | 90 | 85 | 7 | −10 | −10 | 6 | 68 | 68 | 2 | 4 | −6 | 6 | 60 | 60 | 4 | −12 | −1 | 6 | 165 | 162 | 3 | −9 | 3 | 6 | 106 | 108 | 2 |
| 1 | 13 | 5 | 115 | 91 | 7 | −9 | −10 | 6 | 32 | 31 | 5 | 5 | −6 | 6 | 51 | 54 | 4 | −11 | −1 | 6 | 48 | 42 | 6 | −8 | 3 | 6 | 78 | 78 | 2 |
| 2 | 13 | 5 | 65 | 57 | 7 | −8 | −10 | 6 | 29 | 27 | 6 | 6 | −6 | 6 | 162 | 158 | 3 | −10 | −1 | 6 | 71 | 67 | 5 | −7 | 3 | 6 | 85 | 74 | 2 |
| 3 | 13 | 5 | 91 | 99 | 7 | −7 | −10 | 6 | 43 | 45 | 4 | −12 | −5 | 6 | 58 | 64 | 4 | −9 | −1 | 6 | 159 | 153 | 2 | −6 | 3 | 6 | 140 | 142 | 2 |
| 4 | 13 | 5 | 18 | 19 | 18 | −6 | −10 | 6 | 140 | 139 | 3 | −11 | −5 | 6 | 94 | 86 | 3 | −8 | −1 | 6 | 62 | 66 | 2 | −5 | 3 | 6 | 96 | 81 | 3 |
| 5 | 13 | 5 | 54 | 60 | 8 | −5 | −10 | 6 | 71 | 70 | 2 | −10 | −5 | 6 | 75 | 77 | 4 | −7 | −1 | 6 | 183 | 189 | 2 | −4 | 3 | 6 | 103 | 107 | 3 |
| −3 | 3 | 6 | 144 | 147 | 4 | 4 | 7 | 6 | 117 | 108 | 3 | −9 | 13 | 6 | 108 | 112 | 3 | −5 | −9 | 7 | 13 | 14 | 12 | −9 | −4 | 7 | 179 | 175 | 3 |
| −2 | 3 | 6 | 180 | 166 | 3 | 5 | 7 | 6 | 22 | 31 | 11 | −8 | 13 | 6 | 79 | 74 | 7 | −4 | −9 | 7 | 219 | 232 | 2 | −8 | −4 | 7 | 137 | 140 | 2 |
| −1 | 3 | 6 | 115 | 120 | 3 | 6 | 7 | 6 | 195 | 189 | 3 | −7 | 13 | 6 | 46 | 45 | 10 | −3 | −9 | 7 | 178 | 182 | 2 | −7 | −4 | 7 | 111 | 113 | 2 |
| 0 | 3 | 6 | 405 | 427 | 3 | −12 | 8 | 6 | 59 | 63 | 4 | −6 | 13 | 6 | 78 | 72 | 8 | −2 | −9 | 7 | 193 | 199 | 2 | −6 | −4 | 7 | 148 | 147 | 2 |
| 1 | 3 | 6 | 166 | 159 | 2 | −11 | 8 | 6 | 58 | 73 | 4 | −5 | 13 | 6 | 44 | 45 | 13 | −1 | −9 | 7 | 167 | 168 | 2 | −5 | −4 | 7 | 84 | 86 | 2 |
| 2 | 3 | 6 | 94 | 99 | 2 | −10 | 8 | 6 | 121 | 113 | 3 | −4 | 13 | 6 | 82 | 82 | 8 | 0 | −9 | 7 | 147 | 157 | 2 | −4 | −4 | 7 | 109 | 115 | 3 |
| 3 | 3 | 6 | 104 | 98 | 2 | −9 | 8 | 6 | 75 | 72 | 3 | −1 | 13 | 6 | 103 | 77 | 7 | 1 | −9 | 7 | 66 | 64 | 3 | −3 | −4 | 7 | 75 | 68 | 3 |
| 4 | 3 | 6 | 49 | 57 | 4 | −8 | 8 | 6 | 111 | 114 | 3 | 0 | 13 | 6 | 46 | 52 | 10 | 2 | −9 | 7 | 22 | 26 | 8 | −2 | −4 | 7 | 149 | 158 | 3 |
| 5 | 3 | 6 | 134 | 134 | 2 | −7 | 8 | 6 | 131 | 135 | 3 | 1 | 13 | 6 | 180 | 185 | 5 | 3 | −9 | 7 | 55 | 54 | 4 | −1 | −4 | 7 | 250 | 250 | 3 |
| 6 | 3 | 6 | 64 | 60 | 5 | −6 | 8 | 6 | 106 | 108 | 4 | 2 | 13 | 6 | 39 | 26 | 9 | 4 | −9 | 7 | 12 | 8 | 12 | 0 | −4 | 7 | 183 | 192 | 3 |
| 7 | 3 | 6 | 70 | 64 | 4 | −5 | 8 | 6 | 113 | 117 | 4 | 3 | 13 | 6 | 75 | 67 | 5 | −12 | −8 | 7 | 88 | 86 | 4 | 1 | −4 | 7 | 238 | 245 | 3 |
| −13 | 4 | 6 | 43 | 48 | 10 | −4 | 8 | 6 | 149 | 150 | 3 | −9 | 14 | 6 | 76 | 71 | 6 | −11 | −8 | 7 | 104 | 99 | 4 | 2 | −4 | 7 | 162 | 172 | 3 |
| −12 | 4 | 6 | 0 | 15 | 1 | −3 | 8 | 6 | 88 | 87 | 3 | −8 | 14 | 6 | 48 | 62 | 9 | −10 | −8 | 7 | 20 | 18 | 7 | 3 | −4 | 7 | 192 | 201 | 3 |
| −11 | 4 | 6 | 106 | 97 | 3 | −2 | 8 | 6 | 41 | 29 | 6 | −7 | 14 | 6 | 43 | 55 | 9 | −9 | −8 | 7 | 94 | 95 | 2 | 4 | −4 | 7 | 125 | 129 | 3 |
| −10 | 4 | 6 | 30 | 39 | 7 | −1 | 8 | 6 | 142 | 142 | 3 | −6 | 14 | 6 | 45 | 42 | 10 | −8 | −8 | 7 | 202 | 208 | 3 | 5 | −4 | 7 | 0 | 7 | 1 |
| −9 | 4 | 6 | 198 | 198 | 2 | 0 | 8 | 6 | 34 | 34 | 8 | −5 | 14 | 6 | 149 | 144 | 6 | −7 | −8 | 7 | 165 | 165 | 2 | 6 | −4 | 7 | 33 | 32 | 8 |
| −8 | 4 | 6 | 186 | 192 | 2 | 1 | 8 | 6 | 52 | 55 | 5 | −4 | 14 | 6 | 26 | 37 | 25 | −6 | −8 | 7 | 178 | 176 | 2 | −13 | −3 | 7 | 32 | 35 | 10 |
| −7 | 4 | 6 | 62 | 58 | 3 | 2 | 8 | 6 | 161 | 159 | 3 | 0 | 14 | 6 | 123 | 129 | 7 | −5 | −8 | 7 | 188 | 183 | 2 | −12 | −3 | 7 | 66 | 55 | 4 |
| −6 | 4 | 6 | 247 | 257 | 2 | 3 | 8 | 6 | 53 | 49 | 4 | 1 | 14 | 6 | 105 | 98 | 7 | −4 | −8 | 7 | 153 | 149 | 2 | −11 | −3 | 7 | 208 | 199 | 3 |
| −5 | 4 | 6 | 156 | 161 | 3 | 4 | 8 | 6 | 67 | 68 | 3 | 2 | 14 | 6 | 29 | 45 | 20 | −3 | −8 | 7 | 112 | 115 | 2 | −10 | −3 | 7 | 146 | 142 | 3 |
| −4 | 4 | 6 | 67 | 72 | 3 | 5 | 8 | 6 | 64 | 63 | 3 | 3 | 14 | 6 | 30 | 18 | 14 | −2 | −8 | 7 | 191 | 185 | 2 | −9 | −3 | 7 | 212 | 203 | 3 |
| −3 | 4 | 6 | 176 | 170 | 3 | 6 | 8 | 6 | 21 | 14 | 12 | −8 | 15 | 6 | 25 | 15 | 20 | −1 | −8 | 7 | 66 | 72 | 2 | −8 | −3 | 7 | 131 | 122 | 3 |
| −2 | 4 | 6 | 197 | 193 | 3 | −11 | 9 | 6 | 0 | 24 | 1 | −7 | 15 | 6 | 67 | 76 | 7 | 0 | −8 | 7 | 25 | 28 | 6 | −7 | −3 | 7 | 31 | 38 | 6 |
| −1 | 4 | 6 | 167 | 172 | 3 | −10 | 9 | 6 | 41 | 49 | 5 | −6 | 15 | 6 | 58 | 45 | 8 | 1 | −8 | 7 | 181 | 174 | 2 | −6 | −3 | 7 | 153 | 151 | 3 |
| 0 | 4 | 6 | 174 | 181 | 3 | −9 | 9 | 6 | 55 | 54 | 4 | −5 | 15 | 6 | 92 | 94 | 7 | 2 | −8 | 7 | 32 | 34 | 5 | −5 | −3 | 7 | 52 | 55 | 3 |
| 1 | 4 | 6 | 148 | 150 | 2 | −8 | 9 | 6 | 322 | 323 | 5 | 0 | 15 | 6 | 155 | 152 | 6 | 3 | −8 | 7 | 76 | 71 | 3 | −4 | −3 | 7 | 153 | 161 | 2 |
| 2 | 4 | 6 | 105 | 103 | 2 | −7 | 9 | 6 | 147 | 137 | 4 | 1 | 15 | 6 | 58 | 50 | 8 | 4 | −8 | 7 | 62 | 60 | 3 | −3 | −3 | 7 | 135 | 144 | 2 |
| 3 | 4 | 6 | 144 | 140 | 2 | −6 | 9 | 6 | 101 | 97 | 4 | 2 | 15 | 6 | 38 | 24 | 10 | 5 | −8 | 7 | 46 | 39 | 5 | −2 | −3 | 7 | 149 | 154 | 2 |
| 4 | 4 | 6 | 46 | 52 | 4 | −5 | 9 | 6 | 157 | 163 | 4 | −6 | 16 | 6 | 42 | 50 | 10 | −12 | −7 | 7 | 57 | 64 | 4 | −1 | −3 | 7 | 58 | 49 | 3 |
| 5 | 4 | 6 | 43 | 46 | 5 | −4 | 9 | 6 | 317 | 323 | 5 | −3 | −15 | 7 | 113 | 114 | 7 | −11 | −7 | 7 | 60 | 58 | 3 | 0 | −3 | 7 | 267 | 266 | 3 |
| 6 | 4 | 6 | 133 | 138 | 3 | −3 | 9 | 6 | 41 | 44 | 7 | −1 | −15 | 7 | 31 | 21 | 30 | −10 | −7 | 7 | 130 | 141 | 3 | 1 | −3 | 7 | 82 | 78 | 3 |
| 7 | 4 | 6 | 148 | 143 | 4 | −2 | 9 | 6 | 165 | 177 | 5 | 0 | −15 | 7 | 18 | 44 | 18 | −9 | −7 | 7 | 171 | 171 | 2 | 2 | −3 | 7 | 54 | 52 | 4 |
| −12 | 5 | 6 | 67 | 64 | 3 | −1 | 9 | 6 | 259 | 262 | 5 | −3 | −14 | 7 | 71 | 69 | 9 | −8 | −7 | 7 | 80 | 79 | 3 | 3 | −3 | 7 | 222 | 219 | 5 |
| −11 | 5 | 6 | 90 | 86 | 3 | 0 | 9 | 6 | 82 | 77 | 5 | −2 | −14 | 7 | 56 | 58 | 11 | −7 | −7 | 7 | 176 | 172 | 2 | 4 | −3 | 7 | 112 | 114 | 4 |
| −10 | 5 | 6 | 73 | 77 | 3 | 1 | 9 | 6 | 162 | 158 | 4 | −1 | −14 | 7 | 99 | 96 | 8 | −6 | −7 | 7 | 37 | 37 | 3 | 5 | −3 | 7 | 83 | 81 | 6 |
| −9 | 5 | 6 | 140 | 142 | 2 | 2 | 9 | 6 | 118 | 116 | 4 | 0 | −14 | 7 | 39 | 46 | 16 | −5 | −7 | 7 | 43 | 40 | 3 | 6 | −3 | 7 | 96 | 93 | 3 |
| −8 | 5 | 6 | 262 | 263 | 3 | 3 | 9 | 6 | 190 | 191 | 3 | 1 | −14 | 7 | 67 | 73 | 9 | −4 | −7 | 7 | 157 | 158 | 2 | −13 | −2 | 7 | 71 | 73 | 4 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −7 | 5 | 6 | 71 | 71 | 3 | 4 | 9 | 6 | 90 | 85 | 3 | −3 | −13 | 7 | 69 | 56 | 8 | −3 | −7 | 7 | 123 | 131 | 2 | −12 | −2 | 7 | 60 | 52 | 7 |
| −6 | 5 | 6 | 146 | 156 | 2 | 5 | 9 | 6 | 71 | 52 | 3 | −2 | −13 | 7 | 116 | 120 | 8 | −2 | −7 | 7 | 67 | 61 | 2 | −11 | −2 | 7 | 125 | 120 | 4 |
| −5 | 5 | 6 | 147 | 138 | 2 | 6 | 9 | 6 | 70 | 62 | 8 | −1 | −13 | 7 | 92 | 97 | 3 | −1 | −7 | 7 | 98 | 94 | 2 | −10 | −2 | 7 | 110 | 120 | 4 |
| −4 | 5 | 6 | 251 | 254 | 3 | −11 | 10 | 6 | 50 | 55 | 5 | 0 | −13 | 7 | 91 | 96 | 3 | 0 | −7 | 7 | 12 | 9 | 11 | −9 | −2 | 7 | 106 | 104 | 4 |
| −3 | 5 | 6 | 325 | 337 | 4 | −10 | 10 | 6 | 66 | 68 | 3 | 1 | −13 | 7 | 61 | 51 | 2 | 1 | −7 | 7 | 246 | 249 | 3 | −8 | −2 | 7 | 134 | 131 | 3 |
| −2 | 5 | 6 | 139 | 148 | 3 | −9 | 10 | 6 | 33 | 31 | 7 | 2 | −13 | 7 | 87 | 90 | 3 | 2 | −7 | 7 | 85 | 82 | 2 | −7 | −2 | 7 | 67 | 68 | 3 |
| −1 | 5 | 6 | 111 | 109 | 3 | −8 | 10 | 6 | 32 | 27 | 9 | −4 | −12 | 7 | 181 | 171 | 7 | 3 | −7 | 7 | 60 | 59 | 3 | −6 | −2 | 7 | 50 | 48 | 3 |
| 0 | 5 | 6 | 82 | 81 | 3 | −7 | 10 | 6 | 41 | 44 | 7 | −3 | −12 | 7 | 138 | 146 | 3 | 4 | −7 | 7 | 94 | 95 | 4 | −5 | −2 | 7 | 183 | 192 | 2 |
| 1 | 5 | 6 | 63 | 63 | 4 | −6 | 10 | 6 | 140 | 139 | 4 | −2 | −12 | 7 | 38 | 31 | 6 | 5 | −7 | 7 | 105 | 104 | 2 | −4 | −2 | 7 | 109 | 104 | 2 |
| 2 | 5 | 6 | 236 | 234 | 3 | −5 | 10 | 6 | 60 | 70 | 6 | −1 | −12 | 7 | 60 | 68 | 5 | −12 | −6 | 7 | 110 | 113 | 2 | −3 | −2 | 7 | 172 | 162 | 2 |
| 3 | 5 | 6 | 149 | 141 | 2 | −4 | 10 | 6 | 45 | 37 | 11 | 0 | −12 | 7 | 142 | 133 | 5 | −11 | −6 | 7 | 34 | 36 | 6 | −2 | −2 | 7 | 174 | 198 | 2 |
| 4 | 5 | 6 | 183 | 181 | 2 | −3 | 10 | 6 | 137 | 150 | 7 | 1 | −12 | 7 | 148 | 137 | 5 | −10 | −6 | 7 | 68 | 67 | 4 | −1 | −2 | 7 | 96 | 91 | 2 |
| 5 | 5 | 6 | 104 | 97 | 3 | −2 | 10 | 6 | 129 | 124 | 5 | 2 | −12 | 7 | 80 | 82 | 4 | −9 | −6 | 7 | 158 | 156 | 3 | 0 | −2 | 7 | 81 | 83 | 2 |
| 6 | 5 | 6 | 112 | 113 | 2 | −1 | 10 | 6 | 63 | 62 | 6 | 3 | −12 | 7 | 53 | 56 | 4 | −8 | −6 | 7 | 103 | 108 | 3 | 1 | −2 | 7 | 102 | 103 | 3 |
| 7 | 5 | 6 | 78 | 77 | 7 | 0 | 10 | 6 | 48 | 37 | 7 | −10 | −11 | 7 | 122 | 118 | 4 | −7 | −6 | 7 | 103 | 109 | 2 | 2 | −2 | 7 | 81 | 75 | 3 |
| −12 | 6 | 6 | 146 | 145 | 2 | 1 | 10 | 6 | 196 | 198 | 4 | −9 | −11 | 7 | 78 | 76 | 4 | −6 | −6 | 7 | 190 | 191 | 2 | 3 | −2 | 7 | 41 | 35 | 7 |
| −11 | 6 | 6 | 14 | 11 | 13 | 2 | 10 | 6 | 153 | 143 | 4 | −8 | −11 | 7 | 43 | 47 | 3 | −5 | −6 | 7 | 76 | 68 | 2 | 4 | −2 | 7 | 85 | 89 | 5 |
| −10 | 6 | 6 | 86 | 89 | 3 | 3 | 10 | 6 | 16 | 20 | 16 | −7 | −11 | 7 | 74 | 75 | 2 | −4 | −6 | 7 | 201 | 201 | 2 | 5 | −2 | 7 | 185 | 182 | 4 |
| −9 | 6 | 6 | 0 | 15 | 1 | 4 | 10 | 6 | 127 | 124 | 3 | −6 | −11 | 7 | 118 | 127 | 2 | −3 | −6 | 7 | 162 | 161 | 2 | 6 | −2 | 7 | 42 | 36 | 9 |
| −8 | 6 | 6 | 171 | 170 | 3 | 5 | 10 | 6 | 86 | 85 | 3 | −5 | −11 | 7 | 50 | 55 | 3 | −2 | −6 | 7 | 51 | 51 | 2 | −13 | −1 | 7 | 75 | 59 | 6 |
| −7 | 6 | 6 | 80 | 86 | 3 | −10 | 11 | 6 | 59 | 59 | 3 | −4 | −11 | 7 | 53 | 53 | 2 | −1 | −6 | 7 | 197 | 195 | 2 | −12 | −1 | 7 | 88 | 85 | 4 |
| −6 | 6 | 6 | 25 | 38 | 9 | −9 | 11 | 6 | 36 | 32 | 6 | −3 | −11 | 7 | 37 | 37 | 3 | 0 | −6 | 7 | 171 | 172 | 2 | −11 | −1 | 7 | 92 | 92 | 4 |
| −5 | 6 | 6 | 185 | 184 | 3 | −8 | 11 | 6 | 88 | 84 | 4 | −2 | −11 | 7 | 167 | 160 | 5 | 1 | −6 | 7 | 70 | 71 | 3 | −10 | −1 | 7 | 210 | 220 | 4 |
| −4 | 6 | 6 | 138 | 139 | 3 | −7 | 11 | 6 | 133 | 133 | 4 | −1 | −11 | 7 | 31 | 25 | 4 | 2 | −6 | 7 | 162 | 169 | 3 | −9 | −1 | 7 | 105 | 105 | 3 |
| −3 | 6 | 6 | 90 | 81 | 3 | −6 | 11 | 6 | 188 | 191 | 5 | 0 | −11 | 7 | 192 | 207 | 3 | 3 | −6 | 7 | 112 | 117 | 3 | −8 | −1 | 7 | 56 | 51 | 3 |
| −2 | 6 | 6 | 53 | 62 | 4 | −5 | 11 | 6 | 222 | 223 | 7 | 1 | −11 | 7 | 109 | 102 | 3 | 4 | −6 | 7 | 177 | 177 | 3 | −7 | −1 | 7 | 77 | 77 | 2 |
| −1 | 6 | 6 | 146 | 148 | 3 | −4 | 11 | 6 | 97 | 104 | 8 | 2 | −11 | 7 | 0 | 12 | 1 | 5 | −6 | 7 | 49 | 45 | 5 | −6 | −1 | 7 | 250 | 242 | 2 |
| 0 | 6 | 6 | 131 | 130 | 3 | −3 | 11 | 6 | 87 | 79 | 8 | 3 | −11 | 7 | 25 | 21 | 5 | −12 | −5 | 7 | 145 | 142 | 3 | −5 | −1 | 7 | 151 | 145 | 2 |
| 1 | 6 | 6 | 74 | 62 | 3 | −2 | 11 | 6 | 168 | 174 | 5 | −11 | −10 | 7 | 58 | 61 | 5 | −11 | −5 | 7 | 176 | 178 | 3 | −4 | −1 | 7 | 129 | 125 | 2 |
| 2 | 6 | 6 | 93 | 90 | 3 | −1 | 11 | 6 | 197 | 199 | 5 | −10 | −10 | 7 | 99 | 92 | 2 | −10 | −5 | 7 | 152 | 159 | 3 | −3 | −1 | 7 | 66 | 69 | 2 |
| 3 | 6 | 6 | 118 | 114 | 3 | 0 | 11 | 6 | 116 | 111 | 5 | −9 | −10 | 7 | 32 | 27 | 5 | −9 | −5 | 7 | 183 | 179 | 3 | −2 | −1 | 7 | 193 | 194 | 2 |
| 4 | 6 | 6 | 62 | 59 | 3 | 1 | 11 | 6 | 78 | 79 | 5 | −8 | −10 | 7 | 65 | 67 | 3 | −8 | −5 | 7 | 127 | 126 | 3 | −1 | −1 | 7 | 183 | 199 | 2 |
| 5 | 6 | 6 | 57 | 54 | 4 | 2 | 11 | 6 | 140 | 139 | 4 | −7 | −10 | 7 | 72 | 71 | 3 | −7 | −5 | 7 | 94 | 91 | 2 | 0 | −1 | 7 | 226 | 216 | 2 |
| 6 | 6 | 6 | 165 | 159 | 2 | 3 | 11 | 6 | 95 | 82 | 5 | −6 | −10 | 7 | 81 | 78 | 3 | −6 | −5 | 7 | 160 | 160 | 2 | 1 | −1 | 7 | 29 | 23 | 6 |
| −12 | 7 | 6 | 65 | 68 | 3 | 4 | 11 | 6 | 23 | 12 | 10 | −5 | −10 | 7 | 75 | 75 | 3 | −5 | −5 | 7 | 131 | 142 | 2 | 2 | −1 | 7 | 87 | 95 | 3 |
| −11 | 7 | 6 | 64 | 60 | 4 | 5 | 11 | 6 | 89 | 92 | 4 | −4 | −10 | 7 | 334 | 333 | 3 | −4 | −5 | 7 | 226 | 226 | 2 | 3 | −1 | 7 | 198 | 210 | 3 |
| −10 | 7 | 6 | 132 | 131 | 3 | −10 | 12 | 6 | 130 | 129 | 2 | −3 | −10 | 7 | 112 | 110 | 2 | −3 | −5 | 7 | 257 | 268 | 2 | 4 | −1 | 7 | 166 | 162 | 3 |
| −9 | 7 | 6 | 87 | 84 | 3 | −9 | 12 | 6 | 114 | 110 | 3 | −2 | −10 | 7 | 78 | 88 | 2 | −2 | −5 | 7 | 168 | 169 | 2 | 5 | −1 | 7 | 41 | 31 | 8 |
| −8 | 7 | 6 | 0 | 18 | 1 | −8 | 12 | 6 | 80 | 77 | 5 | −1 | −10 | 7 | 28 | 34 | 5 | −1 | −5 | 7 | 349 | 343 | 3 | 6 | −1 | 7 | 84 | 88 | 4 |
| −7 | 7 | 6 | 265 | 260 | 3 | −7 | 12 | 6 | 33 | 30 | 13 | 0 | −10 | 7 | 210 | 217 | 3 | 0 | −5 | 7 | 205 | 209 | 3 | −13 | 0 | 7 | 43 | 34 | 10 |
| −6 | 7 | 6 | 117 | 119 | 3 | −6 | 12 | 6 | 54 | 40 | 9 | 1 | −10 | 7 | 237 | 237 | 4 | 1 | −5 | 7 | 145 | 151 | 3 | −12 | 0 | 7 | 66 | 57 | 5 |
| −5 | 7 | 6 | 172 | 172 | 3 | −5 | 12 | 6 | 150 | 152 | 7 | 2 | −10 | 7 | 80 | 83 | 3 | 2 | −5 | 7 | 98 | 106 | 3 | −11 | 0 | 7 | 109 | 106 | 4 |
| −4 | 7 | 6 | 307 | 311 | 4 | −4 | 12 | 6 | 217 | 230 | 7 | 3 | −10 | 7 | 156 | 152 | 3 | 3 | −5 | 7 | 133 | 137 | 3 | −10 | 0 | 7 | 204 | 203 | 4 |
| −3 | 7 | 6 | 140 | 149 | 3 | −3 | 12 | 6 | 144 | 144 | 7 | 4 | −10 | 7 | 32 | 38 | 5 | 4 | −5 | 7 | 114 | 116 | 3 | −9 | 0 | 7 | 84 | 90 | 2 |
| −2 | 7 | 6 | 246 | 250 | 3 | −1 | 12 | 6 | 55 | 55 | 10 | −11 | −9 | 7 | 76 | 74 | 3 | 5 | −5 | 7 | 43 | 33 | 5 | −8 | 0 | 7 | 114 | 114 | 2 |
| −1 | 7 | 6 | 46 | 34 | 5 | 0 | 12 | 6 | 92 | 84 | 5 | −10 | −9 | 7 | 58 | 59 | 4 | 6 | −5 | 7 | 70 | 69 | 4 | −7 | 0 | 7 | 166 | 167 | 2 |
| 0 | 7 | 6 | 164 | 166 | 3 | 1 | 12 | 6 | 170 | 173 | 5 | −9 | −9 | 7 | 105 | 106 | 3 | −13 | −4 | 7 | 109 | 114 | 4 | −6 | 0 | 7 | 9 | 7 | 9 |
| 1 | 7 | 6 | 263 | 266 | 4 | 2 | 12 | 6 | 1 | 30 | 1 | −8 | −9 | 7 | 96 | 97 | 2 | −12 | −4 | 7 | 63 | 66 | 4 | −5 | 0 | 7 | 127 | 146 | 1 |
| 2 | 7 | 6 | 205 | 198 | 3 | 3 | 12 | 6 | 116 | 116 | 4 | −7 | −9 | 7 | 177 | 178 | 3 | −11 | −4 | 7 | 57 | 63 | 5 | −4 | 0 | 7 | 12 | 2 | 12 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 3 | 7 | 6 | 69 | 66 | 3 | 4 | 12 | 6 | 0 | 19 | 1 | −6 | −9 | 7 | 46 | 40 | 3 | −10 | −4 | 7 | 187 | 183 | 3 | −3 | 0 | 7 | 113 | 111 | 2 |
| −2 | 0 | 7 | 72 | 70 | 2 | 6 | 4 | 7 | 31 | 32 | 10 | 2 | 9 | 7 | 19 | 25 | 19 | −3 | −12 | 8 | 92 | 91 | 3 | −6 | −6 | 8 | 88 | 92 | 3 |
| −1 | 0 | 7 | 73 | 76 | 2 | −12 | 5 | 7 | 147 | 143 | 3 | 3 | 9 | 7 | 55 | 54 | 4 | −2 | −12 | 8 | 85 | 82 | 4 | −5 | −6 | 8 | 172 | 176 | 2 |
| 0 | 0 | 7 | 94 | 107 | 2 | −11 | 5 | 7 | 186 | 179 | 3 | 4 | 9 | 7 | 0 | 7 | 1 | −1 | −12 | 8 | 49 | 43 | 6 | −4 | −6 | 8 | 123 | 124 | 2 |
| 1 | 0 | 7 | 54 | 57 | 3 | −10 | 5 | 7 | 156 | 159 | 2 | −11 | 10 | 7 | 55 | 62 | 5 | 0 | −12 | 8 | 72 | 68 | 5 | −3 | −6 | 8 | 174 | 169 | 2 |
| 2 | 0 | 7 | 45 | 37 | 4 | −9 | 5 | 7 | 173 | 179 | 3 | −10 | 10 | 7 | 96 | 92 | 3 | 1 | −12 | 8 | 21 | 6 | 12 | −2 | −6 | 8 | 168 | 176 | 2 |
| 3 | 0 | 7 | 6 | 27 | 5 | −8 | 5 | 7 | 132 | 125 | 2 | −9 | 10 | 7 | 27 | 27 | 9 | 2 | −12 | 8 | 98 | 91 | 3 | −1 | −6 | 8 | 224 | 221 | 3 |
| 4 | 0 | 7 | 79 | 87 | 4 | −7 | 5 | 7 | 98 | 92 | 3 | −8 | 10 | 7 | 59 | 68 | 5 | −10 | −11 | 8 | 85 | 87 | 3 | 0 | −6 | 8 | 123 | 135 | 3 |
| 5 | 0 | 7 | 140 | 135 | 3 | −6 | 5 | 7 | 170 | 160 | 2 | −7 | 10 | 7 | 75 | 72 | 5 | −9 | −11 | 8 | 153 | 152 | 4 | 1 | −6 | 8 | 195 | 205 | 3 |
| 6 | 0 | 7 | 42 | 49 | 8 | −5 | 5 | 7 | 129 | 141 | 2 | −6 | 10 | 7 | 85 | 78 | 5 | −8 | −11 | 8 | 29 | 27 | 4 | 2 | −6 | 8 | 16 | 14 | 15 |
| −13 | 1 | 7 | 60 | 59 | 7 | −4 | 5 | 7 | 224 | 226 | 3 | −5 | 10 | 7 | 70 | 75 | 5 | −7 | −11 | 8 | 107 | 108 | 2 | 3 | −6 | 8 | 30 | 33 | 9 |
| −12 | 1 | 7 | 90 | 85 | 5 | −3 | 5 | 7 | 258 | 269 | 4 | −4 | 10 | 7 | 326 | 332 | 5 | −6 | −11 | 8 | 127 | 122 | 3 | 4 | −6 | 8 | 27 | 30 | 9 |
| −11 | 1 | 7 | 94 | 92 | 4 | −2 | 5 | 7 | 172 | 169 | 3 | −3 | 10 | 7 | 114 | 110 | 4 | −5 | −11 | 8 | 76 | 80 | 3 | −12 | −5 | 8 | 88 | 91 | 4 |
| −10 | 1 | 7 | 218 | 220 | 3 | −1 | 5 | 7 | 347 | 344 | 4 | −2 | 10 | 7 | 84 | 88 | 6 | −4 | −11 | 8 | 82 | 73 | 2 | −11 | −5 | 8 | 74 | 76 | 4 |
| −9 | 1 | 7 | 112 | 105 | 2 | 0 | 5 | 7 | 206 | 209 | 2 | −1 | 10 | 7 | 17 | 35 | 17 | −3 | −11 | 8 | 117 | 113 | 5 | −10 | −5 | 8 | 92 | 96 | 3 |
| −8 | 1 | 7 | 53 | 51 | 3 | 1 | 5 | 7 | 147 | 151 | 2 | 0 | 10 | 7 | 219 | 217 | 4 | −2 | −11 | 8 | 129 | 117 | 5 | −9 | −5 | 8 | 74 | 77 | 4 |
| −7 | 1 | 7 | 75 | 77 | 2 | 2 | 5 | 7 | 106 | 106 | 2 | 1 | 10 | 7 | 231 | 238 | 4 | −1 | −11 | 8 | 105 | 107 | 2 | −8 | −5 | 8 | 79 | 82 | 4 |
| −6 | 1 | 7 | 250 | 242 | 2 | 3 | 5 | 7 | 134 | 137 | 2 | 2 | 10 | 7 | 83 | 83 | 3 | 0 | −11 | 8 | 126 | 119 | 3 | −7 | −5 | 8 | 166 | 167 | 2 |
| −5 | 1 | 7 | 152 | 146 | 1 | 4 | 5 | 7 | 120 | 115 | 3 | 3 | 10 | 7 | 150 | 152 | 3 | 1 | −11 | 8 | 77 | 81 | 5 | −6 | −5 | 8 | 31 | 31 | 6 |
| −4 | 1 | 7 | 128 | 125 | 2 | 5 | 5 | 7 | 39 | 33 | 4 | 4 | 10 | 7 | 46 | 38 | 5 | 2 | −11 | 8 | 62 | 56 | 5 | −5 | −5 | 8 | 168 | 168 | 3 |
| −3 | 1 | 7 | 70 | 70 | 2 | 6 | 5 | 7 | 74 | 69 | 8 | −10 | 11 | 7 | 123 | 117 | 3 | −11 | −10 | 8 | 48 | 49 | 4 | −4 | −5 | 8 | 225 | 240 | 3 |
| −2 | 1 | 7 | 195 | 194 | 2 | −12 | 6 | 7 | 114 | 113 | 3 | −9 | 11 | 7 | 79 | 75 | 3 | −10 | −10 | 8 | 94 | 92 | 2 | −3 | −5 | 8 | 264 | 267 | 3 |
| −1 | 1 | 7 | 186 | 199 | 2 | −11 | 6 | 7 | 45 | 36 | 5 | −8 | 11 | 7 | 44 | 47 | 7 | −9 | −10 | 8 | 56 | 55 | 3 | −2 | −5 | 8 | 104 | 104 | 3 |
| 0 | 1 | 7 | 225 | 217 | 2 | −10 | 6 | 7 | 68 | 68 | 3 | −7 | 11 | 7 | 78 | 76 | 5 | −8 | −10 | 8 | 50 | 53 | 4 | −1 | −5 | 8 | 211 | 220 | 3 |
| 1 | 1 | 7 | 29 | 23 | 5 | −9 | 6 | 7 | 148 | 155 | 3 | −6 | 11 | 7 | 129 | 127 | 4 | −7 | −10 | 8 | 43 | 38 | 4 | 0 | −5 | 8 | 220 | 222 | 3 |
| 2 | 1 | 7 | 88 | 94 | 2 | −8 | 6 | 7 | 106 | 108 | 3 | −5 | 11 | 7 | 51 | 54 | 6 | −6 | −10 | 8 | 94 | 92 | 3 | 1 | −5 | 8 | 149 | 161 | 3 |
| 3 | 1 | 7 | 197 | 210 | 2 | −7 | 6 | 7 | 100 | 109 | 3 | −4 | 11 | 7 | 57 | 53 | 6 | −5 | −11 | 8 | 112 | 112 | 2 | 2 | −5 | 8 | 36 | 36 | 7 |
| 4 | 1 | 7 | 160 | 162 | 3 | −6 | 6 | 7 | 194 | 190 | 3 | −3 | 11 | 7 | 31 | 36 | 13 | −4 | −10 | 8 | 154 | 166 | 3 | 3 | −5 | 8 | 120 | 123 | 3 |
| 5 | 1 | 7 | 19 | 31 | 19 | −5 | 6 | 7 | 75 | 68 | 3 | −2 | 11 | 7 | 160 | 159 | 5 | −3 | −10 | 8 | 76 | 87 | 2 | 4 | −5 | 8 | 16 | 19 | 16 |
| 6 | 1 | 7 | 100 | 88 | 6 | −4 | 6 | 7 | 202 | 202 | 3 | −1 | 11 | 7 | 28 | 26 | 14 | −2 | −10 | 8 | 92 | 107 | 3 | −12 | −4 | 8 | 27 | 29 | 10 |
| −13 | 2 | 7 | 72 | 73 | 5 | −3 | 6 | 7 | 164 | 161 | 3 | 0 | 11 | 7 | 201 | 207 | 4 | −1 | −10 | 8 | 78 | 76 | 2 | −11 | −4 | 8 | 76 | 76 | 4 |
| −12 | 2 | 7 | 55 | 52 | 5 | −2 | 6 | 7 | 57 | 51 | 5 | 1 | 11 | 7 | 110 | 103 | 4 | 0 | −10 | 8 | 88 | 8 | 4 | −10 | −4 | 8 | 105 | 104 | 4 |
| −11 | 2 | 7 | 127 | 120 | 3 | −1 | 6 | 7 | 201 | 195 | 3 | 2 | 11 | 7 | 15 | 13 | 15 | 1 | −10 | 8 | 86 | 86 | 3 | −9 | −4 | 8 | 41 | 38 | 6 |
| −10 | 2 | 7 | 121 | 120 | 3 | 0 | 6 | 7 | 178 | 173 | 3 | 3 | 11 | 7 | 31 | 21 | 6 | 2 | −10 | 8 | 39 | 29 | 4 | −8 | −4 | 8 | 85 | 88 | 3 |
| −9 | 2 | 7 | 102 | 104 | 2 | 1 | 6 | 7 | 78 | 71 | 3 | −10 | 12 | 7 | 30 | 41 | 6 | 3 | −10 | 8 | 64 | 68 | 3 | −7 | −4 | 8 | 145 | 149 | 2 |
| −8 | 2 | 7 | 135 | 131 | 2 | 2 | 6 | 7 | 163 | 170 | 2 | −9 | 12 | 7 | 89 | 93 | 3 | −11 | −9 | 8 | 53 | 54 | 3 | −6 | −4 | 8 | 20 | 6 | 20 |
| −7 | 2 | 7 | 69 | 68 | 2 | 3 | 6 | 7 | 114 | 117 | 3 | −8 | 12 | 7 | 119 | 115 | 4 | −10 | −9 | 8 | 35 | 32 | 5 | −5 | −4 | 8 | 58 | 58 | 4 |
| −6 | 2 | 7 | 48 | 49 | 2 | 4 | 6 | 7 | 175 | 177 | 2 | −7 | 12 | 7 | 128 | 115 | 4 | −9 | −9 | 8 | 73 | 73 | 3 | −4 | −4 | 8 | 68 | 65 | 4 |
| −5 | 2 | 7 | 186 | 191 | 2 | 5 | 6 | 7 | 49 | 44 | 4 | −6 | 12 | 7 | 142 | 139 | 5 | −8 | −9 | 8 | 78 | 79 | 2 | −3 | −4 | 8 | 82 | 84 | 4 |
| −4 | 2 | 7 | 110 | 104 | 2 | −12 | 7 | 7 | 56 | 63 | 3 | −5 | 12 | 7 | 67 | 65 | 6 | −7 | −9 | 8 | 175 | 165 | 3 | −2 | −4 | 8 | 254 | 257 | 4 |
| −3 | 2 | 7 | 171 | 163 | 1 | −11 | 7 | 7 | 63 | 57 | 4 | −4 | 12 | 7 | 174 | 171 | 5 | −6 | −9 | 8 | 164 | 169 | 3 | −1 | −4 | 8 | 114 | 116 | 4 |
| −2 | 2 | 7 | 172 | 197 | 2 | −10 | 7 | 7 | 139 | 141 | 2 | −3 | 12 | 7 | 149 | 145 | 4 | −5 | −9 | 8 | 96 | 92 | 2 | 0 | −4 | 8 | 118 | 110 | 4 |
| −1 | 2 | 7 | 96 | 91 | 2 | −9 | 7 | 7 | 173 | 171 | 3 | −2 | 12 | 7 | 32 | 31 | 11 | −4 | −9 | 8 | 176 | 179 | 2 | 1 | −4 | 8 | 257 | 270 | 4 |
| 0 | 2 | 7 | 76 | 83 | 2 | −8 | 7 | 7 | 80 | 78 | 3 | −1 | 12 | 7 | 57 | 68 | 6 | −3 | −9 | 8 | 172 | 171 | 2 | 2 | −4 | 8 | 59 | 61 | 6 |
| 1 | 2 | 7 | 108 | 102 | 2 | −7 | 7 | 7 | 178 | 172 | 3 | 0 | 12 | 7 | 128 | 133 | 5 | −2 | −9 | 8 | 91 | 87 | 2 | 3 | −4 | 8 | 63 | 57 | 4 |
| 2 | 2 | 7 | 75 | 74 | 3 | −6 | 7 | 7 | 42 | 37 | 5 | 1 | 12 | 7 | 146 | 136 | 5 | −1 | −9 | 8 | 114 | 116 | 2 | 4 | −4 | 8 | 67 | 59 | 4 |
| 3 | 2 | 7 | 31 | 35 | 6 | −5 | 7 | 7 | 47 | 41 | 5 | 2 | 12 | 7 | 82 | 82 | 4 | 0 | −9 | 8 | 61 | 61 | 3 | 5 | −4 | 8 | 111 | 116 | 8 |
| 4 | 2 | 7 | 93 | 89 | 3 | −4 | 7 | 7 | 158 | 157 | 3 | 3 | 12 | 7 | 63 | 56 | 4 | 1 | −9 | 8 | 36 | 40 | 4 | −12 | −3 | 8 | 24 | 24 | 14 |
| 5 | 2 | 7 | 192 | 182 | 4 | −3 | 7 | 7 | 126 | 131 | 3 | −9 | 13 | 7 | 81 | 86 | 4 | 2 | −9 | 8 | 94 | 92 | 3 | −11 | −3 | 8 | 76 | 81 | 4 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 6 | 2 | 7 | 52 | 36 | 5 | −2 | 7 | 7 | 67 | 62 | 4 | −8 | 13 | 7 | 45 | 50 | 8 | 3 | −9 | 8 | 46 | 46 | 5 | −10 | −3 | 8 | 108 | 116 | 5 |
| −13 | 3 | 7 | 32 | 35 | 10 | −1 | 7 | 7 | 94 | 93 | 4 | −7 | 13 | 7 | 143 | 131 | 6 | −11 | −8 | 8 | 60 | 65 | 3 | −9 | −3 | 8 | 116 | 114 | 3 |
| −12 | 3 | 7 | 54 | 55 | 5 | 0 | 7 | 7 | 12 | 10 | 12 | −6 | 13 | 7 | 130 | 128 | 6 | −10 | −8 | 8 | 75 | 82 | 2 | −8 | −3 | 8 | 118 | 127 | 3 |
| −11 | 3 | 7 | 211 | 199 | 2 | 1 | 7 | 7 | 240 | 248 | 3 | −5 | 13 | 7 | 56 | 68 | 9 | −9 | −8 | 8 | 60 | 60 | 3 | −7 | −3 | 8 | 153 | 150 | 3 |
| −10 | 3 | 7 | 150 | 142 | 3 | 2 | 7 | 7 | 81 | 82 | 3 | −4 | 13 | 7 | 100 | 110 | 7 | −8 | −8 | 8 | 79 | 81 | 3 | −6 | −3 | 8 | 200 | 196 | 3 |
| −9 | 3 | 7 | 211 | 203 | 2 | 3 | 7 | 7 | 56 | 59 | 3 | −3 | 13 | 7 | 70 | 57 | 6 | −7 | −8 | 8 | 128 | 128 | 2 | −5 | −3 | 8 | 107 | 108 | 3 |
| −8 | 3 | 7 | 130 | 122 | 2 | 4 | 7 | 7 | 95 | 95 | 3 | −2 | 13 | 7 | 117 | 119 | 5 | −6 | −8 | 8 | 54 | 55 | 3 | −4 | −3 | 8 | 160 | 156 | 2 |
| −7 | 3 | 7 | 39 | 38 | 4 | 5 | 7 | 7 | 105 | 105 | 2 | −1 | 13 | 7 | 92 | 97 | 5 | −5 | −8 | 8 | 273 | 265 | 2 | −3 | −3 | 8 | 170 | 171 | 2 |
| −6 | 3 | 7 | 149 | 150 | 2 | −12 | 8 | 7 | 76 | 85 | 8 | 0 | 13 | 7 | 98 | 96 | 5 | −4 | −8 | 8 | 183 | 189 | 2 | −2 | −3 | 8 | 320 | 328 | 3 |
| −5 | 3 | 7 | 51 | 55 | 2 | −11 | 8 | 7 | 106 | 99 | 3 | 1 | 13 | 7 | 54 | 51 | 6 | −3 | −8 | 8 | 116 | 116 | 2 | −1 | −3 | 8 | 120 | 120 | 3 |
| −4 | 3 | 7 | 154 | 160 | 2 | −10 | 8 | 7 | 22 | 17 | 11 | 2 | 13 | 7 | 89 | 89 | 4 | −2 | −8 | 8 | 167 | 167 | 2 | 0 | −3 | 8 | 174 | 178 | 3 |
| −3 | 3 | 7 | 138 | 144 | 2 | −9 | 8 | 7 | 93 | 95 | 3 | −8 | 14 | 7 | 0 | 10 | 1 | −1 | −8 | 8 | 184 | 187 | 3 | 1 | −3 | 8 | 117 | 127 | 4 |
| −2 | 3 | 7 | 154 | 154 | 2 | −8 | 8 | 7 | 207 | 207 | 3 | −7 | 14 | 7 | 61 | 57 | 7 | 0 | −8 | 8 | 83 | 88 | 2 | 2 | −3 | 8 | 162 | 157 | 4 |
| −1 | 3 | 7 | 58 | 49 | 2 | −7 | 8 | 7 | 162 | 165 | 3 | −6 | 14 | 7 | 82 | 86 | 7 | 1 | −8 | 8 | 51 | 53 | 3 | 3 | −3 | 8 | 66 | 61 | 5 |
| 0 | 3 | 7 | 266 | 267 | 2 | −6 | 8 | 7 | 181 | 176 | 3 | −5 | 14 | 7 | 47 | 47 | 10 | 2 | −8 | 8 | 91 | 85 | 3 | 4 | −3 | 8 | 61 | 47 | 7 |
| 1 | 3 | 7 | 85 | 78 | 2 | −5 | 8 | 7 | 191 | 184 | 3 | −4 | 14 | 7 | 67 | 69 | 9 | 3 | −8 | 8 | 132 | 135 | 2 | 5 | −3 | 8 | 27 | 32 | 9 |
| 2 | 3 | 7 | 50 | 51 | 3 | −4 | 8 | 7 | 159 | 149 | 3 | −3 | 14 | 7 | 74 | 69 | 8 | −12 | −7 | 8 | 97 | 102 | 4 | −13 | −2 | 8 | 0 | 17 | 1 |
| 3 | 3 | 7 | 222 | 219 | 3 | −3 | 8 | 7 | 112 | 115 | 4 | −2 | 14 | 7 | 61 | 59 | 6 | −11 | −7 | 8 | 57 | 58 | 3 | −12 | −2 | 8 | 56 | 62 | 7 |
| 4 | 3 | 7 | 109 | 114 | 3 | −2 | 8 | 7 | 190 | 184 | 3 | −1 | 14 | 7 | 95 | 96 | 5 | −10 | −7 | 8 | 162 | 157 | 4 | −11 | −2 | 8 | 212 | 206 | 4 |
| 5 | 3 | 7 | 84 | 81 | 4 | −1 | 8 | 7 | 73 | 72 | 4 | 0 | 14 | 7 | 45 | 46 | 7 | −9 | −7 | 8 | 138 | 132 | 2 | −10 | −2 | 8 | 56 | 50 | 5 |
| 6 | 3 | 7 | 98 | 94 | 4 | 0 | 8 | 7 | 19 | 28 | 18 | 1 | 14 | 7 | 69 | 73 | 5 | −8 | −7 | 8 | 127 | 124 | 2 | −9 | −2 | 8 | 225 | 230 | 4 |
| −12 | 4 | 7 | 68 | 66 | 4 | 1 | 8 | 7 | 180 | 175 | 3 | −7 | 15 | 7 | 51 | 53 | 8 | −7 | −7 | 8 | 114 | 119 | 2 | −8 | −2 | 8 | 129 | 123 | 3 |
| −11 | 4 | 7 | 71 | 62 | 3 | 2 | 8 | 7 | 33 | 35 | 6 | −6 | 15 | 7 | 44 | 49 | 9 | −6 | −7 | 8 | 154 | 159 | 2 | −7 | −2 | 8 | 90 | 94 | 3 |
| −10 | 4 | 7 | 185 | 183 | 3 | 3 | 8 | 7 | 80 | 71 | 3 | −5 | 15 | 7 | 16 | 27 | 15 | −5 | −7 | 8 | 285 | 295 | 2 | −6 | −2 | 8 | 13 | 16 | 13 |
| −9 | 4 | 7 | 179 | 174 | 2 | 4 | 8 | 7 | 58 | 61 | 3 | −4 | 15 | 7 | 49 | 56 | 10 | −4 | −7 | 8 | 34 | 35 | 4 | −5 | −2 | 8 | 42 | 50 | 4 |
| −8 | 4 | 7 | 136 | 140 | 2 | 5 | 8 | 7 | 48 | 40 | 4 | −3 | 15 | 7 | 103 | 114 | 7 | −3 | −7 | 8 | 98 | 98 | 2 | −4 | −2 | 8 | 65 | 58 | 3 |
| −7 | 4 | 7 | 114 | 113 | 2 | −11 | 9 | 7 | 68 | 74 | 3 | −1 | 15 | 7 | 39 | 20 | 13 | −2 | −7 | 8 | 100 | 99 | 2 | −3 | −2 | 8 | 162 | 160 | 2 |
| −6 | 4 | 7 | 154 | 147 | 2 | −10 | 9 | 7 | 58 | 60 | 4 | 0 | 15 | 7 | 30 | 44 | 17 | −1 | −7 | 8 | 51 | 58 | 4 | −2 | −2 | 8 | 446 | 460 | 4 |
| −5 | 4 | 7 | 84 | 86 | 2 | −9 | 9 | 7 | 111 | 106 | 3 | −3 | −14 | 8 | 32 | 31 | 24 | 0 | −7 | 8 | 193 | 191 | 3 | −1 | −2 | 8 | 238 | 243 | 2 |
| −4 | 4 | 7 | 107 | 114 | 3 | −8 | 9 | 7 | 104 | 98 | 4 | −2 | −14 | 8 | 56 | 60 | 10 | 1 | −7 | 8 | 33 | 32 | 5 | 0 | −2 | 8 | 75 | 81 | 3 |
| −3 | 4 | 7 | 72 | 68 | 2 | −7 | 9 | 7 | 180 | 177 | 4 | −1 | −14 | 8 | 64 | 4 | 9 | 2 | −7 | 8 | 101 | 9 | 2 | 1 | −2 | 8 | 133 | 133 | 3 |
| −2 | 4 | 7 | 146 | 157 | 2 | −6 | 9 | 7 | 44 | 40 | 7 | 0 | −14 | 8 | 85 | 87 | 7 | 3 | −7 | 8 | 39 | 33 | 5 | 2 | −2 | 8 | 247 | 258 | 4 |
| −1 | 4 | 7 | 249 | 249 | 3 | −5 | 9 | 7 | 17 | 14 | 16 | −3 | −13 | 8 | 85 | 71 | 8 | 4 | −7 | 8 | 83 | 7 | 2 | 3 | −2 | 8 | 75 | 84 | 5 |
| 0 | 4 | 7 | 183 | 192 | 2 | −4 | 9 | 7 | 219 | 232 | 4 | −2 | −13 | 8 | 84 | 85 | 8 | −12 | −6 | 8 | 75 | 86 | 3 | 4 | −2 | 8 | 32 | 42 | 11 |
| 1 | 4 | 7 | 243 | 244 | 2 | −3 | 9 | 7 | 179 | 183 | 3 | −1 | −13 | 8 | 96 | 81 | 8 | −11 | −6 | 8 | 115 | 114 | 3 | 5 | −2 | 8 | 53 | 60 | 7 |
| 2 | 4 | 7 | 157 | 172 | 2 | −2 | 9 | 7 | 195 | 198 | 3 | 0 | −13 | 8 | 0 | 21 | 1 | −10 | −6 | 8 | 45 | 39 | 5 | −13 | −1 | 8 | 50 | 34 | 9 |
| 3 | 4 | 7 | 194 | 200 | 3 | −1 | 9 | 7 | 166 | 168 | 4 | 1 | −13 | 8 | 44 | 77 | 12 | −9 | −6 | 8 | 101 | 110 | 3 | −12 | −1 | 8 | 73 | 67 | 6 |
| 4 | 4 | 7 | 132 | 129 | 2 | 0 | 9 | 7 | 151 | 158 | 4 | −5 | −12 | 8 | 102 | 96 | 3 | −8 | −6 | 8 | 153 | 150 | 3 | −11 | −1 | 8 | 57 | 50 | 5 |
| 5 | 4 | 7 | 6 | 7 | 5 | 1 | 9 | 7 | 71 | 65 | 5 | −4 | −12 | 8 | 114 | 116 | 3 | −7 | −6 | 8 | 226 | 228 | 3 | −10 | −1 | 8 | 109 | 119 | 4 |
| −9 | −1 | 8 | 29 | 34 | 9 | 2 | 3 | 8 | 166 | 157 | 4 | 4 | 8 | 8 | 26 | 19 | 17 | −7 | −11 | 9 | 120 | 117 | 2 | −4 | −5 | 9 | 122 | 120 | 4 |
| −8 | −1 | 8 | 106 | 107 | 3 | 3 | 3 | 8 | 61 | 61 | 4 | −11 | 9 | 8 | 49 | 53 | 5 | −6 | −11 | 9 | 157 | 154 | 3 | −3 | −5 | 9 | 151 | 157 | 4 |
| −7 | −1 | 8 | 157 | 146 | 2 | 4 | 3 | 8 | 58 | 47 | 6 | −10 | 9 | 8 | 40 | 32 | 5 | −5 | −11 | 9 | 118 | 115 | 2 | −2 | −5 | 9 | 165 | 175 | 4 |
| −6 | −1 | 8 | 109 | 102 | 2 | 5 | 3 | 8 | 31 | 32 | 9 | −9 | 9 | 8 | 72 | 72 | 3 | −4 | −11 | 9 | 87 | 84 | 5 | −1 | −5 | 9 | 110 | 108 | 3 |
| −5 | −1 | 8 | 91 | 91 | 2 | −12 | 4 | 8 | 28 | 29 | 10 | −8 | 9 | 8 | 84 | 79 | 3 | −3 | −11 | 9 | 42 | 41 | 7 | 0 | −5 | 9 | 173 | 170 | 3 |
| −4 | −1 | 8 | 84 | 79 | 2 | −11 | 4 | 8 | 81 | 78 | 3 | −7 | 9 | 8 | 174 | 165 | 4 | −2 | −11 | 9 | 163 | 165 | 5 | 1 | −5 | 9 | 61 | 60 | 4 |
| −3 | −1 | 8 | 137 | 129 | 2 | −10 | 4 | 8 | 107 | 104 | 3 | −6 | 9 | 8 | 160 | 169 | 3 | −1 | −11 | 9 | 83 | 80 | 5 | 2 | −5 | 9 | 46 | 46 | 5 |
| −2 | −1 | 8 | 167 | 166 | 2 | −9 | 4 | 8 | 41 | 39 | 4 | −5 | 9 | 8 | 95 | 82 | 4 | 0 | −11 | 9 | 63 | 55 | 5 | 3 | −5 | 9 | 108 | 114 | 3 |
| −1 | −1 | 8 | 117 | 106 | 3 | −8 | 4 | 8 | 90 | 89 | 2 | −4 | 9 | 8 | 130 | 179 | 3 | 1 | −11 | 9 | 70 | 64 | 4 | −12 | −4 | 9 | 0 | 29 | 1 |
| 0 | −1 | 8 | 180 | 176 | 3 | −7 | 4 | 8 | 154 | 149 | 2 | −3 | 9 | 8 | 171 | 171 | 4 | −10 | −10 | 9 | 43 | 38 | 5 | −11 | −4 | 9 | 51 | 57 | 5 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 1 | −1 | 8 | 93 | 86 | 4 | −6 | 4 | 8 | 16 | 7 | 16 | −2 | 9 | 8 | 92 | 87 | 4 | −9 | −10 | 9 | 3 | 42 | 4 | −10 | −4 | 9 | 81 | 92 | 4 |
| 2 | −1 | 8 | 86 | 87 | 4 | −5 | 4 | 8 | 62 | 58 | 2 | −1 | 9 | 8 | 118 | 116 | 4 | −8 | −10 | 9 | 110 | 104 | 3 | −9 | −4 | 9 | 119 | 116 | 3 |
| 3 | −1 | 8 | 68 | 60 | 4 | −4 | 4 | 8 | 68 | 65 | 3 | 0 | 9 | 8 | 64 | 62 | 4 | −7 | −10 | 9 | 72 | 67 | 3 | −8 | −4 | 9 | 48 | 54 | 5 |
| 4 | −1 | 8 | 98 | 100 | 4 | −3 | 4 | 8 | 89 | 85 | 2 | 1 | 9 | 8 | 43 | 40 | 5 | −6 | −10 | 9 | 75 | 75 | 3 | −7 | −4 | 9 | 124 | 140 | 4 |
| 5 | −1 | 8 | 45 | 35 | 6 | −2 | 4 | 8 | 255 | 258 | 2 | 2 | 9 | 8 | 94 | 92 | 2 | −5 | −10 | 9 | 120 | 118 | 2 | −6 | −4 | 9 | 53 | 40 | 6 |
| −13 | 0 | 8 | 48 | 11 | 9 | −1 | 4 | 8 | 116 | 114 | 2 | 3 | 9 | 8 | 48 | 46 | 4 | −4 | −10 | 9 | 111 | 108 | 2 | −5 | −4 | 9 | 32 | 102 | 4 |
| −12 | 0 | 8 | 44 | 45 | 7 | 0 | 4 | 8 | 118 | 110 | 2 | −11 | 10 | 8 | 46 | 49 | 8 | −3 | −10 | 9 | 102 | 100 | 2 | −4 | −4 | 9 | 148 | 147 | 3 |
| −11 | 0 | 8 | 22 | 11 | 22 | 1 | 4 | 8 | 258 | 270 | 3 | −10 | 10 | 8 | 91 | 92 | 3 | −2 | −10 | 9 | 65 | 61 | 2 | −3 | −4 | 9 | 323 | 330 | 5 |
| −10 | 0 | 8 | 72 | 83 | 4 | 2 | 4 | 8 | 53 | 61 | 3 | −9 | 10 | 8 | 48 | 55 | 5 | −1 | −10 | 9 | 122 | 113 | 3 | −2 | −4 | 9 | 144 | 141 | 4 |
| −9 | 0 | 8 | 110 | 99 | 3 | 3 | 4 | 8 | 62 | 57 | 3 | −8 | 10 | 8 | 56 | 53 | 4 | 0 | −10 | 9 | 56 | 44 | 3 | −1 | −4 | 9 | 151 | 168 | 4 |
| −8 | 0 | 8 | 127 | 134 | 2 | 4 | 4 | 8 | 63 | 58 | 4 | −7 | 10 | 8 | 38 | 38 | 7 | 1 | −10 | 9 | 20 | 11 | 8 | 0 | −4 | 9 | 104 | 101 | 5 |
| −7 | 0 | 8 | 80 | 68 | 2 | −12 | 5 | 8 | 89 | 91 | 3 | −6 | 10 | 8 | 89 | 93 | 4 | −11 | −9 | 9 | 86 | 87 | 2 | 1 | −4 | 9 | 7 | 13 | 7 |
| −6 | 0 | 8 | 157 | 155 | 2 | −11 | 5 | 8 | 82 | 76 | 3 | −5 | 10 | 8 | 114 | 112 | 4 | −10 | −9 | 9 | 71 | 67 | 3 | 2 | −4 | 9 | 83 | 82 | 5 |
| −5 | 0 | 8 | 256 | 256 | 2 | −10 | 5 | 8 | 89 | 95 | 3 | −4 | 10 | 8 | 165 | 166 | 4 | −9 | −9 | 9 | 86 | 83 | 3 | 3 | −4 | 9 | 53 | 51 | 4 |
| −4 | 0 | 8 | 229 | 224 | 2 | −9 | 5 | 8 | 68 | 77 | 2 | −3 | 10 | 8 | 88 | 87 | 4 | −8 | −9 | 9 | 42 | 41 | 5 | −12 | −3 | 9 | 89 | 82 | 5 |
| −3 | 0 | 8 | 201 | 210 | 2 | −8 | 5 | 8 | 76 | 82 | 3 | −2 | 10 | 8 | 109 | 107 | 4 | −7 | −9 | 9 | 91 | 94 | 2 | −11 | −3 | 9 | 35 | 34 | 8 |
| −2 | 0 | 8 | 189 | 191 | 2 | −7 | 5 | 8 | 171 | 166 | 2 | −1 | 10 | 8 | 90 | 77 | 4 | −6 | −9 | 9 | 56 | 54 | 3 | −10 | −3 | 9 | 89 | 82 | 5 |
| −1 | 0 | 8 | 213 | 215 | 2 | −6 | 5 | 8 | 26 | 31 | 7 | 0 | 10 | 8 | 92 | 86 | 4 | −5 | −9 | 9 | 91 | 31 | 2 | −9 | −3 | 9 | 47 | 46 | 8 |
| 0 | 0 | 8 | 59 | 51 | 3 | −5 | 5 | 8 | 163 | 167 | 2 | 1 | 10 | 8 | 93 | 86 | 3 | −4 | −9 | 9 | 170 | 165 | 2 | −8 | −3 | 9 | 65 | 79 | 4 |
| 1 | 0 | 8 | 121 | 123 | 3 | −4 | 5 | 8 | 231 | 240 | 3 | 2 | 10 | 8 | 27 | 30 | 8 | −3 | −9 | 9 | 115 | 112 | 2 | −7 | −3 | 9 | 180 | 184 | 3 |
| 2 | 0 | 8 | 252 | 242 | 4 | −3 | 5 | 8 | 267 | 267 | 3 | 3 | 10 | 8 | 68 | 69 | 3 | −2 | −9 | 9 | 81 | 76 | 2 | −6 | −3 | 9 | 11 | 26 | 11 |
| 3 | 0 | 8 | 163 | 159 | 3 | −2 | 5 | 8 | 93 | 104 | 2 | −10 | 11 | 8 | 82 | 87 | 3 | −1 | −9 | 9 | 81 | 71 | 2 | −5 | −3 | 9 | 75 | 79 | 3 |
| 4 | 0 | 8 | 0 | 10 | 1 | −1 | 5 | 8 | 211 | 220 | 2 | −9 | 11 | 8 | 155 | 152 | 3 | 0 | −9 | 9 | 61 | 61 | 3 | −4 | −3 | 9 | 24 | 253 | 4 |
| 5 | 0 | 8 | 39 | 48 | 8 | 0 | 5 | 8 | 223 | 221 | 2 | −8 | 11 | 8 | 28 | 26 | 9 | 1 | −9 | 9 | 56 | 55 | 5 | −3 | −3 | 9 | 112 | 108 | 3 |
| −13 | 1 | 8 | 36 | 34 | 18 | 1 | 5 | 8 | 151 | 161 | 2 | −7 | 11 | 8 | 113 | 108 | 4 | 2 | −9 | 9 | 50 | 48 | 5 | −2 | −3 | 9 | 80 | 88 | 4 |
| −12 | 1 | 8 | 72 | 67 | 5 | 2 | 5 | 8 | 31 | 36 | 5 | −6 | 11 | 8 | 122 | 122 | 4 | −11 | −8 | 9 | 33 | 33 | 5 | −1 | −3 | 9 | 92 | 97 | 4 |
| −11 | 1 | 8 | 52 | 50 | 6 | 3 | 5 | 8 | 114 | 123 | 3 | −5 | 11 | 8 | 77 | 80 | 5 | −10 | −8 | 9 | 98 | 100 | 3 | 0 | −3 | 9 | 147 | 153 | 4 |
| −10 | 1 | 8 | 113 | 119 | 3 | 4 | 5 | 8 | 14 | 19 | 14 | −4 | 11 | 8 | 83 | 72 | 4 | −9 | −8 | 9 | 105 | 100 | 2 | 1 | −3 | 9 | 135 | 141 | 4 |
| −9 | 1 | 8 | 32 | 34 | 6 | −12 | 6 | 8 | 80 | 87 | 3 | −3 | 11 | 8 | 107 | 113 | 5 | −8 | −8 | 9 | 110 | 113 | 2 | 2 | −3 | 9 | 97 | 89 | 6 |
| −8 | 1 | 8 | 110 | 107 | 2 | −11 | 6 | 8 | 125 | 114 | 3 | −2 | 11 | 8 | 127 | 118 | 5 | −7 | −8 | 9 | 119 | 119 | 2 | 3 | −3 | 9 | 98 | 88 | 5 |
| −7 | 1 | 8 | 155 | 146 | 2 | −10 | 6 | 8 | 47 | 39 | 4 | −1 | 11 | 8 | 106 | 107 | 5 | −6 | −8 | 9 | 111 | 111 | 2 | −12 | −2 | 9 | 133 | 127 | 4 |
| −6 | 1 | 8 | 111 | 102 | 2 | −9 | 6 | 8 | 103 | 110 | 3 | 0 | 11 | 8 | 134 | 119 | 4 | −5 | −8 | 9 | 219 | 215 | 2 | −11 | −2 | 9 | 50 | 49 | 9 |
| −5 | 1 | 8 | 93 | 92 | 2 | −8 | 6 | 8 | 158 | 150 | 3 | 1 | 11 | 8 | 89 | 81 | 3 | −4 | −8 | 9 | 80 | 82 | 2 | −10 | −2 | 9 | 53 | 50 | 5 |
| −4 | 1 | 8 | 81 | 80 | 2 | −7 | 6 | 8 | 226 | 229 | 3 | 2 | 11 | 8 | 63 | 56 | 3 | −3 | −8 | 9 | 50 | 51 | 3 | −9 | −2 | 9 | 131 | 126 | 4 |
| −3 | 1 | 8 | 135 | 130 | 2 | −6 | 6 | 8 | 94 | 93 | 3 | −9 | 12 | 8 | 35 | 38 | 6 | −2 | −8 | 9 | 41 | 42 | 4 | −8 | −2 | 9 | 88 | 83 | 4 |
| −2 | 1 | 8 | 165 | 166 | 2 | −5 | 6 | 8 | 175 | 176 | 3 | −8 | 12 | 8 | 94 | 91 | 3 | −1 | −8 | 9 | 183 | 185 | 2 | −7 | −2 | 9 | 138 | 141 | 3 |
| −1 | 1 | 8 | 116 | 106 | 2 | −4 | 6 | 8 | 129 | 125 | 3 | −7 | 12 | 8 | 87 | 84 | 4 | 0 | −8 | 9 | 79 | 79 | 3 | −6 | −2 | 9 | 261 | 263 | 3 |
| 0 | 1 | 8 | 178 | 176 | 2 | −3 | 6 | 8 | 178 | 168 | 3 | −6 | 12 | 8 | 151 | 154 | 5 | 1 | −8 | 9 | 68 | 59 | 3 | −5 | −2 | 9 | 113 | 111 | 3 |
| 1 | 1 | 8 | 85 | 86 | 2 | −2 | 6 | 8 | 168 | 177 | 3 | −5 | 12 | 8 | 97 | 95 | 5 | 2 | −8 | 9 | 28 | 25 | 8 | −4 | −2 | 9 | 336 | 346 | 3 |
| 2 | 1 | 8 | 81 | 87 | 3 | −1 | 6 | 8 | 218 | 221 | 3 | −4 | 12 | 8 | 110 | 115 | 5 | −11 | −7 | 9 | 89 | 93 | 2 | −3 | −2 | 9 | 144 | 138 | 3 |
| 3 | 1 | 8 | 75 | 60 | 5 | 0 | 6 | 8 | 119 | 135 | 2 | −3 | 12 | 8 | 91 | 91 | 5 | −10 | −7 | 9 | 93 | 95 | 3 | −2 | −2 | 9 | 214 | 208 | 2 |
| 4 | 1 | 8 | 99 | 100 | 4 | 1 | 6 | 8 | 198 | 205 | 2 | −2 | 12 | 8 | 83 | 83 | 5 | −9 | −7 | 9 | 158 | 155 | 3 | −1 | −2 | 9 | 121 | 124 | 4 |
| 5 | 1 | 8 | 31 | 35 | 15 | 2 | 6 | 8 | 19 | 14 | 11 | −1 | 12 | 8 | 50 | 43 | 6 | −8 | −7 | 9 | 50 | 48 | 3 | 0 | −2 | 9 | 123 | 130 | 3 |
| −13 | 2 | 8 | 25 | 18 | 24 | 3 | 6 | 8 | 23 | 33 | 10 | 0 | 12 | 8 | 73 | 68 | 5 | −7 | −7 | 9 | 83 | 79 | 2 | 1 | −2 | 9 | 164 | 167 | 4 |
| −12 | 2 | 8 | 65 | 62 | 6 | 4 | 6 | 8 | 17 | 31 | 17 | 1 | 12 | 8 | 17 | 6 | 16 | −6 | −7 | 9 | 62 | 64 | 3 | 2 | −2 | 9 | 98 | 86 | 4 |
| −11 | 2 | 8 | 210 | 206 | 3 | −12 | 7 | 8 | 104 | 102 | 4 | 2 | 12 | 8 | 87 | 91 | 4 | −5 | −7 | 9 | 216 | 206 | 3 | 3 | −2 | 9 | 8 | 17 | 8 |
| −10 | 2 | 8 | 54 | 50 | 3 | −11 | 7 | 8 | 61 | 59 | 4 | −9 | 13 | 8 | 0 | 15 | 1 | −4 | −7 | 9 | 94 | 105 | 3 | 4 | −2 | 9 | 72 | 74 | 5 |
| −9 | 2 | 8 | 227 | 230 | 3 | −10 | 7 | 8 | 164 | 157 | 2 | −8 | 13 | 8 | 51 | 61 | 5 | −3 | −7 | 9 | 207 | 203 | 3 | −12 | −1 | 9 | 91 | 89 | 5 |
| −8 | 2 | 8 | 130 | 123 | 2 | −9 | 7 | 8 | 135 | 131 | 3 | −7 | 13 | 8 | 30 | 12 | 11 | −2 | −7 | 9 | 139 | 134 | 3 | −11 | −1 | 9 | 79 | 87 | 4 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −7 | 2 | 8 | 98 | 94 | 2 | −8 | 7 | 8 | 126 | 124 | 3 | −6 | 13 | 8 | 104 | 97 | 5 | −1 | −7 | 9 | 16 | 8 | 15 | −10 | −1 | 9 | 42 | 42 | 7 |
| −6 | 2 | 8 | 16 | 17 | 11 | −7 | 7 | 8 | 108 | 118 | 3 | −5 | 13 | 8 | 65 | 62 | 6 | 0 | −7 | 9 | 25 | 19 | 8 | −9 | −1 | 9 | 95 | 95 | 4 |
| −5 | 2 | 8 | 43 | 50 | 3 | −6 | 7 | 8 | 157 | 159 | 3 | −4 | 13 | 8 | 60 | 61 | 6 | 1 | −7 | 9 | 71 | 70 | 3 | −8 | −1 | 9 | 156 | 166 | 3 |
| −4 | 2 | 8 | 64 | 59 | 2 | −5 | 7 | 8 | 289 | 296 | 3 | −3 | 13 | 8 | 81 | 70 | 5 | 2 | −7 | 9 | 64 | 59 | 3 | −7 | −1 | 9 | 142 | 139 | 2 |
| −3 | 2 | 8 | 162 | 159 | 2 | −4 | 7 | 8 | 38 | 35 | 7 | −2 | 13 | 8 | 83 | 85 | 5 | −12 | −6 | 9 | 43 | 47 | 3 | −6 | −1 | 9 | 132 | 137 | 3 |
| −2 | 2 | 8 | 445 | 460 | 3 | −3 | 7 | 8 | 103 | 98 | 4 | −1 | 13 | 8 | 88 | 81 | 5 | −11 | −6 | 9 | 35 | 43 | 7 | −5 | −1 | 9 | 9 | 12 | 9 |
| −1 | 2 | 8 | 237 | 243 | 2 | −2 | 7 | 8 | 103 | 99 | 4 | 0 | 13 | 8 | 17 | 21 | 17 | −10 | −6 | 9 | 54 | 49 | 4 | −4 | −1 | 9 | 206 | 210 | 3 |
| 0 | 2 | 8 | 84 | 81 | 2 | −1 | 7 | 8 | 49 | 58 | 5 | 1 | 13 | 8 | 74 | 77 | 5 | −9 | −6 | 9 | 101 | 97 | 3 | −3 | −1 | 9 | 295 | 299 | 3 |
| 1 | 2 | 8 | 130 | 134 | 2 | 0 | 7 | 8 | 186 | 191 | 3 | −7 | 14 | 8 | 23 | 26 | 22 | −8 | −6 | 9 | 73 | 70 | 4 | −2 | −1 | 9 | 215 | 213 | 3 |
| 2 | 2 | 8 | 245 | 258 | 3 | 1 | 7 | 8 | 36 | 32 | 5 | −6 | 14 | 8 | 15 | 18 | 15 | −7 | −6 | 9 | 217 | 218 | 3 | −1 | −1 | 9 | 30 | 34 | 8 |
| 3 | 2 | 8 | 77 | 84 | 3 | 2 | 7 | 8 | 104 | 97 | 2 | −5 | 14 | 8 | 48 | 44 | 7 | −6 | −6 | 9 | 216 | 222 | 3 | 0 | −1 | 9 | 101 | 94 | 4 |
| 4 | 2 | 8 | 51 | 42 | 6 | 3 | 7 | 8 | 45 | 39 | 4 | −4 | 14 | 8 | 85 | 92 | 5 | −5 | −6 | 9 | 107 | 103 | 3 | 1 | −1 | 9 | 101 | 99 | 4 |
| 5 | 2 | 8 | 53 | 60 | 8 | 4 | 7 | 8 | 82 | 77 | 2 | −3 | 14 | 8 | 45 | 31 | 7 | −4 | −6 | 9 | 79 | 80 | 3 | 2 | −1 | 9 | 74 | 71 | 5 |
| −13 | 3 | 8 | 72 | 81 | 7 | −11 | 8 | 8 | 68 | 65 | 3 | −2 | 14 | 8 | 54 | 60 | 6 | −3 | −6 | 9 | 233 | 235 | 3 | 3 | −1 | 9 | 31 | 37 | 11 |
| −12 | 3 | 8 | 17 | 23 | 17 | −10 | 8 | 8 | 77 | 81 | 3 | −1 | 14 | 8 | 46 | 47 | 7 | −2 | −6 | 9 | 67 | 63 | 3 | 4 | −1 | 9 | 0 | 11 | 1 |
| −11 | 3 | 8 | 91 | 81 | 3 | −9 | 8 | 8 | 65 | 60 | 3 | 0 | 14 | 8 | 97 | 86 | 7 | −1 | −6 | 9 | 62 | 63 | 3 | −12 | 0 | 9 | 20 | 32 | 20 |
| −10 | 3 | 8 | 113 | 116 | 3 | −8 | 8 | 8 | 77 | 82 | 3 | −5 | 15 | 8 | 59 | 72 | 8 | 0 | −6 | 9 | 174 | 177 | 3 | −11 | 0 | 9 | 124 | 128 | 4 |
| −9 | 3 | 8 | 112 | 114 | 3 | −7 | 8 | 8 | 124 | 128 | 3 | −4 | 15 | 8 | 67 | 76 | 7 | 1 | −6 | 9 | 50 | 45 | 5 | −10 | 0 | 9 | 19 | 7 | 19 |
| −8 | 3 | 8 | 124 | 127 | 2 | −6 | 8 | 8 | 62 | 54 | 4 | −3 | 15 | 8 | 29 | 32 | 20 | 2 | −6 | 9 | 0 | 5 | 1 | −9 | 0 | 9 | 14 | 7 | 13 |
| −7 | 3 | 8 | 159 | 150 | 2 | −5 | 8 | 8 | 268 | 266 | 4 | −3 | −13 | 9 | 45 | 20 | 11 | 3 | −6 | 9 | 46 | 48 | 4 | −8 | 0 | 9 | 82 | 76 | 3 |
| −6 | 3 | 8 | 202 | 196 | 2 | −4 | 8 | 8 | 185 | 188 | 3 | −2 | −13 | 9 | 71 | 62 | 7 | −12 | −5 | 9 | 71 | 71 | 4 | −7 | 0 | 9 | 99 | 104 | 2 |
| −5 | 3 | 8 | 104 | 108 | 2 | −3 | 8 | 8 | 119 | 116 | 4 | −1 | −13 | 9 | 91 | 82 | 6 | −11 | −5 | 9 | 142 | 143 | 3 | −6 | 0 | 9 | 101 | 97 | 2 |
| −4 | 3 | 8 | 161 | 155 | 2 | −2 | 8 | 8 | 154 | 167 | 4 | −4 | −12 | 9 | 64 | 65 | 2 | −10 | −5 | 9 | 53 | 54 | 5 | −5 | 0 | 9 | 66 | 66 | 2 |
| −3 | 3 | 8 | 173 | 171 | 2 | −1 | 8 | 8 | 188 | 187 | 3 | −3 | −12 | 9 | 0 | 21 | 1 | −9 | −5 | 9 | 190 | 188 | 3 | −4 | 0 | 9 | 279 | 295 | 3 |
| −2 | 3 | 8 | 322 | 327 | 2 | 0 | 8 | 8 | 86 | 88 | 3 | −2 | −12 | 9 | 133 | 138 | 3 | −8 | −5 | 9 | 100 | 105 | 3 | −3 | 0 | 9 | 154 | 158 | 3 |
| −1 | 3 | 8 | 129 | 120 | 2 | 1 | 8 | 8 | 56 | 54 | 4 | −1 | −12 | 9 | 97 | 89 | 3 | −7 | −5 | 9 | 80 | 79 | 3 | −2 | 0 | 9 | 70 | 73 | 3 |
| 0 | 3 | 8 | 184 | 179 | 2 | 2 | 8 | 8 | 91 | 84 | 2 | 0 | −12 | 9 | 59 | 54 | 3 | −6 | −5 | 9 | 9 | 22 | 8 | −1 | 0 | 9 | 116 | 122 | 3 |
| 1 | 3 | 8 | 114 | 127 | 2 | 3 | 8 | 8 | 134 | 135 | 2 | −8 | −11 | 9 | 98 | 94 | 3 | −5 | −5 | 9 | 180 | 182 | 3 | 0 | 0 | 9 | 22 | 14 | 15 |
| 1 | 0 | 9 | 36 | 19 | 8 | −12 | 6 | 9 | 46 | 47 | 5 | −3 | 12 | 9 | 30 | 21 | 10 | −5 | −5 | 10 | 24 | 23 | 13 | −8 | 1 | 10 | 82 | 85 | 3 |
| 2 | 0 | 9 | 29 | 23 | 10 | −11 | 6 | 9 | 61 | 44 | 3 | −2 | 12 | 9 | 140 | 138 | 4 | −4 | −5 | 10 | 82 | 89 | 5 | −7 | 1 | 10 | 109 | 111 | 3 |
| 3 | 0 | 9 | 89 | 89 | 6 | −10 | 6 | 9 | 54 | 49 | 4 | −1 | 12 | 9 | 91 | 89 | 4 | −3 | −5 | 10 | 66 | 68 | 6 | −6 | 1 | 10 | 121 | 121 | 3 |
| 4 | 0 | 9 | 72 | 56 | 14 | −9 | 6 | 9 | 100 | 97 | 2 | 0 | 12 | 9 | 60 | 54 | 4 | −2 | −5 | 10 | 125 | 133 | 5 | −5 | 1 | 10 | 183 | 181 | 3 |
| −13 | 1 | 9 | 72 | 70 | 9 | −8 | 6 | 9 | 65 | 70 | 3 | −8 | 13 | 9 | 49 | 57 | 7 | −1 | −5 | 10 | 96 | 93 | 3 | −4 | 1 | 10 | 372 | 383 | 4 |
| −12 | 1 | 9 | 94 | 89 | 4 | −7 | 6 | 9 | 213 | 218 | 3 | −7 | 13 | 9 | 62 | 45 | 5 | 0 | −5 | 10 | 28 | 16 | 9 | −3 | 1 | 10 | 96 | 96 | 3 |
| −11 | 1 | 9 | 81 | 87 | 5 | −6 | 6 | 9 | 215 | 222 | 3 | −6 | 13 | 9 | 13 | 10 | 13 | 1 | −5 | 10 | 64 | 59 | 4 | −2 | 1 | 10 | 116 | 115 | 3 |
| −10 | 1 | 9 | 31 | 42 | 8 | −5 | 6 | 9 | 105 | 103 | 2 | −5 | 13 | 9 | 88 | 84 | 5 | 2 | −5 | 10 | 75 | 78 | 4 | −1 | 1 | 10 | 77 | 66 | 3 |
| −9 | 1 | 9 | 84 | 95 | 3 | −4 | 6 | 9 | 81 | 79 | 3 | −4 | 13 | 9 | 67 | 58 | 5 | −12 | −4 | 10 | 17 | 25 | 16 | 0 | 1 | 10 | 32 | 34 | 10 |
| −8 | 1 | 9 | 163 | 166 | 2 | −3 | 6 | 9 | 230 | 235 | 3 | −3 | 13 | 9 | 36 | 20 | 8 | −11 | −4 | 10 | 40 | 45 | 6 | 1 | 1 | 10 | 93 | 94 | 3 |
| −7 | 1 | 9 | 150 | 139 | 2 | −2 | 6 | 9 | 64 | 63 | 3 | −2 | 13 | 9 | 59 | 62 | 5 | −10 | −4 | 10 | 0 | 32 | 1 | 2 | 1 | 10 | 58 | 60 | 6 |
| −6 | 1 | 9 | 132 | 137 | 2 | −1 | 6 | 9 | 64 | 62 | 3 | −1 | 13 | 9 | 92 | 83 | 5 | −9 | −4 | 10 | 53 | 59 | 5 | −12 | 2 | 10 | 49 | 46 | 6 |
| −5 | 1 | 9 | 0 | 11 | 1 | 0 | 6 | 9 | 172 | 177 | 2 | −6 | 14 | 9 | 12 | 20 | 11 | −8 | −4 | 10 | 43 | 42 | 8 | −11 | 2 | 10 | 70 | 79 | 4 |
| −4 | 1 | 9 | 209 | 209 | 2 | 1 | 6 | 9 | 49 | 45 | 4 | −5 | 14 | 9 | 56 | 58 | 7 | −7 | −4 | 10 | 154 | 162 | 4 | −10 | 2 | 10 | 38 | 44 | 7 |
| −3 | 1 | 9 | 295 | 300 | 2 | 2 | 6 | 9 | 0 | 6 | 1 | −4 | 14 | 9 | 16 | 20 | 15 | −6 | −4 | 10 | 110 | 109 | 4 | −9 | 2 | 10 | 138 | 136 | 3 |
| −2 | 1 | 9 | 214 | 213 | 2 | 3 | 6 | 9 | 34 | 48 | 5 | −7 | −11 | 10 | 31 | 32 | 5 | −5 | −4 | 10 | 120 | 138 | 5 | −8 | 2 | 10 | 30 | 34 | 6 |
| −1 | 1 | 9 | 28 | 33 | 8 | −11 | 7 | 9 | 97 | 94 | 2 | −6 | −11 | 10 | 42 | 40 | 5 | −4 | −4 | 10 | 84 | 97 | 5 | −7 | 2 | 10 | 101 | 113 | 2 |
| 0 | 1 | 9 | 98 | 94 | 3 | −10 | 7 | 9 | 100 | 95 | 2 | −5 | −11 | 10 | 0 | 12 | 1 | −3 | −4 | 10 | 99 | 106 | 5 | −6 | 2 | 10 | 166 | 168 | 3 |
| 1 | 1 | 9 | 99 | 100 | 3 | −9 | 7 | 9 | 166 | 155 | 2 | −4 | −11 | 10 | 121 | 122 | 4 | −2 | −4 | 10 | 52 | 56 | 7 | −5 | 2 | 10 | 222 | 228 | 3 |
| 2 | 1 | 9 | 58 | 71 | 5 | −8 | 7 | 9 | 52 | 48 | 4 | −3 | −11 | 10 | 154 | 143 | 4 | −1 | −4 | 10 | 0 | 31 | 1 | −4 | 2 | 10 | 142 | 140 | 2 |
| 3 | 1 | 9 | 23 | 37 | 16 | −7 | 7 | 9 | 78 | 79 | 3 | −2 | −11 | 10 | 40 | 36 | 6 | 0 | −4 | 10 | 31 | 10 | 11 | −3 | 2 | 10 | 43 | 45 | 4 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 4 | 1 | 9 | 29 | 11 | 15 | −6 | 7 | 9 | 64 | 65 | 4 | −1 | −11 | 10 | 76 | 72 | 4 | 1 | −4 | 10 | 99 | 85 | 4 | −2 | 2 | 10 | 25 | 25 | 8 |
| −12 | 2 | 9 | 134 | 128 | 5 | −5 | 7 | 9 | 215 | 207 | 3 | −9 | −10 | 10 | 25 | 26 | 4 | 2 | −4 | 10 | 24 | 24 | 10 | −1 | 2 | 10 | 137 | 137 | 3 |
| −11 | 2 | 9 | 57 | 49 | 5 | −4 | 7 | 9 | 94 | 105 | 3 | −8 | −10 | 10 | 72 | 74 | 3 | −12 | −3 | 10 | 26 | 20 | 10 | 0 | 2 | 10 | 82 | 73 | 3 |
| −10 | 2 | 9 | 56 | 50 | 3 | −3 | 7 | 9 | 192 | 203 | 3 | −7 | −10 | 10 | 109 | 103 | 3 | −11 | −3 | 10 | 23 | 9 | 16 | 1 | 2 | 10 | 30 | 35 | 10 |
| −9 | 2 | 9 | 121 | 126 | 3 | −2 | 7 | 9 | 131 | 134 | 2 | −6 | −10 | 10 | 89 | 92 | 3 | −10 | −3 | 10 | 83 | 77 | 5 | 2 | 2 | 10 | 101 | 96 | 4 |
| −8 | 2 | 9 | 91 | 83 | 3 | −1 | 7 | 9 | 22 | 8 | 8 | −5 | −10 | 10 | 128 | 119 | 3 | −9 | −3 | 10 | 79 | 76 | 6 | −12 | 3 | 10 | 28 | 20 | 11 |
| −7 | 2 | 9 | 141 | 141 | 2 | 0 | 7 | 9 | 32 | 19 | 5 | −4 | −10 | 10 | 67 | 68 | 3 | −8 | −3 | 10 | 60 | 62 | 6 | −11 | 3 | 10 | 17 | 9 | 16 |
| −6 | 2 | 9 | 262 | 263 | 2 | 1 | 7 | 9 | 74 | 70 | 2 | −3 | −10 | 10 | 52 | 46 | 3 | −7 | −3 | 10 | 109 | 115 | 5 | −10 | 3 | 10 | 80 | 77 | 3 |
| −5 | 2 | 9 | 114 | 110 | 2 | 2 | 7 | 9 | 68 | 58 | 3 | −2 | −10 | 10 | 0 | 3 | 1 | −6 | −3 | 10 | 144 | 154 | 5 | −9 | 3 | 10 | 92 | 76 | 3 |
| −4 | 2 | 9 | 338 | 346 | 3 | 3 | 7 | 9 | 163 | 158 | 4 | −1 | −10 | 10 | 11 | 32 | 11 | −5 | −3 | 10 | 200 | 215 | 5 | −8 | 3 | 10 | 57 | 61 | 3 |
| −3 | 2 | 9 | 141 | 138 | 2 | −11 | 8 | 9 | 35 | 33 | 5 | −10 | −9 | 10 | 85 | 89 | 3 | −4 | −3 | 10 | 25 | 25 | 19 | −7 | 3 | 10 | 99 | 115 | 3 |
| −2 | 2 | 9 | 213 | 209 | 2 | −10 | 8 | 9 | 97 | 99 | 2 | −9 | −9 | 10 | 26 | 32 | 6 | −3 | −3 | 10 | 137 | 143 | 6 | −6 | 3 | 10 | 147 | 154 | 2 |
| −1 | 2 | 9 | 115 | 123 | 2 | −9 | 8 | 9 | 107 | 101 | 3 | −8 | −9 | 10 | 80 | 76 | 3 | −2 | −3 | 10 | 50 | 71 | 6 | −5 | 3 | 10 | 205 | 215 | 2 |
| 0 | 2 | 9 | 119 | 130 | 2 | −8 | 8 | 9 | 109 | 113 | 3 | −7 | −9 | 10 | 164 | 161 | 2 | −1 | −3 | 10 | 135 | 121 | 4 | −4 | 3 | 10 | 35 | 25 | 3 |
| 1 | 2 | 9 | 164 | 167 | 3 | −7 | 8 | 9 | 114 | 120 | 3 | −6 | −9 | 10 | 143 | 139 | 2 | 0 | −3 | 10 | 79 | 65 | 5 | −3 | 3 | 10 | 142 | 143 | 2 |
| 2 | 2 | 9 | 100 | 87 | 4 | −6 | 8 | 9 | 107 | 111 | 3 | −5 | −9 | 10 | 89 | 91 | 2 | 1 | −3 | 10 | 122 | 102 | 4 | −2 | 3 | 10 | 60 | 72 | 3 |
| 3 | 2 | 9 | 32 | 17 | 9 | −5 | 8 | 9 | 216 | 214 | 4 | −4 | −9 | 10 | 95 | 96 | 2 | 2 | −3 | 10 | 45 | 49 | 7 | −1 | 3 | 10 | 129 | 121 | 3 |
| 4 | 2 | 9 | 72 | 74 | 6 | −4 | 8 | 9 | 79 | 81 | 4 | −3 | −9 | 10 | 65 | 58 | 3 | −12 | −2 | 10 | 59 | 46 | 7 | 0 | 3 | 10 | 78 | 65 | 3 |
| −12 | 3 | 9 | 74 | 82 | 4 | −3 | 8 | 9 | 52 | 51 | 5 | −2 | −9 | 10 | 173 | 167 | 3 | −11 | −2 | 10 | 70 | 79 | 6 | 1 | 3 | 10 | 111 | 102 | 3 |
| −11 | 3 | 9 | 51 | 34 | 5 | −2 | 8 | 9 | 40 | 42 | 5 | −1 | −9 | 10 | 24 | 24 | 5 | −10 | −2 | 10 | 49 | 43 | 9 | 2 | 3 | 10 | 45 | 49 | 6 |
| −10 | 3 | 9 | 95 | 82 | 3 | −1 | 8 | 9 | 178 | 185 | 3 | 0 | −9 | 10 | 60 | 51 | 4 | −9 | −2 | 10 | 140 | 137 | 5 | −12 | 4 | 10 | 28 | 25 | 14 |
| −9 | 3 | 9 | 46 | 46 | 4 | 0 | 8 | 9 | 81 | 79 | 3 | −10 | −8 | 10 | 0 | 2 | 1 | −8 | −2 | 10 | 30 | 34 | 9 | −11 | 4 | 10 | 44 | 46 | 5 |
| −8 | 3 | 9 | 76 | 79 | 3 | 1 | 8 | 9 | 64 | 59 | 3 | −9 | −8 | 10 | 108 | 103 | 2 | −7 | −2 | 10 | 120 | 112 | 3 | −10 | 4 | 10 | 43 | 32 | 4 |
| −7 | 3 | 9 | 187 | 185 | 2 | 2 | 8 | 9 | 37 | 25 | 4 | −8 | −8 | 10 | 38 | 36 | 4 | −6 | −2 | 10 | 172 | 167 | 3 | −9 | 4 | 10 | 61 | 59 | 3 |
| −6 | 3 | 9 | 22 | 25 | 7 | −11 | 9 | 9 | 85 | 87 | 5 | −7 | −8 | 10 | 45 | 45 | 4 | −5 | −2 | 10 | 223 | 228 | 3 | −8 | 4 | 10 | 31 | 42 | 6 |
| −5 | 3 | 9 | 81 | 80 | 2 | −10 | 9 | 9 | 76 | 68 | 3 | −6 | −8 | 10 | 31 | 29 | 5 | −4 | −2 | 10 | 131 | 140 | 4 | −7 | 4 | 10 | 157 | 161 | 2 |
| −4 | 3 | 9 | 250 | 254 | 2 | −9 | 9 | 9 | 89 | 89 | 3 | −5 | −8 | 10 | 25 | 24 | 6 | −3 | −2 | 10 | 51 | 44 | 7 | −6 | 4 | 10 | 108 | 109 | 2 |
| −3 | 3 | 9 | 115 | 108 | 2 | −8 | 9 | 9 | 44 | 41 | 5 | −4 | −8 | 10 | 53 | 51 | 3 | −2 | −2 | 10 | 24 | 25 | 20 | −5 | 4 | 10 | 116 | 139 | 5 |
| −2 | 3 | 9 | 86 | 89 | 2 | −7 | 9 | 9 | 92 | 94 | 3 | −3 | −8 | 10 | 93 | 91 | 2 | −1 | −2 | 10 | 133 | 137 | 4 | −4 | 4 | 10 | 88 | 97 | 2 |
| −1 | 3 | 9 | 91 | 97 | 2 | −6 | 9 | 9 | 57 | 54 | 4 | −2 | −8 | 10 | 92 | 86 | 2 | 0 | −2 | 10 | 87 | 73 | 5 | −3 | 4 | 10 | 93 | 107 | 2 |
| 0 | 3 | 9 | 139 | 153 | 3 | −5 | 9 | 9 | 91 | 90 | 4 | −1 | −8 | 10 | 68 | 66 | 3 | 1 | −2 | 10 | 32 | 35 | 11 | −2 | 4 | 10 | 55 | 56 | 3 |
| 1 | 3 | 9 | 138 | 140 | 2 | −4 | 9 | 9 | 167 | 165 | 4 | 0 | −8 | 10 | 12 | 20 | 11 | 2 | −2 | 10 | 103 | 97 | 5 | −1 | 4 | 10 | 37 | 31 | 4 |
| 2 | 3 | 9 | 90 | 89 | 3 | −3 | 9 | 9 | 123 | 111 | 4 | 1 | −8 | 10 | 16 | 25 | 15 | −12 | −1 | 10 | 31 | 39 | 15 | 0 | 4 | 10 | 13 | 11 | 13 |
| 3 | 3 | 9 | 95 | 87 | 5 | −2 | 9 | 9 | 76 | 76 | 4 | −11 | −7 | 10 | 53 | 62 | 5 | −11 | −1 | 10 | 61 | 57 | 7 | 1 | 4 | 10 | 92 | 85 | 3 |
| −12 | 4 | 9 | 30 | 29 | 8 | −1 | 9 | 9 | 77 | 77 | 3 | −10 | −7 | 10 | 41 | 48 | 4 | −10 | −1 | 10 | 51 | 40 | 5 | 2 | 4 | 10 | 25 | 25 | 11 |
| −11 | 4 | 9 | 65 | 57 | 4 | 0 | 9 | 9 | 65 | 62 | 3 | −9 | −7 | 10 | 59 | 56 | 3 | −9 | −1 | 10 | 146 | 138 | 4 | −12 | 5 | 10 | 96 | 97 | 10 |
| −10 | 4 | 9 | 106 | 92 | 3 | 1 | 9 | 9 | 64 | 55 | 3 | −8 | −7 | 10 | 61 | 57 | 3 | −8 | −1 | 10 | 80 | 85 | 3 | −11 | 5 | 10 | 32 | 36 | 8 |
| −9 | 4 | 9 | 106 | 116 | 3 | 2 | 9 | 9 | 52 | 47 | 4 | −7 | −7 | 10 | 67 | 64 | 3 | −7 | −1 | 10 | 112 | 111 | 3 | −10 | 5 | 10 | 27 | 31 | 7 |
| −8 | 4 | 9 | 48 | 55 | 3 | −10 | 10 | 9 | 38 | 38 | 5 | −6 | −7 | 10 | 112 | 112 | 2 | −6 | −1 | 10 | 120 | 121 | 3 | −9 | 5 | 10 | 63 | 65 | 3 |
| −7 | 4 | 9 | 134 | 139 | 2 | −9 | 10 | 9 | 37 | 42 | 5 | −5 | −7 | 10 | 110 | 117 | 3 | −5 | −1 | 10 | 184 | 181 | 3 | −8 | 5 | 10 | 196 | 199 | 2 |
| −6 | 4 | 9 | 46 | 40 | 3 | −8 | 10 | 9 | 112 | 104 | 3 | −4 | −7 | 10 | 84 | 89 | 3 | −4 | −1 | 10 | 376 | 383 | 4 | −7 | 5 | 10 | 56 | 56 | 3 |
| −5 | 4 | 9 | 101 | 102 | 2 | −7 | 10 | 9 | 66 | 67 | 4 | −3 | −7 | 10 | 73 | 79 | 3 | −3 | −1 | 10 | 102 | 97 | 3 | −6 | 5 | 10 | 132 | 132 | 3 |
| −4 | 4 | 9 | 146 | 147 | 2 | −6 | 10 | 9 | 79 | 75 | 5 | −2 | −7 | 10 | 93 | 88 | 3 | −2 | −1 | 10 | 126 | 115 | 3 | −5 | 5 | 10 | 14 | 22 | 13 |
| −3 | 4 | 9 | 331 | 329 | 3 | −5 | 10 | 9 | 117 | 118 | 4 | −1 | −7 | 10 | 71 | 68 | 3 | −1 | −1 | 10 | 69 | 66 | 4 | −4 | 5 | 10 | 87 | 90 | 2 |
| −2 | 4 | 9 | 146 | 140 | 2 | −4 | 10 | 9 | 104 | 107 | 4 | 0 | −7 | 10 | 106 | 99 | 2 | 0 | −1 | 10 | 14 | 34 | 13 | −3 | 5 | 10 | 69 | 68 | 2 |
| −1 | 4 | 9 | 155 | 167 | 2 | −3 | 10 | 9 | 111 | 101 | 5 | 1 | −7 | 10 | 33 | 28 | 4 | 1 | −1 | 10 | 94 | 95 | 4 | −2 | 5 | 10 | 126 | 132 | 2 |
| 0 | 4 | 9 | 100 | 101 | 2 | −2 | 10 | 9 | 54 | 61 | 5 | −11 | −6 | 10 | 14 | 37 | 14 | 2 | −1 | 10 | 53 | 59 | 6 | −1 | 5 | 10 | 100 | 92 | 2 |
| 1 | 4 | 9 | 0 | 13 | 1 | −1 | 10 | 9 | 113 | 113 | 3 | −10 | −6 | 10 | 99 | 91 | 3 | −12 | 0 | 10 | 28 | 27 | 21 | 0 | 5 | 10 | 24 | 15 | 8 |
| 2 | 4 | 9 | 85 | 82 | 3 | 0 | 10 | 9 | 53 | 44 | 4 | −9 | −6 | 10 | 156 | 148 | 3 | −11 | 0 | 10 | 86 | 80 | 4 | 1 | 5 | 10 | 65 | 58 | 3 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 3 | 4 | 9 | 60 | 51 | 5 | 1 | 10 | 9 | 0 | 11 | 1 | −8 | −6 | 10 | 50 | 59 | 5 | −10 | 0 | 10 | 115 | 110 | 4 | 2 | 5 | 10 | 83 | 77 | 4 |
| −12 | 5 | 9 | 65 | 72 | 4 | −9 | 11 | 9 | 23 | 21 | 9 | −7 | −6 | 10 | 79 | 69 | 3 | −9 | 0 | 10 | 246 | 230 | 3 | −11 | 6 | 10 | 40 | 37 | 5 |
| −11 | 5 | 9 | 149 | 143 | 3 | −8 | 11 | 9 | 95 | 94 | 3 | −6 | −6 | 10 | 81 | 74 | 4 | −8 | 0 | 10 | 56 | 60 | 4 | −10 | 6 | 10 | 95 | 91 | 3 |
| −10 | 5 | 9 | 56 | 54 | 4 | −7 | 11 | 9 | 110 | 116 | 3 | −5 | −6 | 10 | 215 | 206 | 3 | −7 | 0 | 10 | 96 | 108 | 3 | −9 | 6 | 10 | 157 | 148 | 2 |
| −9 | 5 | 9 | 184 | 188 | 2 | −6 | 11 | 9 | 152 | 154 | 4 | −4 | −6 | 10 | 96 | 102 | 3 | −6 | 0 | 10 | 311 | 315 | 3 | −8 | 6 | 10 | 52 | 59 | 3 |
| −8 | 5 | 9 | 94 | 104 | 2 | −5 | 11 | 9 | 123 | 116 | 4 | −3 | −6 | 10 | 61 | 63 | 3 | −5 | 0 | 10 | 15 | 27 | 14 | −7 | 6 | 10 | 78 | 69 | 2 |
| −7 | 5 | 9 | 76 | 79 | 2 | −4 | 11 | 9 | 84 | 83 | 4 | −2 | −6 | 10 | 156 | 151 | 3 | −4 | 0 | 10 | 19 | 2 | 18 | −6 | 6 | 10 | 74 | 74 | 2 |
| −6 | 5 | 9 | 28 | 21 | 6 | −3 | 11 | 9 | 30 | 40 | 10 | −1 | −6 | 10 | 77 | 75 | 3 | −3 | 0 | 10 | 22 | 19 | 14 | −5 | 6 | 10 | 211 | 206 | 2 |
| −5 | 5 | 9 | 179 | 182 | 2 | −2 | 11 | 9 | 175 | 165 | 4 | 0 | −6 | 10 | 29 | 38 | 9 | −2 | 0 | 10 | 111 | 93 | 3 | −4 | 6 | 10 | 106 | 102 | 2 |
| −4 | 5 | 9 | 128 | 120 | 2 | −1 | 11 | 9 | 84 | 80 | 4 | 1 | −6 | 10 | 55 | 50 | 3 | −1 | 0 | 10 | 0 | 12 | 1 | −3 | 6 | 10 | 64 | 63 | 3 |
| −3 | 5 | 9 | 152 | 158 | 2 | 0 | 11 | 9 | 67 | 55 | 3 | −12 | −5 | 10 | 96 | 97 | 3 | 0 | 0 | 10 | 14 | 6 | 14 | −2 | 6 | 10 | 156 | 151 | 2 |
| −2 | 5 | 9 | 163 | 175 | 2 | 1 | 11 | 9 | 65 | 64 | 3 | −11 | −5 | 10 | 28 | 36 | 7 | 1 | 0 | 10 | 0 | 25 | 1 | −1 | 6 | 10 | 78 | 75 | 2 |
| −1 | 5 | 9 | 115 | 108 | 2 | −8 | 12 | 9 | 41 | 34 | 5 | −10 | −5 | 10 | 0 | 32 | 1 | 2 | 0 | 10 | 49 | 58 | 7 | 0 | 6 | 10 | 34 | 38 | 5 |
| 0 | 5 | 9 | 174 | 170 | 3 | −7 | 12 | 9 | 37 | 44 | 6 | −9 | −5 | 10 | 62 | 65 | 4 | −12 | 1 | 10 | 45 | 39 | 10 | 1 | 6 | 10 | 53 | 50 | 4 |
| 1 | 5 | 9 | 62 | 59 | 3 | −6 | 12 | 9 | 61 | 52 | 5 | −8 | −5 | 10 | 200 | 199 | 3 | −11 | 1 | 10 | 61 | 57 | 5 | −11 | 7 | 10 | 69 | 63 | 3 |
| 2 | 5 | 9 | 40 | 46 | 4 | −5 | 12 | 9 | 49 | 52 | 7 | −7 | −5 | 10 | 51 | 56 | 5 | −10 | 1 | 10 | 40 | 40 | 7 | −10 | 7 | 10 | 47 | 48 | 4 |
| 3 | 5 | 9 | 108 | 114 | 2 | −4 | 12 | 9 | 71 | 66 | 5 | −6 | −5 | 10 | 121 | 133 | 3 | −9 | 1 | 10 | 139 | 138 | 3 | −9 | 7 | 10 | 60 | 56 | 3 |
| −8 | 7 | 10 | 64 | 58 | 3 | −3 | −7 | 11 | 94 | 88 | 2 | −2 | 0 | 11 | 30 | 27 | 13 | −8 | 8 | 11 | 43 | 46 | 4 | −11 | 0 | 12 | 49 | 49 | 12 |
| −7 | 7 | 10 | 68 | 65 | 3 | −2 | −7 | 11 | 99 | 91 | 2 | −1 | 0 | 11 | 48 | 50 | 7 | −7 | 8 | 11 | 58 | 61 | 2 | −10 | 0 | 12 | 94 | 94 | 5 |
| −6 | 7 | 10 | 113 | 112 | 2 | −1 | −7 | 11 | 83 | 80 | 2 | 0 | 0 | 11 | 55 | 64 | 6 | −6 | 8 | 11 | 43 | 41 | 3 | −9 | 0 | 12 | 190 | 192 | 6 |
| −5 | 7 | 10 | 109 | 117 | 2 | −10 | −6 | 11 | 53 | 51 | 4 | 1 | 0 | 11 | 0 | 27 | 1 | −5 | 8 | 11 | 58 | 54 | 3 | −8 | 0 | 12 | 59 | 69 | 7 |
| −4 | 7 | 10 | 87 | 90 | 2 | −9 | −6 | 11 | 144 | 140 | 3 | −11 | 1 | 11 | 189 | 183 | 6 | −4 | 8 | 11 | 102 | 97 | 2 | −7 | 0 | 12 | 0 | 18 | 1 |
| −3 | 7 | 10 | 77 | 78 | 2 | −8 | −6 | 11 | 107 | 111 | 3 | −10 | 1 | 11 | 146 | 141 | 4 | −3 | 8 | 11 | 79 | 74 | 2 | −6 | 0 | 12 | 61 | 45 | 6 |
| −2 | 7 | 10 | 92 | 87 | 2 | −7 | −6 | 11 | 85 | 89 | 3 | −9 | 1 | 11 | 34 | 38 | 7 | −2 | 8 | 11 | 7 | 9 | 7 | −5 | 0 | 12 | 31 | 7 | 10 |
| −1 | 7 | 10 | 76 | 68 | 2 | −6 | −6 | 11 | 135 | 132 | 3 | −8 | 1 | 11 | 175 | 172 | 3 | −1 | 8 | 11 | 22 | 17 | 21 | −4 | 0 | 12 | 57 | 61 | 5 |
| 0 | 7 | 10 | 104 | 99 | 2 | −5 | −6 | 11 | 142 | 141 | 2 | −7 | 1 | 11 | 177 | 170 | 3 | −9 | 9 | 11 | 72 | 71 | 3 | −3 | 0 | 12 | 37 | 20 | 9 |
| 1 | 7 | 10 | 37 | 28 | 5 | −4 | −6 | 11 | 121 | 118 | 3 | −6 | 1 | 11 | 124 | 123 | 3 | −8 | 9 | 11 | 47 | 43 | 3 | −2 | 0 | 12 | 18 | 14 | 18 |
| −10 | 8 | 10 | 16 | 2 | 16 | −3 | −6 | 11 | 145 | 131 | 4 | −5 | 1 | 11 | 44 | 39 | 5 | −7 | 9 | 11 | 66 | 68 | 2 | −1 | 0 | 12 | 0 | 1 | 1 |
| −9 | 8 | 10 | 108 | 103 | 2 | −2 | −6 | 11 | 58 | 56 | 3 | −4 | 1 | 11 | 68 | 58 | 4 | −6 | 9 | 11 | 41 | 40 | 3 | −11 | 1 | 12 | 53 | 65 | 11 |
| −8 | 8 | 10 | 36 | 36 | 4 | −1 | −6 | 11 | 64 | 63 | 3 | −3 | 1 | 11 | 111 | 118 | 3 | −5 | 9 | 11 | 105 | 100 | 2 | −10 | 1 | 12 | 50 | 35 | 9 |
| −7 | 8 | 10 | 37 | 44 | 4 | 0 | −6 | 11 | 61 | 57 | 3 | −2 | 1 | 11 | 160 | 152 | 3 | −4 | 9 | 11 | 74 | 74 | 2 | −9 | 1 | 12 | 47 | 52 | 10 |
| −6 | 8 | 10 | 38 | 30 | 4 | −11 | −5 | 11 | 73 | 75 | 4 | −1 | 1 | 11 | 78 | 75 | 3 | −3 | 9 | 11 | 77 | 75 | 2 | −8 | 1 | 12 | 75 | 85 | 3 |
| −5 | 8 | 10 | 14 | 24 | 14 | −10 | −5 | 11 | 16 | 34 | 15 | 0 | 1 | 11 | 30 | 30 | 11 | −2 | 9 | 11 | 118 | 116 | 2 | −7 | 1 | 12 | 52 | 52 | 5 |
| −4 | 8 | 10 | 53 | 51 | 3 | −9 | −5 | 11 | 110 | 102 | 3 | 1 | 1 | 11 | 0 | 43 | 1 | −8 | 10 | 11 | 23 | 9 | 23 | −6 | 1 | 12 | 75 | 80 | 3 |
| −3 | 8 | 10 | 92 | 91 | 2 | −8 | −5 | 11 | 14 | 6 | 14 | −11 | 2 | 11 | 53 | 39 | 5 | −7 | 10 | 11 | 114 | 108 | 2 | −5 | 1 | 12 | 38 | 31 | 8 |
| −2 | 8 | 10 | 94 | 87 | 2 | −7 | −5 | 11 | 12 | 15 | 12 | −10 | 2 | 11 | 90 | 94 | 3 | −6 | 10 | 11 | 99 | 94 | 2 | −4 | 1 | 12 | 60 | 54 | 6 |
| −1 | 8 | 10 | 69 | 66 | 2 | −6 | −5 | 11 | 88 | 93 | 4 | −9 | 2 | 11 | 173 | 160 | 3 | −5 | 10 | 11 | 94 | 95 | 2 | −3 | 1 | 12 | 136 | 122 | 4 |
| 0 | 8 | 10 | 8 | 19 | 8 | −5 | −5 | 11 | 45 | 52 | 6 | −8 | 2 | 11 | 122 | 112 | 3 | −4 | 10 | 11 | 103 | 99 | 2 | −2 | 1 | 12 | 78 | 78 | 4 |
| 1 | 8 | 10 | 1 | 25 | 1 | −4 | −5 | 11 | 70 | 77 | 6 | −7 | 2 | 11 | 41 | 40 | 6 | −3 | 10 | 11 | 78 | 71 | 2 | −1 | 1 | 12 | 110 | 94 | 11 |
| −10 | 9 | 10 | 95 | 89 | 3 | −3 | −5 | 11 | 94 | 82 | 5 | −6 | 2 | 11 | 66 | 67 | 4 | −6 | 11 | 11 | 70 | 65 | 8 | −10 | 2 | 12 | 16 | 26 | 15 |
| −9 | 9 | 10 | 16 | 31 | 15 | −2 | −5 | 11 | 109 | 94 | 4 | −5 | 2 | 11 | 95 | 95 | 3 | −5 | 11 | 11 | 83 | 95 | 4 | −9 | 2 | 12 | 125 | 121 | 3 |
| −8 | 9 | 10 | 76 | 76 | 3 | −1 | −5 | 11 | 70 | 54 | 4 | −4 | 2 | 11 | 54 | 58 | 4 | −7 | −8 | 12 | 0 | 15 | 1 | −8 | 2 | 12 | 78 | 77 | 3 |
| −7 | 9 | 10 | 166 | 161 | 3 | 0 | −5 | 11 | 127 | 116 | 2 | −3 | 2 | 11 | 51 | 51 | 4 | −6 | −8 | 12 | 52 | 52 | 2 | −7 | 2 | 12 | 42 | 44 | 6 |
| −6 | 9 | 10 | 141 | 139 | 3 | −11 | −4 | 11 | 25 | 29 | 9 | −2 | 2 | 11 | 102 | 99 | 3 | −5 | −8 | 12 | 32 | 32 | 4 | −6 | 2 | 12 | 107 | 106 | 3 |
| −5 | 9 | 10 | 86 | 91 | 3 | −10 | −4 | 11 | 131 | 134 | 3 | −1 | 2 | 11 | 54 | 48 | 5 | −8 | −7 | 12 | 69 | 69 | 2 | −5 | 2 | 12 | 23 | 25 | 10 |
| −4 | 9 | 10 | 94 | 95 | 2 | −9 | −4 | 11 | 74 | 80 | 4 | 0 | 2 | 11 | 79 | 72 | 3 | −7 | −7 | 12 | 118 | 115 | 2 | −4 | 2 | 12 | 66 | 60 | 3 |
| −3 | 9 | 10 | 69 | 58 | 3 | −8 | −4 | 11 | 131 | 135 | 4 | −11 | 3 | 11 | 86 | 94 | 3 | −6 | −7 | 12 | 38 | 37 | 4 | −3 | 2 | 12 | 142 | 125 | 7 |
| −2 | 9 | 10 | 172 | 167 | 2 | −7 | −4 | 11 | 42 | 50 | 9 | −10 | 3 | 11 | 79 | 82 | 4 | −5 | −7 | 12 | 69 | 75 | 2 | −2 | 2 | 12 | 91 | 102 | 4 |
| −1 | 9 | 10 | 18 | 24 | 12 | −6 | −4 | 11 | 96 | 103 | 5 | −9 | 3 | 11 | 120 | 127 | 3 | −4 | −7 | 12 | 23 | 17 | 8 | −10 | 3 | 12 | 63 | 62 | 4 |

TABLE 24-continued

Observed and calculated structure factors for Diol-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 0 | 9 | 10 | 53 | 51 | 3 | −5 | −4 | 11 | 84 | 81 | 5 | −8 | 3 | 11 | 89 | 83 | 3 | −3 | −7 | 12 | 56 | 56 | 3 | −9 | 3 | 12 | 0 | 13 | 1 |
| −9 | 10 | 10 | 18 | 26 | 17 | −4 | −4 | 11 | 82 | 79 | 5 | −7 | 3 | 11 | 170 | 167 | 3 | −9 | −6 | 12 | 21 | 16 | 12 | −8 | 3 | 12 | 86 | 80 | 4 |
| −8 | 10 | 10 | 78 | 75 | 3 | −3 | −4 | 11 | 21 | 32 | 21 | −6 | 3 | 11 | 123 | 123 | 3 | −8 | −6 | 12 | 37 | 38 | 5 | −7 | 3 | 12 | 71 | 74 | 3 |
| −7 | 10 | 10 | 102 | 103 | 3 | −2 | −4 | 11 | 115 | 102 | 4 | −5 | 3 | 11 | 76 | 82 | 3 | −7 | −6 | 12 | 60 | 48 | 3 | −6 | 3 | 12 | 54 | 49 | 4 |
| −6 | 10 | 10 | 92 | 91 | 3 | −1 | −4 | 11 | 0 | 19 | 1 | −4 | 3 | 11 | 62 | 69 | 4 | −6 | −6 | 12 | 76 | 69 | 2 | −5 | 3 | 12 | 116 | 110 | 3 |
| −5 | 10 | 10 | 124 | 120 | 3 | 0 | −4 | 11 | 142 | 138 | 3 | −3 | 3 | 11 | 62 | 66 | 4 | −5 | −6 | 12 | 89 | 86 | 2 | −4 | 3 | 12 | 101 | 92 | 3 |
| −4 | 10 | 10 | 67 | 68 | 3 | −11 | −3 | 11 | 98 | 94 | 5 | −2 | 3 | 11 | 72 | 68 | 4 | −4 | −6 | 12 | 19 | 12 | 12 | −3 | 3 | 12 | 70 | 68 | 3 |
| −3 | 10 | 10 | 52 | 46 | 3 | −10 | −3 | 11 | 82 | 82 | 6 | −1 | 3 | 11 | 151 | 142 | 3 | −3 | −6 | 12 | 92 | 93 | 3 | −2 | 3 | 12 | 70 | 73 | 6 |
| −2 | 10 | 10 | 21 | 3 | 8 | −9 | −3 | 11 | 127 | 127 | 5 | 0 | 3 | 11 | 31 | 36 | 12 | −9 | −5 | 12 | 86 | 95 | 3 | −10 | 4 | 12 | 63 | 57 | 5 |
| −1 | 10 | 10 | 31 | 33 | 5 | −8 | −3 | 11 | 77 | 83 | 6 | −11 | 4 | 11 | 32 | 29 | 7 | −8 | −5 | 12 | 79 | 81 | 3 | −9 | 4 | 12 | 96 | 92 | 4 |
| 0 | 10 | 10 | 75 | 93 | 6 | −7 | −3 | 11 | 167 | 167 | 5 | −10 | 4 | 11 | 135 | 134 | 3 | −7 | −5 | 12 | 37 | 34 | 6 | −8 | 4 | 12 | 102 | 97 | 3 |
| −8 | 11 | 10 | 91 | 97 | 2 | −6 | −3 | 11 | 109 | 123 | 5 | −9 | 4 | 11 | 80 | 79 | 3 | −6 | −5 | 12 | 47 | 52 | 5 | −7 | 4 | 12 | 82 | 84 | 3 |
| −7 | 11 | 10 | 44 | 32 | 5 | −5 | −3 | 11 | 77 | 82 | 5 | −8 | 4 | 11 | 139 | 135 | 2 | −5 | −5 | 12 | 46 | 47 | 5 | −6 | 4 | 12 | 101 | 103 | 3 |
| −6 | 11 | 10 | 33 | 39 | 6 | −4 | −3 | 11 | 76 | 69 | 6 | −7 | 4 | 11 | 53 | 50 | 3 | −4 | −5 | 12 | 58 | 49 | 4 | −5 | 4 | 12 | 41 | 33 | 6 |
| −5 | 11 | 10 | 33 | 12 | 7 | −3 | −3 | 11 | 54 | 67 | 7 | −6 | 4 | 11 | 104 | 103 | 2 | −3 | −5 | 12 | 114 | 115 | 3 | −4 | 4 | 12 | 75 | 73 | 3 |
| −4 | 11 | 10 | 126 | 121 | 3 | −2 | −3 | 11 | 67 | 67 | 6 | −5 | 4 | 11 | 76 | 81 | 2 | −2 | −5 | 12 | 43 | 42 | 6 | −3 | 4 | 12 | 151 | 148 | 3 |
| −3 | 11 | 10 | 147 | 144 | 3 | −1 | −3 | 11 | 151 | 142 | 4 | −4 | 4 | 11 | 78 | 79 | 3 | −10 | −4 | 12 | 53 | 57 | 4 | −2 | 4 | 12 | 107 | 105 | 3 |
| −2 | 11 | 10 | 37 | 36 | 4 | 0 | −3 | 11 | 33 | 36 | 11 | −3 | 4 | 11 | 26 | 32 | 8 | −9 | −4 | 12 | 82 | 92 | 3 | −10 | 5 | 12 | 109 | 102 | 10 |
| −1 | 11 | 10 | 66 | 72 | 3 | 1 | −3 | 11 | 48 | 59 | 11 | −2 | 4 | 11 | 113 | 102 | 3 | −8 | −4 | 12 | 93 | 97 | 4 | −9 | 5 | 12 | 94 | 95 | 4 |
| −7 | 12 | 10 | 70 | 69 | 4 | −11 | −2 | 11 | 23 | 39 | 22 | −1 | 4 | 11 | 14 | 18 | 14 | −7 | −4 | 12 | 81 | 84 | 4 | −8 | 5 | 12 | 84 | 81 | 3 |
| −6 | 12 | 10 | 72 | 79 | 4 | −10 | −2 | 11 | 98 | 94 | 5 | 0 | 4 | 11 | 142 | 138 | 3 | −6 | −4 | 12 | 98 | 103 | 4 | −7 | 5 | 12 | 27 | 34 | 9 |
| −5 | 12 | 10 | 27 | 43 | 10 | −9 | −2 | 11 | 160 | 160 | 5 | −11 | 5 | 11 | 81 | 76 | 5 | −5 | −4 | 12 | 26 | 33 | 19 | −6 | 5 | 12 | 55 | 52 | 4 |
| −4 | 12 | 10 | 28 | 34 | 8 | −8 | −2 | 11 | 113 | 112 | 4 | −10 | 5 | 11 | 29 | 33 | 7 | −4 | −4 | 12 | 77 | 73 | 5 | −5 | 5 | 12 | 52 | 47 | 5 |
| −3 | 12 | 10 | 42 | 48 | 7 | −7 | −2 | 11 | 41 | 41 | 10 | −9 | 5 | 11 | 114 | 102 | 2 | −3 | −4 | 12 | 149 | 148 | 4 | −4 | 5 | 12 | 60 | 49 | 4 |
| −2 | 12 | 10 | 12 | 15 | 12 | −6 | −2 | 11 | 55 | 67 | 7 | −8 | 5 | 11 | 0 | 6 | 1 | −2 | −4 | 12 | 116 | 105 | 4 | −3 | 5 | 12 | 123 | 116 | 3 |
| −8 | −10 | 11 | 0 | 9 | 1 | −5 | −2 | 11 | 101 | 95 | 5 | −7 | 5 | 11 | 0 | 15 | 1 | −10 | −3 | 12 | 62 | 62 | 4 | −2 | 5 | 12 | 41 | 41 | 9 |
| −7 | −10 | 11 | 112 | 108 | 4 | −4 | −2 | 11 | 46 | 58 | 9 | −6 | 5 | 11 | 94 | 93 | 2 | −9 | −3 | 12 | 0 | 13 | 1 | −9 | 6 | 12 | 15 | 17 | 15 |
| −6 | −10 | 11 | 95 | 94 | 4 | −3 | −2 | 11 | 31 | 51 | 31 | −5 | 5 | 11 | 50 | 52 | 3 | −8 | −3 | 12 | 77 | 80 | 5 | −8 | 6 | 12 | 42 | 37 | 5 |
| −5 | −10 | 11 | 98 | 95 | 4 | −2 | −2 | 11 | 97 | 100 | 7 | −4 | 5 | 11 | 77 | 77 | 3 | −7 | −3 | 12 | 65 | 74 | 6 | −7 | 6 | 12 | 50 | 48 | 4 |
| −4 | −10 | 11 | 94 | 99 | 5 | −1 | −2 | 11 | 39 | 47 | 12 | −3 | 5 | 11 | 89 | 82 | 3 | −6 | −3 | 12 | 48 | 49 | 8 | −6 | 6 | 12 | 80 | 68 | 3 |
| −3 | −10 | 11 | 67 | 71 | 5 | 0 | −2 | 11 | 72 | 71 | 6 | −2 | 5 | 11 | 103 | 95 | 3 | −5 | −3 | 12 | 109 | 110 | 4 | −5 | 6 | 12 | 89 | 87 | 3 |
| −9 | −9 | 11 | 68 | 71 | 3 | 1 | −2 | 11 | 0 | 4 | 1 | −1 | 5 | 11 | 64 | 54 | 4 | −4 | −3 | 12 | 91 | 93 | 5 | −4 | 6 | 12 | 10 | 12 | 9 |
| −8 | −9 | 11 | 44 | 43 | 4 | −11 | −1 | 11 | 186 | 183 | 4 | 0 | 5 | 11 | 122 | 116 | 4 | −3 | −3 | 12 | 84 | 68 | 6 | −3 | 6 | 12 | 93 | 93 | 3 |
| −7 | −9 | 11 | 61 | 67 | 3 | −10 | −1 | 11 | 142 | 140 | 5 | −10 | 6 | 11 | 48 | 51 | 4 | −2 | −3 | 12 | 80 | 73 | 4 | −8 | 7 | 12 | 73 | 68 | 3 |
| −6 | −9 | 11 | 43 | 41 | 4 | −9 | −1 | 11 | 43 | 37 | 10 | −9 | 6 | 11 | 145 | 139 | 2 | −1 | −3 | 12 | 75 | 93 | 8 | −7 | 7 | 12 | 121 | 115 | 3 |
| −5 | −9 | 11 | 97 | 99 | 2 | −8 | −1 | 11 | 175 | 172 | 3 | −8 | 6 | 11 | 112 | 111 | 3 | −10 | −2 | 12 | 25 | 27 | 25 | −6 | 7 | 12 | 40 | 37 | 5 |
| −4 | −9 | 11 | 70 | 74 | 2 | −7 | −1 | 11 | 175 | 170 | 4 | −7 | 6 | 11 | 92 | 88 | 2 | −9 | −2 | 12 | 110 | 121 | 5 | −5 | 7 | 12 | 74 | 75 | 3 |
| −3 | −9 | 11 | 75 | 74 | 2 | −6 | −1 | 11 | 118 | 123 | 3 | −6 | 6 | 11 | 138 | 132 | 2 | −8 | −2 | 12 | 74 | 77 | 6 | −4 | 7 | 12 | 9 | 18 | 9 |
| −2 | −9 | 11 | 114 | 117 | 3 | −5 | −1 | 11 | 39 | 39 | 9 | −5 | 6 | 11 | 143 | 141 | 2 | −7 | −2 | 12 | 31 | 44 | 19 | −3 | 7 | 12 | 44 | 55 | 9 |
| −9 | −8 | 11 | 100 | 98 | 3 | −4 | −1 | 11 | 57 | 58 | 6 | −4 | 6 | 11 | 116 | 118 | 2 | −6 | −2 | 12 | 110 | 106 | 6 | −7 | 8 | 12 | 0 | 16 | 1 |
| −8 | −8 | 11 | 45 | 46 | 3 | −3 | −1 | 11 | 113 | 118 | 4 | −3 | 6 | 11 | 138 | 132 | 2 | −5 | −2 | 12 | 25 | 26 | 24 | −6 | 8 | 12 | 45 | 52 | 5 |
| −7 | −8 | 11 | 49 | 60 | 3 | −2 | −1 | 11 | 157 | 152 | 4 | −2 | 6 | 11 | 55 | 56 | 4 | −4 | −2 | 12 | 62 | 60 | 6 | −5 | 8 | 12 | 32 | 31 | 7 |
| −6 | −8 | 11 | 38 | 42 | 4 | −1 | −1 | 11 | 69 | 75 | 6 | −1 | 6 | 11 | 65 | 63 | 3 | −3 | −2 | 12 | 13 | 125 | 5 | −4 | 8 | 12 | 95 | 89 | 6 |
| −5 | −8 | 11 | 55 | 53 | 3 | 0 | −1 | 11 | 24 | 30 | 16 | 0 | 6 | 11 | 59 | 57 | 5 | −2 | −2 | 12 | 102 | 103 | 5 | −7 | −4 | 13 | 28 | 50 | 27 |
| −4 | −8 | 11 | 99 | 96 | 2 | 1 | −1 | 11 | 18 | 44 | 17 | −10 | 7 | 11 | 31 | 33 | 6 | −1 | −2 | 12 | 34 | 44 | 14 | −6 | −4 | 13 | 13 | 24 | 12 |
| −3 | −8 | 11 | 69 | 74 | 3 | −12 | 0 | 11 | 73 | 75 | 9 | −9 | 7 | 11 | 65 | 62 | 3 | −10 | −1 | 12 | 42 | 34 | 8 | −5 | −4 | 13 | 66 | 44 | 14 |
| −2 | −8 | 11 | 15 | 10 | 14 | −11 | 0 | 11 | 38 | 32 | 11 | −8 | 7 | 11 | 96 | 95 | 2 | −9 | −1 | 12 | 39 | 52 | 11 | −8 | −3 | 13 | 29 | 45 | 13 |
| −1 | −8 | 11 | 16 | 17 | 16 | −10 | 0 | 11 | 71 | 83 | 6 | −7 | 7 | 11 | 75 | 75 | 3 | −8 | −1 | 12 | 80 | 85 | 5 | −7 | −3 | 13 | 88 | 84 | 4 |
| −10 | −7 | 11 | 27 | 34 | 7 | −9 | 0 | 11 | 112 | 101 | 4 | −6 | 7 | 11 | 26 | 20 | 6 | −7 | −1 | 12 | 65 | 52 | 7 | −6 | −3 | 13 | 46 | 53 | 7 |

TABLE 24-continued

| Observed and calculated structure factors for Diol-2. | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| −9 | −7 | 11 | 58 | 62 | 3 | −8 | 0 | 11 | 84 | 76 | 3 | −5 | 7 | 11 | 73 | 67 | 2 | −6 | −1 | 12 | 92 | 80 | 6 | −5 | −3 | 13 | 57 | 65 | 9 |
| −8 | −7 | 11 | 91 | 95 | 3 | −7 | 0 | 11 | 140 | 134 | 3 | −4 | 7 | 11 | 42 | 36 | 3 | −5 | −1 | 12 | 28 | 31 | 28 | −8 | −2 | 13 | 80 | 90 | 5 |
| −7 | −7 | 11 | 70 | 76 | 3 | −6 | 0 | 11 | 118 | 105 | 3 | −3 | 7 | 11 | 92 | 88 | 2 | −4 | −1 | 12 | 50 | 54 | 13 | −7 | −2 | 13 | 86 | 96 | 4 |
| −6 | −7 | 11 | 12 | 20 | 12 | −5 | 0 | 11 | 75 | 80 | 4 | −2 | 7 | 11 | 101 | 91 | 3 | −3 | −1 | 12 | 125 | 122 | 7 | −6 | −2 | 13 | 67 | 76 | 5 |
| −5 | −7 | 11 | 75 | 67 | 3 | −4 | 0 | 11 | 55 | 50 | 4 | −1 | 7 | 11 | 84 | 81 | 3 | −2 | −1 | 12 | 61 | 78 | 7 | −5 | −2 | 13 | 57 | 62 | 8 |
| −4 | −7 | 11 | 51 | 37 | 4 | −3 | 0 | 11 | 80 | 87 | 4 | −9 | 8 | 11 | 104 | 98 | 2 | −1 | −1 | 12 | 88 | 94 | 6 | −4 | −2 | 13 | 107 | 120 | 5 |
| −9 | −1 | 13 | 27 | 42 | 27 | −4 | −1 | 13 | 24 | 30 | 23 | −5 | 0 | 13 | 114 | 114 | 11 | −5 | 1 | 13 | 51 | 56 | 10 | −8 | 3 | 13 | 0 | 45 | 1 |
| −8 | −1 | 13 | 18 | 15 | 18 | −9 | 0 | 13 | 0 | 9 | 1 | −4 | 0 | 13 | 0 | 27 | 1 | −8 | 2 | 13 | 75 | 91 | 12 | −7 | 3 | 13 | 103 | 84 | 10 |
| −7 | −1 | 13 | 78 | 84 | 5 | −8 | 0 | 13 | 126 | 125 | 7 | −8 | 1 | 13 | 20 | 14 | 20 | −7 | 2 | 13 | 91 | 96 | 8 | −6 | 3 | 13 | 56 | 53 | 6 |
| −6 | −1 | 13 | 6 | 35 | 5 | −7 | 0 | 13 | 55 | 56 | 8 | −7 | 1 | 13 | 81 | 85 | 7 | −6 | 2 | 13 | 80 | 77 | 7 | −7 | 4 | 13 | 56 | 50 | 14 |
| −5 | −1 | 13 | 50 | 56 | 10 | −6 | 0 | 13 | 16 | 33 | 16 | −6 | 1 | 13 | 34 | 35 | 14 | −5 | 2 | 13 | 52 | 63 | 8 | −6 | 4 | 13 | 24 | 24 | 18 |

TABLE 25

| Crystal data and structure refinement for Diol-3. | | |
|---|---|---|
| Empirical formula | C19H36O2 | |
| Formula weight | 296.48 | |
| Temperature | 100(1) K | |
| Wavelength | 1.54178 Å | |
| Crystal system, space group | Monoclinic, P2(1) | |
| Unit cell dimensions | a = 9.6840(19) Å | α = 90° |
| | b = 19.156(4) Å | β = 91.27(3)° |
| | c = 9.6870(19) Å | γ = 90° |
| Volume | 1796.6(6) $Å^3$ | |
| Z | 4 | |
| Calculated density | 1.096 $Mg/m^3$ | |
| Absorption coefficient | 0.521 $mm^{-1}$ | |
| F(000) | 664 | |
| Crystal size | 0.24 × 0.31 × 0.76 mm | |
| Theta range for data collection | 4.57 to 64.68° | |
| Limiting indices | −11 <= h <= 11, −22 <= k <= 20, 0 <= 1 <= 11 | |
| Reflections collected/unique | 8762/5350 [R(int) = 0.0689] | |
| Data/restraints/parameters | 5350/1/379 | |
| Goodness-of-fit on $F^2$ | 1.047 | |
| Final R indices [I > 2□(I)] | R1 = 0.0772, wR2 = 0.1991 | |
| R indices (all data) | R1 = 0.0872, wR2 = 0.2084 | |
| Absolute structure parameter | −0.1(4) | |
| Largest diff. peak and hole | 0.358 and −0.427 e/$Å^{-3}$ | |

TABLE 26

Atomic coordinates ($Å^2 \times 10^4$) and equivalent isotropic displacement parameters $Å^2 \times 10^3$) for Diol-3 U9eq) is defined as one third of the trace of the orthogonalized Uij tensor.

| | x | y | z | U(eq) |
|---|---|---|---|---|
| O(8A) | 3815(3) | 3378(2) | 9792(3) | 26(1) |
| O(25A) | 9202(3) | 3271(2) | 17725(3) | 24(1) |
| O(8B) | 11330(3) | 2585(2) | −415(3) | 23(1) |
| O(25B) | 6157(3) | 2765(2) | 8258(3) | 27(1) |
| C(17A) | 6814(4) | 4768(2) | 12027(4) | 21(1) |
| C(13B) | 9534(5) | 1736(3) | 1576(4) | 21(1) |
| C(17B) | 8211(4) | 1268(3) | 1505(5) | 22(1) |
| C(13A) | 5505(4) | 4291(3) | 11951(4) | 21(1) |
| C(18A) | 5933(5) | 3534(2) | 12112(5) | 23(1) |
| C(18B) | 9103(4) | 2503(2) | 1616(4) | 20(1) |
| C(25A) | 10092(4) | 3402(3) | 16552(4) | 23(1) |
| C(21A) | 9163(5) | 5138(3) | 12942(5) | 30(1) |
| C(16A) | 7413(5) | 4700(3) | 10550(4) | 26(1) |
| C(15B) | 8999(4) | 1542(3) | −862(4) | 23(1) |
| C(12B) | 10604(4) | 1567(3) | 2717(4) | 21(1) |
| C(23B) | 6171(4) | 1824(3) | 4809(5) | 22(1) |
| C(24A) | 9177(4) | 3713(3) | 15410(5) | 23(1) |
| C(16B) | 7729(5) | 1315(3) | −29(5) | 33(1) |
| C(22A) | 7439(4) | 4646(3) | 14644(4) | 23(1) |
| C(21B) | 5823(5) | 910(3) | 2180(5) | 27(1) |
| C(14B) | 10179(4) | 1521(3) | 190(4) | 20(1) |
| C(14A) | 4969(5) | 4485(3) | 10503(5) | 24(1) |
| C(11B) | 11976(5) | 1929(3) | 2467(5) | 25(1) |
| C(15A) | 6236(4) | 4459(3) | 9587(5) | 24(1) |
| C(20B) | 6997(4) | 1438(2) | 2468(5) | 21(1) |
| C(20A) | 7947(4) | 4631(3) | 13144(4) | 23(1) |
| C(25B) | 5508(4) | 2497(3) | 7018(4) | 21(1) |
| C(8A) | 3650(5) | 4112(3) | 9996(5) | 24(1) |
| C(8B) | 11548(4) | 1867(3) | −143(5) | 23(1) |
| C(23A) | 8533(5) | 4418(3) | 15715(5) | 26(1) |
| C(24B) | 6603(5) | 2086(3) | 6215(5) | 24(1) |
| C(9B) | 12571(4) | 1746(3) | 1067(4) | 23(1) |
| C(28A) | 6859(6) | 5353(3) | 15049(5) | 33(1) |
| C(11A) | 2995(5) | 4084(3) | 12535(5) | 29(1) |
| C(27B) | 4354(5) | 2017(3) | 7461(5) | 31(1) |
| C(27A) | 11239(5) | 3903(3) | 17027(5) | 31(1) |
| C(12A) | 4342(5) | 4469(3) | 12953(4) | 24(1) |
| C(22B) | 7357(4) | 1484(3) | 3999(5) | 22(1) |
| C(9A) | 2523(5) | 4229(3) | 11062(5) | 29(1) |
| C(26A) | 10699(5) | 2712(3) | 16084(5) | 28(1) |
| C(28B) | 7802(5) | 791(3) | 4656(5) | 30(1) |
| C(26B) | 4937(5) | 3104(3) | 6177(5) | 30(1) |

TABLE 27

| Bond lengths (Å) for Diol-3. | | | |
|---|---|---|---|
| O(8A)—C(8A) | 1.430(6) | O(25A)—C(25A) | 1.463(5) |
| O(8B)—C(8B) | 1.414(6) | O(25B)—C(25B) | 1.438(6) |
| C(17A)—C(16A) | 1.561(6) | C(17A)—C(20A) | 1.547(6) |
| C(17A)—C(13A) | 1.563(6) | C(13B)—C(18B) | 1.529(7) |
| C(13B)—C(14B) | 1.549(6) | C(13B)—C(12B) | 1.533(6) |
| C(13B)—C(17B) | 1.563(6) | C(17B)—C(20B) | 1.551(5) |
| C(17B)—C(16B) | 1.550(7) | C(13A)—C(18A) | 1.516(7) |
| C(13A)—C(14A) | 1.531(7) | C(13A)—C(12A) | 1.541(6) |
| C(25A)—C(24A) | 1.524(7) | C(25A)—C(26A) | 1.519(7) |
| C(25A)—C(27A) | 1.531(7) | C(21A)—C(20A) | 1.543(6) |
| C(16A)—C(15A) | 1.528(7) | C(15B)—C(14B) | 1.515(6) |
| C(15B)—C(16B) | 1.549(6) | C(12B)—C(11B) | 1.523(6) |
| C(23B)—C(24B) | 1.503(6) | C(23B)—C(22B) | 1.548(6) |
| C(24A)—C(23A) | 1.519(7) | C(22A)—C(28A) | 1.521(7) |
| C(22A)—C(23A) | 1.531(6) | C(22A)—C(20A) | 1.544(6) |
| C(21B)—C(20B) | 1.543(7) | C(14B)—C(8B) | 1.524(6) |
| C(14A)—C(15A) | 1.531(6) | C(14A)—C(8A) | 1.535(7) |
| C(11B)—C(9B) | 1.526(6) | C(20B)—C(22B) | 1.519(7) |
| C(25B)—C(27B) | 1.515(7) | C(25B)—C(26B) | 1.517(7) |
| C(25B)—C(24B) | 1.544(6) | C(8A)—C(9A) | 1.534(6) |
| C(8B)—C(9B) | 1.536(6) | C(11A)—C(9A) | 1.515(7) |
| C(11A)—C(12A) | 1.545(7) | C(22B)—C(28B) | 1.531(7) |

TABLE 28

| Bond angles (°) for Diol-3. | |
|---|---|
| C(16A)—C(17A)—C(20A) | 110.8(4) |
| C(16A)—C(17A)—C(13A) | 103.0(4) |
| C(20A)—C(17A)—C(13A) | 119.7(4) |
| C(18B)—C(13B)—C(14B) | 113.1(4) |
| C(18B)—C(13B)—C(12B) | 111.4(4) |
| C(14B)—C(13B)—C(12B) | 106.9(3) |
| C(18B)—C(13B)—C(17B) | 109.1(4) |
| C(14B)—C(13B)—C(17B) | 98.9(3) |
| C(12B)—C(13B)—C(17B) | 116.8(4) |
| C(20B)—C(17B)—C(16B) | 110.3(4) |
| C(20B)—C(17B)—C(13B) | 119.0(4) |
| C(16B)—C(17B)—C(13B) | 103.8(3) |
| C(18A)—C(13A)—C(14A) | 114.4(4) |
| C(18A)—C(13A)—C(12A) | 110.4(4) |
| C(14A)—C(13A)—C(12A) | 106.6(3) |
| C(18A)—C(13A)—C(17A) | 109.6(4) |
| C(14A)—C(13A)—C(17A) | 99.2(4) |
| C(12A)—C(13A)—C(17A) | 116.4(4) |
| O(25A)—C(25A)—C(24A) | 106.7(3) |
| O(25A)—C(25A)—C(26A) | 108.8(4) |
| C(24A)—C(25A)—C(26A) | 110.2(4) |
| O(25A)—C(25A)—C(27A) | 108.0(4) |
| C(24A)—C(25A)—C(27A) | 112.3(4) |
| C(26A)—C(25A)—C(27A) | 110.6(4) |
| C(15A)—C(16A)—C(17A) | 107.3(4) |
| C(14B)—C(15B)—C(16B) | 103.7(3) |
| C(11B)—C(12B)—C(13B) | 111.6(4) |
| C(24B)—C(23B)—C(22B) | 113.9(4) |
| C(23A)—C(24A)—C(25A) | 116.2(4) |
| C(15B)—C(16B)—C(17B) | 106.9(4) |
| C(28A)—C(22A)—C(23A) | 109.5(4) |
| C(28A)—C(22A)—C(20A) | 112.8(4) |
| C(23A)—C(22A)—C(20A) | 113.7(4) |
| C(15B)—C(14B)—C(13B) | 105.3(3) |
| C(15B)—C(14B)—C(8B) | 119.5(4) |
| C(13B)—C(14B)—C(8B) | 115.9(4) |
| C(15A)—C(14A)—C(8A) | 118.1(4) |
| C(15A)—C(14A)—C(13A) | 105.2(4) |
| C(8A)—C(14A)—C(13A) | 116.3(4) |
| C(12B)—C(11B)—C(9B) | 112.6(4) |
| C(16A)—C(15A)—C(14A) | 103.4(4) |
| C(22B)—O(20B)—O(21B) | 111.6(4) |
| C(22B)—C(20B)—C(17B) | 116.0(4) |
| C(21B)—C(20B)—C(17B) | 108.6(3) |
| C(21A)—C(20A)—C(22A) | 111.6(4) |
| C(21A)—C(20A)—C(17A) | 109.6(4) |
| C(22A)—C(20A)—C(17A) | 114.7(4) |
| O(25B)—C(25B)—C(27B) | 106.9(3) |

TABLE 28-continued

| Bond angles (°) for Diol-3. | |
|---|---|
| O(25B)—C(25B)—C(26B) | 108.8(4) |
| C(27B)—C(25B)—C(26B) | 110.8(4) |
| O(25B)—C(25B)—C(24B) | 108.1(3) |
| C(27B)—C(25B)—C(24B) | 110.6(4) |
| C(26B)—C(25B)—C(24B) | 111.5(4) |
| O(8A)—C(8A)—C(14A) | 114.0(4) |
| O(8A)—C(8A)—C(9A) | 108.6(4) |
| C(14A)—C(8A)—C(9A) | 108.5(4) |
| O(8B)—C(8B)—C(9B) | 112.3(4) |
| O(8B)—C(8B)—C(14B) | 109.6(4) |
| C(9B)—C(8B)—C(14B) | 108.8(4) |
| C(24A)—C(23A)—C(22A) | 113.8(4) |
| C(23B)—C(24B)—C(25B) | 116.5(4) |
| C(8B)—C(9B)—C(11B) | 113.2(4) |
| C(9A)—C(11A)—C(12A) | 113.2(4) |
| C(11A)—C(12A)—C(13A) | 110.7(4) |
| C(28B)—C(22B) C(20B) | 114.3(4) |
| C(28B)—C(22B)—C(23B) | 111.3(4) |
| C(20B)—C(22B)—C(23B) | 111.3(4) |
| C(8A)—C(9A)—C(11A) | 113.8(4) |

TABLE 29

Anisotropic displacement parameters (Å$^2$ × 10$^3$) for Diol-3. The anisotropic displacement factor exponent takes the form "$-2\pi^2$[h$^2$a * 2U$_{11}$ + + 2hka * b * U$_{12}$]

| | $U_{11}$ | $U_{22}$ | $U_{33}$ | $U_{23}$ | $U_{13}$ | $U_{12}$ |
|---|---|---|---|---|---|---|
| O(8A) | 28(2) | 18(2) | 32(2) | −2(1) | 9(1) | −5(1) |
| O(25A) | 30(2) | 27(2) | 16(2) | 3(1) | 8(1) | 0(1) |
| O(8B) | 26(2) | 16(2) | 26(2) | 3(1) | 9(1) | −4(1) |
| O(25B) | 33(2) | 24(2) | 24(2) | −6(1) | 13(1) | 3(1) |
| C(17A) | 27(2) | 15(3) | 22(2) | 2(2) | 7(2) | −2(2) |
| C(13B) | 27(2) | 19(3) | 17(2) | −2(2) | 10(2) | 1(2) |
| C(17B) | 25(2) | 16(3) | 25(2) | 0(2) | 15(2) | 0(2) |
| C(13A) | 23(2) | 14(2) | 27(2) | −3(2) | 9(2) | 0(2) |
| C(18A) | 28(2) | 16(3) | 24(2) | 2(2) | 10(2) | −2(2) |
| C(18B) | 25(2) | 17(2) | 18(2) | −2(2) | 12(2) | 0(2) |
| C(25A) | 25(2) | 28(3) | 17(2) | 3(2) | 12(2) | −4(2) |
| C(21A) | 27(2) | 32(3) | 30(3) | 5(2) | 3(2) | −8(2) |
| C(16A) | 33(2) | 23(3) | 22(2) | 5(2) | 13(2) | −2(2) |
| C(15B) | 29(2) | 23(3) | 19(2) | −2(2) | 14(2) | −2(2) |
| C(12B) | 26(2) | 18(3) | 20(2) | 2(2) | 9(2) | 4(2) |
| C(23B) | 21(2) | 22(3) | 25(2) | −5(2) | 15(2) | 3(2) |
| C(24A) | 24(2) | 18(3) | 28(2) | −1(2) | 6(2) | −3(2) |
| C(16B) | 26(2) | 18(3) | 26(2) | −4(2) | 12(2) | −1(2) |
| C(22A) | 26(2) | 19(3) | 23(2) | 3(2) | 6(2) | −5(2) |
| C(21B) | 27(2) | 30(3) | 25(2) | −5(2) | 14(2) | −5(2) |
| C(14B) | 23(2) | 14(2) | 23(2) | −1(2) | 13(2) | 4(2) |
| C(14A) | 26(2) | 18(3) | 29(2) | −1(2) | 13(2) | −1(2) |
| C(11B) | 26(2) | 26(3) | 24(2) | −1(2) | 9(2) | −1(2) |
| C(15A) | 27(2) | 19(3) | 27(2) | 4(2) | 11(2) | −2(2) |
| C(20B) | 23(2) | 13(3) | 27(2) | −5(2) | 14(2) | −1(2) |
| C(20A) | 30(2) | 13(3) | 25(2) | 1(2) | 7(2) | −1(2) |
| C(25B) | 27(2) | 17(3) | 21(2) | −2(2) | 13(2) | 0(2) |
| C(8A) | 30(2) | 20(3) | 22(2) | 2(2) | 6(2) | −2(2) |
| C(8B) | 26(2) | 17(3) | 26(2) | −6(2) | 14(2) | −2(2) |
| C(23A) | 27(2) | 25(3) | 26(2) | −3(2) | 3(2) | −4(2) |
| C(24B) | 28(2) | 21(3) | 23(2) | −1(2) | 17(2) | 3(2) |
| C(9B) | 23(2) | 20(3) | 24(2) | −1(2) | 10(2) | 0(2) |
| C(28A) | 41(3) | 32(3) | 26(3) | −5(2) | 8(2) | 12(2) |
| C(11A) | 27(2) | 24(3) | 38(3) | −1(2) | 17(2) | −1(2) |
| C(27B) | 34(3) | 31(3) | 29(2) | −7(2) | 18(2) | −6(2) |
| C(27A) | 30(2) | 30(3) | 32(3) | 4(2) | 4(2) | −6(2) |
| C(12A) | 33(2) | 20(3) | 20(2) | −3(2) | 11(2) | 2(2) |
| C(22B) | 21(2) | 18(3) | 29(2) | −1(2) | 15(2) | 1(2) |
| C(9A) | 23(2) | 25(3) | 40(3) | −5(2) | 13(2) | 3(2) |
| C(26A) | 32(3) | 23(3) | 29(2) | 2(2) | 7(2) | 5(2) |
| C(28B) | 38(3) | 28(3) | 23(2) | 1(2) | 14(2) | 9(2) |
| C(26B) | 35(3) | 27(3) | 29(3) | −3(2) | 12(2) | 5(2) |

TABLE 30

Hydrogen coordinates (Å$^2$ × 10$^4$) and isotropic displacement parameters (Å × 10$^3$) for Diol-3.

| | x | y | z | U(eq) |
|---|---|---|---|---|
| H(8AA) | 3053 | 3192 | 9743 | 38 |
| H(25A) | 9650 | 3078 | 18343 | 37 |
| H(8BA) | 12067 | 2794 | −342 | 34 |
| H(25B) | 5572 | 2945 | 8742 | 40 |
| H(17A) | 6498 | 5251 | 12138 | 25 |
| H(17B) | 8497 | 785 | 1687 | 26 |
| H(18A) | 5127 | 3242 | 12071 | 34 |
| H(18B) | 6403 | 3471 | 12986 | 34 |
| H(18C) | 6539 | 3408 | 11381 | 34 |
| H(18D) | 9911 | 2793 | 1648 | 30 |
| H(18E) | 8566 | 2586 | 2421 | 30 |
| H(18F) | 8559 | 2612 | 803 | 30 |
| H(21A) | 9868 | 5050 | 13632 | 44 |
| H(21B) | 8842 | 5610 | 13026 | 44 |
| H(21C) | 9536 | 5071 | 12042 | 44 |
| H(16A) | 7769 | 5146 | 10246 | 31 |
| H(16B) | 8159 | 4362 | 10553 | 31 |
| H(15A) | 9160 | 1222 | −1618 | 28 |
| H(15B) | 8875 | 2009 | −1232 | 28 |
| H(12A) | 10254 | 1714 | 3601 | 26 |
| H(12B) | 10750 | 1066 | 2754 | 26 |
| H(23A) | 5798 | 2211 | 4274 | 27 |
| H(23B) | 5439 | 1483 | 4911 | 27 |
| H(24A) | 9723 | 3759 | 14587 | 28 |
| H(24B) | 8438 | 3385 | 15199 | 28 |
| H(16C) | 7392 | 865 | −349 | 28 |
| H(16D) | 6990 | 1654 | −136 | 28 |
| H(22A) | 6678 | 4311 | 14693 | 27 |
| H(21D) | 5062 | 1010 | 2766 | 41 |
| H(21E) | 6153 | 445 | 2363 | 41 |
| H(21F) | 5524 | 944 | 1231 | 41 |
| H(14A) | 10399 | 1024 | 297 | 24 |
| H(14B) | 4721 | 4981 | 10558 | 29 |
| H(11A) | 12633 | 1797 | 3190 | 30 |
| H(11B) | 11844 | 2430 | 2519 | 30 |
| H(15C) | 6398 | 3989 | 9255 | 29 |
| H(15D) | 6128 | 4770 | 8802 | 29 |
| H(20A) | 6643 | 1897 | 2189 | 25 |
| H(20B) | 8301 | 4159 | 12981 | 27 |
| H(8AB) | 3345 | 4323 | 9120 | 29 |
| H(8BB) | 11916 | 1648 | −972 | 27 |
| H(23C) | 9258 | 4767 | 15761 | 31 |
| H(23D) | 8114 | 4398 | 16615 | 31 |
| H(24C) | 7405 | 2383 | 6114 | 28 |
| H(24D) | 6889 | 1688 | 6772 | 28 |
| H(9BA) | 13391 | 2026 | 926 | 27 |
| H(9BB) | 12848 | 1259 | 1074 | 27 |
| H(28A) | 6551 | 5334 | 15984 | 49 |
| H(28B) | 6094 | 5470 | 14444 | 49 |
| H(28C) | 7564 | 5702 | 14976 | 49 |
| H(11C) | 3137 | 3586 | 12647 | 35 |
| H(11D) | 2271 | 4224 | 13154 | 35 |
| H(27A) | 3679 | 2282 | 7948 | 47 |
| H(27B) | 4726 | 1660 | 8055 | 47 |
| H(27C) | 3927 | 1807 | 6660 | 47 |
| H(27D) | 10836 | 4332 | 17334 | 46 |
| H(27E) | 11837 | 3996 | 16271 | 46 |
| H(27F) | 11762 | 3695 | 17773 | 46 |
| H(12C) | 4622 | 4336 | 13883 | 29 |
| H(12D) | 4180 | 4969 | 12945 | 29 |
| H(22B) | 8151 | 1800 | 4089 | 27 |
| H(9AA) | 1744 | 3929 | 10834 | 35 |
| H(9AB) | 2207 | 4708 | 10997 | 35 |
| H(26A) | 9966 | 2404 | 15797 | 42 |
| H(26B) | 11215 | 2504 | 16835 | 42 |
| H(26C) | 11299 | 2793 | 15325 | 42 |
| H(28D) | 8548 | 595 | 4146 | 45 |
| H(28E) | 7036 | 472 | 4638 | 45 |
| H(28F) | 8101 | 869 | 5594 | 45 |
| H(26D) | 4247 | 3342 | 6695 | 45 |
| H(26E) | 4531 | 2932 | 5330 | 45 |
| H(26F) | 5671 | 3422 | 5973 | 45 |

TABLE 31

| Torsion angles [deg] for Diol-3 | |
|---|---|
| C(18B)—C(13B)—C(17B)—C(20B) | −44.8(5) |
| C(14B)—C(13B)—C(17B)—C(20B) | −163.2(4) |
| C(12B)—C(13B)—C(17B)—C(20B) | 82.7(5) |
| C(18B)—C(13B)—C(17B)—C(16B) | 78.3(4) |
| C(14B)—C(13B)—C(17B)—C(16B) | −40.1(4) |
| C(12B)—C(13B)—C(17B)—C(16B) | −154.2(4) |
| C(16A)—C(17A)—C(13A)—C(18A) | 79.5(4) |
| C(20A)—C(17A)—C(13A)—C(18A) | −43.9(5) |
| C(16A)—C(17A)—C(13A)—C(14A) | −40.7(4) |
| C(20A)—C(17A)—C(13A)—C(14A) | −164.1(4) |
| C(16A)—C(17A)—C(13A)—C(12A) | −154.4(4) |
| C(20A)—C(17A)—C(13A)—C(12A) | 82.2(5) |
| C(20A)—C(17A)—C(16A)—C(15A) | 150.7(4) |
| C(13A)—C(17A)—C(16A)—C(15A) | 21.5(5) |
| C(18B)—C(13B)—C(12B)—C(11B) | −67.7(5) |
| C(14B)—C(13B)—C(12B)—C(11B) | 56.4(5) |
| C(17B)—C(13B)—C(12B)—C(11B) | 166.0(4) |
| O(25A)—C(25A)—C(24A)—C(23A) | 63.9(5) |
| C(26A)—C(25A)—C(24A)—C(23A) | −178.1(4) |
| C(27A)—C(25A)—C(24A)—C(23A) | −54.3(5) |
| C(14B)—C(15B)—C(16B)—C(17B) | 7.3(5) |
| C(20B)—C(17B)—C(16B)—C(15B) | 149.8(4) |
| C(13B)—C(17B)—C(16B)—C(15B) | 21.2(5) |
| C(16B)—C(15B)—C(14B)—C(13B) | −33.7(5) |
| C(16B)—C(15B)—C(14B)—C(8B) | −166.1(4) |
| C(18B)—C(13B)—C(14B)—C(15B) | −69.2(5) |
| C(12B)—C(13B)—C(14B)—C(15B) | 167.8(4) |
| C(17B)—C(13B)—C(14B)—C(15B) | 46.2(4) |
| C(18B)—C(13B)—C(14B)—C(8B) | 65.3(5) |
| C(12B)—C(13B)—C(14B)—C(8B) | −57.7(5) |
| C(17B)—C(13B)—C(14B)—C(8B) | −179.4(4) |
| C(18A)—C(13A)—C(14A)—C(15A) | −70.0(5) |
| C(12A)—C(13A)—C(14A)—C(15A) | 167.7(4) |
| C(17A)—C(13A)—C(14A)—C(15A) | 46.6(4) |
| C(18A)—C(13A)—C(14A)—C(8A) | 62.9(5) |
| C(12A)—C(13A)—C(14A)—C(8A) | −59.5(5) |
| C(17A)—C(13A)—C(14A)—C(8A) | 179.4(4) |
| C(13B)—C(12B)—C(11B)—C(9B) | −56.8(5) |
| C(17A)—C(16A)—C(15A)—C(14A) | 6.8(5) |
| C(8A)—C(14A)—C(15A)—C(16A) | −165.5(4) |
| C(13A)—C(14A)—C(15A)—C(16A) | −33.7(5) |
| C(16B)—C(17B)—C(20B)—C(22B) | −173.9(4) |
| C(13B)—C(17B)—C(20B)—C(22B) | −54.2(6) |

TABLE 31-continued

| Torsion angles [deg] for Diol-3 | |
|---|---|
| C(16B)—C(17B)—C(20B)—C(21B) | 59.5(5) |
| C(13B)—C(17B)—C(20B)—C(21B) | 179.2(4) |
| C(28A)—C(22A)—C(20A)—C(21A) | 63.5(5) |
| C(23A)—C(22A)—C(20A)—C(21A) | −62.0(5) |
| C(28A)—C(22A)—C(20A)—C(17A) | −62.0(5) |
| C(23A)—C(22A)—C(20A)—C(17A) | 172.6(4) |
| C(16A)—C(17A)—C(20A)—C(21A) | 56.8(5) |
| C(13A)—C(17A)—C(20A)—C(21A) | 176.3(4) |
| C(16A)—C(17A)—C(20A)—C(22A) | −176.8(4) |
| C(13A)—C(17A)—C(20A)—C(22A) | −57.3(6) |
| C(15A)—C(14A)—C(8A)—O(8A) | 60.3(5) |
| C(13A)—C(14A)—C(8A)—O(8A) | −66.3(5) |
| C(15A)—C(14A)—C(8A)—C(9A) | −178.5(4) |
| C(13A)—C(14A)—C(8A)—C(9A) | 54.9(5) |
| C(15B)—C(14B)—C(8B)—O(8B) | 58.8(5) |
| C(13B)—C(14B)—C(8B)—O(8B) | −68.9(5) |
| C(15B)—C(14B)—C(8B)—C(9B) | −178.0(4) |
| C(13B)—C(14B)—C(8B)—C(9B) | 54.3(5) |
| C(25A)—C(24A)—C(23A)—C(22A) | −170.2(4) |
| C(28A)—C(22A)—C(23A)—C(24A) | 179.7(4) |
| C(20A)—C(22A)—C(23A)—C(24A) | −53.1(5) |
| C(22B)—C(23B)—C(24B)—C(25B) | 173.9(4) |
| O(25B)—C(25B)—C(24B)—C(23B) | −173.9(4) |
| C(27B)—C(25B)—C(24B)—C(23B) | 69.4(5) |
| C(26B)—C(25B)—C(24B)—C(23B) | −54.3(6) |
| O(8B)—C(8B)—C(9B)—C(11B) | 71.8(5) |
| C(14B)—C(8B)—C(9B)—C(11B) | −49.8(5) |
| C(12B)—C(11B)—C(9B)—C(8B) | 53.0(6) |
| C(9A)—C(11A)—C(12A)—C(13A) | −55.8(5) |
| C(18A)—C(13A)—C(12A)—C(11A) | −68.1(5) |
| C(14A)—C(13A)—C(12A)—C(11A) | 56.7(5) |
| C(17A)—C(13A)—C(12A)—C(11A) | 166.2(4) |
| C(21B)—C(20B)—C(22B)—C(28B) | 58.3(5) |
| C(17B)—C(20B)—C(22B)—C(28B) | −66.8(5) |
| C(21B)—C(20B)—C(22B)—C(23B) | −68.4(5) |
| C(17B)—C(20B)—C(22B)—C(23B) | 166.4(4) |
| C(24B)—C(23B)—C(22B)—C(28B) | 69.3(5) |
| C(24B)—C(23B)—C(22B)—C(20B) | −162.2(4) |
| O(8A)—C(8A)—C(9A)—C(11A) | 75.9(5) |
| C(14A)—C(8A)—C(9A)—C(11A) | −48.5(6) |
| C(12A)—C(11A)—C(9A)—C(8A) | 51.6(6) |

TABLE 32

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 0 | −22 | 0 | 10 | 28 | 10 | 5 | −9 | 0 | 168 | 162 | 4 | 7 | −1 | 0 | 100 | 98 | 3 | 9 | 9 | 0 | 59 | 54 | 6 | −1 | −16 | 1 | 136 | 141 | 5 |
| 1 | −22 | 0 | 90 | 90 | 7 | 6 | −9 | 0 | 117 | 120 | 4 | 8 | −1 | 0 | 108 | 109 | 2 | 10 | 9 | 0 | 90 | 78 | 7 | 0 | −16 | 1 | 0 | 13 | 1 |
| 1 | −21 | 0 | 73 | 79 | 6 | 7 | −9 | 0 | 112 | 98 | 3 | 9 | −1 | 0 | 150 | 124 | 5 | 4 | 10 | 0 | 56 | 50 | 11 | 1 | −16 | 1 | 44 | 35 | 5 |
| 2 | −21 | 0 | 89 | 89 | 6 | 8 | −9 | 0 | 22 | 18 | 12 | 10 | −1 | 0 | 75 | 73 | 4 | 5 | 10 | 0 | 58 | 70 | 12 | 2 | −16 | 1 | 188 | 174 | 5 |
| 3 | −21 | 0 | 41 | 45 | 11 | 9 | −9 | 0 | 55 | 53 | 4 | 11 | −1 | 0 | 57 | 61 | 10 | 6 | 10 | 0 | 165 | 150 | 7 | 3 | −16 | 1 | 148 | 128 | 6 |
| 0 | −20 | 0 | 44 | 38 | 14 | 10 | −9 | 0 | 86 | 79 | 8 | 1 | 0 | 0 | 49 | 47 | 2 | 7 | 10 | 0 | 70 | 70 | 8 | 4 | −16 | 1 | 177 | 178 | 8 |
| 1 | −20 | 0 | 103 | 97 | 6 | 0 | −8 | 0 | 379 | 377 | 17 | 2 | 0 | 0 | 91 | 94 | 4 | 8 | 10 | 0 | 80 | 81 | 8 | 5 | −16 | 1 | 93 | 92 | 4 |
| 2 | −20 | 0 | 147 | 131 | 6 | 1 | −8 | 0 | 598 | 553 | 14 | 3 | 0 | 0 | 64 | 61 | 4 | 9 | 10 | 0 | 76 | 62 | 6 | −4 | −15 | 1 | 64 | 80 | 13 |
| 3 | −20 | 0 | 35 | 27 | 12 | 2 | −8 | 0 | 53 | 22 | 5 | 4 | 0 | 0 | 238 | 239 | 9 | 10 | 10 | 0 | 27 | 20 | 27 | −3 | −15 | 1 | 140 | 146 | 8 |
| 4 | −20 | 0 | 59 | 63 | 12 | 3 | −8 | 0 | 155 | 129 | 7 | 5 | 0 | 0 | 11 | 3 | 11 | 3 | 11 | 0 | 194 | 194 | 11 | −2 | −15 | 1 | 192 | 135 | 8 |
| 1 | −19 | 0 | 43 | 40 | 8 | 4 | −8 | 0 | 121 | 117 | 3 | 6 | 0 | 0 | 259 | 244 | 5 | 4 | 11 | 0 | 92 | 95 | 11 | −1 | −15 | 1 | 98 | 86 | 5 |
| 2 | −19 | 0 | 48 | 49 | 9 | 5 | −8 | 0 | 297 | 281 | 6 | 7 | 0 | 0 | 67 | 61 | 3 | 5 | 11 | 0 | 66 | 78 | 12 | 0 | −15 | 1 | 148 | 137 | 4 |
| 3 | −19 | 0 | 65 | 66 | 7 | 6 | −8 | 0 | 85 | 77 | 3 | 8 | 0 | 0 | 47 | 51 | 3 | 6 | 11 | 0 | 233 | 231 | 9 | 1 | −15 | 1 | 77 | 80 | 4 |
| 4 | −19 | 0 | 46 | 43 | 11 | 7 | −8 | 0 | 57 | 54 | 4 | 9 | 0 | 0 | 56 | 57 | 6 | 7 | 11 | 0 | 94 | 91 | 7 | 2 | −15 | 1 | 400 | 365 | 8 |
| 0 | −18 | 0 | 114 | 127 | 7 | 8 | −8 | 0 | 66 | 67 | 5 | 10 | 0 | 0 | 17 | 19 | 16 | 8 | 11 | 0 | 101 | 101 | 7 | 3 | −15 | 1 | 61 | 48 | 4 |
| 1 | −18 | 0 | 68 | 67 | 6 | 9 | −8 | 0 | 105 | 95 | 4 | 11 | 0 | 0 | 40 | 44 | 10 | 9 | 11 | 0 | 118 | 107 | 7 | 4 | −15 | 1 | 72 | 73 | 3 |
| 2 | −18 | 0 | 285 | 241 | 9 | 10 | −8 | 0 | 74 | 67 | 4 | 1 | 1 | 0 | 339 | 303 | 13 | 4 | 12 | 0 | 262 | 270 | 13 | 5 | −15 | 1 | 104 | 103 | 3 |
| 3 | −18 | 0 | 68 | 67 | 7 | 1 | −7 | 0 | 175 | 155 | 4 | 2 | 1 | 0 | 370 | 361 | 14 | 5 | 12 | 0 | 208 | 211 | 12 | 6 | −15 | 1 | 132 | 149 | 5 |
| 4 | −18 | 0 | 110 | 111 | 7 | 2 | −7 | 0 | 168 | 206 | 6 | 3 | 1 | 0 | 242 | 257 | 9 | 6 | 12 | 0 | 121 | 132 | 11 | 7 | −15 | 1 | 123 | 112 | 5 |
| 8 | −14 | 0 | 24 | 23 | 13 | 6 | −5 | 0 | 155 | 152 | 3 | 8 | 3 | 0 | 61 | 54 | 5 | −2 | −21 | 1 | 87 | 72 | 6 | 0 | −13 | 1 | 44 | 38 | 4 |
| 1 | −13 | 0 | 430 | 401 | 10 | 7 | −5 | 0 | 62 | 61 | 3 | 9 | 3 | 0 | 59 | 51 | 4 | −1 | −21 | 1 | 64 | 60 | 7 | 1 | −13 | 1 | 112 | 99 | 3 |
| 2 | −13 | 0 | 47 | 50 | 3 | 8 | −5 | 0 | 41 | 44 | 5 | 10 | 3 | 0 | 32 | 24 | 11 | 0 | −21 | 1 | 71 | 76 | 6 | 2 | −13 | 1 | 195 | 209 | 5 |
| 3 | −13 | 0 | 229 | 222 | 5 | 9 | −5 | 0 | 163 | 159 | 6 | 11 | 3 | 0 | 86 | 86 | 6 | 1 | −21 | 1 | 61 | 44 | 7 | 3 | −13 | 1 | 138 | 123 | 3 |
| 4 | −13 | 0 | 72 | 66 | 3 | 10 | −5 | 0 | 26 | 14 | 15 | 2 | 4 | 0 | 528 | 505 | 20 | 2 | −21 | 1 | 86 | 83 | 5 | 4 | −13 | 1 | 197 | 199 | 5 |
| 5 | −13 | 0 | 200 | 203 | 7 | 0 | −4 | 0 | 1156 | 1139 | 33 | 3 | 4 | 0 | 138 | 150 | 6 | 3 | −21 | 1 | 36 | 44 | 11 | 5 | −13 | 1 | 173 | 187 | 5 |
| 6 | −13 | 0 | 59 | 65 | 6 | 1 | −4 | 0 | 216 | 239 | 8 | 6 | 4 | 0 | 55 | 54 | 3 | −3 | −20 | 1 | 35 | 34 | 20 | 6 | −13 | 1 | 86 | 92 | 6 |
| 7 | −13 | 0 | 93 | 94 | 5 | 2 | −4 | 0 | 460 | 506 | 18 | 7 | 4 | 0 | 93 | 88 | 3 | −2 | −20 | 1 | 150 | 142 | 6 | 7 | −13 | 1 | 113 | 129 | 6 |
| 8 | −13 | 0 | 40 | 42 | 8 | 4 | −4 | 0 | 242 | 236 | 12 | 8 | 4 | 0 | 28 | 16 | 10 | −1 | −20 | 1 | 69 | 72 | 7 | 8 | −13 | 1 | 26 | 44 | 18 |
| 9 | −13 | 0 | 90 | 81 | 6 | 5 | −4 | 0 | 130 | 131 | 7 | 9 | 4 | 0 | 60 | 57 | 5 | 0 | −20 | 1 | 0 | 21 | 1 | 9 | −13 | 1 | 78 | 79 | 7 |
| 0 | −12 | 0 | 397 | 341 | 15 | 6 | −4 | 0 | 56 | 54 | 3 | 10 | 4 | 0 | 174 | 164 | 5 | 1 | −20 | 1 | 51 | 49 | 7 | −9 | −12 | 1 | 36 | 33 | 8 |
| 1 | −12 | 0 | 226 | 210 | 4 | 7 | −4 | 0 | 89 | 89 | 3 | 11 | 4 | 0 | 43 | 41 | 15 | 2 | −20 | 1 | 122 | 110 | 6 | −8 | −12 | 1 | 95 | 92 | 4 |
| 2 | −12 | 0 | 281 | 272 | 5 | 8 | −4 | 0 | 19 | 16 | 9 | 2 | 5 | 0 | 251 | 241 | 10 | 3 | −20 | 1 | 20 | 15 | 20 | −7 | −12 | 1 | 34 | 39 | 5 |
| 3 | −12 | 0 | 129 | 137 | 3 | 9 | −4 | 0 | 66 | 56 | 6 | 3 | 5 | 0 | 259 | 235 | 10 | 4 | −20 | 1 | 100 | 108 | 6 | −6 | −12 | 1 | 106 | 113 | 3 |
| 4 | −12 | 0 | 256 | 269 | 6 | 10 | −4 | 0 | 183 | 164 | 6 | 5 | 5 | 0 | 86 | 95 | 9 | −3 | −19 | 1 | 94 | 81 | 8 | −5 | −12 | 1 | 110 | 122 | 3 |
| 5 | −12 | 0 | 199 | 211 | 55 | 11 | −4 | 0 | 23 | 40 | 22 | 6 | 5 | 0 | 160 | 151 | 7 | −2 | −19 | 1 | 91 | 93 | 7 | −4 | −12 | 1 | 154 | 160 | 3 |
| 6 | −12 | 0 | 120 | 132 | 4 | 2 | −3 | 0 | 534 | 497 | 21 | 7 | 5 | 0 | 61 | 61 | 4 | −1 | −19 | 1 | 59 | 31 | 8 | −3 | −12 | 1 | 369 | 360 | 6 |
| 7 | −12 | 0 | 32 | 36 | 11 | 3 | −3 | 0 | 299 | 294 | 12 | 8 | 5 | 0 | 48 | 44 | 7 | 0 | −19 | 1 | 157 | 152 | 6 | −2 | −12 | 1 | 125 | 132 | 3 |
| 8 | −12 | 0 | 45 | 45 | 9 | 4 | −3 | 0 | 470 | 435 | 12 | 9 | 5 | 0 | 167 | 159 | 5 | 1 | −19 | 1 | 125 | 119 | 6 | −1 | −12 | 1 | 145 | 117 | 3 |
| 9 | −12 | 0 | 55 | 56 | 6 | 5 | −3 | 0 | 186 | 173 | 5 | 10 | 5 | 0 | 30 | 13 | 13 | 2 | −19 | 1 | 61 | 49 | 7 | 0 | −12 | 1 | 272 | 252 | 5 |
| 1 | −11 | 0 | 95 | 105 | 2 | 6 | −3 | 0 | 27 | 24 | 6 | 11 | 5 | 0 | 37 | 38 | 20 | 3 | −19 | 1 | 77 | 79 | 6 | 1 | −12 | 1 | 247 | 251 | 5 |
| 2 | −11 | 0 | 393 | 379 | 7 | 7 | −3 | 0 | 33 | 36 | 4 | 5 | 6 | 0 | 23 | 19 | 16 | 4 | −19 | 1 | 104 | 102 | 6 | 2 | −12 | 1 | 63 | 69 | 3 |
| 3 | −11 | 0 | 203 | 194 | 3 | 8 | −3 | 0 | 57 | 54 | 3 | 6 | 6 | 0 | 73 | 62 | 7 | 5 | −19 | 1 | 0 | 7 | 1 | 3 | −12 | 1 | 262 | 254 | 5 |
| 4 | −11 | 0 | 93 | 96 | 2 | 9 | −3 | 0 | 57 | 51 | 4 | 7 | 6 | 0 | 108 | 104 | 4 | −3 | −18 | 1 | 126 | 124 | 8 | 4 | −12 | 1 | 155 | 161 | 4 |
| 5 | −11 | 0 | 75 | 79 | 3 | 10 | −3 | 0 | 0 | 24 | 1 | 8 | 6 | 0 | 87 | 73 | 5 | −2 | −18 | 1 | 165 | 175 | 8 | 5 | −12 | 1 | 183 | 191 | 5 |
| 6 | −11 | 0 | 236 | 230 | 4 | 11 | −3 | 0 | 88 | 86 | 5 | 9 | 6 | 0 | 147 | 138 | 5 | −1 | −18 | 1 | 94 | 81 | 6 | 6 | −12 | 1 | 34 | 33 | 12 |
| 7 | −11 | 0 | 85 | 92 | 4 | 0 | −2 | 0 | 401 | 408 | 12 | 10 | 6 | 0 | 78 | 75 | 8 | 0 | −18 | 1 | 49 | 50 | 8 | 7 | −12 | 1 | 17 | 25 | 16 |
| 8 | −11 | 0 | 102 | 101 | 5 | 1 | −2 | 0 | 535 | 567 | 16 | 5 | 7 | 0 | 219 | 215 | 8 | 1 | −18 | 1 | 232 | 231 | 10 | 8 | −12 | 1 | 59 | 60 | 10 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 9 | −11 | 0 | 105 | 107 | 7 | 2 | −2 | 0 | 783 | 727 | 31 | 6 | 7 | 0 | 48 | 39 | 8 | 2 | −18 | 1 | 153 | 130 | 6 | 9 | −12 | 1 | 110 | 102 | 5 |
| 0 | −10 | 0 | 512 | 530 | 23 | 3 | −2 | 0 | 20 | 11 | 7 | 7 | 7 | 0 | 105 | 94 | 7 | 3 | −18 | 1 | 81 | 67 | 6 | −9 | −11 | 1 | 139 | 136 | 4 |
| 1 | −10 | 0 | 254 | 236 | 12 | 4 | −2 | 0 | 476 | 440 | 14 | 8 | 7 | 0 | 75 | 72 | 6 | 4 | −18 | 1 | 64 | 48 | 7 | −8 | −11 | 1 | 83 | 74 | 3 |
| 2 | −10 | 0 | 148 | 123 | 4 | 5 | −2 | 0 | 95 | 90 | 3 | 9 | 7 | 0 | 101 | 93 | 5 | 5 | −18 | 1 | 73 | 57 | 10 | −7 | −11 | 1 | 77 | 71 | 4 |
| 3 | −10 | 0 | 49 | 48 | 2 | 6 | −2 | 0 | 18 | 24 | 7 | 10 | 7 | 0 | 49 | 41 | 11 | −3 | −17 | 1 | 61 | 36 | 10 | −6 | −11 | 1 | 113 | 111 | 3 |
| 4 | −10 | 0 | 51 | 49 | 2 | 7 | −2 | 0 | 44 | 43 | 4 | 5 | 8 | 0 | 292 | 281 | 11 | −2 | −17 | 1 | 139 | 134 | 5 | −5 | −11 | 1 | 121 | 115 | 3 |
| 5 | −10 | 0 | 63 | 70 | 3 | 8 | −2 | 0 | 145 | 143 | 3 | 6 | 8 | 0 | 87 | 77 | 7 | −1 | −17 | 1 | 46 | 42 | 8 | −4 | −11 | 1 | 148 | 153 | 3 |
| 6 | −10 | 0 | 167 | 150 | 4 | 9 | −2 | 0 | 61 | 49 | 5 | 7 | 8 | 0 | 56 | 53 | 9 | 0 | −17 | 1 | 187 | 183 | 8 | −3 | −11 | 1 | 120 | 114 | 2 |
| 7 | −10 | 0 | 68 | 71 | 4 | 10 | −2 | 0 | 29 | 29 | 12 | 8 | 8 | 0 | 70 | 68 | 6 | 1 | −17 | 1 | 98 | 100 | 5 | −2 | −11 | 1 | 227 | 201 | 4 |
| 8 | −10 | 0 | 90 | 81 | 4 | 11 | −2 | 0 | 54 | 44 | 7 | 9 | 8 | 0 | 111 | 94 | 5 | 2 | −17 | 1 | 164 | 143 | 6 | −1 | −11 | 1 | 299 | 298 | 6 |
| 9 | −10 | 0 | 66 | 62 | 4 | 1 | −1 | 0 | 336 | 303 | 13 | 10 | 8 | 0 | 78 | 67 | 8 | 3 | −17 | 1 | 118 | 114 | 6 | 0 | −11 | 1 | 153 | 160 | 5 |
| 10 | −10 | 0 | 18 | 19 | 17 | 2 | −1 | 0 | 377 | 361 | 15 | 4 | 9 | 0 | 84 | 72 | 9 | 4 | −17 | 1 | 76 | 67 | 6 | 1 | −11 | 1 | 184 | 165 | 5 |
| 1 | −9 | 0 | 524 | 482 | 14 | 3 | −1 | 0 | 238 | 257 | 9 | 5 | 9 | 0 | 165 | 163 | 7 | 5 | −17 | 1 | 40 | 29 | 20 | 2 | −11 | 1 | 351 | 357 | 8 |
| 2 | −9 | 0 | 342 | 331 | 15 | 4 | −1 | 0 | 256 | 222 | 10 | 6 | 9 | 0 | 116 | 121 | 7 | −4 | −16 | 1 | 120 | 120 | 12 | 3 | −11 | 1 | 204 | 209 | 4 |
| 3 | −9 | 0 | 308 | 294 | 14 | 5 | −1 | 0 | 103 | 105 | 3 | 7 | 9 | 0 | 106 | 97 | 7 | −3 | −16 | 1 | 173 | 174 | 9 | 4 | −11 | 1 | 111 | 113 | 3 |
| 4 | −9 | 0 | 83 | 73 | 3 | 6 | −1 | 0 | 78 | 70 | 2 | 8 | 9 | 0 | 18 | 18 | 18 | −2 | −16 | 1 | 186 | 189 | 7 | 5 | −11 | 1 | 100 | 103 | 5 |
| 6 | −11 | 1 | 194 | 190 | 5 | −10 | −6 | 1 | 113 | 102 | 5 | −8 | −2 | 1 | 207 | 199 | 5 | −10 | 2 | 1 | 59 | 54 | 7 | −9 | 6 | 1 | 112 | 104 | 5 |
| 7 | −11 | 1 | 39 | 44 | 12 | −9 | −6 | 1 | 104 | 103 | 4 | −7 | −2 | 1 | 171 | 172 | 4 | −9 | 2 | 1 | 163 | 147 | 4 | −8 | 6 | 1 | 198 | 198 | 6 |
| 8 | −11 | 1 | 74 | 74 | 9 | −8 | −6 | 1 | 171 | 198 | 7 | −6 | −2 | 1 | 127 | 123 | 2 | −8 | 2 | 1 | 211 | 200 | 4 | −7 | 6 | 1 | 245 | 240 | 9 |
| 9 | −11 | 1 | 69 | 68 | 8 | −7 | −6 | 1 | 248 | 241 | 8 | −5 | −2 | 1 | 151 | 159 | 4 | −7 | 2 | 1 | 175 | 173 | 4 | −6 | 6 | 1 | 60 | 55 | 8 |
| −9 | −10 | 1 | 49 | 39 | 4 | −6 | −6 | 1 | 68 | 55 | 4 | −4 | −2 | 1 | 262 | 255 | 7 | −6 | 2 | 1 | 122 | 123 | 4 | −5 | 6 | 1 | 96 | 85 | 6 |
| −8 | −10 | 1 | 97 | 80 | 3 | −5 | −6 | 1 | 96 | 86 | 3 | −3 | −2 | 1 | 367 | 352 | 14 | −5 | 2 | 1 | 142 | 160 | 8 | 1 | 6 | 1 | 289 | 306 | 11 |
| −7 | −10 | 1 | 202 | 190 | 6 | −3 | −6 | 1 | 800 | 687 | 36 | −2 | −2 | 1 | 523 | 524 | 20 | −4 | 2 | 1 | 257 | 256 | 11 | 2 | 6 | 1 | 495 | 534 | 19 |
| −6 | −10 | 1 | 161 | 164 | 4 | −2 | −6 | 1 | 469 | 387 | 21 | −1 | −2 | 1 | 1124 | 1057 | 44 | −3 | 2 | 1 | 359 | 353 | 14 | 5 | 6 | 1 | 58 | 52 | 6 |
| −5 | −10 | 1 | 169 | 161 | 4 | −1 | −6 | 1 | 214 | 215 | 7 | 0 | −2 | 1 | 231 | 248 | 6 | −2 | 2 | 1 | 497 | 525 | 19 | 6 | 6 | 1 | 25 | 24 | 25 |
| −4 | −10 | 1 | 233 | 232 | 4 | 0 | −6 | 1 | 479 | 488 | 11 | 1 | −2 | 1 | 1070 | 1007 | 25 | −1 | 2 | 1 | 977 | 1057 | 38 | 7 | 6 | 1 | 99 | 97 | 11 |
| −3 | −10 | 1 | 206 | 215 | 4 | 1 | −6 | 1 | 329 | 306 | 15 | 3 | −2 | 1 | 345 | 323 | 15 | 0 | 2 | 1 | 227 | 246 | 9 | 8 | 6 | 1 | 66 | 33 | 6 |
| −2 | −10 | 1 | 195 | 191 | 5 | 3 | −6 | 1 | 383 | 360 | 14 | 4 | −2 | 1 | 318 | 313 | 10 | 1 | 2 | 1 | 1004 | 1008 | 39 | 9 | 6 | 1 | 65 | 58 | 5 |
| −1 | −10 | 1 | 193 | 192 | 9 | 4 | −6 | 1 | 54 | 63 | 3 | 5 | −2 | 1 | 38 | 38 | 3 | 2 | 2 | 1 | 252 | 231 | 7 | 10 | 6 | 1 | 45 | 57 | 9 |
| 0 | −10 | 1 | 153 | 153 | 8 | 5 | −6 | 1 | 59 | 52 | 2 | 6 | −2 | 1 | 105 | 98 | 3 | 3 | 2 | 1 | 340 | 322 | 9 | −10 | 7 | 1 | 136 | 128 | 7 |
| 1 | −10 | 1 | 176 | 158 | 8 | 6 | −6 | 1 | 27 | 24 | 4 | 7 | −2 | 1 | 158 | 150 | 3 | 4 | 2 | 1 | 329 | 313 | 13 | −9 | 7 | 1 | 57 | 54 | 7 |
| 2 | −10 | 1 | 213 | 198 | 10 | 7 | −6 | 1 | 103 | 96 | 2 | 8 | −2 | 1 | 97 | 93 | 3 | 5 | 2 | 1 | 41 | 38 | 4 | −8 | 7 | 1 | 191 | 209 | 8 |
| 3 | −10 | 1 | 261 | 254 | 6 | 8 | −6 | 1 | 48 | 33 | 6 | 9 | −2 | 1 | 82 | 75 | 4 | 6 | 2 | 1 | 100 | 97 | 2 | −7 | 7 | 1 | 126 | 120 | 7 |
| 4 | −10 | 1 | 122 | 116 | 2 | 9 | −6 | 1 | 60 | 58 | 5 | 10 | −2 | 1 | 41 | 41 | 8 | 7 | 2 | 1 | 157 | 149 | 3 | −6 | 7 | 1 | 197 | 184 | 8 |
| 5 | −10 | 1 | 140 | 134 | 3 | 10 | −6 | 1 | 54 | 57 | 5 | 11 | −2 | 1 | 50 | 59 | 10 | 8 | 2 | 1 | 95 | 93 | 4 | −5 | 7 | 1 | 154 | 153 | 7 |
| 6 | −10 | 1 | 138 | 136 | 3 | −10 | −5 | 1 | 108 | 93 | 5 | −11 | −1 | 1 | 49 | 38 | 8 | 9 | 2 | 1 | 81 | 75 | 6 | 5 | 7 | 1 | 110 | 97 | 6 |
| 7 | −10 | 1 | 189 | 192 | 11 | −9 | −5 | 1 | 185 | 180 | 5 | −10 | −1 | 1 | 51 | 36 | 7 | 10 | 2 | 1 | 45 | 41 | 7 | 6 | 7 | 1 | 128 | 128 | 7 |
| 8 | −10 | 1 | 119 | 115 | 5 | −8 | −5 | 1 | 56 | 73 | 4 | −9 | −1 | 1 | 284 | 257 | 6 | 11 | 2 | 1 | 55 | 59 | 7 | 7 | 7 | 1 | 121 | 125 | 5 |
| 9 | −10 | 1 | 0 | 23 | 1 | −7 | −5 | 1 | 90 | 77 | 4 | −8 | −1 | 1 | 199 | 192 | 4 | −11 | 3 | 1 | 51 | 58 | 15 | 8 | 7 | 1 | 87 | 77 | 5 |
| 10 | −10 | 1 | 73 | 72 | 8 | −6 | −5 | 1 | 117 | 114 | 4 | −7 | −1 | 1 | 92 | 89 | 3 | −10 | 3 | 1 | 45 | 40 | 7 | 9 | 7 | 1 | 128 | 122 | 5 |
| −10 | −9 | 1 | 45 | 37 | 4 | −5 | −5 | 1 | 77 | 63 | 3 | −6 | −1 | 1 | 45 | 37 | 3 | −9 | 3 | 1 | 145 | 143 | 4 | 10 | 7 | 1 | 121 | 117 | 7 |
| −9 | −9 | 1 | 99 | 85 | 4 | −4 | −5 | 1 | 250 | 289 | 10 | −5 | −1 | 1 | 241 | 236 | 6 | −8 | 3 | 1 | 187 | 173 | 4 | −10 | 8 | 1 | 87 | 77 | 8 |
| −8 | −9 | 1 | 87 | 83 | 5 | −3 | −5 | 1 | 38 | 26 | 4 | −4 | −1 | 1 | 423 | 377 | 16 | −7 | 3 | 1 | 234 | 229 | 6 | −9 | 8 | 1 | 177 | 165 | 6 |
| −7 | −9 | 1 | 67 | 72 | 4 | −2 | −5 | 1 | 409 | 382 | 16 | −3 | −1 | 1 | 166 | 186 | 7 | −6 | 3 | 1 | 217 | 205 | 6 | −8 | 8 | 1 | 139 | 130 | 8 |
| −6 | −9 | 1 | 150 | 150 | 4 | −1 | −5 | 1 | 318 | 285 | 14 | −2 | −1 | 1 | 455 | 444 | 18 | −4 | 3 | 1 | 237 | 215 | 10 | −7 | 8 | 1 | 116 | 107 | 7 |
| −5 | −9 | 1 | 239 | 240 | 5 | 0 | −5 | 1 | 36 | 36 | 2 | −1 | −1 | 1 | 730 | 724 | 28 | −3 | 3 | 1 | 238 | 208 | 9 | −6 | 8 | 1 | 134 | 136 | 7 |
| −4 | −9 | 1 | 216 | 208 | 4 | 1 | −5 | 1 | 379 | 356 | 17 | 0 | −1 | 1 | 94 | 112 | 3 | −2 | 3 | 1 | 170 | 165 | 7 | −5 | 8 | 1 | 211 | 214 | 8 |
| −3 | −9 | 1 | 323 | 303 | 14 | 2 | −5 | 1 | 538 | 512 | 15 | 1 | −1 | 1 | 558 | 507 | 16 | −1 | 3 | 1 | 772 | 823 | 30 | 4 | 8 | 1 | 185 | 197 | 11 |
| −2 | −9 | 1 | 188 | 177 | 9 | 3 | −5 | 1 | 392 | 399 | 13 | 2 | −1 | 1 | 648 | 634 | 30 | 0 | 3 | 1 | 1390 | 1499 | 55 | 5 | 8 | 1 | 89 | 80 | 9 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −1 | −9 | 1 | 386 | 376 | 12 | 4 | −5 | 1 | 145 | 156 | 5 | 4 | −1 | 1 | 294 | 278 | 14 | 1 | 3 | 1 | 915 | 967 | 36 | 6 | 8 | 1 | 87 | 81 | 7 |
| 0 | −9 | 1 | 97 | 95 | 6 | 5 | −5 | 1 | 97 | 86 | 3 | 5 | −1 | 1 | 161 | 151 | 6 | 2 | 3 | 1 | 215 | 226 | 8 | 7 | 8 | 1 | 76 | 67 | 8 |
| 1 | −9 | 1 | 383 | 369 | 17 | 6 | −5 | 1 | 95 | 89 | 3 | 6 | −1 | 1 | 50 | 46 | 2 | 3 | 3 | 1 | 89 | 60 | 3 | 8 | 8 | 1 | 53 | 34 | 6 |
| 2 | −9 | 1 | 108 | 76 | 6 | 7 | −5 | 1 | 110 | 107 | 2 | 7 | −1 | 1 | 18 | 12 | 6 | 4 | 3 | 1 | 368 | 334 | 14 | 9 | 8 | 1 | 134 | 116 | 5 |
| 3 | −9 | 1 | 231 | 222 | 6 | 8 | −5 | 1 | 65 | 59 | 4 | 8 | −1 | 1 | 123 | 110 | 3 | 5 | 3 | 1 | 210 | 213 | 5 | 10 | 8 | 1 | 71 | 73 | 8 |
| 4 | −9 | 1 | 58 | 58 | 3 | 9 | −5 | 1 | 187 | 165 | 6 | 9 | −1 | 1 | 104 | 83 | 5 | 6 | 3 | 1 | 147 | 144 | 3 | −10 | 9 | 1 | 31 | 38 | 25 |
| 5 | −9 | 1 | 51 | 44 | 2 | 10 | −5 | 1 | 177 | 167 | 5 | 10 | −1 | 1 | 26 | 18 | 15 | 7 | 3 | 1 | 94 | 67 | 4 | −9 | 9 | 1 | 98 | 85 | 6 |
| 6 | −9 | 1 | 53 | 54 | 3 | −11 | −4 | 1 | 34 | 34 | 13 | 11 | −1 | 1 | 52 | 45 | 10 | 8 | 3 | 1 | 149 | 136 | 4 | −8 | 9 | 1 | 92 | 82 | 7 |
| 7 | −9 | 1 | 51 | 46 | 4 | −10 | −4 | 1 | 69 | 56 | 7 | −11 | 0 | 1 | 34 | 21 | 17 | 9 | 3 | 1 | 19 | 9 | 19 | −7 | 9 | 1 | 76 | 72 | 8 |
| 8 | −9 | 1 | 41 | 33 | 5 | −9 | −4 | 1 | 42 | 45 | 6 | −10 | 0 | 1 | 103 | 86 | 4 | 10 | 3 | 1 | 112 | 99 | 5 | −6 | 9 | 1 | 147 | 149 | 7 |
| 9 | −9 | 1 | 27 | 20 | 8 | −8 | −4 | 1 | 187 | 191 | 5 | −9 | 0 | 1 | 24 | 23 | 10 | 11 | 3 | 1 | 0 | 31 | 1 | −5 | 9 | 1 | 224 | 238 | 9 |
| 10 | −9 | 1 | 44 | 45 | 12 | −7 | −4 | 1 | 137 | 137 | 3 | −8 | 0 | 1 | 141 | 120 | 3 | −11 | 4 | 1 | 49 | 34 | 15 | −4 | 9 | 1 | 201 | 208 | 8 |
| −10 | −8 | 1 | 88 | 76 | 4 | −6 | −4 | 1 | 95 | 99 | 3 | −7 | 0 | 1 | 55 | 49 | 3 | −10 | 4 | 1 | 66 | 56 | 5 | 4 | 9 | 1 | 60 | 59 | 10 |
| −9 | −8 | 1 | 185 | 165 | 5 | −5 | −4 | 1 | 278 | 266 | 6 | −6 | 0 | 1 | 98 | 91 | 2 | −9 | 4 | 1 | 44 | 45 | 6 | 5 | 9 | 1 | 68 | 45 | 10 |
| −8 | −8 | 1 | 141 | 130 | 5 | −4 | −4 | 1 | 560 | 539 | 14 | −5 | 0 | 1 | 172 | 174 | 5 | −8 | 4 | 1 | 193 | 190 | 5 | 6 | 9 | 1 | 64 | 52 | 8 |
| −7 | −8 | 1 | 113 | 107 | 4 | −3 | −4 | 1 | 206 | 219 | 8 | −4 | 0 | 1 | 48 | 57 | 5 | −7 | 4 | 1 | 134 | 138 | 5 | 7 | 9 | 1 | 45 | 47 | 11 |
| −6 | −8 | 1 | 133 | 136 | 4 | −2 | −4 | 1 | 460 | 415 | 18 | −3 | 0 | 1 | 222 | 195 | 9 | −6 | 4 | 1 | 101 | 98 | 6 | 8 | 9 | 1 | 50 | 34 | 7 |
| −5 | −8 | 1 | 223 | 214 | 5 | −1 | −4 | 1 | 295 | 292 | 8 | −2 | 0 | 1 | 146 | 148 | 6 | −5 | 4 | 1 | 255 | 266 | 14 | 9 | 9 | 1 | 31 | 19 | 13 |
| −4 | −8 | 1 | 215 | 198 | 5 | 0 | −4 | 1 | 524 | 519 | 15 | −1 | 0 | 1 | 320 | 346 | 12 | −3 | 4 | 1 | 203 | 220 | 8 | 10 | 9 | 1 | 33 | 45 | 18 |
| −3 | −8 | 1 | 140 | 130 | 7 | 1 | −4 | 1 | 134 | 106 | 4 | 0 | 0 | 1 | 430 | 460 | 12 | −2 | 4 | 1 | 416 | 415 | 16 | −10 | 10 | 1 | 138 | 145 | 7 |
| −2 | −8 | 1 | 577 | 530 | 26 | 2 | −4 | 1 | 534 | 498 | 15 | 1 | 0 | 1 | 214 | 184 | 6 | −1 | 4 | 1 | 251 | 291 | 10 | −9 | 10 | 1 | 40 | 38 | 10 |
| −1 | −8 | 1 | 491 | 474 | 15 | 3 | −4 | 1 | 187 | 196 | 8 | 3 | 0 | 1 | 176 | 167 | 7 | 0 | 4 | 1 | 495 | 519 | 21 | −8 | 10 | 1 | 102 | 79 | 8 |
| 0 | −8 | 1 | 164 | 165 | 5 | 4 | −4 | 1 | 492 | 475 | 17 | 4 | 0 | 1 | 330 | 312 | 10 | 1 | 4 | 1 | 142 | 108 | 5 | −7 | 10 | 1 | 203 | 190 | 8 |
| 1 | −8 | 1 | 381 | 335 | 17 | 5 | −4 | 1 | 127 | 103 | 4 | 5 | 0 | 1 | 121 | 99 | 7 | 2 | 4 | 1 | 497 | 498 | 19 | −6 | 10 | 1 | 165 | 164 | 7 |
| 2 | −8 | 1 | 345 | 293 | 16 | 6 | −4 | 1 | 55 | 60 | 3 | 6 | 0 | 1 | 77 | 71 | 2 | 3 | 4 | 1 | 188 | 196 | 7 | −5 | 10 | 1 | 165 | 162 | 7 |
| 3 | −8 | 1 | 188 | 166 | 9 | 7 | −4 | 1 | 39 | 36 | 3 | 7 | 0 | 1 | 31 | 28 | 3 | 4 | 4 | 1 | 515 | 477 | 19 | −4 | 10 | 1 | 219 | 232 | 9 |
| 4 | −8 | 1 | 201 | 197 | 5 | 8 | −4 | 1 | 66 | 68 | 3 | 8 | 0 | 1 | 239 | 229 | 5 | 5 | 4 | 1 | 121 | 102 | 3 | 3 | 10 | 1 | 243 | 254 | 12 |
| 5 | −8 | 1 | 88 | 80 | 3 | 9 | −4 | 1 | 80 | 72 | 5 | 9 | 0 | 1 | 112 | 95 | 5 | 6 | 4 | 1 | 64 | 60 | 4 | 4 | 10 | 1 | 124 | 115 | 10 |
| 6 | −8 | 1 | 84 | 81 | 2 | 10 | −4 | 1 | 32 | 22 | 11 | 10 | 0 | 1 | 51 | 51 | 7 | 7 | 4 | 1 | 48 | 36 | 5 | 5 | 10 | 1 | 139 | 134 | 10 |
| 7 | −8 | 1 | 69 | 67 | 3 | −11 | −3 | 1 | 53 | 58 | 7 | 11 | 0 | 1 | 35 | 30 | 10 | 8 | 4 | 1 | 77 | 68 | 4 | 6 | 10 | 1 | 137 | 136 | 11 |
| 8 | −8 | 1 | 31 | 34 | 7 | −10 | −3 | 1 | 52 | 39 | 7 | −11 | 1 | 1 | 43 | 37 | 14 | 9 | 4 | 1 | 85 | 72 | 4 | 7 | 10 | 1 | 216 | 193 | 12 |
| 9 | −8 | 1 | 136 | 116 | 4 | −9 | −3 | 1 | 143 | 143 | 4 | −10 | 1 | 1 | 45 | 36 | 7 | 10 | 4 | 1 | 28 | 23 | 16 | 8 | 10 | 1 | 117 | 116 | 5 |
| 10 | −8 | 1 | 74 | 73 | 4 | −8 | −3 | 1 | 183 | 173 | 4 | −9 | 1 | 1 | 278 | 257 | 5 | 11 | 4 | 1 | 67 | 53 | 10 | 9 | 10 | 1 | 33 | 23 | 11 |
| −10 | −7 | 1 | 142 | 128 | 4 | −7 | −3 | 1 | 231 | 229 | 6 | −8 | 1 | 1 | 194 | 192 | 5 | −10 | 5 | 1 | 105 | 94 | 4 | −9 | 11 | 1 | 148 | 136 | 7 |
| −9 | −7 | 1 | 60 | 54 | 5 | −6 | −3 | 1 | 216 | 205 | 4 | −7 | 1 | 1 | 92 | 89 | 3 | −9 | 5 | 1 | 193 | 180 | 8 | −8 | 11 | 1 | 74 | 73 | 9 |
| −8 | −7 | 1 | 181 | 208 | 6 | −5 | −3 | 1 | 113 | 104 | 3 | −6 | 1 | 1 | 46 | 36 | 4 | −8 | 5 | 1 | 66 | 73 | 5 | −7 | 11 | 1 | 72 | 70 | 8 |
| −7 | −7 | 1 | 121 | 121 | 4 | −4 | −3 | 1 | 243 | 216 | 6 | −5 | 1 | 1 | 234 | 236 | 6 | −7 | 5 | 1 | 91 | 77 | 7 | −6 | 11 | 1 | 134 | 112 | 6 |
| −6 | −7 | 1 | 202 | 184 | 5 | −3 | −3 | 1 | 254 | 207 | 10 | −4 | 1 | 1 | 408 | 376 | 16 | −6 | 5 | 1 | 119 | 114 | 6 | −5 | 11 | 1 | 119 | 116 | 7 |
| −5 | −7 | 1 | 163 | 153 | 4 | −2 | −3 | 1 | 184 | 165 | 7 | −3 | 1 | 1 | 162 | 186 | 7 | −5 | 5 | 1 | 82 | 63 | 6 | −4 | 11 | 1 | 144 | 153 | 10 |
| −4 | −7 | 1 | 374 | 327 | 17 | −1 | −3 | 1 | 876 | 823 | 25 | −2 | 1 | 1 | 447 | 444 | 17 | −2 | 5 | 1 | 375 | 382 | 15 | 3 | 11 | 1 | 192 | 208 | 11 |
| −3 | −7 | 1 | 319 | 287 | 14 | 0 | −3 | 1 | 1415 | 1499 | 64 | −1 | 1 | 1 | 661 | 724 | 26 | −1 | 5 | 1 | 270 | 285 | 10 | 4 | 11 | 1 | 109 | 113 | 11 |
| −2 | −7 | 1 | 238 | 207 | 11 | 1 | −3 | 1 | 1034 | 967 | 24 | 0 | 1 | 1 | 92 | 111 | 4 | 0 | 5 | 1 | 31 | 35 | 5 | 5 | 11 | 1 | 99 | 102 | 11 |
| −1 | −7 | 1 | 257 | 265 | 8 | 2 | −3 | 1 | 232 | 227 | 7 | 1 | 1 | 1 | 555 | 507 | 16 | 1 | 5 | 1 | 326 | 355 | 13 | 6 | 11 | 1 | 181 | 189 | 12 |
| 0 | −7 | 1 | 173 | 157 | 5 | 4 | −3 | 1 | 364 | 334 | 12 | 2 | 1 | 1 | 649 | 634 | 17 | 2 | 5 | 1 | 499 | 513 | 19 | 7 | 11 | 1 | 40 | 45 | 12 |
| 1 | −7 | 1 | 161 | 132 | 7 | 5 | −3 | 1 | 215 | 214 | 7 | 3 | 1 | 1 | 90 | 94 | 4 | 3 | 5 | 1 | 400 | 399 | 14 | 8 | 11 | 1 | 81 | 75 | 8 |
| 2 | −7 | 1 | 143 | 159 | 5 | 6 | −3 | 1 | 150 | 145 | 3 | 4 | 1 | 1 | 276 | 278 | 12 | 4 | 5 | 1 | 176 | 156 | 6 | 9 | 11 | 1 | 75 | 68 | 8 |
| 3 | −7 | 1 | 229 | 219 | 10 | 7 | −3 | 1 | 86 | 66 | 2 | 5 | 1 | 1 | 153 | 151 | 5 | 5 | 5 | 1 | 92 | 86 | 9 | −9 | 12 | 1 | 54 | 34 | 10 |
| 4 | −7 | 1 | 285 | 273 | 9 | 8 | −3 | 1 | 139 | 136 | 4 | 6 | 1 | 1 | 54 | 46 | 3 | 6 | 5 | 1 | 94 | 90 | 4 | −8 | 12 | 1 | 86 | 92 | 8 |
| 5 | −7 | 1 | 104 | 97 | 3 | 9 | −3 | 1 | 0 | 9 | 1 | 7 | 1 | 1 | 8 | 12 | 7 | 7 | 5 | 1 | 118 | 107 | 5 | −7 | 12 | 1 | 6 | 39 | 6 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 6 | −7 | 1 | 139 | 127 | 2 | 10 | −3 | 1 | 113 | 98 | 5 | 8 | 1 | 1 | 124 | 110 | 4 | 8 | 5 | 1 | 75 | 59 | 5 | −6 | 12 | 1 | 111 | 114 | 7 |
| 7 | −7 | 1 | 122 | 125 | 3 | 11 | −3 | 1 | 25 | 31 | 24 | 9 | 1 | 1 | 107 | 84 | 5 | 9 | 5 | 1 | 173 | 164 | 5 | −5 | 12 | 1 | 124 | 121 | 10 |
| 8 | −7 | 1 | 84 | 78 | 4 | −11 | −2 | 1 | 39 | 36 | 9 | 10 | 1 | 1 | 25 | 18 | 18 | 10 | 5 | 1 | 160 | 167 | 6 | 2 | 12 | 1 | 55 | 69 | 14 |
| 9 | −7 | 1 | 136 | 122 | 4 | −10 | −2 | 1 | 61 | 54 | 7 | 11 | 1 | 1 | 49 | 45 | 8 | 11 | 5 | 1 | 45 | 34 | 13 | 3 | 12 | 1 | 251 | 254 | 13 |
| 10 | −7 | 1 | 135 | 118 | 4 | −9 | −2 | 1 | 162 | 147 | 4 | −11 | 2 | 1 | 39 | 36 | 11 | −10 | 6 | 1 | 112 | 102 | 8 | 4 | 12 | 1 | 147 | 160 | 11 |
| 5 | 12 | 1 | 177 | 191 | 12 | 5 | −17 | 2 | 50 | 46 | 13 | 4 | −11 | 2 | 96 | 95 | 4 | −10 | −6 | 2 | 76 | 63 | 6 | −9 | −2 | 2 | 139 | 125 | 6 |
| 6 | 12 | 1 | 39 | 33 | 29 | 6 | −17 | 2 | 249 | 227 | 14 | 5 | −11 | 2 | 232 | 229 | 6 | −9 | −6 | 2 | 30 | 31 | 11 | −8 | −2 | 2 | 77 | 62 | 4 |
| 7 | 12 | 1 | 48 | 25 | 19 | −3 | −16 | 2 | 110 | 115 | 7 | 6 | −11 | 2 | 124 | 154 | 9 | −8 | −6 | 2 | 91 | 102 | 5 | −7 | −2 | 2 | 100 | 100 | 3 |
| 8 | 12 | 1 | 51 | 60 | 21 | −2 | −16 | 2 | 140 | 161 | 6 | 7 | −11 | 2 | 22 | 28 | 21 | −7 | −6 | 2 | 140 | 142 | 4 | −6 | −2 | 2 | 171 | 164 | 3 |
| 9 | 12 | 1 | 111 | 102 | 7 | −1 | −16 | 2 | 82 | 67 | 4 | 8 | −11 | 2 | 8 | 18 | 7 | −6 | −6 | 2 | 236 | 229 | 8 | −5 | −2 | 2 | 110 | 103 | 3 |
| −9 | 13 | 1 | 88 | 93 | 11 | 0 | −16 | 2 | 32 | 35 | 6 | 9 | −11 | 2 | 30 | 31 | 19 | −5 | −6 | 2 | 189 | 187 | 5 | −4 | −2 | 2 | 283 | 273 | 7 |
| −8 | 13 | 1 | 20 | 15 | 20 | 1 | −16 | 2 | 120 | 136 | 5 | −9 | −10 | 2 | 32 | 23 | 7 | −4 | −6 | 2 | 331 | 315 | 13 | −3 | −2 | 2 | 102 | 105 | 5 |
| −7 | 13 | 1 | 85 | 87 | 8 | 2 | −16 | 2 | 144 | 130 | 4 | −8 | −10 | 2 | 122 | 120 | 4 | −3 | −6 | 2 | 132 | 142 | 5 | −2 | −2 | 2 | 261 | 222 | 10 |
| −6 | 13 | 1 | 100 | 97 | 7 | 3 | −16 | 2 | 129 | 119 | 3 | −7 | −10 | 2 | 37 | 41 | 6 | −2 | −6 | 2 | 298 | 272 | 11 | −1 | −2 | 2 | 302 | 280 | 12 |
| −5 | 13 | 1 | 130 | 130 | 11 | 4 | −16 | 2 | 126 | 121 | 4 | −6 | −10 | 2 | 106 | 106 | 4 | −1 | −6 | 2 | 331 | 295 | 10 | 0 | −2 | 2 | 288 | 279 | 8 |
| 3 | 13 | 1 | 112 | 123 | 12 | 5 | −16 | 2 | 19 | 18 | 19 | −5 | −10 | 2 | 222 | 226 | 4 | 0 | −6 | 2 | 123 | 125 | 6 | 1 | −2 | 2 | 273 | 279 | 8 |
| 4 | 13 | 1 | 183 | 199 | 12 | 6 | −16 | 2 | 32 | 2 | 8 | −4 | −10 | 2 | 133 | 126 | 4 | 1 | −6 | 2 | 384 | 384 | 17 | 2 | −2 | 2 | 279 | 248 | 8 |
| 5 | 13 | 1 | 168 | 186 | 11 | −3 | −15 | 2 | 115 | 102 | 4 | −3 | −10 | 2 | 185 | 216 | 3 | 2 | −6 | 2 | 178 | 165 | 5 | 3 | −2 | 2 | 142 | 148 | 4 |
| 6 | 13 | 1 | 77 | 92 | 13 | −2 | −15 | 2 | 259 | 245 | 6 | −2 | −10 | 2 | 131 | 127 | 4 | 3 | −6 | 2 | 252 | 242 | 8 | 4 | −2 | 2 | 254 | 219 | 7 |
| 7 | 13 | 1 | 110 | 129 | 11 | −1 | −15 | 2 | 77 | 67 | 3 | −1 | −10 | 2 | 314 | 334 | 14 | 4 | −6 | 2 | 96 | 74 | 3 | 5 | −2 | 2 | 54 | 59 | 2 |
| 8 | 13 | 1 | 38 | 45 | 28 | 0 | −15 | 2 | 98 | 88 | 4 | 0 | −10 | 2 | 252 | 240 | 12 | 5 | −6 | 2 | 43 | 48 | 2 | 6 | −2 | 2 | 143 | 138 | 3 |
| 9 | 13 | 1 | 79 | 79 | 11 | 1 | −15 | 2 | 81 | 66 | 4 | 1 | −10 | 2 | 155 | 127 | 5 | 6 | −6 | 2 | 208 | 205 | 4 | 7 | −2 | 2 | 239 | 226 | 4 |
| −8 | 14 | 1 | 31 | 7 | 19 | 2 | −15 | 2 | 273 | 262 | 6 | 2 | −10 | 2 | 131 | 131 | 4 | 7 | −6 | 2 | 186 | 186 | 3 | 8 | −2 | 2 | 73 | 71 | 4 |
| −7 | 14 | 1 | 67 | 74 | 8 | 3 | −15 | 2 | 246 | 259 | 5 | 3 | −10 | 2 | 168 | 176 | 6 | 8 | −6 | 2 | 224 | 210 | 6 | 9 | −2 | 2 | 133 | 129 | 5 |
| −6 | 14 | 1 | 79 | 93 | 13 | 4 | −15 | 2 | 99 | 87 | 4 | 4 | −10 | 2 | 221 | 225 | 5 | 9 | −6 | 2 | 19 | 13 | 18 | 10 | −2 | 2 | 52 | 47 | 5 |
| −5 | 14 | 1 | 66 | 45 | 12 | 5 | −15 | 2 | 164 | 151 | 5 | 5 | −10 | 2 | 72 | 71 | 4 | 10 | −6 | 2 | 26 | 22 | 9 | −11 | −1 | 2 | 17 | 42 | 16 |
| 3 | 14 | 1 | 63 | 69 | 16 | 6 | −15 | 2 | 143 | 152 | 5 | 6 | −10 | 2 | 153 | 154 | 4 | −10 | −5 | 2 | 125 | 117 | 6 | −10 | −1 | 2 | 35 | 31 | 13 |
| 4 | 14 | 1 | 106 | 117 | 12 | 7 | −15 | 2 | 37 | 29 | 7 | 7 | −10 | 2 | 26 | 54 | 26 | −9 | −5 | 2 | 134 | 127 | 5 | −9 | −1 | 2 | 45 | 47 | 5 |
| 5 | 14 | 1 | 139 | 177 | 10 | 8 | −15 | 2 | 54 | 49 | 6 | 8 | −10 | 2 | 85 | 101 | 10 | −8 | −5 | 2 | 114 | 123 | 6 | −8 | −1 | 2 | 331 | 317 | 6 |
| 6 | 14 | 1 | 56 | 82 | 17 | −6 | −14 | 2 | 52 | 57 | 6 | 9 | −10 | 2 | 0 | 16 | 1 | −7 | −5 | 2 | 121 | 115 | 5 | −7 | −1 | 2 | 80 | 75 | 3 |
| 7 | 14 | 1 | 43 | 41 | 22 | −5 | −14 | 2 | 120 | 120 | 5 | −10 | −9 | 2 | 101 | 94 | 5 | −6 | −5 | 2 | 142 | 137 | 4 | −6 | −1 | 2 | 228 | 226 | 4 |
| 8 | 14 | 1 | 11 | 50 | 11 | −4 | −14 | 2 | 169 | 164 | 6 | −9 | −9 | 2 | 142 | 136 | 3 | −5 | −5 | 2 | 299 | 279 | 6 | −5 | −1 | 2 | 249 | 229 | 6 |
| −8 | 15 | 1 | 0 | 15 | 1 | −3 | −14 | 2 | 85 | 77 | 4 | −8 | −9 | 2 | 176 | 170 | 5 | −4 | −5 | 2 | 66 | 49 | 3 | −4 | −1 | 2 | 314 | 296 | 9 |
| −7 | 15 | 1 | 92 | 88 | 10 | −2 | −14 | 2 | 86 | 85 | 3 | −7 | −9 | 2 | 158 | 166 | 6 | −3 | −5 | 2 | 485 | 541 | 17 | −3 | −1 | 2 | 475 | 427 | 18 |
| −6 | 15 | 1 | 152 | 182 | 10 | −1 | −14 | 2 | 200 | 190 | 4 | −6 | −9 | 2 | 100 | 104 | 4 | −2 | −5 | 2 | 221 | 215 | 9 | −2 | −1 | 2 | 379 | 369 | 15 |
| 3 | 15 | 1 | 41 | 48 | 26 | 0 | −14 | 2 | 53 | 50 | 4 | −5 | −9 | 2 | 149 | 149 | 3 | −1 | −5 | 2 | 388 | 358 | 11 | −1 | −1 | 2 | 120 | 113 | 5 |
| 4 | 15 | 1 | 45 | 73 | 23 | 1 | −14 | 2 | 146 | 130 | 4 | −4 | −9 | 2 | 78 | 65 | 3 | 0 | −5 | 2 | 167 | 178 | 8 | 0 | −1 | 2 | 543 | 571 | 16 |
| 5 | 15 | 1 | 74 | 103 | 13 | 2 | −14 | 2 | 36 | 18 | 6 | −3 | −9 | 2 | 153 | 154 | 4 | 1 | −5 | 2 | 238 | 218 | 11 | 1 | −1 | 2 | 197 | 209 | 5 |
| 6 | 15 | 1 | 121 | 149 | 12 | 3 | −14 | 2 | 128 | 129 | 3 | −2 | −9 | 2 | 220 | 233 | 10 | 2 | −5 | 2 | 228 | 208 | 5 | 2 | −1 | 2 | 153 | 103 | 7 |
| 7 | 15 | 1 | 95 | 112 | 12 | 4 | −14 | 2 | 102 | 104 | 4 | −1 | −9 | 2 | 113 | 70 | 7 | 3 | −5 | 2 | 315 | 283 | 8 | 3 | −1 | 2 | 348 | 302 | 10 |
| 8 | 15 | 1 | 16 | 45 | 16 | 5 | −14 | 2 | 74 | 72 | 4 | 0 | −9 | 2 | 177 | 163 | 9 | 4 | −5 | 2 | 131 | 138 | 3 | 4 | −1 | 2 | 272 | 255 | 7 |
| −7 | 16 | 1 | 42 | 49 | 18 | 6 | −14 | 2 | 113 | 110 | 6 | 1 | −9 | 2 | 272 | 280 | 12 | 5 | −5 | 2 | 254 | 246 | 4 | 5 | −1 | 2 | 238 | 238 | 5 |
| −6 | 16 | 1 | 81 | 119 | 10 | 7 | −14 | 2 | 57 | 59 | 6 | 2 | −9 | 2 | 83 | 69 | 6 | 6 | −5 | 2 | 187 | 190 | 3 | 6 | −1 | 2 | 203 | 197 | 4 |
| 4 | 16 | 1 | 138 | 179 | 11 | 8 | −14 | 2 | 36 | 43 | 8 | 3 | −9 | 2 | 32 | 23 | 6 | 7 | −5 | 2 | 18 | 20 | 6 | 7 | −1 | 2 | 26 | 20 | 5 |
| 5 | 16 | 1 | 53 | 92 | 16 | −8 | −13 | 2 | 88 | 85 | 5 | 4 | −9 | 2 | 106 | 117 | 2 | 8 | −5 | 2 | 155 | 152 | 4 | 8 | −1 | 2 | 107 | 92 | 6 |
| 6 | 16 | 1 | 5 | 36 | 4 | −7 | −13 | 2 | 132 | 135 | 3 | 5 | −9 | 2 | 127 | 128 | 2 | 9 | −5 | 2 | 179 | 165 | 5 | 9 | −1 | 2 | 72 | 60 | 5 |
| 7 | 16 | 1 | 58 | 73 | 14 | −6 | −13 | 2 | 159 | 158 | 3 | 6 | −9 | 2 | 131 | 121 | 3 | 10 | −5 | 2 | 48 | 30 | 5 | 10 | −1 | 2 | 77 | 61 | 5 |
| 4 | 17 | 1 | 57 | 67 | 14 | −5 | −13 | 2 | 66 | 57 | 3 | 7 | −9 | 2 | 93 | 104 | 4 | −10 | −4 | 2 | 113 | 95 | 6 | 11 | −1 | 2 | 31 | 11 | 16 |
| 5 | 17 | 1 | 0 | 30 | 1 | −4 | −13 | 2 | 160 | 150 | 6 | 8 | −9 | 2 | 54 | 55 | 4 | −9 | −4 | 2 | 226 | 208 | 8 | −11 | 0 | 2 | 35 | 55 | 18 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 6 | 17 | 1 | 0 | 28 | 1 | −3 | −13 | 2 | 164 | 153 | 5 | 9 | −9 | 2 | 103 | 97 | 9 | −8 | −4 | 2 | 276 | 291 | 11 | −10 | 0 | 2 | 179 | 165 | 6 |
| 7 | 17 | 1 | 88 | 92 | 10 | −2 | −13 | 2 | 92 | 87 | 3 | 10 | −9 | 2 | 124 | 128 | 8 | −7 | −4 | 2 | 331 | 331 | 8 | −9 | 0 | 2 | 28 | 29 | 9 |
| 5 | 18 | 1 | 38 | 56 | 21 | −1 | −13 | 2 | 213 | 180 | 6 | −10 | −8 | 2 | 28 | 28 | 9 | −6 | −4 | 2 | 265 | 258 | 6 | −8 | 0 | 2 | 465 | 440 | 9 |
| 6 | 18 | 1 | 92 | 141 | 9 | 0 | −13 | 2 | 133 | 131 | 4 | −9 | −8 | 2 | 205 | 195 | 7 | −5 | −4 | 2 | 226 | 212 | 4 | −7 | 0 | 2 | 375 | 358 | 7 |
| −2 | −21 | 2 | 106 | 92 | 6 | 1 | −13 | 2 | 296 | 302 | 7 | −8 | −8 | 2 | 80 | 90 | 5 | −4 | −4 | 2 | 284 | 262 | 9 | −6 | 0 | 2 | 278 | 273 | 5 |
| −1 | −21 | 2 | 46 | 32 | 9 | 2 | −13 | 2 | 87 | 77 | 4 | −7 | −8 | 2 | 105 | 101 | 4 | −3 | −4 | 2 | 206 | 207 | 6 | −5 | 0 | 2 | 241 | 254 | 6 |
| 0 | −21 | 2 | 28 | 21 | 6 | 3 | −13 | 2 | 292 | 297 | 7 | −6 | −8 | 2 | 122 | 114 | 4 | −2 | −4 | 2 | 226 | 239 | 9 | −4 | 0 | 2 | 171 | 167 | 5 |
| 1 | −21 | 2 | 81 | 75 | 5 | 4 | −13 | 2 | 128 | 122 | 4 | −5 | −8 | 2 | 92 | 90 | 3 | −1 | −4 | 2 | 183 | 167 | 5 | −3 | 0 | 2 | 258 | 208 | 10 |
| 2 | −21 | 2 | 97 | 85 | 7 | 5 | −13 | 2 | 30 | 37 | 10 | −4 | −8 | 2 | 181 | 168 | 4 | 0 | −4 | 2 | 92 | 72 | 3 | −2 | 0 | 2 | 456 | 466 | 18 |
| −3 | −20 | 2 | 39 | 21 | 16 | 6 | −13 | 2 | 126 | 136 | 8 | −3 | −8 | 2 | 89 | 66 | 5 | 1 | −4 | 2 | 178 | 168 | 4 | −1 | 0 | 2 | 168 | 187 | 7 |
| −2 | −20 | 2 | 99 | 95 | 6 | 7 | −13 | 2 | 75 | 103 | 8 | −1 | −8 | 2 | 297 | 272 | 14 | 2 | −4 | 2 | 228 | 219 | 5 | 0 | 0 | 2 | 22 | 18 | 4 |
| −1 | −20 | 2 | 26 | 30 | 26 | 8 | −13 | 2 | 51 | 51 | 7 | 0 | −8 | 2 | 150 | 140 | 8 | 3 | −4 | 2 | 341 | 372 | 10 | 1 | 0 | 2 | 90 | 4 | 4 |
| 0 | −20 | 2 | 61 | 58 | 4 | −9 | −12 | 2 | 115 | 107 | 4 | 1 | −8 | 2 | 400 | 404 | 18 | 4 | −4 | 2 | 149 | 143 | 4 | 2 | 0 | 2 | 577 | 593 | 17 |
| 1 | −20 | 2 | 64 | 64 | 4 | −8 | −12 | 2 | 83 | 83 | 3 | 2 | −8 | 2 | 290 | 291 | 13 | 5 | −4 | 2 | 180 | 182 | 3 | 3 | 0 | 2 | 239 | 220 | 7 |
| 2 | −20 | 2 | 36 | 30 | 5 | −7 | −12 | 2 | 45 | 45 | 5 | 3 | −8 | 2 | 171 | 172 | 4 | 6 | −4 | 2 | 136 | 125 | 3 | 4 | 0 | 2 | 75 | 50 | 2 |
| 3 | −20 | 2 | 47 | 49 | 6 | −6 | −12 | 2 | 255 | 260 | 6 | 4 | −8 | 2 | 163 | 141 | 3 | 7 | −4 | 2 | 183 | 177 | 3 | 5 | 0 | 2 | 46 | 70 | 5 |
| 4 | −20 | 2 | 85 | 83 | 7 | −5 | −12 | 2 | 270 | 272 | 6 | 5 | −8 | 2 | 98 | 91 | 2 | 8 | −4 | 2 | 230 | 219 | 6 | 6 | 0 | 2 | 36 | 37 | 3 |
| −3 | −19 | 2 | 88 | 86 | 8 | −4 | −12 | 2 | 110 | 98 | 4 | 6 | −8 | 2 | 131 | 131 | 3 | 9 | −4 | 2 | 135 | 122 | 4 | 7 | 0 | 2 | 167 | 153 | 4 |
| −2 | −19 | 2 | 80 | 79 | 7 | −3 | −12 | 2 | 194 | 191 | 5 | 7 | −8 | 2 | 189 | 180 | 4 | 10 | −4 | 2 | 67 | 53 | 5 | 8 | 0 | 2 | 439 | 411 | 12 |
| −1 | −19 | 2 | 188 | 193 | 7 | −2 | −12 | 2 | 196 | 199 | 4 | 8 | −8 | 2 | 151 | 144 | 4 | −11 | −3 | 2 | 87 | 67 | 6 | 9 | 0 | 2 | 150 | 137 | 5 |
| 0 | −19 | 2 | 71 | 69 | 4 | −1 | −12 | 2 | 91 | 54 | 5 | 9 | −8 | 2 | 141 | 132 | 4 | −10 | −3 | 2 | 177 | 164 | 5 | 10 | 0 | 2 | 33 | 18 | 9 |
| 1 | −19 | 2 | 136 | 110 | 4 | 0 | −12 | 2 | 89 | 93 | 3 | 10 | −8 | 2 | 85 | 79 | 8 | −9 | −3 | 2 | 30 | 30 | 11 | 11 | 0 | 2 | 54 | 66 | 9 |
| 2 | −19 | 2 | 71 | 77 | 4 | 1 | −12 | 2 | 163 | 166 | 4 | −10 | −7 | 2 | 88 | 80 | 5 | −8 | −3 | 2 | 94 | 88 | 6 | −10 | 1 | 2 | 35 | 32 | 12 |
| 3 | −19 | 2 | 112 | 107 | 4 | 2 | −12 | 2 | 127 | 122 | 4 | −9 | −7 | 2 | 96 | 93 | 5 | −7 | −3 | 2 | 251 | 244 | 4 | −9 | 1 | 2 | 50 | 47 | 4 |
| 4 | −19 | 2 | 89 | 84 | 5 | 3 | −12 | 2 | 110 | 112 | 3 | −8 | −7 | 2 | 118 | 133 | 5 | −6 | −3 | 2 | 259 | 258 | 4 | −8 | 1 | 2 | 336 | 317 | 6 |
| 5 | −19 | 2 | 46 | 44 | 12 | 4 | −12 | 2 | 279 | 296 | 6 | −7 | −7 | 2 | 136 | 139 | 4 | −5 | −3 | 2 | 179 | 168 | 4 | −7 | 1 | 2 | 80 | 76 | 3 |
| −3 | −18 | 2 | 93 | 94 | 7 | 5 | −12 | 2 | 247 | 249 | 6 | −6 | −7 | 2 | 126 | 122 | 4 | −4 | −3 | 2 | 202 | 180 | 5 | −6 | 1 | 2 | 225 | 226 | 4 |
| −2 | −18 | 2 | 38 | 54 | 13 | 7 | −12 | 2 | 43 | 41 | 11 | −5 | −7 | 2 | 67 | 60 | 3 | −3 | −3 | 2 | 443 | 412 | 17 | −5 | 1 | 2 | 233 | 229 | 6 |
| −1 | −18 | 2 | 151 | 142 | 6 | 8 | −12 | 2 | 73 | 78 | 8 | −4 | −7 | 2 | 240 | 221 | 6 | −2 | −3 | 2 | 759 | 735 | 30 | −4 | 1 | 2 | 317 | 297 | 12 |
| 0 | −18 | 2 | 26 | 30 | 9 | 9 | −12 | 2 | 56 | 48 | 8 | −3 | −7 | 2 | 309 | 281 | 9 | −1 | −3 | 2 | 486 | 423 | 14 | −3 | 1 | 2 | 465 | 428 | 18 |
| 1 | −18 | 2 | 230 | 228 | 7 | −9 | −11 | 2 | 53 | 51 | 4 | −2 | −7 | 2 | 86 | 68 | 5 | 0 | −3 | 2 | 107 | 107 | 3 | −2 | 1 | 2 | 365 | 369 | 14 |
| 2 | −18 | 2 | 32 | 28 | 6 | −8 | −11 | 2 | 110 | 104 | 4 | −1 | −7 | 2 | 141 | 148 | 5 | 1 | −3 | 2 | 579 | 609 | 13 | −1 | 1 | 2 | 116 | 112 | 5 |
| 3 | −18 | 2 | 105 | 91 | 5 | −7 | −11 | 2 | 151 | 146 | 4 | 0 | −7 | 2 | 132 | 136 | 7 | 2 | −3 | 2 | 576 | 519 | 13 | 0 | 1 | 2 | 529 | 570 | 21 |
| 4 | −18 | 2 | 60 | 54 | 6 | −6 | −11 | 2 | 56 | 61 | 4 | 1 | −7 | 2 | 189 | 192 | 9 | 3 | −3 | 2 | 251 | 264 | 10 | 1 | 1 | 2 | 187 | 208 | 5 |
| 5 | −18 | 2 | 61 | 71 | 10 | −5 | −11 | 2 | 93 | 92 | 6 | 2 | −7 | 2 | 117 | 130 | 4 | 4 | −3 | 2 | 211 | 220 | 6 | 2 | 1 | 2 | 143 | 103 | 6 |
| −3 | −17 | 2 | 70 | 69 | 8 | −4 | −11 | 2 | 197 | 203 | 4 | 3 | −7 | 2 | 332 | 314 | 12 | 5 | −3 | 2 | 92 | 92 | 2 | 3 | 1 | 2 | 337 | 301 | 10 |
| −2 | −17 | 2 | 73 | 66 | 7 | −3 | −11 | 2 | 200 | 201 | 4 | 4 | −7 | 2 | 343 | 344 | 6 | 6 | −3 | 2 | 167 | 157 | 3 | 4 | 1 | 2 | 278 | 255 | 7 |
| −1 | −17 | 2 | 41 | 41 | 7 | −2 | −11 | 2 | 118 | 112 | 3 | 5 | −7 | 2 | 101 | 103 | 2 | 7 | −3 | 2 | 312 | 306 | 5 | 5 | 1 | 2 | 247 | 238 | 6 |
| 0 | −17 | 2 | 165 | 160 | 6 | −1 | −11 | 2 | 247 | 261 | 6 | 6 | −7 | 2 | 135 | 136 | 2 | 8 | −3 | 2 | 94 | 89 | 3 | 6 | 1 | 2 | 200 | 197 | 4 |
| 1 | −17 | 2 | 89 | 90 | 4 | 0 | −11 | 2 | 33 | 28 | 5 | 7 | −7 | 2 | 127 | 124 | 4 | 9 | −3 | 2 | 121 | 106 | 5 | 7 | 1 | 2 | 24 | 19 | 7 |
| 2 | −17 | 2 | 58 | 51 | 4 | 1 | −11 | 2 | 156 | 148 | 4 | 8 | −7 | 2 | 84 | 71 | 4 | 10 | −3 | 2 | 15 | 12 | 14 | 8 | 1 | 2 | 111 | 93 | 6 |
| 3 | −17 | 2 | 107 | 106 | 4 | 2 | −11 | 2 | 161 | 163 | 6 | 9 | −7 | 2 | 102 | 96 | 4 | −11 | −2 | 2 | 54 | 50 | 7 | 9 | 1 | 2 | 61 | 60 | 6 |
| 4 | −17 | 2 | 73 | 64 | 6 | 3 | −11 | 2 | 161 | 168 | 4 | 10 | −7 | 2 | 17 | 26 | 16 | −10 | −2 | 2 | 53 | 35 | 8 | 10 | 1 | 2 | 78 | 61 | 5 |
| 11 | 1 | 2 | 0 | 11 | 1 | −5 | 6 | 2 | 181 | 186 | 7 | −7 | 12 | 2 | 49 | 44 | 11 | 1 | −18 | 3 | 50 | 50 | 12 | 8 | −12 | 3 | 75 | 72 | 8 |
| −10 | 2 | 2 | 39 | 36 | 8 | 0 | 6 | 2 | 112 | 125 | 5 | −6 | 12 | 2 | 245 | 260 | 10 | 2 | −18 | 3 | 94 | 93 | 8 | −9 | −11 | 3 | 14 | 15 | 14 |
| −9 | 2 | 2 | 140 | 125 | 3 | 1 | 6 | 2 | 329 | 384 | 13 | −5 | 12 | 2 | 269 | 271 | 10 | 3 | −18 | 3 | 139 | 138 | 4 | −8 | −11 | 3 | 17 | 5 | 17 |
| −8 | 2 | 2 | 75 | 62 | 4 | 2 | 6 | 2 | 185 | 166 | 6 | −3 | 12 | 2 | 196 | 191 | 12 | 4 | −18 | 3 | 63 | 52 | 5 | −7 | −11 | 3 | 129 | 130 | 4 |
| −7 | 2 | 2 | 99 | 100 | 3 | 3 | 6 | 2 | 233 | 243 | 8 | −2 | 12 | 2 | 198 | 199 | 9 | 5 | −18 | 3 | 56 | 50 | 9 | −6 | −11 | 3 | 89 | 88 | 4 |
| −6 | 2 | 2 | 169 | 165 | 4 | 5 | 6 | 2 | 53 | 49 | 5 | −1 | 12 | 2 | 90 | 54 | 13 | −3 | −17 | 3 | 62 | 75 | 10 | −5 | −11 | 3 | 151 | 167 | 3 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −5 | 2 | 2 | 103 | 102 | 3 | 6 | 6 | 2 | 199 | 206 | 6 | 0 | 12 | 2 | 73 | 94 | 13 | −2 | −17 | 3 | 118 | 112 | 6 | −4 | −11 | 3 | 222 | 222 | 5 |
| −4 | 2 | 2 | 277 | 273 | 11 | 7 | 6 | 2 | 190 | 187 | 5 | 1 | 12 | 2 | 127 | 165 | 13 | −1 | −7 | 3 | 44 | 38 | 6 | −3 | −11 | 3 | 104 | 106 | 7 |
| −3 | 2 | 2 | 99 | 105 | 5 | 8 | 6 | 2 | 215 | 209 | 6 | 2 | 12 | 2 | 110 | 122 | 11 | 0 | −17 | 3 | 88 | 94 | 4 | −2 | −11 | 3 | 69 | 70 | 3 |
| −2 | 2 | 2 | 234 | 221 | 9 | 9 | 6 | 2 | 10 | 13 | 10 | 3 | 12 | 2 | 101 | 112 | 12 | 1 | −17 | 3 | 59 | 71 | 5 | −1 | −11 | 3 | 294 | 305 | 7 |
| −1 | 2 | 2 | 271 | 280 | 10 | 10 | 6 | 2 | 0 | 22 | 1 | 4 | 12 | 2 | 259 | 297 | 14 | 2 | −17 | 3 | 200 | 186 | 5 | 0 | −11 | 3 | 135 | 128 | 4 |
| 0 | 2 | 2 | 274 | 279 | 11 | −10 | 7 | 2 | 71 | 80 | 9 | 5 | 12 | 2 | 237 | 250 | 13 | 3 | −17 | 3 | 46 | 38 | 4 | 1 | −11 | 3 | 104 | 46 | 6 |
| 1 | 2 | 2 | 268 | 280 | 8 | −9 | 7 | 2 | 99 | 94 | 5 | 6 | 12 | 2 | 111 | 107 | 13 | 4 | −17 | 3 | 49 | 32 | 4 | 2 | −11 | 3 | 92 | 93 | 5 |
| 2 | 2 | 2 | 263 | 248 | 7 | −8 | 7 | 2 | 124 | 132 | 7 | 7 | 12 | 2 | 19 | 41 | 18 | 5 | −17 | 3 | 101 | 90 | 3 | 3 | −11 | 3 | 203 | 201 | 7 |
| 3 | 2 | 2 | 144 | 148 | 4 | −7 | 7 | 2 | 141 | 140 | 7 | 8 | 12 | 2 | 81 | 78 | 7 | 6 | −17 | 3 | 131 | 123 | 9 | 4 | −11 | 3 | 225 | 230 | 6 |
| 4 | 2 | 2 | 255 | 219 | 6 | −6 | 7 | 2 | 134 | 122 | 7 | 9 | 12 | 2 | 53 | 48 | 15 | −3 | −16 | 3 | 145 | 158 | 5 | 5 | −11 | 3 | 14 | 31 | 14 |
| 5 | 2 | 2 | 55 | 59 | 2 | −5 | 7 | 2 | 68 | 60 | 7 | −9 | 13 | 2 | 44 | 34 | 19 | −2 | −16 | 3 | 33 | 42 | 6 | 6 | −11 | 3 | 105 | 140 | 9 |
| 6 | 2 | 2 | 141 | 138 | 3 | −4 | 7 | 2 | 274 | 221 | 15 | −8 | 13 | 2 | 95 | 86 | 8 | −1 | −16 | 3 | 148 | 146 | 3 | 7 | −11 | 3 | 75 | 93 | 10 |
| 7 | 2 | 2 | 233 | 225 | 5 | 4 | 7 | 2 | 311 | 344 | 16 | −7 | 13 | 2 | 132 | 135 | 7 | 0 | −16 | 3 | 241 | 230 | 7 | 8 | −11 | 3 | 72 | 81 | 9 |
| 8 | 2 | 2 | 75 | 71 | 7 | 5 | 7 | 2 | 97 | 104 | 10 | −6 | 13 | 2 | 155 | 158 | 7 | 1 | −16 | 3 | 171 | 159 | 4 | 9 | −11 | 3 | 33 | 35 | 16 |
| 9 | 2 | 2 | 128 | 129 | 7 | 6 | 7 | 2 | 135 | 136 | 5 | −5 | 13 | 2 | 61 | 58 | 15 | 2 | −16 | 3 | 114 | 109 | 4 | −9 | −10 | 3 | 62 | 62 | 3 |
| 10 | 2 | 2 | 57 | 47 | 6 | 7 | 7 | 2 | 135 | 124 | 6 | −4 | 13 | 2 | 168 | 149 | 11 | 3 | −16 | 3 | 40 | 29 | 5 | −8 | −10 | 3 | 131 | 137 | 4 |
| −10 | 3 | 2 | 164 | 164 | 5 | 8 | 7 | 2 | 90 | 71 | 5 | −3 | 13 | 2 | 204 | 153 | 10 | 4 | −16 | 3 | 105 | 94 | 3 | −7 | −10 | 3 | 138 | 142 | 5 |
| −9 | 3 | 2 | 32 | 30 | 9 | 9 | 7 | 2 | 101 | 96 | 5 | 2 | 13 | 2 | 82 | 77 | 13 | 5 | −16 | 3 | 141 | 135 | 4 | −6 | −10 | 3 | 88 | 90 | 4 |
| −8 | 3 | 2 | 94 | 87 | 4 | 10 | 7 | 2 | 38 | 26 | 18 | 3 | 13 | 2 | 252 | 297 | 14 | 6 | −16 | 3 | 25 | 7 | 9 | −5 | −10 | 3 | 180 | 168 | 5 |
| −7 | 3 | 2 | 254 | 245 | 6 | −10 | 8 | 2 | 45 | 28 | 12 | 4 | 13 | 2 | 97 | 123 | 13 | 7 | −16 | 3 | 120 | 112 | 4 | −4 | −10 | 3 | 112 | 117 | 3 |
| −6 | 3 | 2 | 260 | 258 | 9 | −9 | 8 | 2 | 204 | 194 | 7 | 5 | 13 | 2 | 30 | 38 | 30 | −5 | −15 | 3 | 132 | 133 | 5 | −3 | −10 | 3 | 166 | 167 | 4 |
| −5 | 3 | 2 | 165 | 167 | 7 | −8 | 8 | 2 | 93 | 90 | 8 | 6 | 13 | 2 | 123 | 136 | 12 | −4 | −15 | 3 | 87 | 90 | 5 | −2 | −10 | 3 | 122 | 128 | 4 |
| −4 | 3 | 2 | 193 | 181 | 8 | −7 | 8 | 2 | 126 | 102 | 7 | 7 | 13 | 2 | 87 | 104 | 11 | −3 | −15 | 3 | 135 | 132 | 3 | −1 | −10 | 3 | 120 | 93 | 4 |
| −3 | 3 | 2 | 427 | 414 | 17 | −6 | 8 | 2 | 136 | 114 | 6 | 8 | 13 | 2 | 48 | 51 | 17 | −2 | −15 | 3 | 195 | 181 | 4 | 0 | −10 | 3 | 233 | 236 | 6 |
| −2 | 3 | 2 | 697 | 734 | 27 | −5 | 8 | 2 | 92 | 90 | 6 | −8 | 14 | 2 | 68 | 70 | 8 | −1 | −15 | 3 | 93 | 91 | 3 | 1 | −10 | 3 | 208 | 212 | 6 |
| −1 | 3 | 2 | 423 | 423 | 16 | −4 | 8 | 2 | 182 | 167 | 7 | −7 | 14 | 2 | 123 | 149 | 7 | 0 | −15 | 3 | 88 | 86 | 4 | 2 | −10 | 3 | 84 | 70 | 5 |
| 0 | 3 | 2 | 96 | 105 | 4 | 4 | 8 | 2 | 157 | 141 | 10 | −6 | 14 | 2 | 53 | 56 | 9 | 1 | −15 | 3 | 110 | 100 | 4 | 3 | −10 | 3 | 267 | 272 | 8 |
| 1 | 3 | 2 | 527 | 609 | 20 | 5 | 8 | 2 | 90 | 91 | 10 | −5 | 14 | 2 | 127 | 121 | 11 | 2 | −15 | 3 | 223 | 237 | 5 | 4 | −10 | 3 | 97 | 85 | 4 |
| 2 | 3 | 2 | 530 | 519 | 15 | 6 | 8 | 2 | 135 | 130 | 7 | −4 | 14 | 2 | 164 | 164 | 11 | 3 | −15 | 3 | 86 | 82 | 3 | 5 | −10 | 3 | 252 | 268 | 7 |
| 3 | 3 | 2 | 300 | 263 | 9 | 7 | 8 | 2 | 183 | 181 | 6 | 2 | 14 | 2 | 23 | 18 | 22 | 4 | −15 | 3 | 40 | 27 | 6 | 6 | −10 | 3 | 88 | 87 | 6 |
| 4 | 3 | 2 | 235 | 219 | 6 | 8 | 8 | 2 | 145 | 143 | 6 | 3 | 14 | 2 | 112 | 129 | 12 | 5 | −15 | 3 | 162 | 168 | 6 | 7 | −10 | 3 | 60 | 92 | 11 |
| 5 | 3 | 2 | 95 | 92 | 2 | 9 | 8 | 2 | 133 | 132 | 5 | 4 | 14 | 2 | 73 | 105 | 14 | 6 | −15 | 3 | 140 | 144 | 5 | 8 | −10 | 3 | 70 | 85 | 10 |
| 6 | 3 | 2 | 166 | 158 | 4 | 10 | 8 | 2 | 79 | 79 | 7 | 5 | 14 | 2 | 67 | 72 | 15 | 7 | −15 | 3 | 42 | 42 | 7 | 9 | −10 | 3 | 112 | 107 | 8 |
| 7 | 3 | 2 | 307 | 306 | 7 | −10 | 9 | 2 | 109 | 94 | 7 | 6 | 14 | 2 | 93 | 110 | 13 | −6 | −14 | 3 | 75 | 83 | 5 | −9 | −9 | 3 | 46 | 46 | 6 |
| 8 | 3 | 2 | 92 | 88 | 4 | −9 | 9 | 2 | 144 | 136 | 8 | 7 | 14 | 2 | 33 | 58 | 33 | −5 | −14 | 3 | 117 | 112 | 5 | −8 | −9 | 3 | 115 | 118 | 5 |
| 9 | 3 | 2 | 127 | 106 | 7 | −8 | 9 | 2 | 170 | 170 | 8 | 8 | 14 | 2 | 11 | 42 | 10 | −4 | −14 | 3 | 93 | 97 | 5 | −7 | −9 | 3 | 146 | 158 | 5 |
| 10 | 3 | 2 | 28 | 12 | 14 | −7 | 9 | 2 | 159 | 166 | 8 | −7 | 15 | 2 | 82 | 97 | 7 | −3 | −14 | 3 | 306 | 317 | 7 | −6 | −9 | 3 | 142 | 147 | 4 |
| −10 | 4 | 2 | 101 | 94 | 5 | −6 | 9 | 2 | 104 | 103 | 7 | −6 | 15 | 2 | 81 | 82 | 11 | −2 | −14 | 3 | 165 | 163 | 4 | −5 | −9 | 3 | 286 | 293 | 6 |
| −9 | 4 | 2 | 224 | 208 | 6 | −5 | 9 | 2 | 154 | 149 | 7 | 1 | 15 | 2 | 58 | 66 | 18 | −1 | −14 | 3 | 222 | 220 | 6 | −4 | −9 | 3 | 100 | 99 | 4 |
| −8 | 4 | 2 | 265 | 291 | 8 | −4 | 9 | 2 | 72 | 65 | 6 | 3 | 15 | 2 | 213 | 260 | 14 | 0 | −14 | 3 | 16 | 31 | 15 | −3 | −9 | 3 | 138 | 148 | 3 |
| −7 | 4 | 2 | 329 | 331 | 12 | 3 | 9 | 2 | 31 | 23 | 25 | 4 | 15 | 2 | 66 | 87 | 16 | 1 | −14 | 3 | 195 | 193 | 5 | −2 | −9 | 3 | 245 | 252 | 8 |
| −6 | 4 | 2 | 259 | 257 | 10 | 4 | 9 | 2 | 106 | 117 | 10 | 5 | 15 | 2 | 125 | 150 | 13 | 2 | −14 | 3 | 111 | 93 | 4 | −1 | −9 | 3 | 290 | 286 | 9 |
| −5 | 4 | 2 | 222 | 212 | 8 | 5 | 9 | 2 | 110 | 128 | 11 | 6 | 15 | 2 | 128 | 152 | 12 | 3 | −14 | 3 | 144 | 124 | 4 | 0 | −9 | 3 | 43 | 42 | 6 |
| −3 | 4 | 2 | 205 | 206 | 9 | 6 | 9 | 2 | 126 | 121 | 12 | 7 | 15 | 2 | 8 | 29 | 7 | 4 | −14 | 3 | 36 | 37 | 7 | 1 | −9 | 3 | 215 | 220 | 6 |
| −2 | 4 | 2 | 219 | 239 | 9 | 7 | 9 | 2 | 107 | 104 | 6 | 8 | 15 | 2 | 68 | 49 | 12 | 5 | −14 | 3 | 90 | 91 | 5 | 2 | −9 | 3 | 115 | 102 | 4 |
| −1 | 4 | 2 | 158 | 166 | 6 | 8 | 9 | 2 | 61 | 55 | 6 | 4 | 16 | 2 | 100 | 121 | 13 | 6 | −14 | 3 | 37 | 35 | 9 | 3 | −9 | 3 | 81 | 61 | 3 |
| 0 | 4 | 2 | 81 | 72 | 4 | 9 | 9 | 2 | 103 | 97 | 5 | 5 | 16 | 2 | 37 | 19 | 36 | 7 | −14 | 3 | 72 | 74 | 6 | 4 | −9 | 3 | 293 | 284 | 8 |
| 1 | 4 | 2 | 163 | 169 | 6 | −10 | 10 | 2 | 56 | 67 | 16 | 6 | 16 | 2 | 12 | 1 | 12 | 8 | −14 | 3 | 53 | 50 | 5 | 5 | −9 | 3 | 103 | 99 | 4 |
| 2 | 4 | 2 | 205 | 218 | 8 | −9 | 10 | 2 | 0 | 23 | 1 | 7 | 16 | 2 | 49 | 21 | 16 | −8 | −13 | 3 | 110 | 100 | 6 | 6 | −9 | 3 | 168 | 176 | 5 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 3 | 4 | 2 | 359 | 373 | 10 | −8 | 10 | 2 | 126 | 120 | 8 | 3 | 17 | 2 | 78 | 107 | 13 | −7 | −13 | 3 | 25 | 27 | 11 | 7 | −9 | 3 | 77 | 90 | 11 |
| 4 | 4 | 2 | 156 | 143 | 5 | −7 | 10 | 2 | 47 | 41 | 11 | 4 | 17 | 2 | 63 | 64 | 14 | −6 | −13 | 3 | 225 | 221 | 7 | 8 | −9 | 3 | 81 | 98 | 10 |
| 5 | 4 | 2 | 182 | 183 | 4 | −6 | 10 | 2 | 128 | 105 | 7 | 5 | 17 | 2 | 32 | 46 | 32 | −5 | −13 | 3 | 85 | 73 | 5 | 9 | −9 | 3 | 91 | 80 | 9 |
| 6 | 4 | 2 | 138 | 125 | 4 | −5 | 10 | 2 | 222 | 225 | 9 | 6 | 17 | 2 | 183 | 227 | 11 | −4 | −13 | 3 | 223 | 214 | 7 | −10 | −8 | 3 | 105 | 103 | 5 |
| 7 | 4 | 2 | 188 | 176 | 5 | −3 | 10 | 2 | 193 | 216 | 11 | 4 | 18 | 2 | 32 | 54 | 31 | −3 | −13 | 3 | 134 | 110 | 5 | −9 | −8 | 3 | 107 | 106 | 5 |
| 8 | 4 | 2 | 229 | 219 | 6 | 2 | 10 | 2 | 115 | 131 | 10 | 5 | 18 | 2 | 65 | 72 | 12 | −2 | −13 | 3 | 155 | 156 | 4 | −8 | −8 | 3 | 98 | 92 | 6 |
| 9 | 4 | 2 | 134 | 123 | 6 | 3 | 10 | 2 | 152 | 176 | 10 | 6 | 18 | 2 | 62 | 64 | 11 | −1 | −13 | 3 | 168 | 153 | 5 | −7 | −8 | 3 | 97 | 100 | 6 |
| 10 | 4 | 2 | 48 | 53 | 10 | 4 | 10 | 2 | 206 | 224 | 12 | 5 | 19 | 2 | 0 | 44 | 1 | 0 | −13 | 3 | 131 | 126 | 4 | −6 | −8 | 3 | 106 | 104 | 4 |
| −10 | 5 | 2 | 122 | 117 | 8 | 5 | 10 | 2 | 68 | 71 | 13 | −2 | −21 | 3 | 83 | 72 | 9 | 1 | −13 | 3 | 204 | 208 | 5 | −5 | −8 | 3 | 59 | 54 | 3 |
| −9 | 5 | 2 | 143 | 126 | 5 | 6 | 10 | 2 | 135 | 154 | 11 | −1 | −21 | 3 | 32 | 30 | 19 | 2 | −13 | 3 | 62 | 45 | 4 | −4 | −8 | 3 | 214 | 218 | 5 |
| −8 | 5 | 2 | 110 | 124 | 5 | 7 | 10 | 2 | 30 | 53 | 29 | 0 | −21 | 3 | 89 | 81 | 7 | 3 | −13 | 3 | 181 | 174 | 4 | −3 | −8 | 3 | 210 | 212 | 5 |
| −7 | 5 | 2 | 116 | 115 | 7 | 8 | 10 | 2 | 113 | 102 | 5 | 1 | −21 | 3 | 44 | 39 | 11 | 4 | −13 | 3 | 139 | 143 | 4 | −1 | −8 | 3 | 228 | 226 | 11 |
| −6 | 5 | 2 | 146 | 138 | 7 | 9 | 10 | 2 | 0 | 16 | 1 | 2 | −21 | 3 | 132 | 133 | 7 | 5 | −13 | 3 | 140 | 159 | 7 | 0 | −8 | 3 | 49 | 49 | 7 |
| −5 | 5 | 2 | 289 | 279 | 11 | −9 | 11 | 2 | 37 | 51 | 19 | −3 | −20 | 3 | 145 | 121 | 11 | 6 | −13 | 3 | 72 | 68 | 9 | 1 | −8 | 3 | 203 | 233 | 10 |
| −2 | 5 | 2 | 213 | 214 | 8 | −8 | 11 | 2 | 120 | 104 | 8 | −2 | −20 | 3 | 72 | 64 | 7 | 7 | −13 | 3 | 87 | 104 | 8 | 2 | −8 | 3 | 166 | 182 | 6 |
| −1 | 5 | 2 | 329 | 358 | 13 | −7 | 11 | 2 | 149 | 146 | 7 | −1 | −20 | 3 | 66 | 67 | 4 | 8 | −13 | 3 | 15 | 25 | 15 | 3 | −8 | 3 | 44 | 25 | 3 |
| 0 | 5 | 2 | 161 | 179 | 7 | −6 | 11 | 2 | 63 | 60 | 8 | 0 | −20 | 3 | 228 | 220 | 10 | −8 | −12 | 3 | 67 | 64 | 4 | 4 | −8 | 3 | 36 | 30 | 2 |
| 1 | 5 | 2 | 222 | 217 | 9 | −5 | 11 | 2 | 126 | 91 | 8 | 1 | −20 | 3 | 33 | 35 | 22 | −7 | −12 | 3 | 66 | 67 | 3 | 5 | −8 | 3 | 139 | 143 | 2 |
| 2 | 5 | 2 | 203 | 208 | 8 | −4 | 11 | 2 | 210 | 203 | 12 | 2 | −20 | 3 | 36 | 44 | 16 | −6 | −12 | 3 | 98 | 101 | 3 | 6 | −8 | 3 | 173 | 169 | 3 |
| 3 | 5 | 2 | 303 | 283 | 11 | −3 | 11 | 2 | 202 | 201 | 12 | 3 | −20 | 3 | 39 | 33 | 13 | −5 | −12 | 3 | 117 | 112 | 3 | 7 | −8 | 3 | 108 | 96 | 4 |
| 4 | 5 | 2 | 128 | 138 | 4 | −2 | 11 | 2 | 140 | 112 | 12 | −3 | −19 | 3 | 57 | 45 | 17 | −4 | −12 | 3 | 176 | 178 | 6 | 8 | −8 | 3 | 68 | 73 | 4 |
| 5 | 5 | 2 | 251 | 246 | 7 | 1 | 11 | 2 | 142 | 147 | 11 | −2 | −19 | 3 | 88 | 82 | 6 | −3 | −12 | 3 | 82 | 92 | 7 | 9 | −8 | 3 | 172 | 178 | 9 |
| 6 | 5 | 2 | 187 | 190 | 5 | 2 | 11 | 2 | 137 | 164 | 10 | −1 | −19 | 3 | 40 | 29 | 6 | −2 | −12 | 3 | 103 | 101 | 3 | −10 | −7 | 3 | 62 | 50 | 5 |
| 7 | 5 | 2 | 27 | 21 | 11 | 3 | 11 | 2 | 155 | 169 | 10 | 0 | −19 | 3 | 100 | 98 | 8 | −1 | −12 | 3 | 135 | 137 | 5 | −9 | −7 | 3 | 140 | 132 | 5 |
| 8 | 5 | 2 | 149 | 152 | 5 | 4 | 11 | 2 | 81 | 94 | 12 | 1 | −19 | 3 | 112 | 105 | 8 | 0 | −12 | 3 | 99 | 96 | 4 | −8 | −7 | 3 | 83 | 103 | 6 |
| 9 | 5 | 2 | 174 | 165 | 6 | 5 | 11 | 2 | 217 | 230 | 13 | 2 | −19 | 3 | 75 | 70 | 9 | 1 | −12 | 3 | 103 | 98 | 4 | −7 | −7 | 3 | 145 | 160 | 4 |
| 10 | 5 | 2 | 0 | 31 | 1 | 6 | 11 | 2 | 133 | 154 | 11 | 3 | −19 | 3 | 62 | 50 | 6 | 2 | −12 | 3 | 71 | 67 | 5 | −6 | −7 | 3 | 201 | 197 | 7 |
| −10 | 6 | 2 | 71 | 63 | 9 | 7 | 11 | 2 | 0 | 28 | 1 | 4 | −19 | 3 | 121 | 112 | 5 | 3 | −12 | 3 | 234 | 243 | 7 | −5 | −7 | 3 | 304 | 307 | 6 |
| −9 | 6 | 2 | 32 | 32 | 11 | 8 | 11 | 2 | 21 | 18 | 21 | −3 | −18 | 3 | 43 | 44 | 27 | 4 | −12 | 3 | 31 | 14 | 7 | −4 | −7 | 3 | 107 | 104 | 3 |
| −8 | 6 | 2 | 87 | 102 | 8 | 9 | 11 | 2 | 0 | 30 | 1 | −2 | −18 | 3 | 121 | 116 | 6 | 5 | −12 | 3 | 197 | 195 | 7 | −3 | −7 | 3 | 49 | 59 | 4 |
| −7 | 6 | 2 | 149 | 143 | 7 | −9 | 12 | 2 | 101 | 108 | 8 | −1 | −18 | 3 | 104 | 104 | 6 | 6 | −12 | 3 | 82 | 111 | 9 | −2 | −7 | 3 | 124 | 115 | 4 |
| −6 | 6 | 2 | 241 | 228 | 9 | −8 | 12 | 2 | 92 | 83 | 8 | 0 | −18 | 3 | 83 | 66 | 9 | 7 | −12 | 3 | 136 | 141 | 9 | −1 | −7 | 3 | 187 | 187 | 6 |
| 0 | −7 | 3 | 114 | 120 | 4 | 5 | −3 | 3 | 88 | 86 | 2 | 10 | 1 | 3 | 124 | 115 | 6 | −1 | 6 | 3 | 119 | 122 | 6 | 3 | 11 | 3 | 180 | 201 | 11 |
| 1 | −7 | 3 | 101 | 113 | 4 | 6 | −3 | 3 | 138 | 128 | 3 | −10 | 2 | 3 | 49 | 36 | 7 | 0 | 6 | 3 | 116 | 128 | 5 | 4 | 11 | 3 | 205 | 230 | 12 |
| 2 | −7 | 3 | 158 | 193 | 5 | 7 | −3 | 3 | 251 | 254 | 5 | −9 | 2 | 3 | 116 | 109 | 4 | 2 | 6 | 3 | 68 | 63 | 4 | 5 | 11 | 3 | 36 | 32 | 33 |
| 3 | −7 | 3 | 259 | 267 | 5 | 8 | −3 | 3 | 266 | 258 | 7 | −8 | 2 | 3 | 66 | 67 | 4 | 3 | 6 | 3 | 118 | 124 | 5 | 6 | 11 | 3 | 90 | 140 | 12 |
| 4 | −7 | 3 | 128 | 130 | 2 | 9 | −3 | 3 | 73 | 53 | 5 | −7 | 2 | 3 | 156 | 160 | 4 | 4 | 6 | 3 | 220 | 227 | 8 | 7 | 11 | 3 | 92 | 94 | 7 |
| 5 | −7 | 3 | 79 | 84 | 2 | 10 | −3 | 3 | 20 | 9 | 19 | −6 | 2 | 3 | 245 | 248 | 6 | 5 | 6 | 3 | 192 | 195 | 5 | 8 | 11 | 3 | 74 | 80 | 7 |
| 6 | −7 | 3 | 97 | 104 | 3 | −10 | −2 | 3 | 44 | 36 | 6 | −5 | 2 | 3 | 115 | 101 | 4 | 6 | 6 | 3 | 122 | 123 | 5 | 9 | 11 | 3 | 25 | 35 | 24 |
| 7 | −7 | 3 | 79 | 77 | 3 | −9 | −2 | 3 | 111 | 109 | 6 | −4 | −2 | 3 | 371 | 382 | 11 | 7 | 6 | 3 | 146 | 156 | 5 | −9 | 12 | 3 | 65 | 76 | 9 |
| 8 | −7 | 3 | 108 | 104 | 4 | −8 | −2 | 3 | 74 | 67 | 4 | −3 | 2 | 3 | 344 | 326 | 14 | 8 | 6 | 3 | 69 | 72 | 5 | −8 | 12 | 3 | 70 | 65 | 9 |
| 9 | −7 | 3 | 0 | 10 | 1 | −7 | −2 | 3 | 152 | 161 | 3 | −2 | 2 | 3 | 496 | 533 | 19 | 9 | 6 | 3 | 82 | 73 | 6 | −7 | 12 | 3 | 70 | 66 | 9 |
| 10 | −7 | 3 | 15 | 26 | 14 | −6 | −2 | 3 | 251 | 248 | 4 | −1 | 2 | 3 | 326 | 325 | 13 | 10 | 6 | 3 | 33 | 27 | 14 | −6 | 12 | 3 | 93 | 100 | 8 |
| −10 | −6 | 3 | 151 | 153 | 4 | −5 | −2 | 3 | 119 | 101 | 2 | 0 | 2 | 3 | 245 | 264 | 10 | −10 | 7 | 3 | 46 | 50 | 13 | −5 | 12 | 3 | 146 | 112 | 11 |
| −9 | −6 | 3 | 51 | 45 | 7 | −4 | −2 | 3 | 391 | 382 | 10 | 1 | 2 | 3 | 255 | 269 | 7 | −9 | 7 | 3 | 129 | 132 | 4 | −4 | 12 | 3 | 182 | 178 | 12 |
| −8 | −6 | 3 | 25 | 32 | 14 | −3 | −2 | 3 | 353 | 326 | 11 | 2 | 2 | 3 | 273 | 267 | 8 | −8 | 7 | 3 | 85 | 103 | 8 | −2 | 12 | 3 | 115 | 102 | 8 |
| −7 | −6 | 3 | 70 | 71 | 6 | −2 | −2 | 3 | 472 | 533 | 18 | 3 | 2 | 3 | 311 | 349 | 7 | −7 | 7 | 3 | 143 | 160 | 8 | −1 | 12 | 3 | 148 | 137 | 12 |
| −6 | −6 | 3 | 157 | 156 | 4 | −1 | −2 | 3 | 337 | 326 | 13 | 4 | 2 | 3 | 155 | 140 | 5 | −6 | 7 | 3 | 194 | 197 | 8 | 0 | 12 | 3 | 81 | 96 | 13 |
| −5 | −6 | 3 | 175 | 171 | 5 | 0 | −2 | 3 | 256 | 264 | 7 | 5 | 2 | 3 | 209 | 224 | 4 | −5 | 7 | 3 | 306 | 307 | 11 | 1 | 12 | 3 | 74 | 97 | 13 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −4 | −6 | 3 | 222 | 221 | 5 | 1 | −2 | 3 | 262 | 270 | 7 | 6 | 2 | 3 | 182 | 186 | 4 | −4 | 7 | 3 | 119 | 105 | 6 | 2 | 12 | 3 | 47 | 67 | 19 |
| −3 | −6 | 3 | 172 | 161 | 5 | 2 | −2 | 3 | 279 | 267 | 8 | 7 | 2 | 3 | 185 | 180 | 5 | 3 | 7 | 3 | 233 | 268 | 13 | 3 | 12 | 3 | 220 | 243 | 13 |
| −2 | −6 | 3 | 66 | 34 | 3 | 3 | −2 | 3 | 235 | 310 | 9 | 8 | 2 | 3 | 74 | 70 | 7 | 4 | 7 | 3 | 115 | 130 | 10 | 4 | 12 | 3 | 28 | 13 | 27 |
| −1 | −6 | 3 | 137 | 122 | 4 | 4 | −2 | 3 | 148 | 140 | 4 | 9 | 2 | 3 | 114 | 103 | 7 | 5 | 7 | 3 | 68 | 84 | 11 | 5 | 12 | 3 | 160 | 194 | 11 |
| 0 | −6 | 3 | 104 | 129 | 4 | 5 | −2 | 3 | 216 | 224 | 5 | 10 | 2 | 3 | 140 | 135 | 6 | 6 | 7 | 3 | 102 | 104 | 5 | 6 | 12 | 3 | 75 | 111 | 13 |
| 1 | −6 | 3 | 77 | 81 | 4 | 6 | −2 | 3 | 192 | 186 | 4 | −10 | 3 | 3 | 120 | 119 | 8 | 7 | 7 | 3 | 79 | 77 | 5 | 7 | 12 | 3 | 137 | 141 | 7 |
| 2 | −6 | 3 | 74 | 62 | 2 | 7 | −2 | 3 | 180 | 180 | 4 | −9 | 3 | 3 | 112 | 104 | 4 | 8 | 7 | 3 | 102 | 105 | 5 | 8 | 12 | 3 | 83 | 71 | 11 |
| 3 | −6 | 3 | 122 | 125 | 3 | 8 | −2 | 3 | 69 | 70 | 5 | −8 | 3 | 3 | 214 | 210 | 6 | 9 | 7 | 3 | 0 | 10 | 1 | −8 | 13 | 3 | 115 | 100 | 9 |
| 4 | −6 | 3 | 230 | 227 | 4 | 9 | −2 | 3 | 118 | 104 | 5 | −7 | 3 | 3 | 267 | 270 | 6 | 10 | 7 | 3 | 11 | 26 | 11 | −7 | 13 | 3 | 35 | 26 | 18 |
| 5 | −6 | 3 | 206 | 196 | 3 | 10 | −2 | 3 | 146 | 136 | 6 | −6 | 3 | 3 | 149 | 156 | 5 | −10 | 8 | 3 | 109 | 103 | 7 | −6 | 13 | 3 | 200 | 220 | 8 |
| 6 | −6 | 3 | 126 | 123 | 2 | −10 | −1 | 3 | 45 | 51 | 7 | −5 | 3 | 3 | 230 | 224 | 9 | −9 | 8 | 3 | 106 | 106 | 6 | −5 | 13 | 3 | 102 | 72 | 12 |
| 7 | −6 | 3 | 151 | 157 | 3 | −9 | −1 | 3 | 48 | 45 | 7 | −4 | 3 | 3 | 432 | 427 | 17 | −8 | 8 | 3 | 87 | 92 | 9 | −4 | 13 | 3 | 228 | 215 | 13 |
| 8 | −6 | 3 | 83 | 72 | 3 | −8 | −1 | 3 | 120 | 115 | 3 | −3 | 3 | 3 | 268 | 266 | 10 | −7 | 8 | 3 | 100 | 100 | 8 | −3 | 13 | 3 | 153 | 110 | 11 |
| 9 | −6 | 3 | 77 | 72 | 4 | −7 | −1 | 3 | 115 | 119 | 3 | −1 | 3 | 3 | 422 | 408 | 16 | −6 | 8 | 3 | 104 | 103 | 7 | −2 | 13 | 3 | 171 | 156 | 8 |
| 10 | −6 | 3 | 30 | 27 | 29 | −6 | −1 | 3 | 301 | 301 | 5 | 0 | 3 | 3 | 23 | 12 | 7 | −5 | 8 | 3 | 62 | 54 | 7 | −1 | 13 | 3 | 172 | 153 | 12 |
| −10 | −5 | 3 | 45 | 41 | 6 | −5 | −1 | 3 | 156 | 151 | 3 | 1 | 3 | 3 | 542 | 625 | 21 | −4 | 8 | 3 | 210 | 217 | 8 | 0 | 13 | 3 | 114 | 126 | 13 |
| −9 | −5 | 3 | 51 | 49 | 7 | −4 | −1 | 3 | 198 | 176 | 5 | 2 | 3 | 3 | 282 | 317 | 11 | −3 | 8 | 3 | 199 | 212 | 12 | 1 | 13 | 3 | 181 | 207 | 13 |
| −8 | −5 | 3 | 111 | 119 | 5 | −3 | −1 | 3 | 688 | 722 | 21 | 4 | 3 | 3 | 321 | 299 | 10 | 3 | 8 | 3 | 38 | 25 | 16 | 2 | 13 | 3 | 24 | 45 | 24 |
| −7 | −5 | 3 | 93 | 81 | 4 | −2 | −1 | 3 | 409 | 412 | 16 | 5 | 3 | 3 | 88 | 86 | 3 | 4 | 8 | 3 | 23 | 30 | 22 | 3 | 13 | 3 | 151 | 174 | 13 |
| −6 | −5 | 3 | 147 | 133 | 4 | −1 | −1 | 3 | 555 | 549 | 22 | 6 | 3 | 3 | 134 | 127 | 4 | 5 | 8 | 3 | 132 | 144 | 11 | 4 | 13 | 3 | 118 | 143 | 13 |
| −5 | −5 | 3 | 105 | 105 | 3 | 0 | −1 | 3 | 382 | 406 | 11 | 7 | 3 | 3 | 257 | 255 | 7 | 6 | 8 | 3 | 173 | 169 | 7 | 5 | 13 | 3 | 137 | 159 | 11 |
| −4 | −5 | 3 | 170 | 170 | 4 | 1 | −1 | 3 | 450 | 480 | 13 | 8 | 3 | 3 | 272 | 258 | 9 | 7 | 8 | 3 | 99 | 96 | 6 | 6 | 13 | 3 | 61 | 67 | 15 |
| −3 | −5 | 3 | 168 | 165 | 5 | 2 | −1 | 3 | 406 | 400 | 12 | 9 | 3 | 3 | 51 | 54 | 9 | 8 | 8 | 3 | 74 | 74 | 6 | 7 | 13 | 3 | 92 | 104 | 7 |
| −1 | −5 | 3 | 158 | 129 | 4 | 4 | −1 | 3 | 364 | 337 | 10 | 10 | 3 | 3 | 38 | 9 | 11 | 9 | 8 | 3 | 163 | 177 | 7 | 8 | 13 | 3 | 43 | 26 | 19 |
| 0 | −5 | 3 | 87 | 84 | 3 | 5 | −1 | 3 | 91 | 83 | 3 | −10 | 4 | 3 | 75 | 84 | 8 | −10 | 9 | 3 | 80 | 68 | 8 | −8 | 14 | 3 | 25 | 24 | 25 |
| 1 | −5 | 3 | 297 | 283 | 8 | 6 | −1 | 3 | 180 | 181 | 4 | −9 | 4 | 3 | 109 | 106 | 4 | −9 | 9 | 3 | 46 | 47 | 13 | −7 | 14 | 3 | 83 | 87 | 10 |
| 2 | −5 | 3 | 352 | 380 | 9 | 7 | −1 | 3 | 57 | 63 | 4 | −8 | 4 | 3 | 240 | 231 | 7 | −8 | 9 | 3 | 119 | 117 | 8 | −6 | 14 | 3 | 59 | 82 | 16 |
| 3 | −5 | 3 | 118 | 93 | 3 | 8 | −1 | 3 | 131 | 144 | 6 | −7 | 4 | 3 | 131 | 129 | 6 | −7 | 9 | 3 | 157 | 158 | 7 | −5 | 14 | 3 | 125 | 113 | 12 |
| 4 | −5 | 3 | 84 | 71 | 2 | 9 | −1 | 3 | 12 | 22 | 11 | −6 | 4 | 3 | 55 | 60 | 7 | −6 | 9 | 3 | 160 | 147 | 7 | −4 | 14 | 3 | 100 | 97 | 12 |
| 5 | −5 | 3 | 54 | 41 | 2 | 10 | −1 | 3 | 130 | 116 | 5 | −5 | 4 | 3 | 116 | 111 | 6 | −5 | 9 | 3 | 286 | 293 | 10 | −3 | 14 | 3 | 303 | 317 | 17 |
| 6 | −5 | 3 | 210 | 215 | 4 | −10 | 0 | 3 | 58 | 71 | 6 | −3 | 4 | 3 | 483 | 502 | 20 | −3 | 9 | 3 | 136 | 148 | 11 | −2 | 14 | 3 | 177 | 164 | 12 |
| 7 | −5 | 3 | 163 | 169 | 3 | −9 | 0 | 3 | 79 | 67 | 4 | −2 | 4 | 3 | 119 | 81 | 5 | −2 | 9 | 3 | 252 | 252 | 9 | −1 | 14 | 3 | 225 | 219 | 14 |
| 8 | −5 | 3 | 78 | 78 | 3 | −8 | 0 | 3 | 146 | 143 | 3 | −1 | 4 | 3 | 185 | 168 | 8 | 2 | 9 | 3 | 91 | 102 | 11 | 0 | 14 | 3 | 0 | 31 | 1 |
| 9 | −5 | 3 | 48 | 28 | 5 | −7 | 0 | 3 | 29 | 16 | 6 | 0 | 4 | 3 | 277 | 290 | 11 | 3 | 9 | 3 | 62 | 61 | 12 | 1 | 14 | 3 | 175 | 193 | 14 |
| 10 | −5 | 3 | 92 | 95 | 4 | −6 | 0 | 3 | 98 | 83 | 3 | 1 | 4 | 3 | 234 | 273 | 9 | 4 | 9 | 3 | 253 | 285 | 14 | 2 | 14 | 3 | 80 | 93 | 15 |
| −10 | −4 | 3 | 87 | 84 | 4 | −5 | 0 | 3 | 47 | 47 | 3 | 2 | 4 | 3 | 257 | 270 | 10 | 5 | 9 | 3 | 87 | 99 | 11 | 3 | 14 | 3 | 121 | 125 | 14 |
| −9 | −4 | 3 | 102 | 106 | 6 | −4 | 0 | 3 | 84 | 80 | 4 | 3 | 4 | 3 | 351 | 320 | 10 | 6 | 9 | 3 | 166 | 176 | 7 | 4 | 14 | 3 | 29 | 37 | 29 |
| −8 | −4 | 3 | 245 | 231 | 8 | −3 | 0 | 3 | 26 | 21 | 6 | 4 | 4 | 3 | 193 | 206 | 6 | 7 | 9 | 3 | 84 | 90 | 6 | 5 | 14 | 3 | 75 | 91 | 14 |
| −7 | −4 | 3 | 130 | 129 | 4 | −2 | 0 | 3 | 179 | 154 | 7 | 5 | 4 | 3 | 88 | 96 | 3 | 8 | 9 | 3 | 87 | 98 | 5 | 6 | 14 | 3 | 31 | 35 | 31 |
| −6 | −4 | 3 | 62 | 60 | 3 | −1 | 0 | 3 | 112 | 122 | 5 | 6 | 4 | 3 | 167 | 184 | 5 | 9 | 9 | 3 | 82 | 80 | 7 | 7 | 14 | 3 | 85 | 74 | 11 |
| −5 | −4 | 3 | 118 | 110 | 3 | 0 | 0 | 3 | 171 | 183 | 5 | 7 | 4 | 3 | 74 | 76 | 4 | −9 | 10 | 3 | 68 | 63 | 9 | 8 | 14 | 3 | 45 | 50 | 19 |
| −4 | −4 | 3 | 129 | 115 | 4 | 1 | 0 | 3 | 69 | 63 | 3 | 8 | 4 | 3 | 100 | 96 | 6 | −8 | 10 | 3 | 136 | 137 | 8 | −7 | 15 | 3 | 51 | 57 | 17 |
| −3 | −4 | 3 | 485 | 503 | 14 | 2 | 0 | 3 | 348 | 356 | 10 | 9 | 4 | 3 | 21 | 42 | 20 | −7 | 10 | 3 | 151 | 142 | 7 | −6 | 15 | 3 | 135 | 127 | 11 |
| −2 | −4 | 3 | 114 | 82 | 5 | 3 | 0 | 3 | 283 | 263 | 8 | 10 | 4 | 3 | 30 | 20 | 15 | −6 | 10 | 3 | 92 | 90 | 8 | −5 | 15 | 3 | 148 | 133 | 10 |
| −1 | −4 | 3 | 191 | 169 | 6 | 4 | 0 | 3 | 58 | 57 | 2 | −10 | 5 | 3 | 24 | 40 | 23 | −5 | 10 | 3 | 191 | 168 | 8 | −4 | 15 | 3 | 94 | 90 | 12 |
| 0 | −4 | 3 | 303 | 289 | 9 | 5 | 0 | 3 | 171 | 170 | 4 | −9 | 5 | 3 | 46 | 48 | 5 | −4 | 10 | 3 | 114 | 116 | 11 | −3 | 15 | 3 | 138 | 132 | 12 |
| 1 | −4 | 3 | 260 | 272 | 7 | 6 | 0 | 3 | 258 | 253 | 6 | −8 | 5 | 3 | 105 | 120 | 5 | −3 | 10 | 3 | 193 | 167 | 12 | −2 | 15 | 3 | 197 | 180 | 12 |
| 2 | −4 | 3 | 282 | 269 | 8 | 7 | 0 | 3 | 53 | 47 | 4 | −7 | 5 | 3 | 86 | 81 | 6 | −2 | 10 | 3 | 137 | 128 | 7 | −1 | 15 | 3 | 93 | 91 | 15 |
| 3 | −4 | 3 | 332 | 319 | 8 | 8 | 0 | 3 | 126 | 155 | 10 | −6 | 5 | 3 | 146 | 134 | 7 | −1 | 10 | 3 | 138 | 93 | 10 | 0 | 15 | 3 | 63 | 86 | 19 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 4 | −4 | 3 | 205 | 206 | 5 | 9 | 0 | 3 | 72 | 47 | 6 | −5 | 5 | 3 | 106 | 105 | 6 | 0 | 10 | 3 | 216 | 235 | 13 | 1 | 15 | 3 | 84 | 100 | 14 |
| 5 | −4 | 3 | 85 | 95 | 2 | 10 | 0 | 3 | 111 | 90 | 6 | −4 | 5 | 3 | 158 | 170 | 10 | 1 | 10 | 3 | 183 | 212 | 12 | 2 | 15 | 3 | 211 | 238 | 15 |
| 6 | −4 | 3 | 175 | 184 | 3 | −10 | 1 | 3 | 43 | 50 | 8 | −1 | 5 | 3 | 153 | 128 | 6 | 2 | 10 | 3 | 62 | 70 | 12 | 3 | 15 | 3 | 56 | 81 | 21 |
| 7 | −4 | 3 | 76 | 77 | 2 | −9 | 1 | 3 | 54 | 46 | 4 | 0 | 5 | 3 | 81 | 85 | 5 | 3 | 10 | 3 | 234 | 273 | 13 | 4 | 15 | 3 | 0 | 27 | 1 |
| 8 | −4 | 3 | 104 | 96 | 4 | −8 | 1 | 3 | 115 | 114 | 3 | 1 | 5 | 3 | 245 | 283 | 10 | 4 | 10 | 3 | 76 | 85 | 12 | 5 | 15 | 3 | 149 | 168 | 12 |
| 9 | −4 | 3 | 41 | 41 | 5 | −7 | 1 | 3 | 119 | 119 | 3 | 2 | 5 | 3 | 331 | 380 | 12 | 5 | 10 | 3 | 229 | 269 | 14 | 6 | 15 | 3 | 121 | 144 | 12 |
| 10 | −4 | 3 | 12 | 20 | 12 | −6 | 1 | 3 | 300 | 300 | 6 | 3 | 5 | 3 | 115 | 93 | 5 | 6 | 10 | 3 | 59 | 87 | 16 | 7 | 15 | 3 | 39 | 42 | 26 |
| −10 | −3 | 3 | 127 | 119 | 4 | −5 | 1 | 3 | 154 | 151 | 4 | 4 | 5 | 3 | 79 | 71 | 3 | 7 | 10 | 3 | 73 | 92 | 11 | −7 | 16 | 3 | 54 | 85 | 14 |
| −9 | −3 | 3 | 112 | 105 | 6 | −4 | 1 | 3 | 187 | 177 | 6 | 5 | 5 | 3 | 54 | 41 | 5 | 8 | 10 | 3 | 76 | 84 | 7 | −6 | 16 | 3 | 24 | 49 | 24 |
| −8 | −3 | 3 | 213 | 210 | 7 | −2 | 1 | 3 | 421 | 413 | 16 | 6 | 5 | 3 | 207 | 215 | 5 | 9 | 10 | 3 | 97 | 106 | 7 | −5 | 16 | 3 | 119 | 113 | 11 |
| −7 | −3 | 3 | 270 | 270 | 6 | −1 | 1 | 3 | 536 | 549 | 21 | 7 | 5 | 3 | 160 | 168 | 5 | −9 | 11 | 3 | 0 | 15 | 1 | −4 | 16 | 3 | 93 | 92 | 11 |
| −6 | −3 | 3 | 157 | 157 | 3 | 0 | 1 | 3 | 366 | 406 | 14 | 8 | 5 | 3 | 66 | 78 | 5 | −8 | 11 | 3 | 0 | 4 | 1 | −2 | 16 | 3 | 28 | 41 | 28 |
| −5 | −3 | 3 | 231 | 224 | 4 | 1 | 1 | 3 | 457 | 480 | 13 | 9 | 5 | 3 | 17 | 28 | 17 | −7 | 11 | 3 | 132 | 131 | 8 | −1 | 16 | 3 | 147 | 146 | 9 |
| −4 | −3 | 3 | 453 | 428 | 14 | 2 | 1 | 3 | 407 | 400 | 12 | 10 | 5 | 3 | 106 | 95 | 6 | −6 | 11 | 3 | 89 | 88 | 7 | 0 | 16 | 3 | 236 | 230 | 14 |
| −3 | −3 | 3 | 265 | 265 | 8 | 3 | 1 | 3 | 656 | 651 | 16 | −10 | 6 | 3 | 135 | 152 | 8 | −5 | 11 | 3 | 151 | 167 | 8 | 2 | 16 | 3 | 92 | 109 | 14 |
| −1 | −3 | 3 | 426 | 409 | 12 | 4 | 1 | 3 | 351 | 338 | 8 | −9 | 6 | 3 | 42 | 44 | 6 | −4 | 11 | 3 | 252 | 222 | 13 | 3 | 16 | 3 | 45 | 29 | 22 |
| 0 | −3 | 3 | 18 | 12 | 5 | 5 | 1 | 3 | 92 | 84 | 2 | −8 | 6 | 3 | 34 | 31 | 12 | −3 | 11 | 3 | 138 | 106 | 10 | 4 | 16 | 3 | 79 | 94 | 14 |
| 1 | −3 | 3 | 573 | 624 | 17 | 6 | 1 | 3 | 179 | 181 | 4 | −7 | 6 | 3 | 59 | 71 | 9 | −2 | 11 | 3 | 78 | 70 | 8 | 5 | 16 | 3 | 114 | 134 | 12 |
| 2 | −3 | 3 | 235 | 316 | 9 | 7 | 1 | 3 | 63 | 64 | 4 | −6 | 6 | 3 | 161 | 155 | 7 | −1 | 11 | 3 | 298 | 305 | 16 | 6 | 16 | 3 | 0 | 8 | 1 |
| 3 | −3 | 3 | 64 | 65 | 3 | 8 | 1 | 3 | 144 | 144 | 6 | −5 | 6 | 3 | 184 | 171 | 7 | 0 | 11 | 3 | 125 | 127 | 11 | 7 | 16 | 3 | 91 | 112 | 12 |
| 4 | −3 | 3 | 322 | 299 | 8 | 9 | 1 | 3 | 27 | 22 | 14 | −4 | 6 | 3 | 233 | 222 | 12 | 2 | 11 | 3 | 76 | 93 | 12 | 0 | 17 | 3 | 109 | 94 | 12 |
| 1 | 17 | 3 | 40 | 71 | 33 | −1 | −13 | 4 | 119 | 104 | 5 | −5 | −8 | 4 | 170 | 173 | 5 | 2 | −4 | 4 | 364 | 378 | 9 | 5 | 0 | 4 | 215 | 218 | 6 |
| 3 | 17 | 3 | 40 | 37 | 27 | 0 | −13 | 4 | 223 | 218 | 6 | −4 | −8 | 4 | 175 | 176 | 4 | 3 | −4 | 4 | 344 | 343 | 8 | 6 | 0 | 4 | 44 | 40 | 5 |
| 4 | 17 | 3 | 33 | 32 | 33 | 1 | −13 | 4 | 123 | 122 | 5 | −3 | −8 | 4 | 111 | 97 | 2 | 4 | −4 | 4 | 107 | 113 | 2 | 7 | 0 | 4 | 59 | 65 | 4 |
| 5 | 17 | 3 | 89 | 90 | 12 | 2 | −13 | 4 | 179 | 179 | 6 | −2 | −8 | 4 | 153 | 164 | 4 | 5 | −4 | 4 | 64 | 54 | 2 | 8 | 0 | 4 | 57 | 70 | 8 |
| 6 | 17 | 3 | 97 | 122 | 10 | 3 | −13 | 4 | 58 | 53 | 4 | −1 | −8 | 4 | 91 | 91 | 3 | 6 | −4 | 4 | 154 | 153 | 3 | 9 | 0 | 4 | 38 | 30 | 9 |
| 1 | 18 | 3 | 36 | 49 | 35 | 4 | −13 | 4 | 203 | 197 | 8 | 0 | −8 | 4 | 115 | 112 | 3 | 7 | −4 | 4 | 71 | 77 | 3 | 10 | 0 | 4 | 53 | 40 | 6 |
| 2 | 18 | 3 | 54 | 93 | 17 | 5 | −13 | 4 | 160 | 182 | 11 | 1 | −8 | 4 | 105 | 105 | 3 | 8 | −4 | 4 | 92 | 88 | 4 | −10 | 1 | 4 | 31 | 24 | 23 |
| 4 | 18 | 3 | 22 | 52 | 21 | 6 | −13 | 4 | 71 | 90 | 9 | 2 | −8 | 4 | 153 | 157 | 4 | 9 | −4 | 4 | 63 | 52 | 4 | −9 | 1 | 4 | 122 | 113 | 4 |
| 5 | 18 | 3 | 28 | 50 | 28 | 7 | −13 | 4 | 51 | 43 | 10 | 3 | −8 | 4 | 201 | 197 | 4 | 10 | −4 | 4 | 98 | 83 | 4 | −8 | 1 | 4 | 85 | 78 | 4 |
| 3 | 19 | 3 | 34 | 50 | 34 | 8 | −13 | 4 | 22 | 24 | 21 | 4 | −8 | 4 | 164 | 166 | 4 | −10 | −3 | 4 | 39 | 44 | 9 | −7 | 1 | 4 | 221 | 234 | 6 |
| −2 | −20 | 4 | 53 | 56 | 5 | −8 | −12 | 4 | 91 | 97 | 5 | 5 | −8 | 4 | 170 | 176 | 4 | −9 | −3 | 4 | 87 | 82 | 6 | −6 | 1 | 4 | 100 | 99 | 3 |
| −1 | −20 | 4 | 59 | 38 | 9 | −7 | −12 | 4 | 65 | 63 | 6 | 6 | −8 | 4 | 156 | 164 | 4 | −8 | −3 | 4 | 85 | 80 | 5 | −5 | 1 | 4 | 197 | 186 | 4 |
| 0 | −20 | 4 | 130 | 115 | 8 | −6 | −12 | 4 | 99 | 104 | 5 | 7 | −8 | 4 | 46 | 48 | 16 | −7 | −3 | 4 | 109 | 106 | 3 | −4 | 1 | 4 | 227 | 241 | 6 |
| 1 | −20 | 4 | 99 | 91 | 7 | −5 | −12 | 4 | 237 | 237 | 8 | 8 | −8 | 4 | 42 | 37 | 18 | −6 | −3 | 4 | 76 | 68 | 3 | −3 | 1 | 4 | 246 | 256 | 8 |
| 2 | −20 | 4 | 80 | 74 | 13 | −4 | −12 | 4 | 262 | 274 | 9 | 9 | −8 | 4 | 88 | 90 | 9 | −5 | −3 | 4 | 106 | 80 | 3 | −2 | 1 | 4 | 195 | 186 | 6 |
| −3 | −19 | 4 | 69 | 50 | 12 | −3 | −12 | 4 | 175 | 158 | 7 | −10 | −7 | 4 | 115 | 111 | 5 | −4 | −3 | 4 | 178 | 173 | 4 | −1 | 1 | 4 | 254 | 277 | 7 |
| −2 | −19 | 4 | 52 | 44 | 10 | −2 | −12 | 4 | 95 | 94 | 4 | −9 | −7 | 4 | 115 | 113 | 5 | −3 | −3 | 4 | 471 | 463 | 14 | 0 | 1 | 4 | 407 | 425 | 12 |
| −1 | −19 | 4 | 71 | 74 | 9 | −1 | −12 | 4 | 207 | 197 | 8 | −8 | −7 | 4 | 6 | 11 | 6 | −2 | −3 | 4 | 306 | 365 | 12 | 1 | 1 | 4 | 184 | 194 | 4 |
| 0 | −19 | 4 | 86 | 84 | 8 | 0 | −12 | 4 | 54 | 48 | 6 | −7 | −7 | 4 | 97 | 96 | 6 | −1 | −3 | 4 | 273 | 334 | 11 | 2 | 1 | 4 | 319 | 334 | 8 |
| 1 | −19 | 4 | 127 | 115 | 8 | 1 | −12 | 4 | 154 | 144 | 5 | −6 | −7 | 4 | 78 | 72 | 4 | 0 | −3 | 4 | 21 | 31 | 5 | 3 | 1 | 4 | 354 | 376 | 8 |
| 2 | −19 | 4 | 86 | 65 | 8 | 2 | −12 | 4 | 110 | 105 | 5 | −5 | −7 | 4 | 175 | 185 | 4 | 1 | −3 | 4 | 107 | 77 | 3 | 4 | 1 | 4 | 83 | 90 | 3 |
| 3 | −19 | 4 | 75 | 66 | 14 | 3 | −12 | 4 | 184 | 172 | 5 | −4 | −7 | 4 | 152 | 161 | 4 | 2 | −3 | 4 | 368 | 471 | 14 | 5 | 1 | 4 | 214 | 225 | 6 |
| −3 | −18 | 4 | 94 | 77 | 11 | 4 | −12 | 4 | 171 | 163 | 5 | −3 | −7 | 4 | 358 | 359 | 6 | 3 | −3 | 4 | 263 | 243 | 8 | 6 | 1 | 4 | 67 | 69 | 4 |
| −2 | −18 | 4 | 148 | 149 | 6 | 5 | −12 | 4 | 81 | 88 | 6 | −2 | −7 | 4 | 94 | 81 | 2 | 4 | −3 | 4 | 219 | 217 | 4 | 7 | 1 | 4 | 103 | 109 | 4 |
| −1 | −18 | 4 | 111 | 118 | 4 | 6 | −12 | 4 | 60 | 63 | 11 | −1 | −7 | 4 | 115 | 110 | 4 | 5 | −3 | 4 | 210 | 214 | 4 | 8 | 1 | 4 | 27 | 30 | 18 |
| 0 | −18 | 4 | 132 | 128 | 9 | 7 | −12 | 4 | 38 | 42 | 16 | 0 | −7 | 4 | 165 | 189 | 5 | 6 | −3 | 4 | 55 | 57 | 3 | 9 | 1 | 4 | 43 | 38 | 10 |
| 1 | −18 | 4 | 123 | 107 | 8 | 8 | −12 | 4 | 23 | 27 | 23 | 1 | −7 | 4 | 126 | 133 | 5 | 7 | −3 | 4 | 178 | 180 | 5 | 10 | 1 | 4 | 55 | 49 | 7 |
| 2 | −18 | 4 | 112 | 101 | 8 | −9 | −11 | 4 | 94 | 90 | 5 | 2 | −7 | 4 | 151 | 154 | 3 | 8 | −3 | 4 | 60 | 57 | 4 | −10 | 2 | 4 | 60 | 66 | 10 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 3 | −18 | 4 | 41 | 12 | 36 | −8 | −11 | 4 | 63 | 72 | 4 | 3 | −7 | 4 | 280 | 282 | 4 | 9 | −3 | 4 | 0 | 12 | 1 | −9 | 2 | 4 | 90 | 93 | 5 |
| 4 | −18 | 4 | 38 | 41 | 10 | −7 | −11 | 4 | 116 | 120 | 4 | 4 | −7 | 4 | 74 | 70 | 2 | 10 | −3 | 4 | 80 | 66 | 4 | −8 | 2 | 4 | 77 | 72 | 4 |
| 5 | −18 | 4 | 83 | 64 | 7 | −6 | −11 | 4 | 85 | 84 | 4 | 5 | −7 | 4 | 144 | 154 | 3 | −10 | −2 | 4 | 63 | 65 | 6 | −7 | 2 | 4 | 121 | 122 | 4 |
| −3 | −17 | 4 | 122 | 107 | 11 | −5 | −11 | 4 | 85 | 89 | 3 | 6 | −7 | 4 | 61 | 70 | 2 | −9 | −2 | 4 | 84 | 93 | 6 | −6 | 2 | 4 | 166 | 161 | 5 |
| −2 | −17 | 4 | 218 | 222 | 6 | −4 | −11 | 4 | 132 | 123 | 8 | 7 | −7 | 4 | 133 | 139 | 3 | −8 | −2 | 4 | 67 | 72 | 6 | −5 | 2 | 4 | 317 | 333 | 6 |
| −1 | −17 | 4 | 105 | 102 | 3 | −3 | −11 | 4 | 82 | 77 | 6 | 8 | −7 | 4 | 90 | 85 | 4 | −7 | −2 | 4 | 117 | 122 | 3 | −4 | 2 | 4 | 364 | 376 | 8 |
| 0 | −17 | 4 | 153 | 150 | 5 | −2 | −11 | 4 | 232 | 229 | 6 | 9 | −7 | 4 | 39 | 45 | 16 | −6 | −2 | 4 | 161 | 160 | 4 | −3 | 2 | 4 | 280 | 291 | 8 |
| 1 | −17 | 4 | 56 | 43 | 5 | −1 | −11 | 4 | 125 | 120 | 6 | −10 | −6 | 4 | 78 | 84 | 5 | −5 | −2 | 4 | 324 | 333 | 6 | −2 | 2 | 4 | 413 | 447 | 12 |
| 2 | −17 | 4 | 128 | 106 | 4 | 0 | −11 | 4 | 161 | 158 | 5 | −9 | −6 | 4 | 60 | 52 | 6 | −4 | −2 | 4 | 375 | 376 | 8 | −1 | 2 | 4 | 330 | 336 | 10 |
| 3 | −17 | 4 | 86 | 74 | 4 | 1 | −11 | 4 | 121 | 125 | 5 | −8 | −6 | 4 | 49 | 48 | 7 | −3 | −2 | 4 | 287 | 292 | 9 | 0 | 2 | 4 | 218 | 212 | 9 |
| 4 | −17 | 4 | 66 | 55 | 3 | 2 | −11 | 4 | 166 | 147 | 5 | −7 | −6 | 4 | 106 | 117 | 6 | −2 | −2 | 4 | 398 | 447 | 16 | 1 | 2 | 4 | 307 | 330 | 9 |
| 5 | −17 | 4 | 57 | 50 | 4 | 3 | −11 | 4 | 107 | 90 | 3 | −6 | −6 | 4 | 139 | 141 | 4 | −1 | −2 | 4 | 291 | 336 | 11 | 2 | 2 | 4 | 300 | 316 | 9 |
| −4 | −16 | 4 | 147 | 151 | 5 | 4 | −11 | 4 | 99 | 103 | 4 | −5 | −6 | 4 | 158 | 160 | 3 | 0 | −2 | 4 | 203 | 211 | 6 | 3 | 2 | 4 | 236 | 253 | 7 |
| −3 | −16 | 4 | 183 | 175 | 6 | 5 | −11 | 4 | 45 | 50 | 9 | −4 | −6 | 4 | 191 | 196 | 4 | 1 | −2 | 4 | 233 | 329 | 9 | 4 | 2 | 4 | 202 | 204 | 4 |
| −2 | −16 | 4 | 146 | 144 | 3 | 6 | −11 | 4 | 93 | 95 | 9 | −3 | −6 | 4 | 229 | 230 | 4 | 2 | −2 | 4 | 230 | 315 | 9 | 5 | 2 | 4 | 93 | 103 | 3 |
| −1 | −16 | 4 | 85 | 78 | 3 | 7 | −11 | 4 | 60 | 59 | 11 | −2 | −6 | 4 | 132 | 122 | 4 | 3 | −2 | 4 | 251 | 252 | 7 | 6 | 2 | 4 | 21 | 24 | 10 |
| 0 | −16 | 4 | 141 | 138 | 4 | 8 | −11 | 4 | 19 | 35 | 18 | −1 | −6 | 4 | 130 | 124 | 4 | 4 | −2 | 4 | 199 | 204 | 4 | 7 | 2 | 4 | 96 | 98 | 4 |
| 1 | −16 | 4 | 123 | 116 | 5 | −9 | −10 | 4 | 45 | 51 | 4 | 0 | −6 | 4 | 141 | 173 | 8 | 5 | −2 | 4 | 94 | 103 | 3 | 8 | 2 | 4 | 40 | 51 | 11 |
| 2 | −16 | 4 | 134 | 119 | 5 | −8 | −10 | 4 | 42 | 52 | 6 | 1 | −6 | 4 | 87 | 84 | 3 | 6 | −2 | 4 | 17 | 24 | 9 | 9 | 2 | 4 | 60 | 55 | 8 |
| 3 | −16 | 4 | 90 | 82 | 4 | −7 | −10 | 4 | 109 | 113 | 4 | 2 | −6 | 4 | 89 | 77 | 2 | 7 | −2 | 4 | 91 | 97 | 5 | 10 | 2 | 4 | 37 | 42 | 10 |
| 4 | −16 | 4 | 108 | 101 | 3 | −6 | −10 | 4 | 128 | 137 | 5 | 3 | −6 | 4 | 124 | 121 | 2 | 8 | −2 | 4 | 51 | 51 | 5 | −10 | 3 | 4 | 49 | 44 | 12 |
| 5 | −16 | 4 | 22 | 15 | 15 | −5 | −10 | 4 | 130 | 150 | 4 | 4 | −6 | 4 | 191 | 190 | 3 | 9 | −2 | 4 | 61 | 55 | 5 | −9 | 3 | 4 | 83 | 83 | 5 |
| 6 | −16 | 4 | 113 | 114 | 4 | −4 | −10 | 4 | 202 | 209 | 5 | 5 | −6 | 4 | 177 | 171 | 3 | 10 | −2 | 4 | 41 | 42 | 6 | −8 | 3 | 4 | 86 | 80 | 4 |
| −6 | −15 | 4 | 62 | 57 | 6 | −3 | −10 | 4 | 239 | 240 | 8 | 6 | −6 | 4 | 84 | 87 | 2 | −10 | −1 | 4 | 21 | 25 | 21 | −7 | 3 | 4 | 113 | 106 | 5 |
| −5 | −15 | 4 | 132 | 141 | 4 | −2 | −10 | 4 | 48 | 31 | 5 | 7 | −6 | 4 | 62 | 66 | 4 | −9 | −1 | 4 | 108 | 112 | 5 | −6 | 3 | 4 | 67 | 67 | 5 |
| −4 | −15 | 4 | 235 | 233 | 8 | −1 | −10 | 4 | 69 | 49 | 6 | 8 | −6 | 4 | 168 | 169 | 3 | −8 | −1 | 4 | 86 | 78 | 4 | −5 | 3 | 4 | 103 | 80 | 4 |
| −3 | −15 | 4 | 53 | 37 | 5 | 0 | −10 | 4 | 67 | 60 | 5 | 9 | −6 | 4 | 131 | 129 | 5 | −7 | −1 | 4 | 223 | 234 | 4 | −4 | 3 | 4 | 177 | 172 | 4 |
| −2 | −15 | 4 | 168 | 169 | 4 | 1 | −10 | 4 | 124 | 130 | 4 | −10 | −5 | 4 | 62 | 66 | 5 | −6 | −1 | 4 | 109 | 99 | 3 | −3 | 3 | 4 | 404 | 463 | 22 |
| −1 | −15 | 4 | 132 | 128 | 3 | 2 | −10 | 4 | 113 | 113 | 5 | −9 | −5 | 4 | 117 | 110 | 5 | −5 | −1 | 4 | 197 | 185 | 3 | −2 | 3 | 4 | 285 | 365 | 15 |
| 0 | −15 | 4 | 58 | 53 | 5 | 3 | −10 | 4 | 156 | 144 | 4 | −8 | −5 | 4 | 122 | 142 | 6 | −4 | −1 | 4 | 233 | 241 | 5 | −1 | 3 | 4 | 323 | 334 | 13 |
| 1 | −15 | 4 | 80 | 61 | 5 | 4 | −10 | 4 | 99 | 99 | 4 | −7 | −5 | 4 | 76 | 78 | 6 | −3 | −1 | 4 | 275 | 257 | 8 | 0 | 3 | 4 | 19 | 31 | 12 |
| 2 | −15 | 4 | 138 | 127 | 5 | 5 | −10 | 4 | 131 | 138 | 5 | −6 | −5 | 4 | 184 | 183 | 4 | −2 | −1 | 4 | 214 | 185 | 7 | 1 | 3 | 4 | 118 | 76 | 4 |
| 3 | −15 | 4 | 101 | 104 | 4 | 6 | −10 | 4 | 70 | 88 | 10 | −5 | −5 | 4 | 249 | 250 | 5 | −1 | −1 | 4 | 262 | 278 | 10 | 2 | 3 | 4 | 427 | 470 | 13 |
| 4 | −15 | 4 | 126 | 105 | 4 | 7 | −10 | 4 | 42 | 40 | 17 | −4 | −5 | 4 | 38 | 23 | 4 | 0 | −1 | 4 | 415 | 425 | 12 | 3 | 3 | 4 | 240 | 242 | 7 |
| 5 | −15 | 4 | 75 | 58 | 4 | 8 | −10 | 4 | 47 | 57 | 13 | −3 | −5 | 4 | 84 | 69 | 3 | 1 | −1 | 4 | 191 | 195 | 6 | 4 | 3 | 4 | 206 | 217 | 4 |
| 6 | −15 | 4 | 82 | 89 | 4 | 9 | −10 | 4 | 23 | 27 | 22 | −2 | −5 | 4 | 214 | 219 | 6 | 2 | −1 | 4 | 254 | 333 | 10 | 5 | 3 | 4 | 196 | 214 | 4 |
| 7 | −15 | 4 | 72 | 76 | 5 | −9 | −9 | 4 | 91 | 94 | 4 | −1 | −5 | 4 | 320 | 307 | 11 | 3 | −1 | 4 | 370 | 376 | 11 | 6 | 3 | 4 | 49 | 57 | 4 |
| −7 | −14 | 4 | 86 | 86 | 4 | −8 | −9 | 4 | 55 | 50 | 5 | 0 | −5 | 4 | 165 | 151 | 5 | 4 | −1 | 4 | 81 | 90 | 3 | 7 | 3 | 4 | 180 | 180 | 7 |
| −6 | −14 | 4 | 62 | 59 | 5 | −7 | −9 | 4 | 37 | 44 | 7 | 1 | −5 | 4 | 242 | 228 | 7 | 5 | −1 | 4 | 216 | 226 | 5 | 8 | 3 | 4 | 40 | 57 | 12 |
| −5 | −14 | 4 | 95 | 101 | 5 | −6 | −9 | 4 | 62 | 56 | 5 | 2 | −5 | 4 | 128 | 117 | 4 | 6 | −1 | 4 | 66 | 69 | 4 | 9 | 3 | 4 | 19 | 12 | 18 |
| −4 | −14 | 4 | 66 | 42 | 5 | −5 | −9 | 4 | 146 | 138 | 5 | 3 | −5 | 4 | 57 | 61 | 2 | 7 | −1 | 4 | 103 | 108 | 7 | 10 | 3 | 4 | 75 | 66 | 6 |
| −3 | −14 | 4 | 150 | 148 | 5 | −4 | −9 | 4 | 100 | 108 | 3 | 4 | −5 | 4 | 174 | 174 | 3 | 8 | −1 | 4 | 36 | 30 | 8 | −10 | 4 | 4 | 71 | 74 | 8 |
| −2 | −14 | 4 | 168 | 165 | 4 | −3 | −9 | 4 | 152 | 158 | 4 | 5 | −5 | 4 | 100 | 106 | 2 | 9 | −1 | 4 | 38 | 38 | 8 | −9 | 4 | 4 | 26 | 8 | 12 |
| −1 | −14 | 4 | 160 | 178 | 5 | −2 | −9 | −4 | 91 | 95 | 5 | 6 | −5 | 4 | 42 | 50 | 3 | 10 | −1 | 4 | 51 | 49 | 7 | −8 | 4 | 4 | 80 | 78 | 5 |
| 0 | −14 | 4 | 94 | 91 | 5 | −1 | −9 | 4 | 164 | 159 | 5 | 7 | −5 | 4 | 130 | 127 | 3 | −10 | 0 | 4 | 94 | 96 | 5 | −7 | 4 | 4 | 180 | 177 | 5 |
| 1 | −14 | 4 | 84 | 63 | 4 | 0 | −9 | 4 | 107 | 87 | 4 | 8 | −5 | 4 | 67 | 60 | 4 | −9 | 0 | 4 | 27 | 16 | 10 | −6 | 4 | 4 | 193 | 197 | 5 |
| 2 | −14 | 4 | 181 | 177 | 5 | 1 | −9 | 4 | 128 | 125 | 4 | 9 | −5 | 4 | 133 | 137 | 4 | −8 | 0 | 4 | 107 | 109 | 4 | −5 | 4 | 4 | 189 | 199 | 5 |
| 3 | −14 | 4 | 63 | 47 | 5 | 2 | −9 | 4 | 194 | 195 | 7 | −10 | −4 | 4 | 62 | 74 | 5 | −7 | 0 | 4 | 138 | 139 | 3 | −4 | 4 | 4 | 260 | 268 | 10 |
| 4 | −14 | 4 | 163 | 166 | 6 | 3 | −9 | 4 | 199 | 189 | 5 | −9 | −4 | 4 | 0 | 8 | 1 | −6 | 0 | 4 | 86 | 89 | 3 | −3 | 4 | 4 | 204 | 209 | 9 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 5 | −14 | 4 | 41 | 41 | 9 | 4 | −9 | 4 | 105 | 95 | 4 | −8 | −4 | 4 | 85 | 78 | 6 | −5 | 0 | 4 | 418 | 421 | 8 | −2 | 4 | 4 | 193 | 185 | 8 |
| 6 | −14 | 4 | 42 | 49 | 9 | 5 | −9 | 4 | 221 | 222 | 6 | −7 | −4 | 4 | 187 | 177 | 5 | −4 | 0 | 4 | 281 | 287 | 6 | −1 | 4 | 4 | 220 | 198 | 8 |
| 7 | −14 | 4 | 32 | 34 | 14 | 6 | −9 | 4 | 49 | 73 | 14 | −6 | −4 | 4 | 199 | 197 | 5 | −3 | 0 | 4 | 74 | 69 | 4 | 0 | 4 | 4 | 214 | 216 | 9 |
| −8 | −13 | 4 | 59 | 52 | 5 | 7 | −9 | 4 | 127 | 119 | 9 | −5 | −4 | 4 | 199 | 199 | 4 | −2 | 0 | 4 | 483 | 486 | 14 | 1 | 4 | 4 | 301 | 337 | 9 |
| −7 | −13 | 4 | 93 | 83 | 5 | 8 | −9 | 4 | 41 | 35 | 17 | −4 | −4 | 4 | 263 | 268 | 5 | −1 | 0 | 4 | 115 | 77 | 4 | 2 | 4 | 4 | 332 | 378 | 10 |
| −6 | −13 | 4 | 71 | 69 | 6 | 9 | −9 | 4 | 25 | 12 | 25 | −3 | −4 | 4 | 221 | 209 | 7 | 0 | 0 | 4 | 597 | 676 | 18 | 3 | 4 | 4 | 324 | 343 | 9 |
| −5 | −13 | 4 | 124 | 123 | 6 | −9 | −8 | 4 | 119 | 117 | 5 | −2 | −4 | 4 | 185 | 185 | 6 | 1 | 0 | 4 | 304 | 316 | 7 | 4 | 4 | 4 | 108 | 113 | 3 |
| −4 | −13 | 4 | 59 | 56 | 7 | −8 | −8 | 4 | 107 | 106 | 5 | −1 | −4 | 4 | 203 | 199 | 6 | 2 | 0 | 4 | 335 | 325 | 10 | 5 | 4 | 4 | 56 | 53 | 3 |
| −3 | −13 | 4 | 69 | 84 | 5 | −7 | −8 | 4 | 140 | 154 | 5 | 0 | −4 | 4 | 219 | 215 | 6 | 3 | 0 | 4 | 71 | 82 | 3 | 6 | 4 | 4 | 147 | 153 | 4 |
| −2 | −13 | 4 | 151 | 142 | 4 | −6 | −8 | 4 | 284 | 295 | 8 | 1 | −4 | 4 | 337 | 337 | 10 | 4 | 0 | 4 | 177 | 175 | 4 | 7 | 4 | 4 | 76 | 78 | 6 |
| 8 | 4 | 4 | 91 | 88 | 7 | −4 | 9 | 4 | 121 | 108 | 11 | −4 | 14 | 4 | 65 | 41 | 15 | 4 | −17 | 5 | 110 | 104 | 3 | 8 | −11 | 5 | 75 | 106 | 8 |
| 9 | 4 | 4 | 70 | 53 | 7 | −3 | 9 | 4 | 162 | 158 | 11 | −3 | 14 | 4 | 142 | 148 | 12 | 5 | −17 | 5 | 72 | 72 | 4 | −8 | −10 | 5 | 146 | 150 | 8 |
| 10 | 4 | 4 | 97 | 83 | 6 | −2 | 9 | 4 | 115 | 95 | 7 | −2 | 14 | 4 | 178 | 165 | 12 | −5 | −16 | 5 | 77 | 78 | 6 | −7 | −10 | 5 | 147 | 157 | 4 |
| −10 | 5 | 4 | 62 | 66 | 9 | −1 | 9 | 4 | 178 | 160 | 11 | −1 | 14 | 4 | 181 | 177 | 12 | −4 | −16 | 5 | 11 | 21 | 10 | −6 | −10 | 5 | 80 | 87 | 4 |
| −9 | 5 | 4 | 112 | 110 | 4 | 0 | 9 | 4 | 90 | 88 | 11 | 0 | 14 | 4 | 95 | 91 | 13 | −3 | −16 | 5 | 171 | 159 | 5 | −5 | −10 | 5 | 71 | 74 | 4 |
| −8 | 5 | 4 | 133 | 142 | 6 | 1 | 9 | 4 | 102 | 125 | 12 | 1 | 14 | 4 | 61 | 62 | 17 | −2 | −16 | 5 | 103 | 100 | 4 | −4 | −10 | 5 | 52 | 46 | 3 |
| −7 | 5 | 4 | 82 | 77 | 6 | 2 | 9 | 4 | 167 | 195 | 11 | 2 | 14 | 4 | 171 | 176 | 13 | −1 | −16 | 5 | 222 | 215 | 4 | −3 | −10 | 5 | 268 | 258 | 9 |
| −6 | 5 | 4 | 182 | 183 | 6 | 3 | 9 | 4 | 171 | 190 | 11 | 3 | 14 | 4 | 47 | 48 | 22 | 0 | −16 | 5 | 60 | 57 | 5 | −2 | −10 | 5 | 39 | 38 | 9 |
| −5 | 5 | 4 | 248 | 249 | 9 | 4 | 9 | 4 | 80 | 95 | 12 | 4 | 14 | 4 | 149 | 166 | 12 | 1 | −16 | 5 | 111 | 77 | 4 | −1 | −10 | 5 | 146 | 125 | 4 |
| −4 | 5 | 4 | 52 | 23 | 6 | 5 | 9 | 4 | 208 | 222 | 8 | 5 | 14 | 4 | 43 | 41 | 22 | 2 | −16 | 5 | 105 | 89 | 5 | 0 | −10 | 5 | 114 | 106 | 4 |
| −3 | 5 | 4 | 84 | 69 | 10 | 6 | 9 | 4 | 69 | 73 | 8 | 6 | 14 | 4 | 45 | 48 | 22 | 3 | −16 | 5 | 169 | 159 | 6 | 1 | −10 | 5 | 195 | 196 | 6 |
| −2 | 5 | 4 | 201 | 218 | 9 | 7 | 9 | 4 | 114 | 119 | 7 | 7 | 14 | 4 | 32 | 34 | 32 | 4 | −16 | 5 | 113 | 108 | 4 | 2 | −10 | 5 | 61 | 52 | 3 |
| −1 | 5 | 4 | 288 | 306 | 11 | 8 | 9 | 4 | 39 | 35 | 10 | −7 | 15 | 4 | 68 | 63 | 13 | 5 | −16 | 5 | 71 | 67 | 4 | 3 | −10 | 5 | 133 | 134 | 4 |
| 0 | 5 | 4 | 149 | 151 | 6 | 9 | 9 | 4 | 19 | 13 | 18 | −6 | 15 | 4 | 52 | 58 | 19 | −6 | −15 | 5 | 33 | 40 | 6 | 4 | −10 | 5 | 116 | 115 | 5 |
| 1 | 5 | 4 | 221 | 229 | 7 | −9 | 10 | 4 | 53 | 51 | 11 | −5 | 15 | 4 | 134 | 141 | 11 | −5 | −15 | 5 | 73 | 69 | 5 | 5 | −10 | 5 | 74 | 69 | 7 |
| 2 | 5 | 4 | 118 | 117 | 5 | −8 | 10 | 4 | 39 | 53 | 17 | −4 | 15 | 4 | 236 | 233 | 14 | −4 | −15 | 5 | 183 | 181 | 6 | 6 | −10 | 5 | 83 | 95 | 10 |
| 3 | 5 | 4 | 54 | 60 | 4 | −7 | 10 | 4 | 126 | 114 | 8 | −3 | 15 | 4 | 61 | 37 | 14 | −3 | −15 | 5 | 139 | 132 | 5 | 7 | −10 | 5 | 49 | 18 | 13 |
| 4 | 5 | 4 | 159 | 174 | 4 | −6 | 10 | 4 | 136 | 137 | 8 | −2 | 15 | 4 | 173 | 169 | 11 | −2 | −15 | 5 | 138 | 118 | 4 | −9 | −9 | 5 | 66 | 72 | 7 |
| 5 | 5 | 4 | 99 | 106 | 4 | −5 | 10 | 4 | 149 | 150 | 7 | −1 | 15 | 4 | 130 | 128 | 8 | −1 | −15 | 5 | 181 | 176 | 4 | −8 | −9 | 5 | 38 | 51 | 7 |
| 6 | 5 | 4 | 44 | 50 | 6 | −4 | 10 | 4 | 213 | 208 | 12 | 0 | 15 | 4 | 55 | 53 | 22 | 0 | −15 | 5 | 213 | 207 | 7 | −7 | −9 | 5 | 118 | 132 | 5 |
| 7 | 5 | 4 | 114 | 128 | 4 | −3 | 10 | 4 | 240 | 240 | 14 | 1 | 15 | 4 | 63 | 61 | 17 | 1 | −15 | 5 | 134 | 112 | 5 | −6 | −9 | 5 | 21 | 24 | 20 |
| 8 | 5 | 4 | 67 | 60 | 8 | −2 | 10 | 4 | 56 | 31 | 9 | 2 | 15 | 4 | 118 | 127 | 14 | 2 | −15 | 5 | 135 | 123 | 5 | −5 | −9 | 5 | 124 | 130 | 4 |
| 9 | 5 | 4 | 139 | 137 | 6 | −1 | 10 | 4 | 80 | 49 | 12 | 3 | 15 | 4 | 85 | 104 | 13 | 3 | −15 | 5 | 113 | 121 | 5 | −4 | −9 | 5 | 239 | 253 | 6 |
| 10 | 5 | 4 | 92 | 81 | 6 | 0 | 10 | 4 | 49 | 60 | 17 | 4 | 15 | 4 | 111 | 105 | 13 | 4 | −15 | 5 | 46 | 31 | 7 | −3 | −9 | 5 | 174 | 158 | 5 |
| −10 | 6 | 4 | 82 | 85 | 8 | 1 | 10 | 4 | 117 | 131 | 10 | 5 | 15 | 4 | 65 | 58 | 14 | 5 | −15 | 5 | 37 | 26 | 9 | −2 | −9 | 5 | 139 | 131 | 6 |
| −9 | 6 | 4 | 53 | 52 | 6 | 2 | 10 | 4 | 93 | 113 | 11 | 6 | 15 | 4 | 80 | 89 | 12 | 6 | −15 | 5 | 14 | 9 | 14 | −1 | −9 | 5 | 92 | 76 | 4 |
| −8 | 6 | 4 | 48 | 47 | 9 | 3 | 10 | 4 | 133 | 144 | 11 | 7 | 15 | 4 | 69 | 76 | 12 | −7 | −14 | 5 | 0 | 21 | 1 | 0 | −9 | 5 | 108 | 105 | 3 |
| −7 | 6 | 4 | 105 | 117 | 6 | 4 | 10 | 4 | 88 | 100 | 12 | −6 | 16 | 4 | 63 | 66 | 13 | −6 | −14 | 5 | 92 | 92 | 5 | 1 | −9 | 5 | 107 | 101 | 3 |
| −6 | 6 | 4 | 131 | 140 | 6 | 5 | 10 | 4 | 125 | 138 | 7 | −5 | 16 | 4 | 94 | 83 | 11 | −5 | −14 | 5 | 59 | 53 | 6 | 2 | −9 | 5 | 83 | 73 | 2 |
| −5 | 6 | 4 | 171 | 160 | 7 | 6 | 10 | 4 | 75 | 87 | 7 | −4 | 16 | 4 | 153 | 150 | 11 | −4 | −14 | 5 | 181 | 175 | 7 | 3 | −9 | 5 | 237 | 246 | 5 |
| −4 | 6 | 4 | 207 | 197 | 7 | 7 | 10 | 4 | 37 | 40 | 13 | −3 | 16 | 4 | 182 | 174 | 12 | −3 | −14 | 5 | 159 | 139 | 5 | 4 | −9 | 5 | 161 | 160 | 4 |
| −3 | 6 | 4 | 221 | 230 | 12 | 8 | 10 | 4 | 48 | 57 | 8 | −2 | 16 | 4 | 145 | 145 | 11 | −2 | −14 | 5 | 50 | 46 | 5 | 5 | −9 | 5 | 133 | 136 | 6 |
| −1 | 6 | 4 | 113 | 124 | 6 | −9 | 11 | 4 | 94 | 89 | 7 | −1 | 16 | 4 | 74 | 77 | 9 | −1 | −14 | 5 | 153 | 148 | 4 | 6 | −9 | 5 | 81 | 83 | 10 |
| 0 | 6 | 4 | 145 | 174 | 6 | −8 | 11 | 4 | 64 | 72 | 10 | 0 | 16 | 4 | 149 | 138 | 12 | 0 | −14 | 5 | 240 | 231 | 9 | 7 | −9 | 5 | 76 | 95 | 10 |
| 1 | 6 | 4 | 75 | 84 | 4 | −7 | 11 | 4 | 122 | 120 | 8 | 1 | 16 | 4 | 124 | 115 | 12 | 1 | −14 | 5 | 117 | 117 | 6 | 8 | −9 | 5 | 59 | 67 | 11 |
| 2 | 6 | 4 | 86 | 77 | 4 | −6 | 11 | 4 | 88 | 84 | 8 | 3 | 16 | 4 | 65 | 83 | 16 | 2 | −14 | 5 | 66 | 85 | 7 | −9 | −8 | 5 | 22 | 41 | 15 |
| 3 | 6 | 4 | 121 | 121 | 4 | −5 | 11 | 4 | 84 | 90 | 14 | 4 | 16 | 4 | 89 | 101 | 13 | 3 | −14 | 5 | 164 | 177 | 7 | −8 | −8 | 5 | 68 | 65 | 5 |
| 4 | 6 | 4 | 181 | 190 | 5 | −4 | 11 | 4 | 144 | 124 | 11 | 5 | 16 | 4 | 0 | 15 | 1 | 4 | −14 | 5 | 120 | 106 | 5 | −7 | −8 | 5 | 16 | 27 | 16 |
| 5 | 6 | 4 | 173 | 171 | 5 | −3 | 11 | 4 | 73 | 77 | 12 | 6 | 16 | 4 | 89 | 114 | 12 | 5 | −14 | 5 | 99 | 92 | 5 | −6 | −8 | 5 | 114 | 108 | 5 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 6 | 6 | 4 | 84 | 87 | 5 | −2 | 11 | 4 | 246 | 229 | 9 | −5 | 17 | 4 | 50 | 54 | 16 | 6 | −14 | 5 | 66 | 63 | 6 | −5 | −8 | 5 | 278 | 290 | 7 |
| 7 | 6 | 4 | 54 | 67 | 6 | −1 | 11 | 4 | 129 | 121 | 11 | −4 | 17 | 4 | 69 | 77 | 13 | −7 | −13 | 5 | 77 | 78 | 5 | −4 | −8 | 5 | 225 | 225 | 5 |
| 8 | 6 | 4 | 156 | 169 | 6 | 0 | 11 | 4 | 150 | 158 | 11 | −3 | 17 | 4 | 94 | 107 | 11 | −6 | −13 | 5 | 31 | 36 | 13 | −3 | −8 | 5 | 141 | 128 | 3 |
| 9 | 6 | 4 | 129 | 130 | 6 | 1 | 11 | 4 | 109 | 124 | 11 | −2 | 17 | 4 | 201 | 222 | 13 | −5 | −13 | 5 | 204 | 198 | 7 | −2 | −8 | 5 | 237 | 233 | 4 |
| 10 | 6 | 4 | 30 | 32 | 19 | 2 | 11 | 4 | 144 | 146 | 12 | −1 | 17 | 4 | 104 | 103 | 11 | −4 | −13 | 5 | 241 | 240 | 11 | −1 | −8 | 5 | 77 | 72 | 3 |
| −10 | 7 | 4 | 106 | 111 | 11 | 3 | 11 | 4 | 82 | 89 | 13 | 0 | 17 | 4 | 170 | 149 | 11 | −3 | −13 | 5 | 59 | 51 | 7 | 0 | −8 | 5 | 81 | 81 | 2 |
| −9 | 7 | 4 | 112 | 113 | 6 | 4 | 11 | 4 | 89 | 102 | 12 | 1 | 17 | 4 | 55 | 42 | 19 | −2 | −13 | 5 | 118 | 100 | 6 | 1 | −8 | 5 | 43 | 36 | 3 |
| −8 | 7 | 4 | 26 | 11 | 25 | 5 | 11 | 4 | 31 | 51 | 30 | 3 | 17 | 4 | 48 | 73 | 22 | −1 | −13 | 5 | 135 | 129 | 4 | 2 | −8 | 5 | 175 | 162 | 4 |
| −7 | 7 | 4 | 91 | 96 | 7 | 6 | 11 | 4 | 73 | 95 | 8 | 4 | 17 | 4 | 0 | 54 | 1 | 0 | −13 | 5 | 102 | 97 | 6 | 3 | −8 | 5 | 132 | 129 | 3 |
| −6 | 7 | 4 | 74 | 72 | 8 | 7 | 11 | 4 | 56 | 59 | 9 | 5 | 17 | 4 | 19 | 50 | 18 | 1 | −13 | 5 | 44 | 33 | 8 | 4 | −8 | 5 | 153 | 152 | 4 |
| −5 | 7 | 4 | 179 | 185 | 7 | 8 | 11 | 4 | 0 | 36 | 1 | 6 | 17 | 4 | 0 | 24 | 1 | 2 | −13 | 5 | 169 | 212 | 7 | 5 | −8 | 5 | 46 | 42 | 5 |
| −4 | 7 | 4 | 157 | 160 | 7 | −8 | 12 | 4 | 79 | 97 | 9 | −4 | 18 | 4 | 54 | 66 | 13 | 3 | −13 | 5 | 124 | 121 | 7 | 6 | −8 | 5 | 89 | 102 | 7 |
| −3 | 7 | 4 | 359 | 358 | 18 | −7 | 12 | 4 | 63 | 64 | 9 | −3 | 18 | 4 | 67 | 78 | 11 | 4 | −13 | 5 | 125 | 132 | 9 | 7 | −8 | 5 | 42 | 16 | 20 |
| −2 | 7 | 4 | 110 | 82 | 6 | −6 | 12 | 4 | 100 | 103 | 7 | −2 | 18 | 4 | 150 | 148 | 10 | 5 | −13 | 5 | 53 | 41 | 8 | 8 | −8 | 5 | 60 | 68 | 11 |
| −1 | 7 | 4 | 121 | 110 | 9 | −5 | 12 | 4 | 245 | 237 | 14 | −1 | 18 | 4 | 118 | 118 | 10 | 6 | −13 | 5 | 0 | 36 | 1 | 9 | −8 | 5 | 39 | 40 | 15 |
| 1 | 7 | 4 | 118 | 134 | 10 | −4 | 12 | 4 | 290 | 275 | 14 | 0 | 18 | 4 | 133 | 128 | 7 | 7 | −13 | 5 | 50 | 62 | 9 | −9 | −7 | 5 | 0 | 20 | 1 |
| 1 | 7 | 4 | 136 | 155 | 11 | −3 | 12 | 4 | 182 | 159 | 12 | 1 | 18 | 4 | 108 | 107 | 12 | −8 | −12 | 5 | 54 | 49 | 10 | −8 | −7 | 5 | 66 | 60 | 5 |
| 3 | 7 | 4 | 262 | 282 | 9 | −2 | 12 | 4 | 109 | 94 | 8 | 2 | 18 | 4 | 83 | 101 | 13 | −7 | −12 | 5 | 93 | 92 | 6 | −7 | −7 | 5 | 133 | 131 | 5 |
| 4 | 7 | 4 | 76 | 71 | 5 | −1 | 12 | 4 | 222 | 197 | 13 | 3 | 18 | 4 | 0 | 11 | 1 | −6 | −12 | 5 | 64 | 57 | 8 | −6 | −7 | 5 | 41 | 41 | 8 |
| 5 | 7 | 4 | 142 | 155 | 5 | 0 | 12 | 4 | 50 | 48 | 18 | 4 | 18 | 4 | 20 | 41 | 19 | −5 | −12 | 5 | 170 | 176 | 9 | −5 | −7 | 5 | 53 | 39 | 4 |
| 6 | 7 | 4 | 55 | 70 | 6 | 1 | 12 | 4 | 139 | 144 | 12 | 5 | 18 | 4 | 50 | 65 | 15 | −4 | −12 | 5 | 139 | 166 | 8 | −4 | −7 | 5 | 256 | 260 | 5 |
| 7 | 7 | 4 | 121 | 139 | 5 | 2 | 12 | 4 | 80 | 106 | 13 | −1 | 19 | 4 | 67 | 74 | 11 | −3 | −12 | 5 | 253 | 248 | 9 | −3 | −7 | 5 | 62 | 57 | 3 |
| 8 | 7 | 4 | 86 | 85 | 6 | 3 | 12 | 4 | 156 | 172 | 12 | 0 | 19 | 4 | 81 | 83 | 10 | −2 | −12 | 5 | 69 | 64 | 6 | −2 | −7 | 5 | 151 | 139 | 3 |
| 9 | 7 | 4 | 43 | 46 | 11 | 4 | 12 | 4 | 146 | 163 | 12 | 1 | 19 | 4 | 124 | 115 | 7 | −1 | −12 | 5 | 53 | 52 | 5 | −1 | −7 | 5 | 78 | 63 | 2 |
| −9 | 8 | 4 | 130 | 116 | 8 | 5 | 12 | 4 | 67 | 87 | 14 | 2 | 19 | 4 | 73 | 64 | 12 | 0 | −12 | 5 | 40 | 47 | 8 | 0 | −7 | 5 | 86 | 85 | 2 |
| −8 | 8 | 4 | 114 | 106 | 6 | 6 | 12 | 4 | 54 | 63 | 10 | 3 | 19 | 4 | 67 | 66 | 12 | 1 | −12 | 5 | 40 | 40 | 8 | 1 | −7 | 5 | 179 | 177 | 3 |
| −7 | 8 | 4 | 140 | 154 | 8 | 7 | 12 | 4 | 33 | 42 | 16 | 4 | 19 | 4 | 99 | 117 | 10 | 2 | −12 | 5 | 103 | 103 | 4 | 2 | −7 | 5 | 111 | 95 | 3 |
| −6 | 8 | 4 | 288 | 295 | 11 | 8 | 12 | 4 | 36 | 26 | 32 | 2 | 20 | 4 | 81 | 74 | 10 | 3 | −12 | 5 | 49 | 15 | 7 | 3 | −7 | 5 | 196 | 204 | 4 |
| −5 | 8 | 4 | 180 | 173 | 7 | −8 | 13 | 4 | 45 | 51 | 12 | −2 | −19 | 5 | 124 | 139 | 5 | 4 | −12 | 5 | 232 | 252 | 10 | 4 | −7 | 5 | 98 | 92 | 3 |
| −4 | 8 | 4 | 191 | 175 | 7 | −7 | 13 | 4 | 69 | 83 | 9 | −1 | −19 | 5 | 19 | 51 | 18 | 5 | −12 | 5 | 90 | 94 | 7 | 5 | −7 | 5 | 221 | 215 | 5 |
| −3 | 8 | 4 | 146 | 96 | 10 | −6 | 13 | 4 | 74 | 69 | 15 | 0 | −19 | 5 | 118 | 104 | 11 | 6 | −12 | 5 | 23 | 42 | 22 | 6 | −7 | 5 | 92 | 93 | 3 |
| −2 | 8 | 4 | 177 | 163 | 7 | −5 | 13 | 4 | 119 | 123 | 12 | 1 | −19 | 5 | 75 | 61 | 14 | 7 | −12 | 5 | 0 | 8 | 1 | 7 | −7 | 5 | 77 | 80 | 6 |
| −1 | 8 | 4 | 102 | 91 | 10 | −4 | 13 | 4 | 87 | 57 | 12 | 2 | −19 | 5 | 47 | 27 | 19 | −8 | −11 | 5 | 103 | 104 | 5 | 8 | −7 | 5 | 95 | 100 | 6 |
| 0 | 8 | 4 | 113 | 112 | 9 | −3 | 13 | 4 | 87 | 84 | 12 | −2 | −18 | 5 | 87 | 57 | 9 | −7 | −11 | 5 | 109 | 110 | 7 | 9 | −7 | 5 | 67 | 97 | 10 |
| 1 | 8 | 4 | 96 | 105 | 11 | −2 | 13 | 4 | 163 | 143 | 11 | −1 | −18 | 5 | 77 | 78 | 14 | −6 | −11 | 5 | 69 | 82 | 8 | −9 | −6 | 5 | 33 | 40 | 10 |
| 2 | 8 | 4 | 132 | 157 | 11 | −1 | 13 | 4 | 119 | 104 | 12 | 0 | −18 | 5 | 106 | 93 | 5 | −5 | −11 | 5 | 174 | 248 | 9 | −8 | −6 | 5 | 43 | 41 | 8 |
| 3 | 8 | 4 | 182 | 197 | 12 | 0 | 13 | 4 | 232 | 217 | 14 | 1 | −18 | 5 | 65 | 43 | 16 | −4 | −11 | 5 | 59 | 67 | 9 | −7 | −6 | 5 | 109 | 113 | 6 |
| 4 | 8 | 4 | 163 | 165 | 7 | 1 | 13 | 4 | 110 | 122 | 12 | 2 | −18 | 5 | 26 | 14 | 12 | −3 | −11 | 5 | 115 | 108 | 6 | −6 | −6 | 5 | 178 | 176 | 6 |
| 5 | 8 | 4 | 179 | 176 | 7 | 2 | 13 | 4 | 173 | 179 | 12 | 3 | −18 | 5 | 13 | 22 | 13 | −2 | −11 | 5 | 231 | 224 | 8 | −5 | −6 | 5 | 191 | 191 | 4 |
| 6 | 8 | 4 | 149 | 164 | 6 | 3 | 13 | 4 | 27 | 53 | 26 | 4 | −18 | 5 | 38 | 15 | 38 | −1 | −11 | 5 | 174 | 162 | 5 | −4 | −6 | 5 | 169 | 163 | 3 |
| 7 | 8 | 4 | 53 | 48 | 6 | 4 | 13 | 4 | 167 | 197 | 11 | −4 | −17 | 5 | 37 | 43 | 9 | 0 | −11 | 5 | 102 | 104 | 5 | −3 | −6 | 5 | 219 | 217 | 4 |
| 8 | 8 | 4 | 30 | 37 | 10 | 5 | 13 | 4 | 119 | 183 | 12 | −3 | −17 | 5 | 75 | 63 | 5 | 1 | −11 | 5 | 63 | 18 | 5 | −2 | −6 | 5 | 185 | 176 | 3 |
| 9 | 8 | 4 | 94 | 89 | 8 | 6 | 13 | 4 | 83 | 90 | 8 | −2 | −17 | 5 | 57 | 52 | 4 | 2 | −11 | 5 | 167 | 145 | 4 | −1 | −6 | 5 | 40 | 42 | 3 |
| −9 | 9 | 4 | 93 | 94 | 8 | 7 | 13 | 4 | 44 | 42 | 20 | −1 | −17 | 5 | 95 | 88 | 3 | 3 | −11 | 5 | 183 | 177 | 5 | 0 | −6 | 5 | 185 | 172 | 3 |
| −8 | 9 | 4 | 52 | 51 | 10 | 8 | 13 | 4 | 34 | 24 | 34 | 0 | −17 | 5 | 104 | 93 | 4 | 4 | −11 | 5 | 175 | 172 | 6 | 1 | −6 | 5 | 73 | 83 | 2 |
| −7 | 9 | 4 | 49 | 45 | 11 | −7 | 14 | 4 | 97 | 85 | 11 | 1 | −17 | 5 | 110 | 106 | 4 | 5 | −11 | 5 | 132 | 128 | 6 | 2 | −6 | 5 | 231 | 231 | 4 |
| −6 | 9 | 4 | 59 | 56 | 9 | −6 | 14 | 4 | 36 | 60 | 35 | 2 | −17 | 5 | 129 | 119 | 5 | 6 | −11 | 5 | 74 | 76 | 10 | 3 | −6 | 5 | 144 | 140 | 2 |
| −5 | 9 | 4 | 152 | 138 | 7 | −5 | 14 | 4 | 111 | 101 | 12 | 3 | −17 | 5 | 63 | 55 | 4 | 7 | −11 | 5 | 55 | 63 | 11 | 4 | −6 | 5 | 147 | 145 | 2 |
| 5 | −6 | 5 | 59 | 56 | 2 | −7 | −1 | 5 | 149 | 148 | 4 | −1 | 3 | 5 | 161 | 206 | 9 | −9 | 8 | 5 | 32 | 41 | 25 | −2 | 13 | 5 | 127 | 99 | 10 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 6 | −6 | 5 | 53 | 45 | 3 | −6 | −2 | 5 | 123 | 117 | 4 | 0 | 3 | 5 | 191 | 188 | 6 | −8 | 8 | 5 | 65 | 65 | 7 | −1 | 13 | 5 | 127 | 129 | 8 |
| 7 | −6 | 5 | 49 | 46 | 4 | −5 | −1 | 5 | 245 | 248 | 6 | 1 | 3 | 5 | 136 | 136 | 5 | −7 | 8 | 5 | 39 | 27 | 12 | 0 | 13 | 5 | 108 | 98 | 12 |
| 8 | −6 | 5 | 51 | 40 | 4 | −4 | −1 | 5 | 295 | 294 | 7 | 2 | 3 | 5 | 102 | 79 | 4 | −6 | 8 | 5 | 102 | 109 | 7 | 1 | 13 | 5 | 46 | 33 | 22 |
| 9 | −6 | 5 | 0 | 20 | 1 | −3 | −1 | 5 | 147 | 128 | 5 | 3 | 3 | 5 | 198 | 232 | 4 | −5 | 8 | 5 | 278 | 291 | 10 | 2 | 13 | 5 | 187 | 212 | 11 |
| −9 | −5 | 5 | 88 | 88 | 6 | −2 | −1 | 5 | 154 | 129 | 7 | 4 | 3 | 5 | 191 | 208 | 4 | −4 | 8 | 5 | 229 | 225 | 9 | 3 | 13 | 5 | 87 | 121 | 13 |
| −8 | −5 | 5 | 118 | 116 | 6 | −1 | −1 | 5 | 172 | 147 | 7 | 5 | 3 | 5 | 240 | 269 | 7 | −3 | 8 | 5 | 157 | 129 | 10 | 4 | 13 | 5 | 87 | 132 | 12 |
| −7 | 5 | 5 | 107 | 106 | 6 | 0 | −1 | 5 | 18 | 21 | 17 | 6 | 3 | 5 | 132 | 144 | 5 | −2 | 8 | 5 | 236 | 233 | 14 | 5 | 13 | 5 | 42 | 41 | 13 |
| −6 | −5 | 5 | 149 | 146 | 4 | 1 | −1 | 5 | 353 | 366 | 10 | 7 | 3 | 5 | 99 | 119 | 7 | −1 | 8 | 5 | 77 | 71 | 12 | 6 | 13 | 5 | 48 | 37 | 10 |
| −5 | −5 | 5 | 221 | 229 | 4 | 2 | −1 | 5 | 24 | 27 | 5 | 8 | 3 | 5 | 40 | 33 | 12 | 0 | 8 | 5 | 81 | 81 | 13 | 7 | 13 | 5 | 63 | 62 | 12 |
| −4 | −5 | 5 | 105 | 98 | 3 | 3 | −1 | 5 | 291 | 301 | 6 | 9 | 3 | 5 | 62 | 75 | 7 | 1 | 8 | 5 | 22 | 36 | 21 | −7 | 14 | 5 | 51 | 21 | 16 |
| −3 | −5 | 5 | 159 | 157 | 3 | 4 | −1 | 5 | 242 | 271 | 6 | −9 | 4 | 5 | 93 | 96 | 5 | 2 | 8 | 5 | 163 | 163 | 8 | −6 | 14 | 5 | 87 | 93 | 13 |
| −2 | −5 | 5 | 225 | 230 | 4 | 5 | −1 | 5 | 45 | 36 | 4 | −8 | 4 | 5 | 55 | 52 | 5 | 3 | 8 | 5 | 111 | 129 | 6 | −5 | 14 | 5 | 50 | 54 | 20 |
| −1 | −5 | 5 | 153 | 145 | 4 | 6 | −1 | 5 | 166 | 171 | 5 | −7 | 4 | 5 | 118 | 111 | 5 | 4 | 8 | 5 | 139 | 152 | 6 | −4 | 14 | 5 | 179 | 174 | 12 |
| 0 | −5 | 5 | 83 | 80 | 2 | 7 | −1 | 5 | 44 | 55 | 9 | −6 | 4 | 5 | 387 | 398 | 9 | 5 | 8 | 5 | 40 | 42 | 17 | −3 | 14 | 5 | 164 | 139 | 11 |
| 1 | −5 | 5 | 112 | 107 | 2 | 8 | −1 | 5 | 0 | 8 | 1 | −5 | 4 | 5 | 200 | 188 | 5 | 6 | 8 | 5 | 92 | 102 | 6 | −2 | 14 | 5 | 40 | 45 | 22 |
| 2 | −5 | 5 | 197 | 199 | 3 | 9 | −1 | 5 | 56 | 43 | 5 | −4 | 4 | 5 | 171 | 175 | 5 | 7 | 8 | 5 | 0 | 16 | 1 | −1 | 14 | 5 | 153 | 149 | 8 |
| 3 | −5 | 5 | 202 | 197 | 3 | −10 | 0 | 5 | 76 | 86 | 10 | −3 | 4 | 5 | 134 | 134 | 4 | 8 | 8 | 5 | 69 | 68 | 7 | 0 | 14 | 5 | 245 | 232 | 14 |
| 4 | −5 | 5 | 113 | 110 | 2 | −9 | 0 | 5 | 207 | 218 | 8 | −2 | 4 | 5 | 129 | 155 | 5 | −9 | 9 | 5 | 62 | 72 | 9 | 1 | 14 | 5 | 127 | 117 | 12 |
| 5 | −5 | 5 | 126 | 136 | 3 | −8 | 0 | 5 | 36 | 42 | 8 | −1 | 4 | 5 | 141 | 127 | 5 | −8 | 9 | 5 | 44 | 50 | 10 | 2 | 14 | 5 | 89 | 85 | 13 |
| 6 | −5 | 5 | 149 | 155 | 3 | −7 | 0 | 5 | 158 | 159 | 5 | 0 | 4 | 5 | 154 | 213 | 10 | −7 | 9 | 5 | 128 | 133 | 6 | 3 | 14 | 5 | 164 | 177 | 11 |
| 7 | −5 | 5 | 113 | 116 | 4 | −6 | 0 | 5 | 228 | 244 | 5 | 1 | 4 | 5 | 273 | 331 | 8 | −6 | 9 | 5 | 11 | 24 | 10 | 4 | 14 | 5 | 105 | 106 | 12 |
| 8 | −5 | 5 | 25 | 23 | 8 | −5 | 0 | 5 | 202 | 203 | 4 | 2 | 4 | 5 | 122 | 128 | 4 | −5 | 9 | 5 | 121 | 130 | 7 | 5 | 14 | 5 | 67 | 92 | 10 |
| 9 | −5 | 5 | 41 | 44 | 13 | −4 | 0 | 5 | 55 | 31 | 3 | 3 | 4 | 5 | 93 | 95 | 3 | −4 | 9 | 5 | 252 | 254 | 14 | 6 | 14 | 5 | 70 | 64 | 12 |
| −10 | −4 | 5 | 64 | 66 | 9 | −3 | 0 | 5 | 331 | 306 | 8 | 4 | 4 | 5 | 102 | 108 | 3 | −3 | 9 | 5 | 182 | 157 | 11 | −6 | 15 | 5 | 0 | 39 | 1 |
| −9 | −4 | 5 | 104 | 97 | 6 | −2 | 0 | 5 | 569 | 559 | 17 | 5 | 4 | 5 | 103 | 115 | 4 | −2 | 9 | 5 | 131 | 131 | 10 | −5 | 15 | 5 | 79 | 69 | 12 |
| −8 | −4 | 5 | 60 | 52 | 7 | −1 | 0 | 5 | 233 | 244 | 9 | 6 | 4 | 5 | 92 | 96 | 8 | −1 | 9 | 5 | 102 | 77 | 11 | −4 | 15 | 5 | 180 | 181 | 12 |
| −7 | −4 | 5 | 110 | 111 | 4 | 0 | 0 | 5 | 226 | 211 | 9 | 7 | 4 | 5 | 47 | 45 | 10 | 0 | 9 | 5 | 128 | 106 | 11 | −3 | 15 | 5 | 148 | 133 | 10 |
| −6 | −4 | 5 | 385 | 398 | 8 | 1 | 0 | 5 | 86 | 2 | 6 | 8 | 4 | 5 | 78 | 77 | 7 | 1 | 9 | 5 | 98 | 101 | 12 | −2 | 15 | 5 | 134 | 118 | 11 |
| −5 | −4 | 5 | 200 | 188 | 4 | 2 | 0 | 5 | 257 | 219 | 8 | 9 | 4 | 5 | 57 | 68 | 8 | 2 | 9 | 5 | 59 | 71 | 15 | −1 | 15 | 5 | 174 | 175 | 12 |
| −4 | −4 | 5 | 176 | 175 | 4 | 3 | 0 | 5 | 20 | 9 | 8 | −9 | 5 | 5 | 91 | 87 | 8 | 3 | 9 | 5 | 233 | 246 | 14 | 0 | 15 | 5 | 235 | 206 | 13 |
| −3 | −4 | 5 | 139 | 133 | 3 | 4 | 0 | 5 | 244 | 270 | 6 | −8 | 5 | 5 | 119 | 117 | 6 | 4 | 9 | 5 | 142 | 159 | 8 | 1 | 15 | 5 | 133 | 112 | 12 |
| −2 | −4 | 5 | 149 | 154 | 4 | 5 | 0 | 5 | 23 | 28 | 8 | −7 | 5 | 5 | 110 | 105 | 5 | 5 | 9 | 5 | 119 | 136 | 7 | 2 | 15 | 5 | 112 | 123 | 13 |
| −1 | −4 | 5 | 162 | 126 | 7 | 6 | 0 | 5 | 24 | 21 | 9 | −6 | 5 | 5 | 159 | 146 | 5 | 6 | 9 | 5 | 83 | 83 | 6 | 3 | 15 | 5 | 115 | 121 | 13 |
| 0 | −4 | 5 | 205 | 213 | 7 | 7 | 0 | 5 | 149 | 165 | 7 | −5 | 5 | 5 | 222 | 230 | 6 | 7 | 9 | 5 | 80 | 96 | 5 | 4 | 15 | 5 | 0 | 31 | 1 |
| 1 | −4 | 5 | 295 | 331 | 8 | 8 | 0 | 5 | 79 | 92 | 7 | −4 | 5 | 5 | 104 | 97 | 5 | 8 | 9 | 5 | 66 | 67 | 8 | 5 | 15 | 5 | 6 | 26 | 5 |
| 2 | −4 | 5 | 135 | 128 | 3 | 9 | 0 | 5 | 31 | 12 | 9 | −3 | 5 | 5 | 163 | 157 | 5 | −8 | 10 | 5 | 144 | 150 | 7 | 6 | 15 | 5 | 43 | 9 | 19 |
| 3 | −4 | 5 | 106 | 95 | 2 | 10 | 0 | 5 | 46 | 51 | 10 | −2 | 5 | 5 | 213 | 230 | 7 | −7 | 10 | 5 | 153 | 157 | 6 | −6 | 16 | 5 | 81 | 87 | 11 |
| 4 | −4 | 5 | 110 | 109 | 2 | −10 | 1 | 5 | 150 | 147 | 9 | −1 | 5 | 5 | 146 | 145 | 4 | −6 | 10 | 5 | 79 | 87 | 8 | −5 | 16 | 5 | 91 | 79 | 10 |
| 5 | −4 | 5 | 109 | 115 | 3 | −9 | 1 | 5 | 54 | 49 | 10 | 0 | 5 | 5 | 82 | 81 | 4 | −5 | 10 | 5 | 73 | 73 | 8 | −4 | 16 | 5 | 54 | 22 | 15 |
| 6 | −4 | 5 | 81 | 96 | 4 | −8 | 1 | 5 | 89 | 84 | 5 | 1 | 5 | 5 | 107 | 107 | 4 | −4 | 10 | 5 | 62 | 46 | 13 | −3 | 16 | 5 | 161 | 158 | 11 |
| 7 | −4 | 5 | 47 | 46 | 5 | −7 | 1 | 5 | 141 | 148 | 5 | 2 | 5 | 5 | 175 | 200 | 4 | −3 | 10 | 5 | 257 | 258 | 14 | −2 | 16 | 5 | 94 | 101 | 12 |
| 8 | −4 | 5 | 72 | 77 | 4 | −6 | 1 | 5 | 111 | 117 | 5 | 3 | 5 | 5 | 177 | 197 | 4 | −2 | 10 | 5 | 36 | 38 | 19 | −1 | 16 | 5 | 206 | 215 | 13 |
| 9 | −4 | 5 | 84 | 69 | 4 | −5 | 1 | 5 | 240 | 248 | 5 | 4 | 5 | 5 | 101 | 110 | 3 | −1 | 10 | 5 | 158 | 125 | 11 | 0 | 16 | 5 | 76 | 57 | 8 |
| −10 | −3 | 5 | 68 | 82 | 9 | −4 | 1 | 5 | 295 | 294 | 6 | 5 | 5 | 5 | 120 | 136 | 6 | 0 | 10 | 5 | 108 | 106 | 11 | 1 | 16 | 5 | 111 | 77 | 12 |
| −9 | −3 | 5 | 48 | 55 | 9 | −3 | 1 | 5 | 141 | 128 | 4 | 6 | 5 | 5 | 142 | 156 | 5 | 1 | 10 | 5 | 196 | 196 | 12 | 2 | 16 | 5 | 92 | 88 | 14 |
| −8 | −3 | 5 | 47 | 48 | 8 | −2 | 1 | 5 | 147 | 130 | 5 | 7 | 5 | 5 | 114 | 117 | 7 | 2 | 10 | 5 | 63 | 52 | 13 | 4 | 16 | 5 | 100 | 109 | 12 |
| −7 | −3 | 5 | 147 | 154 | 4 | −1 | 1 | 5 | 178 | 148 | 6 | 8 | 5 | 5 | 0 | 23 | 1 | 3 | 10 | 5 | 117 | 135 | 13 | 5 | 16 | 5 | 47 | 66 | 19 |
| −6 | −3 | 5 | 258 | 273 | 6 | 0 | 1 | 5 | 14 | 22 | 13 | 9 | 5 | 5 | 34 | 44 | 12 | 4 | 10 | 5 | 86 | 115 | 8 | 6 | 16 | 5 | 58 | 62 | 14 |
| −5 | −3 | 5 | 67 | 61 | 3 | 1 | 1 | 5 | 339 | 366 | 10 | −9 | 6 | 5 | 50 | 39 | 11 | 5 | 10 | 5 | 53 | 70 | 9 | −5 | 17 | 5 | 81 | 90 | 11 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −4 | −3 | 5 | 65 | 53 | 4 | 2 | 1 | 5 | 23 | 27 | 6 | −8 | 6 | 5 | 38 | 41 | 11 | 6 | 10 | 5 | 90 | 95 | 7 | −4 | 17 | 5 | 22 | 42 | 21 |
| −3 | −3 | 5 | 163 | 150 | 5 | 3 | 1 | 5 | 286 | 301 | 7 | −7 | 6 | 5 | 103 | 113 | 6 | 7 | 10 | 5 | 15 | 18 | 14 | −3 | 17 | 5 | 57 | 64 | 15 |
| −2 | −3 | 5 | 276 | 292 | 7 | 4 | 1 | 5 | 238 | 271 | 6 | −6 | 6 | 5 | 181 | 176 | 6 | −8 | 11 | 5 | 107 | 103 | 7 | −2 | 17 | 5 | 82 | 52 | 10 |
| −1 | −3 | 5 | 195 | 206 | 9 | 5 | 1 | 5 | 39 | 36 | 5 | −5 | 6 | 5 | 189 | 191 | 6 | −7 | 11 | 5 | 115 | 109 | 8 | −1 | 17 | 5 | 97 | 87 | 10 |
| 0 | −3 | 5 | 210 | 188 | 6 | 6 | 1 | 5 | 164 | 170 | 5 | −4 | 6 | 5 | 163 | 163 | 5 | −6 | 11 | 5 | 83 | 82 | 8 | 0 | 17 | 5 | 91 | 93 | 8 |
| 1 | −3 | 5 | 157 | 136 | 5 | 7 | 1 | 5 | 37 | 55 | 12 | −3 | 6 | 5 | 216 | 216 | 7 | −4 | 11 | 5 | 81 | 67 | 12 | 1 | 17 | 5 | 107 | 105 | 12 |
| 2 | −3 | 5 | 104 | 80 | 3 | 8 | 1 | 5 | 18 | 9 | 18 | −2 | 6 | 5 | 179 | 176 | 7 | −3 | 11 | 5 | 132 | 108 | 10 | 2 | 17 | 5 | 139 | 119 | 11 |
| 3 | −3 | 5 | 219 | 233 | 4 | 9 | 1 | 5 | 51 | 43 | 8 | −1 | 6 | 5 | 0 | 42 | 1 | −2 | 11 | 5 | 221 | 224 | 13 | 3 | 17 | 5 | 41 | 55 | 33 |
| 4 | −3 | 5 | 205 | 205 | 4 | 10 | 1 | 5 | 76 | 66 | 8 | 0 | 6 | 5 | 163 | 172 | 6 | −1 | 11 | 5 | 182 | 162 | 11 | 4 | 17 | 5 | 125 | 104 | 11 |
| 5 | −3 | 5 | 260 | 269 | 5 | −10 | 2 | 5 | 64 | 75 | 12 | 1 | 6 | 5 | 63 | 84 | 5 | 0 | 11 | 5 | 100 | 104 | 12 | 5 | 17 | 5 | 67 | 72 | 13 |
| 6 | −3 | 5 | 136 | 144 | 3 | −9 | 2 | 5 | 170 | 178 | 7 | 2 | 6 | 5 | 196 | 232 | 5 | 1 | 11 | 5 | 44 | 18 | 21 | −4 | 18 | 5 | 102 | 109 | 9 |
| 7 | −3 | 5 | 109 | 119 | 5 | −8 | 2 | 5 | 67 | 67 | 5 | 3 | 6 | 5 | 127 | 140 | 6 | 2 | 11 | 5 | 154 | 144 | 12 | −3 | 18 | 5 | 49 | 57 | 13 |
| 8 | −3 | 5 | 37 | 34 | 6 | −7 | 2 | 5 | 170 | 176 | 4 | 4 | 6 | 5 | 131 | 145 | 5 | 3 | 11 | 5 | 170 | 176 | 12 | −2 | 18 | 5 | 66 | 55 | 11 |
| 9 | −3 | 5 | 70 | 75 | 4 | −6 | 2 | 5 | 184 | 181 | 6 | 5 | 6 | 5 | 51 | 56 | 6 | 4 | 11 | 5 | 139 | 173 | 8 | −1 | 18 | 5 | 67 | 78 | 11 |
| −10 | −2 | 5 | 68 | 75 | 10 | −5 | 2 | 5 | 232 | 239 | 5 | 6 | 6 | 5 | 48 | 45 | 6 | 5 | 11 | 5 | 111 | 128 | 7 | 0 | 18 | 5 | 84 | 92 | 11 |
| −9 | −2 | 5 | 172 | 177 | 6 | −4 | 2 | 5 | 188 | 182 | 4 | 7 | 6 | 5 | 38 | 46 | 11 | 6 | 11 | 5 | 71 | 76 | 8 | 1 | 18 | 5 | 72 | 42 | 8 |
| −8 | −2 | 5 | 71 | 67 | 4 | −3 | 2 | 5 | 160 | 164 | 4 | 8 | 6 | 5 | 0 | 41 | 1 | 7 | 11 | 5 | 61 | 63 | 7 | 2 | 18 | 5 | 33 | 14 | 32 |
| −7 | −2 | 5 | 167 | 176 | 5 | −2 | 2 | 5 | 173 | 167 | 6 | 9 | 6 | 5 | 0 | 19 | 1 | −8 | 12 | 5 | 35 | 49 | 34 | 3 | 18 | 5 | 55 | 22 | 15 |
| −6 | −2 | 5 | 178 | 181 | 4 | −1 | 2 | 5 | 139 | 115 | 5 | −9 | 7 | 5 | 0 | 20 | 1 | −7 | 12 | 5 | 85 | 92 | 8 | 4 | 18 | 5 | 0 | 16 | 1 |
| −5 | −2 | 5 | 240 | 240 | 5 | 0 | 2 | 5 | 286 | 324 | 8 | −8 | 7 | 5 | 68 | 60 | 7 | −6 | 12 | 5 | 57 | 57 | 17 | −2 | 19 | 5 | 115 | 139 | 9 |
| −4 | −2 | 5 | 194 | 181 | 4 | 1 | 2 | 5 | 244 | 270 | 7 | −7 | 7 | 5 | 138 | 131 | 6 | −5 | 12 | 5 | 173 | 176 | 12 | −1 | 19 | 5 | 65 | 51 | 9 |
| −3 | −2 | 5 | 166 | 164 | 4 | 2 | 2 | 5 | 302 | 322 | 7 | −6 | 7 | 5 | 36 | 41 | 13 | −3 | 12 | 5 | 232 | 248 | 14 | 0 | 19 | 5 | 111 | 104 | 9 |
| −2 | −2 | 5 | 182 | 168 | 8 | 3 | 2 | 5 | 118 | 124 | 3 | −5 | 7 | 5 | 48 | 39 | 13 | −2 | 12 | 5 | 65 | 64 | 13 | 1 | 19 | 5 | 61 | 62 | 11 |
| −1 | −2 | 5 | 133 | 114 | 6 | 4 | 2 | 5 | 220 | 239 | 5 | −4 | 7 | 5 | 250 | 259 | 10 | −1 | 12 | 5 | 37 | 51 | 16 | 2 | 19 | 5 | 62 | 27 | 7 |
| 0 | −2 | 5 | 299 | 325 | 12 | 5 | 2 | 5 | 197 | 212 | 5 | −3 | 7 | 5 | 45 | 56 | 11 | 0 | 12 | 5 | 48 | 47 | 21 | −2 | −18 | 6 | 64 | 68 | 5 |
| 1 | −2 | 5 | 274 | 271 | 8 | 6 | 2 | 5 | 122 | 124 | 4 | −2 | 7 | 5 | 137 | 139 | 11 | 1 | 12 | 5 | 39 | 40 | 30 | −1 | −18 | 6 | 127 | 131 | 13 |
| 2 | −2 | 5 | 327 | 322 | 7 | 7 | 2 | 5 | 102 | 109 | 7 | −1 | 7 | 5 | 87 | 63 | 9 | 2 | 12 | 5 | 77 | 103 | 13 | 0 | −18 | 6 | 166 | 155 | 6 |
| 3 | −2 | 5 | 124 | 125 | 3 | 8 | 2 | 5 | 67 | 65 | 7 | 0 | 7 | 5 | 90 | 86 | 8 | 3 | 12 | 5 | 12 | 16 | 12 | 1 | −18 | 6 | 111 | 104 | 5 |
| 4 | −2 | 5 | 230 | 239 | 4 | 9 | 2 | 5 | 0 | 24 | 1 | 1 | 7 | 5 | 179 | 177 | 8 | 4 | 12 | 5 | 182 | 252 | 14 | 2 | −18 | 6 | 85 | 81 | 5 |
| 5 | −2 | 5 | 199 | 212 | 5 | −9 | 3 | 5 | 51 | 55 | 7 | 2 | 7 | 5 | 92 | 96 | 6 | 5 | 12 | 5 | 82 | 93 | 8 | −3 | −17 | 6 | 107 | 105 | 3 |
| 6 | −2 | 5 | 114 | 124 | 4 | −8 | 3 | 5 | 51 | 48 | 5 | 3 | 7 | 5 | 175 | 205 | 6 | 6 | 12 | 5 | 40 | 42 | 13 | −2 | −17 | 6 | 84 | 88 | 3 |
| 7 | −2 | 5 | 92 | 108 | 6 | −7 | 3 | 5 | 152 | 154 | 5 | 4 | 7 | 5 | 88 | 92 | 6 | 7 | 12 | 5 | 36 | 8 | 28 | −1 | −17 | 6 | 110 | 95 | 3 |
| 8 | −2 | 5 | 55 | 65 | 5 | −6 | 3 | 5 | 253 | 273 | 7 | 5 | 7 | 5 | 189 | 214 | 6 | −7 | 13 | 5 | 82 | 78 | 13 | 0 | −17 | 6 | 85 | 73 | 4 |
| 9 | −2 | 5 | 21 | 24 | 14 | −5 | 3 | 5 | 62 | 62 | 5 | 6 | 7 | 5 | 87 | 93 | 6 | −6 | 13 | 5 | 41 | 36 | 29 | 1 | −17 | 6 | 150 | 141 | 5 |
| −10 | −1 | 5 | 141 | 147 | 9 | −4 | 3 | 5 | 57 | 54 | 5 | 7 | 7 | 5 | 74 | 80 | 7 | −5 | 13 | 5 | 204 | 199 | 13 | 2 | −17 | 6 | 37 | 41 | 7 |
| −9 | −1 | 5 | 45 | 49 | 9 | −3 | 3 | 5 | 156 | 151 | 4 | 8 | 7 | 5 | 98 | 100 | 8 | −4 | 13 | 5 | 243 | 238 | 14 | 3 | −17 | 6 | 112 | 101 | 4 |
| −8 | −1 | 5 | 91 | 84 | 4 | −2 | 3 | 5 | 256 | 292 | 8 | 9 | 7 | 5 | 90 | 97 | 6 | −3 | 13 | 5 | 43 | 51 | 20 | 4 | −17 | 6 | 141 | 131 | 7 |
| −4 | −16 | 6 | 73 | 74 | 4 | 4 | −10 | 6 | 106 | 98 | 6 | 4 | −5 | 6 | 43 | 42 | 3 | −3 | 0 | 6 | 28 | 34 | 8 | 8 | 4 | 6 | 60 | 55 | 8 |
| −3 | −16 | 6 | 60 | 72 | 4 | 5 | −10 | 6 | 86 | 89 | 10 | 5 | −5 | 6 | 179 | 191 | 5 | −2 | 0 | 6 | 189 | 196 | 5 | 9 | 4 | 6 | 36 | 41 | 9 |
| −2 | −16 | 6 | 102 | 101 | 4 | 6 | −10 | 6 | 22 | 53 | 21 | 6 | −5 | 6 | 83 | 74 | 3 | −1 | 0 | 6 | 118 | 138 | 4 | −9 | 5 | 6 | 91 | 94 | 8 |
| −1 | −16 | 6 | 121 | 119 | 3 | 7 | −10 | 6 | 0 | 19 | 1 | 7 | −5 | 6 | 69 | 69 | 4 | 0 | 0 | 6 | 88 | 92 | 4 | −8 | 5 | 6 | 89 | 84 | 6 |
| 0 | −16 | 6 | 59 | 57 | 4 | −8 | −9 | 6 | 71 | 77 | 8 | 8 | −5 | 6 | 20 | 24 | 20 | 1 | 0 | 6 | 82 | 94 | 4 | −7 | 5 | 6 | 134 | 137 | 5 |
| 1 | −16 | 6 | 121 | 105 | 6 | −7 | −9 | 6 | 85 | 79 | 4 | −9 | −4 | 6 | 73 | 84 | 6 | 2 | 0 | 6 | 21 | 12 | 8 | −6 | 5 | 6 | 99 | 105 | 5 |
| 2 | −16 | 6 | 61 | 54 | 6 | −6 | −9 | 6 | 144 | 158 | 4 | −8 | −4 | 6 | 59 | 52 | 7 | 3 | 0 | 6 | 182 | 196 | 5 | −5 | 5 | 6 | 101 | 96 | 5 |
| 3 | −16 | 6 | 54 | 49 | 5 | −5 | −9 | 6 | 149 | 156 | 4 | −7 | −4 | 6 | 130 | 124 | 5 | 4 | 0 | 6 | 141 | 147 | 5 | −4 | 5 | 6 | 131 | 132 | 5 |
| 4 | −16 | 6 | 59 | 60 | 4 | −4 | −9 | 6 | 35 | 24 | 7 | −6 | −4 | 6 | 139 | 153 | 4 | 5 | 0 | 6 | 276 | 297 | 7 | −3 | 5 | 6 | 187 | 180 | 5 |
| −6 | −15 | 6 | 85 | 92 | 6 | −3 | −9 | 6 | 259 | 268 | 12 | −5 | −4 | 6 | 160 | 165 | 4 | 6 | 0 | 6 | 30 | 57 | 16 | −2 | 5 | 6 | 132 | 130 | 5 |
| −5 | −15 | 6 | 75 | 76 | 5 | −2 | −9 | 6 | 129 | 131 | 5 | −4 | −4 | 6 | 69 | 70 | 3 | 7 | 0 | 6 | 25 | 33 | 18 | −1 | 5 | 6 | 124 | 130 | 4 |
| −4 | −15 | 6 | 92 | 80 | 5 | −1 | −9 | 6 | 103 | 111 | 5 | −3 | −4 | 6 | 102 | 95 | 3 | 8 | 0 | 6 | 124 | 132 | 6 | 0 | 5 | 6 | 81 | 79 | 4 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −3 | −15 | 6 | 24 | 14 | 9 | 0 | −9 | 6 | 147 | 146 | 4 | −2 | −4 | 6 | 191 | 179 | 4 | 9 | 0 | 6 | 30 | 26 | 9 | 1 | 5 | 6 | 159 | 179 | 5 |
| −2 | −15 | 6 | 21 | 24 | 10 | 1 | −9 | 6 | 38 | 33 | 5 | −1 | −4 | 6 | 56 | 43 | 3 | −9 | 1 | 6 | 55 | 64 | 9 | 2 | 5 | 6 | 167 | 195 | 5 |
| −1 | −15 | 6 | 79 | 80 | 3 | 2 | −9 | 6 | 108 | 99 | 3 | 0 | −4 | 6 | 167 | 160 | 3 | −8 | 1 | 6 | 117 | 128 | 5 | 3 | 5 | 6 | 175 | 174 | 5 |
| 0 | −15 | 6 | 166 | 159 | 5 | 3 | −9 | 6 | 52 | 40 | 4 | 1 | −4 | 6 | 100 | 90 | 3 | −7 | 1 | 6 | 153 | 162 | 6 | 4 | 5 | 6 | 37 | 43 | 5 |
| 1 | −15 | 6 | 101 | 93 | 4 | 4 | −9 | 6 | 151 | 140 | 5 | 2 | −4 | 6 | 235 | 242 | 4 | −6 | 1 | 6 | 89 | 91 | 8 | 5 | 5 | 6 | 164 | 192 | 8 |
| 2 | −15 | 6 | 59 | 48 | 4 | 5 | −9 | 6 | 49 | 12 | 15 | 3 | −4 | 6 | 109 | 102 | 3 | −5 | 1 | 6 | 161 | 155 | 5 | 6 | 5 | 6 | 79 | 74 | 8 |
| 3 | −15 | 6 | 87 | 72 | 4 | 6 | −9 | 6 | 80 | 92 | 10 | 4 | −4 | 6 | 77 | 74 | 3 | −4 | 1 | 6 | 112 | 109 | 4 | 7 | 5 | 6 | 69 | 69 | 7 |
| 4 | −15 | 6 | 121 | 121 | 5 | 7 | −9 | 6 | 29 | 33 | 29 | 5 | −4 | 6 | 221 | 233 | 5 | −3 | 1 | 6 | 184 | 186 | 4 | 8 | 5 | 6 | 4 | 23 | 4 |
| 5 | −15 | 6 | 56 | 55 | 6 | 8 | −9 | 6 | 22 | 59 | 22 | 6 | −4 | 6 | 155 | 166 | 4 | −2 | 1 | 6 | 108 | 113 | 3 | 9 | 5 | 6 | 15 | 39 | 14 |
| −6 | −14 | 6 | 26 | 9 | 11 | −8 | −8 | 6 | 90 | 111 | 5 | 7 | −4 | 6 | 104 | 97 | 4 | −1 | 1 | 6 | 55 | 12 | 4 | −9 | 6 | 6 | 82 | 77 | 12 |
| −5 | −14 | 6 | 99 | 103 | 5 | −7 | −8 | 6 | 47 | 53 | 7 | 8 | −4 | 6 | 62 | 54 | 4 | 0 | 1 | 6 | 255 | 255 | 7 | −8 | 6 | 6 | 39 | 32 | 15 |
| −4 | −14 | 6 | 133 | 128 | 6 | −6 | −8 | 6 | 105 | 117 | 5 | 9 | −4 | 6 | 37 | 41 | 12 | 1 | 1 | 6 | 146 | 156 | 4 | −7 | 6 | 6 | 152 | 168 | 5 |
| −3 | −14 | 6 | 68 | 76 | 4 | −5 | −8 | 6 | 29 | 32 | 8 | −9 | −3 | 6 | 0 | 38 | 1 | 2 | 1 | 6 | 97 | 92 | 4 | −6 | 6 | 6 | 139 | 132 | 5 |
| −2 | −14 | 6 | 28 | 13 | 8 | −4 | −8 | 6 | 140 | 150 | 4 | −8 | −3 | 6 | 28 | 36 | 16 | 3 | 1 | 6 | 57 | 55 | 5 | −5 | 6 | 6 | 271 | 278 | 7 |
| −1 | −14 | 6 | 55 | 56 | 4 | −3 | −8 | 6 | 240 | 243 | 4 | −7 | −3 | 6 | 105 | 109 | 4 | 4 | 1 | 6 | 111 | 115 | 4 | −4 | 6 | 6 | 31 | 25 | 12 |
| 0 | −14 | 6 | 139 | 149 | 5 | −2 | −8 | 6 | 73 | 11 | 7 | −6 | −3 | 6 | 277 | 286 | 7 | 5 | 1 | 6 | 121 | 137 | 4 | −3 | 6 | 6 | 246 | 264 | 6 |
| 1 | −14 | 6 | 37 | 30 | 4 | −1 | −8 | 6 | 141 | 147 | 4 | −5 | −3 | 6 | 133 | 128 | 3 | 6 | 1 | 6 | 163 | 192 | 7 | −2 | 6 | 6 | 128 | 127 | 6 |
| 2 | −14 | 6 | 71 | 64 | 4 | 0 | −8 | 6 | 91 | 85 | 3 | −4 | −3 | 6 | 208 | 210 | 4 | 7 | 1 | 6 | 65 | 77 | 8 | −1 | 6 | 6 | 101 | 112 | 6 |
| 3 | −14 | 6 | 31 | 28 | 8 | 1 | −8 | 6 | 118 | 108 | 3 | −3 | −3 | 6 | 256 | 258 | 5 | 8 | 1 | 6 | 12 | 17 | 11 | 0 | 6 | 6 | 24 | 22 | 23 |
| 4 | −14 | 6 | 57 | 62 | 5 | 2 | −8 | 6 | 186 | 185 | 4 | −2 | −3 | 6 | 237 | 230 | 5 | 9 | 1 | 6 | 112 | 103 | 5 | 1 | 6 | 6 | 68 | 70 | 7 |
| 5 | −14 | 6 | 108 | 101 | 5 | 3 | −8 | 6 | 138 | 119 | 5 | −1 | −3 | 6 | 106 | 102 | 3 | −9 | 2 | 6 | 130 | 142 | 7 | 2 | 6 | 6 | 67 | 77 | 6 |
| −6 | −13 | 6 | 68 | 76 | 6 | 4 | −8 | 6 | 85 | 79 | 4 | 0 | −3 | 6 | 169 | 151 | 4 | −8 | 2 | 6 | 145 | 155 | 5 | 3 | 6 | 6 | 62 | 67 | 6 |
| −5 | −13 | 6 | 163 | 152 | 8 | 5 | −8 | 6 | 116 | 123 | 5 | 1 | −3 | 6 | 176 | 188 | 3 | −7 | 2 | 6 | 96 | 108 | 5 | 4 | 6 | 6 | 92 | 97 | 8 |
| −4 | −13 | 6 | 110 | 93 | 7 | 6 | −8 | 6 | 35 | 37 | 12 | 2 | −3 | 6 | 105 | 87 | 3 | −6 | 2 | 6 | 119 | 131 | 6 | 5 | 6 | 6 | 172 | 176 | 9 |
| −3 | −13 | 6 | 45 | 54 | 6 | 7 | −8 | 6 | 66 | 51 | 11 | 3 | −3 | 6 | 150 | 149 | 3 | −5 | 2 | 6 | 42 | 41 | 5 | 6 | 6 | 6 | 161 | 187 | 7 |
| −2 | −13 | 6 | 8 | 1 | 7 | 8 | −8 | 6 | 49 | 64 | 12 | 4 | −3 | 6 | 149 | 139 | 4 | −4 | 2 | 6 | 49 | 42 | 5 | 7 | 6 | 6 | 44 | 39 | 10 |
| −1 | −13 | 6 | 99 | 105 | 4 | −9 | −7 | 6 | 100 | 93 | 7 | 5 | −3 | 6 | 175 | 197 | 4 | −3 | 2 | 6 | 54 | 54 | 4 | 8 | 6 | 6 | 50 | 59 | 8 |
| 0 | −13 | 6 | 105 | 101 | 4 | −8 | −7 | 6 | 4 | 53 | 6 | 6 | −3 | 6 | 44 | 42 | 6 | −2 | 2 | 6 | 146 | 141 | 4 | −9 | 7 | 6 | 99 | 92 | 11 |
| 1 | −13 | 6 | 158 | 172 | 7 | −7 | −7 | 6 | 65 | 56 | 6 | 7 | −3 | 6 | 25 | 29 | 10 | −1 | 2 | 6 | 187 | 193 | 4 | −8 | 7 | 6 | 67 | 52 | 9 |
| 2 | −13 | 6 | 73 | 64 | 4 | −6 | −7 | 6 | 265 | 280 | 7 | 8 | −3 | 6 | 84 | 77 | 4 | 0 | 2 | 6 | 52 | 40 | 4 | −7 | 7 | 6 | 58 | 57 | 8 |
| 3 | −13 | 6 | 111 | 107 | 6 | −5 | −7 | 6 | 49 | 46 | 6 | 9 | −3 | 6 | 46 | 42 | 4 | 1 | 2 | 6 | 72 | 75 | 3 | −6 | 7 | 6 | 262 | 281 | 8 |
| 4 | −13 | 6 | 127 | 125 | 6 | −4 | −7 | 6 | 82 | 75 | 3 | −9 | −2 | 6 | 128 | 144 | 6 | 2 | 2 | 6 | 212 | 243 | 6 | −5 | 7 | 6 | 55 | 47 | 8 |
| 5 | −13 | 6 | 35 | 18 | 12 | −3 | −7 | 6 | 111 | 108 | 3 | −8 | −2 | 6 | 151 | 155 | 5 | 3 | 2 | 6 | 120 | 125 | 4 | −4 | 7 | 6 | 75 | 76 | 6 |
| 6 | −13 | 6 | 54 | 76 | 8 | −2 | −7 | 6 | 168 | 174 | 3 | −7 | −2 | 6 | 96 | 108 | 4 | 4 | 2 | 6 | 131 | 150 | 5 | −3 | 7 | 6 | 105 | 108 | 6 |
| −7 | −12 | 6 | 39 | 47 | 9 | −1 | −7 | 6 | 63 | 46 | 2 | −6 | −2 | 6 | 139 | 132 | 4 | 5 | 2 | 6 | 63 | 73 | 5 | −2 | 7 | 6 | 170 | 174 | 7 |
| −6 | −12 | 6 | 65 | 62 | 8 | 0 | −7 | 6 | 163 | 157 | 4 | −5 | −2 | 6 | 45 | 41 | 6 | 6 | 2 | 6 | 0 | 9 | 1 | −1 | 7 | 6 | 68 | 46 | 7 |
| −5 | −12 | 6 | 148 | 143 | 8 | 1 | −7 | 6 | 158 | 160 | 4 | −4 | −2 | 6 | 53 | 42 | 5 | 7 | 2 | 6 | 51 | 45 | 9 | 0 | 7 | 6 | 162 | 157 | 7 |
| −4 | −12 | 6 | 81 | 73 | 7 | 2 | −7 | 6 | 36 | 31 | 6 | −3 | −2 | 6 | 51 | 54 | 5 | 8 | 2 | 6 | 78 | 74 | 7 | 1 | 7 | 6 | 148 | 160 | 6 |
| −3 | −12 | 6 | 56 | 58 | 5 | 3 | −7 | 6 | 35 | 38 | 5 | −2 | −2 | 6 | 152 | 141 | 4 | 9 | 2 | 6 | 26 | 22 | 14 | 2 | 7 | 6 | 40 | 31 | 10 |
| −2 | −12 | 6 | 197 | 253 | 7 | 4 | −7 | 6 | 108 | 105 | 4 | −1 | −2 | 6 | 195 | 193 | 5 | −9 | 3 | 6 | 20 | 38 | 19 | 3 | 7 | 6 | 40 | 38 | 10 |
| −1 | −12 | 6 | 146 | 169 | 5 | 5 | −7 | 6 | 86 | 94 | 5 | 0 | −2 | 6 | 47 | 40 | 4 | −8 | 3 | 6 | 35 | 36 | 11 | 4 | 7 | 6 | 92 | 105 | 6 |
| 0 | −12 | 6 | 104 | 99 | 4 | 6 | −7 | 6 | 23 | 16 | 15 | 1 | −2 | 6 | 83 | 74 | 4 | −7 | 3 | 6 | 97 | 110 | 6 | 5 | 7 | 6 | 80 | 94 | 5 |
| 1 | −12 | 6 | 94 | 74 | 4 | 7 | −7 | 6 | 18 | 9 | 17 | 2 | −2 | 6 | 230 | 243 | 4 | −6 | 3 | 6 | 287 | 285 | 7 | 6 | 7 | 6 | 26 | 15 | 26 |
| 2 | −12 | 6 | 148 | 101 | 8 | 8 | −7 | 6 | 30 | 25 | 30 | 3 | −2 | 6 | 126 | 125 | 4 | −5 | 3 | 6 | 125 | 128 | 5 | 7 | 7 | 6 | 0 | 9 | 1 |
| 3 | −12 | 6 | 171 | 151 | 10 | −9 | −6 | 6 | 61 | 77 | 6 | 4 | −2 | 6 | 141 | 150 | 4 | −4 | 3 | 6 | 197 | 209 | 5 | 8 | 7 | 6 | 23 | 25 | 22 |
| 4 | −12 | 6 | 178 | 171 | 7 | −8 | −6 | 6 | 43 | 32 | 8 | 5 | −2 | 6 | 71 | 73 | 4 | −3 | 3 | 6 | 242 | 258 | 5 | −8 | 8 | 6 | 114 | 111 | 7 |
| 5 | −12 | 6 | 47 | 29 | 9 | −7 | −6 | 6 | 152 | 169 | 5 | 6 | −2 | 6 | 17 | 9 | 16 | −2 | 3 | 6 | 222 | 229 | 5 | −7 | 8 | 6 | 48 | 53 | 9 |
| 6 | −12 | 6 | 44 | 65 | 12 | −6 | −6 | 6 | 134 | 131 | 5 | 7 | −2 | 6 | 50 | 46 | 5 | −1 | 3 | 6 | 110 | 102 | 3 | −6 | 8 | 6 | 108 | 117 | 6 |
| 7 | −12 | 6 | 0 | 1 | 1 | −5 | −6 | 6 | 275 | 278 | 6 | 8 | −2 | 6 | 82 | 75 | 4 | 0 | 3 | 6 | 155 | 150 | 4 | −5 | 8 | 6 | 33 | 32 | 14 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −7 | −11 | 6 | 95 | 97 | 7 | −4 | −6 | 6 | 21 | 24 | 8 | 9 | −2 | 6 | 30 | 22 | 10 | 1 | 3 | 6 | 158 | 187 | 4 | −4 | 8 | 6 | 134 | 150 | 6 |
| −6 | −11 | 6 | 131 | 137 | 8 | −3 | −6 | 6 | 252 | 264 | 4 | −9 | −1 | 6 | 65 | 65 | 8 | 2 | 3 | 6 | 89 | 87 | 5 | −3 | 8 | 6 | 239 | 243 | 14 |
| −5 | −11 | 6 | 100 | 109 | 8 | −2 | −6 | 6 | 132 | 128 | 3 | −8 | −1 | 6 | 114 | 128 | 5 | 3 | 3 | 6 | 139 | 149 | 4 | −2 | 8 | 6 | 33 | 12 | 32 |
| −4 | −11 | 6 | 151 | 197 | 8 | −1 | −6 | 6 | 104 | 112 | 2 | −7 | −1 | 6 | 166 | 162 | 5 | 4 | 3 | 6 | 130 | 138 | 5 | −1 | 8 | 6 | 154 | 148 | 7 |
| −3 | −11 | 6 | 69 | 82 | 5 | 0 | −6 | 6 | 19 | 22 | 6 | −6 | −1 | 6 | 74 | 91 | 6 | 5 | 3 | 6 | 171 | 198 | 5 | 0 | 8 | 6 | 73 | 85 | 7 |
| −2 | −11 | 6 | 59 | 56 | 5 | 1 | −6 | 6 | 76 | 71 | 2 | −5 | −1 | 6 | 163 | 155 | 4 | 6 | 3 | 6 | 31 | 43 | 18 | 1 | 8 | 6 | 114 | 108 | 6 |
| −1 | −11 | 6 | 196 | 223 | 7 | 2 | −6 | 6 | 77 | 78 | 2 | −4 | −1 | 6 | 110 | 108 | 5 | 7 | 3 | 6 | 29 | 29 | 18 | 2 | 8 | 6 | 147 | 187 | 8 |
| 0 | −11 | 6 | 94 | 91 | 4 | 3 | −6 | 6 | 7 | 67 | 2 | −3 | −1 | 6 | 186 | 187 | 5 | 8 | 3 | 6 | 87 | 77 | 7 | 3 | 8 | 6 | 125 | 119 | 5 |
| 1 | −11 | 6 | 152 | 131 | 4 | 4 | −6 | 6 | 97 | 97 | 2 | −2 | −1 | 6 | 108 | 112 | 4 | 9 | 3 | 6 | 42 | 42 | 9 | 4 | 8 | 6 | 68 | 79 | 7 |
| 2 | −11 | 6 | 151 | 153 | 8 | 5 | −6 | 6 | 182 | 176 | 4 | −1 | −1 | 6 | 58 | 12 | 4 | −9 | 4 | 6 | 80 | 83 | 8 | 5 | 8 | 6 | 118 | 123 | 8 |
| 3 | −11 | 6 | 116 | 98 | 5 | 6 | −6 | 6 | 169 | 187 | 4 | 0 | −1 | 6 | 269 | 266 | 7 | −8 | 4 | 6 | 62 | 52 | 6 | 6 | 8 | 6 | 39 | 37 | 16 |
| 4 | −11 | 6 | 90 | 88 | 6 | 7 | −6 | 6 | 34 | 39 | 8 | 1 | −1 | 6 | 153 | 156 | 4 | −7 | 4 | 6 | 120 | 124 | 5 | 7 | 8 | 6 | 45 | 51 | 22 |
| 5 | −11 | 6 | 79 | 88 | 7 | 8 | −6 | 6 | 67 | 58 | 8 | 2 | −1 | 6 | 99 | 92 | 4 | −6 | 4 | 6 | 146 | 152 | 5 | 8 | 8 | 6 | 38 | 64 | 20 |
| 6 | −11 | 6 | 105 | 118 | 9 | −9 | −5 | 6 | 91 | 94 | 5 | 3 | −1 | 6 | 53 | 55 | 4 | −5 | 4 | 6 | 161 | 166 | 5 | −8 | 9 | 6 | 82 | 7 | 8 |
| 7 | −11 | 6 | 17 | 25 | 17 | −8 | −5 | 6 | 89 | 84 | 6 | 4 | −1 | 6 | 115 | 115 | 4 | −4 | 4 | 6 | 67 | 69 | 5 | −7 | 9 | 6 | 87 | 77 | 6 |
| −8 | −10 | 6 | 57 | 74 | 7 | −7 | −5 | 6 | 141 | 138 | 6 | 5 | −1 | 6 | 116 | 137 | 4 | −3 | 4 | 6 | 98 | 95 | 4 | −6 | 9 | 6 | 141 | 158 | 6 |
| −7 | −10 | 6 | 7 | 26 | 6 | −6 | −5 | 6 | 99 | 105 | 4 | 6 | −1 | 6 | 167 | 192 | 7 | −2 | 4 | 6 | 186 | 180 | 4 | −5 | 9 | 6 | 144 | 156 | 6 |
| −6 | −10 | 6 | 107 | 90 | 8 | −5 | −5 | 6 | 37 | 96 | 4 | 7 | −1 | 6 | 79 | 77 | 6 | −1 | 4 | 6 | 54 | 42 | 4 | −4 | 9 | 6 | 36 | 24 | 17 |
| −5 | −10 | 6 | 71 | 91 | 9 | −4 | −5 | 6 | 128 | 132 | 3 | 8 | −1 | 6 | 20 | 16 | 19 | 0 | 4 | 6 | 151 | 161 | 4 | −3 | 9 | 6 | 245 | 268 | 14 |
| −3 | −10 | 6 | 120 | 124 | 8 | −3 | −5 | 6 | 189 | 179 | 4 | 9 | −1 | 6 | 113 | 103 | 4 | 1 | 4 | 6 | 94 | 89 | 3 | −2 | 9 | 6 | 139 | 131 | 10 |
| −2 | −10 | 6 | 80 | 83 | 5 | −2 | −5 | 6 | 138 | 129 | 3 | −9 | 0 | 6 | 36 | 29 | 15 | 2 | 4 | 6 | 196 | 241 | 5 | −1 | 9 | 6 | 126 | 112 | 7 |
| −1 | −10 | 6 | 133 | 135 | 5 | −1 | −5 | 6 | 133 | 131 | 3 | −8 | 0 | 6 | 37 | 22 | 8 | 3 | 4 | 6 | 101 | 102 | 3 | 0 | 9 | 6 | 157 | 146 | 11 |
| 0 | −10 | 6 | 62 | 61 | 4 | 0 | −5 | 6 | 96 | 79 | 2 | −7 | 0 | 6 | 59 | 68 | 6 | 4 | 4 | 6 | 70 | 74 | 4 | 1 | 9 | 6 | 44 | 33 | 14 |
| 1 | −10 | 6 | 92 | 80 | 4 | 1 | −5 | 6 | 186 | 179 | 3 | −6 | 0 | 6 | 302 | 357 | 9 | 5 | 4 | 6 | 202 | 233 | 6 | 2 | 9 | 6 | 82 | 100 | 7 |
| 2 | −10 | 6 | 123 | 124 | 4 | 2 | −5 | 6 | 208 | 196 | 3 | −5 | 0 | 6 | 157 | 160 | 5 | 6 | 4 | 6 | 144 | 166 | 7 | 3 | 9 | 6 | 51 | 40 | 9 |
| 3 | −10 | 6 | 160 | 163 | 5 | 3 | −5 | 6 | 195 | 174 | 3 | −4 | 0 | 6 | 23 | 19 | 14 | 7 | 4 | 6 | 92 | 97 | 7 | 4 | 9 | 6 | 136 | 140 | 6 |
| 5 | 9 | 6 | 18 | 12 | 17 | −4 | 16 | 6 | 75 | 74 | 11 | 0 | −11 | 7 | 103 | 95 | 5 | −4 | −5 | 7 | 247 | 252 | 5 | −3 | 0 | 7 | 46 | 22 | 7 |
| 6 | 9 | 6 | 80 | 92 | 6 | −3 | 16 | 6 | 52 | 72 | 15 | 1 | −11 | 7 | 101 | 91 | 5 | −3 | −5 | 7 | 210 | 206 | 4 | −2 | 0 | 7 | 209 | 196 | 6 |
| 7 | 9 | 6 | 34 | 33 | 17 | −2 | 16 | 6 | 119 | 102 | 9 | 2 | −11 | 7 | 143 | 131 | 6 | −2 | −5 | 7 | 127 | 127 | 3 | −1 | 0 | 7 | 174 | 142 | 6 |
| 8 | 9 | 6 | 60 | 59 | 12 | −1 | 16 | 6 | 130 | 120 | 10 | 3 | −11 | 7 | 43 | 22 | 8 | −1 | −5 | 7 | 197 | 188 | 4 | 0 | 0 | 7 | 67 | 64 | 4 |
| −8 | 10 | 6 | 64 | 74 | 9 | 0 | 16 | 6 | 62 | 58 | 12 | 4 | −11 | 7 | 71 | 61 | 7 | 0 | −5 | 7 | 177 | 174 | 3 | 1 | 0 | 7 | 421 | 438 | 10 |
| −7 | 10 | 6 | 26 | 27 | 26 | 1 | 16 | 6 | 134 | 104 | 7 | 5 | −11 | 7 | 36 | 18 | 16 | 1 | −5 | 7 | 106 | 90 | 2 | 2 | 0 | 7 | 171 | 172 | 5 |
| −6 | 10 | 6 | 85 | 90 | 6 | 2 | 16 | 6 | 59 | 54 | 17 | 6 | −11 | 7 | 58 | 69 | 8 | 2 | −5 | 7 | 224 | 212 | 4 | 3 | 0 | 7 | 158 | 166 | 5 |
| −5 | 10 | 6 | 67 | 91 | 9 | 4 | 16 | 6 | 57 | 60 | 16 | −7 | −10 | 7 | 42 | 57 | 10 | 3 | −5 | 7 | 175 | 153 | 4 | 4 | 0 | 7 | 58 | 53 | 9 |
| −4 | 10 | 6 | 166 | 208 | 8 | 5 | 16 | 6 | 89 | 63 | 10 | −6 | −10 | 7 | 51 | 53 | 10 | 4 | −5 | 7 | 182 | 171 | 4 | 5 | 0 | 7 | 40 | 54 | 11 |
| −3 | 10 | 6 | 116 | 124 | 11 | −4 | 17 | 6 | 63 | 71 | 10 | −5 | −10 | 7 | 87 | 81 | 8 | 5 | −5 | 7 | 20 | 22 | 16 | 6 | 0 | 7 | 0 | 13 | 1 |
| −2 | 10 | 6 | 87 | 84 | 11 | −3 | 17 | 6 | 116 | 104 | 9 | −4 | −10 | 7 | 106 | 108 | 7 | 6 | −5 | 7 | 41 | 44 | 8 | 7 | 0 | 7 | 52 | 51 | 6 |
| −1 | 10 | 6 | 151 | 136 | 7 | −2 | 17 | 6 | 90 | 88 | 10 | −3 | −10 | 7 | 168 | 187 | 9 | 7 | −5 | 7 | 36 | 34 | 8 | 8 | 0 | 7 | 32 | 36 | 8 |
| 0 | 10 | 6 | 24 | 60 | 23 | −1 | 17 | 6 | 115 | 95 | 10 | −2 | −10 | 7 | 95 | 87 | 7 | 8 | −5 | 7 | 56 | 53 | 8 | −8 | 1 | 7 | 113 | 112 | 7 |
| 1 | 10 | 6 | 75 | 80 | 9 | 0 | 17 | 6 | 76 | 73 | 11 | −1 | −10 | 7 | 57 | 23 | 5 | −8 | −4 | 7 | 54 | 61 | 7 | −7 | 1 | 7 | 38 | 47 | 10 |
| 2 | 10 | 6 | 111 | 123 | 8 | 1 | 17 | 6 | 135 | 140 | 10 | 0 | −10 | 7 | 43 | 39 | 5 | −7 | −4 | 7 | 97 | 97 | 5 | −6 | 1 | 7 | 44 | 26 | 11 |
| 3 | 10 | 6 | 140 | 163 | 8 | 2 | 17 | 6 | 69 | 40 | 7 | 1 | −10 | 7 | 153 | 152 | 5 | −6 | −4 | 7 | 67 | 60 | 4 | −5 | 1 | 7 | 92 | 102 | 8 |
| 4 | 10 | 6 | 92 | 97 | 0 | 3 | 17 | 6 | 127 | 100 | 10 | 2 | −10 | 7 | 164 | 162 | 9 | −5 | −4 | 7 | 38 | 34 | 7 | −4 | 1 | 7 | 145 | 136 | 5 |
| 5 | 10 | 6 | 86 | 89 | 7 | 4 | 17 | 6 | 137 | 130 | 10 | 3 | −10 | 7 | 143 | 131 | 9 | −4 | −4 | 7 | 119 | 121 | 4 | −3 | 1 | 7 | 167 | 164 | 5 |
| 6 | 10 | 6 | 56 | 53 | 6 | −2 | 18 | 6 | 62 | 69 | 11 | 4 | −10 | 7 | 32 | 10 | 32 | −3 | −4 | 7 | 99 | 91 | 3 | −2 | 1 | 7 | 302 | 296 | 8 |
| 7 | 10 | 6 | 33 | 19 | 19 | −1 | 18 | 6 | 151 | 131 | 9 | 5 | −10 | 7 | 66 | 82 | 10 | −2 | −4 | 7 | 84 | 83 | 4 | −1 | 1 | 7 | 179 | 184 | 5 |
| −7 | 11 | 6 | 98 | 97 | 7 | 0 | 18 | 6 | 154 | 155 | 10 | 6 | −10 | 7 | 34 | 22 | 18 | −1 | −4 | 7 | 120 | 92 | 4 | 0 | 1 | 7 | 127 | 116 | 4 |
| −6 | 11 | 6 | 132 | 137 | 6 | 1 | 18 | 6 | 113 | 104 | 9 | −7 | −9 | 7 | 57 | 52 | 8 | 0 | −4 | 7 | 173 | 161 | 4 | 1 | 1 | 7 | 106 | 95 | 4 |
| −5 | 11 | 6 | 88 | 109 | 8 | 2 | 18 | 6 | 80 | 82 | 10 | −6 | −9 | 7 | 29 | 26 | 28 | 1 | −4 | 7 | 256 | 255 | 5 | 2 | 1 | 7 | 194 | 191 | 5 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −4 | 11 | 6 | 151 | 197 | 10 | −2 | −17 | 7 | 87 | 79 | 4 | −5 | −9 | 7 | 164 | 177 | 9 | 2 | −4 | 7 | 272 | 266 | 5 | 3 | 1 | 7 | 154 | 164 | 5 |
| −3 | 11 | 6 | 58 | 83 | 13 | −1 | −17 | 7 | 64 | 52 | 8 | −4 | −9 | 7 | 30 | 10 | 22 | 3 | −4 | 7 | 174 | 166 | 4 | 4 | 1 | 7 | 130 | 143 | 7 |
| −2 | 11 | 6 | 61 | 56 | 12 | 0 | −17 | 7 | 21 | 27 | 20 | −3 | −9 | 7 | 179 | 179 | 8 | 4 | −4 | 7 | 28 | 21 | 10 | 5 | 1 | 7 | 72 | 84 | 7 |
| −1 | 11 | 6 | 212 | 223 | 8 | 1 | −17 | 7 | 127 | 129 | 6 | −2 | −9 | 7 | 166 | 161 | 9 | 5 | −4 | 7 | 48 | 57 | 5 | 6 | 1 | 7 | 23 | 29 | 23 |
| 0 | 11 | 6 | 81 | 91 | 14 | 2 | −17 | 7 | 110 | 119 | 12 | −1 | −9 | 7 | 164 | 169 | 5 | 6 | −4 | 7 | 147 | 142 | 4 | 7 | 1 | 7 | 130 | 124 | 6 |
| 1 | 11 | 6 | 146 | 131 | 12 | −3 | −16 | 7 | 72 | 73 | 3 | 0 | −9 | 7 | 141 | 128 | 4 | 7 | −4 | 7 | 66 | 60 | 4 | 8 | 1 | 7 | 66 | 61 | 5 |
| 2 | 11 | 6 | 116 | 153 | 8 | −2 | −16 | 7 | 167 | 168 | 5 | 1 | −9 | 7 | 89 | 68 | 3 | 8 | −4 | 7 | 59 | 52 | 8 | −8 | 2 | 7 | 63 | 62 | 9 |
| 3 | 11 | 6 | 85 | 97 | 8 | −1 | −16 | 7 | 59 | 55 | 3 | 2 | −9 | 7 | 180 | 164 | 5 | −8 | −3 | 7 | 52 | 58 | 7 | −7 | 2 | 7 | 43 | 47 | 9 |
| 4 | 11 | 6 | 77 | 88 | 8 | 0 | −16 | 7 | 128 | 116 | 4 | 3 | −9 | 7 | 32 | 26 | 9 | −7 | −3 | 7 | 114 | 111 | 4 | −6 | 2 | 7 | 109 | 116 | 7 |
| 5 | 11 | 6 | 84 | 88 | 7 | 1 | −16 | 7 | 75 | 80 | 5 | 4 | −9 | 7 | 137 | 129 | 6 | −6 | −3 | 7 | 130 | 140 | 5 | −5 | 2 | 7 | 173 | 184 | 11 |
| 6 | 11 | 6 | 105 | 119 | 8 | 2 | −16 | 7 | 95 | 68 | 5 | 5 | −9 | 7 | 61 | 56 | 12 | −5 | −3 | 7 | 131 | 135 | 5 | −4 | 2 | 7 | 226 | 235 | 6 |
| 7 | 11 | 6 | 37 | 25 | 30 | 3 | −16 | 7 | 35 | 30 | 7 | 6 | −9 | 7 | 26 | 7 | 26 | −4 | −3 | 7 | 159 | 162 | 5 | −3 | 2 | 7 | 159 | 152 | 5 |
| −7 | 12 | 6 | 27 | 48 | 27 | −4 | −15 | 7 | 117 | 113 | 5 | 7 | −9 | 7 | 0 | 10 | 1 | −3 | −3 | 7 | 362 | 378 | 8 | −2 | 2 | 7 | 124 | 122 | 5 |
| −6 | 12 | 6 | 69 | 62 | 9 | −3 | −15 | 7 | 104 | 114 | 4 | −7 | −8 | 7 | 109 | 113 | 8 | −2 | −3 | 7 | 219 | 214 | 5 | −1 | 2 | 7 | 190 | 200 | 5 |
| −5 | 12 | 6 | 138 | 142 | 11 | −2 | −15 | 7 | 48 | 48 | 4 | −6 | −8 | 7 | 82 | 95 | 5 | −1 | −3 | 7 | 81 | 81 | 4 | 0 | 2 | 7 | 99 | 103 | 4 |
| −4 | 12 | 6 | 85 | 74 | 12 | −1 | −15 | 7 | 67 | 41 | 4 | −5 | −8 | 7 | 67 | 74 | 6 | 0 | −3 | 7 | 154 | 141 | 4 | 1 | 2 | 7 | 147 | 142 | 5 |
| −3 | 12 | 6 | 58 | 58 | 12 | 0 | −15 | 7 | 38 | 31 | 5 | −4 | −8 | 7 | 95 | 98 | 5 | 1 | −3 | 7 | 39 | 25 | 5 | 2 | 2 | 7 | 162 | 166 | 5 |
| −2 | 12 | 6 | 218 | 253 | 12 | 1 | −15 | 7 | 165 | 52 | 6 | −3 | −8 | 7 | 98 | 88 | 6 | 2 | −3 | 7 | 155 | 148 | 4 | 3 | 2 | 7 | 140 | 153 | 5 |
| −1 | 12 | 6 | 151 | 169 | 10 | 2 | −15 | 7 | 68 | 62 | 4 | −2 | −8 | 7 | 55 | 44 | 4 | 3 | −3 | 7 | 57 | 43 | 4 | 4 | 2 | 7 | 154 | 165 | 7 |
| 0 | 12 | 6 | 87 | 98 | 12 | 3 | −15 | 7 | 46 | 31 | 6 | −1 | −8 | 7 | 209 | 226 | 6 | 4 | −3 | 7 | 31 | 23 | 11 | 5 | 2 | 7 | 108 | 127 | 7 |
| 1 | 12 | 6 | 73 | 74 | 13 | 4 | −15 | 7 | 149 | 134 | 6 | 0 | −8 | 7 | 212 | 209 | 5 | 5 | −3 | 7 | 162 | 167 | 5 | 6 | 2 | 7 | 92 | 93 | 7 |
| 2 | 12 | 6 | 89 | 101 | 9 | −5 | −14 | 7 | 101 | 111 | 5 | 1 | −8 | 7 | 150 | 132 | 5 | 6 | −3 | 7 | 52 | 58 | 5 | 7 | 2 | 7 | 44 | 28 | 9 |
| 3 | 12 | 6 | 104 | 151 | 8 | −4 | −14 | 7 | 115 | 114 | 6 | 2 | −8 | 7 | 124 | 123 | 3 | 7 | −3 | 7 | 61 | 58 | 4 | 8 | 2 | 7 | 89 | 83 | 5 |
| 4 | 12 | 6 | 168 | 171 | 12 | −3 | −14 | 7 | 56 | 66 | 5 | 3 | −8 | 7 | 154 | 155 | 5 | 8 | −3 | 7 | 48 | 40 | 10 | −8 | 3 | 7 | 55 | 58 | 10 |
| 5 | 12 | 6 | 45 | 29 | 10 | −2 | −14 | 7 | 33 | 13 | 6 | 4 | −8 | 7 | 18 | 25 | 17 | −8 | −2 | 7 | 62 | 62 | 8 | −7 | 3 | 7 | 123 | 111 | 7 |
| 6 | 12 | 6 | 65 | 65 | 12 | −1 | −14 | 7 | 255 | 263 | 8 | 5 | −8 | 7 | 110 | 121 | 6 | −7 | −2 | 7 | 53 | 47 | 6 | −6 | 3 | 7 | 123 | 140 | 8 |
| −7 | 13 | 6 | 106 | 105 | 10 | 0 | −14 | 7 | 24 | 22 | 8 | 6 | −8 | 7 | 132 | 130 | 8 | −6 | −2 | 7 | 113 | 115 | 5 | −5 | 3 | 7 | 131 | 135 | 8 |
| −6 | 13 | 6 | 80 | 77 | 12 | 1 | −14 | 7 | 164 | 123 | 6 | 7 | −8 | 7 | 61 | 82 | 10 | −5 | −2 | 7 | 161 | 185 | 6 | −4 | 3 | 7 | 163 | 163 | 6 |
| −5 | 13 | 6 | 146 | 152 | 12 | 2 | −14 | 7 | 130 | 126 | 5 | −8 | −7 | 7 | 69 | 72 | 8 | −4 | −2 | 7 | 225 | 235 | 6 | −3 | 3 | 7 | 366 | 379 | 7 |
| −4 | 13 | 6 | 109 | 93 | 11 | 3 | −14 | 7 | 82 | 74 | 5 | −7 | −7 | 7 | 101 | 99 | 4 | −3 | −2 | 7 | 162 | 152 | 5 | −2 | 3 | 7 | 210 | 213 | 4 |
| −3 | 13 | 6 | 59 | 54 | 12 | 4 | −14 | 7 | 47 | 32 | 7 | −6 | −7 | 7 | 95 | 93 | 5 | −2 | −2 | 7 | 134 | 123 | 6 | −1 | 3 | 7 | 73 | 81 | 3 |
| −2 | 13 | 6 | 0 | 1 | 1 | 5 | −14 | 7 | 41 | 35 | 10 | −5 | −7 | 7 | 144 | 150 | 4 | −1 | −2 | 7 | 196 | 199 | 5 | 0 | 3 | 7 | 136 | 141 | 5 |
| −1 | 13 | 6 | 98 | 105 | 10 | −6 | −13 | 7 | 94 | 113 | 6 | −4 | −7 | 7 | 74 | 79 | 3 | 0 | −2 | 7 | 111 | 102 | 4 | 1 | 3 | 7 | 40 | 25 | 6 |
| 0 | 13 | 6 | 96 | 102 | 7 | −5 | −13 | 7 | 74 | 58 | 6 | −3 | −7 | 7 | 211 | 215 | 4 | 1 | −2 | 7 | 157 | 142 | 4 | 2 | 3 | 7 | 144 | 147 | 5 |
| 1 | 13 | 6 | 131 | 172 | 12 | −4 | −13 | 7 | 43 | 47 | 9 | −2 | −7 | 7 | 161 | 153 | 3 | 2 | −2 | 7 | 171 | 167 | 4 | 3 | 3 | 7 | 42 | 43 | 6 |
| 2 | 13 | 6 | 54 | 64 | 16 | −3 | −13 | 7 | 124 | 126 | 7 | −1 | −7 | 7 | 226 | 240 | 6 | 3 | −2 | 7 | 155 | 153 | 4 | 4 | 3 | 7 | 23 | 24 | 22 |
| 3 | 13 | 6 | 85 | 106 | 8 | −2 | −13 | 7 | 157 | 171 | 6 | 0 | −7 | 7 | 208 | 190 | 6 | 4 | −2 | 7 | 163 | 165 | 5 | 5 | 3 | 7 | 154 | 167 | 7 |
| 4 | 13 | 6 | 127 | 126 | 8 | −1 | −13 | 7 | 71 | 52 | 4 | 1 | −7 | 7 | 79 | 38 | 4 | 5 | −2 | 7 | 122 | 126 | 5 | 6 | 3 | 7 | 41 | 58 | 11 |
| 5 | 13 | 6 | 25 | 18 | 24 | 0 | −13 | 7 | 125 | 122 | 5 | 2 | −7 | 7 | 208 | 204 | 5 | 6 | −2 | 7 | 74 | 92 | 5 | 7 | 3 | 7 | 55 | 58 | 8 |
| 6 | 13 | 6 | 53 | 76 | 15 | 1 | −13 | 7 | 148 | 160 | 6 | 3 | −7 | 7 | 46 | 43 | 7 | 7 | −2 | 7 | 32 | 28 | 7 | 8 | 3 | 7 | 42 | 41 | 8 |
| −6 | 14 | 6 | 10 | 9 | 9 | 2 | −13 | 7 | 60 | 34 | 5 | 4 | −7 | 7 | 66 | 67 | 5 | 8 | −2 | 7 | 91 | 83 | 4 | −8 | 4 | 7 | 53 | 61 | 10 |
| −5 | 14 | 6 | 109 | 104 | 10 | 3 | −13 | 7 | 76 | 67 | 6 | 5 | −7 | 7 | 81 | 74 | 5 | −9 | −1 | 7 | 60 | 96 | 10 | −7 | 4 | 7 | 105 | 98 | 8 |
| −4 | 14 | 6 | 132 | 127 | 10 | 4 | −13 | 7 | 137 | 120 | 6 | 6 | −7 | 7 | 25 | 38 | 12 | −8 | −1 | 7 | 113 | 112 | 7 | −6 | 4 | 7 | 60 | 61 | 8 |
| −3 | 14 | 6 | 62 | 76 | 13 | 5 | −13 | 7 | 111 | 104 | 6 | 7 | −7 | 7 | 13 | 9 | 13 | −7 | −1 | 7 | 49 | 47 | 7 | −5 | 4 | 7 | 31 | 34 | 18 |
| −2 | 14 | 6 | 29 | 13 | 29 | −6 | −12 | 7 | 45 | 55 | 8 | −8 | −6 | 7 | 32 | 45 | 9 | −6 | −1 | 7 | 13 | 26 | 12 | −4 | 4 | 7 | 123 | 121 | 5 |
| −1 | 14 | 6 | 48 | 57 | 15 | −5 | −12 | 7 | 157 | 165 | 8 | −7 | −6 | 7 | 38 | 41 | 9 | −5 | −1 | 7 | 91 | 101 | 5 | −3 | 4 | 7 | 93 | 91 | 5 |
| 0 | 14 | 6 | 158 | 148 | 7 | −4 | −12 | 7 | 58 | 64 | 9 | −6 | −6 | 7 | 190 | 195 | 6 | −4 | −1 | 7 | 139 | 136 | 5 | −2 | 4 | 7 | 77 | 84 | 4 |
| 1 | 14 | 6 | 48 | 31 | 20 | −3 | −12 | 7 | 55 | 50 | 8 | −5 | −6 | 7 | 77 | 71 | 3 | −3 | −1 | 7 | 164 | 165 | 5 | −1 | 4 | 7 | 113 | 91 | 4 |
| 2 | 14 | 6 | 51 | 64 | 18 | −2 | −12 | 7 | 43 | 56 | 6 | −4 | −6 | 7 | 65 | 65 | 4 | −2 | −1 | 7 | 307 | 296 | 8 | 0 | 4 | 7 | 160 | 161 | 4 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 3 | 14 | 6 | 40 | 29 | 16 | −1 | −12 | 7 | 145 | 145 | 5 | −3 | −6 | 7 | 209 | 203 | 4 | −1 | −1 | 7 | 183 | 184 | 5 | 1 | 4 | 7 | 233 | 255 | 5 |
| 4 | 14 | 6 | 41 | 61 | 14 | 0 | −12 | 7 | 14 | 11 | 13 | −2 | −6 | 7 | 175 | 178 | 3 | 0 | −1 | 7 | 130 | 117 | 4 | 2 | 4 | 7 | 237 | 265 | 7 |
| 6 | 14 | 6 | 62 | 54 | 13 | 1 | −12 | 7 | 89 | 59 | 5 | −1 | −6 | 7 | 57 | 46 | 3 | 1 | −1 | 7 | 106 | 95 | 4 | 3 | 4 | 7 | 151 | 166 | 5 |
| −5 | 15 | 6 | 84 | 75 | 11 | 2 | −12 | 7 | 38 | 26 | 7 | 0 | −6 | 7 | 98 | 106 | 3 | 2 | −1 | 7 | 198 | 191 | 5 | 4 | 4 | 7 | 0 | 21 | 1 |
| −4 | 15 | 6 | 94 | 80 | 11 | 3 | −12 | 7 | 265 | 240 | 14 | 1 | −6 | 7 | 75 | 65 | 2 | 3 | −1 | 7 | 166 | 164 | 4 | 5 | 4 | 7 | 33 | 57 | 17 |
| −3 | 15 | 6 | 0 | 14 | 1 | 4 | −12 | 7 | 77 | 77 | 6 | 2 | −6 | 7 | 87 | 78 | 4 | 4 | −1 | 7 | 133 | 143 | 5 | 6 | 4 | 7 | 134 | 142 | 10 |
| −2 | 15 | 6 | 50 | 23 | 14 | 5 | −12 | 7 | 62 | 82 | 9 | 3 | −6 | 7 | 123 | 116 | 5 | 5 | −1 | 7 | 86 | 84 | 6 | 7 | 4 | 7 | 65 | 60 | 7 |
| −1 | 15 | 6 | 80 | 80 | 11 | 6 | −12 | 7 | 0 | 27 | 1 | 4 | −6 | 7 | 54 | 62 | 6 | 6 | −1 | 7 | 23 | 29 | 17 | 8 | 4 | 7 | 54 | 52 | 7 |
| 0 | 15 | 6 | 165 | 159 | 8 | −7 | −11 | 7 | 66 | 73 | 7 | 5 | −6 | 7 | 180 | 182 | 10 | 7 | −1 | 7 | 128 | 124 | 5 | −8 | 5 | 7 | 73 | 74 | 8 |
| 1 | 15 | 6 | 106 | 93 | 12 | −6 | −11 | 7 | 100 | 107 | 7 | 6 | −6 | 7 | 107 | 109 | 8 | 8 | −1 | 7 | 60 | 61 | 4 | −7 | 5 | 7 | 103 | 108 | 8 |
| 2 | 15 | 6 | 46 | 49 | 24 | −5 | −11 | 7 | 68 | 60 | 8 | 7 | −6 | 7 | 38 | 35 | 12 | −8 | 0 | 7 | 39 | 21 | 13 | −6 | 5 | 7 | 95 | 97 | 7 |
| 3 | 15 | 6 | 90 | 73 | 13 | −4 | −11 | 7 | 242 | 248 | 11 | −8 | −5 | 7 | 68 | 74 | 5 | −7 | 0 | 7 | 38 | 40 | 9 | −5 | 5 | 7 | 224 | 218 | 6 |
| 4 | 15 | 6 | 129 | 121 | 10 | −3 | −11 | 7 | 127 | 143 | 8 | −7 | −5 | 7 | 102 | 108 | 5 | −6 | 0 | 7 | 53 | 53 | 7 | −4 | 5 | 7 | 243 | 252 | 6 |
| 5 | 15 | 6 | 63 | 55 | 13 | −2 | −11 | 7 | 134 | 135 | 5 | −6 | −5 | 7 | 95 | 97 | 4 | −5 | 0 | 7 | 96 | 103 | 7 | −3 | 5 | 7 | 214 | 207 | 7 |
| −5 | 16 | 6 | 156 | 166 | 10 | −1 | −11 | 7 | 142 | 136 | 5 | −5 | −5 | 7 | 221 | 219 | 5 | −4 | 0 | 7 | 73 | 69 | 6 | −2 | 5 | 7 | 141 | 126 | 7 |
| −1 | 5 | 7 | 191 | 188 | 6 | 6 | 10 | 7 | 0 | 21 | 1 | 1 | −13 | 8 | 159 | 156 | 6 | 5 | −6 | 8 | 99 | 90 | 8 | 1 | 0 | 8 | 64 | 61 | 5 |
| 0 | 5 | 7 | 160 | 174 | 5 | −7 | 11 | 7 | 64 | 73 | 11 | 2 | −13 | 8 | 115 | 106 | 5 | 6 | −6 | 8 | 42 | 43 | 11 | 2 | 0 | 8 | 276 | 218 | 10 |
| 1 | 5 | 7 | 102 | 90 | 4 | −6 | 11 | 7 | 103 | 107 | 9 | 3 | −13 | 8 | 58 | 44 | 6 | −7 | −5 | 8 | 72 | 85 | 5 | 3 | 0 | 8 | 133 | 145 | 7 |
| 2 | 5 | 7 | 189 | 212 | 5 | −5 | 11 | 7 | 74 | 60 | 8 | 4 | −13 | 8 | 57 | 48 | 9 | −6 | −5 | 8 | 57 | 52 | 5 | 4 | 0 | 8 | 179 | 181 | 7 |
| 3 | 5 | 7 | 143 | 153 | 5 | −4 | 11 | 7 | 239 | 249 | 13 | −5 | −12 | 8 | 27 | 25 | 18 | −5 | −5 | 8 | 26 | 35 | 9 | 5 | 0 | 8 | 23 | 7 | 22 |
| 4 | 5 | 7 | 158 | 170 | 8 | −3 | 11 | 7 | 124 | 143 | 7 | −4 | −12 | 8 | 130 | 135 | 7 | −4 | −5 | 8 | 95 | 88 | 4 | 6 | 0 | 8 | 15 | 6 | 14 |
| 5 | 5 | 7 | 29 | 21 | 21 | −2 | 11 | 7 | 113 | 135 | 7 | −3 | −12 | 8 | 62 | 65 | 7 | −3 | −5 | 8 | 76 | 74 | 4 | 7 | 0 | 8 | 106 | 97 | 4 |
| 6 | 5 | 7 | 35 | 44 | 14 | −1 | 11 | 7 | 121 | 136 | 8 | −2 | −12 | 8 | 180 | 189 | 8 | −2 | −5 | 8 | 49 | 41 | 6 | −8 | 1 | 8 | 110 | 127 | 6 |
| 7 | 5 | 7 | 32 | 34 | 13 | 0 | 11 | 7 | 88 | 94 | 8 | −1 | −12 | 8 | 77 | 71 | 4 | −1 | −5 | 8 | 355 | 371 | 8 | −7 | 1 | 8 | 98 | 80 | 7 |
| 8 | 5 | 7 | 58 | 52 | 6 | 1 | 11 | 7 | 79 | 92 | 9 | 0 | −12 | 8 | 77 | 76 | 5 | 0 | −5 | 8 | 248 | 246 | 6 | −6 | 1 | 8 | 68 | 63 | 6 |
| −8 | 6 | 7 | 52 | 45 | 11 | 2 | 11 | 7 | 151 | 131 | 11 | 1 | −12 | 8 | 95 | 86 | 5 | 1 | −5 | 8 | 82 | 51 | 6 | −5 | 1 | 8 | 175 | 185 | 7 |
| −7 | 6 | 7 | 32 | 40 | 16 | 3 | 11 | 7 | 40 | 22 | 13 | 2 | −12 | 8 | 43 | 11 | 7 | 2 | −5 | 8 | 75 | 77 | 4 | −4 | 1 | 8 | 175 | 183 | 7 |
| −6 | 6 | 7 | 187 | 195 | 5 | 4 | 11 | 7 | 76 | 62 | 7 | 3 | −12 | 8 | 89 | 92 | 6 | 3 | −5 | 8 | 95 | 99 | 4 | −3 | 1 | 8 | 63 | 43 | 8 |
| −5 | 6 | 7 | 77 | 71 | 5 | 5 | 11 | 7 | 28 | 18 | 28 | −5 | −11 | 8 | 127 | 137 | 7 | 4 | −5 | 8 | 51 | 47 | 7 | −2 | 1 | 8 | 189 | 189 | 7 |
| −4 | 6 | 7 | 70 | 65 | 6 | 6 | 11 | 7 | 52 | 69 | 16 | −4 | −11 | 8 | 119 | 137 | 7 | 5 | −5 | 8 | 58 | 53 | 6 | −1 | 1 | 8 | 269 | 238 | 8 |
| −3 | 6 | 7 | 204 | 203 | 6 | −6 | 12 | 7 | 56 | 55 | 11 | −3 | −11 | 8 | 45 | 33 | 10 | 6 | −5 | 8 | 40 | 29 | 7 | 0 | 1 | 8 | 73 | 72 | 5 |
| −2 | 6 | 7 | 172 | 179 | 5 | −5 | 12 | 7 | 161 | 164 | 10 | −2 | −11 | 8 | 69 | 70 | 8 | 7 | −5 | 8 | 9 | 25 | 9 | 1 | 1 | 8 | 339 | 334 | 9 |
| −1 | 6 | 7 | 46 | 47 | 9 | −4 | 12 | 7 | 38 | 64 | 16 | −1 | −11 | 8 | 183 | 189 | 6 | −7 | −4 | 8 | 66 | 58 | 6 | 2 | 1 | 8 | 86 | 73 | 7 |
| 0 | 6 | 7 | 90 | 106 | 5 | −3 | 12 | 7 | 45 | 50 | 29 | 0 | −11 | 8 | 186 | 176 | 7 | −6 | −4 | 8 | 0 | 2 | 1 | 3 | 1 | 8 | 135 | 130 | 7 |
| 1 | 6 | 7 | 68 | 65 | 5 | −2 | 12 | 7 | 37 | 56 | 14 | 1 | −11 | 8 | 157 | 138 | 6 | −5 | −4 | 8 | 58 | 60 | 5 | 4 | 1 | 8 | 44 | 43 | 9 |
| 2 | 6 | 7 | 84 | 78 | 6 | −1 | 12 | 7 | 122 | 144 | 8 | 2 | −11 | 8 | 163 | 153 | 6 | −4 | −4 | 8 | 80 | 73 | 4 | 5 | 1 | 8 | 34 | 24 | 11 |
| 3 | 6 | 7 | 117 | 116 | 5 | 0 | 12 | 7 | 25 | 11 | 24 | 3 | −11 | 8 | 156 | 138 | 6 | −3 | −4 | 8 | 225 | 231 | 6 | 6 | 1 | 8 | 41 | 35 | 9 |
| 4 | 6 | 7 | 56 | 62 | 18 | 1 | 12 | 7 | 67 | 59 | 7 | 4 | −11 | 8 | 53 | 39 | 10 | −2 | −4 | 8 | 151 | 142 | 4 | 7 | 1 | 8 | 40 | 46 | 6 |
| 5 | 6 | 7 | 161 | 181 | 11 | 2 | 12 | 7 | 0 | 25 | 1 | −6 | −10 | 8 | 59 | 58 | 7 | −1 | −4 | 8 | 83 | 90 | 4 | −8 | 2 | 8 | 88 | 103 | 6 |
| 6 | 6 | 7 | 89 | 108 | 7 | 3 | 12 | 7 | 184 | 239 | 11 | −5 | −10 | 8 | 18 | 29 | 17 | 0 | −4 | 8 | 203 | 194 | 6 | −7 | 2 | 8 | 38 | 28 | 13 |
| 7 | 6 | 7 | 26 | 35 | 16 | 4 | 12 | 7 | 74 | 77 | 7 | −4 | −10 | 8 | 57 | 57 | 9 | 1 | −4 | 8 | 34 | 34 | 8 | −6 | 2 | 8 | 90 | 91 | 7 |
| 8 | 6 | 7 | 56 | 57 | 10 | 5 | 12 | 7 | 89 | 82 | 10 | −3 | −10 | 8 | 160 | 163 | 8 | 2 | −4 | 8 | 107 | 114 | 4 | −5 | 2 | 8 | 71 | 81 | 8 |
| −8 | 7 | 7 | 65 | 71 | 15 | −6 | 13 | 7 | 106 | 114 | 8 | −2 | −10 | 8 | 86 | 75 | 7 | 3 | −4 | 8 | 35 | 28 | 10 | −4 | 2 | 8 | 96 | 97 | 7 |
| −7 | 7 | 7 | 106 | 99 | 7 | −5 | 13 | 7 | 64 | 58 | 12 | −1 | −10 | 8 | 137 | 136 | 8 | 4 | −4 | 8 | 77 | 82 | 4 | −3 | 2 | 8 | 139 | 127 | 7 |
| −6 | 7 | 7 | 98 | 93 | 5 | −4 | 13 | 7 | 22 | 48 | 21 | 0 | −10 | 8 | 229 | 207 | 7 | 5 | −4 | 8 | 106 | 98 | 4 | −2 | 2 | 8 | 108 | 107 | 7 |
| −5 | 7 | 7 | 149 | 150 | 5 | −3 | 13 | 7 | 128 | 126 | 9 | 1 | −10 | 8 | 113 | 104 | 5 | 6 | −4 | 8 | 27 | 26 | 13 | −1 | 2 | 8 | 127 | 128 | 5 |
| −4 | 7 | 7 | 81 | 78 | 5 | −2 | 13 | 7 | 156 | 171 | 11 | 2 | −10 | 8 | 191 | 166 | 10 | 7 | −4 | 8 | 24 | 13 | 23 | 0 | 2 | 8 | 317 | 300 | 8 |
| −3 | 7 | 7 | 204 | 214 | 6 | −1 | 13 | 7 | 73 | 52 | 8 | 3 | −10 | 8 | 94 | 92 | 9 | −7 | −3 | 8 | 48 | 45 | 8 | 1 | 2 | 8 | 131 | 127 | 5 |
| −2 | 7 | 7 | 165 | 153 | 6 | 0 | 13 | 7 | 110 | 122 | 7 | 4 | −10 | 8 | 76 | 77 | 9 | −6 | −3 | 8 | 90 | 96 | 4 | 2 | 2 | 8 | 94 | 93 | 7 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −1 | 7 | 7 | 231 | 239 | 8 | 1 | 13 | 7 | 150 | 159 | 6 | 5 | −10 | 8 | 51 | 55 | 11 | −5 | −3 | 8 | 73 | 79 | 5 | 3 | 2 | 8 | 110 | 105 | 7 |
| 0 | 7 | 7 | 206 | 190 | 8 | 2 | 13 | 7 | 50 | 35 | 12 | −6 | −9 | 8 | 109 | 120 | 7 | −4 | −3 | 8 | 103 | 103 | 5 | 4 | 2 | 8 | 71 | 74 | 7 |
| 1 | 7 | 7 | 69 | 37 | 6 | 3 | 13 | 7 | 81 | 68 | 13 | −5 | −9 | 8 | 41 | 43 | 12 | −3 | −3 | 8 | 47 | 41 | 6 | 5 | 2 | 8 | 22 | 25 | 21 |
| 2 | 7 | 7 | 212 | 204 | 8 | 4 | 13 | 7 | 139 | 120 | 10 | −4 | −9 | 8 | 129 | 123 | 7 | −2 | −3 | 8 | 165 | 135 | 6 | 6 | 2 | 8 | 41 | 47 | 9 |
| 3 | 7 | 7 | 43 | 43 | 9 | −5 | 14 | 7 | 95 | 112 | 9 | −3 | −9 | 8 | 84 | 81 | 8 | −1 | −3 | 8 | 92 | 88 | 5 | 7 | 2 | 8 | 92 | 86 | 5 |
| 4 | 7 | 7 | 54 | 67 | 12 | −4 | 14 | 7 | 112 | 114 | 9 | −2 | −9 | 8 | 33 | 21 | 19 | 0 | −3 | 8 | 66 | 65 | 6 | −8 | 3 | 8 | 17 | 33 | 16 |
| 5 | 7 | 7 | 73 | 75 | 13 | −3 | 14 | 7 | 67 | 66 | 9 | −1 | −9 | 8 | 111 | 100 | 6 | 1 | −3 | 8 | 112 | 98 | 5 | −7 | 3 | 8 | 47 | 44 | 10 |
| 6 | 7 | 7 | 46 | 38 | 18 | −2 | 14 | 7 | 18 | 13 | 18 | 0 | −9 | 8 | 106 | 93 | 6 | 2 | −3 | 8 | 272 | 238 | 8 | −6 | 3 | 8 | 95 | 95 | 7 |
| 7 | 7 | 7 | 44 | 9 | 15 | −1 | 14 | 7 | 254 | 263 | 14 | 1 | −9 | 8 | 51 | 22 | 7 | 3 | −3 | 8 | 90 | 77 | 5 | −5 | 3 | 8 | 74 | 79 | 8 |
| −8 | 8 | 7 | 54 | 23 | 15 | 0 | 14 | 7 | 37 | 22 | 15 | 2 | −9 | 8 | 36 | 24 | 11 | 4 | −3 | 8 | 62 | 62 | 5 | −4 | 3 | 8 | 106 | 102 | 7 |
| −7 | 8 | 7 | 111 | 112 | 7 | 1 | 14 | 7 | 154 | 123 | 8 | 3 | −9 | 8 | 55 | 53 | 7 | 5 | −3 | 8 | 93 | 83 | 3 | −3 | 3 | 8 | 56 | 41 | 10 |
| −6 | 8 | 7 | 92 | 95 | 5 | 2 | 14 | 7 | 128 | 125 | 7 | 4 | −9 | 8 | 136 | 122 | 8 | 6 | −3 | 8 | 70 | 57 | 3 | −2 | 3 | 8 | 161 | 136 | 11 |
| −5 | 8 | 7 | 82 | 75 | 5 | 3 | 14 | 7 | 66 | 74 | 8 | 5 | −9 | 8 | 27 | 53 | 27 | 7 | −3 | 8 | 23 | 17 | 23 | −1 | 3 | 8 | 93 | 87 | 5 |
| −4 | 8 | 7 | 94 | 98 | 5 | 4 | 14 | 7 | 34 | 32 | 34 | 6 | −9 | 8 | 0 | 8 | 1 | −7 | −2 | 8 | 26 | 28 | 25 | 0 | 3 | 8 | 64 | 65 | 6 |
| −3 | 8 | 7 | 96 | 89 | 6 | 5 | 14 | 7 | 37 | 35 | 32 | −6 | −8 | 8 | 73 | −76 | 8 | −6 | −2 | 8 | 96 | 91 | 5 | 1 | 3 | 8 | 107 | 98 | 7 |
| −2 | 8 | 7 | 47 | 45 | 10 | −4 | 15 | 7 | 104 | 112 | 10 | −5 | −8 | 8 | 122 | 142 | 8 | −5 | −2 | 8 | 83 | 81 | 5 | 2 | 3 | 8 | 241 | 238 | 9 |
| −1 | 8 | 7 | 201 | 226 | 6 | −3 | 15 | 7 | 119 | 115 | 10 | −4 | −8 | 8 | 171 | 178 | 9 | −4 | −2 | 8 | 81 | 97 | 5 | 3 | 3 | 8 | 78 | 77 | 8 |
| 0 | 8 | 7 | 196 | 209 | 7 | −2 | 15 | 7 | 57 | 48 | 12 | −3 | −8 | 8 | 123 | 117 | 6 | −3 | −2 | 8 | 121 | 127 | 5 | 4 | 3 | 8 | 53 | 62 | 9 |
| 1 | 8 | 7 | 125 | 132 | 8 | −1 | 15 | 7 | 74 | 41 | 11 | −2 | −8 | 8 | 155 | 161 | 6 | −2 | −2 | 8 | 101 | 107 | 6 | 5 | 3 | 8 | 83 | 84 | 7 |
| 2 | 8 | 7 | 116 | 123 | 6 | 0 | 15 | 7 | 48 | 32 | 11 | −1 | −8 | 8 | 147 | 134 | 5 | −1 | −2 | 8 | 129 | 128 | 5 | 6 | 3 | 8 | 57 | 57 | 7 |
| 3 | 8 | 7 | 149 | 155 | 8 | 1 | 15 | 7 | 155 | 153 | 10 | 0 | −8 | 8 | 168 | 160 | 5 | 0 | −2 | 8 | 334 | 299 | 7 | 7 | 3 | 8 | 15 | 16 | 14 |
| 4 | 8 | 7 | 31 | 25 | 12 | 2 | 15 | 7 | 60 | 62 | 9 | 1 | −8 | 8 | 126 | 108 | 4 | 1 | −2 | 8 | 148 | 127 | 5 | −7 | 4 | 8 | 58 | 58 | 9 |
| 5 | 8 | 7 | 104 | 120 | 8 | 3 | 15 | 7 | 51 | 31 | 18 | 2 | −8 | 8 | 75 | 70 | 5 | 2 | −2 | 8 | 92 | 92 | 6 | −6 | 4 | 8 | 33 | 3 | 17 |
| 6 | 8 | 7 | 99 | 130 | 11 | 4 | 15 | 7 | 154 | 134 | 10 | 3 | −8 | 8 | 76 | 57 | 4 | 3 | −2 | 8 | 102 | 104 | 5 | −5 | 4 | 8 | 58 | 60 | 9 |
| 7 | 8 | 7 | 59 | 82 | 12 | −3 | 16 | 7 | 78 | 73 | 10 | 4 | −8 | 8 | 110 | 101 | 6 | 4 | −2 | 8 | 74 | 74 | 5 | −4 | 4 | 8 | 87 | 72 | 7 |
| −7 | 9 | 7 | 69 | 53 | 7 | −2 | 16 | 7 | 163 | 168 | 11 | 5 | −8 | 8 | 0 | 22 | 1 | 5 | −2 | 8 | 21 | 25 | 21 | −3 | 4 | 8 | 229 | 230 | 8 |
| −6 | 9 | 7 | 31 | 26 | 13 | −1 | 16 | 7 | 76 | 56 | 10 | 6 | −8 | 8 | 0 | 34 | 1 | 6 | −2 | 8 | 53 | 48 | 5 | −2 | 4 | 8 | 154 | 141 | 7 |
| −5 | 9 | 7 | 170 | 178 | 6 | 0 | 16 | 7 | 120 | 116 | 10 | −7 | −7 | 8 | 15 | 35 | 14 | 7 | −2 | 8 | 103 | 86 | 4 | −1 | 4 | 8 | 97 | 90 | 7 |
| −4 | 9 | 7 | 30 | 10 | 29 | 1 | 16 | 7 | 76 | 79 | 10 | −6 | −7 | 8 | 39 | 46 | 14 | −8 | −1 | 8 | 119 | 127 | 7 | 0 | 4 | 8 | 183 | 195 | 7 |
| −3 | 9 | 7 | 160 | 179 | 8 | 2 | 16 | 7 | 84 | 68 | 9 | −5 | −7 | 8 | 98 | 122 | 8 | −7 | −1 | 8 | 79 | 80 | 7 | 1 | 4 | 8 | 41 | 34 | 11 |
| −2 | 9 | 7 | 164 | 160 | 11 | 3 | 16 | 7 | 22 | 30 | 22 | −4 | −7 | 8 | 115 | 107 | 6 | −6 | −1 | 8 | 68 | 63 | 5 | 2 | 4 | 8 | 118 | 114 | 7 |
| −1 | 9 | 7 | 160 | 169 | 6 | −2 | 17 | 7 | 78 | 79 | 10 | −3 | −7 | 8 | 127 | 132 | 4 | −5 | −1 | 8 | 158 | 186 | 6 | 3 | 4 | 8 | 42 | 27 | 12 |
| 0 | 9 | 7 | 139 | 129 | 5 | −1 | 17 | 7 | 65 | 52 | 10 | −2 | −7 | 8 | 77 | 68 | 7 | −4 | −1 | 8 | 142 | 184 | 7 | 4 | 4 | 8 | 70 | 83 | 7 |
| 1 | 9 | 7 | 68 | 68 | 8 | 0 | 17 | 7 | 46 | 27 | 13 | −1 | −7 | 8 | 87 | 55 | 5 | −3 | −1 | 8 | 53 | 44 | 9 | 5 | 4 | 8 | 90 | 99 | 7 |
| 2 | 9 | 7 | 179 | 164 | 9 | 1 | 17 | 7 | 132 | 129 | 9 | 0 | −7 | 8 | 80 | 83 | 5 | −2 | −1 | 8 | 187 | 188 | 7 | 6 | 4 | 8 | 0 | 26 | 1 |
| 3 | 9 | 7 | 23 | 25 | 22 | 2 | 17 | 7 | 125 | 119 | 8 | 1 | −7 | 8 | 197 | 196 | 6 | −1 | −1 | 8 | 275 | 239 | 7 | 7 | 4 | 8 | 12 | 14 | 12 |
| 4 | 9 | 7 | 142 | 129 | 11 | −2 | −15 | 8 | 43 | 43 | 7 | 2 | −7 | 8 | 210 | 206 | 6 | 0 | −1 | 8 | 69 | 72 | 5 | −7 | 5 | 8 | 80 | 85 | 7 |
| 5 | 9 | 7 | 53 | 56 | 11 | −1 | −15 | 8 | 56 | 46 | 4 | 3 | −7 | 8 | 142 | 133 | 7 | 1 | −1 | 8 | 353 | 334 | 9 | −6 | 5 | 8 | 69 | 52 | 8 |
| 6 | 9 | 7 | 20 | 7 | 19 | 0 | −15 | 8 | 61 | 61 | 4 | 4 | −7 | 8 | 57 | 55 | 5 | 2 | −1 | 8 | 86 | 73 | 6 | −5 | 5 | 8 | 43 | 35 | 12 |
| 7 | 9 | 7 | 0 | 10 | 1 | 1 | −15 | 8 | 70 | 67 | 4 | 5 | −7 | 8 | 40 | 30 | 6 | 3 | −1 | 8 | 128 | 130 | 5 | −4 | 5 | 8 | 93 | 88 | 7 |
| −7 | 10 | 7 | 65 | 59 | 7 | 2 | −15 | 8 | 66 | 66 | 6 | 6 | −7 | 8 | 44 | 32 | 8 | 4 | −1 | 8 | 41 | 43 | 8 | −3 | 5 | 8 | 76 | 74 | 8 |
| −6 | 10 | 7 | 49 | 53 | 7 | −3 | −14 | 8 | 118 | 120 | 7 | −7 | −6 | 8 | 58 | 68 | 9 | 5 | −1 | 8 | 33 | 23 | 10 | −2 | 5 | 8 | 55 | 40 | 9 |
| −5 | 10 | 7 | 80 | 80 | 7 | −2 | −14 | 8 | 42 | 35 | 5 | −6 | −6 | 8 | 53 | 61 | 5 | 6 | −1 | 8 | 43 | 35 | 6 | −1 | 5 | 8 | 363 | 372 | 12 |
| −4 | 10 | 7 | 97 | 108 | 8 | −1 | −14 | 8 | 81 | 89 | 4 | −5 | −6 | 8 | 41 | 46 | 5 | 7 | −1 | 8 | 50 | 45 | 5 | 0 | 5 | 8 | 254 | 246 | 9 |
| −3 | 10 | 7 | 163 | 187 | 8 | 0 | −14 | 8 | 162 | 144 | 6 | −4 | −6 | 8 | 85 | 80 | 3 | −8 | 0 | 8 | 0 | 25 | 1 | 1 | 5 | 8 | 105 | 52 | 11 |
| −2 | 10 | 7 | 76 | 86 | 8 | 1 | −14 | 8 | 55 | 46 | 5 | −3 | −6 | 8 | 136 | 133 | 4 | −7 | 0 | 8 | 42 | 37 | 12 | 2 | 5 | 8 | 74 | 76 | 8 |
| −1 | 10 | 7 | 54 | 21 | 10 | 2 | −14 | 8 | 113 | 107 | 5 | −2 | −6 | 8 | 122 | 118 | 3 | −6 | 0 | 8 | 151 | 168 | 7 | 3 | 5 | 8 | 97 | 99 | 7 |
| 0 | 10 | 7 | 45 | 39 | 10 | 3 | −14 | 8 | 71 | 54 | 5 | −1 | −6 | 8 | 195 | 198 | 5 | −5 | 0 | 8 | 0 | 19 | 1 | 4 | 5 | 8 | 49 | 47 | 9 |
| 1 | 10 | 7 | 162 | 152 | 9 | −4 | −13 | 8 | 107 | 109 | 6 | 0 | −6 | 8 | 246 | 234 | 7 | −4 | 0 | 8 | 68 | 85 | 8 | 5 | 5 | 8 | 44 | 53 | 9 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 2 | 10 | 7 | 116 | 162 | 7 | −3 | −13 | 8 | 188 | 195 | 9 | 1 | −6 | 8 | 95 | 85 | 6 | −3 | 0 | 8 | 155 | 145 | 7 | 6 | 5 | 8 | 26 | 30 | 16 |
| 3 | 10 | 7 | 89 | 131 | 7 | −2 | −13 | 8 | 130 | 136 | 5 | 2 | −6 | 8 | 88 | 86 | 6 | −2 | 0 | 8 | 467 | 461 | 15 | 7 | 5 | 8 | 5 | 25 | 5 |
| 4 | 10 | 7 | 32 | 11 | 13 | −1 | −13 | 8 | 79 | 50 | 4 | 3 | −6 | 8 | 72 | 74 | 9 | −1 | 0 | 8 | 64 | 67 | 5 | −7 | 6 | 8 | 66 | 68 | 8 |
| 5 | 10 | 7 | 65 | 82 | 10 | 0 | −13 | 8 | 139 | 122 | 5 | 4 | −6 | 8 | 55 | 50 | 7 | 0 | 0 | 8 | 39 | 56 | 8 | −6 | 6 | 8 | 78 | 60 | 7 |
| −5 | 6 | 8 | 40 | 46 | 13 | −1 | 13 | 8 | 61 | 50 | 8 | −2 | −5 | 9 | 30 | 25 | 8 | −5 | 2 | 9 | 35 | 22 | 13 | −2 | 9 | 9 | 121 | 123 | 7 |
| −4 | 6 | 8 | 84 | 81 | 6 | 0 | 13 | 8 | 140 | 122 | 10 | −1 | −5 | 9 | 52 | 39 | 5 | −4 | 2 | 9 | 111 | 90 | 7 | −1 | 9 | 9 | 105 | 99 | 7 |
| −3 | 6 | 8 | 137 | 133 | 6 | 1 | 13 | 8 | 157 | 155 | 10 | 0 | −5 | 9 | 52 | 45 | 7 | −3 | 2 | 9 | 194 | 199 | 8 | 0 | 9 | 9 | 143 | 144 | 12 |
| −2 | 6 | 8 | 122 | 117 | 4 | 2 | 13 | 8 | 114 | 106 | 9 | 1 | −5 | 9 | 115 | 118 | 6 | −2 | 2 | 9 | 69 | 73 | 8 | 1 | 9 | 9 | 95 | 89 | 12 |
| −1 | 6 | 8 | 194 | 198 | 6 | 3 | 13 | 8 | 56 | 44 | 10 | 2 | −5 | 9 | 36 | 29 | 11 | −1 | 2 | 9 | 183 | 181 | 12 | 2 | 9 | 9 | 111 | 104 | 10 |
| 0 | 6 | 8 | 238 | 234 | 9 | −3 | 14 | 8 | 122 | 120 | 8 | 3 | −5 | 9 | 48 | 60 | 8 | 0 | 2 | 9 | 102 | 100 | 8 | 3 | 9 | 9 | 88 | 83 | 11 |
| 1 | 6 | 8 | 93 | 85 | 7 | −2 | 14 | 8 | 47 | 35 | 12 | 4 | −5 | 9 | 59 | 56 | 6 | 1 | 2 | 9 | 50 | 57 | 15 | 4 | 9 | 9 | 73 | 69 | 10 |
| 2 | 6 | 8 | 72 | 87 | 14 | −1 | 14 | 8 | 92 | 89 | 9 | −6 | −4 | 9 | 202 | 228 | 11 | 2 | 2 | 9 | 60 | 55 | 8 | −3 | 10 | 9 | 84 | 81 | 9 |
| 3 | 6 | 8 | 53 | 75 | 16 | 0 | 14 | 8 | 158 | 144 | 10 | −5 | −4 | 9 | 103 | 106 | 5 | 3 | 2 | 9 | 138 | 105 | 7 | −2 | 10 | 9 | 19 | 48 | 18 |
| 4 | 6 | 8 | 30 | 50 | 30 | 1 | 14 | 8 | 43 | 47 | 14 | −4 | −4 | 3 | 92 | 95 | 4 | 4 | 2 | 9 | 85 | 81 | 6 | −1 | 10 | 9 | 94 | 86 | 9 |
| 5 | 6 | 8 | 80 | 90 | 11 | 2 | 14 | 8 | 117 | 106 | 9 | −3 | −4 | 9 | 165 | 165 | 5 | 5 | 2 | 9 | 31 | 33 | 11 | 0 | 10 | 9 | 54 | 67 | 10 |
| 6 | 6 | 8 | 36 | 43 | 21 | 3 | 14 | 8 | 56 | 53 | 10 | −2 | −4 | 9 | 173 | 178 | 4 | 6 | 2 | 9 | 16 | 32 | 15 | 1 | 10 | 9 | 92 | 95 | 13 |
| 7 | 6 | 8 | 0 | 23 | 1 | −2 | 15 | 8 | 33 | 44 | 14 | −1 | −4 | 9 | 40 | 34 | 6 | −6 | 3 | 9 | 65 | 74 | 7 | 2 | 10 | 9 | 60 | 63 | 14 |
| −7 | 7 | 8 | 39 | 35 | 21 | −1 | 15 | 8 | 51 | 46 | 11 | 0 | −4 | 9 | 218 | 219 | 6 | −5 | 3 | 9 | 69 | 66 | 8 | 3 | 10 | 9 | 62 | 44 | 12 |
| −6 | 7 | 8 | 68 | 46 | 8 | 0 | 15 | 8 | 60 | 61 | 10 | 1 | −4 | 9 | 24 | 20 | 13 | −4 | 3 | 9 | 82 | 74 | 7 | 4 | 10 | 9 | 49 | 46 | 14 |
| −5 | 7 | 8 | 116 | 122 | 6 | 1 | 15 | 8 | 73 | 68 | 8 | 2 | −4 | 9 | 69 | 78 | 7 | −3 | 3 | 9 | 59 | 45 | 8 | −3 | 11 | 9 | 38 | 41 | 17 |
| −4 | 7 | 8 | 123 | 107 | 6 | 2 | 15 | 8 | 55 | 66 | 10 | 3 | −4 | 9 | 35 | 24 | 23 | −2 | 3 | 9 | 121 | 115 | 7 | −2 | 11 | 9 | 50 | 50 | 13 |
| −3 | 7 | 8 | 125 | 131 | 5 | −2 | −13 | 9 | 87 | 71 | 6 | 4 | −4 | 9 | 30 | 26 | 12 | −1 | 3 | 9 | 176 | 153 | 10 | −1 | 11 | 9 | 47 | 11 | 12 |
| −2 | 7 | 8 | 75 | 68 | 5 | −1 | −13 | 9 | 101 | 104 | 7 | 5 | −4 | 9 | 67 | 50 | 7 | 0 | 3 | 9 | 102 | 94 | 7 | 0 | 11 | 9 | 0 | 28 | 1 |
| −1 | 7 | 8 | 80 | 56 | 5 | 0 | −13 | 9 | 96 | 95 | 7 | 6 | −4 | 9 | 35 | 17 | 10 | 1 | 3 | 9 | 182 | 168 | 9 | 1 | 11 | 9 | 0 | 35 | 1 |
| 0 | 7 | 8 | 68 | 82 | 6 | 1 | −13 | 9 | 48 | 21 | 10 | −6 | −3 | 9 | 62 | 74 | 6 | 2 | 3 | 9 | 140 | 111 | 7 | 2 | 11 | 9 | 0 | 7 | 1 |
| 1 | 7 | 8 | 181 | 196 | 8 | −3 | −12 | 9 | 76 | 85 | 7 | −5 | −3 | 9 | 60 | 67 | 5 | 3 | 3 | 9 | 83 | 78 | 1 | 3 | 11 | 9 | 43 | 32 | 17 |
| 2 | 7 | 8 | 201 | 205 | 8 | −2 | −12 | 9 | 50 | 64 | 8 | −4 | −3 | 9 | 77 | 75 | 4 | 4 | 3 | 9 | 62 | 6 | 7 | −2 | 12 | 9 | 62 | 63 | 10 |
| 4 | 7 | 8 | 22 | 55 | 21 | −1 | −12 | 9 | 146 | 144 | 8 | −3 | −3 | 9 | 48 | 45 | 6 | 5 | 3 | 9 | 100 | 99 | 6 | −1 | 12 | 9 | 156 | 143 | 9 |
| 5 | 7 | 8 | 0 | 30 | 1 | 0 | −12 | 9 | 82 | 76 | 8 | −2 | −3 | 9 | 121 | 116 | 4 | 6 | 3 | 9 | 70 | 60 | 5 | 0 | 12 | 9 | 84 | 77 | 9 |
| 6 | 7 | 8 | 0 | 32 | 1 | 1 | −12 | 9 | 80 | 63 | 5 | −1 | −3 | 9 | 149 | 153 | 4 | −6 | 4 | 9 | 211 | 229 | 8 | 1 | 12 | 9 | 65 | 64 | 10 |
| −6 | 8 | 8 | 83 | 76 | 5 | 2 | −12 | 9 | 40 | 25 | 13 | 0 | −3 | 9 | 92 | 94 | 4 | −5 | 4 | 9 | 119 | 106 | 6 | −1 | −9 | 10 | 43 | 46 | 12 |
| −5 | 8 | 8 | 131 | 142 | 5 | −4 | −11 | 9 | 10 | 5 | 10 | 1 | −3 | 9 | 167 | 167 | 6 | −4 | 4 | 9 | 102 | 94 | 7 | 0 | −9 | 10 | 79 | 63 | 9 |
| −4 | 8 | 8 | 167 | 178 | 5 | −3 | −11 | 9 | 49 | 41 | 8 | 2 | −3 | 9 | 137 | 110 | 4 | −3 | 4 | 9 | 174 | 165 | 7 | −2 | −8 | 10 | 64 | 78 | 9 |
| −3 | 8 | 8 | 120 | 118 | 6 | −2 | −11 | 9 | 59 | 50 | 8 | 3 | −3 | 9 | 77 | 78 | 4 | −2 | 4 | 9 | 180 | 178 | 7 | −1 | −8 | 10 | 55 | 64 | 12 |
| −2 | 8 | 8 | 158 | 161 | 6 | −1 | −11 | 9 | 0 | 11 | 1 | 4 | −3 | 9 | 60 | 67 | 5 | −1 | 4 | 9 | 34 | 34 | 17 | 0 | −8 | 10 | 127 | 107 | 8 |
| −1 | 8 | 8 | 143 | 134 | 8 | 0 | −11 | 9 | 39 | 28 | 13 | 5 | −3 | 9 | 108 | 98 | 8 | 0 | 4 | 9 | 240 | 220 | 8 | 1 | −8 | 10 | 78 | 68 | 8 |
| 0 | 8 | 8 | 162 | 159 | 7 | 1 | −11 | 9 | 47 | 35 | 12 | 6 | −3 | 9 | 77 | 59 | 7 | 1 | 4 | 9 | 46 | 20 | 10 | −2 | −7 | 10 | 80 | 69 | 8 |
| 1 | 8 | 8 | 113 | 108 | 7 | 2 | −11 | 9 | 35 | 8 | 18 | −6 | −2 | 9 | 108 | 114 | 5 | 2 | 4 | 9 | 102 | 78 | 7 | −1 | −7 | 10 | 47 | 22 | 10 |
| 2 | 8 | 8 | 65 | 69 | 7 | 3 | −11 | 9 | 22 | 31 | 21 | −5 | −2 | 9 | 0 | 22 | 1 | 3 | 4 | 9 | 28 | 24 | 18 | 0 | −7 | 10 | 97 | 88 | 8 |
| 3 | 8 | 8 | 61 | 58 | 9 | −4 | −10 | 9 | 0 | 19 | 1 | −4 | −2 | 9 | 89 | 91 | 5 | 4 | 4 | 9 | 46 | 25 | 8 | 1 | −7 | 10 | 76 | 75 | 8 |
| 4 | 8 | 8 | 83 | 101 | 13 | −3 | −10 | 9 | 71 | 81 | 7 | −3 | −2 | 9 | 195 | 199 | 5 | 5 | 4 | 9 | 47 | 50 | 7 | 2 | −7 | 10 | 95 | 79 | 8 |
| 5 | 8 | 8 | 0 | 22 | 1 | −2 | −10 | 9 | 59 | 49 | 8 | −2 | −2 | 9 | 68 | 73 | 6 | 6 | 4 | 9 | 0 | 17 | 1 | 3 | −7 | 10 | 102 | 89 | 7 |
| 6 | 8 | 8 | 0 | 34 | 1 | −1 | −10 | 9 | 94 | 86 | 8 | −1 | −2 | 9 | 192 | 181 | 8 | −6 | 5 | 9 | 108 | 106 | 10 | −3 | −6 | 10 | 25 | 26 | 24 |
| −6 | 9 | 8 | 111 | 120 | 6 | 0 | −10 | 9 | 85 | 68 | 8 | 0 | −2 | 9 | 105 | 100 | 5 | −5 | 5 | 9 | 68 | 73 | 7 | −2 | −6 | 10 | 147 | 136 | 8 |
| −5 | 9 | 8 | 52 | 43 | 13 | 1 | −10 | 9 | 111 | 95 | 8 | 1 | −2 | 9 | 94 | 57 | 5 | −4 | 5 | 9 | 48 | 32 | 9 | −1 | −6 | 10 | 65 | 41 | 8 |
| −4 | 9 | 8 | 115 | 123 | 6 | 2 | −10 | 9 | 78 | 63 | 9 | 2 | −2 | 9 | 70 | 55 | 6 | −3 | 5 | 9 | 74 | 77 | 7 | 0 | −6 | 10 | 22 | 17 | 22 |
| −3 | 9 | 8 | 87 | 81 | 6 | 3 | −10 | 9 | 35 | 45 | 21 | 3 | −2 | 9 | 127 | 105 | 5 | −2 | 5 | 9 | 33 | 24 | 16 | 1 | −6 | 10 | 66 | 43 | 8 |
| −2 | 9 | 8 | 0 | 21 | 1 | 4 | −10 | 9 | 60 | 47 | 10 | 4 | −2 | 9 | 86 | 81 | 4 | −1 | 5 | 9 | 49 | 38 | 10 | 2 | −6 | 10 | 69 | 55 | 8 |
| −1 | 9 | 8 | 119 | 101 | 8 | −4 | −9 | 9 | 49 | 71 | 9 | 5 | −2 | 9 | 35 | 34 | 7 | 0 | 5 | 9 | 35 | 45 | 15 | 3 | −6 | 10 | 28 | 28 | 18 |

TABLE 32-continued

Observed and calculated structure factors for Diol-3.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 0 | 9 | 8 | 104 | 93 | 8 | −3 | −9 | 9 | 63 | 71 | 8 | 6 | −2 | 9 | 28 | 32 | 22 | 1 | 5 | 9 | 130 | 118 | 6 | −4 | −5 | 10 | 64 | 70 | 9 |
| 1 | 9 | 8 | 31 | 21 | 12 | −2 | −9 | 9 | 126 | 123 | 7 | −6 | −1 | 9 | 61 | 62 | 7 | 2 | 5 | 9 | 45 | 29 | 11 | −3 | −5 | 10 | 78 | 67 | 8 |
| 2 | 9 | 8 | 34 | 24 | 9 | −1 | −9 | 3 | 116 | 98 | 8 | −5 | −1 | 3 | 97 | 95 | 5 | 3 | 5 | 9 | 46 | 60 | 9 | −2 | −5 | 10 | 103 | 94 | 8 |
| 3 | 9 | 8 | 39 | 53 | 11 | 0 | −9 | 9 | 166 | 145 | 8 | −4 | −1 | 3 | 37 | 34 | 9 | 4 | 5 | 9 | 68 | 56 | 6 | −1 | −5 | 10 | 87 | 71 | 5 |
| 4 | 9 | 8 | 108 | 122 | 12 | 1 | −9 | 9 | 123 | 89 | 9 | −3 | −1 | 9 | 71 | 68 | 7 | 5 | 5 | 9 | 43 | 15 | 7 | 0 | −5 | 10 | 29 | 16 | 13 |
| 5 | 9 | 8 | 0 | 53 | 1 | 2 | −9 | 9 | 117 | 104 | 9 | −2 | −1 | 9 | 110 | 95 | 6 | 6 | 5 | 9 | 45 | 51 | 11 | 1 | −5 | 10 | 74 | 72 | 6 |
| 6 | 9 | 8 | 0 | 8 | 1 | 3 | −9 | 9 | 108 | 83 | 9 | −1 | −1 | 3 | 51 | 23 | 8 | −6 | 6 | 9 | 77 | 94 | 7 | 2 | −5 | 10 | 25 | 23 | 24 |
| −6 | 10 | 8 | 58 | 58 | 12 | 4 | −9 | 9 | 81 | 69 | 9 | 0 | −1 | 9 | 192 | 171 | 6 | −5 | 6 | 9 | 15 | 26 | 14 | 3 | −5 | 10 | 57 | 53 | 8 |
| −5 | 10 | 8 | 0 | 29 | 1 | −5 | −8 | 9 | 74 | 81 | 7 | 1 | −1 | 9 | 107 | 98 | 5 | −4 | 6 | 9 | 95 | 97 | 6 | 4 | −5 | 10 | 88 | 72 | 7 |
| −4 | 10 | 8 | 56 | 58 | 8 | −4 | −8 | 9 | 101 | 103 | 8 | 2 | −1 | 9 | 172 | 158 | 6 | −3 | 6 | 9 | 60 | 58 | 8 | −4 | −4 | 10 | 80 | 86 | 8 |
| −3 | 10 | 8 | 160 | 162 | 7 | −3 | −8 | 9 | 85 | 99 | 8 | 3 | −1 | 9 | 81 | 64 | 5 | −2 | 6 | 9 | 181 | 182 | 7 | −3 | −4 | 10 | 115 | 122 | 8 |
| −2 | 10 | 8 | 76 | 75 | 7 | −2 | −8 | 9 | 96 | 96 | 5 | 4 | −1 | 9 | 47 | 35 | 7 | −1 | 6 | 9 | 71 | 78 | 7 | −2 | −4 | 10 | 147 | 151 | 6 |
| −1 | 10 | 8 | 136 | 135 | 10 | −1 | −8 | 9 | 144 | 124 | 6 | 5 | −1 | 9 | 67 | 57 | 4 | 0 | 6 | 9 | 104 | 111 | 12 | −1 | −4 | 10 | 77 | 65 | 6 |
| 0 | 10 | 8 | 220 | 207 | 9 | 0 | −8 | 9 | 166 | 143 | 6 | 6 | −1 | 9 | 96 | 71 | 4 | 1 | 6 | 9 | 118 | 99 | 10 | 0 | −4 | 10 | 33 | 19 | 12 |
| 1 | 10 | 8 | 102 | 104 | 5 | 1 | −8 | 9 | 161 | 137 | 6 | −6 | 0 | 9 | 28 | 3 | 20 | 2 | 6 | 9 | 60 | 38 | 15 | 1 | −4 | 10 | 38 | 19 | 10 |
| 2 | 10 | 8 | 191 | 166 | 6 | 2 | −8 | 9 | 66 | 79 | 7 | −5 | 0 | 9 | 142 | 151 | 5 | 3 | 6 | 9 | 57 | 38 | 15 | 2 | −4 | 10 | 98 | 71 | 8 |
| 3 | 10 | 8 | 93 | 33 | 6 | 3 | −8 | 9 | 32 | 21 | 12 | −4 | 0 | 9 | 140 | 154 | 6 | 4 | 6 | 9 | 51 | 23 | 14 | 3 | −4 | 10 | 44 | 15 | 11 |
| 4 | 10 | 8 | 58 | 76 | 7 | 4 | −8 | 9 | 54 | 57 | 9 | −3 | 0 | 9 | 39 | 36 | 10 | 5 | 6 | 9 | 76 | 48 | 9 | 4 | −4 | 10 | 53 | 37 | 9 |
| 5 | 10 | 8 | 40 | 55 | 22 | −5 | −7 | 9 | 70 | 71 | 9 | −2 | 0 | 9 | 94 | 87 | 7 | −5 | 7 | 9 | 68 | 71 | 7 | −5 | −3 | 10 | 47 | 29 | 12 |
| −5 | 11 | 8 | 131 | 137 | 9 | −4 | −7 | 9 | 43 | 55 | 9 | −1 | 0 | 9 | 25 | 4 | 24 | −4 | 7 | 9 | 54 | 55 | 8 | −4 | −3 | 10 | 39 | 51 | 6 |
| −4 | 11 | 8 | 121 | 137 | 9 | −3 | −7 | 9 | 103 | 107 | 6 | 0 | 0 | 9 | 76 | 53 | 7 | −3 | 7 | 9 | 109 | 107 | 6 | −3 | −3 | 10 | 93 | 94 | 5 |
| −3 | 11 | 8 | 39 | 33 | 13 | −2 | −7 | 9 | 136 | 136 | 4 | 1 | 0 | 9 | 81 | 81 | 6 | −2 | 7 | 9 | 132 | 136 | 10 | −2 | −3 | 10 | 42 | 49 | 6 |
| −2 | 11 | 8 | 84 | 70 | 7 | −1 | −7 | 9 | 79 | 66 | 4 | 2 | 0 | 9 | 114 | 104 | 5 | −1 | 7 | 9 | 58 | 66 | 17 | −1 | −3 | 10 | 80 | 69 | 6 |
| −1 | 11 | 8 | 189 | 189 | 11 | 0 | −7 | 9 | 166 | 140 | 5 | 3 | 0 | 9 | 48 | 36 | 8 | 0 | 7 | 9 | 138 | 140 | 12 | 0 | −3 | 10 | 45 | 41 | 5 |
| 0 | 11 | 8 | 192 | 177 | 11 | 1 | −7 | 9 | 114 | 111 | 5 | 4 | 0 | 9 | 58 | 55 | 6 | 1 | 7 | 9 | 108 | 111 | 11 | 1 | −3 | 10 | 150 | 137 | 9 |
| 1 | 11 | 8 | 155 | 138 | 10 | 2 | −7 | 9 | 47 | 42 | 7 | 5 | 0 | 9 | 92 | 90 | 5 | 2 | 7 | 9 | 61 | 42 | 13 | 2 | −3 | 10 | 56 | 41 | 7 |
| 2 | 11 | 8 | 156 | 153 | 10 | 3 | −7 | 9 | 102 | 88 | 8 | 6 | 0 | 9 | 48 | 43 | 5 | 3 | 7 | 9 | 103 | 88 | 10 | 3 | −3 | 10 | 15 | 5 | 14 |
| 3 | 11 | 8 | 148 | 138 | 6 | 4 | −7 | 9 | 96 | 87 | 8 | −7 | 1 | 9 | 123 | 137 | 6 | 4 | 7 | 9 | 97 | 87 | 10 | 4 | −3 | 10 | 48 | 54 | 10 |
| 4 | 11 | 8 | 47 | 39 | 8 | −5 | −6 | 9 | 39 | 26 | 10 | −6 | 1 | 9 | 50 | 63 | 9 | 5 | 7 | 9 | 53 | 32 | 11 | −5 | −2 | 10 | 82 | 89 | 6 |
| −5 | 12 | 8 | 35 | 24 | 17 | −4 | −6 | 9 | 102 | 98 | 8 | −5 | 1 | 9 | 102 | 94 | 6 | −5 | 8 | 9 | 79 | 81 | 7 | −4 | −2 | 10 | 30 | 91 | 5 |
| −4 | 12 | 8 | 132 | 136 | 9 | −3 | −6 | 3 | 66 | 58 | 5 | −4 | 1 | 3 | 39 | 33 | 12 | −4 | 8 | 9 | 108 | 103 | 9 | −3 | −2 | 10 | 22 | 16 | 22 |
| −3 | 12 | 8 | 52 | 65 | 9 | −2 | −6 | 9 | 183 | 181 | 7 | −3 | 1 | 9 | 82 | 69 | 7 | −3 | 8 | 9 | 89 | 99 | 10 | −2 | −2 | 10 | 89 | 95 | 4 |
| −2 | 12 | 8 | 168 | 189 | 7 | −1 | −6 | 9 | 81 | 78 | 5 | −2 | 1 | 9 | 120 | 95 | 8 | −2 | 8 | 9 | 81 | 97 | 11 | −1 | −2 | 10 | 131 | 125 | 5 |
| −1 | 12 | 8 | 67 | 70 | 8 | 0 | −6 | 9 | 128 | 110 | 6 | −1 | 1 | 9 | 58 | 23 | 8 | −1 | 8 | 9 | 134 | 124 | 11 | 0 | −2 | 10 | 46 | 54 | 7 |
| 0 | 12 | 8 | 54 | 76 | 9 | 1 | −6 | 9 | 108 | 99 | 6 | 0 | 1 | 9 | 191 | 172 | 8 | 0 | 8 | 9 | 136 | 144 | 12 | 1 | −2 | 10 | 62 | 53 | 6 |
| 1 | 12 | 8 | 100 | 87 | 10 | 2 | −6 | 9 | 65 | 38 | 6 | 1 | 1 | 9 | 107 | 98 | 6 | 1 | 8 | 9 | 140 | 138 | 11 | 2 | −2 | 10 | 53 | 60 | 5 |
| 2 | 12 | 8 | 40 | 12 | 10 | 3 | −6 | 3 | 54 | 38 | 6 | 2 | 1 | 3 | 172 | 159 | 7 | 2 | 8 | 9 | 73 | 78 | 11 | 3 | −2 | 10 | 85 | 70 | 8 |
| 3 | 12 | 8 | 95 | 91 | 7 | 4 | −6 | 9 | 30 | 22 | 11 | 3 | 1 | 9 | 79 | 64 | 7 | 3 | 8 | 9 | 40 | 21 | 22 | 4 | −2 | 10 | 119 | 86 | 8 |
| 4 | 12 | 8 | 91 | 92 | 8 | 5 | −6 | 9 | 53 | 47 | 9 | 4 | 1 | 9 | 42 | 35 | 8 | 4 | 8 | 9 | 62 | 58 | 11 | −5 | −1 | 10 | 29 | 38 | 13 |
| −4 | 13 | 8 | 107 | 110 | 9 | −5 | −5 | 9 | 74 | 73 | 5 | 5 | 1 | 9 | 59 | 57 | 5 | 5 | 8 | 9 | 61 | 59 | 10 | −4 | −1 | 10 | 99 | 106 | 5 |
| −3 | 13 | 8 | 184 | 195 | 11 | −4 | −5 | 9 | 35 | 32 | 6 | 6 | 1 | 9 | 84 | 71 | 4 | −4 | 9 | 9 | 63 | 72 | 10 | −3 | −1 | 10 | 50 | 58 | 7 |
| −2 | 13 | 8 | 146 | 135 | 9 | −3 | −5 | 9 | 72 | 77 | 4 | −6 | 2 | 9 | 117 | 115 | 6 | −3 | 9 | 9 | 54 | 71 | 14 | −2 | −1 | 10 | 63 | 61 | 6 |
| −1 | −1 | 10 | 107 | 105 | 5 | 3 | 1 | 10 | 42 | 20 | 7 | −2 | 4 | 10 | 159 | 151 | 7 | −2 | 7 | 10 | 64 | 70 | 11 | −2 | −1 | 11 | 40 | 37 | 7 |
| 0 | −1 | 10 | 57 | 51 | 7 | 4 | 1 | 10 | 137 | 117 | 4 | −1 | 4 | 10 | 77 | 65 | 7 | −1 | 7 | 10 | 0 | 22 | 1 | −1 | −1 | 11 | 89 | 64 | 8 |
| 1 | −1 | 10 | 77 | 67 | 5 | 5 | 1 | 10 | 48 | 24 | 7 | 0 | 4 | 10 | 0 | 19 | 1 | 0 | 7 | 10 | 96 | 88 | 10 | 0 | −1 | 11 | 107 | 72 | 8 |
| 2 | −1 | 10 | 61 | 59 | 5 | −5 | 2 | 10 | 80 | 89 | 6 | 1 | 4 | 10 | 0 | 19 | 1 | 1 | 7 | 10 | 53 | 75 | 13 | 2 | −1 | 11 | 0 | 20 | 1 |
| 3 | −1 | 10 | 40 | 20 | 7 | −4 | 2 | 10 | 105 | 91 | 6 | 2 | 4 | 10 | 83 | 70 | 6 | 3 | 7 | 10 | 97 | 89 | 9 | −3 | 0 | 11 | 8 | 18 | 8 |
| 4 | −1 | 10 | 145 | 117 | 8 | −3 | 2 | 10 | 0 | 17 | 1 | 3 | 4 | 10 | 38 | 15 | 9 | −3 | 8 | 10 | 30 | 11 | 29 | −2 | 0 | 11 | 0 | 5 | 1 |
| 5 | −1 | 10 | 39 | 23 | 11 | −2 | 2 | 10 | 101 | 95 | 6 | 4 | 4 | 10 | 54 | 37 | 5 | −2 | 8 | 10 | 63 | 79 | 10 | −1 | 0 | 11 | 55 | 37 | 6 |

TABLE 32-continued

| Observed and calculated structure factors for Diol-3. | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| −5 | 0 | 10 | 101 | 111 | 5 | −1 | 2 | 10 | 137 | 125 | 6 | −4 | 5 | 10 | 66 | 70 | 7 | −1 | 8 | 10 | 43 | 64 | 17 | 0 | 0 | 11 | 0 | 8 | 1 |
| −4 | 0 | 10 | 18 | 13 | 18 | 0 | 2 | 10 | 66 | 54 | 7 | −3 | 5 | 10 | 71 | 67 | 7 | 0 | 8 | 10 | 106 | 107 | 10 | 1 | 0 | 11 | 63 | 75 | 5 |
| −3 | 0 | 10 | 54 | 57 | 7 | 1 | 2 | 10 | 84 | 53 | 6 | −2 | 5 | 10 | 99 | 95 | 6 | 1 | 8 | 10 | 53 | 68 | 14 | 2 | 0 | 11 | 0 | 23 | 1 |
| −2 | 0 | 10 | 102 | 88 | 6 | 2 | 2 | 10 | 67 | 60 | 7 | −1 | 5 | 10 | 80 | 70 | 7 | 2 | 8 | 10 | 22 | 49 | 21 | −2 | 1 | 11 | 43 | 37 | 11 |
| −1 | 0 | 10 | 145 | 133 | 5 | 3 | 2 | 10 | 75 | 69 | 5 | 0 | 5 | 10 | 0 | 16 | 1 | −2 | 9 | 10 | 0 | 10 | 1 | −1 | 1 | 11 | 75 | 64 | 5 |
| 0 | 0 | 10 | 67 | 59 | 6 | 4 | 2 | 10 | 112 | 87 | 5 | 1 | 5 | 10 | 82 | 73 | 6 | −1 | 9 | 10 | 0 | 46 | 1 | 0 | 1 | 11 | 83 | 72 | 5 |
| 1 | 0 | 10 | 106 | 105 | 5 | −5 | 3 | 10 | 18 | 29 | 18 | 2 | 5 | 10 | 20 | 23 | 19 | 0 | 9 | 10 | 55 | 63 | 12 | 1 | 1 | 11 | 79 | 80 | 6 |
| 2 | 0 | 10 | 116 | 97 | 5 | −4 | 3 | 10 | 47 | 52 | 9 | 3 | 5 | 10 | 31 | 53 | 31 | 1 | 9 | 10 | 0 | 38 | 1 | 2 | 1 | 11 | 18 | 20 | 18 |
| 3 | 0 | 10 | 74 | 61 | 5 | −3 | 3 | 10 | 114 | 94 | 9 | 4 | 5 | 10 | 90 | 72 | 8 | −1 | −4 | 11 | 100 | 83 | 7 | −2 | 2 | 11 | 13 | 25 | 13 |
| 4 | 0 | 10 | 45 | 60 | 6 | −2 | 3 | 10 | 56 | 49 | 8 | −4 | 6 | 10 | 95 | 111 | 8 | 0 | −4 | 11 | 106 | 85 | 7 | −1 | 2 | 11 | 130 | 125 | 5 |
| 5 | 0 | 10 | 72 | 70 | 7 | −1 | 3 | 10 | 89 | 69 | 11 | −3 | 6 | 10 | 10 | 26 | 9 | 1 | −4 | 11 | 70 | 59 | 8 | 0 | 2 | 11 | 53 | 53 | 6 |
| −5 | 1 | 10 | 27 | 38 | 17 | 0 | 3 | 10 | 65 | 42 | 8 | −2 | 6 | 10 | 134 | 136 | 6 | −2 | −3 | 11 | 93 | 83 | 8 | 1 | 2 | 11 | 82 | 69 | 5 |
| −4 | 1 | 10 | 114 | 107 | 6 | 1 | 3 | 10 | 158 | 137 | 7 | −1 | 6 | 10 | 57 | 41 | 13 | −1 | −3 | 11 | 132 | 104 | 8 | 2 | 2 | 11 | 41 | 36 | 15 |
| −3 | 1 | 10 | 65 | 57 | 7 | 2 | 3 | 10 | 73 | 41 | 6 | 0 | 6 | 10 | 0 | 17 | 1 | 1 | −3 | 11 | 75 | 47 | 8 | −2 | 3 | 11 | 88 | 82 | 8 |
| −2 | 1 | 10 | 71 | 61 | 7 | 3 | 3 | 10 | 42 | 5 | 8 | 1 | 6 | 10 | 49 | 43 | 16 | 2 | −3 | 11 | 43 | 7 | 11 | −1 | 3 | 11 | 120 | 104 | 6 |
| −1 | 1 | 10 | 117 | 105 | 6 | 4 | 3 | 10 | 48 | 54 | 5 | 2 | 6 | 10 | 44 | 55 | 18 | −2 | −2 | 11 | 15 | 25 | 14 | 0 | 3 | 11 | 125 | 127 | 5 |
| 0 | 1 | 10 | 63 | 51 | 8 | −5 | 4 | 10 | 52 | 38 | 11 | 3 | 6 | 10 | 0 | 27 | 1 | 0 | −2 | 11 | 70 | 53 | 8 | 1 | 3 | 11 | 68 | 48 | 6 |
| 1 | 1 | 10 | 80 | 67 | 6 | −4 | 4 | 10 | 76 | 86 | 6 | 4 | 6 | 10 | 49 | 48 | 11 | 1 | −2 | 11 | 96 | 69 | 7 | −1 | 4 | 11 | 79 | 83 | 9 |
| 2 | 1 | 10 | 70 | 60 | 6 | −3 | 4 | 10 | 122 | 122 | 6 | −3 | 7 | 10 | 40 | 53 | 13 | 2 | −2 | 11 | 33 | 36 | 15 | 0 | 4 | 11 | 91 | 85 | 8 |

REFERENCES

1. CrysAlis RED, Oxford Diffraction Ltd., Version 1.171.28 cycle2 beta (release 25 Oct. 2005 CrysAlis171.NET) (compiled Oct. 25, 2005, 08:50:05). Empirical absorption correction using spherical harmonics, implemented in SCALE3 ABSPACK scaling algorithm.
2. CrysAlis CCD, Oxford Diffraction Ltd. Version 1.171.28 cycle2 beta; CrysAlis RED, Oxford Diffraction Ltd., Version 1.171.28 cycle2 beta.
3. G. M. Sheldrick, Acta Crystallogr. 1990, A46, 467-473.
4. G. M. Sheldrick, SHELXL93. *Program for the Refinement of Crystal Structures*., Univ. of Göttingen, Germany.
5. *International Tables for Crystallography*, Ed. A. J. C. Wilson, Kluwer: Dordrecth, 1992, Vol. C.

Example 4

Synthesis of SAG-1 and SAG-2

The preparation of SAG-1 and SAG-2 having the basic structures I and II can be accomplished by a common general method otherwise referred to as the condensation of a bicyclic Windaus-Grundman type ketone III or IV with the allylic phosphine oxide IX to the corresponding 2-methylene-19-nor-vitamin D analog VIa or VIb followed by deprotection at C-1 and C-3 in the latter compound VIa or VIb to obtain compound I (SAG-1) or compound II (SAG-2).

III

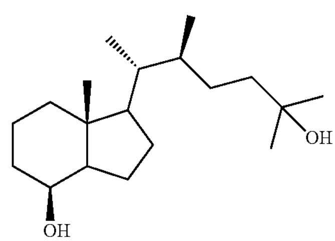

Diol-1 (precursor of SAG-1)
(8S,20R,22S)-Des-A,B-22-methyl-cholestan-8,25-diol

IV

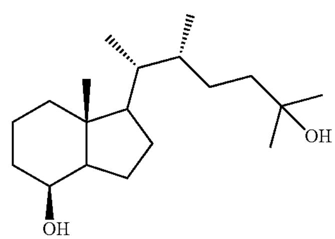

Diol-2 (precursor of SAG-2)
(2S,20R,22R)-Des-A,B-22-methyl-cholestan-8,25-diol

IX

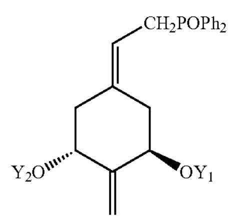

-continued

VIa

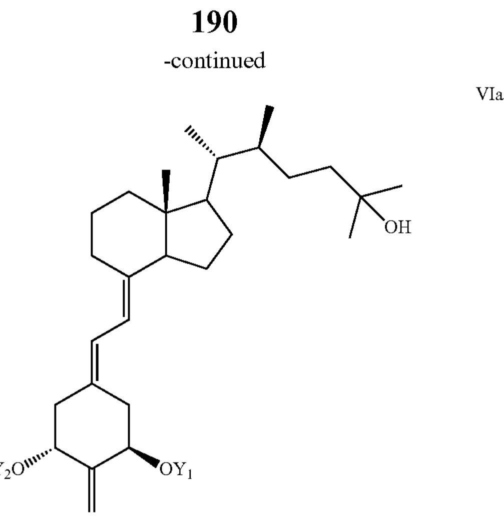

VIb

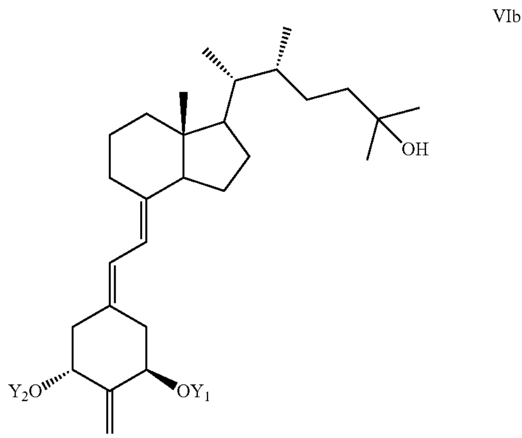

Example 5

Synthesis of AGS-1 and AGS-2

The preparation of AGS-1 and AGS-2 having the basic structures V and VI can be accomplished by a common general method otherwise referred to as the condensation of a bicyclic Windaus-Grundmann type ketone VII or VIII with the allylic phosphine oxide IX to the corresponding 2-methylene-19-nor-vitamin D analog VIc or VId followed by deprotection at C-1 and C-3 in the latter compound VIc or VId to obtain compound V, (AGS-1) or compound VI (AGS-2).

VII

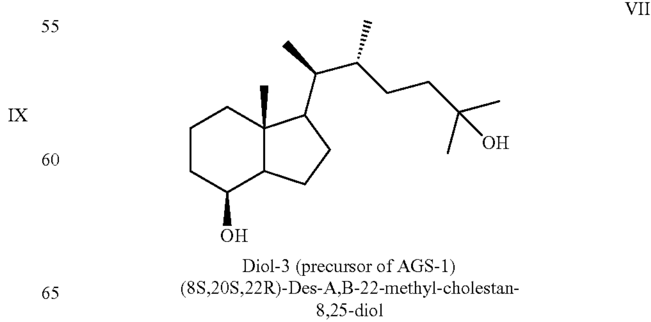

Diol-3 (precursor of AGS-1)
(8S,20S,22R)-Des-A,B-22-methyl-cholestan-8,25-diol

-continued

VIII

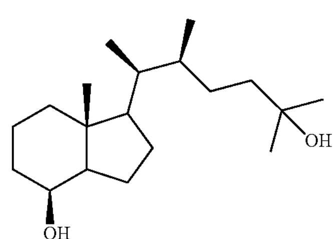

Diol-4 (precursor of AGS-2)
(8S,20S,22S)-Des-A,B-22-methyl-cholestan-8,25-diol

IX

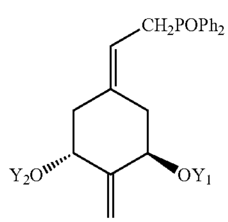

VIc

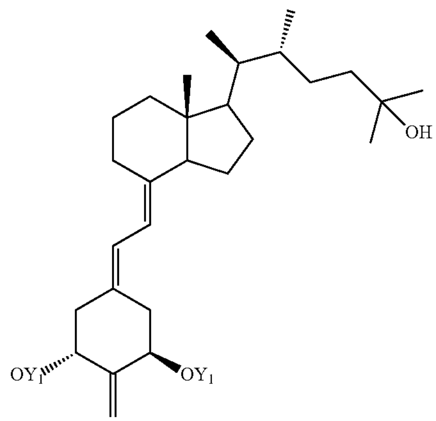

VId

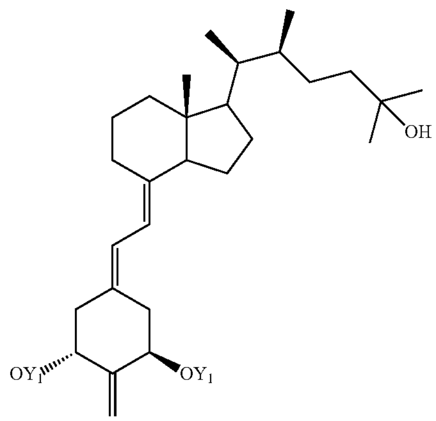

In phosphine oxide IX, $Y_1$ and $Y_2$ are preferably hydroxy-protecting groups such as silyl protecting groups. The t-butyldimethylsilyl (TMDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans. I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1.986); DeLuca et al., U.S. Pat. No. 5,086,191; De Luca et al., U.S. Pat. No. 5,536,713; and DeLuca et al., U.S. Pat. No. 5,843,928 all of which are hereby incorporated by reference in their entirety and for all purposes as if fully set forth herein.

Phosphine oxide IX is a convenient reagent that can be used to prepare a large number of 19-nor-vitamin D compounds and is prepared according to the procedures described by Sicinski et al., *J. Med. Chem.,* 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191 which are hereby incorporated by reference in their entirety as if fully set forth herein.

An overall process for the synthesis of compounds I, II, V and VI is illustrated and described more completely in U.S. Pat. No. 5,843,928 entitled "2-Alkylidene-9-Nor-Vitamin D Compounds" and in U.S. patent application Ser. No. 13/069,074, filed Mar. 22, 2011, entitled "Diastereomers of 2-Methylene-9-Nor-22-Methyl-1α,25-Dihydroxyvitamin $D_3$" and published as U.S. Publication No. U.S. 2011/0237557, the content of which is incorporated herein by reference in its entirety.

We claim:

1. (20R,22R)-2-methylene-19-nor-22-methyl-1α,25-dihydroxyvitamin $D_3$ having the formula

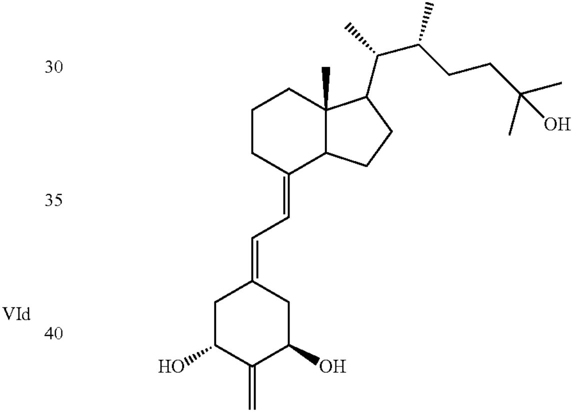

in crystalline form.

2. A crystalline form of (20R,22R)-2-methylene-19-nor-22-methyl-1α,25-dihydroxyvitamin $D_3$ having molecular packing arrangement defined by space group C2 and unit cell dimensions a=27.03 Å b==6.47 Å c=17.41 Å α=90°, β=103.35° and γ=90°.

3. A three dimensional structure for (20R,22R)-2-methylene-19-nor-22-methyl-1α,25-dihydroxyvitamin $D_3$ as defined by the molecular packing arrangement set forth in claim 2.

4. A method of purifying (20R,22R)-2-methylene-19-nor-22-methyl-1α,25-dihydroxyvitamin $D_3$, comprising the steps of:

(a) preparing a solvent comprising hexane;

(b) adding a product containing (20R,22R)-2-methylene-19-nor-22-methyl-1α,25-dihydroxyvitamin $D_3$ to be purified to said hexane to form a suspension of the product in the hexane;

(c) adding 2-propanol dropwise to the suspension to form a mixture of the product in the hexane and 2-propanol;

(d) heating the mixture to dissolve the product containing (20R,22R)-2-methylene-19-nor-22-methyl-1α,25-dihydroxyvitamin $D_3$ to be purified in said mixture;

(e) cooling said mixture and dissolved product below ambient temperature for a sufficient amount of time to form a precipitate of (20R,22R)-2-methylene-19-nor-22-methyl-1α,25-dihydroxyvitamin $D_3$ crystals; and (f) separating the (20R,22R)-2-methylene-19-nor-22-methyl-1α,25-dihydroxyvitamin $D_3$ crystals from the mixture.

5. The method of claim 4 including the further step of allowing said mixture and dissolved product to cool to ambient temperature prior to cooling below ambient temperature.

6. The method of claim 4 wherein the step of separating comprises filtering the mixture and precipitate to obtain the crystals.

7. The method of claim 4 including a further step (g) comprising repeating steps (a) through (f) using the recovered crystals from step (f) as the product of step (b).

8. The method of claim 4 wherein said mixture comprises about 15% 2-propanol and about 85% hexane, by volume.

9. A compound having the formula

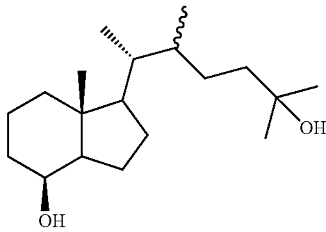 [SMILES: CC(CCC(C)(C)O)[C@@H](C)C1CCC2[C@@H](O)CCC[C@]12C]

in crystalline form, wherein the wavy line at carbon 22 indicates the methyl group attached to carbon 22 may be in its R or S orientation.

10. (8S,20R,22S)-Des-A,B-22-methyl-cholestan-8,25-diol having the formula

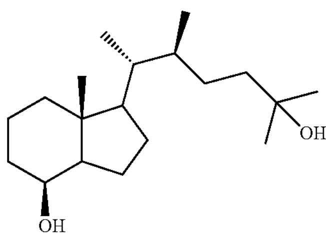 [SMILES: C[C@@H](CCC(C)(C)O)[C@@H](C)C1CCC2[C@@H](O)CCC[C@@]21C]

in crystalline form.

11. A crystalline form of (8S,20R,22S)-Des-A,B-22-methyl-cholestan-8,25-diol having molecular packaging arrangement defined by space group C2 and unit cell dimensions a=26.39 Å b=6.08 Å c=12.68 Å α=90°, β=118.38° and γ=90°.

12. A three dimensional structure for (8S,20R,22S)-Des-A,B-22-methyl-cholestan-8,25-diol as defined by the molecular packaging arrangement set forth in claim 11.

13. A method of purifying (8S,20R,22S)-Des-A,B-22-methyl-cholestan-8,25-diol comprising the steps of:

(a) preparing a solvent comprising ethyl acetate;

(b) dissolving a product containing (8S,20R,22S)-Des-A,B-22-methyl-cholestan-8,25-diol to be purified in said solvent;

(c) cooling said solvent and dissolved product below ambient temperature for a sufficient amount of time to form a precipitate of (8S,20R,22S)-Des-A,B-22-methyl-cholestan-8,25-diol crystals; and (d) separating the (8S,20R,22S)-Des-A,B-22-methyl-cholestan-8,25-diol crystals from the solvent.

14. The method of claim 13 including the further step of allowing said solvent and dissolved product to cool to ambient temperature prior to cooling below ambient temperature.

15. The method of claim 13 wherein said solvent comprises 100% ethyl acetate, by volume.

16. The method of claim 13 wherein the step of separating comprises filtering the solvent and precipitate to obtain the crystals.

17. The method of claim 13 including a further step (e) comprising repeating steps (a) through (d) using the recovered crystals from step (d) as the product of step (b).

18. (8S,20R,22R)-Des-A,B-22-methyl-cholestan-8,25-diol having the formula

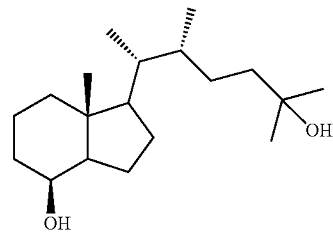 [SMILES: C[C@H](CCC(C)(C)O)[C@@H](C)C1CCC2[C@@H](O)CCC[C@@]21C]

in crystalline form.

19. A crystalline form of (8S,20R,22R)-Des-A,B-22-methyl-cholestan-8,25-diol having molecular packaging arrangement defined by space group P2(1) and unit cell dimensions a=11.39 Å b=16.53 Å c=11.45 Å α=90°, β=119.26° and γ=90°.

20. A three dimensional structure for (8S,20R,22R)-Des-A,B-22-methyl-cholestan-8,25-diol as defined by the molecular packaging arrangement set forth in claim 19.

21. A method of purifying (8S,20R,22R)-Des-A,B-22-methyl-cholestan-8,25-diol comprising the steps of:

(a) preparing a solvent comprising ethyl acetate;

(b) dissolving a product containing (8S,20R,22R)-Des-A,B-22-methyl-cholestan-8,25-diol to be purified in said solvent;

(c) cooling said solvent and dissolved product below ambient temperature for a sufficient amount of time to form a precipitate of (8S,20R,22R)-Des-A,B-22-methyl-cholestan-8,25-diol crystals; and (d) separating the (8S,20R,22R)-Des-A,B-22-methyl-cholestan-8,25-diol crystals from the solvent.

22. The method of claim 21 including the further step of allowing said solvent and dissolved product to cool to ambient temperature prior to cooling below ambient temperature.

23. The method of claim 21 wherein the step of separating comprises filtering the solvent and precipitate to obtain the crystals.

24. The method of claim 21 including a further step (e) comprising repeating steps (a) through (d) using the recovered crystals from step (d) as the product of step (b).

25. The method of claim 21 wherein said solvent comprises 100% ethyl acetate, by volume.

26. (8S,20S,22R)-Des-A,B-22-methyl-cholestan-8,25-diol having the formula

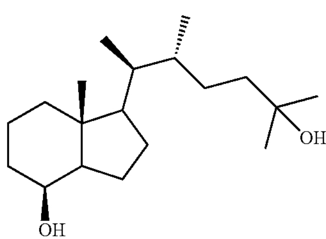 [SMILES: C[C@H](CCC(C)(C)O)[C@H](C)C1CCC2[C@@H](O)CCC[C@]12C]

in crystalline form.

27. A crystalline form of (8S,20S,22R)-Des-A,B-22-methyl-cholestan-8,25-diol having molecular packaging arrangement defined by space group P2(1) and unit cell dimensions a=9.68 Å b=19.15 Å c=9.68 Å $\alpha$=90°, $\beta$=91.27° and $\gamma$=90°.

28. A three dimensional structure for (8S,20S,22R)-Des-A,B-22-methyl-cholestan-8,25-diol as defined by the molecular packaging arrangement set forth in claim 27.

29. A method of purifying (8S,20S,22R)-Des-A,B-22-methyl-cholestan-8,25-diol comprising the steps of:

(a) preparing a solvent comprising ethyl acetate;

(b) dissolving a product containing (8S,20S,22R)-Des-A,B-22-methyl-cholestan-8,25-diol to be purified in said solvent;

(c) cooling said solvent and dissolved product below ambient temperature for a sufficient amount of time to form a precipitate of (8S,20S,22R)-Des-A,B-22-methyl-cholestan-8,25-diol crystals; and (d) separating the (8S,20S,22R)-Des-A,B-22-methyl-cholestan-8,25-diol crystals from the solvent.

30. The method of claim 29 including the further step of allowing said solvent and dissolved product to cool to ambient temperature prior to cooling below ambient temperature.

31. The method of claim 29 wherein the step of separating comprises filtering the solvent and precipitate to obtain the crystals.

32. The method of claim 29 including a further step (e) comprising repeating steps (a) through (d) using the recovered crystals from step (d) as the product of step (b).

33. The method of claim 29 wherein said solvent comprises 100% ethyl acetate, by volume.

* * * * *